(12) United States Patent
Sakamuri et al.

(10) Patent No.: US 11,203,611 B2
(45) Date of Patent: Dec. 21, 2021

(54) IMMUNOMODULATING POLYNUCLEOTIDES, ANTIBODY CONJUGATES THEREOF, AND METHODS OF THEIR USE

(71) Applicant: SOLSTICE BIOLOGICS, LTD., Dublin (IE)

(72) Inventors: Sukumar Sakamuri, San Diego, CA (US); Curt W. Bradshaw, San Diego, CA (US); Son Lam, San Diego, CA (US); Joseph Stock, San Diego, CA (US); Edward Hyungsuk Ha, Solana Beach, CA (US); Laxman Eltepu, San Diego, CA (US); Dingguo Liu, San Diego, CA (US); Bin Liu, San Diego, CA (US); Giuseppe Dello Iacono, Oceanside, CA (US); Bryan R. Meade, San Diego, CA (US); Ayman Kabakibi, San Diego, CA (US)

(73) Assignee: TOLLNINE, INC., San Francisco, CA (US)

( * ) Notice: Subject to any disclaimer, the term of this patent is extended or adjusted under 35 U.S.C. 154(b) by 298 days.

(21) Appl. No.: 15/953,290

(22) Filed: Apr. 13, 2018

(65) Prior Publication Data
US 2018/0312536 A1  Nov. 1, 2018

Related U.S. Application Data

(60) Provisional application No. 62/537,925, filed on Jul. 27, 2017, provisional application No. 62/485,748, filed on Apr. 14, 2017.

(51) Int. Cl.
| | |
|---|---|
| C07H 21/04 | (2006.01) |
| C12N 15/117 | (2010.01) |
| A61P 35/00 | (2006.01) |
| C07K 7/06 | (2006.01) |
| C07K 16/28 | (2006.01) |
| C07K 16/30 | (2006.01) |
| A61K 47/68 | (2017.01) |
| A61K 47/60 | (2017.01) |
| A61K 31/7125 | (2006.01) |
| A61K 39/00 | (2006.01) |
| A61K 39/39 | (2006.01) |

(52) U.S. Cl.
CPC ......... *C07H 21/04* (2013.01); *A61K 31/7125* (2013.01); *A61K 39/0011* (2013.01); *A61K 39/39* (2013.01); *A61K 47/60* (2017.08); *A61K 47/6807* (2017.08); *A61K 47/6849* (2017.08); *A61K 47/6883* (2017.08); *A61P 35/00* (2018.01); *C07K 7/06* (2013.01); *C07K 16/2803* (2013.01); *C07K 16/2812* (2013.01); *C07K 16/2815* (2013.01); *C07K 16/2818* (2013.01); *C07K 16/2827* (2013.01); *C07K 16/2833* (2013.01); *C07K 16/2851* (2013.01); *C07K 16/2863* (2013.01); *C07K 16/2878* (2013.01); *C07K 16/2887* (2013.01); *C07K 16/2896* (2013.01); *C07K 16/3084* (2013.01); *C12N 15/117* (2013.01); *A61K 2039/505* (2013.01); *A61K 2039/507* (2013.01); *A61K 2039/53* (2013.01); *A61K 2039/54* (2013.01); *A61K 2039/55516* (2013.01); *A61K 2039/55561* (2013.01); *A61K 2039/572* (2013.01); *C07K 2319/40* (2013.01); *C12N 2310/17* (2013.01); *C12N 2310/311* (2013.01); *C12N 2310/315* (2013.01); *C12N 2310/332* (2013.01); *C12N 2310/3513* (2013.01); *C12N 2310/3515* (2013.01); *C12N 2310/51* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |

(Continued)

FOREIGN PATENT DOCUMENTS

| | | |
|---|---|---|
| EP | 2368579 | 9/2011 |
| EP | 1809671 | 7/2014 |

(Continued)

OTHER PUBLICATIONS

Jain et al., Bioorganic & Medical Chemistry vol. 21(20):6224-6232.*

(Continued)

*Primary Examiner* — Sean McGarry
(74) *Attorney, Agent, or Firm* — Jones Day

(57) ABSTRACT

Immunomodulating polynucleotides are disclosed. The immunomodulating polynucleotides may contain 5-modified uridine, 5-modified cytidine, a total of from 6 to 16 nucleotides, and/or one or more abasic spacers and/or internucleoside phosphotriesters. Also disclosed are conjugates containing a targeting moiety and one or more immunomodulating polynucleotides. The immunomodulating polynucleotides and conjugates may further contain one or more auxiliary moieties. Also disclosed are compositions containing the immunomodulating polynucleotides or the conjugates containing one or more stereochemically enriched internucleoside phosphorothioates. Further disclosed are pharmaceutical compositions containing the immunomodulating polynucleotides or the conjugates and methods of their use.

35 Claims, 105 Drawing Sheets
Specification includes a Sequence Listing.

(56) References Cited

U.S. PATENT DOCUMENTS

| | | | |
|---|---|---|---|
| 5,130,302 | A | 7/1992 | Spielvogel et al. |
| 5,134,066 | A | 7/1992 | Rogers et al. |
| 5,175,273 | A | 12/1992 | Bischofberger et al. |
| 5,367,066 | A | 11/1994 | Urdea et al. |
| 5,432,272 | A | 7/1995 | Benner |
| 5,457,187 | A | 10/1995 | Gmeiner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,506,212 | A | 4/1996 | Hoke et al. |
| 5,525,711 | A | 6/1996 | Hawkins et al. |
| 5,552,540 | A | 9/1996 | Haralambidis |
| 5,576,302 | A | 11/1996 | Cook et al. |
| 5,587,361 | A | 12/1996 | Cook et al. |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,681,941 | A | 10/1997 | Cook et al. |
| 5,734,041 | A | 3/1998 | Just et al. |
| 5,852,188 | A | 12/1998 | Cook |
| 5,883,237 | A | 3/1999 | Stec et al. |
| 6,017,700 | A | 1/2000 | Horn et al. |
| 6,242,589 | B1 | 6/2001 | Cook et al. |
| 6,322,996 | B1 | 11/2001 | Sato et al. |
| 6,867,294 | B1 | 3/2005 | Sanghvi et al. |
| 7,534,772 | B2 | 5/2009 | Weiner et al. |
| 8,580,268 | B2 | 11/2013 | Debelak et al. |
| 8,859,755 | B2 | 10/2014 | Wada et al. |
| 8,871,908 | B2 | 10/2014 | Liu et al. |
| 9,676,871 | B2 | 6/2017 | Strop et al. |
| 2003/0059773 | A1 | 3/2003 | Nest et al. |
| 2004/0266690 | A1 | 12/2004 | Pool |
| 2005/0136491 | A1 | 6/2005 | Chen et al. |
| 2006/0135459 | A1 | 6/2006 | Epstein et al. |
| 2007/0105770 | A1 | 5/2007 | Johansen et al. |
| 2007/0184537 | A1 | 8/2007 | Schibli et al. |
| 2010/0098704 | A1 | 4/2010 | Keler et al. |
| 2010/0261779 | A1* | 10/2010 | Uhlmann ............... A61K 45/06 514/44 R |
| 2011/0184147 | A1 | 7/2011 | Kamiya et al. |
| 2013/0184450 | A1 | 7/2013 | Wada et al. |
| 2013/0189287 | A1 | 7/2013 | Bregeon et al. |
| 2013/0230543 | A1 | 9/2013 | Pons et al. |
| 2014/0127197 | A1 | 5/2014 | Ebens et al. |
| 2014/0163213 | A1 | 6/2014 | Debelak et al. |
| 2014/0356385 | A1 | 12/2014 | Dennler et al. |
| 2015/0111246 | A1 | 4/2015 | Samant et al. |
| 2015/0166999 | A1 | 6/2015 | Gemba |
| 2015/0197540 | A1 | 7/2015 | Shimizu et al. |
| 2016/0022833 | A1 | 1/2016 | Bregeon |
| 2016/0257961 | A1* | 9/2016 | Bradshaw ........... C07F 9/65616 |
| 2016/0333349 | A1 | 11/2016 | Gemba et al. |
| 2016/0355859 | A1 | 12/2016 | Johansen et al. |
| 2016/0361434 | A1 | 12/2016 | El Alaoui et al. |
| 2017/0014442 | A1 | 1/2017 | Admyre et al. |
| 2017/0340734 | A1* | 11/2017 | Robert .................... A61P 43/00 |
| 2019/0194655 | A1* | 6/2019 | Bradshaw ............ C12N 15/113 |

FOREIGN PATENT DOCUMENTS

| | | |
|---|---|---|
| WO | WO 2006/052900 | 5/2006 |
| WO | WO 2010/002042 | 1/2010 |
| WO | WO 2010/132622 | 11/2010 |
| WO | WO 2012/085291 | 6/2012 |
| WO | WO 2012/092616 | 7/2012 |
| WO | WO 2014/011521 | 1/2014 |
| WO | WO 2015/031837 | 3/2015 |
| WO | WO 2015/069932 | 5/2015 |
| WO | WO 2015/097267 | 7/2015 |
| WO | WO 2015/107425 | 7/2015 |
| WO | WO 2015/188197 | 12/2015 |
| WO | WO 2016/096785 | 6/2016 |
| WO | WO 2016/096938 | 6/2016 |

OTHER PUBLICATIONS

Puig et al. Nucleic Acids Research vol. 34(22):6488-6495, 2006.*

Mongis et al., Bioconjugat Chemistry, vol. 28(4):1151-1165, Mar. 2017.*

Aaronson et al., "Rapid HATU-mediated solution phase siRNA conjugation," Bioconjug. Chem., 22(8):1723-1728 (2011).

Anami et al., "Enzymatic conjugation using branched linkers for constructing homogeneous antibody-drug conjugates with high potency," Org. Biomol. Chem., 15:5635-5642 (2017).

Aoshi et al., "Development of Nonaggregating Poly-A Tailed Immunostimulatory A/D Type CpG Oligodeoxynucleotides Applicable for Clinical Use," J. Immunol. Res., Article ID 316364 (2015).

Avalos et al., "Differential Cytokine Production and Bystander Activation of Autoreactive B Cells in Response to CpG-A and CpG-B ODNs1," J. Immunol., 183(10):6262-6268 (2009).

Ballas et al., "Divergent Therapeutic and Immunologic Effects of Oligodeoxynucleotides with Distinct CpG Motifs," J. Immunol., 167(9):4878-4886 (2001).

Betting et al., "Intratumoral But Not Systemic Delivery of CpG Oligodeoxynucleotide Augments the Efficacy of Anti-CD20 Monoclonal Antibody Therapy Against B Cell Lymphoma," J. Immunother., 32(6):622-631 (2009).

Bhagat et al., "CpG penta- and hexadeoxyribonucleotides as potent immunomodulatory agents," Biochem. Biophys. Res. Comm., 300:853-861 (2003).

Bradshaw et al., "5-Substituted Pyrimidine Nucleosides and Nucleotides," Chem. Soc. Rev., 6:43-62 (1977).

Buhe et al., "Development of a Murine model to dissect the CpG-oligonucleotide-enhancement of the killing of human B Cells by rituximab," J. Autoimmun., 34:134-144 (2010).

Caporale et al., "The LQSP tetrapeptide is a new highly efficient substrate of microbial transglutaminase for the site-specific derivatization of peptides and proteins," Biotechnol. J., 10:154-161 (2015).

Clarke et al., "The Incorporation of Amines into Protein," Arch. Biochem. Biophys., 79:338-354 (1959).

Cornelie et al., "Direct Evidence that Toll-like Receptor 9 (TLR9) Functionally Binds Plasmid DNA by Specific Cytosine-phosphate-guanine Motif Recognition," J. Biol. Chem., 279(15):15124-15129 (2004).

D'Arpa et al., "Toll-Like Receptor Signaling in Burn Wound Healing and Scarring," Adv. Wound Care, 6(10):330-343 (2017).

Dale et al., "Stimulated platelets use serotonin to enhance their retention of procoagulant proteins on the cell surface," Nature, 415:175-179 (2002).

Dennler et al., "Microbial Transglutaminaseand c-myc-Tag:AStrong Couple for the Functionalization of Antibody-Like Protein Scaffolds from Discovery Platforms," Chem. Bio. Chem., 16:861-867 (2015).

Dennler et al., "Transglutaminase-Based Chemo-Enzymatic Conjugation Approach Yields Homogeneous Antibody—Drug Conjugates," Bioconjugate Chem., 25:569-578 (2014).

Dorywalska et al., "Effect of Attachment Site on Stability of Cleavable Antibody Drug Conjugates," Bioconjugate Chem., 26:650-659 (2015).

Englisch et al., "Chemically Modified Oligonucleotides as Probes and Inhibitors," Angew. Chem. Int. Ed. Engl., 30(6):613-629 (1991).

Fearon et al., "A minimal human immunostimulatory CpG motif that potently induces IFN-gamma and IFN-alpha production," Eur. J. Immunol., 33:2114-2122 (2003).

Gangloff et al., "Baseless Assumptions: Activation of TLR9 by DNA," Immunity, 28:293-294 (2008).

Guiducci et al., "Properties regulating the nature of the plasmacytoid dendritic cell response to Toll-like receptor 9 activation," J. Exp. Med., 203(8):1999-2008 (2006).

Gundersen et al., "Microbial transglutaminase displays broad acyl-acceptor substrate specificity," Appl. Microbiol. Biotechnol., 98:219-230 (2014).

Guo et al., "Solid-Phase Stereoselective Synthesis of 2'-O-Methyl-Oligoribonucleoside Phosphorothioates Using Nucleoside Bicyclic Oxazaphospholidines," Bioorg. Med. Chem. Lett., 8:2539-2544 (1998).

(56) References Cited

OTHER PUBLICATIONS

Haas et al., "Supplemental Data: The DNA Sugar Backbone 2' Deoxyribose Determines Toll-like Receptor 9 Activation," *Immunity*, 28:1-10 (2008).
Haas et al., "The DNA Sugar Backbone 2' Deoxyribose Determines Toll-like Receptor 9 Activation," *Immunity*, 28:315-323 (2008).
Hornung et al., "Sequence-specific potent induction of IFN-α by short interfering RNA in plasmacytoid dendritic cells through TLR7," *Nat. Med.*, 11(3):263-270 (2005).
Hu et al., "Rational Design of Transglutaminase Substrate Peptides for Rapid Enzymatic Formation of Hydrogels," *J. Am. Chem. Soc.*, 125(47):14298-14299 (2003).
Jahns et al., "Stereochemical bias introduced during RNA synthesis modulates the activity of phosphorothioate siRNAs," *Nat. Comm.*, 6:6317 (2015).
Jain et al., "Assessment of the cellular internalization of thermolytic phosphorothioate DNA oligonucleotide prodrugs," *Bioorg. Med. Chem.*, 21:6224-6232 (2013).
Jang et al., "Systemic delivery and mechanistic studies of novel chTNT-3/CpG immunoconjugates for immunotherapy of solid tumors," *Cancer Immunology, Immunotherapy.*, pp. 1-34 (2016).
Jeger et al., "Site-Specific and Stoichiometric Modification of Antibodies by Bacterial Transglutaminase," *Angew. Chem. Int. Ed.*, 49:9995-9997 (2010).
Jeger, "Site-Specific Conjugation of Tumour-Targeting Antibodies Using Transglutaminase," Dissertation, University of Basel, pp. 1-138 (2009).
Josten et al., "Use of microbial transglutaminase for the enzymatic biotinylation of antibodies," *J. Immunol. Meth.*, 240:47-54 (2000).
Kandimalla et al., "A dinucleotide motif in oligonucleotides shows potent immunomodulatory activity and overrides species-specific recognition observed with CpG motif," *Proc. Natl. Acad. Sci. USA*, 100(24):14303-14308 (2003).
Kandimalla et al., "Conjugation of Ligands at the 5'-End of CpG DNA Affects Immunostimulatory Activity," *Bioconjugate Chem.*, 13(5):966-974 (2002).
Kandimalla et al., "Divergent synthetic nucleotide motif recognition pattern: design and development of potent immunomodulatory oligodeoxyribonucleotide agents with distinct cytokine induction profiles," *Nucl. Acids Res.*, 31(9):2393-2400 (2003).
Kandimalla et al., "Effect of Chemical Modifications of Cytosine and Guanine in a CpG-Motif of Oligonucleotides: Structure-Immunostimulatory Activity Relationships," *Bioorg. Med. Chem.*, 9:807-813 (2001).
Kandimalla et al., "Secondary structures in CpG oligonucleotides affect immunostimulatory activity," *Biochem. Biophys. Res. Comm.*, 306:948-953 (2003).
Kapp et al., "Genuine Immunomodulation With dSLIM," *Mol. Ther. Nucl. Acids*, 3:e170 (2014).
Kolar et al., "Halogen Bonding in Nucleic Acid Complexes," *J. Med. Chem.*, 1-35 (2017).
Koziolkiewicz et al., "Stereodifferentiation—the effect of P chirality of oligo(nucleoside phosphorothioates) on the activity of bacterial RNase H," *Nucl. Acids Res.*, 23(24):5000-5005 (1995).
Kreutz et al., "Antibody-Antigen-Adjuvant Conjugates Enable Co-Delivery of Antigen and Adjuvant to Dendritic Cells in Cis but Only Have Partial Targeting Specificity," *PLoS One*, 7(7):e40208 (2012).
Krieg et al., "P-Chirality-Dependent Immune Activation by Phosphorothioate CpG Oligodeoxynucleotides," *Oligonucleotides*, 13:491-499 (2003).
Kroschwitz ed., "Polynucleotides," *The Concise Encyclopedia of Polymer Science and Engineering*, John Wiley & Sons, New York, NY, pp. 858-859 (1990).
Langston et al., "Substrate Specificity of Streptomyces Transglutaminases," *Appl. Biochem. Biotechnol.*, 136:291-308 (2007).
Lee et al., "Glutamine (Q)-Peptide Screening for Transglutaminase Reaction Using mRNA Display," *Biotechnol. Bioeng.*, 110(2):353-362 (2013).
Lesnikowski, "Stereocontrolled Synthesis of P-Chiral Analogues of Oligonucleotides," *Bioorg. Chem.*, 21:127-155 (1993).
Li et al., "Generation of tumor-targeted antibody—CpG conjugates," *J. Immunol. Methods*, 389:45-51 (2013).
Li et al., "Lymphoma Immunotherapy with CpG Oligodeoxynucleotides Requires TLR9 Either in the Host or in the Tumor Itself," *J. Immunol.*, 179:2493-2500 (2007).
Makkouk et al., "Biodegradable Microparticles Loaded with Doxorubicin and CpG ODN for In Situ Immunization Against Cancer," *AAPS J.*, 17(1):184-193 (2015).
Mallikarjuna et al., "Agonists of Toll-like Receptor 9 Containing Synthetic Dinucleotide Motifs," *J. Med. Chem.*, 50(25):6411-6418 (2007).
Marabelle et al., "Depleting tumor-specific Tregs at a single site eradicates disseminated tumors," *J. Clin. Investigation*, 123(6):2447-2463 (2013).
Marshall et al., "Identification of a novel CpG DNA class and motif that optimally stimulate B cell and plasmacytoid dendritic cell functions," *J. Leukocyte Biol.*, 73:781-792 (2003).
Martínez-Campos et al., "Role of TLR9 in Oncogenic Virus-Produced Cancer," *Viral Immunol.*, 30(2):98-105 (2017).
Meng et al., "Nuclease-resistant immunostimulatory phosphodiester CpG oligodeoxynucleotides as human Toll-like receptor 9 agonists," *BMC Biotechnol.*, 11:88 (2011).
Mindt et al., "Modification of Different IgG1 Antibodies via Glutamine and Lysine using Bacterial and Human Tissue Transglutaminase," *Bioconjugate Chem.*, 19:271-278 (2008).
Mongis et al., "Coupling of Immunostimulants to Live Cells through Metabolic Glycoengineering and Bioorthogonal Click Chemistry," *Bioconjugate Chem.*, 28:1151-1165 (2017).
Narayanan et al., "CpG Oligonucleotides with Modified Termini and Nicked Dumbbell Structure Show Enhanced Immunostimulatory Activity," *J. Med. Chem.*, 46(23):5031-5044.
Nawrot et al., "DNA Oligonucleotides Containing Stereodefined Phosphorothioate Linkages in Selected Positions," *Curr. Protocols Nucl. Acid Chem.*, 36:4.34.1-4.34.15 (2009).
Nierkens et al., "Route of Administration of the TLR9 Agonist CpG Critically Determines the Efficacy of Cancer Immunotherapy in Mice," *PLoS One*, 4(12):e8368 (2009).
Notley et al., "DNA methylation governs the dynamic regulation of inflammation by apoptotic cells during efferocytosis," *Sci. Rep.*, 7:42204 (2017).
Nukaga et al., "Stereocontrolled Solid-Phase Synthesis of Phosphorothioate Oligoribonucleotides Using 2'-O-(2-Cyanoethoxymethyl)-nucleoside 3'-O-Oxazaphospholidine Monomers," *J. Org. Chem.*, 77:7913-7922 (2012).
Ohto et al., "Structural basis of CpG and inhibitory DNA recognition by Toll-like receptor 9," *Nature*, (2015). doi: 10.1038/nature14138.
Ohtsuka et al., "Comparison of Substrate Specificities of Transglutaminases Using Synthetic Peptides as Acyl donors," *Biosci. Biotechnol. Biochem.*, 64(12):2608-2613 (2000).
Oka et al., "An Oxazaphospholidine Approach for the Stereocontrolled Synthesis of Oligonucleoside Phosphorothioates," *J. Am. Chem. Soc.*, 125(27):8307-8317 (2003).
Oka et al., "Solid-Phase Synthesis of Stereoregular Oligodeoxyribonucleoside Phosphorothioates Using Bicyclic Oxazaphospholidine Derivatives as Monomer Units," *J. Am. Chem. Soc.*, 130(47):16031-16037 (2008).
Oka et al., "Stereocontrolled synthesis of oligonucleotide analogs containing chiral internucleotidic phosphorus atoms," *Chem. Soc. Rev.*, 40:5829-5843 (2011).
Oka et al., "Stereocontrolled Synthesis of Oligoribonucleoside Phosphorothioates by an Oxazaphospholidine Approach," *Org. Lett.*, 11(4):967-970 (2009).
Palma et al., "Improved systemic pharmacokinetics, biodistribution, and antitumor activity of CpG oligodeoxynucleotides complexed to endogenous antibodies in vivo," *J. Control Rel.*, 120(1-2):95-103 (2007).
Paz et al., "The Distinct and Cooperative Roles of Toll-Like Receptor 9 and Receptor for Advanced Glycation End Products in Modulating In Vivo Inflammatory Responses to Select CpG and Non-CpG Oligonucleotides," *Nucl. Acid Therapeutics*, 1-13 (2017).

(56) References Cited

OTHER PUBLICATIONS

Pohar et al., "Minimal Sequence Requirements for Oligodeoxyribonucleotides Activating Human TLR9," *J. Immunol.*, 194:3901-3908 (2015).

Puig et al., "Use of thermolytic protective groups to prevent G-tetrad formation in CpG ODN type D: structural studies and immunomodulatory activity in primates," *Nucl. Acids Res.*, 34(22):6488-6495 (2006).

Putta et al., "Immune-Stimulatory Dinucleotide at the 5'-End of Oligodeoxynucleotides Is Critical for TLR9-Mediated Immune Responses," *ACS Med. Chem. Lett.*, 4:302-305 (2013).

Putta et al., "Impact of Nature and Length of Linker Incorporated in Agonists on Toll-Like Receptor 9-Mediated Immune Responses," *J. Med. Chem.*, 53:3730-3738 (2010).

Rachel et al., "Biotechnological Applications of Transglutaminases," *Biomolecules*, 3:870-888 (2013).

Radhakrishnan et al., "Solid-Phase Stereoselective Synthesis of Oligonucleoside Phosphorothioates: The Nucleoside Bicyclic Oxazaphospholidines as Novel Synthons," *Tetrahedron Lett.*, 39:2491-2494 (1998).

Roberts et al., "Cutting Edge: Species-Specific TLR9-Mediated Recognition of CpG and Non-CpG Phosphorothioate-Modified Oligonucleotides," *J. Immunol.*, 174(2):605-608 (2005).

Samulowitz et al., "A Novel Class of Immune-Stimulatory CpG Oligodeoxynucleotides Unifies High Potency in Type I Interferon Induction with Preferred Structural Properties," *Oligonucleotides*, 20(2):93-101 (2010).

Sanghvi, "Chapter 16: Oligonucleotides" *Antisense Research and Applications*, Crooke et al. eds., CRC Press, Boca Raton, FL, pp. 289-302 (1993).

Sanghvi, "Chapter 15: Heterocyclic Base Modifications in Nucleic Acids and Their Applications in Antisense Oligonucleotides," *Antisense Research and Applications*, Crooke et al. eds., CRC Press, Boca Raton, FL, pp. 276-278 (1993).

Schettini et al., "Intratumoral delivery of CpG-conjugated anti-MUC1 antibody enhances NK cell anti-tumor activity," *Cancer Immunol. Immunother.*, 61:2055-2065 (2012).

Schmidt et al., "Cytokine and Ig-production by CG-containing sequences with phosphorodiester backbone and dumbbell-shape," *Allergy*, 61:56-63 (2006).

Schmidt et al., "Design and Structural Requirements of the Potent and Safe TLR-9 Agonistic Immunomodulator MGN1703," *Nucleic Acid Therapeutics*, (2015). doi: 10.1089/nat.2015.0533.

Schraml et al., "Defining dendritic cells," *Curr. Opin. Immunol.*, 32:13-20 (2015).

Seio et al., "Enhanced Stereoselectivity in Internucleotidic Bond Formation by the Use of the Chiral Ribose Moiety of Thymidine," *J. Org. Chem.*, 68:3849-3859 (2003).

Sharma et al., "Systemic Targeting of CpG-ODN to the Tumor Microenvironment with Anti-neu-CpG HybridMolecule and T Regulatory Cell Depletion Induces Memory Responses in BALB-neuT Tolerant Mice," *Cancer Res.*, 68(18):7530-7540 (2008).

Sheng et al., "Synthesis, structure and imaging of oligodeoxyribonucleotides with tellurium-nucleobase derivatization," *Nucleic Acids Res.*, 39(9):3962-3971 (2011).

Siegmund et al., "Locked by Design: A Conformationally Constrained Transglutaminase Tag Enables Efficient Site-Specific Conjugation," *Angew. Chem. Int. Ed.*, 54:1-6 (2015).

Spolaore et al., "Site-Specific Transglutaminase-mediated Conjugation of Interferon Alpha-2b at Glutamine or Lysine Residues," *Bioconjugate Chem.*, pp. 1-31 (2016).

St.-Jacques et al., "Specificity of Transglutaminase-Catalyzed Peptide Synthesis," *J. Mol. Catal., B Enzym.*, (2015). doi: http://dx.doi.org/doi:10.1016/j.molcatb.2015.11.009.

Strop et al., "Location Matters: Site of Conjugation Modulates Stability and Pharmacokinetics of Antibody Drug Conjugates," *Chem. Biol.*, 20:161-167 (2013).

Strop et al., "Supplemental Information: Location Matters: Site of Conjugation Modulates Stability and Pharmacokinetics of Antibody Drug Conjugates," *Chem. Biol.*, 20: pp. 1-20 (2013).

Strop, "Versatility of Microbial Transglutaminase," *Bioconjugate Chem.*, 25:855-862 (2014).

Sugimura et al., "Identification of preferred substrate sequences of microbial transglutaminase from Strep-to-my-ces mo-baraen-sis using a phage-displayed peptide library," *Arch. Biochem. Biophys.*, 477:379-383 (2008).

Sugimura et al., "Screening for the Preferred Substrate Sequence of Transglutaminase Using a Phage-displayed Peptide Library," *J. Biol. Chem.*, 281(26):17699-17706 (2006).

Tabatadze et al., "A Novel Thymidine Phosphoramidite Synthon for Incorporation of Internucleoside Phosphate Linkers During Automated Oligodeoxynucleotide Synthesis," *Nucleosides Nucleotides Nucleic Acids*, 27:157-172 (2008).

Tagami et al., "Substrate specificity of microbial transglutaminase as revealed by three-dimensional docking simulation and mutagenesis," *Protein Eng. Des. Sel.*, 22(12):747-752 (2009).

Taguchi et al., "Substrate Specificity Analysis of Microbial Transglutaminase Using Proteinaceous Protease Inhibitos as Natural Model Substrates," *J. Biochem.*, 128:415-425 (2000).

Tominaga et al., "An enzymatic method for site-specific labeling of recombinant proteins with oligonucleotides," *Chem. Comm.*, Supplmentary Information:1-7 (2006).

Verthelyi et al., "Differential signaling by CpG DNA in DCs and B cells: not just TLR9," *Trends Immunol.*, 24(10):519-522 (2003).

Verthelyi et al., "Human Peripheral Blood Cells Differentially Recognize and Respond to Two Distinct CpG Motifs," *J. Immunol.*, 166:2372-2377 (2001).

Wada et al., "Stereocontrolled synthesis of phosphorothioate DNA by an oxazaphospholidine approach," *Nucl. Acids Res. Suppl.*, 3:109-110 (2003).

Wan et al., "Synthesis, biophysical properties and biological activity of second generation antisense oligonucleotides containing chiral phosphorothioate linkages," *Nucl. Acids Res.*, 42(22):13456-13468 (2014).

Wang et al., "An Immunosuppressive Antibody—Drug Conjugate," *J. Am. Chem. Soc.*, 137:3229-3232 (2015).

Wittig et al., "MGN1703, an immunomodulator and toll-like receptor 9 (TLR-9) agonist: From bench to bedside," *Crit. Rev. Oncol. Hematol.*, 94:31-44 (2015).

Wu et al., "Inflammatory arthritis can be reined in by CpG-induced DC—NK cell cross talk," *J. Exp. Med.*, 204(8):1911-1922 (2007).

Yasuda et al., "Endosomal Translocation of Vertebrate DNA Activates Dendritic Cells via TLR9-Dependent and -Independent Pathways," *J. Immunol.*, 174:6129-6136 (2005).

Yu et al., "Immunostimulatory Activity of CpG Oligonucleotides Containing Non-Ionic Methylphosphonate Linkages," *Biorg. Med. Chem.*, 9:2803-2808 (2001).

Yu et al., "Immunostimulatory properties of phosphorothioate CpG DNA containing both 3'-5'- and 2'-5'-internucleotide linkages," *Nucl. Acids. Res.*, 30(7):1613-1619 (2002).

Yu et al., "Modulation of Immunostimulatory Activity of CpG Oligonucleotides by Site-Specific Deletion of Nucleobases," *Bioorg. Med. Chem. Lett.*, 11:2263-2267 (2001).

Yu et al., "Potent CpG oligonucleotides containing phosphodiester linkages: in vitro and in vivo immunostimulatory properties," *Biochem. Biophys. Res. Comm.*, 297:83-90 (2002).

Yu et al., "Requirement of Nucleobase Proximal to CpG Dinucleotide for Immunostimulatory Activity of Synthetic CpG DNA," *Biorg. Med. Chem.*, 11:459-464 (2003).

Yu et al., "Stereo-Enriched Phosphorothioate Oligodeoxynucleotides: Synthesis, Biophysical and Biological Properties," *Bioorg. Med. Chem.*, 8:275-284 (2000).

Zhang et al., "Identification of tumor-associated antigens as diagnostic and predictive biomarkers in cancer," *Methods Mol. Biol.*, 520:1-10 (2009).

Zhao et al., "Immunostimulatory Activity of CpG Containing Phosphorothioate Oligodeoxynucleotide is Modulated by Modi® cation of a Single Deoxynucleoside," *Bioorg. Med. Chem. Lett.*, 10:1051-1054 (2000).

(56) References Cited

OTHER PUBLICATIONS

Zhao et al., "Site of Chemical Modifications in CpG Containing Phosphorothioate Oligodeoxynucleotide Modulates its Immunostimulatory Activity," *Bioorg. Med. Chem. Lett.*, 9:3453-3458 (1999).

* cited by examiner

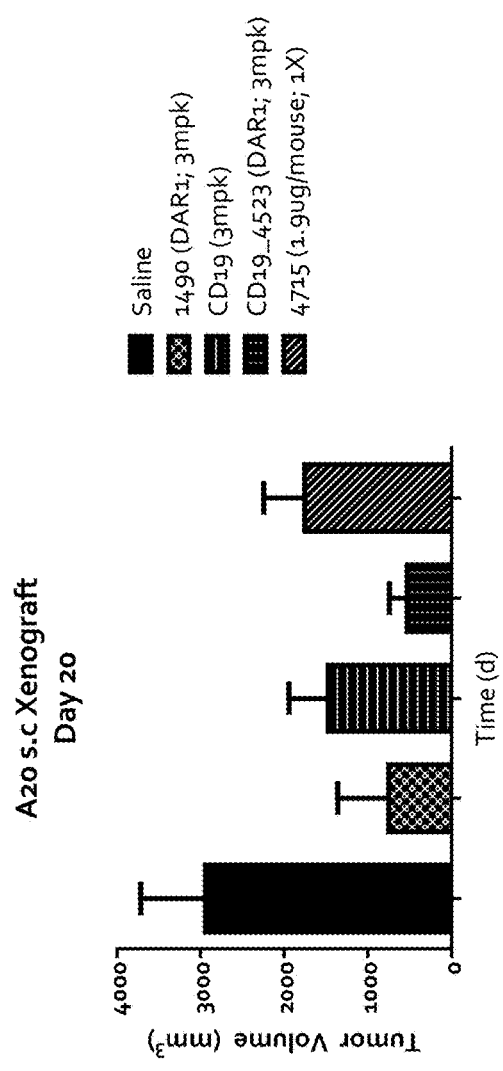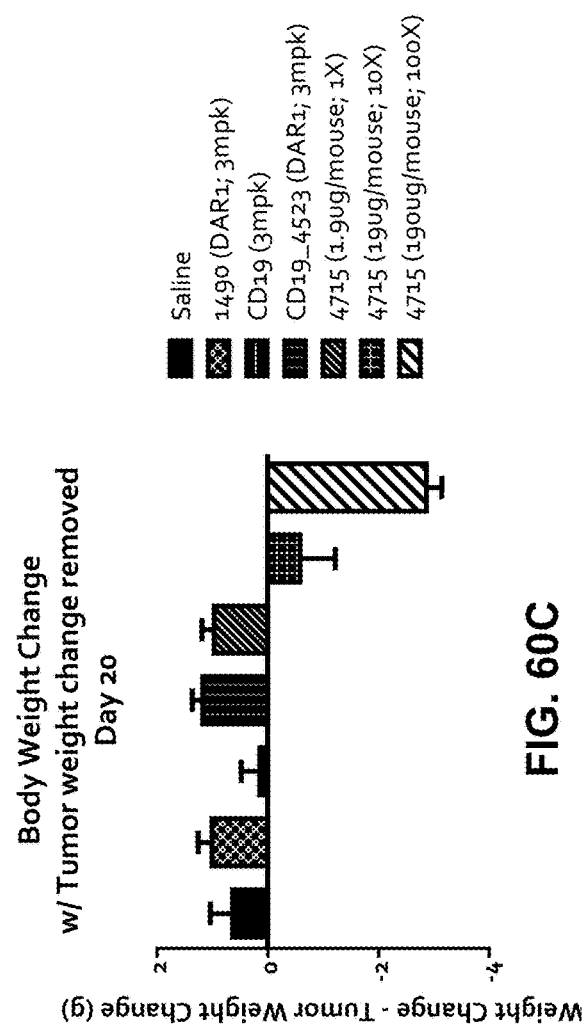
FIG. 60B
FIG. 60C

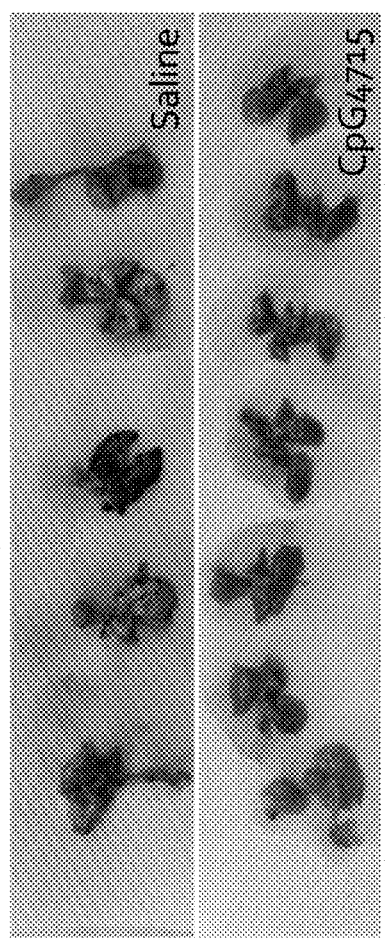
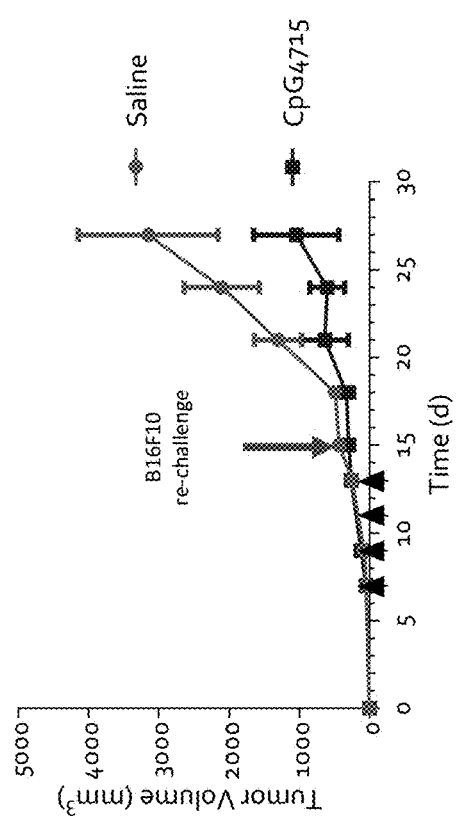
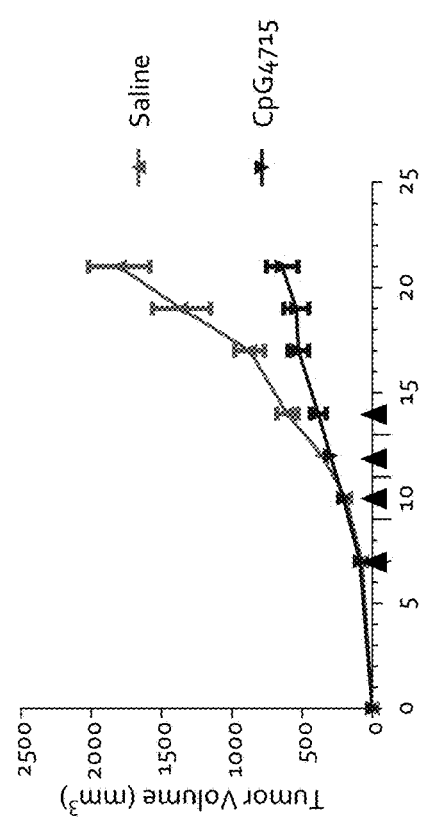
FIG. 61A
FIG. 61B
FIG. 61C

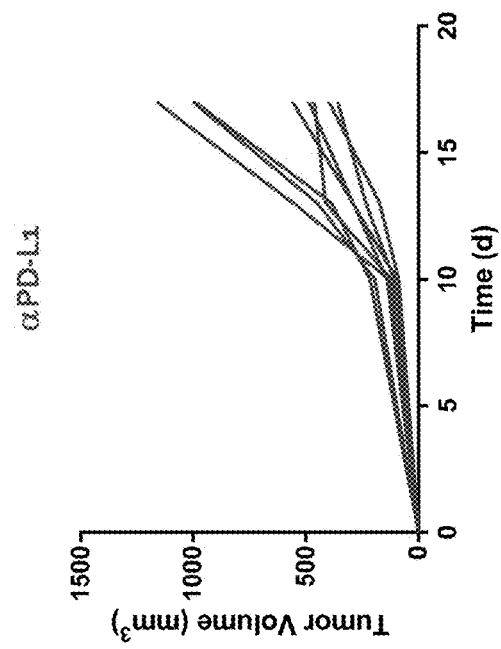
FIG. 63C
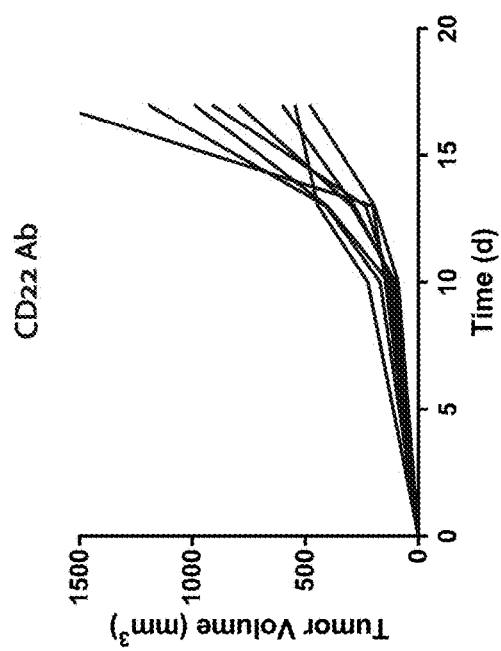
FIG. 63E
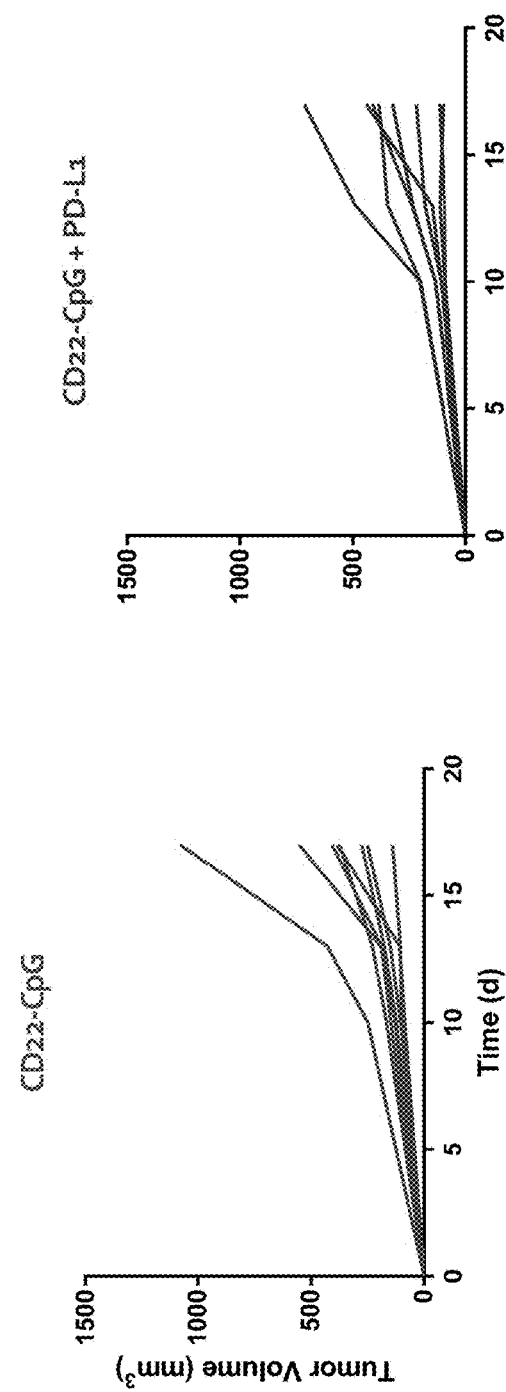
FIG. 63D
FIG. 63F

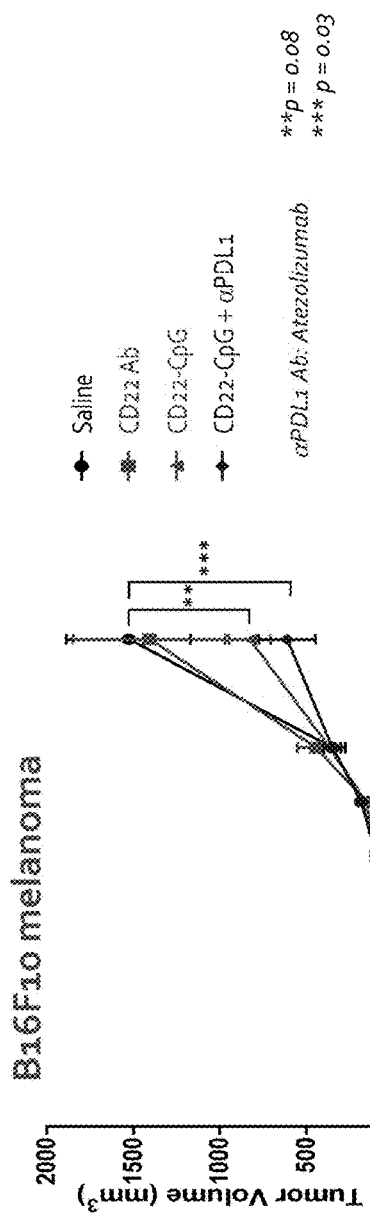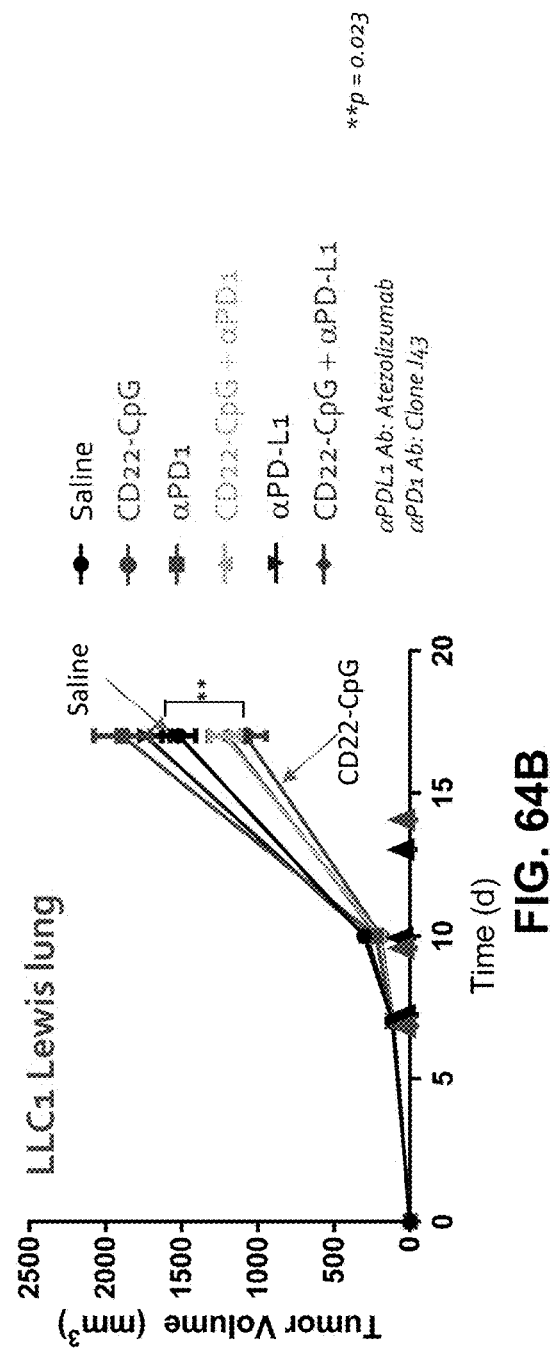
FIG. 64A
FIG. 64B

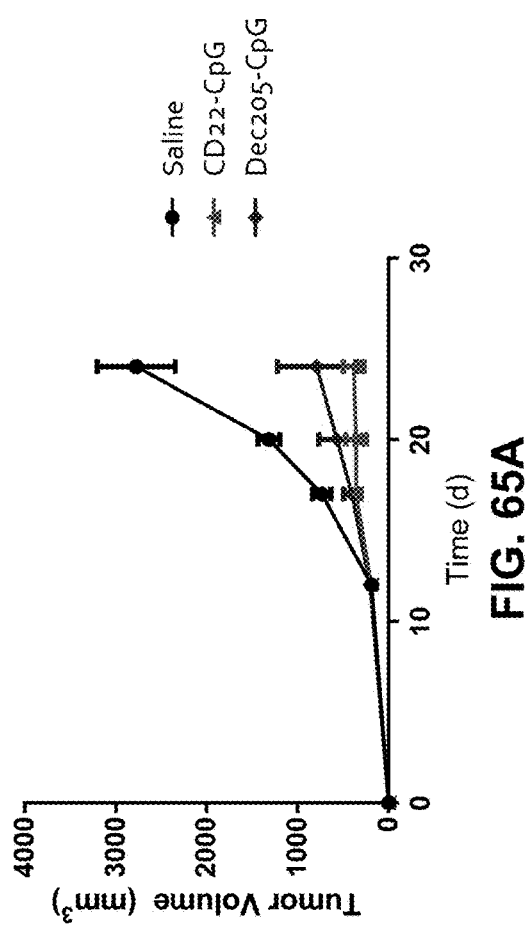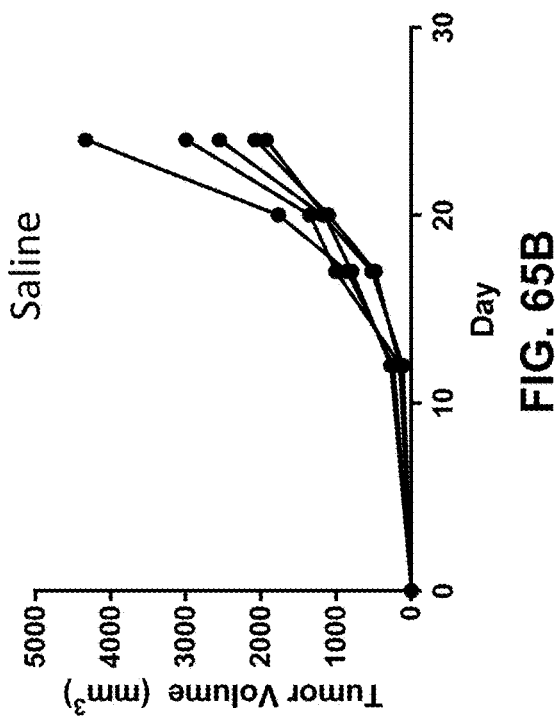
FIG. 65A
FIG. 65B

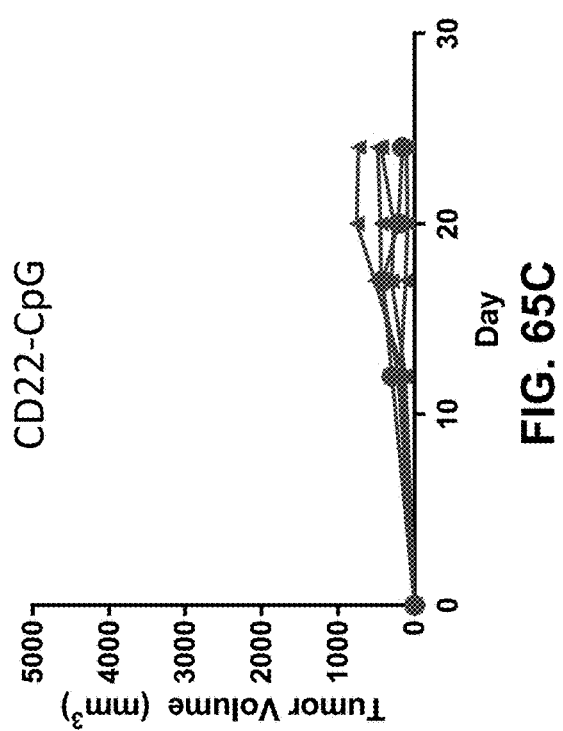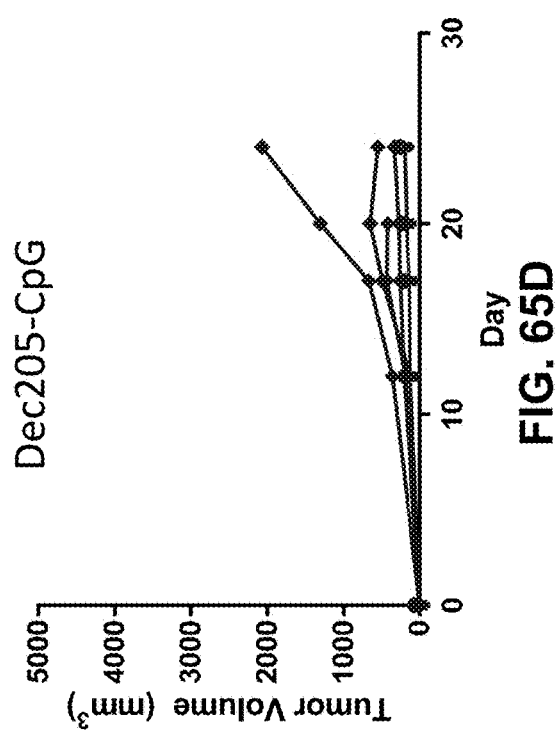

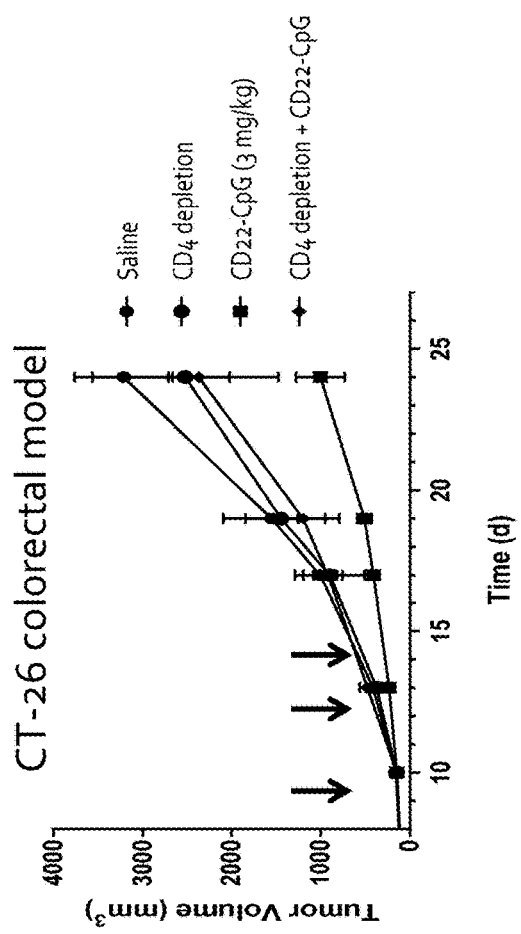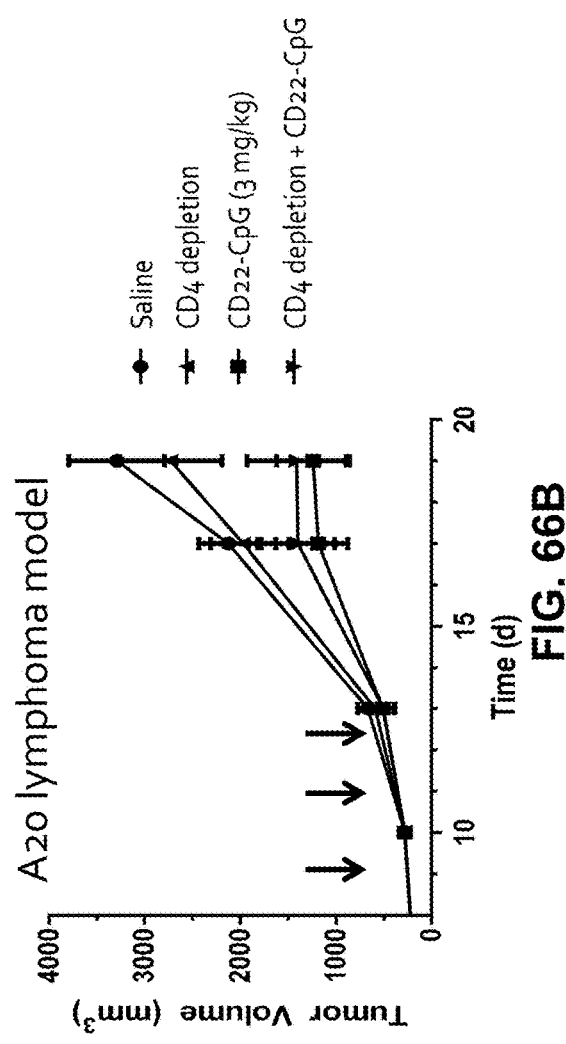
FIG. 66A
FIG. 66B

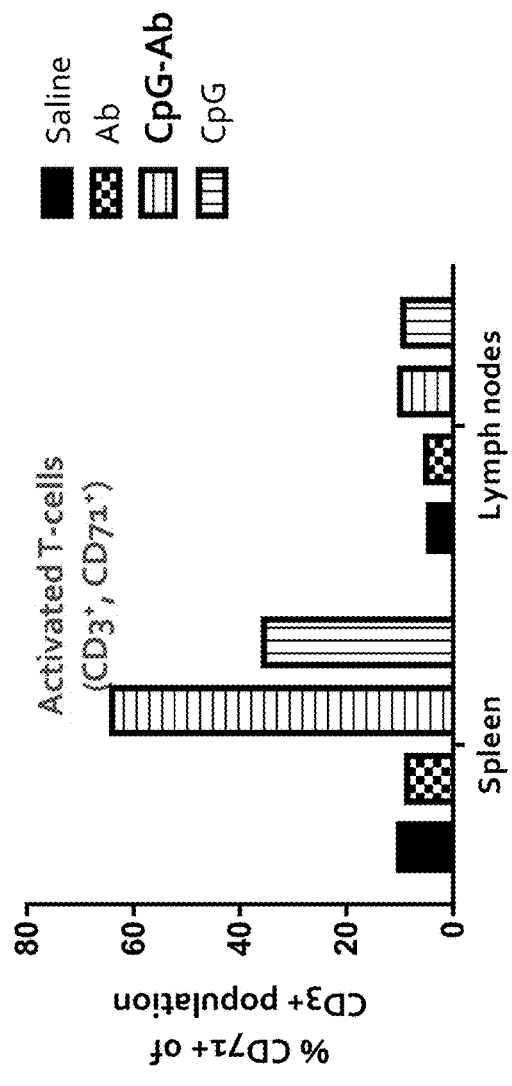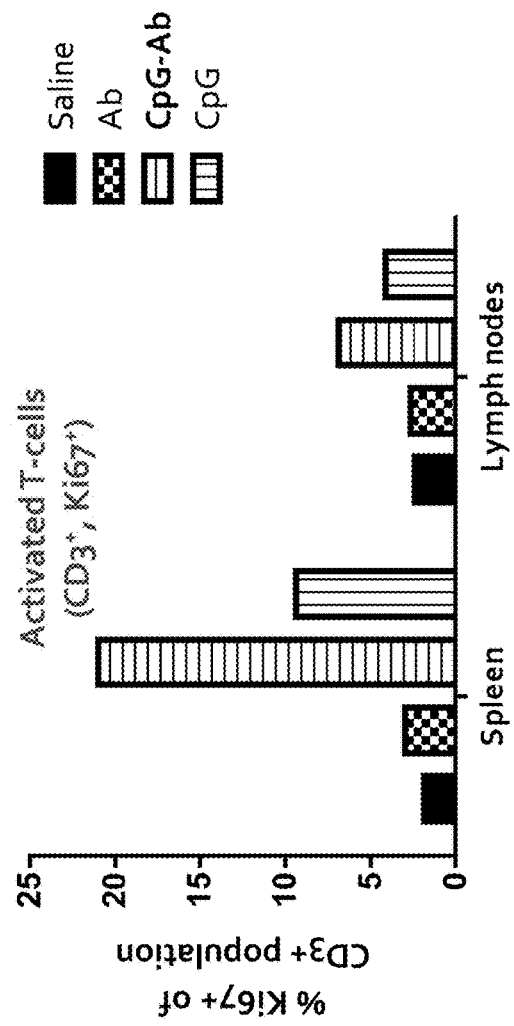
FIG. 68A
FIG. 68B

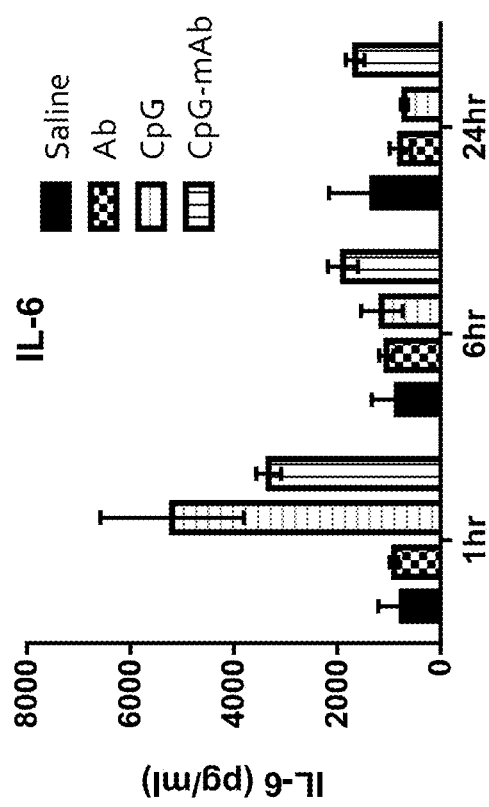
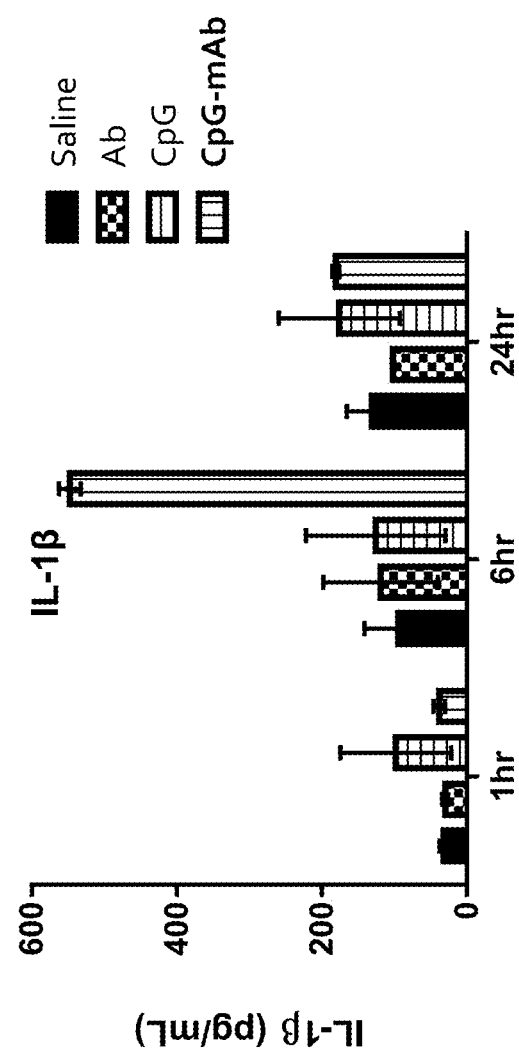
FIG. 70A
FIG. 70B

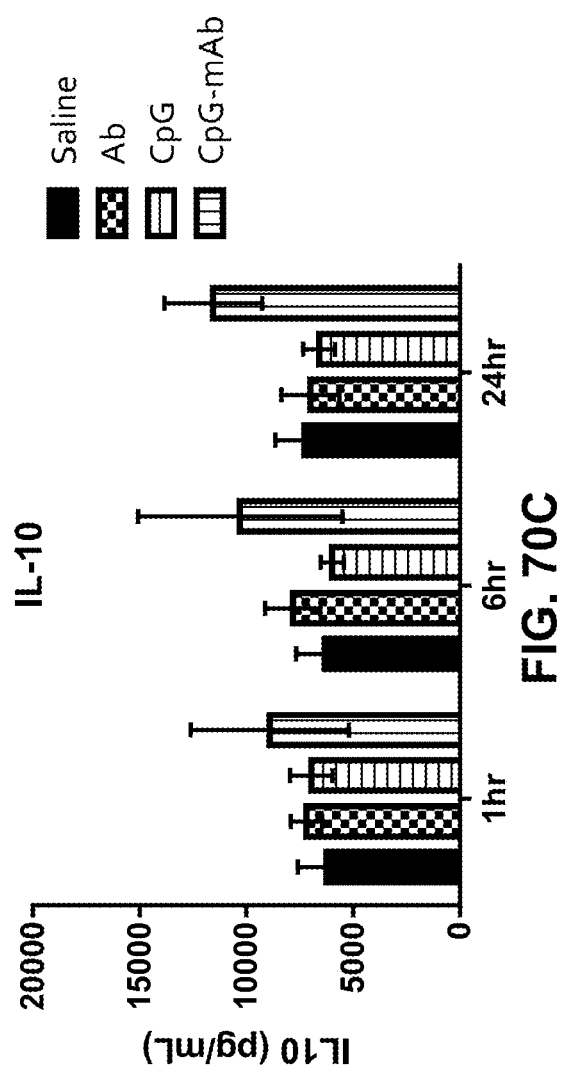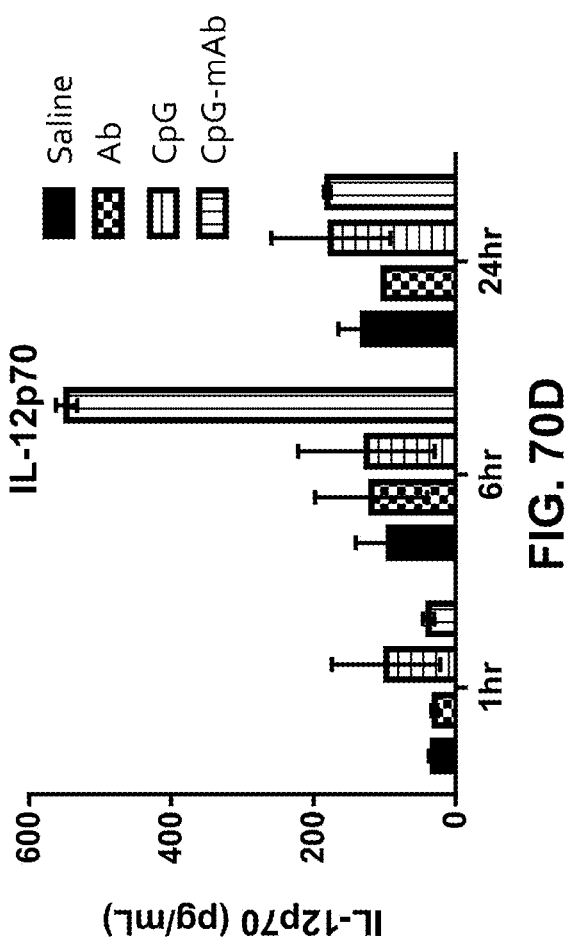

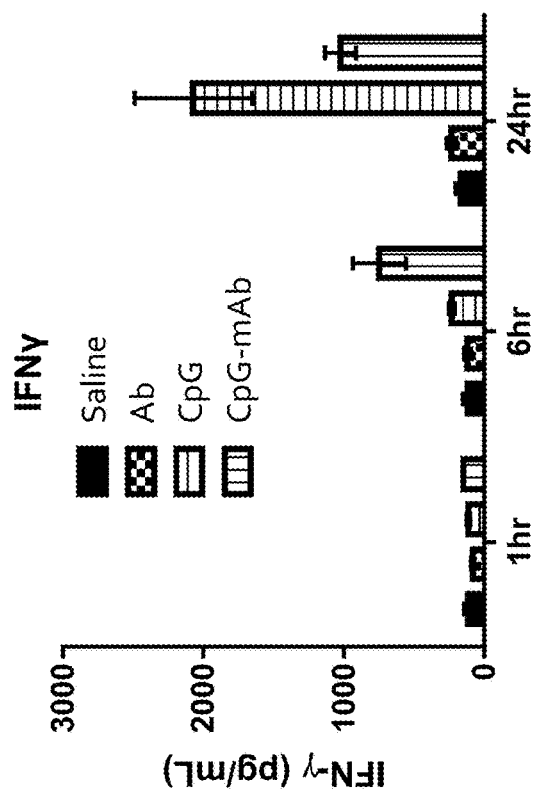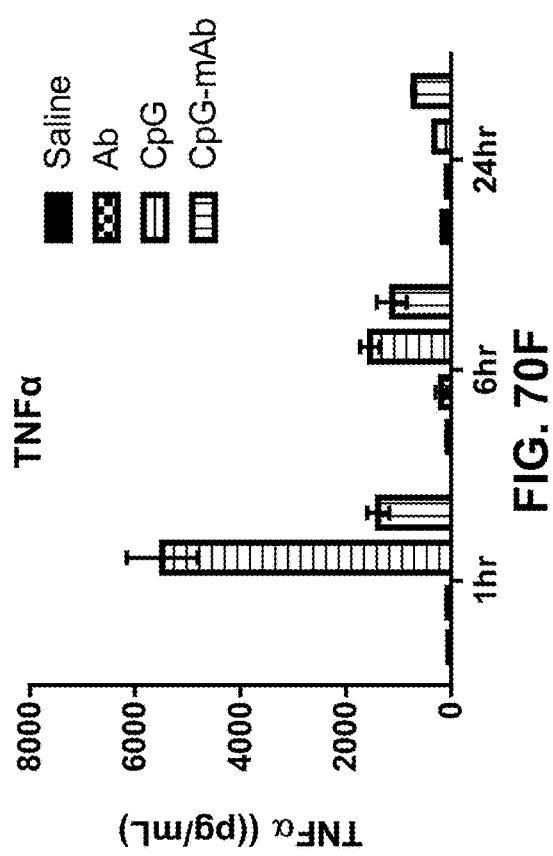

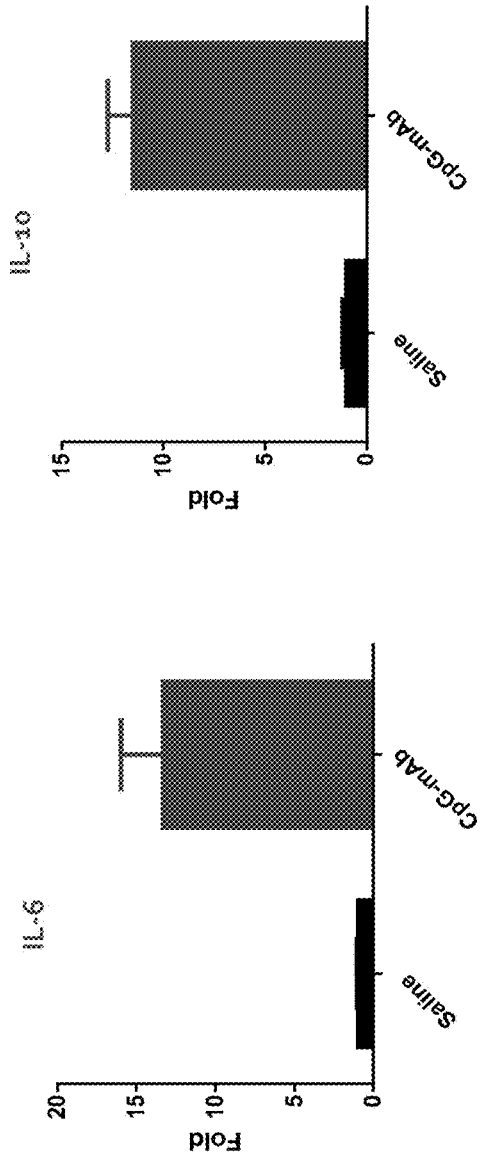
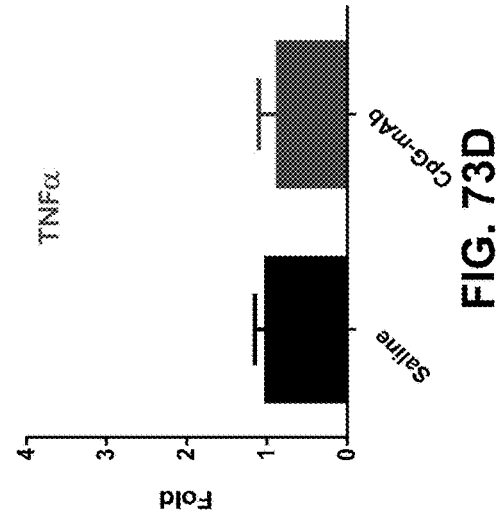
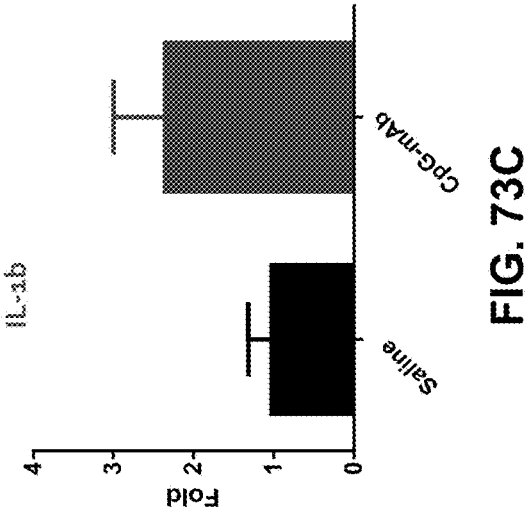
FIG. 73A · FIG. 73B · FIG. 73C · FIG. 73D

SEQUENCE LISTING

<160> NUMBER OF SEQ ID NOS: 497

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
tcgtcgtttt gtcgttttgt cgtt                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide -continued

```
<400> SEQUENCE: 2
tcgtcgtttt gtcgttttgt cgtt                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
tcgtcgtttt gtcgttttgt cgtt                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
tcgtcgtttt gtcgttttgt cgtt                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
tcgtcgtttt gtcgttttgt cgtt                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
tcgtcgtttt gtcgttttgt cgtt                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
tcgtcgtttt gtcgttttgt cgtt                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
tgctgctttt gtgcttttgt gctt                                              24

<210> SEQ ID NO 9
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 9
tgctgctttt gtgcttttgt gctt                                            24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tcgtcgtttt gtcgttttgt cgtt                                            24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
tcgtcgtttt gtcgttttgt cgtt                                            24

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
tcgtcgtttt gtcgttttgt cgtt                                            24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
tcgtcgtttt gtcgttttgt cgtt                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
tcgtcgtttt gtcgttttgt cgtt                                            24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
```

```
tcgtcgtttt gtcgttttgt cgtt                                          24

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tccatgacgt tcctgacgtt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tccatgacgt tcctgacgtt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tccatgacgt tcctgacgtt                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tccatgacgt tcctgacgtt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tccatgacgt tcctgacgtt                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tccatgacgt tcctgacgtt                                               20

<210> SEQ ID NO 22
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 22
tccatgagct tcctgagctt                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
tccatgagct tcctgagctt                                                    20

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
dtcgtcgttt tgtcgttttg tcgtt                                              25

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
tcgtcgttdt tgtcgttttg tcgtt                                              25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
tcgtcgtttt gdtcgttttg tcgtt                                              25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
tcgtcgtttt gtcgttdttg tcgtt                                              25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
tcgtcgtttt gtcgttttgt cgtdt                                              25
```

<210> SEQ ID NO 29
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 29
tcgcgacgtt cgcccgacgt tcggta                                   26

<210> SEQ ID NO 30
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 30
tcgcgacgtt cgcccgacgt tcggta                                   26

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
tccatgacgt tcctgatgct                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tccatgacgt tcctgatgct                                          20

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 33
tcgacgttcg tcgttcgtcg ttc                                      23

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
tcgacgttcg tcgttcgtcg ttc                                      23

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 35
tcgtcgtttt gtcgttttgt cgtt                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
tcgtcgtttt gtcgttttgt cgtt                                          24

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
tccatgacgt tcctgacgtt                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tccatgacgt tcctgacgtt                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tccatgacgt tcctgacgtt                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tccatgacgt tcctgacgtt                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
tccatgacgt tcctgacgtt                                               20

<210> SEQ ID NO 42
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tccatgacgt tcctgacgtt                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
tccatgacgt tcctgacgtt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
tccatgacgt tcctgacgtt                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
tccatgacgt tcctgacgtt                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
tccatgacgt tcctgacgtt                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tccatgacgt tcctgacgtt                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
```
tccatgacgt tcctgacgtt                                          20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tccatgacgt tcctgacgtt                                          20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
tccatgacgt tcctgacgtt                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
tccatgacgt tcctgacgtt                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
tccatgacgt tcctgacgtt                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gggggacgat cgtcgggggg                                          20

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
tcgtcgtcgt tcgaacgacg ttgat                                    25

<210> SEQ ID NO 55
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 55
tcgtcgtttt cggcgcgcgc cg                                           22

<210> SEQ ID NO 56
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 56
tcgcgaacgt tcgccgcgtt cgaacgcgg                                    29

<210> SEQ ID NO 57
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 57
tcgtcgacga tcggcgcgcg ccg                                          23

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tccatgacgt tcctgacgtt                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
tccatgacgt tcctgacgtt                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tccatgacgt tcctgacgtt                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
tccatgacgt tcctgacgtt                                              20
```

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tccatgacgt tcctgacgtt					20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
tccatgacgt tcctgacgtt					20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
tccatgacgt tcctgacgtt					20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
tccatgacgt tcctgacgtt					20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tccatgacgt tcctgacgtt					20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
tccatgacgt tcctgacgtt					20

<210> SEQ ID NO 68
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 68
tccatgacgt tcctgacgtt                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tccatgacgt tcctgacgtt                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
tccatgacgt tcctgacgtt                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
tccatgacgt tcctgacgtt                                               20

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 72
tcgtcgtttt gtcgttttgt cgtt                                          24

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
tcgtcgtttt gtcgttttgt cgtt                                          24

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
tccatgacgt tcctgatgct                                               20
```

```
<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
tccatgacgt tcctgatgct                                                   20

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 76
tcgtcgtttt gtcgttttgt cgtt                                              24

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 77
tcgtcgtttt gtcgttttgt cgtt                                              24

<210> SEQ ID NO 78
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 78
tcgtcgtttt gtcgttttgt cgtt                                              24

<210> SEQ ID NO 79
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 79
tcgtcgtttt gtcgttttgt cgtt                                              24

<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 80
tcgtcgtttt gtcgttttgt cgtt                                              24

<210> SEQ ID NO 81
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 81
tcgtcgtttt gtcgttttgt cgtt                                    24

<210> SEQ ID NO 82
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 82
tcgtcgtttt gtcgttttgt cgtt                                    24

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 83
tcgtcgtttt gtcgttttgt cgtt                                    24

<210> SEQ ID NO 84
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 84
tcgtcgtttt gtcgttttgt cgtt                                    24

<210> SEQ ID NO 85
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 85
tcgtcgtttt gtcgttttgt cgtt                                    24

<210> SEQ ID NO 86
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 86
tcgtcgtttt gtcgttttgt cgtt                                    24

<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 87
tcgtcgtttt gtcgttttgt cgtt                                    24

<210> SEQ ID NO 88
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 88
tcgtcgtttt gtcgttttgt cgtt                                          24

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tccatgacgt tcctgacgtt                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
tccatgacgt tcctgacgtt                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
tccatgacgt tcctgacgtt                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
tccatgacgt tcctgacgtt                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
tccatgacgt tcctgacgtt                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
```

```
tccatgacgt tcctgacgtt                                              20

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 95
tcgtcgtttt gtcgttttgt cgtt                                         24

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 96
tcgtcgtttt gtcgttttgt cgtt                                         24

<210> SEQ ID NO 97
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 97
tcgtcgtttt gtcgttttgt cgtt                                         24

<210> SEQ ID NO 98
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 98
tcgtcgtttt gtcgttttgt cgtt                                         24

<210> SEQ ID NO 99
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 99
tcgtcgtttt gtcgttttgt cgtt                                         24

<210> SEQ ID NO 100
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 100
tcgtcgtttt gtcgttttgt cgtt                                         24

<210> SEQ ID NO 101
<211> LENGTH: 24
<212> TYPE: DNA
<213> ORGANISM: Artificial Sequence
```

```
<220> FEATURE:
<223> OTHER INFORMATION: Synthetic oligonucleotide

<400> SEQUENCE: 101
tcgtcgtttt gtcgttttgt cgtt                                          24

<210> SEQ ID NO 102
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 102
tcgtcgtttt gtcgttttgt cgtt                                          24

<210> SEQ ID NO 103
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 103
tcgtcgtttt gtcgttttgt cgtt                                          24

<210> SEQ ID NO 104
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 104
tcgtcgtttt gtcgttttgt cgtt                                          24

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
tccatgacgt tcctgacgtt                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
tccatgacgt tcctgacgtt                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
tccatgacgt tcctgacgtt                                               20
```

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
tccatgacgt tcctgacgtt                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
tccatgacgt tcctgacgtt                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
tccatgacgt tcctgacgtt                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
tccatgacgt tcctgacgtt                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 112
tccatgacgt tcctgacgtt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
tccatgacgt tcctgacgtt                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 114
tccatgacgt tcctgacgtt                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
tccatgacgt tcctgacgtt                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 116
tccatgacgt tcctgacgtt                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 117
tccatgacgt tcctgacgtt                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 118
tccatgacgt tcctgacgtt                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
tccatgacgt tcctgacgtt                                              20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
tccatgacgt tcctgacgtt                                              20

<210> SEQ ID NO 121
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
tccatgacgt tcctgacgtt                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
tccatgacgt tcctgacgtt                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
tccatgacgt tcctgacgtt                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
tccatgacgt tcctgacgtt                                              20

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 125
tcgtcgtttc gtcgttttgt cgtt                                         24

<210> SEQ ID NO 126
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 126
tcgtcgtttt gtcgttttgt cgtt                                         24

<210> SEQ ID NO 127
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 127
```

```
tcgtcgtttt gtcgttttgt cgtt                                          24

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 128
tgctgctttt gtgcttttgt gctt                                          24

<210> SEQ ID NO 129
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 129
tcattggaaa acgttcttcg gggcgttctt                                    30

<210> SEQ ID NO 130
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 130
tcattggaaa agcttcttgc ggggcttctt                                    30

<210> SEQ ID NO 131
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 131
tcattggaaa acgttcttcg gggcgttctt                                    30

<210> SEQ ID NO 132
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 132
aagaacgccc cgaagaacgt tttccaatga                                    30

<210> SEQ ID NO 133
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 133
tcattggaaa acgttcttcg gggcgttctt                                    30

<210> SEQ ID NO 134
<211> LENGTH: 30
<212> TYPE: DNA
```

<213> ORGANISM: Artificial Sequence
<220> FEATURE:
<223> OTHER INFORMATION: Synthetic oligonucleotide

<400> SEQUENCE: 134
aagaacgccc cgaagaacgt tttccaatga                    30

<210> SEQ ID NO 135
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 135
tcattggaaa acgttcttcg gggcgttctt                    30

<210> SEQ ID NO 136
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 136
aagaacgccc cgaagaacgt tttccaatga                    30

<210> SEQ ID NO 137
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 137
tcattggaaa acgttcttcg gggcgttctt                    30

<210> SEQ ID NO 138
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 138
aagaacgccc cgaagaacgt tttccaatga                    30

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
tccatgacgt tcctgacgtt                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
tccatgacgt tcctgacgtt                               20

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
tccatgacgt tcctgacgtt                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
tccatgacgt tcctgacgtt                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 143
tccatgacgt tcctgacgtt                                              20

<210> SEQ ID NO 144
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 144
aacgacaaaa cgacaaaacg acga                                         24

<210> SEQ ID NO 145
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 145
aacgacaaaa cgacaaaacg acga                                         24

<210> SEQ ID NO 146
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 146
tcgtcgtttt gtcgttttgt cgtt                                         24

<210> SEQ ID NO 147
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 147
tcgtcgtttt gtcgttttgt cgtt                                              24

<210> SEQ ID NO 148
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 148
tcgtcgtttt gtcgttttgt cgtt                                              24

<210> SEQ ID NO 149
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 149
tcgtcgtttt gtcgttttgt cgtt                                              24

<210> SEQ ID NO 150
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 150
tcgtcgtttt gtcgttttgt cgtt                                              24

<210> SEQ ID NO 151
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 151
tcgtcgtttt gtcgttttgt cgtt                                              24

<210> SEQ ID NO 152
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 152
tcgtcgtttt gtcgttttgt cgtt                                              24

<210> SEQ ID NO 153
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 153
tcgtcgtttt gtcgttttgt cgtt                                              24

```
<210> SEQ ID NO 154
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 154
tcgtcgtttt gtcgttttgt cgtt                                          24

<210> SEQ ID NO 155
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 155
ttcgtcgttt tgtcgttttg tcgtt                                         25

<210> SEQ ID NO 156
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 156
tttcgtcgtt ttgtcgtttt gtcgtt                                        26

<210> SEQ ID NO 157
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 157
gtttcgtcgt tttgtcgttt tgtcgtt                                       27

<210> SEQ ID NO 158
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 158
gtttcgtcgt tttgtcgttt tgtcgtt                                       27

<210> SEQ ID NO 159
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 159
gtttcgtcgt tttgtcgttt tgtcgtt                                       27

<210> SEQ ID NO 160
<211> LENGTH: 27
<212> TYPE: DNA
<213> ORGANISM: Artificial Sequence
<220> FEATURE:
<223> OTHER INFORMATION: Synthetic oligonucleotide
```

```
<400> SEQUENCE: 160
gtttcgtcgt tttgtcgttt tgtcgtt                                   27

<210> SEQ ID NO 161
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 161
tcgtcgtttt gtcgttttgt cgtt                                      24

<210> SEQ ID NO 162
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 162
tcgtcgtttt gtcgtttt                                             18

<210> SEQ ID NO 163
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 163
ucgtcgtttt gtcgttttgt cgtt                                      24

<210> SEQ ID NO 164
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 164
ucgtcgtttt gtcgttttgt cgtt                                      24

<210> SEQ ID NO 165
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 165
tcgucgtttt gtcgttttgt cgtt                                      24

<210> SEQ ID NO 166
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 166
tcgucgtttt gtcgttttgt cgtt                                      24

<210> SEQ ID NO 167
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 167
ucgucgtttt gtcgttttgt cgtt                                              24

<210> SEQ ID NO 168
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 168
ucgucgtttt gtcgttttgt cgtt                                              24

<210> SEQ ID NO 169
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 169
ucgtcgtttt gtcgttttgt cgtt                                              24

<210> SEQ ID NO 170
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 170
ucgtcgtttt gtcgttttgt cgtt                                              24

<210> SEQ ID NO 171
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 171
tcgtcgtttt gtcgtttt                                                     18

<210> SEQ ID NO 172
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 172
tcgtcgtttt gtcgtt                                                       16

<210> SEQ ID NO 173
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 173
```

```
tcgtcgtttt gtcg                                                     14

<210> SEQ ID NO 174
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 174
tcgtcgtttt gt                                                       12

<210> SEQ ID NO 175
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 175
ucgtcgtttt gtcgtttt                                                 18

<210> SEQ ID NO 176
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 176
utcgtcgttt tgtcgtt                                                  17

<210> SEQ ID NO 177
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 177
ucgtcgtttt gtcg                                                     14

<210> SEQ ID NO 178
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 178
ucgtcgtttt gt                                                       12

<210> SEQ ID NO 179
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 179
ucgucgtttt gtcgttttgt cgtt                                          24

<210> SEQ ID NO 180
<211> LENGTH: 24
<212> TYPE: DNA
<213> ORGANISM: Artificial Sequence
```

```
<220> FEATURE:
<223> OTHER INFORMATION: Synthetic oligonucleotide

<400> SEQUENCE: 180
ucgtcgtttt gtcgttttgt cgtt                                          24

<210> SEQ ID NO 181
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 181
ucgtcgtttt gtcgttttgt cgtt                                          24

<210> SEQ ID NO 182
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 182
ucgtcgtttt gtcgttttgt cgtt                                          24

<210> SEQ ID NO 183
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 183
ucgtcgtttt gtcgttttgt cgtt                                          24

<210> SEQ ID NO 184
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 184
tccatgacgt tcctgatgct                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 185
tccatgacgt tcctgatgct                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 186
tccatgacgt tcctgatgct                                               20
```

```
<210> SEQ ID NO 187
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 187
ucgtcgtttg tcgtt                                                           15

<210> SEQ ID NO 188
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 188
ucgtcgttgt cgtt                                                            14

<210> SEQ ID NO 189
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 189
ucgtcgtgtc gtt                                                             13

<210> SEQ ID NO 190
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 190
ucgtcgttcg tt                                                              12

<210> SEQ ID NO 191
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 191
ucgtcgtcgt t                                                               11

<210> SEQ ID NO 192
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 192
ugctgctttt gtgcttttgt gctt                                                 24

<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 193
tccatgacgt tcctgacgtt                                          20

<210> SEQ ID NO 194
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 194
tccatgacgt tcctgacgtt                                          20

<210> SEQ ID NO 195
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 195
tccatgacgt tcctgacgtt                                          20

<210> SEQ ID NO 196
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 196
tccatgacgt tcctgacgtt                                          20

<210> SEQ ID NO 197
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 197
taacgacaaa acgacaaaac gacga                                    25

<210> SEQ ID NO 198
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 198
aacgacaaaa cgacaaaacg acgat                                    25

<210> SEQ ID NO 199
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 199
ucgtcgtttt gtcgtt                                              16

<210> SEQ ID NO 200
```

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 200
ucgtcgtttt gtcgtt                                                      16

<210> SEQ ID NO 201
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 201
ucgtcgtttt gtcgtt                                                      16

<210> SEQ ID NO 202
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 202
ucgtcgtttt gtcgtt                                                      16

<210> SEQ ID NO 203
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 203
ucgtcgtttt gtcgtt                                                      16

<210> SEQ ID NO 204
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 204
ucgtcgtttt gtcgtt                                                      16

<210> SEQ ID NO 205
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 205
ucgtcgtttt gtcgtt                                                      16

<210> SEQ ID NO 206
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 206
```

```
ucgtcgtttt gtcgtt                                                     16

<210> SEQ ID NO 207
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 207
ucgtcgtttt gtcgtt                                                     16

<210> SEQ ID NO 208
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 208
ucgtcgtttt gtcgtt                                                     16

<210> SEQ ID NO 209
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 209 ucgtcgtt                                                               8

<210> SEQ ID NO 210
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 210 ucgtcgtt                                                               8

<210> SEQ ID NO 211
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 211 ucgttt                                                                 6

<210> SEQ ID NO 212
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 212 ucgttt                                                                 6

<210> SEQ ID NO 213
<211> LENGTH: 13
<212> TYPE: DNA
```

```
<213> ORGANISM: Artificial Sequence
<220> FEATURE:
<223> OTHER INFORMATION: Synthetic oligonucleotide

<400> SEQUENCE: 213
ucgtcgtgtc gtt                                                        13

<210> SEQ ID NO 214
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 214
ucgtcgtgtt ttt                                                        13

<210> SEQ ID NO 215
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 215
ucgttttgtc gtt                                                        13

<210> SEQ ID NO 216
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 216
ucgtttgtcg tt                                                         12

<210> SEQ ID NO 217
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 217
ucgttgtcgt t                                                          11

<210> SEQ ID NO 218
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 218
ucgtgtcgtt                                                            10

<210> SEQ ID NO 219
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 219
ugctgctttt gtgctt                                                     16
```

<210> SEQ ID NO 220
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 220
ucgtcgtttt gtcgtt                                                      16

<210> SEQ ID NO 221
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 221
ucgtcgtttt gtcgtt                                                      16

<210> SEQ ID NO 222
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 222
gggacgatcg tct                                                         13

<210> SEQ ID NO 223
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 223
gggacgatcg tctgg                                                       15

<210> SEQ ID NO 224
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 224
gggacgatcg tctgg                                                       15

<210> SEQ ID NO 225
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 225
ucgtcgtgtc gtt                                                         13

<210> SEQ ID NO 226
<211> LENGTH: 13
<212> TYPE: DNA
<213> ORGANISM: Artificial Sequence
<220> FEATURE:

<223> OTHER INFORMATION: Synthetic oligonucleotide

<400> SEQUENCE: 226
ucgtcgtgtc gtt                                                          13

<210> SEQ ID NO 227
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 227
ucgtcgtgtc gtt                                                          13

<210> SEQ ID NO 228
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 228
ucgtcgtgtc gtt                                                          13

<210> SEQ ID NO 229
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 229
ucgtcgtgtc gtt                                                          13

<210> SEQ ID NO 230
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 230
ucgtcgtgtc gtt                                                          13

<210> SEQ ID NO 231
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 231
ucgtcgtgtc gtt                                                          13

<210> SEQ ID NO 232
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 232
tcgtcgtttt gtcgttttgt cgtt                                              24

```
<210> SEQ ID NO 233
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 233
ucgtcgtttt gtcgttttgt cgtt                                              24

<210> SEQ ID NO 234
<211> LENGTH: 24
<212> TYPE: DNA
<213> ORGANISM: Artificial Sequence
<220> FEATURE:
<223> OTHER INFORMATION: Synthetic oligonucleotide - Double stranded-
      CpG using p88/p144

<400> SEQUENCE: 234
tcgtcgtttt gtcgttttgt cgtt                                              24

<210> SEQ ID NO 235
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 235
tcgtcgtttt gtcgtt                                                       16

<210> SEQ ID NO 236
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 236
ucgtcgtttt gtcgtt                                                       16

<210> SEQ ID NO 237
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 237
tcgtcgtgtc gtt                                                          13

<210> SEQ ID NO 238
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 238
ucgtcgtgtc gtt                                                          13

<210> SEQ ID NO 239
<211> LENGTH: 13
<212> TYPE: DNA
<213> ORGANISM: Artificial Sequence
<220> FEATURE:
<223> OTHER INFORMATION: Synthetic oligonucleotide
```

```
<400> SEQUENCE: 239
ucgtcgtgtc gtt                                                        13

<210> SEQ ID NO 240
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 240
ucgtcgtgtc gtt                                                        13

<210> SEQ ID NO 241
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 241
ucgtcgtgtc gtt                                                        13

<210> SEQ ID NO 242
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 242
ucgtcgtgtc gtt                                                        13

<210> SEQ ID NO 243
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 243
ucgtcgtgtc gtt                                                        13

<210> SEQ ID NO 244
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 244
ucgtcgtgtc gtt                                                        13

<210> SEQ ID NO 245
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 245
ucgtcgtgtc gtt                                                        13

<210> SEQ ID NO 246
```

```
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 246
ucgtcgtgtc gtt                                                             13

<210> SEQ ID NO 247
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 247
ucgtcgtttt gtcgttttgt cgtt                                                 24

<210> SEQ ID NO 248
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 248
ucgtcgtttt gtcgttttgt cgtt                                                 24

<210> SEQ ID NO 249
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 249
ucgtcgtttt gtcgttttgt cgtt                                                 24

<210> SEQ ID NO 250
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 250
ucgtcgtgtc gtt                                                             13

<210> SEQ ID NO 251
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 251
ucgtcgtgtc gtt                                                             13

<210> SEQ ID NO 252
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 252
```
ucgtcgtgtc gtt                                                    13

<210> SEQ ID NO 253
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 253
ucgtcgtgtc gtt                                                    13

<210> SEQ ID NO 254
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 254
ucgtcgtgtc gtt                                                    13

<210> SEQ ID NO 255
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 255
ucgtcgtgtc gtt                                                    13

<210> SEQ ID NO 256
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 256
ucgtcgtgtc gtt                                                    13

<210> SEQ ID NO 257
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 257
ucgtcgtgtc gtt                                                    13

<210> SEQ ID NO 258
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 258
ucgtcgtgtc gtt                                                    13

<210> SEQ ID NO 259
<211> LENGTH: 13
<212> TYPE: DNA

```
<213> ORGANISM: Artificial Sequence
<220> FEATURE:
<223> OTHER INFORMATION: Synthetic oligonucleotide

<400> SEQUENCE: 259
ucgtcgtgtc gtt                                                          13

<210> SEQ ID NO 260
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 260
ucgtcgtgtc gtt                                                          13

<210> SEQ ID NO 261
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 261
ucgtcgtgtc gtt                                                          13

<210> SEQ ID NO 262
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 262
ucgucgtgtc gtt                                                          13

<210> SEQ ID NO 263
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 263
ucgtcgtguc gtt                                                          13

<210> SEQ ID NO 264
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 264
taacgacacg acga                                                         14

<210> SEQ ID NO 265
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 265
aacgacacga cgat                                                         14
```

<210> SEQ ID NO 266
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 266
ucgtcgtguc gtt                                                          13

<210> SEQ ID NO 267
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 267
cgtcgtgtcg tt                                                           12

<210> SEQ ID NO 268
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 268
cgtcgtgucg tt                                                           12

<210> SEQ ID NO 269
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 269
tcgtcgtgtc gtt                                                          13

<210> SEQ ID NO 270
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 270
tcgtcgtgtc gtt                                                          13

<210> SEQ ID NO 271
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 271
ucgtcgtgtc gtt                                                          13

<210> SEQ ID NO 272
<211> LENGTH: 13
<212> TYPE: DNA
<213> ORGANISM: Artificial Sequence
<220> FEATURE:

<223> OTHER INFORMATION: Synthetic oligonucleotide

<400> SEQUENCE: 272
ucgtcgtgtc gtt                                              13

<210> SEQ ID NO 273
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 273
ugctgctgtg ctt                                              13

<210> SEQ ID NO 274
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 274
ucgagctgtc gtt                                              13

<210> SEQ ID NO 275
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 275
ucgtcgtgac gtt                                              13

<210> SEQ ID NO 276
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 276
ucgacgtgac gtt                                              13

<210> SEQ ID NO 277
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 277
acgacgtgac gtt                                              13

<210> SEQ ID NO 278
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 278
acgacgtgac gtt                                              13

```
<210> SEQ ID NO 279
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 279
ucgtcgtgtc gtt                                                          13

<210> SEQ ID NO 280
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 280
ucgtcgtgtc gtt                                                          13

<210> SEQ ID NO 281
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 281
ucgtcgtgtc gtt                                                          13

<210> SEQ ID NO 282
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 282
ucgtcgtgtc gtt                                                          13

<210> SEQ ID NO 283
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 283
acgacgtgac gtt                                                          13

<210> SEQ ID NO 284
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 284
acgacgtgac gtt                                                          13

<210> SEQ ID NO 285
<211> LENGTH: 13
<212> TYPE: DNA
<213> ORGANISM: Artificial Sequence
<220> FEATURE:
<223> OTHER INFORMATION: Synthetic oligonucleotide
```

```
<400> SEQUENCE: 285
ucgtcgtgtc gtt                                                          13

<210> SEQ ID NO 286
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 286
ucgtcgtgtc gtt                                                          13

<210> SEQ ID NO 287
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 287
ucgtcgtgtc gtt                                                          13

<210> SEQ ID NO 288
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 288
ucgtcgtgtc gtt                                                          13

<210> SEQ ID NO 289
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 289
ucgtcgtgtc gtt                                                          13

<210> SEQ ID NO 290
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 290
tcgtcgtgtc gtt                                                          13

<210> SEQ ID NO 291
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 291
tcgtcgtgtc gtt                                                          13

<210> SEQ ID NO 292
<211> LENGTH: 13
```

```
<212> TYPE: DNA
<213> ORGANISM: Artificial Sequence
<220> FEATURE:
<223> OTHER INFORMATION: Synthetic oligonucleotide

<400> SEQUENCE: 292
ucgtcgtgac gtt                                                          13

<210> SEQ ID NO 293
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 293
ucgacgtgac gtt                                                          13

<210> SEQ ID NO 294
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 294
tccatgucgt tccttgatt                                                    19

<210> SEQ ID NO 295
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 295
tccatgucgt tccttt                                                       16

<210> SEQ ID NO 296
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 296
tccatgucgt tctt                                                         14

<210> SEQ ID NO 297
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 297
tccatgucgt t                                                            11

<210> SEQ ID NO 298
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 298
```
tucgtcgtgt cgtt                                                          14

<210> SEQ ID NO 299
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 299
uucgtcgtgt cgtt                                                          14

<210> SEQ ID NO 300
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 300
uucgtcgtgt cgtt                                                          14

<210> SEQ ID NO 301
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 301
tcgucgtgtc gtt                                                           13

<210> SEQ ID NO 302
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 302
tcgucgtgtc gtt                                                           13

<210> SEQ ID NO 303
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 303
tcgucgtgtc gtt                                                           13

<210> SEQ ID NO 304
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 304
ucgtcgtgac gtt                                                           13

<210> SEQ ID NO 305
<211> LENGTH: 13
<212> TYPE: DNA
<213> ORGANISM: Artificial Sequence

```
<220> FEATURE:
<223> OTHER INFORMATION: Synthetic oligonucleotide

<400> SEQUENCE: 305
ucgacgtgac gtt                                                          13

<210> SEQ ID NO 306
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 306
ucgtcgtgtc gtt                                                          13

<210> SEQ ID NO 307
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 307
cgtcgtgtcg tt                                                           12

<210> SEQ ID NO 308
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 308
cgtcgtgtcg tt                                                           12

<210> SEQ ID NO 309
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 309
ucgtcgtgtc gtt                                                          13

<210> SEQ ID NO 310
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 310
ucgtcgtgtc gtt                                                          13

<210> SEQ ID NO 311
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 311
ucgtcgtgtc gtt                                                          13
```

```
<210> SEQ ID NO 312
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 312
tcgucgtgtc gtt                                                        13

<210> SEQ ID NO 313
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 313
tucgtcgtga cgtt                                                       14

<210> SEQ ID NO 314
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 314
uucgtcgtga cgtt                                                       14

<210> SEQ ID NO 315
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 315
ucgtcgtgac gtt                                                        13

<210> SEQ ID NO 316
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 316
uucgtcgtga cgtt                                                       14

<210> SEQ ID NO 317
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 317
tcgacgtguc gtt                                                        13

<210> SEQ ID NO 318
<211> LENGTH: 13
<212> TYPE: DNA
<213> ORGANISM: Artificial Sequence
<220> FEATURE:
<223> OTHER INFORMATION: Synthetic oligonucleotide
```

```
<400> SEQUENCE: 318
tcgacgtgac gtt                                                    13

<210> SEQ ID NO 319
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 319
ucgacgtguc gtt                                                    13

<210> SEQ ID NO 320
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 320
ucgtccatga cgtt                                                   14

<210> SEQ ID NO 321
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 321
ucgtccatgu cgtt                                                   14

<210> SEQ ID NO 322
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 322
tcgtccatgu cgtt                                                   14

<210> SEQ ID NO 323
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 323
cgtcgtgacg tt                                                     12

<210> SEQ ID NO 324
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 324
catgucgttc cttt                                                   14

<210> SEQ ID NO 325
```

-continued

```
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 325
tgucgttcct tt                                                         12

<210> SEQ ID NO 326
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 326
tatgucgttc cttt                                                       14

<210> SEQ ID NO 327
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 327
tccatgacgt tccttt                                                     16

<210> SEQ ID NO 328
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 328
ugctgctgag ctt                                                        13

<210> SEQ ID NO 329
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 329
ugcagctgag ctt                                                        13

<210> SEQ ID NO 330
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 330
tcgtcgtgtc gtt                                                        13

<210> SEQ ID NO 331
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 331
```

```
tcgtcgtgtc gtt                                                    13

<210> SEQ ID NO 332
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 332
ucgtcgtgtc gtt                                                    13

<210> SEQ ID NO 333
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 333
ucgtcgtgtc gtt                                                    13

<210> SEQ ID NO 334
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 334
ucgtcgtgtc gtt                                                    13

<210> SEQ ID NO 335
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 335
ucgtcgtgtc gtt                                                    13

<210> SEQ ID NO 336
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 336
ucgtcgtgtc gtt                                                    13

<210> SEQ ID NO 337
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 337
ucgtcgtgtc gtt                                                    13

<210> SEQ ID NO 338
<211> LENGTH: 14
<212> TYPE: DNA
```

-continued

<213> ORGANISM: Artificial Sequence
<220> FEATURE:
<223> OTHER INFORMATION: Synthetic oligonucleotide

<400> SEQUENCE: 338
tatgugcttc cttt                                                        14

<210> SEQ ID NO 339
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 339
cgtcgtgtcg tt                                                          12

<210> SEQ ID NO 340
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 340
cgtcgtgtcg tt                                                          12

<210> SEQ ID NO 341
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 341
cgtcgtgtcg tt                                                          12

<210> SEQ ID NO 342
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 342
cgtcgtgtcg tt                                                          12

<210> SEQ ID NO 343
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 343
cgtcgtgtcg tt                                                          12

<210> SEQ ID NO 344
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 344
cgtcgtgtcg tt                                                          12

<210> SEQ ID NO 345
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 345
tugctgctga gctt                                                          14

<210> SEQ ID NO 346
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 346
tugctgctga gctt                                                          14

<210> SEQ ID NO 347
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 347
tugctgctga gctt                                                          14

<210> SEQ ID NO 348
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 348
ucgtcgtgtc gtt                                                           13

<210> SEQ ID NO 349
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 349
ucgtcgtgtc gtt                                                           13

<210> SEQ ID NO 350
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 350
ucgtcgtgtc gtt                                                           13

<210> SEQ ID NO 351
<211> LENGTH: 13
<212> TYPE: DNA
<213> ORGANISM: Artificial Sequence
<220> FEATURE:

<223> OTHER INFORMATION: Synthetic oligonucleotide

<400> SEQUENCE: 351
ucgtcgtgtc gtt					13

<210> SEQ ID NO 352
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 352
ucgtcgtgtc gtt					13

<210> SEQ ID NO 353
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 353
tucgtcgtga cgtt					14

<210> SEQ ID NO 354
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 354
tugctgctga gctt					14

<210> SEQ ID NO 355
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 355
ucgtcgtgtc gtt					13

<210> SEQ ID NO 356
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 356
ucgtcgtgtc gtt					13

<210> SEQ ID NO 357
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 357
ucgtcgtgtc gtt					13

```
<210> SEQ ID NO 358
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 358
ucgtcgtgtc gtt                                                          13

<210> SEQ ID NO 359
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 359
ucgtcgtgtc gtt                                                          13

<210> SEQ ID NO 360
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 360
ucgtcgtgtc gtt                                                          13

<210> SEQ ID NO 361
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 361
ucgtcgtgtc gtt                                                          13

<210> SEQ ID NO 362
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 362
ucgtcgtgtc gtt                                                          13

<210> SEQ ID NO 363
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 363
ucgtcgtgtc gtt                                                          13

<210> SEQ ID NO 364
<211> LENGTH: 13
<212> TYPE: DNA
<213> ORGANISM: Artificial Sequence
<220> FEATURE:
<223> OTHER INFORMATION: Synthetic oligonucleotide
```

```
<400> SEQUENCE: 364
ucgtcgtgtc gtt                                                          13

<210> SEQ ID NO 365
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 365
ucgtcgtgtc gtt                                                          13

<210> SEQ ID NO 366
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 366
ucgtcgtgtc gtt                                                          13

<210> SEQ ID NO 367
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 367
ucgtcgtgtc gtt                                                          13

<210> SEQ ID NO 368
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 368
ucgtcgtgtc gtt                                                          13

<210> SEQ ID NO 369
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 369
ucgtcgtgtc gtt                                                          13

<210> SEQ ID NO 370
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 370
ucgtcgtgtc gtt                                                          13

<210> SEQ ID NO 371
<211> LENGTH: 13
```

```
<212> TYPE: DNA
<213> ORGANISM: Artificial Sequence
<220> FEATURE:
<223> OTHER INFORMATION: Synthetic oligonucleotide

<400> SEQUENCE: 371
ucgtcgtgtc gtt                                                      13

<210> SEQ ID NO 372
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 372
ucgtcgtgtc gtt                                                      13

<210> SEQ ID NO 373
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 373
tucgtcgtga cgtt                                                     14

<210> SEQ ID NO 374
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 374
tucgtcgtga cgtt                                                     14

<210> SEQ ID NO 375
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 375
tucgtcgtga cgtt                                                     14

<210> SEQ ID NO 376
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 376
tucgtcgtga cgtt                                                     14

<210> SEQ ID NO 377
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 377
```
tucgtcgtga cgtt                    14

<210> SEQ ID NO 378
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 378
tucgtcgtga cgtt                    14

<210> SEQ ID NO 379
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 379
tucgtcgtga cgtt                    14

<210> SEQ ID NO 380
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 380
tucgtcgtga cgtt                    14

<210> SEQ ID NO 381
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 381
tucgtcgtga cgtt                    14

<210> SEQ ID NO 382
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 382
tucgtcgtga cgtt                    14

<210> SEQ ID NO 383
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 383
tucgtcgtga cgtt                    14

<210> SEQ ID NO 384
<211> LENGTH: 14
<212> TYPE: DNA
<213> ORGANISM: Artificial Sequence

```
<220> FEATURE:
<223> OTHER INFORMATION: Synthetic oligonucleotide

<400> SEQUENCE: 384
tucgtcgtga cgtt                                                        14

<210> SEQ ID NO 385
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 385
tucgtcgtga cgtt                                                        14

<210> SEQ ID NO 386
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 386
tucgtcgtga cgtt                                                        14

<210> SEQ ID NO 387
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 387
tucgtcgtga cgtt                                                        14

<210> SEQ ID NO 388
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 388
tucgcgtgac gtt                                                         13

<210> SEQ ID NO 389
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 389
tucgcgtgac gtt                                                         13

<210> SEQ ID NO 390
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 390
ucgtcgtgtc gtt                                                         13
```

<210> SEQ ID NO 391
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 391
ucgtcgtgtc gtt                                                          13

<210> SEQ ID NO 392
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 392
ucgtcgtgtc gtt                                                          13

<210> SEQ ID NO 393
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 393
ucgtcgtgtc gtt                                                          13

<210> SEQ ID NO 394
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 394
ucgtcgtgtc gtt                                                          13

<210> SEQ ID NO 395
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 395
ucgtcgtgtc gtt                                                          13

<210> SEQ ID NO 396
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 396
ucgtcgtgtc gtt                                                          13

<210> SEQ ID NO 397
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 397
ucgtcgtgtc gtt                                                        13

<210> SEQ ID NO 398
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 398
ucgtcgtgtc gtt                                                        13

<210> SEQ ID NO 399
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 399
ucgtcgtgtc gtt                                                        13

<210> SEQ ID NO 400
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 400
ucgtcgtgtc gtt                                                        13

<210> SEQ ID NO 401
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 401
ucgtcgtgtc gtt                                                        13

<210> SEQ ID NO 402
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 402
ucgtcgtgtc gtt                                                        13

<210> SEQ ID NO 403
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 403
ucgtcgtgtc gtt                                                        13

<210> SEQ ID NO 404

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 404
ucgtcgttgt cgtt                                                      14

<210> SEQ ID NO 405
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 405
ucgtcgttgt cgtt                                                      14

<210> SEQ ID NO 406
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 406
ucgtcgttgt cgtt                                                      14

<210> SEQ ID NO 407
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 407
ucgtcgtgtc gtt                                                       13

<210> SEQ ID NO 408
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 408
ucgtcgtgtc gtt                                                       13

<210> SEQ ID NO 409
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 409
ucgtcgttgt cgtt                                                      14

<210> SEQ ID NO 410
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 410
```
ucgtcgtgtc gtt                                                          13

<210> SEQ ID NO 411
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 411
ucgtcgtgtc gtt                                                          13

<210> SEQ ID NO 412
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 412
ucgtcgtgtc gtt                                                          13

<210> SEQ ID NO 413
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 413
ucgtcgtgtc gtt                                                          13

<210> SEQ ID NO 414
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 414
ucgtcgtgtc gtt                                                          13

<210> SEQ ID NO 415
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 415
ucgtcgtgtc gtt                                                          13

<210> SEQ ID NO 416
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 416
ucgtcgtgtc gtt                                                          13

<210> SEQ ID NO 417
<211> LENGTH: 13
<212> TYPE: DNA

```
<213> ORGANISM: Artificial Sequence
<220> FEATURE:
<223> OTHER INFORMATION: Synthetic oligonucleotide

<400> SEQUENCE: 417
ucgtcgtgtc gtt                                                              13

<210> SEQ ID NO 418
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 418
ucgtcgtgtc gtt                                                              13

<210> SEQ ID NO 419
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 419
ucgtcgtgtc gtt                                                              13

<210> SEQ ID NO 420
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 420
ucgtcgtgtc gtt                                                              13

<210> SEQ ID NO 421
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 421
ucgtcgtgtc gtt                                                              13

<210> SEQ ID NO 422
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 422
ucgtcgtgtc gtt                                                              13

<210> SEQ ID NO 423
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 423
ucgtcgtgtc gtt                                                              13
```

<210> SEQ ID NO 424
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 424
ucgtcgtgtc gtt                                                          13

<210> SEQ ID NO 425
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 425
cgtcgtgtcg tt                                                           12

<210> SEQ ID NO 426
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 426
ccgtcgtgtc gtt                                                          13

<210> SEQ ID NO 427
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 427
ucgtcgtgtc gtt                                                          13

<210> SEQ ID NO 428
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 428
ucgtcgtgtc gtt                                                          13

<210> SEQ ID NO 429
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 429
ucgtcgtgtc gtt                                                          13

<210> SEQ ID NO 430
<211> LENGTH: 13
<212> TYPE: DNA
<213> ORGANISM: Artificial Sequence
<220> FEATURE:

<223> OTHER INFORMATION: Synthetic oligonucleotide

<400> SEQUENCE: 430
ucgtcgtgtc gtt                                                    13

<210> SEQ ID NO 431
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 431
ucgtcgtgtc gtt                                                    13

<210> SEQ ID NO 432
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 432
ucgtcgtgtc gtt                                                    13

<210> SEQ ID NO 433
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 433
cgtcgtgtcg tt                                                     12

<210> SEQ ID NO 434
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 434
cgtcgtgtcg tt                                                     12

<210> SEQ ID NO 435
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 435
cgtcgtgtcg tt                                                     12

<210> SEQ ID NO 436
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 436
cgtcgtgtcg tt                                                     12

```
<210> SEQ ID NO 437
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 437
cgtcgtgtcg tt                                                             12

<210> SEQ ID NO 438
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 438
cgtcgtgtcg tt                                                             12

<210> SEQ ID NO 439
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 439
cgtcgtgtcg tt                                                             12

<210> SEQ ID NO 440
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 440
cgtcgtgtcg tt                                                             12

<210> SEQ ID NO 441
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 441
cgtcgtgtcg tt                                                             12

<210> SEQ ID NO 442
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 442
cgtcgtgtcg tt                                                             12

<210> SEQ ID NO 443
<211> LENGTH: 12
<212> TYPE: DNA
<213> ORGANISM: Artificial Sequence
<220> FEATURE:
<223> OTHER INFORMATION: Synthetic oligonucleotide
```

```
<400> SEQUENCE: 443
cgtcgtgtcg tt                                                        12

<210> SEQ ID NO 444
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 444
aacgacacga cga                                                       13

<210> SEQ ID NO 445
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 445
cgtcgtgtcg tt                                                        12

<210> SEQ ID NO 446
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 446
cgtcgtgtcg tt                                                        12

<210> SEQ ID NO 447
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 447
cgtcgtgtcg tt                                                        12

<210> SEQ ID NO 448
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 448
cgtcgtgtcg tt                                                        12

<210> SEQ ID NO 449
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 449
cgtcgtgtcg tt                                                        12

<210> SEQ ID NO 450
<211> LENGTH: 14
```

```
<212> TYPE: DNA
<213> ORGANISM: Artificial Sequence
<220> FEATURE:
<223> OTHER INFORMATION: Synthetic oligonucleotide

<400> SEQUENCE: 450
tucgtcgtga cgtt                                                          14

<210> SEQ ID NO 451
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 451
tucgacgtga cgtt                                                          14

<210> SEQ ID NO 452
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 452 tucgacgtt                                                                 9

<210> SEQ ID NO 453
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 453 tuacgtt                                                                   7

<210> SEQ ID NO 454
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 454 tacgtt                                                                    6

<210> SEQ ID NO 455
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 455 tucgtt                                                                    6

<210> SEQ ID NO 456
<211> LENGTH: 5
<212> TYPE: DNA
<213> ORGANISM: Artificial Sequence
<220> FEATURE:
<223> OTHER INFORMATION: Synthetic oligonucleotide

<400> SEQUENCE: 456
```

```
tacgt                                                             5

<210> SEQ ID NO 457
<211> LENGTH: 5
<212> TYPE: DNA
<213> ORGANISM: Artificial Sequence
<220> FEATURE:
<223> OTHER INFORMATION: Synthetic oligonucleotide

<400> SEQUENCE: 457 tucgt                                                             5

<210> SEQ ID NO 458
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 458
tucgucgtga cgtt                                                  14

<210> SEQ ID NO 459
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 459 tucgucgtt                                                         9

<210> SEQ ID NO 460
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 460 tuacgut                                                           7

<210> SEQ ID NO 461
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 461 tacgut                                                            6

<210> SEQ ID NO 462
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 462 tucgut                                                            6

<210> SEQ ID NO 463
<211> LENGTH: 6
<212> TYPE: DNA
<213> ORGANISM: Artificial Sequence
```

```
<220> FEATURE:
<223> OTHER INFORMATION: Synthetic oligonucleotide

<400> SEQUENCE: 463 gucgtt                                                                     6

<210> SEQ ID NO 464
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 464 gacgtt                                                                     6

<210> SEQ ID NO 465
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 465 gucgut                                                                     6

<210> SEQ ID NO 466
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 466 gacgut                                                                     6

<210> SEQ ID NO 467
<211> LENGTH: 24
<212> TYPE: DNA
<213> ORGANISM: Artificial Sequence
<220> FEATURE:
<223> OTHER INFORMATION: Synthetic oligonucleotide - Double stranded-CpG
      using p88/p145

<400> SEQUENCE: 467
tcgtcgtttt gtcgttttgt cgtt                                                24

<210> SEQ ID NO 468
<211> LENGTH: 214
<212> TYPE: PRT
<213> ORGANISM: Artificial Sequence
<220> FEATURE:
<223> OTHER INFORMATION: light chain of anti-DEC205 antibody

<400> SEQUENCE: 468

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Arg Asn Trp Pro Leu
                    85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 469
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 469
tcgtcgtgac gtt                                                          13

<210> SEQ ID NO 470
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 470
cgtcgtgtcg                                                              10

<210> SEQ ID NO 471
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 471 cgtcgtgt                                                                 8

<210> SEQ ID NO 472
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 472 cgtcgtgt                                                                 8

<210> SEQ ID NO 473

```
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 473 cgtcgt                                                                    6

<210> SEQ ID NO 474
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 474 cgtcgt                                                                    6

<210> SEQ ID NO 475
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 475 cgtt                                                                      4

<210> SEQ ID NO 476
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 476 cgtt                                                                      4

<210> SEQ ID NO 477
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 477
tucgtcgtga cgtt                                                          14

<210> SEQ ID NO 478
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 478
ttucgtcgtg acgtt                                                         15

<210> SEQ ID NO 479
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 479
```
ttucgtcgtg acgtt    15

<210> SEQ ID NO 480
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 480
tucgtcgtga cgtt    14

<210> SEQ ID NO 481
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 481
ttucgtcgtg acgtt    15

<210> SEQ ID NO 482
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 482
tucgtcgtga cgtt    14

<210> SEQ ID NO 483
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 483
tucgtcgtga cgtt    14

<210> SEQ ID NO 484
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 484
tucgtcgtga cgtt    14

<210> SEQ ID NO 485
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 485
tucgtcgtga cgtt    14

<210> SEQ ID NO 486
<211> LENGTH: 15
<212> TYPE: DNA

```
<213> ORGANISM: Artificial Sequence
<220> FEATURE:
<223> OTHER INFORMATION: Synthetic oligonucleotide

<400> SEQUENCE: 486
ttucgtcgtg acgtt                                                      15

<210> SEQ ID NO 487
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 487
cgtcgtgtcg tt                                                         12

<210> SEQ ID NO 488
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 488
cgtcgtgtcg tt                                                         12

<210> SEQ ID NO 489
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 489
cgtcgtgtcg tt                                                         12

<210> SEQ ID NO 490
<211> LENGTH: 452
<212> TYPE: PRT
<213> ORGANISM: Artificial Sequence
<220> FEATURE:
<223> OTHER INFORMATION: heavy chain of anti-DEC205 antibody

<400> SEQUENCE: 490

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Gly Trp Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
            130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Leu
            435                 440                 445

Leu Gln Gly Gly
450

<210> SEQ ID NO 491
<211> LENGTH: 216
<212> TYPE: PRT
<213> ORGANISM: Artificial Sequence
<220> FEATURE:
<223> OTHER INFORMATION: light chain of anti-CD303 antibody

<400> SEQUENCE: 491

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Trp Tyr Gln Gln Lys Pro Gly Lys Ala Pro Lys
```

35                  40                  45
Leu Leu Ile Tyr Ala Ala Ser Thr Leu Glu Ser Gly Val Pro Ser Arg
    50                  55                  60
Phe Ser Gly Ser Gly Ser Gly Thr Asp Phe Thr Leu Thr Ile Ser Ser
65                  70                  75                  80
Leu Gln Pro Glu Asp Phe Ala Thr Tyr Tyr Cys Gln Gln Ala Asn Glu
                85                  90                  95
Asp Pro Arg Thr Phe Gly Gln Gly Thr Lys Val Glu Ile Lys Arg Thr
                100                 105                 110
Val Ala Ala Pro Ser Val Phe Ile Phe Pro Pro Ser Asp Glu Gln Leu
                115                 120                 125
Lys Ser Gly Thr Ala Ser Trp Cys Leu Leu Asn Asn Phe Tyr Pro Arg
                130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Ala Tyr Glu Lys His Lys
                180                 185                 190
Val Tyr Ala Cys Glu Val Thr His Gln Gly Leu Ser Ser Pro Val Thr
                195                 200                 205
Lys Ser Phe Asn Arg Gly Glu Cys
210                 215

<210> SEQ ID NO 492
<211> LENGTH: 454
<212> TYPE: PRT
<213> ORGANISM: Artificial Sequence
<220> FEATURE:
<223> OTHER INFORMATION: heavy chain of anti-CD303 antibody

<400> SEQUENCE: 492

Asp Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Thr Tyr
                20                  25                  30
Thr Met Ser Trp Val Arg Gln Ala Pro Gly Lys Gly Leu Glu Trp Val
                35                  40                  45
Ala Thr Ile Ser Pro Gly Asp Ser Phe Gly Tyr Tyr Pro Asp Ser
    50                  55                  60
Val Gln Gly Arg Phe Thr Ile Ser Arg Asp Asn Ala Lys Asn Ser Leu
65                  70                  75                  80
Tyr Leu Gln Met Asn Ser Leu Arg Ala Glu Asp Thr Ala Val Tyr Tyr
                85                  90                  95
Cys Thr Arg Asp Ile Tyr Tyr Asn Tyr Gly Ala Trp Phe Ala Tyr Trp
                100                 105                 110
Gly Gln Gly Thr Leu Val Thr Val Ser Ala Ser Thr Lys Gly Pro
                115                 120                 125
Ser Val Phe Pro Leu Ala Pro Ser Ser Lys Ser Thr Ser Gly Gly Thr
                130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr

-continued

```
              180                 185                 190
Val Pro Ser Ser Leu Gly Thr Gln Thr Tyr Ile Cys Asn Val Asn
            195                 200                 205
His Lys Pro Ser Asn Thr Lys Val Asp Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Leu Leu Gln Gly Gly
    450

<210> SEQ ID NO 493
<211> LENGTH: 5
<212> TYPE: PRT
<213> ORGANISM: Artificial Sequence
<220> FEATURE:
<223> OTHER INFORMATION: heavy chain Q-tag

<400> SEQUENCE: 493

Leu Leu Gln Gly Gly
1               5

<210> SEQ ID NO 494
<211> LENGTH: 8
<212> TYPE: PRT
<213> ORGANISM: Artificial Sequence
<220> FEATURE:
<223> OTHER INFORMATION: light chain Q-tag

<400> SEQUENCE: 494

Gly Gly Gly Leu Leu Gln Gly Gly
1               5
```

<210> SEQ ID NO 495
<211> LENGTH: 213
<212> TYPE: PRT
<213> ORGANISM: Artificial Sequence
<220> FEATURE:
<223> OTHER INFORMATION: light chain of anti-PD-L1 antibody

<400> SEQUENCE: 495

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 496
<211> LENGTH: 452
<212> TYPE: PRT
<213> ORGANISM: Artificial Sequence
<220> FEATURE:
<223> OTHER INFORMATION: heavy chain of anti-PD-L1 antibody

<400> SEQUENCE: 496

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Arg His Trp Pro Gly Gly Phe Asp Tyr Trp Gly Gln Gly Thr
            100                 105                 110

Leu Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
            165                 170                 175

Ser Asp Leu Tyr Thr Leu Ser Ser Val Thr Val Thr Ser Ser Thr
        180                 185                 190

Trp Pro Ser Gln Ser Ile Thr Cys Asn Val Ala His Pro Ala Ser Ser
    195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
            245                 250                 255

Ser Pro Ile Val Thr Cys Val Val Val Ala Val Ser Glu Asp Asp Pro
        260                 265                 270

Asp Val Gln Ile Ser Trp Phe Val Asn Asn Val Glu Val His Thr Ala
    275                 280                 285

Gln Thr Gln Thr His Arg Glu Asp Tyr Ala Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
            325                 330                 335

Ile Ser Lys Pro Lys Gly Ser Val Arg Ala Pro Gln Val Tyr Val Leu
        340                 345                 350

Pro Pro Pro Glu Glu Met Thr Lys Lys Gln Val Thr Leu Thr Cys
    355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
            405                 410                 415

Asn Trp Val Glu Arg Asn Ser Tyr Ser Cys Ser Val Val His Glu Gly
        420                 425                 430

Leu His Asn His His Thr Thr Lys Ser Phe Ser Arg Thr Pro Gly Leu
    435                 440                 445

Leu Gln Gly Gly
    450

<210> SEQ ID NO 497
<211> LENGTH: 14
<212> TYPE: DNA
<213> ORGANISM: Artificial Sequence
<220> FEATURE:
<223> OTHER INFORMATION: Synthetic Oligonucleotide - a stereoisomer,
      a mixture of two or more diastereomers, a tautomer,
      or a mixture of two or more tautomers thereof

```
<220> FEATURE:
<221> NAME/KEY: misc_feature
<222> LOCATION: (1)..(1)
<223> OTHER INFORMATION: N is absent or 2-Prime-deoxythymidine
<220> FEATURE:
<221> NAME/KEY: modified_base
<222> LOCATION: (2)..(2)
<223> OTHER INFORMATION: N is a 2-Prime-deoxyribonucleotide with a
      modified nucleobase
<220> FEATURE:
<221> NAME/KEY: modified_base
<222> LOCATION: (5)..(5)
<223> OTHER INFORMATION: N is 2-Prime-deoxyadenosine or 2-Prime-
      deoxythymidine, each optionally comprising a 3-Prime-
      phosphotriester
<220> FEATURE:
<221> NAME/KEY: repeat_unit
<222> LOCATION: (8)..(8)
<223> OTHER INFORMATION: t can be repeated 1 to 4 times, i.e. it can be
      t, tt, ttt, tttt
<220> FEATURE:
<221> NAME/KEY: modified_base
<222> LOCATION: (10)..(10)
<223> OTHER INFORMATION: N is 2-Prime-deoxyadenosine or 2-Prime-
      deoxythymidine
<220> FEATURE:
<221> NAME/KEY: modified_base
<222> LOCATION: (13)..(13)
<223> OTHER INFORMATION: N is 2-Prime-deoxythymidine optionally
      comprising a 3-Prime-phosphotriester

<400> SEQUENCE: 497
nncgncgtgn cgnt                                                    14
```

IMMUNOMODULATING POLYNUCLEOTIDES, ANTIBODY CONJUGATES THEREOF, AND METHODS OF THEIR USE

CROSS REFERENCE TO RELATED APPLICATIONS

This application claims the benefit of U.S. Provisional Application Nos. 62/485,748 and 62/537,925, filed April 14 and Jul. 27, 2017, respectively; the disclosure of each of which is incorporated herein by reference in its entirety.

REFERENCE TO A SEQUENCE LISTING

This application is being filed with a computer readable form (CRF) copy of a Sequence Listing named 14465-001-999_ST25.txt, created on Apr. 11, 2018, and being 116,262 bytes in size; which is incorporated herein by reference in its entirety.

FIELD OF THE INVENTION

This invention relates to compositions and methods for modulating the immune system response. Provided herein is an immunomodulating polynucleotide. Also provided herein is an immunomodulating polynucleotide comprising a 5-modified uridine or a 5-modified cytidine and having a length ranging from about 6 to about 16 nucleotides. Further provided herein is a conjugate comprising a targeting moiety and one or more immunomodulating polynucleotides. Provided herein is a pharmaceutical composition comprising an immunomodulating polynucleotide or a conjugate comprising a targeting moiety and one or more immunomodulating polynucleotides. Provided herein are methods of their use for treating a disease, such as cancer.

BACKGROUND

Pathogen-associated molecular patterns (PAMPs) are molecules associated with various pathogens and are recognized by toll-like receptors (TLRs) and other pattern recognition receptors (PRRs) activating innate immune responses. The ability of PAMPs to recruit immune system in the absence of pathogens provides a strategy for treating a variety of diseases involving cell destruction (e.g., anticancer therapy) through the use of innate immune system response. One class of PAMPs that has been investigated for a variety of therapeutic applications is immunostimulating polynucleotides, such as CpG ODN (e.g., agatolimod). It is thought that CpG ODNs mediate TLR9 dimerization in immune cells (e.g., B cells, monocytes, and plasmacytoid dendritic cells (pDCs)) to upregulate cytokines (e.g., type I interferon and interleukins), thereby activating natural killer cells.

CpG ODNs are generally divided into three classes: class A, class B, and class C. Class A CpG ODNs typically contain poly-G tails with phosphorothioate backbones at 3'- and 5'-termini and a central palindromic sequence including a phosphate backbone. Class A CpG ODNs typically contain CpG within the central palindrome sequence. Class B CpG ODNs typically include fully phosphorothioate backbone, and the sequence at the 5' end of class B CpG ODN is often critical for TLR9 activation. Class C CpG ODNs include fully phosphorothioate backbone with a 3'-end sequence enabling formation of a duplex. CpG ODNs are often susceptible to degradation in serum. Thus, pharmacokinetics of CpG ODNs may be one of the limiting factors in their development as therapeutics. Further, CpG ODNs often exhibit uneven tissue distribution in vivo, with primary sites of accumulation being in liver, kidney, and spleen. Such distribution can elicit off-target activity and local toxicity associated with PAMPs. Thus, therapeutic applications of CpG ODNs may be facilitated by addressing the pharmacokinetic/pharmacodynamic challenges described herein.

Accordingly, there is a need for new immunomodulating polynucleotides.

SUMMARY OF THE INVENTION

In general, the present invention relates to immunomodulating (e.g., immunostimulating) polynucleotides and conjugates containing a targeting moiety and one or more immunomodulating (e.g., immunostimulating) polynucleotides.

In one aspect, disclosed are immunomodulating polynucleotides. The immunomodulating polynucleotide may be an immunostimulating polynucleotide. Alternatively, the immunomodulating polynucleotide may be an immunosuppressive polynucleotide.

In some embodiments, the immunomodulating polynucleotide contains one or more (e.g., 1 or 2) abasic spacers or phosphotriesters. In particular embodiments, the immunomodulating polynucleotide contains one or more (e.g., 1 to 5) internucleoside phosphotriesters. In further embodiments, at least one of the internucleoside phosphotriesters contains a conjugating group. In yet further embodiments, the immunomodulating polynucleotide further contains a terminal phosphoester (e.g., a 5'-terminal phosphoester or 3'-terminal phosphoester). In still further embodiments, the terminal phosphoester contains a conjugating group. In other embodiments, the immunomodulating polynucleotide includes a 5'-cap or 3'-cap. In yet other embodiments, the immunomodulating polynucleotide contains the 5'-cap that is a 5'-5' cap. In still other embodiments, the 5'-5' cap contains a conjugating group covalently bonded to an internucleoside phosphate, internucleoside phosphorothioate, or internucleoside phosphorodithioate. In some embodiments, the immunomodulating polynucleotide includes the 3'-cap containing a conjugating group covalently bonded to an internucleoside phosphate, internucleoside phosphorothioate, or internucleoside phosphorodithioate.

In further embodiments, the immunomodulating polynucleotide contains a 5'-capping group that is monophosphate, diphosphate, triphosphate, an auxiliary moiety, a terminal phosphodiester, a terminal phosphotriester, a 5'-5' cap, or a group —OR', where R' is a bioreversible group, a non-bioreversible group, or an O-protecting group. In yet further embodiments, the 5'-capping group is monophosphate or the terminal phosphodiester including optionally substituted $C_{1-6}$ alkyl bonded to phosphate, phosphorothioate, or phosphorodithioate. In still further embodiments, the immunomodulating polynucleotide contains a 3'-capping group that is monophosphate, diphosphate, triphosphate, an auxiliary moiety, a terminal phosphodiester, a terminal phosphotriester, and a group —OR', where R' is a bioreversible group, a non-bioreversible group, or an O-protecting group. In some embodiments, the 3'-capping group is monophosphate or the terminal phosphodiester comprising optionally substituted $C_{1-6}$ alkyl bonded to phosphate, phosphorothioate, or phosphorodithioate.

In particular embodiments, the immunomodulating polynucleotide contains one or more (e.g., 1 or 2) abasic spacers. In further embodiments, at least one of the abasic spacers is an internucleoside abasic spacer. In yet further embodiments, at least one of the abasic spacers is a 3'-terminal abasic spacer. In still further embodiments, at least one of the abasic spacers comprises a conjugating group.

In certain embodiments, the immunomodulating polynucleotide contains a 5-modified uridine (e.g., 5-halouridine (e.g., 5-bromouridine or 5-iodouridine) or 5-modified cytidine). In further embodiments, the 5-modified uridine (e.g., 5-halouridine (e.g., 5-bromouridine or 5-iodouridine)) is at least one of two 5'-terminal nucleosides or is present in an immunostimulating sequence (ISS) in the immunomodulating polynucleotide. In yet further embodiments, the 5-modified uridine (e.g., 5-halouridine) includes a 3'-position bonded to an internucleoside phosphodiester phosphate. In certain embodiments, the 5-modified uridine (e.g., 5-halouridine) includes a 3'-position bonded to an internucleoside phosphodiester phosphorothioate. In still further embodiments, the 5-modified uridine (e.g., 5-halouridine) is 5'-terminal. In some embodiments, the 5-modified uridine is 5-bromouridine. In particular embodiments, the immunomodulating polynucleotide contains cytidine and guanosine as the second and third nucleosides or as the third and fourth nucleosides.

In particular embodiments, the immunomodulating polynucleotide contains a 5'-terminal immunostimulating sequence. In certain embodiments, at least one of the internucleoside phosphotriesters is bonded to a 3'-carbon atom of a nucleoside having a 5'-carbon atom which is bonded to a 5'-terminal immunostimulating sequence.

In further embodiments, the immunomodulating polynucleotide comprises a total of from 6 to 16 (e.g., 6, 7, 8, 9, 10, 11, 12, 13, 14, 15, or 16) nucleotides. In yet further embodiments, at least 10% (e.g., at least 20%, at least 30%, at least 40%, at least 50%, at least 60%, at least 70%, at least 80%, or at least 90%) of internucleoside bridging groups in the immunomodulating polynucleotide contain phosphorothioates. In still further embodiments, at least 50% of internucleoside bridging groups in the immunomodulating polynucleotide contain phosphorothioates.

In some embodiments, the immunomodulating polynucleotide includes a conjugating group covalently bonded to a nucleobase in the immunomodulating polynucleotide.

In certain embodiments, the immunomodulating polynucleotide includes one or more auxiliary moieties. In particular embodiments, the immunomodulating polynucleotide includes a conjugating moiety containing at least one of the auxiliary moieties. In some embodiments, at least of the one auxiliary moieties contains a polyethylene glycol) (PEG) having a molecular weight of from 100 Da to 2,500 Da. In further embodiments, each PEG contains independently a total of at least 3 ethylene glycol repeating units. In yet further embodiments, each PEG contains independently a total of at least 20 ethylene glycol repeating units. In still further embodiments, each PEG contains independently a total of 50 or fewer ethylene glycol repairing units. In other embodiments, the immunomodulating polynucleotide contains from one to eight PEGs.

In particular embodiments, the immunomodulating polynucleotide is a polynucleotide disclosed herein (e.g., in Table 2).

In another aspect, disclosed are hybridized immunomodulating polynucleotides containing an immunomodulating polynucleotide hybridized to a complementary polynucleotide.

In yet another aspect, disclosed are compositions containing an immunomodulating polynucleotide, in which the immunomodulating polynucleotide contains at least one stereochemically enriched internucleoside phosphorothioate.

In some embodiments, at least one stereochemically enriched internucleoside phosphorothioate is disposed between a 5'-terminal nucleoside and cytidine of CpG in an immunostimulating sequence in the immunomodulating polynucleotide. In further embodiments, one stereochemically enriched internucleoside phosphorothioate connects the first and the second nucleosides in the immunomodulating polynucleotide. In yet further embodiments, one stereochemically enriched internucleoside phosphorothioate is bonded to 5'-carbon atom of cytidine of CpG in an immunostimulating sequence in the immunomodulating polynucleotide. In still further embodiments, one stereochemically enriched internucleoside phosphorothioate connects the fourth and the fifth nucleosides in the immunomodulating polynucleotide. In certain embodiments, the stereochemically enriched internucleoside phosphorothioate is S-stereogenic. In particular embodiments, the stereochemically enriched internucleoside phosphorothioate is R-stereogenic.

In still another aspect, disclosed are conjugates containing a targeting moiety and one or more immunomodulating polynucleotides.

In some embodiments, the targeting moiety is an antigen-binding moiety, a polypeptide, an aptamer, or a group including one or more small molecules. In certain embodiments, the targeting moiety is an antigen-binding moiety (e.g., an antibody or an antigen-binding fragment thereof). In further embodiments, the antibody or the antibody fragment includes an N-terminal or C-terminal Q-tag, where the immunomodulating polynucleotide(s) are independently covalently bonded to the N-terminal or C-terminal Q-tag. In yet further embodiments, the Q-tag is disposed in a heavy chain or light chain of the antibody or the antibody fragment.

In particular embodiments, the immunomodulating polynucleotide is as disclosed in other aspects.

In certain embodiments, at least one of the immunomodulating polynucleotides contains a 5-modified uridine or 5-modified cytidine. In further embodiments, at least one of the immunomodulating polynucleotides comprises a 5-modified uridine that is 5-halouridine, 5-alkynyluridine, or 5-heterocyclyluridine. In yet further embodiments, the 5-modified uridine is 5-halouridine (e.g., 5-bromouridine or 5-iodouridine). In some embodiments, the 5-modified uridine is one of two 5'-terminal nucleotides of at least one of the immunomodulating polynucleotides. In other embodiments, the 5-modified uridine comprises a 3'-position bonded to an internucleoside phosphoester phosphate. In yet other embodiments, the 5-modified uridine comprises a 3'-position bonded to an internucleoside phosphoester phosphorothioate. In still other embodiments, at least one of the immunomodulating polynucleotides contains cytidine and guanosine as the second and third nucleosides. In particular embodiments, at least one of the immunomodulating polynucleotides contains cytidine and guanosine as the third and fourth nucleosides.

In some embodiments, at least one of the immunomodulating polynucleotides contains a total of from 6 to 16 (e.g., 6, 7, 8, 9, 10, 11, 12, 13, 14, 15, or 16) nucleotides.

In further embodiments, at least one of the immunomodulating polynucleotides contains one or more abasic spacers or internucleoside phosphotriesters. In yet further embodiments, at least one abasic spacer or at least one phosphotriester contains the linker.

In particular embodiments, at least one of the immunomodulating polynucleotides contains one or more (e.g., 1 or 2) abasic spacers. In other embodiments, at least one of the abasic spacers is an internucleoside abasic spacer. In yet other embodiments, at least one of the abasic spacers is a 3'-terminal abasic spacer.

In certain embodiments, at least one of the immunomodulating polynucleotides contains one or more (e.g., 1 to 5) internucleoside phosphotriesters.

In some embodiments, the conjugate further contains one or more auxiliary moieties bonded to the linker. In further embodiments, at least of the one auxiliary moieties contains a polyethylene glycol) (PEG) having a molecular weight of from 100 Da to 2,500 Da. In yet further embodiments, each PEG independently contains a total of at least 3 (e.g., at least 5, at least 6, at least, 7 at least 8, at least 9, at least 10, at least 12, at least 14, at least 16, at least 18, or at least 20) ethylene glycol repeating units. In still further embodiments, each PEG independently contains a total of 50 or fewer (e.g., 45 or fewer, 40 or fewer, 35 or fewer, or 30 or fewer) ethylene glycol repearing units. In certain embodiments, the conjugate contains from one to eight PEGs.

In particular embodiments, a 5'-capping group in at least one of the immunomodulating polynucleotides is monophosphate, diphosphate, triphosphate, an auxiliary moiety, a terminal phosphodiester, a terminal phosphotriester, or a group-OR', where R' is a bioreversible group, a non-bioreversible group, or an O-protecting group. In further embodiments, the 5'-capping group is monophosphate or the terminal phosphodiester containing optionally substituted $C_{1-6}$ alkyl bonded to phosphate, phosphorothioate, or phosphorodithioate. In yet further embodiments, the 3'-capping group in at least one of the immunomodulating polynucleotides is monophosphate, diphosphate, triphosphate, an auxiliary moiety, a terminal phosphodiester, a terminal phosphotriester, or a group —OR', where R' is a bioreversible group, a non-bioreversible group, or an O-protecting group. In other embodiments, the 3'-capping group is monophosphate or the terminal phosphodiester containing optionally substituted $C_{1-6}$ alkyl bonded to phosphate, phosphorothioate, or phosphorodithioate.

In certain embodiments, at least one of immunomodulating polynucleotides contains a nucleobase bonded to the linker.

In further embodiments, the conjugate contains from one to six (e.g., 1 to 4) immunomodulating polynucleotides. In yet further embodiments, the conjugate contains only one immunomodulating polynucleotide. In still further embodiments, the conjugate contains only two immunomodulating polynucleotides. In other embodiments, the conjugate contains one targeting moiety.

In some embodiments, the immunomodulating polynucleotide contains a human immunostimulating sequence within four 5'-terminal nucleotides. In certain embodiments, the human immunostimulating sequence within four 5'-terminal nucleotides of the immunomodulating polynucleotide includes cytidine containing a 5'-carbon atom bonded to a phosphoester substituted with a nucleoside.

In particular embodiments, at least one of the immunomodulating polynucleotides contains a 5-modified uridine or 5-modified cytidine.

In certain embodiments, at least one of the immunomodulating polynucleotides is hybridized to its complement.

In further embodiments, at least one of the immunomodulating polynucleotides contains at least one stereochemically enriched internucleoside phosphorothioate.

In a further aspect, disclosed are compositions containing a conjugate including a targeting moiety and one or more immunomodulating polynucleotides, each of the immunomodulating polynucleotides including independently a linker, where the targeting moiety is covalently bonded to the linker, and at least one of the immunomodulating polynucleotides containing at least one stereochemically enriched internucleoside phosphorothioate.

In some embodiments, at least one stereochemically enriched internucleoside phosphorothioate is disposed between a 5'-terminal nucleoside and cytidine of CpG in an immunostimulating sequence in the immunomodulating polynucleotide. In certain embodiments, at least one stereochemically enriched internucleoside phosphorothioate is bonded to 5'-carbon atom of cytidine of CpG in an immunostimulating sequence in the immunomodulating polynucleotide. In particular embodiments, at least one stereochemically enriched internucleoside phosphorothioate connects the first and the second nucleosides in the immunomodulating polynucleotide. In further embodiments, at least one stereochemically enriched internucleoside phosphorothioate connects the fourth and the fifth nucleosides in the immunomodulating polynucleotide. In yet further embodiments, the stereochemically enriched internucleoside phosphorothioate is S-stereogenic. In still further embodiments, the stereochemically enriched internucleoside phosphorothioate is R-stereogenic.

In yet further aspect, disclosed are pharmaceutical compositions containing a pharmaceutically acceptable carrier and the immunomodulating polynucleotide of invention, the stereochemically enriched composition of the invention, or the conjugate of the invention.

In still further aspect, disclosed are methods of modulating an endosomal toll-like receptor in a cell comprising the endosomal toll-like receptor by contacting the cell with the immunomodulating polynucleotide of the invention, the composition of the invention, the conjugate of the invention, or the pharmaceutical composition of the invention under conditions permitting the immunomodulating polynucleotides to be transported into the cell, where, after the contacting, the activity of the endosomal toll-like receptor is modulated.

In some embodiments, the immunomodulating polynucleotide is an immunostimulating polynucleotide, and the method is for agonizing an endosomal toll-like receptor.

In particular embodiments, the immunomodulating polynucleotide is an immunosuppressive polynucleotide, and the method is for antagonizing an endosomal toll-like receptor.

In another aspect, disclosed are methods of inducing one or more cytokines in an antigen-presenting cell containing an endosomal toll-like receptor by contacting the antigen-presenting cell with the immunomodulating polynucleotide of the invention, the composition of the invention, the conjugate of the invention, or the pharmaceutical composition of the invention under conditions permitting the one or more immunomodulating polynucleotides to be transported into the cell, where, after the contacting, the level of at least one cytokine in the cell is increased, where the targeting moiety targets the antigen-presenting cell, and where the immunomodulating polynucleotide is an immunostimulating polynucleotide.

In some embodiments, the antigen-presenting cell is a B cell. In certain embodiments, at least one of the one or more cytokines is an inflammatory cytokine. In particular embodiments, the antigen-presenting cell is a plasmacytoid dendritic cell, and where the targeting moiety targets the plasmacytoid dendritic cell. In certain embodiments, the antigen-presenting cell is a macrophage. In further embodiments, at least one of the cytokines is a type I interferon. In yet further embodiments, the toll-like receptor is TLR9.

In yet another aspect, disclosed are methods of treating a liquid tumor in a patient by administering to the patient an effective amount of the immunomodulating polynucleotide of the invention, the composition of the invention, the conjugate of the invention, or the pharmaceutical composition of the invention, where the targeting moiety targets B cells, and where the immunomodulating polynucleotide is an immunostimulating polynucleotide that is a TLR9 agonist.

In certain embodiments, the liquid tumor is a hematologic tumor (e.g., the hematologic tumor is a lymphoma). In particular embodiments, the lymphoma is a non-Hodgkin B-cell lymphoma. In further embodiments, the lymphoma is mantle cell lymphoma, diffuse large B cell lymphoma, follicular lymphoma, chronic lymphocytic leukemia, or multiple myeloma.

In still another aspect, disclosed are methods of treating a solid tumor in a patient by administering to the patient the immunomodulating polynucleotide of the invention, the composition of the invention, the conjugate of the invention, or the pharmaceutical composition of the invention, where the targeting moiety targets plasmacytoid dendritic cells, and where the immunomodulating polynucleotide is an immunostimulating polynucleotide that is a TLR9 agonist. In some embodiments, the method for treating a solid tumor in a patient comprises administering to the patient an immunomodulating polynucleotide as disclosed herein, wherein the immunomodulating polynucleotide targets B cell in the patient.

It is to be understood that the present invention also provides uses of the immunomodulating polynucleotides of the invention, conjugates of the invention, compositions of the invention, or pharmaceutical compositions of the invention in the manufacture of products (e.g., medicaments) for the purposes described herein (e.g., for treating a liquid or solid tumor in a patient). It is also to be understood that the present invention also provides uses of the immunomodulating polynucleotides of the invention, conjugates of the invention, compositions of the invention, or pharmaceutical compositions of the invention for the purposes described herein (e.g., for treating a liquid or solid tumor in a patient). Further, it is to be understood that the present invention also provides the immunomodulating polynucleotides of the invention, conjugates of the invention, compositions of the invention, or pharmaceutical compositions of the invention for use according to the purposes described herein (e.g., for treating a liquid or solid tumor in a patient).

In any aspect of the invention, the linker can be as disclosed herein (e.g., according to any one of formulae (II), (V), and (VI)-(XV)). In any aspect of the invention, the conjugating group can be as disclosed herein.

Provided herein is an oligonucleotide of Formula (A):

$$X^{5'}-(X^N)_b-Y^P-(X^N)_c-X^{3'} \quad (A)$$

or a stereoisomer, a mixture of two or more diastereomers, a tautomer, or a mixture of two or more tautomers thereof; or a pharmaceutically acceptable salt, solvate, or hydrate thereof; wherein:

each $X^N$ is independently a nucleotide;
$X^{3'}$ is a 3' terminal nucleotide;
$X^{5'}$ is a 5' terminal nucleotide;
$Y^P$ is an internucleoside phosphotriester; and
b and c are each an integer ranging from about 0 to about 25; with the proviso that their sum is no less than 5;

wherein the oligonucleotide comprises a nucleotide with a modified nucleobase.

Also provided herein is an oligonucleotide having a sequence of $N^1N^2CGN^3CG(T)_xGN^4CGN^5T$ (SEQ ID NO: 497), or a stereoisomer, a mixture of two or more diastereomers, a tautomer, or a mixture of two or more tautomers thereof; or a pharmaceutically acceptable salt, solvate, or hydrate thereof; wherein:

x is an integer ranging from 1 to 4;
$N^1$ is absent or 2'-deoxythymidine;
$N^2$ is a 2'-deoxyribonucleotide with a modified nucleobase;
$N^3$ is 2'-deoxyadenosine or 2'-deoxythymidine, each optionally comprising a 3'-phosphotriester;
$N^4$ is 2'-deoxyadenosine or 2'-deoxythymidine; and
$N^5$ is 2'-deoxythymidine optionally comprising a 3'-phosphotriester.

Additionally provided herein is a compound of Formula (B):

$$R^x-L^N-(Q)_e \quad (B)$$

or a stereoisomer, a mixture of two or more diastereomers, a tautomer, or a mixture of two or more tautomers thereof; or a pharmaceutically acceptable salt, solvate, or hydrate thereof; wherein:

$R^x$ is a conjugating group;
$L^N$ is a linker;
each Q is independently an oligonucleotide comprising a phosphotriester; and
e is an integer of 1, 2, 3, or 4.

Further provided herein is a compound of Formula (C):

$$Ab-[-L^N-(Q)_e]_f \quad (C)$$

or a stereoisomer, a mixture of two or more diastereomers, a tautomer, or a mixture of two or more tautomers thereof; or a pharmaceutically acceptable salt, solvate, or hydrate thereof; wherein:

Ab is an antibody;
each $L^N$ is independently a linker;
each Q is independently an oligonucleotide comprising a phosphotriester;
each e is independently an integer of 1, 2, 3, or 4; and
f is an integer of 1, 2, 3, or 4.

In one aspect, provided herein are methods for treating cancer in a subject having cancer, comprising administering a therapeutically effective amount of a CpG-Ab immunoconjugate to the subject, wherein the CpG-Ab immunoconjugate does not bind to a tumor associated antigen (TAA). In some embodiments, the CpG-Ab immunoconjugate specifically binds to a target antigen associated with a normal immune cell that expresses at least one toll-like receptor. In some embodiments, the normal immune cell expresses TLR9. In some embodiments, the normal immune cell is an antigen presenting cell (APC). In some embodiments, the APC is a B cell, a dendritic cells or a macrophage. In some embodiments, the target antigen is selected from the group consisting of a MHC molecule, a T cell costimulatory molecule, an immune checkpoint molecule, a B cell specific antigen, a dendritic cell specific antigen and a macrophage specific antigen. In some embodiments, the MHC molecule is selected from MHC class I and MHC class II molecules. In some embodiments, the T cell costimulatory molecule is selected from the list consisting of OX40, CD2, CD27, CDS, ICAM-1, LFA-1/CD11a/CD18, ICOS/CD278, 4-1BB/CD137, GITR, CD30, CD40, BAFFR, HVEM, CD7, LIGHT, NKG2C, SLAMF7, NKp80, CD160, B7-H3, and CD83. In some embodiments, the immune checkpoint molecule is selected from the list consisting of PD-1, PD-L1, PD-L2, TIM-1, TIM-3, LAG-3, CEACAM-1, CEACAM-5, CLTA-4, VISTA, BTLA, TIGIT, LAIR1, CD47, CD160, 2B4, CD172a, and TGFβ. In some embodiments, target antigen is selected from the group consisting of CD1, CD2, CD3, CD5, CD6, CD9, CD11, CD14, CD17, CD18, CD19, CD20, CD21, CD22, CD23, CD24, CD25, CD26, CD27, CD30, CD32, CD37, CD38, CD39, CD40, CD44, CD45R (B220), CD49, CD52, CD55, CD56, CD64, CD66 (Carcinoembrionic antigen, CEA), CD68, CD70, CD74, CD79b, CD80, CD93, CD115, CD123, CD126, CD127, CD137, CD138, CD163, CD196, CD197, CD200R, CD205, CD206, CD207, CD208, CD209, CD267, CD269, CD274, CD300a, CD301, CD303, CD304, CD319, CD336, CLEC5a, CLEC6, CLEC9a, CXCL16, CX3CR1, and DC-STAMP. In some embodiments, the CpG-Ab immunoconjugates comprises an immunostimulating polynucleotide selected from Table 2. In some embodiments, the CpG-Ab immunoconjugates comprises an immunostimulating polynucleotide selected from the group consisting of p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489. In some embodiments, the CpG-Ab immunoconjugates is not conjugated to a T cell epitope. In some embodiments, the T cell epitope is an epitope of ovalbumin (OVA). In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of treating cancer in a subject having cancer, comprises administering a therapeutically effective amount of a CpG-Ab immunoconjugate to the subject, wherein the CpG-Ab immunoconjugate specifically binds to a tumor associated antigen (TAA), wherein the TAA is not an antigen selected from the group consisting of CD19, CD20, CD22, exportin 7, Her2, Src, EGFR, CD52, CXCR-4, Muc-1 and DNA. In some embodiments, binding of the CpG-Ab immunoconjugate to the TAA facilitates internalization of the CpG-Ab immunoconjugate into a cancer cell expressing the TAA. In some embodiments, binding of the CpG-Ab immunoconjugate to the TAA facilitates transportation of the CpG-Ab immunoconjugate to endosome of the cancer cell expressing the TAA. In some embodiments, binding of the CpG-Ab immunoconjugate to the TAA facilitates activation of a TLR9 signaling pathway in a cancer cell expressing the TAA. In some embodiments, the TAA and the TLR9 are located on a same cellular membrane of the cancer cell expressing the TAA. In some embodiments, both the TAA and the TLR9 are located on the cell membrane of the cancer cell expressing the TAA. In some embodiments, both the TAA and the TLR9 are located on the endosomal membrane of the cancer cell expressing the TAA. In some embodiments, binding of the CpG-Ab immunoconjugate to the TAA induces apoptosis of the cancer cell expressing the TAA. In some embodiments, the TAA is not expressed by a normal immune cell. In some embodiments, the TAA is expressed by a normal immune cell. In some embodiments, the normal immune cell is an antigen presenting cell (APC). In some embodiments, the TAA is selected from the group consisting of CD8, CD11 b, CD11c, CD14, CD33, CD40, CD123, CD157, CD168, CD169, CD172a, CD200, CD204, CD205, CD301, CD302, CD303, CD304, and CD206. In some embodiments, the CpG-Ab immunoconjugate is not conjugated to the TAA or any other TAA expressed by the cancer. In some embodiments, the CpG-Ab immunoconjugates comprises an immunostimulating polynucleotide selected from Table 2. In some embodiments, the CpG-Ab immunoconjugates comprises an immunostimulating polynucleotide selected from the group consisting of p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489. In some embodiments, the CpG-Ab immunoconjugate is not conjugated to a T cell epitope. In some embodiments, the T cell epitope is ovalbumin (OVA). In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of treating an immunotherapy resistant or refractory cancer in a subject having immunotherapy resistant or refractory cancer, comprising administering a therapeutically effective amount of a CpG-Ab immunoconjugate to the subject. In some embodiments, the CpG-Ab immunoconjugate does not bind to a tumor associated antigen. In some embodiments, the CpG-Ab immunoconjugate specifically binds to a target antigen associated with a normal immune cell that expresses at least one toll-like receptor. In some embodiments, the CpG-Ab immunoconjugate specifically binds to a tumor associated antigen. In some embodiments, the cancer is resistant to treatment with an immune checkpoint modulator. In some embodiments, the method further comprising co-administering to the subject the immune checkpoint modulator. In some embodiments, the CpG-Ab immunoconjugates comprises an immunostimulating polynucleotide selected from Table 2. In some embodiments, the CpG-Ab immunoconjugates comprises an immunostimulating polynucleotide selected from the group consisting of p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489 as shown in Table 2. In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of preventing cancer in a subject in need thereof, comprising administering a therapeutically effective amount of a CpG-Ab immunoconjugate to the subject, wherein the CpG-Ab immunoconjugate specifically binds to a target antigen associated with a normal immune cell expressing at least one toll-like receptor. In some embodiments, such method further comprises co-administering a tumor associated antigen with the CpG-Ab immunoconjugate. In some embodiments, the CpG-Ab immunoconjugate is not conjugated to the tumor associated antigen. In some embodiments, the normal immune cell expresses TLR9. In some embodiments, the normal immune cell is an antigen presenting cell (APC). In some embodiments, the CpG-Ab immunoconjugates comprises an immunostimulating polynucleotide selected from Table 2. In some embodiments, the CpG-Ab immunoconjugates comprises an immunostimulating polynucleotide selected from the group consisting of p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489 as shown in Table 2. In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of preventing cancer in a subject in need thereof, comprising co-administering a therapeutic effective amount of a CpG-Ab immunoconjugate with a cancer vaccine, wherein the CpG-Ab immunoconjugate specifically binds to a target antigen associated with a normal immune cell expressing at least one toll-like receptor. In some embodiments, the CpG-Ab immunoconjugate is formulated as an adjuvant of the cancer vaccine. In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of inducing an adaptive immune response in a subject, comprising administering a therapeutically effective amount of a CpG-Ab immunoconjugate to the subject, wherein the CpG-Ab immunoconjugate specifically binds to a target antigen associated with a normal immune cell expressing at least one toll-like receptor. In some embodiments, the subject has cancer. In some embodiments, the target antigen is not a TAA. In some embodiments, the target antigen is a TAA that is not an antigen selected from the group consisting of CD19, CD20, CD22, STAT3, exportin 7, Her2, Src, EGFR, CD52, CXCR-4, Muc-1 and DNA. In some embodiments, the subject has an infectious disease. In some embodiments, the normal immune cell expresses TLR9. In some embodiments, the normal immune cell is an antigen presenting cell (APC). In some embodiments, the adaptive immune response is CD8+ T cell dependent. In some embodiments, the CpG-Ab immunoconjugates comprises an immunostimulating polynucleotide selected from Table 2. In some embodiments, the CpG-Ab immunoconjugates comprises an immunostimulating polynucleotide selected from the group consisting of p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489 as shown in Table 2. In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments, provided herein are methods of treating cancer in a subject having cancer, comprising administering to the subject a therapeutic effective amount of a CpG-Ab immunoconjugates selected from Table 6. In some embodiments, the CpG-Ab immunoconjugates binds to a tumor associated antigen (TAA). In some embodiments, the CpG-Ab immunoconjugates binds to a target antigen other than the TAA. In some embodiments, the CpG-Ab immunoconjugates binds to the target antigen associated with a normal immune cell expressing a TLR receptor. In some embodiments, the CpG-Ab immunoconjugates is selected from the group consisting of CpG-Ab immunoconjugates comprising p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489 as shown in Table 2. In some embodiments, further comprising co-administering a therapeutic effective amount of at least one additional cancer therapeutic agent. In some embodiments, the at least one additional cancer therapeutic agent is selected from a second TAA, a T cell costimulatory molecule, and an immune checkpoint modulator. In some embodiments, the second TAA is the same as the TAA. In some embodiments, the second TAA is different from the TAA. In some embodiments, the T cell costimulatory molecule is selected from the list consisting of OX40, CD2, CD27, CDS, ICAM-1, LFA-1/CD11a/CD18, ICOS/CD278, 4-1BB/CD137, GITR, CD30, CD40, BAFFR, HVEM, CD7, LIGHT, NKG2C, SLAMF7, NKp80, CD160, B7-H3, and CD83 or an ligand thereof. In some embodiments, the T cell costimulatory molecule is an anti-OX40 antibody, anti-ICOS/CD278 antibody or anti-4-1 BB/CD137 antibody, or an antigen-binding fragment thereof. In some embodiments, wherein the immune checkpoint modulator is an inhibitor of immune checkpoint molecules selected from the list consisting of PD-1, PD-L1, PD-L2, TIM-3, LAG-3, CEACAM-1, CEACAM-5, CLTA-4, VISTA, BTLA, TIGIT, LAIR1, CD47, CD160, 2B4, CD172a, and TGFR. In some embodiments, the immune checkpoint modulator is an anti-CD47 antibody, anti-PD-1 antibody, anti-PD-L1 antibody, or an antigen-binding fragment thereof. In some embodiments, the cancer is a solid tumor. In some embodiments the cancer is a liquid tumor. In some embodiments of the methods provided herein, the cancer is recurrent cancer. In some embodiments of the methods provided herein, the administering or co-administering is through systemic administration. In some embodiments of the methods provided herein, the therapeutic effective amount of the CpG-Ab immunoconjugate is not effective to activate the complement pathway in the subject. In some embodiments of the methods provided herein, the amount is not effective to activate complement C3 in the subject.

In some embodiments of any of the methods provided herein, wherein the CpG-Ab immunoconjugate comprises an oligonucleotide of Formula (A) as defined above. In some embodiments of any of the methods provided herein, wherein the CpG-Ab immunoconjugate comprises a compound of Formula (B) as defined above. In some embodiments of any of the methods provided herein, wherein the CpG-Ab immunoconjugate is a compound of Formula (C) as defined above.

BRIEF DESCRIPTION OF THE DRAWINGS

FIG. 60B shows the average tumor volume at Day 20 of mice with A20 mouse B-cell lymphoma cell xenografts following intravenous doses of (i) saline solution (solid); (ii) 3 mg/kg CpG-Ab (SB-337) (checkered); (iii) 3 mg/kg CD19-mAb (horizontal); (iv) 3 mg/kg CpG-Ab (SB-388) (vertical); (v) 1.9 µg/mouse naked CpG (P347) (downward diagonal); on each of Days 10, 12 and 14.

FIG. 60C shows the average body weight change with the tumor weight change removed at Day 20 of mice with A20 mouse B-cell lymphoma cell xenografts following intravenous doses of (i) saline solution (filled); (ii) 3 mg/kg CpG-Ab (SB-337) (checkered); (iii) 3 mg/kg CD19-mAb (horizontal); (iv) 3 mg/kg CpG-Ab (SB-388) (vertical); (v) 1.9 µg/mouse naked CpG (P347) (downward diagonal); (vi) 19 µg/mouse naked CpG (P347) (grid); (vii) 190 µg/mouse naked CpG (P347) (upward diagonal); on each of Days 10, 12 and 14.

FIG. 61A shows the average tumor volume growth progression of mice after B16F10 melanoma re-challenge following intratumoral dosing of (i) saline solution (closed circle); or (ii) p347 (closed square); on each of Days 7, 9, 11, and 13, and re-challenge on day 14.

FIG. 61B shows the lung metastases from mice after B16F10 melanoma re-challenge following intratumoral dosing of saline solution (top panel), or p347 (bottom panel); on each of Days 7, 9, 11, and 13, and re-challenge on day 14.

FIG. 61C shows the average tumor volume growth progression of mice inoculated with CT26 colorectal xenografts following intratumoral dosing of (i) saline solution (upward triangle); or (ii) p347 (downward triangle); on each of Days 7, 10, 12, and 14.

FIG. 63C shows the tumor volume growth progression of each mouse using a MC38 colorectal syngeneic model following intravenous dosing of 10 mg/kg of anti-CD22 mAb on Days 10, 12, and 14.

FIG. 63D shows the tumor volume growth progression of each mouse using a MC38 colorectal syngeneic model following intraperitoneal dosing of 10 mg/kg of anti-PD-L1 on Days 10, 13, and 17.

FIG. 63E shows the tumor volume growth progression of each mouse using a MC38 colorectal syngeneic model following intravenous dosing of 10 mg/kg of CD22-CpG (SB-337) on Days 10, 12, and 14.

FIG. 63F shows the tumor volume growth progression of each mouse using a MC38 colorectal syngeneic model following intravenous dosing of 10 mg/kg of CD22-CpG (SB-337) on Days 10, 12, and 14, plus intraperitoneal dosing of 10 mg/kg of anti-PD-L1 on Days 10, 13, and 17.

FIG. 64A shows the average tumor volume growth progression of mice using a B16F10 melanoma model following dosing of (i) saline solution (circle); (ii) 10 mg/kg anti-CD22 (square); (iii) 10 mg/kg CD22-CpG (SB-337) (triangle); or (iv) 10 mg/kg CD22-CpG (SB-337)+10 mg/kg anti-PD-L1 (diamond) on Days 10, 12, and 14. Anti-CD22 and CD22-CpG were dosed intravenously; anti-PD-L1 was dosed intraperitoneally.  p=0.08; * p=0.03.

FIG. 64B shows the average tumor volume growth progression of mice using a LLC1 Lewis lung carcinoma model following dosing of (i) saline solution (circle); (ii) 10 mg/kg CD22-CpG (SB-337) (circle); (iii) 10 mg/kg anti-PD1 (square); (iv) 10 mg/kg CD22-CpG (SB-337)+10 mg/kg anti-PD1 (upward triangle) (v) 10 mg/kg anti-PD-L1 (downward triangle); (vi) 10 mg/kg CD22-CpG+10 mg/kg anti-PD-L1 (diamond). Anti-CD22 and CD22-CpG were dosed intravenously on Days 7, 10, and 13; anti-PD-L1 and anti-PD1 were dosed intraperitoneally on Days 7, 10, and 14. ** p=0.023.

FIG. 65A shows the average tumor volume growth progression of mice using the CT26 colorectal model following intravenous dosing of (i) saline solution (circle); (ii) 10 mg/kg CD22-CpG (SB-337) (triangle); or (iii) 10 mg/kg DEC205-CpG (SB-3096) on each of Days 12, 17, 20, and 24.

FIG. 65B shows the tumor volume growth progression of each mouse using the CT26 colorectal model following intravenous dosing of saline on each of Days 12, 17, 20, and 24.

FIG. 65C shows the tumor volume growth progression of each mouse using the CT26 colorectal model following intravenous dosing of 10 mg/kg CD22-CpG (SB-337) on each of Days 12, 17, 20, and 24.

FIG. 65D shows the tumor volume growth progression of each mouse using the CT26 colorectal model following intravenous dosing of 10 mg/kg DEC205-CpG (SB-3096) on each of Days 12, 17, 20, and 24.

FIG. 66A shows the average tumor volume growth progression of mice using a CT26 colorectal model following dosing of (i) saline solution (small circle); (ii) CD4 depletion (big circle); (iii) 3 mg/kg CD22-CpG (SB-337) (square); or (iv) CD4 depletion+3 mg/kg CD22-CpG (SB-337) (diamond). CD22-CpG was dosed intravenously on Days 10, 13; and 15. CD4 depletion was performed using anti-CD4.

FIG. 66B shows the average tumor volume growth progression of mice using an A20 lymphoma model following dosing of (i) saline solution (circle); (ii) CD4 depletion (upward triangle); (iii) 3 mg/kg CD22-CpG (SB-337) (square); or (iv) CD4 depletion+3 mg/kg CD22-CpG (SB-337) (downward triangle). CD22-CpG was dosed intravenously on Days 10, 12; and 14. CD4 depletion was performed using anti-CD4

Figure 67A:
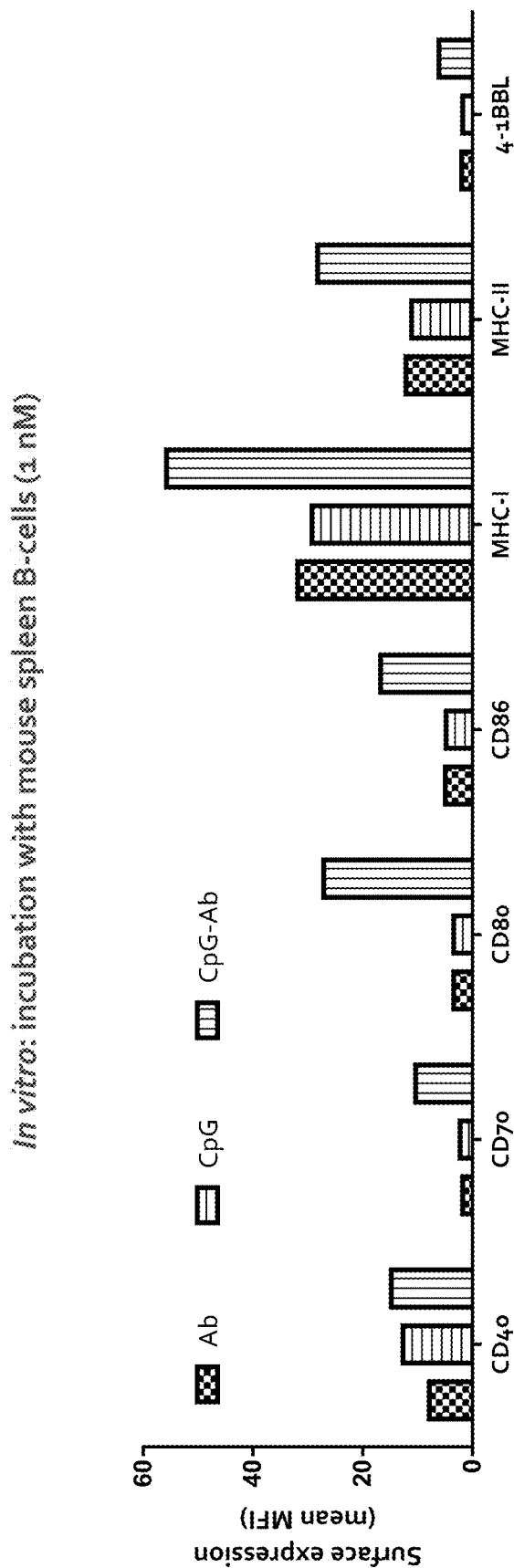

FIG. 67A shows the mean fluorescence intensity (MFI) of CD40, CD70, CD80, CD86, MHC-I, MHC II, and 4-1 BBL surface expression on CD19+/B220+ B-cells after in vitro incubation with 1 nM CD22 Ab (checkered); 1 nM CpG (SB-4715) (horizontal line); or 1 nM CpG-Ab (SB-337) (vertical line).

Figure 67B:
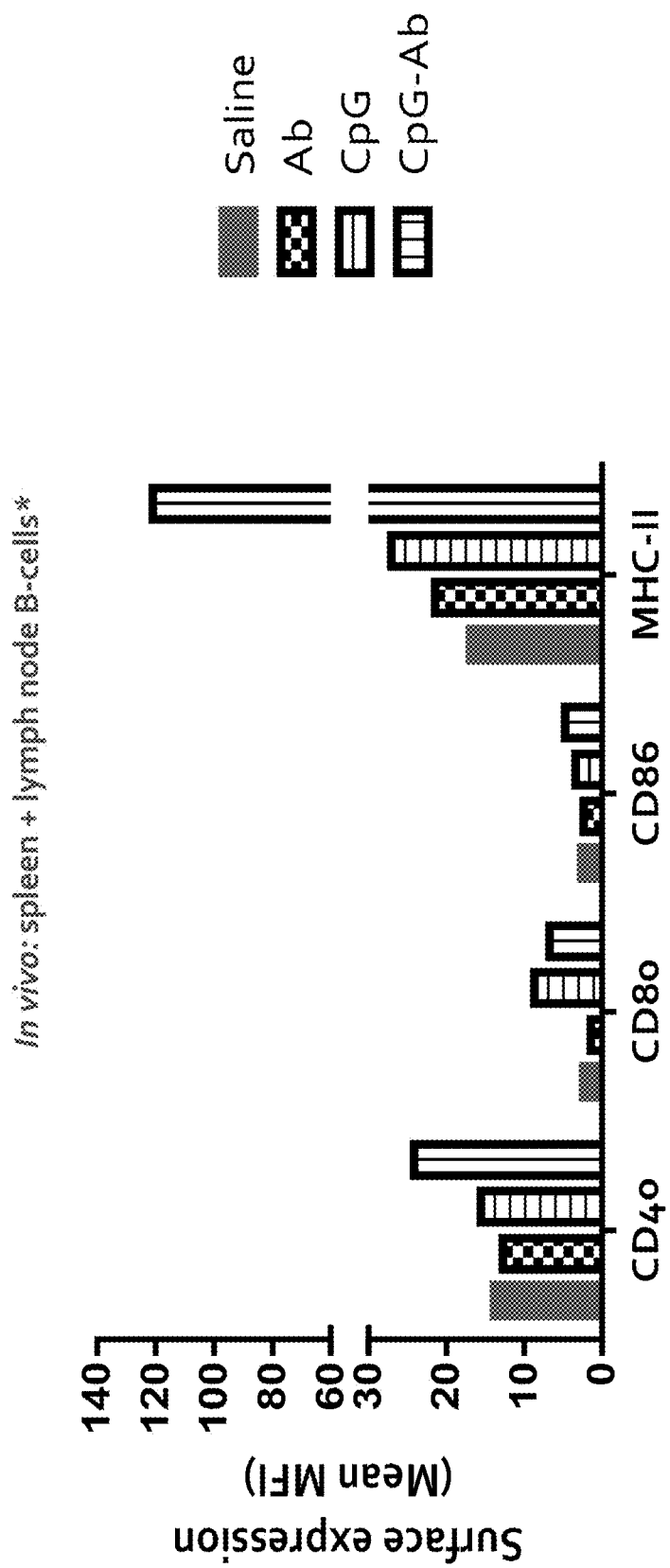

FIG. 67B shows the mean fluorescence intensity (MFI) of CD40, CD80, CD86, and MHC II surface expression on CD19+/B220+ B-cells after in vivo dosing with saline (solid); 10 mg/kg CD22 Ab (checkered); 10 mg/kg CpG (SB-4715) (horizontal line); or 10 mg/kg CpG-Ab (SB-337) (vertical line).

FIG. 68A shows the percent of activated T-cells (CD71+, CD3+) relative to total T-cell (CD3+) population in mice treated with (i) saline (solid); (ii) Ab (anti-CD22) (checkered); (iii) CpG-Ab (SB-337) (horizontal); or (iv) CpG (SB-4715) (vertical).

FIG. 68B shows the percent of activated T-cells (Ki67+, CD3+) relative to total T-cell (CD3+) population in mice treated with (i) saline (solid); (ii) Ab (anti-CD22) (checkered); (iii) CpG-Ab (SB-337) (horizontal); or (iv) CpG (SB-4715) (vertical).

Figure 69A:
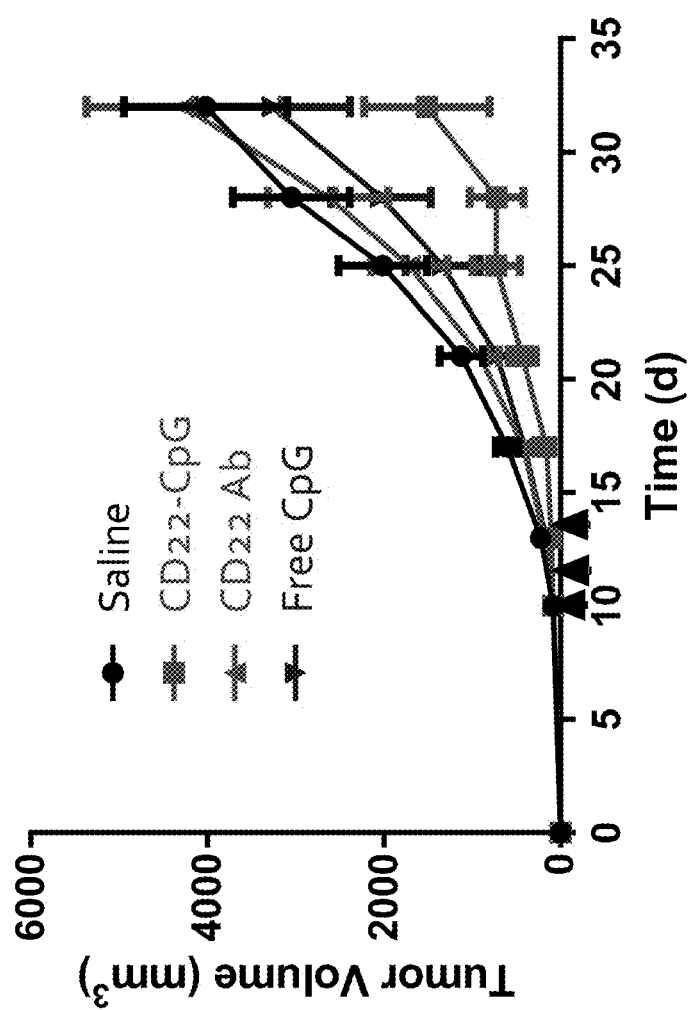

FIG. 69A shows the average tumor volume growth progression of mice using the CT26 colorectal model following intravenous dosing of (i) saline solution (circle); (ii) 10 mg/kg CD22-CpG (SB-337) (square); (iii) 10 mg/kg CD22 (upward triangle); or (iv) Free CpG (P347) (downward triangle) on each of Days 10, 12, 14.

Figure 69B:
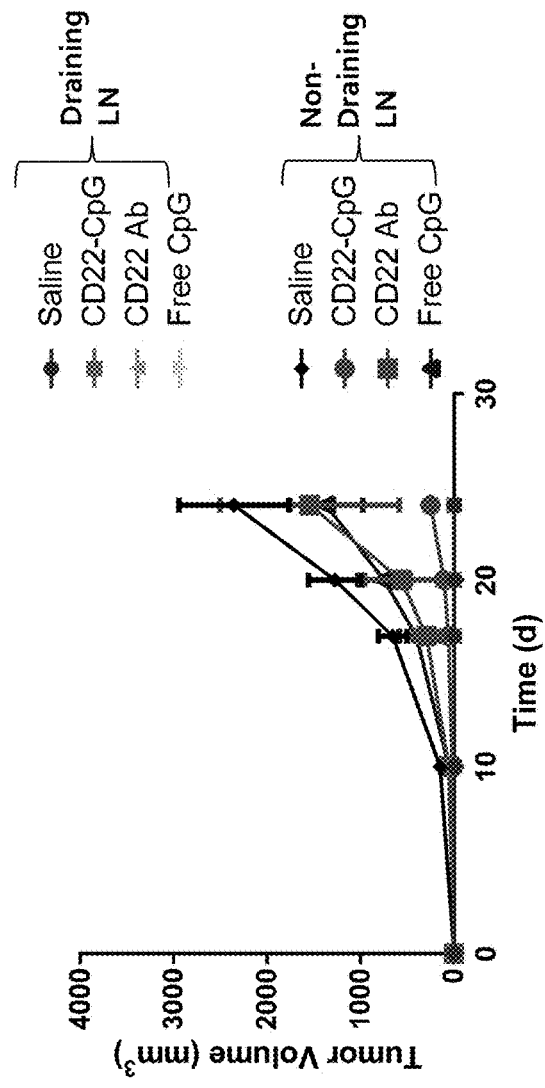

FIG. 69B shows the average tumor volume growth progression of mice using the CT26 colorectal model following adoptively transferred draining lymph node cells from mice treated with (i) saline solution (small circle); (ii) 10 mg/kg CD22-CpG (SB-337) (small square); (iii) 10 mg/kg CD22 (small upward triangle); or (iv) Free CpG (P347) (small downward triangle); or non-draining lymph node cells from mice treated with (v) saline solution (diamond); (vi) 10 mg/kg CD22-CpG (SB-337) (large circle); (vii) 10 mg/kg CD22 (large square); or (viii) Free CpG (P347) (large upward triangle).

Figure 69C:
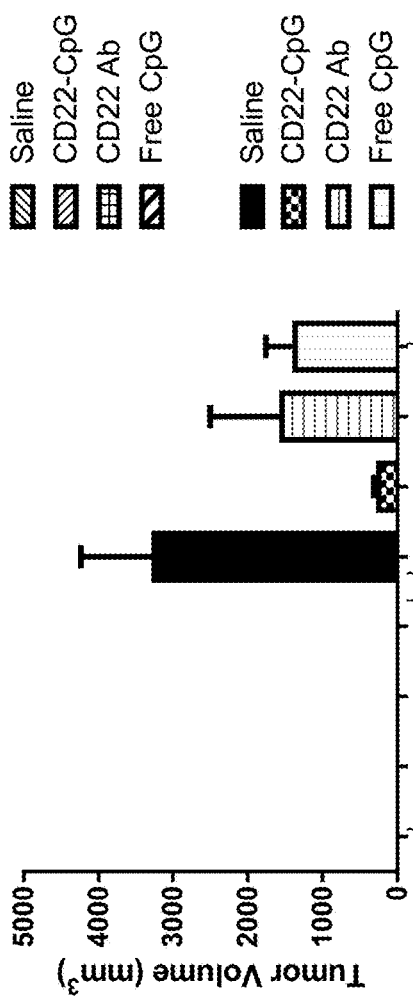

FIG. 69C shows the average tumor volume on Day 24 for mice using the CT26 colorectal model following adoptively transferred draining lymph node cells from mice treated with (i) saline solution (upward narrow diagonal); (ii) 10 mg/kg CD22-CpG (SB-337) (downward narrow diagonal); (iii) 10 mg/kg CD22 (grid); or (iv) Free CpG (P347) (wide downward diagonal); or non-draining lymph node cells from mice treated with (v) saline solution (solid); (vi) 10 mg/kg CD22-CpG (SB-337) (checkered); (vii) 10 mg/kg CD22 (horizontal); or (viii) Free CpG (P347) (empty).

FIG. 70A shows the plasma concentration of IL-6 in naïve mice treated intravenously with (i) saline (solid); (ii) 10 mg/kg Ab (CD22) (checkered); (iii) 5.7 ug/dose free CpG (p347) (horizontal); or (iv) 10 mg/kg CpG-mAb (SB-337) (vertical).

FIG. 70B shows the plasma concentration of IL-1β in naïve mice treated intravenously with (i) saline (solid); (ii) 10 mg/kg Ab (CD22) (checkered); (iii) 5.7 ug/dose free CpG (p347) (horizontal); or (iv) 10 mg/kg CpG-mAb (SB-337) (vertical).

FIG. 70C shows the plasma concentration of IL-10 in naïve mice treated intravenously with (i) saline (solid); (ii) 10 mg/kg Ab (CD22) (checkered); (iii) 5.7 ug/dose free CpG (p347) (horizontal); or (iv) 10 mg/kg CpG-mAb (SB-337) (vertical).

FIG. 70D shows the plasma concentration of IL-12p70 in naïve mice treated intravenously with (i) saline (solid); (ii) 10 mg/kg Ab (CD22) (checkered); (iii) 5.7 ug/dose free CpG (Sp347) (horizontal); or (iv) 10 mg/kg CpG-mAb (SB-337) (vertical).

FIG. 70E shows the plasma concentration of IFNγ in naïve mice treated intravenously with (i) saline (solid); (ii) 10 mg/kg Ab (CD22) (checkered); (iii) 5.7 ug/dose free CpG (p347) (horizontal); or (iv) 10 mg/kg CpG-mAb (SB-337) (vertical).

FIG. 70F shows the plasma concentration of TNFα in naïve mice treated intravenously with (i) saline (solid); (ii) 10 mg/kg Ab (CD22) (checkered); (iii) 5.7 ug/dose free CpG (p347) (horizontal); or (iv) 10 mg/kg CpG-mAb (SB-337) (vertical).

Figure 71B:
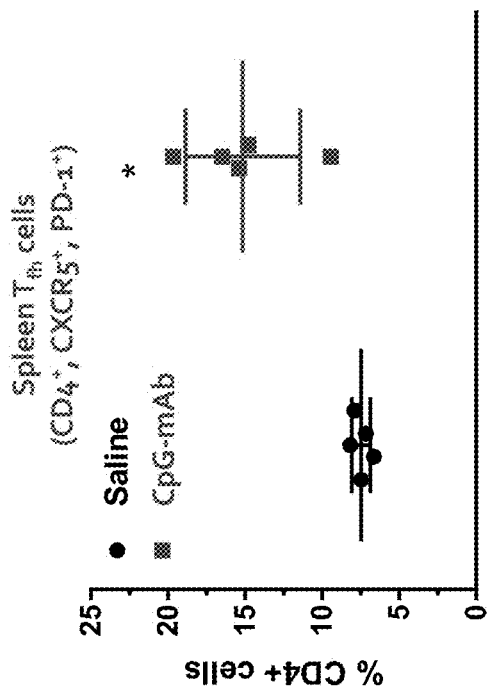
Figure 71A:
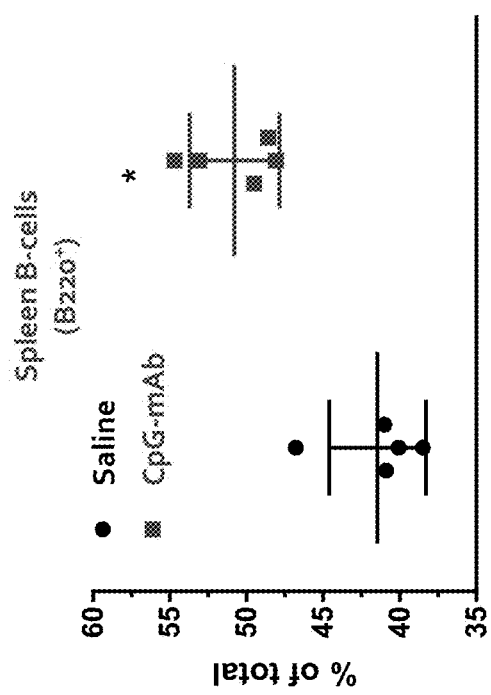

FIG. 71A shows the percentage of B-cells (B220+) relative to total cell in spleen from mice using the CT26 colorectal model following intravenous dosing of (i) saline (circle); or (ii) 10 mg/kg CpG-mAb (SB-337) (square) on each of Days 10, 13, and 17. * p<0.05

FIG. 71B shows the percentage of germinal center (GC) cells (B220$^+$, IgD$^{lo}$, Fas$^+$) relative to total cell in spleen from mice using the CT26 colorectal model following intravenous dosing of (i) saline (circle); or (ii) 10 mg/kg CpG-mAb (SB-337) (square) on each of Days 10, 13, and 17. * p<0.05

Figure 71C:
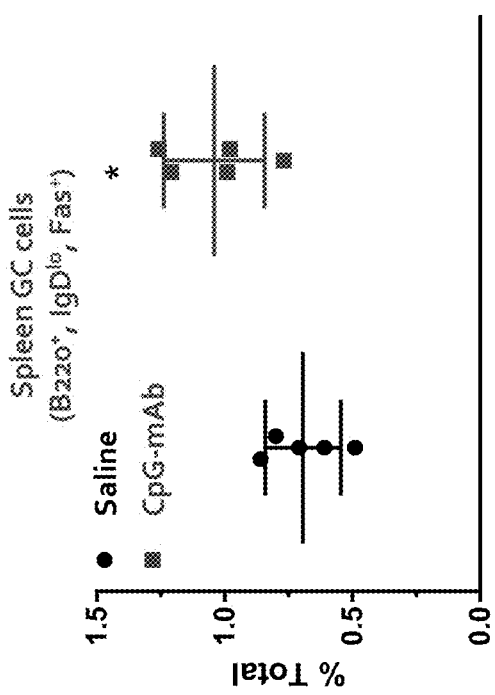

FIG. 71C shows the percentage of T follicular helper ($T_{fh}$) cells (CD4$^+$, CXCR5$^+$, PD-1$^+$) relative to total cell in spleen from mice using the CT26 colorectal model following intravenous dosing of (i) saline (circle); or (ii) 10 mg/kg CpG-mAb (SB-337) (square) on each of Days 10, 13, and 17. * p<0.05

Figure 71E:
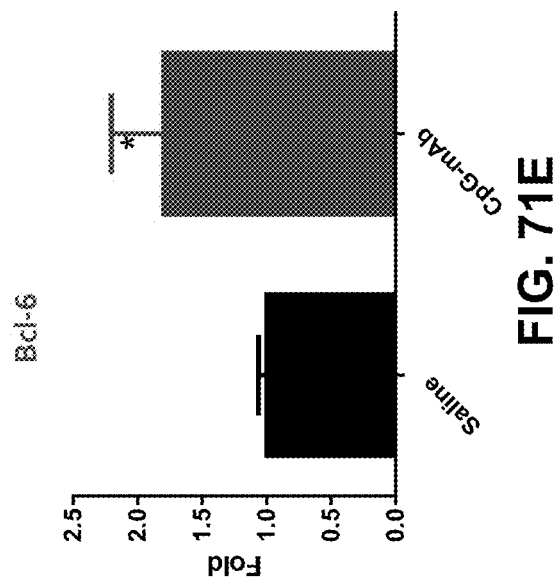
Figure 71D:
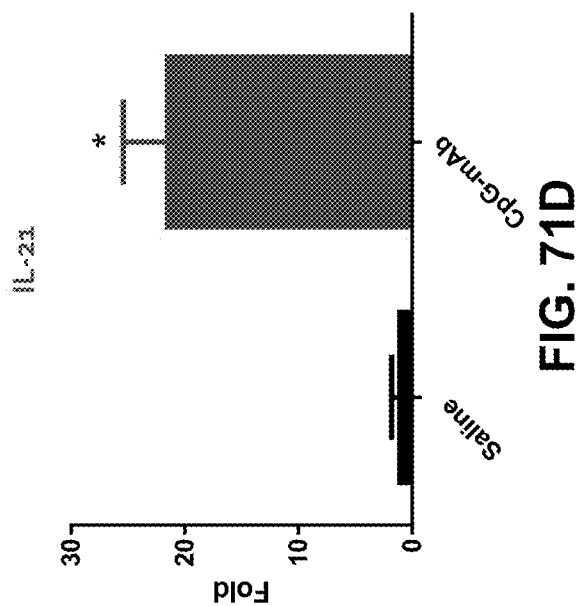

FIG. 71D shows the relative fold change of IL-21 from mice using the CT26 colorectal model following intravenous dosing of (i) saline; or (ii) 10 mg/kg CpG-mAb (SB-337) on each of Days 10, 13, and 17. *p<0.05

FIG. 71E shows the relative fold change of Bcl-6 from mice using the CT26 colorectal model following intravenous dosing of (i) saline; or (ii) 10 mg/kg CpG-mAb (SB-337) on each of Days 10, 13, and 17. *p<0.05

Figure 71F:
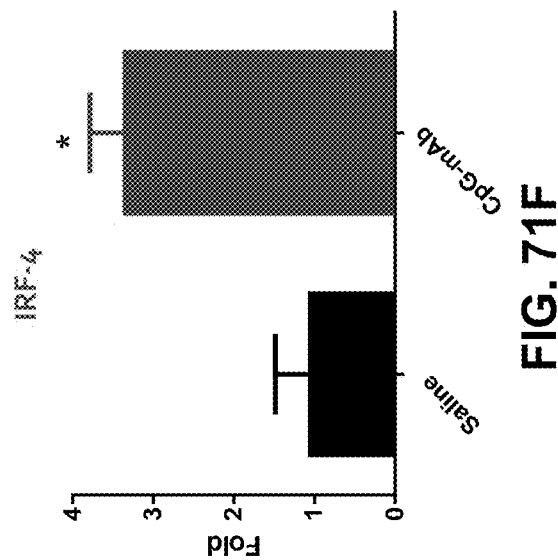

FIG. 71F shows the relative fold change of IRF-4 from mice using the CT26 colorectal model following intravenous dosing of (i) saline; or (ii) 10 mg/kg CpG-mAb (SB-337) on each of Days 10, 13, and 17. *p<0.05

Figure 72A:
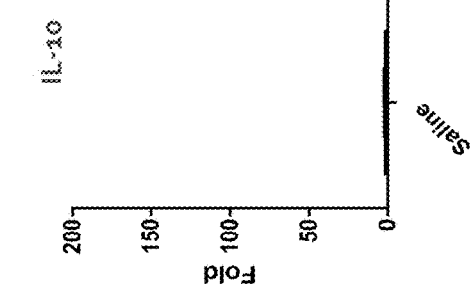

FIG. 72A shows the relative fold change of IL-6 in the spleen from mice using the CT26 colorectal model following intravenous dosing of (i) saline; or (ii) 3 mg/kg CpG-mAb (SB-337) on each of Days 10, 13, and 17.

Figure 72B:
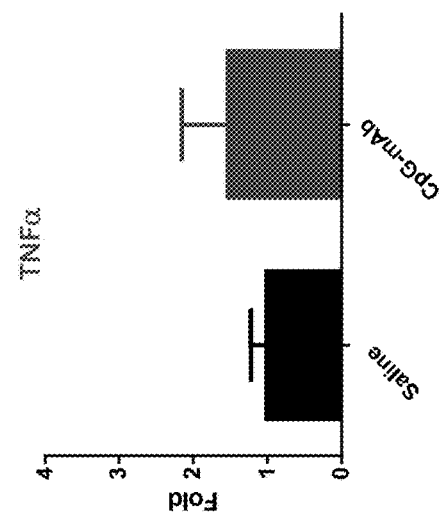

FIG. 72B shows the relative fold change of IL-10 in the spleen from mice using the CT26 colorectal model following intravenous dosing of (i) saline; or (ii) 3 mg/kg CpG-mAb (SB-337) on each of Days 10, 13, and 17.

Figure 72C:
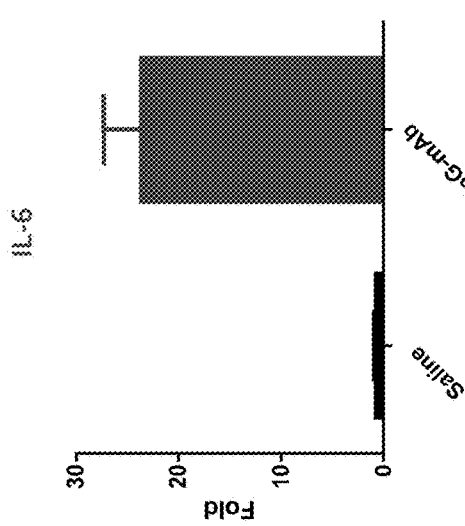

FIG. 72C shows the relative fold change of IL-1β in the spleen from mice using the CT26 colorectal model following intravenous dosing of (i) saline; or (ii) 3 mg/kg CpG-mAb (SB-337) on each of Days 10, 13, and 17.

Figure 72D:
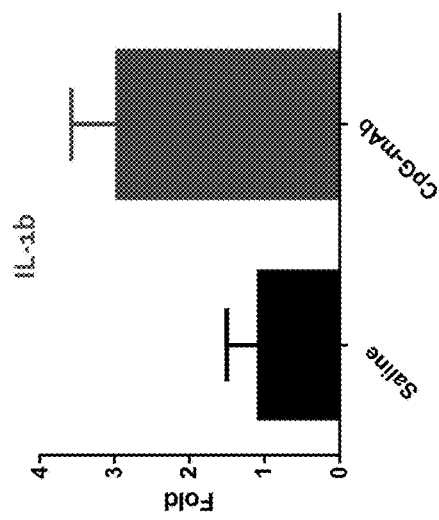

FIG. 72D shows the relative fold change of TNFα in the spleen from mice using the CT26 colorectal model following intravenous dosing of (i) saline; or (ii) 3 mg/kg CpG-mAb (SB-337) on each of Days 10, 13, and 17.

FIG. 73A shows the relative fold change of IL-6 in the draining lymph node from mice using the CT26 colorectal model following intravenous dosing of (i) saline; or (ii) 3 mg/kg CpG-mAb (SB-337) on each of Days 10, 13, and 17.

FIG. 73B shows the relative fold change of IL-10 in the draining lymph node from mice using the CT26 colorectal model following intravenous dosing of (i) saline; or (ii) 3 mg/kg CpG-mAb (SB-337) on each of Days 10, 13, and 17.

FIG. 73C shows the relative fold change of IL-1β in the draining lymph node from mice using the CT26 colorectal model following intravenous dosing of (i) saline; or (ii) 3 mg/kg CpG-mAb (SB-337) on each of Days 10, 13, and 17.

FIG. 73D shows the relative fold change of TNFα in the draining lymph node from mice using the CT26 colorectal model following intravenous dosing of (i) saline; or (ii) 3 mg/kg CpG-mAb (SB-337) on each of Days 10, 13, and 17.

Figure 74B:
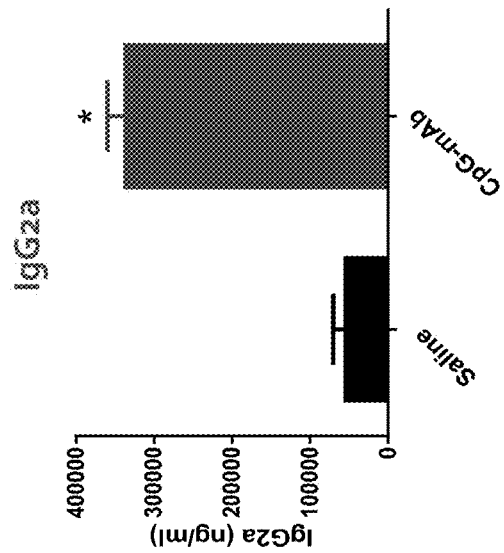
Figure 74A:
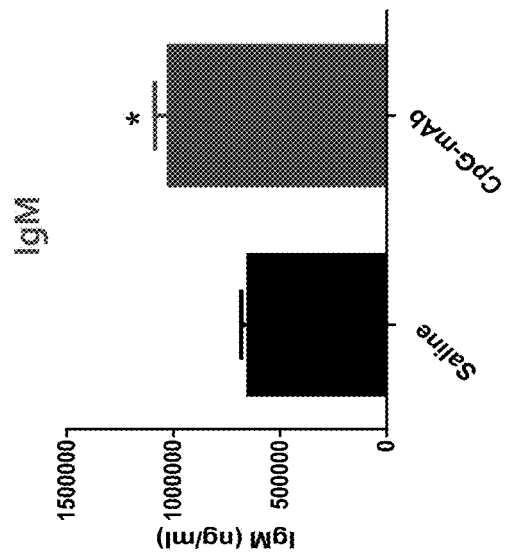

FIG. 74A shows the concentration of IgM in mice using the CT26 colorectal model following intravenous dosing of (i) saline; or (ii) 3 mg/kg CpG-mAb (SB-337) on each of Days 10, 13, and 16. * p<0.05.

FIG. 74B shows the concentration of IgG2a in mice using the CT26 colorectal model following intravenous dosing of (i) saline; or (ii) 3 mg/kg CpG-mAb (SB-337) on each of Days 10, 13, and 16. *p<0.05

Figure 74C:
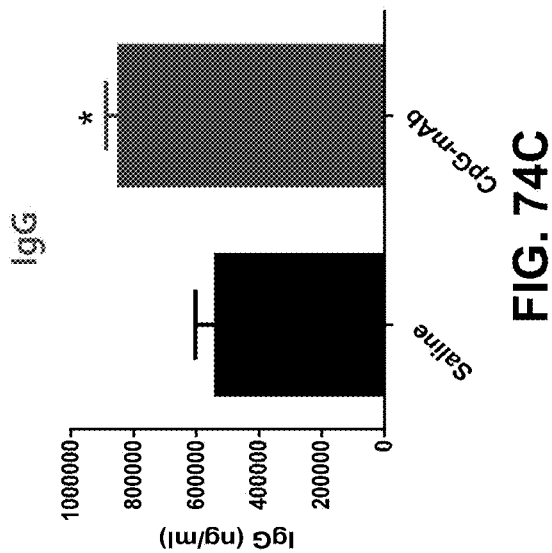

FIG. 74C shows the concentration of IgG in mice using the CT26 colorectal model following intravenous dosing of (i) saline; or (ii) 3 mg/kg CpG-mAb (SB-337) on each of Days 10, 13, and 16. * p<0.05

Figure 75:
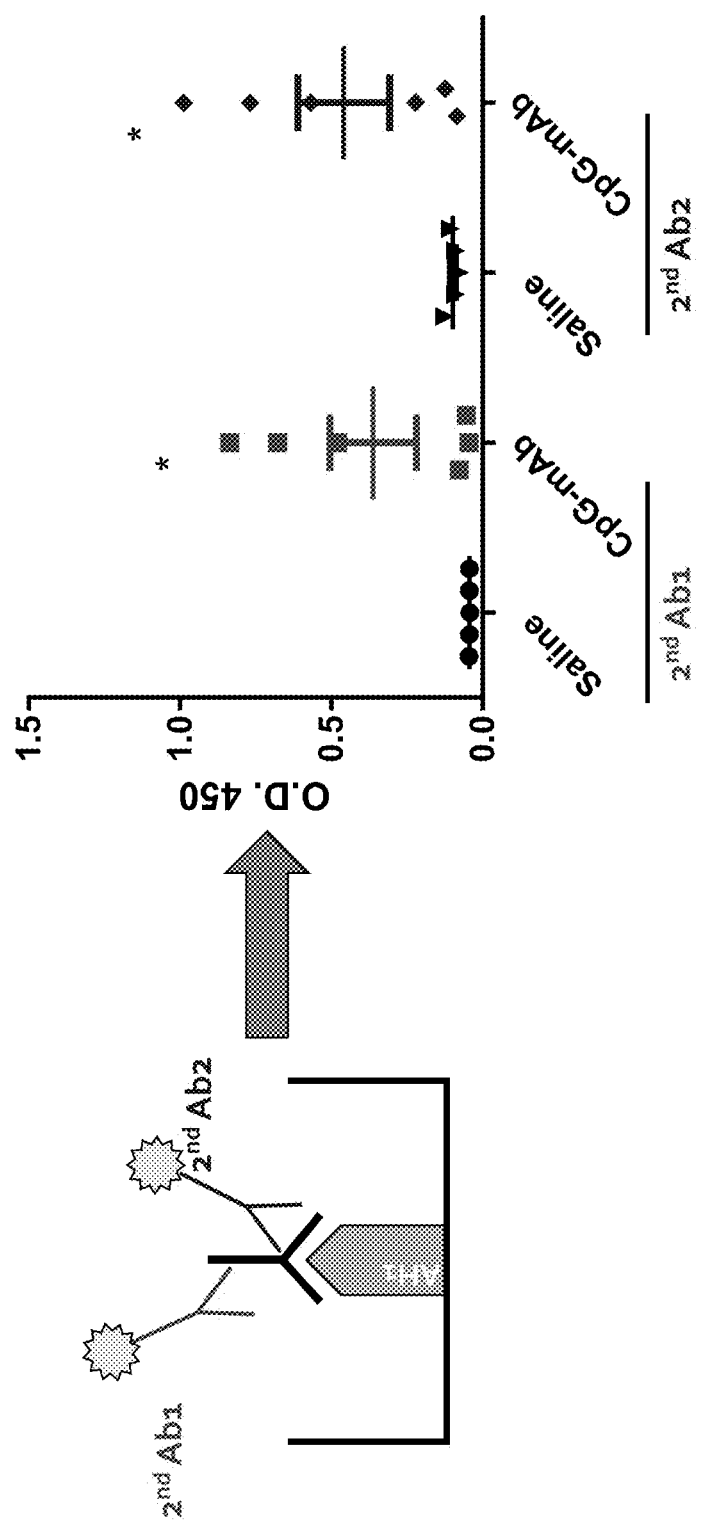

FIG. 75 shows the scheme and quantification of mouse anti-AH1 IgG2a in the serum from mice treated intravenously with saline (circle), or 3 mg/kg of CpG-mAb (SB-337) (square) measured using a commercially available secondary anti-mouse IgG2a-HRP antibodies, $2^{nd}$ Ab1; or measuring treatment with saline (downward triangle), or 3 mg/kg of CpG-mAb (SB-337) (diamond) using a second commercially available secondary anti-mouse IgG2a-HRP antibodies, $2^{nd}$ Ab2.

Figure 76A:
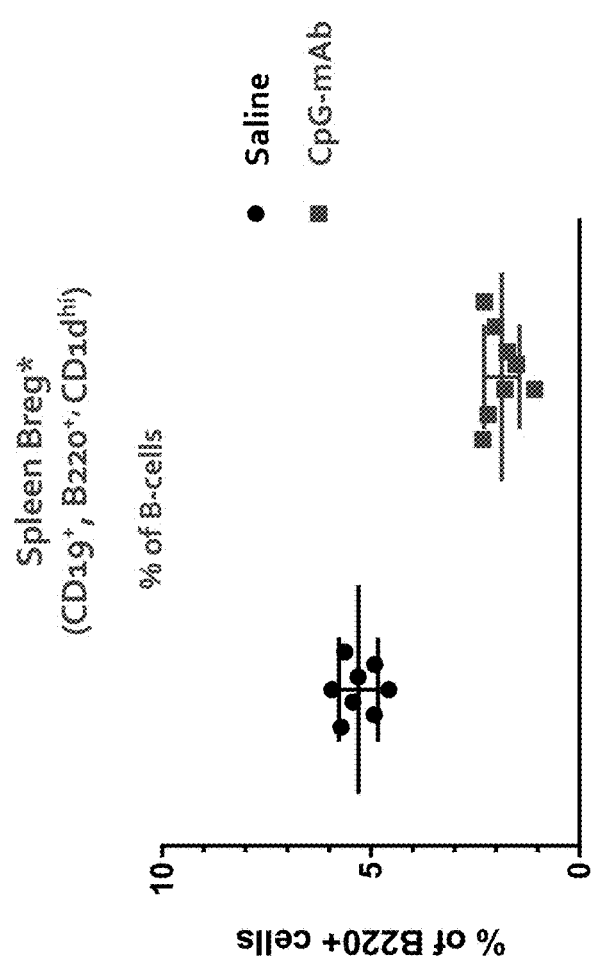

FIG. 76A shows the percentage of regulatory B cells (Bregs; CD19$^+$, B220$^+$, CD1d$^{hi}$) relative to total B-cells (B220+) in spleen from mice following weekly intravenous dosing of (i) saline (circle); or (ii) 10 mg/kg CpG-mAb (SB-337) (square). * p<0.001

Figure 76B:
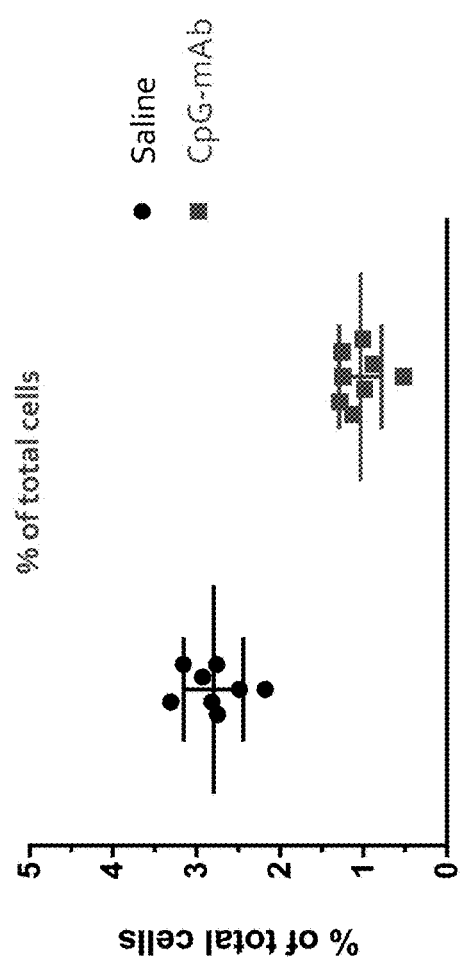

FIG. 76B shows the percentage of regulatory B cells (Bregs; CD19$^+$, B220$^+$, CD1d$^{hi}$) relative to total cells in spleen from mice following weekly intravenous dosing of (i) saline (circle); or (ii) 10 mg/kg CpG-mAb (SB-337) (square). * p<0.001

Figure 77A:
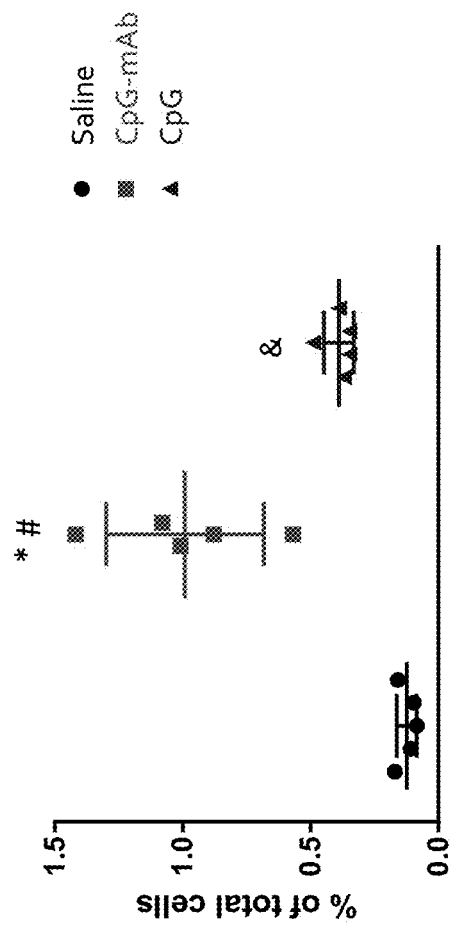

FIG. 77A shows the percentage of spleen myeloid dendritic cells (mDC; B220$^-$, CD11C$^+$; DEC205$^{hi}$) relative to total cells in spleen lymph nodes from mice using the CT26 colorectal model treated intravenously with (i) saline (circle); (ii) 10 mg/kg CpG-mAb (SB-337) (square); or (iii) 10 mg/kg CpG; (triangle) on each of Days 14, 17, and 30. * p=0.0002, $^\&$ p=0.003, $^\#$ p=0.002.

Figure 77B:
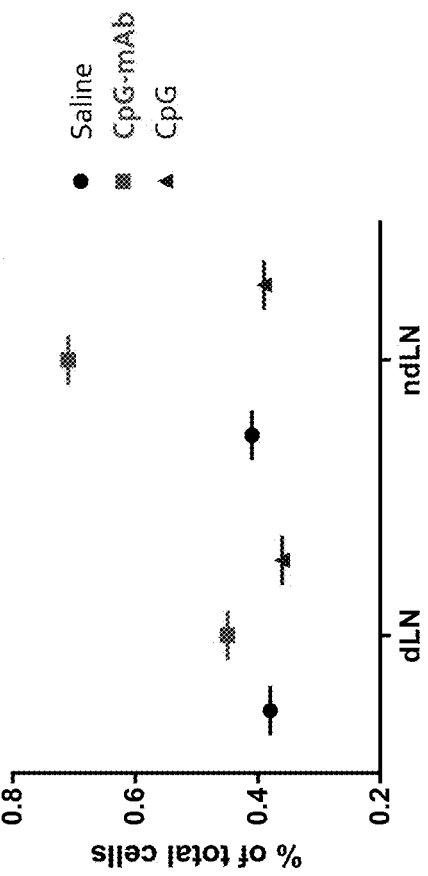

FIG. 77B shows the percentage of pooled lymph node (LN) myeloid dendritic cells (mDC; B220$^-$, CD11C$^+$; CD8$^+$) relative to total cells from mice using the CT26 colorectal model treated intravenously with (i) saline (circle); (ii) 10 mg/kg CpG-mAb (SB-337) (square); or (iii) 10 mg/kg CpG (triangle); on each of Days 14, 17, and 30. Sample were taken from drained lymph nodes (dLN) and non-drained lymph nodes (ndLN).

Figure 78A:
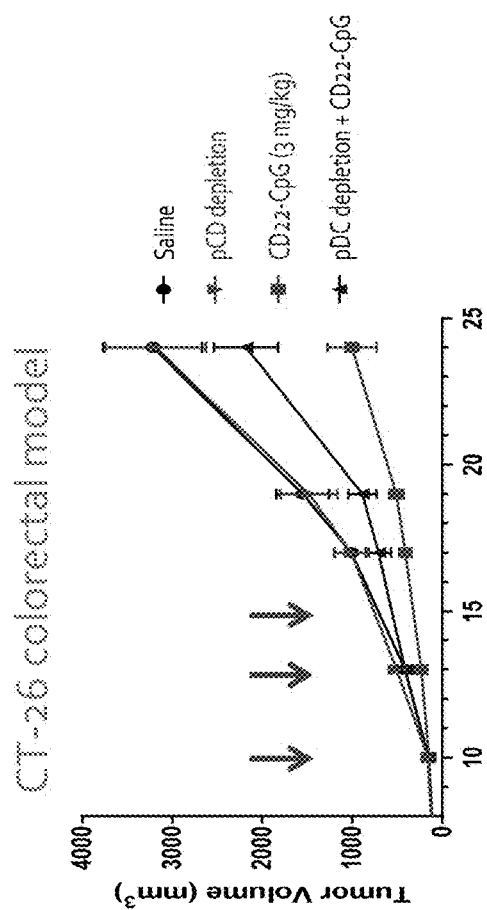

FIG. 78A shows the average tumor volume growth progression of mice using the CT26 colorectal model following treatment with (i) saline solution (circle); (ii) plasmacytoid dendritic cell (pDC) depletion (downward triangle); (iii) 3 mg/kg CD22-CpG (SB-337) (square); or (iv) pDC depletion+3 mg/kg CD22-CpG (SB-337) (upward triangle) on each of Days 10, 13, and 15.

Figure 78B:
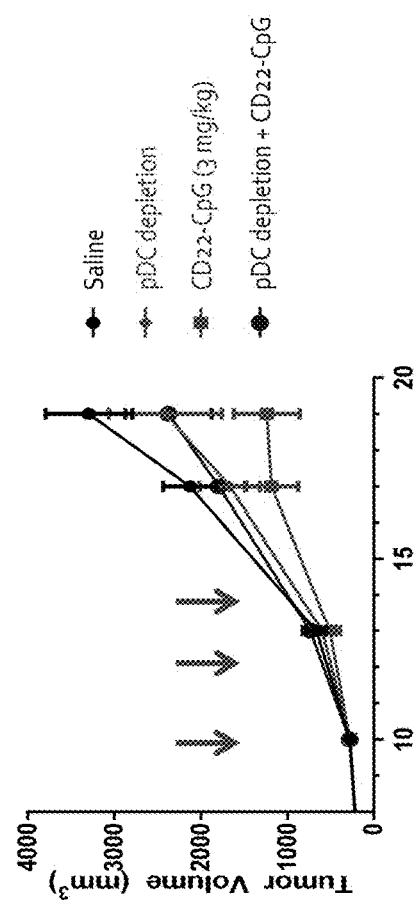

FIG. 78B shows the average tumor volume growth progression of mice using the A20 lymphoma model following treatment with (i) saline solution (small circle); (ii) plasmacytoid dendritic cell (pDC) depletion (diamond); (iii) 3 mg/kg CD22-CpG (SB-337) (square); or (iv) pDC depletion+3 mg/kg CD22-CpG (SB-337) (large circle) on each of Days 10, 12, and 14.

Figure 79A:
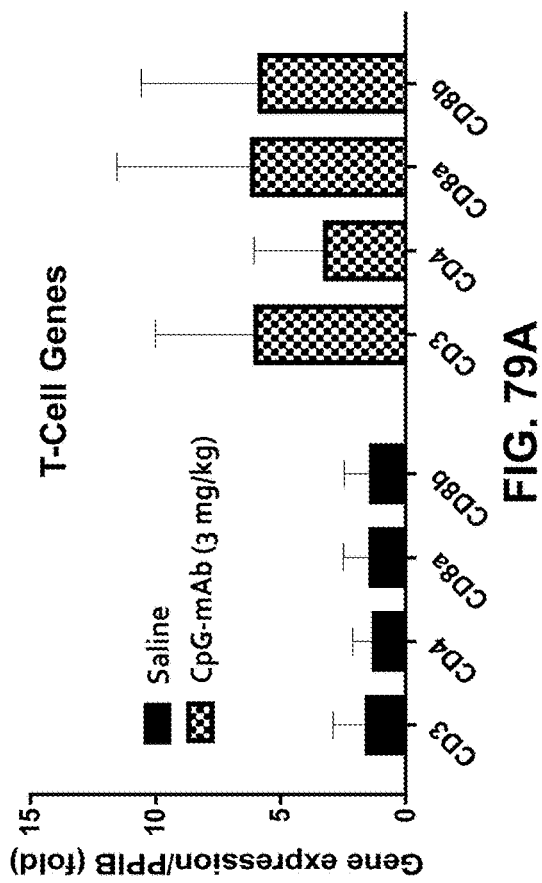

FIG. 79A shows the relative fold change in gene expression of T-cell genes from mice using the CT26 colorectal model following intravenous dosing of (i) saline (solid); or (ii) 3 mg/kg CpG-mAb (SB-337) (checkered) on each of Days 10, 12, and 14.

Figure 79B:
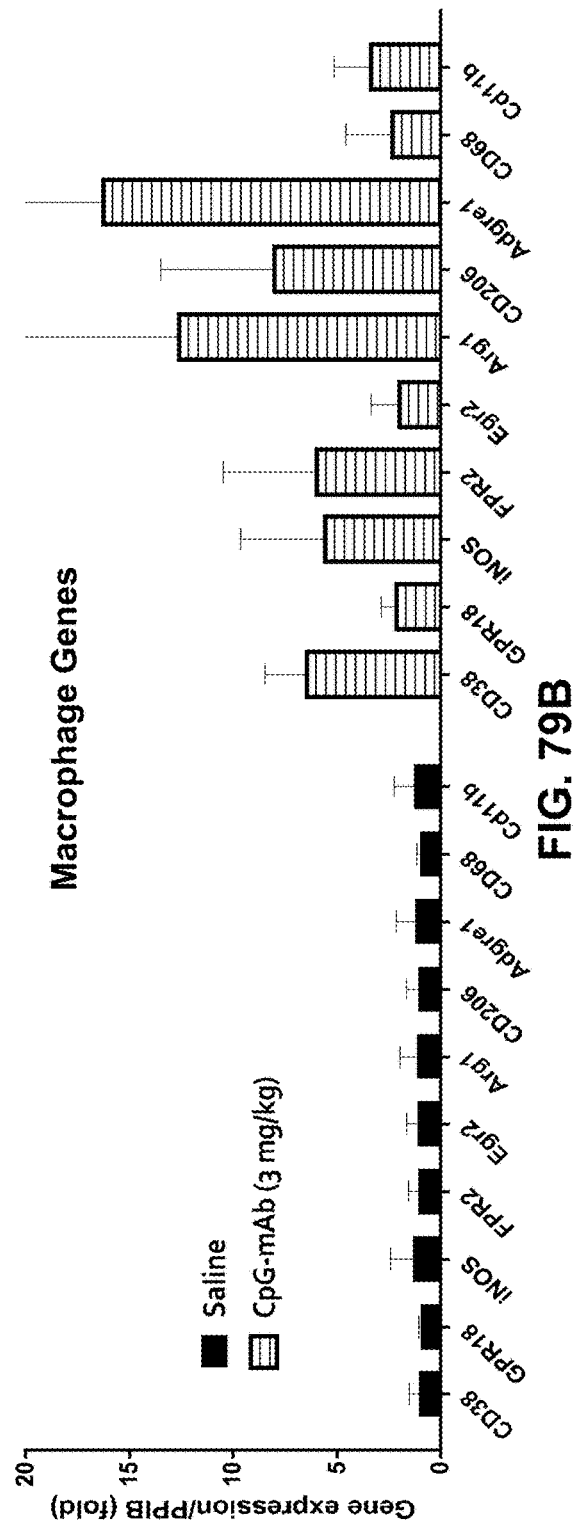

FIG. 79B shows the relative fold change in gene expression of macrophage genes from mice using the CT26 colorectal model following intravenous dosing of (i) saline (solid); or (ii) 3 mg/kg CpG-mAb (SB-337) (horizontal) on each of Days 10, 12, and 14.

Figure 79C:
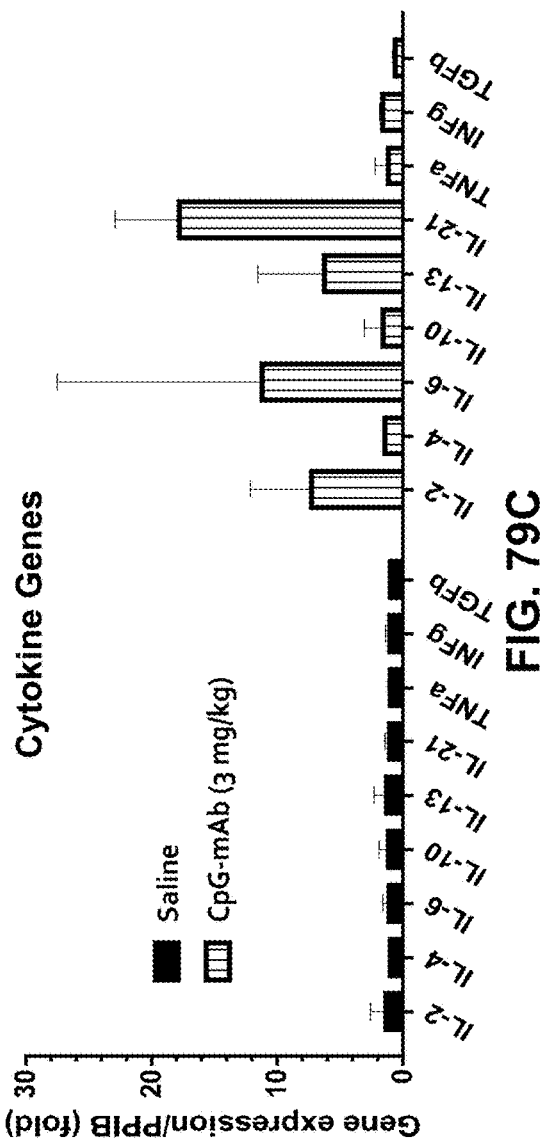

FIG. 79C shows the relative fold change in gene expression of cytokine genes from mice using the CT26 colorectal model following intravenous dosing of (i) saline (solid); or (ii) 3 mg/kg CpG-mAb (SB-337) (vertical) on each of Days 10, 12, and 14.

Figure 79D:
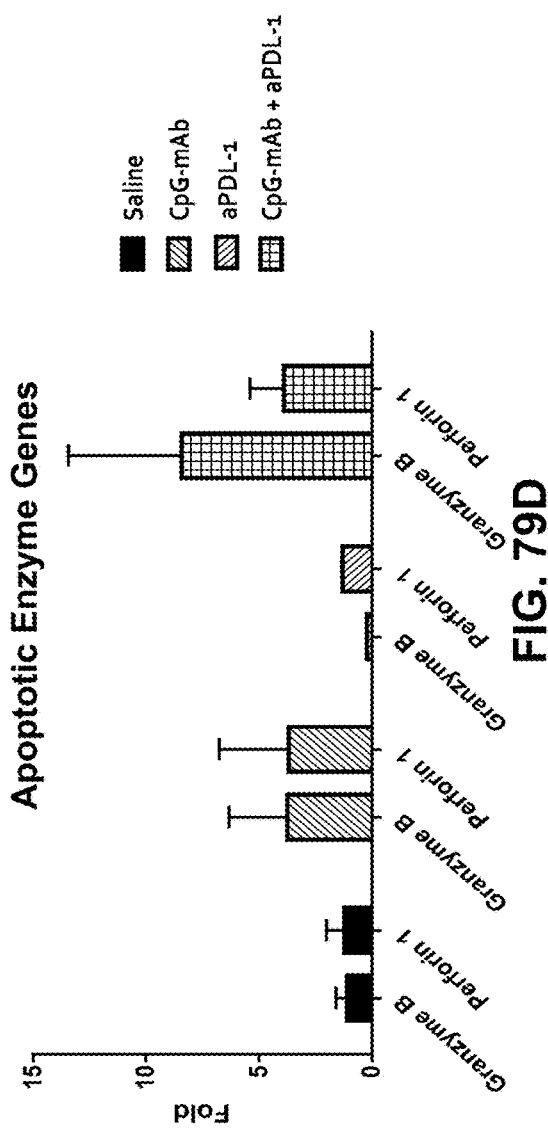

FIG. 79D shows the relative fold change in gene expression of apoptotic enzyme genes from mice using the CT26 colorectal model following intravenous dosing of (i) saline (solid); (ii) 3 mg/kg CpG-mAb (SB-337) (upward diagonal); (iii) anti-PD-L1 (downward diagonal); (iv) 3 mg/kg CpG-mAb+anti-PD-L1 (SB-337) (grid) on each of Days 10, 12, and 14.

Figure 80A:
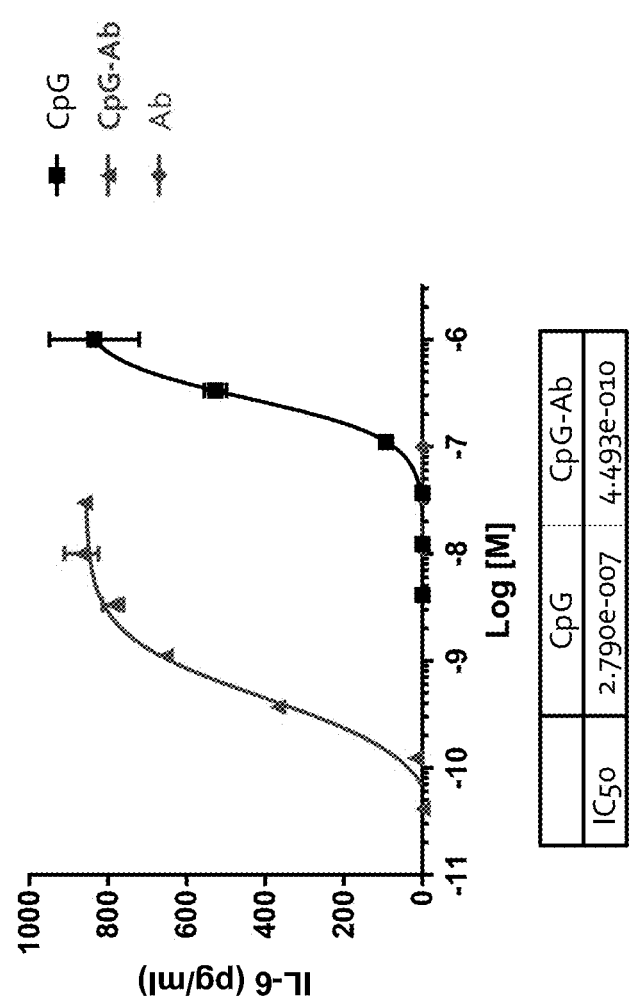

FIG. 80A shows a dose response curve for the concentration of IL-6 from human primary B-cells in response to in vitro treatment with (i) CpG (p425) (square); (ii) CpG-Ab (SB-430) (triangle); or (iii) Ab (diamond) for 24-72 hours.

Figure 80B:
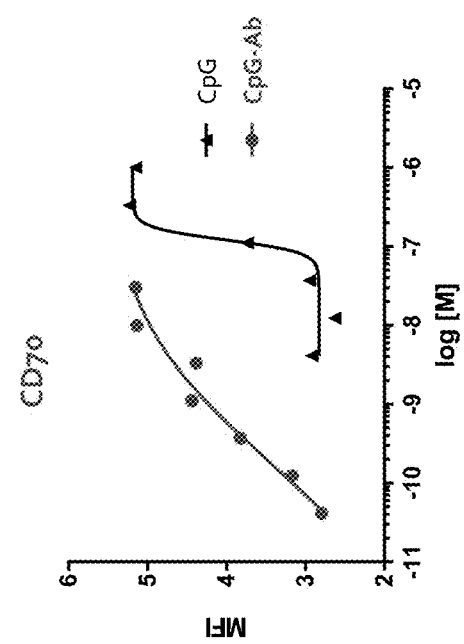

FIG. 80B shows a dose response curve for the mean fluorescence intensity (MFI) of MHC II expression on human primary B-cells in response to in vitro treatment with (i) CpG (p425) (triangle); or (ii) CpG-Ab (SB-430) (circle) for 24-72 hours.

Figure 80C:
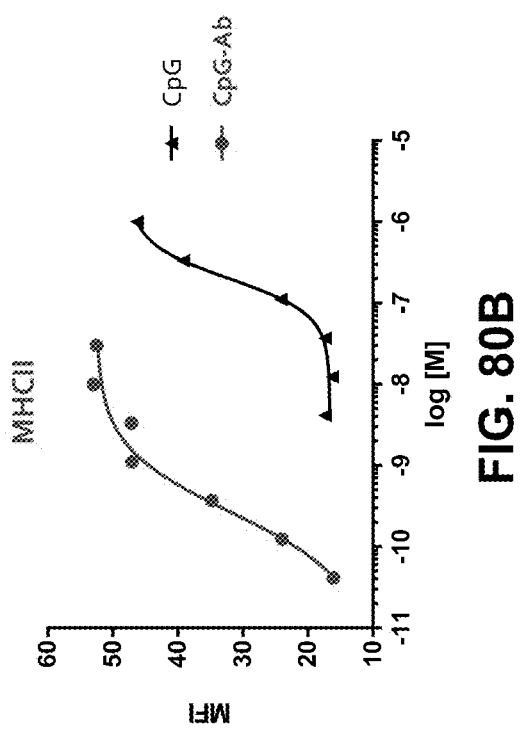

FIG. 80C shows a dose response curve for the mean fluorescence intensity (MFI) of CD86 expression on human primary B-cells in response to in vitro treatment with (i) CpG (p425) (triangle); or (ii) CpG-Ab (SB-430) (circle) for 24-72 hours.

Figure 80D:
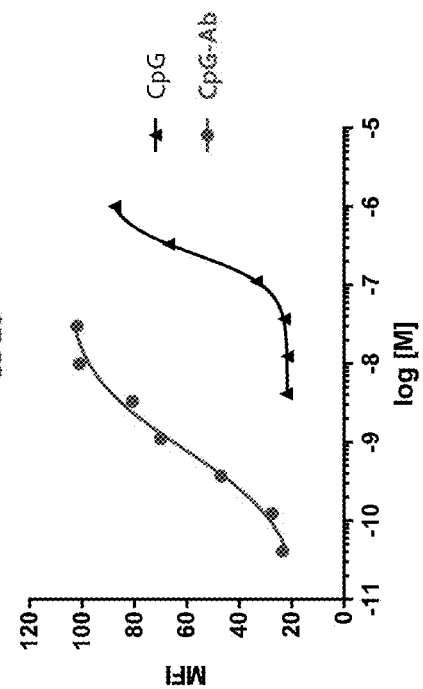

FIG. 80D shows a dose response curve for the mean fluorescence intensity (MFI) of CD70 expression on human primary B-cells in response to in vitro treatment with (i) CpG (p425) (triangle); or (ii) CpG-Ab (SB-430) (circle) for 24-72 hours.

Figure 80E:
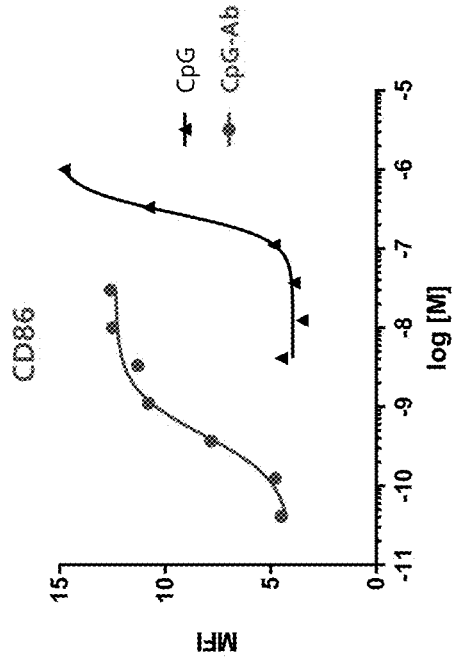

FIG. 80E shows a dose response curve for the mean fluorescence intensity (MFI) of CD20 expression on human primary B-cells in response to in vitro treatment with (i) CpG (p425) (triangle); or (ii) CpG-Ab (SB-430) (circle) for 24-72 hours.

Figure 81:
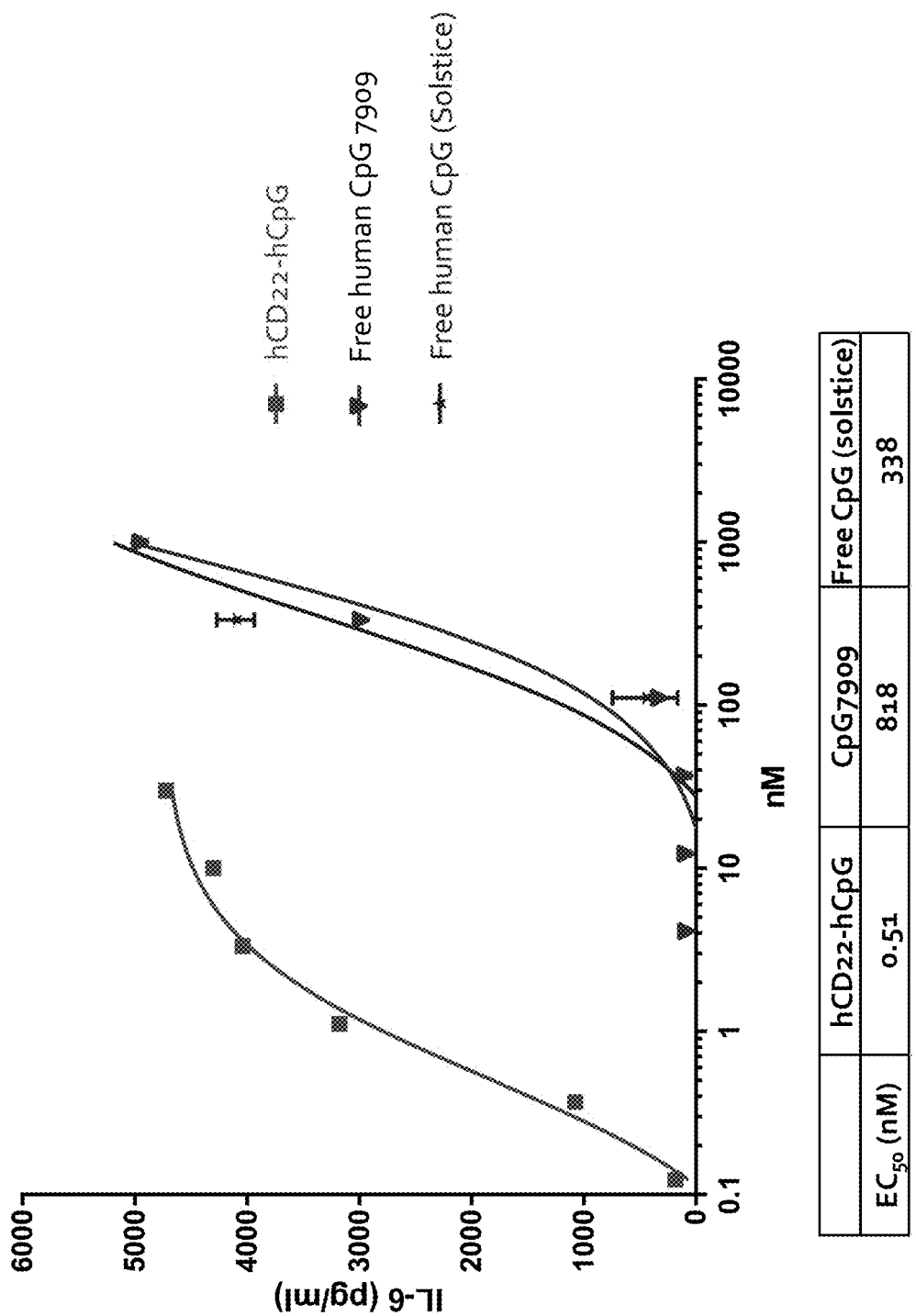
Figure 82A:
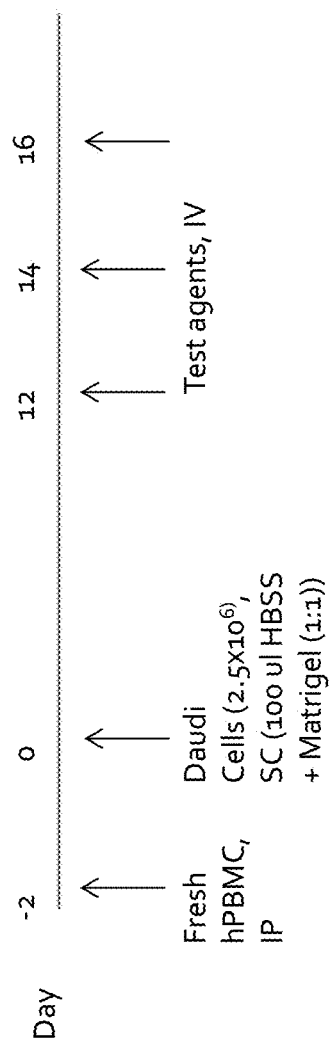

FIG. 81 shows a dose response curve for the concentration of IL-6 from primary human splenocytes in response to in vitro treatment with (i) hCD22-hCpG (SB-430) (square); (ii) Free human CpG 7909 (downward triangle); or (iii) Free human CpG Solstice (p425) (upward arrow) for 24 hours FIG. 82A shows the scheme for the humanized mouse model experiment using intraperitoneally (IP) injected fresh human peripheral blood mononuclear cells (hPBMC) prior to subcutaneous transplantation of Daudi Burkitt lymphoma cells and intravenous (IV) treatment at each of Days 12, 14, and 16.

Figure 82B:
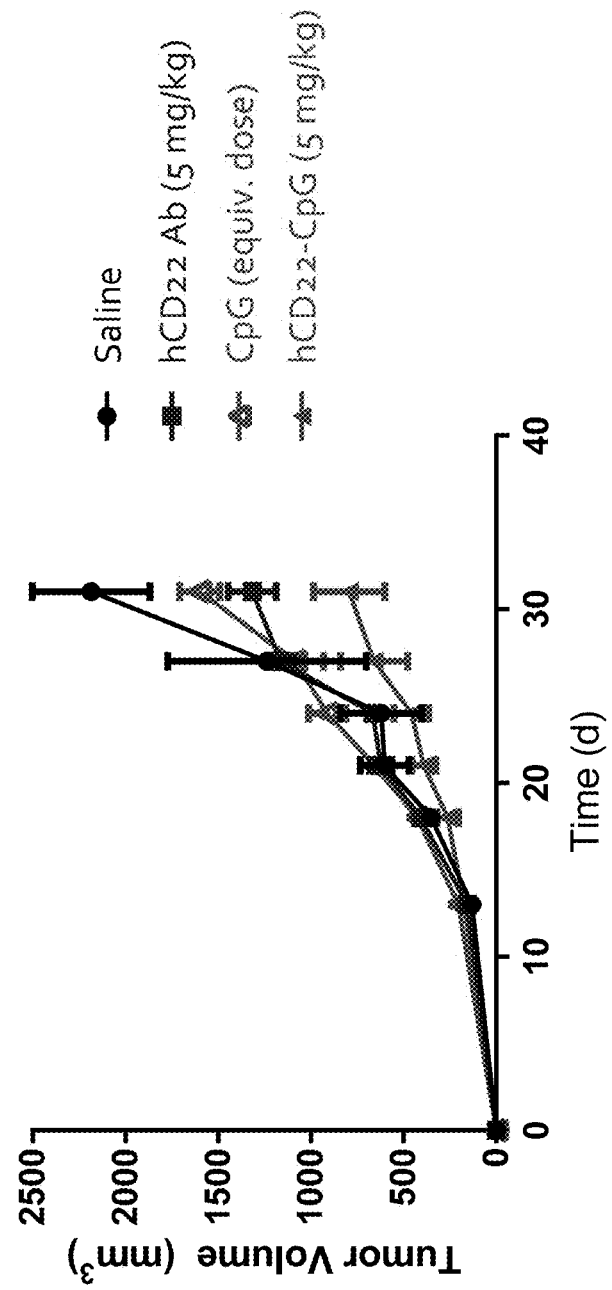

FIG. 82B shows the average tumor volume growth progression in a humanized mouse model intraperitoneally injected with fresh human peripheral blood mononuclear cells prior to subcutaneous transplantation of Daudi Burkitt lymphoma cells and intravenous (IV) treatment with (i) saline (circle); (ii) 5 mg/kg hCD22 Ab (square); (iii) 5.7 µg/dose CpG (p425) (open triangle); or (iv) 5 mg/kg hCD22-CpG (SB-430) (closed triangle), at each of Days 12, 14, and 16.

Figure 83:
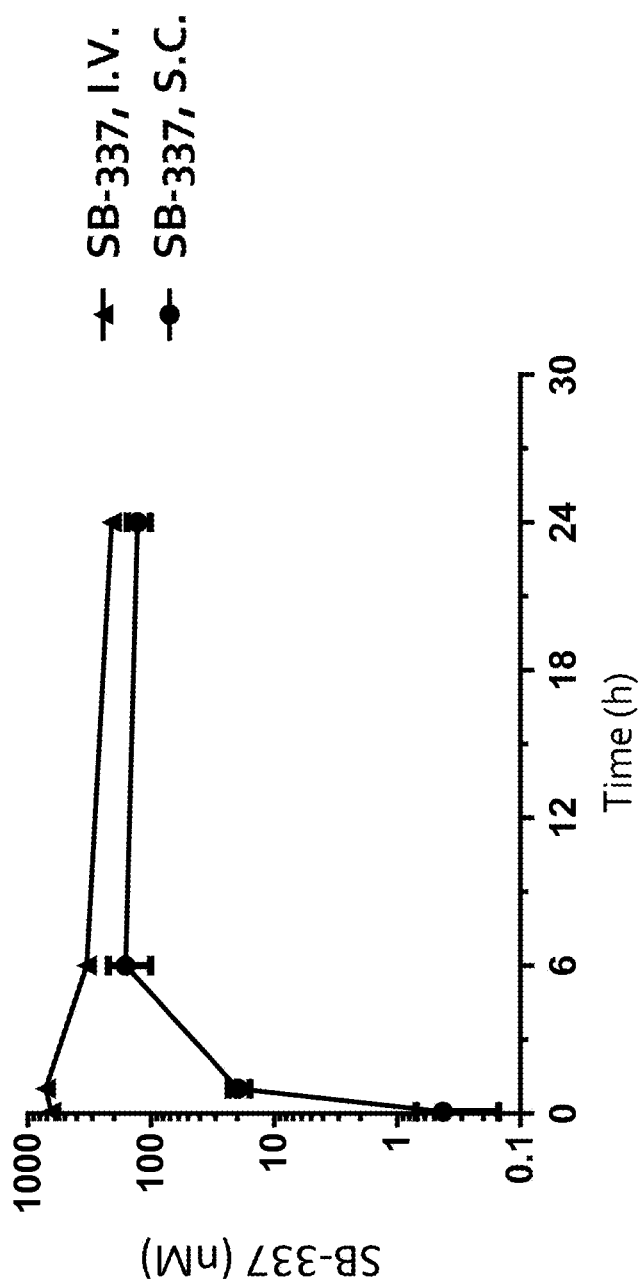

FIG. 83 shows pharmacokinetic profiles of CpG-antibody conjugate SB-337 DAR1 in mice administered intravenously or subcutaneously.

Figure 84:
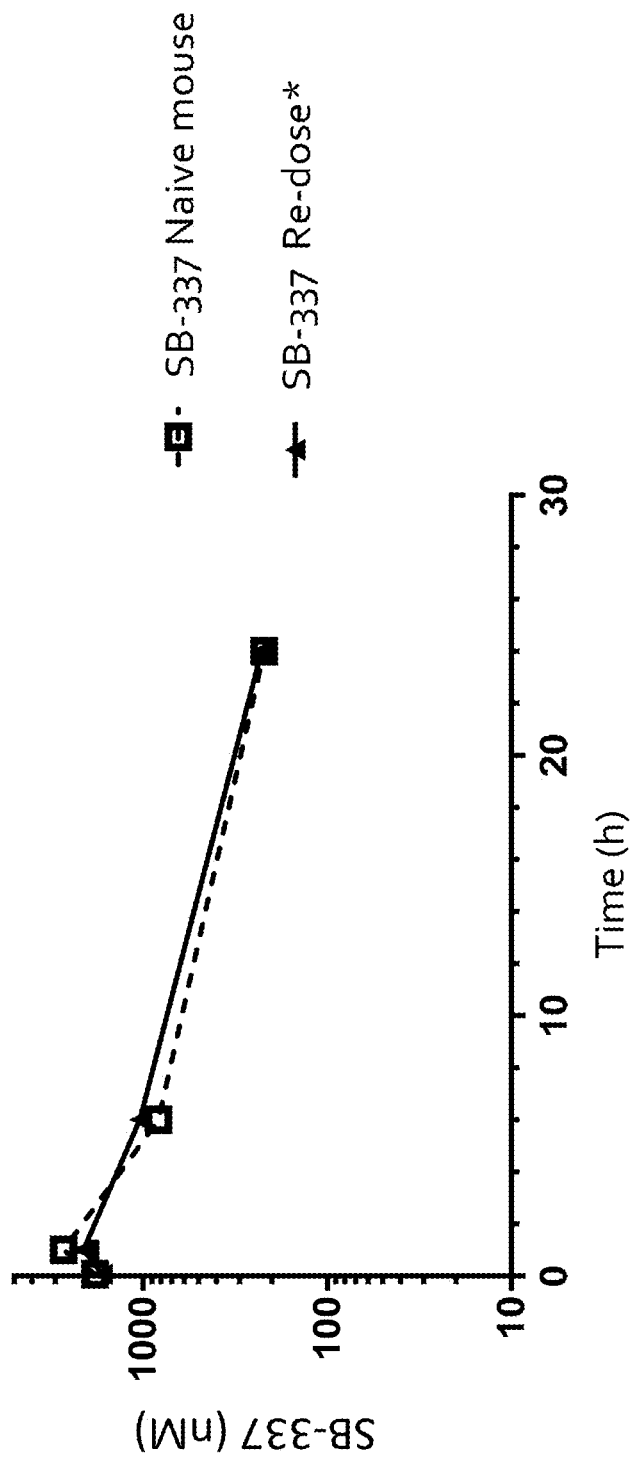

FIG. 84 shows pharmacokinetic profiles of CpG-antibody conjugate SB-337 DAR1 in mice administered intravenously.

Figure 85:
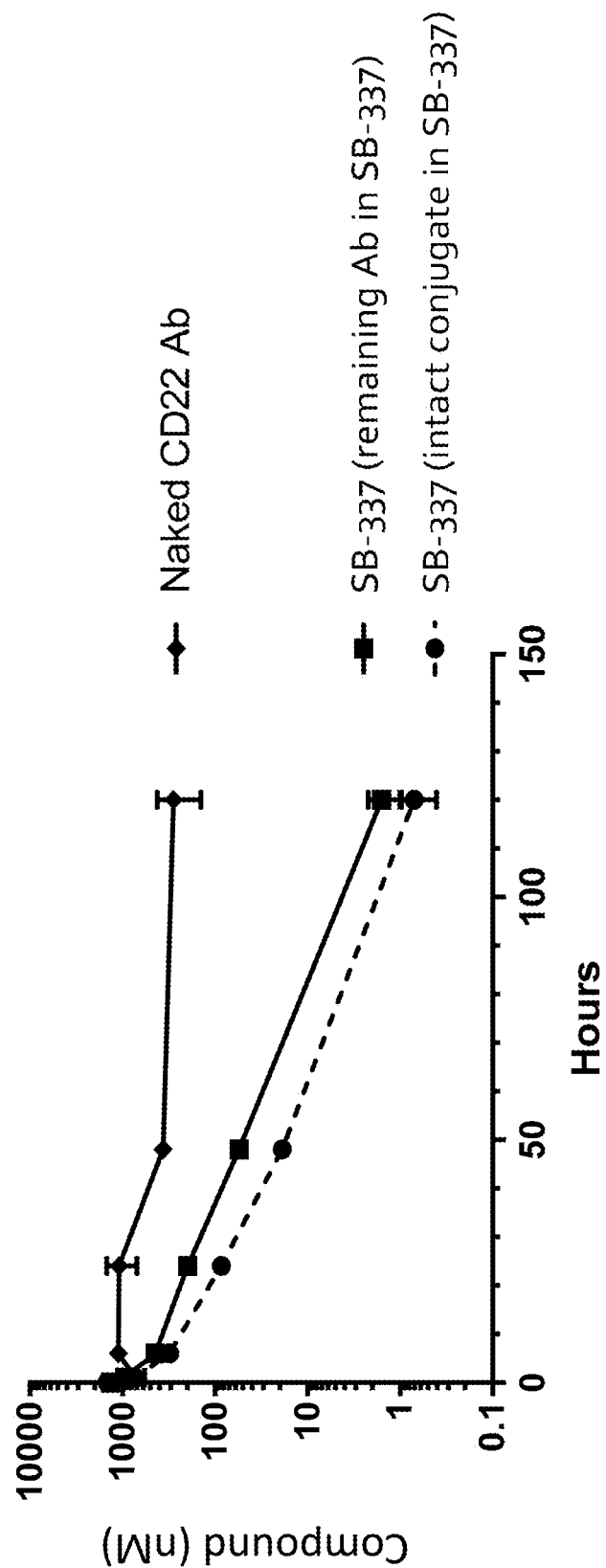

FIG. 85 shows pharmacokinetic profiles of CpG-antibody conjugate SB-337 DAR1 in mice administered intravenously.

Figure 86:
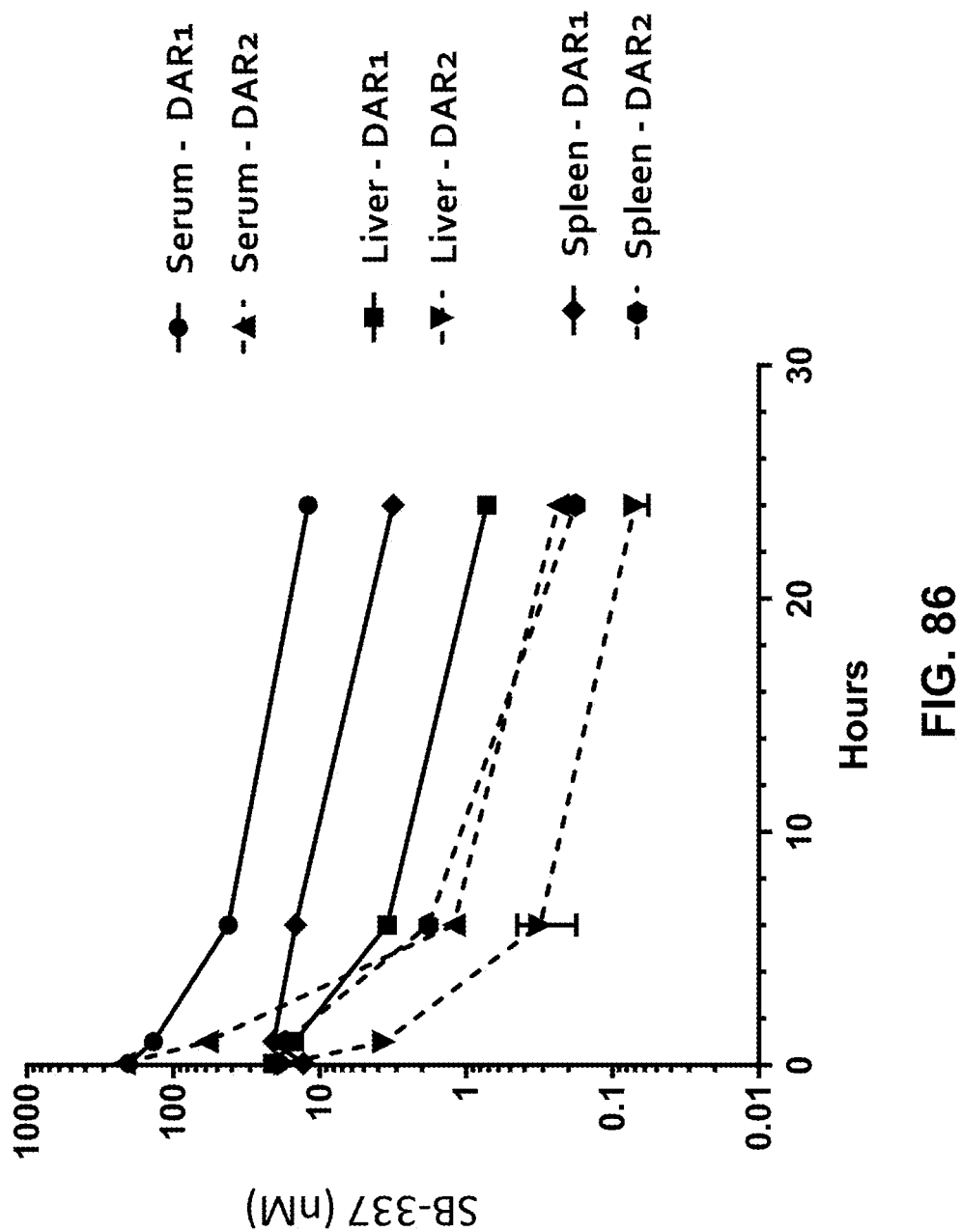

FIG. 86 shows pharmacokinetic profiles of CpG-antibody conjugates SB-337 DAR1 and SB-337 DAR2 in mice administered intravenously.

Figure 87A:
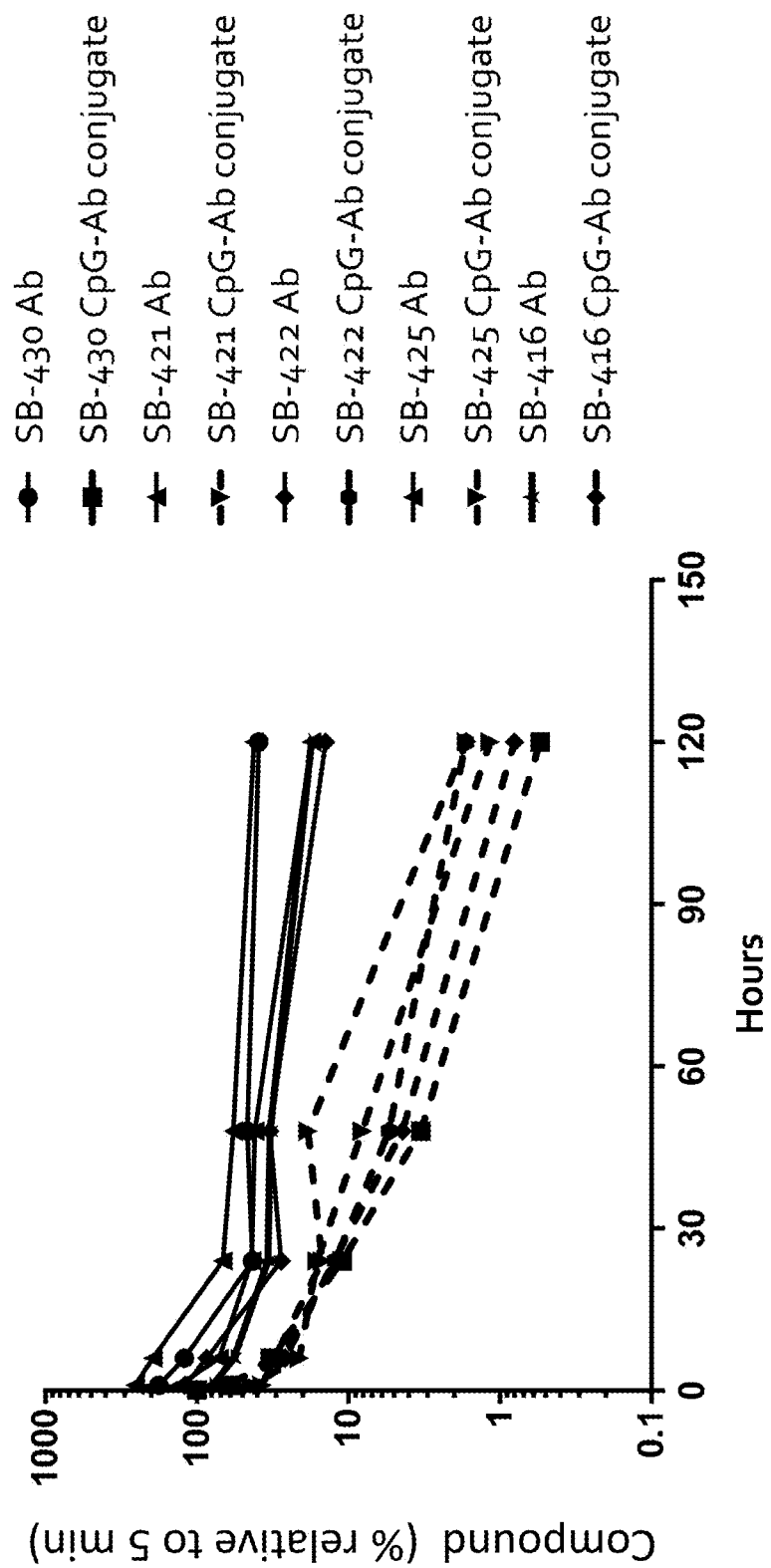
Figure 87B:
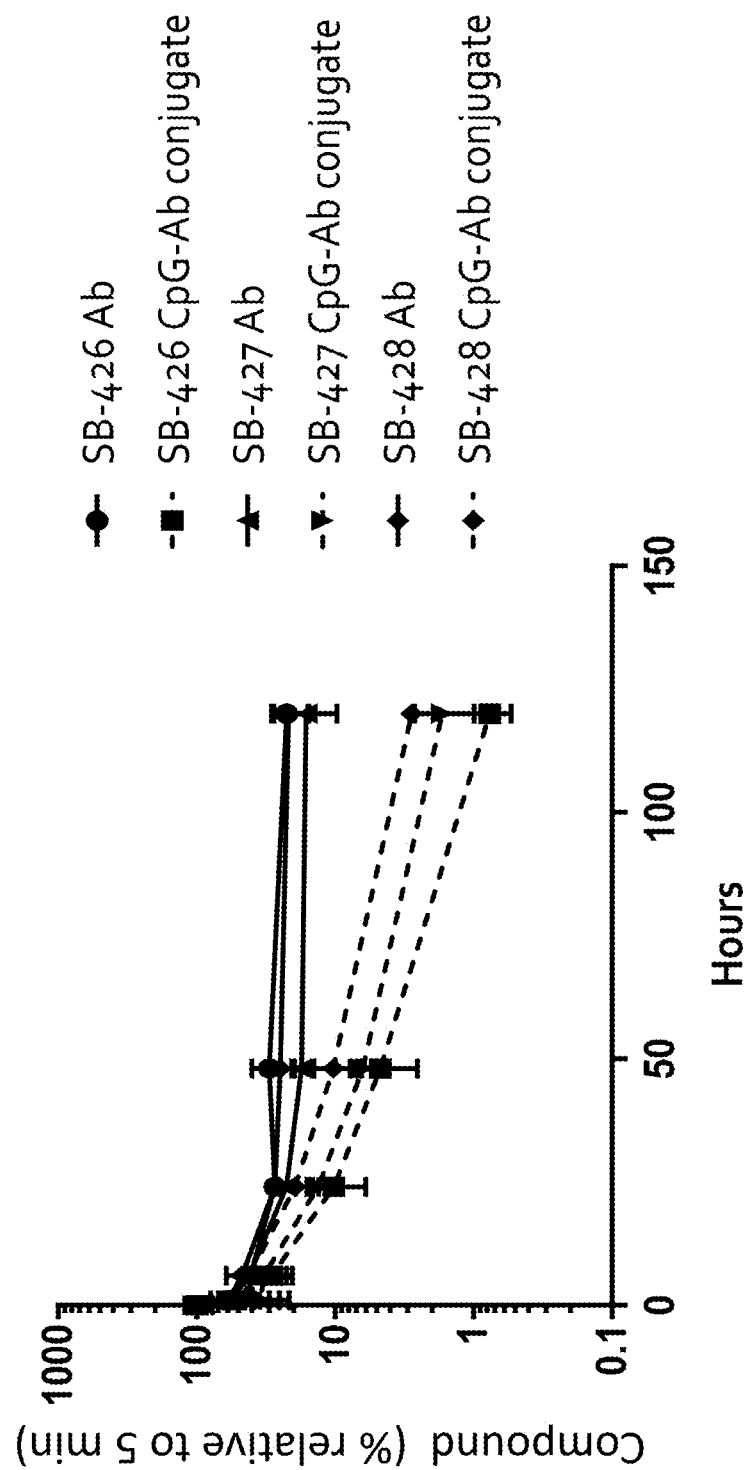

FIGS. 87A and 87B show pharmacokinetic profiles of CpG-antibody conjugates in mice administered intravenously.

DETAILED DESCRIPTION

Definitions

The term "abasic spacer," as used herein, represents a divalent group of the following structure:

$$R^1-L^1-[-L^2-(L^1)_{n1}-]_{n2}-R^2, \quad (I)$$

wherein:
n1 is 0 or 1,
n2 is an integer from 1 to 6,
$R^1$ is a bond to a nucleoside in the immunomodulating polynucleotide,
$R^2$ is a bond to a nucleoside in the immunomodulating polynucleotide or to a capping group,
each $L^1$ is independently a phosphodiester or a phosphotriester, and
each $L^2$ is a sugar analogue,
provided that,
if the abasic spacer is an internucleoside, abasic spacer, each n1 is 1, and $R^2$ is a bond to a nucleoside, and
if the abasic spacer is a terminal, abasic spacer, each n1 is independently 0 or 1, and $R^2$ is a bond to a capping group.

The term "about," as used herein, represents a value that is ±10% of the recited value.

The term "alkane-tetrayl," as used herein, represents a tetravalent, acyclic, straight or branched chain, saturated hydrocarbon group having from 1 to 16 carbons, unless otherwise specified. Alkane-tetrayl may be optionally substituted as described for alkyl.

The term "alkane-triyl," as used herein, represents a trivalent, acyclic, straight or branched chain, saturated hydrocarbon group having from 1 to 16 carbons, unless otherwise specified. Alkane-triyl may be optionally substituted as described for alkyl.

The term "alkanoyl," as used herein, represents hydrogen or an alkyl group that is attached to the parent molecular group through a carbonyl group and is exemplified by formyl (i.e., a carboxyaldehyde group), acetyl, propionyl, butyryl, and iso-butyryl. Unsubstituted alkanoyl groups contain from 1 to 7 carbons. The alkanoyl group may be unsubstituted of substituted (e.g., optionally substituted $C_{1-7}$ alkanoyl) as described herein for alkyl group. The ending "-oyl" may be added to another group defined herein, e.g., aryl, cycloalkyl, and heterocyclyl, to define "aryloyl," "cycloalkanoyl," and "(heterocyclyl)oyl." These groups represent a carbonyl group attached to aryl, cycloalkyl, or heterocyclyl, respectively. Each of "aryloyl," "cycloalkanoyl," and "(heterocyclyl)oyl" may be optionally substituted as defined for "aryl," "cycloalkyl," or "heterocyclyl," respectively.

The term "alkenyl," as used herein, represents acyclic monovalent straight or branched chain hydrocarbon groups of containing one, two, or three carbon-carbon double bonds. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkenylene," as used herein, refers to a straight or branched chain alkenyl group with one hydrogen removed, thereby rendering this group divalent. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. The alkenylene group may be unsubstituted or substituted (e.g., optionally substituted alkenylene) as described for alkyl.

The term "alkoxy," as used herein, represents a chemical substituent of formula —OR, where R is a $C_{1-6}$ alkyl group, unless otherwise specified. In some embodiments, the alkyl group can be further substituted as defined herein. The term "alkoxy" can be combined with other terms defined herein, e.g., aryl, cycloalkyl, or heterocyclyl, to define an "aryl alkoxy," "cycloalkyl alkoxy," and "(heterocyclyl)alkoxy" groups. These groups represent an alkoxy that is substituted by aryl, cycloalkyl, or heterocyclyl, respectively. Each of "aryl alkoxy," "cycloalkyl alkoxy," and "(heterocyclyl)alkoxy" may optionally substituted as defined herein for each individual portion.

The term "alkyl," as used herein, refers to an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: amino; aryl; aryloxy; azido; cycloalkyl; cycloalkoxy; cycloalkenyl; cycloalkynyl; halo; heterocyclyl; (heterocyclyl)oxy; hydroxy; nitro; thiol; silyl; cyano; =O; =S; =NR', where R' is H, alkyl, aryl, or heterocyclyl. Each of the substituents may itself be unsubstituted or, valency permitting, substituted with unsubstituted substituent(s) defined herein for each respective group.

The term "alkylamino," as used herein, refers to a group having the formula —N($R^{N1}$)$_2$ or —NHR$^{N1}$, in which $R^{N1}$ is alkyl, as defined herein. The alkyl portion of alkylamino can be optionally substituted as defined for alkyl. Each optional substituent on the substituted alkylamino may itself be unsubstituted or, valency permitting, substituted with unsubstituted substituent(s) defined herein for each respective group.

The term "alkyl cycloalkylene," as used herein, refers to a saturated divalent hydrocarbon group that is an alkyl cycloalkane, in which two valencies replace two hydrogen atoms. Preferably, at least one of the two valencies is present on the cycloalkane portion. The alkane and cycloalkane portions may be optionally substituted as the individual groups as described herein.

The term "alkylene," as used herein, refers to a saturated divalent hydrocarbon group that is a straight or branched chain saturated hydrocarbon, in which two valencies replace two hydrogen atoms. The valency of alkylene defined herein does not include the optional substituents. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. The term "C$_{x-y}$ alkylene" represents alkylene groups having between x and y carbons. Exemplary values for x are 1, 2, 3, 4, 5, and 6, and exemplary values for y are 2, 3, 4, 5, 6, 7, 8, 9, 10, 11, and 12. Alkylene can be optionally substituted as described herein for alkyl.

The term "alkylsulfenyl," as used herein, represents a group of formula —S-(alkyl). Alkylsulfenyl may be optionally substituted as defined for alkyl.

The term "alkylsulfinyl," as used herein, represents a group of formula —S(O)-(alkyl). Alkylsulfinyl may be optionally substituted as defined for alkyl.

The term "alkylsulfonyl," as used herein, represents a group of formula —S(O)$_2$-(alkyl). Alkylsulfonyl may be optionally substituted as defined for alkyl.

The term "alkynyl," as used herein, represents monovalent straight or branched chain hydrocarbon groups of from two to six carbon atoms containing at least one carbon-carbon triple bond and is exemplified by ethynyl, 1-propynyl, and the like. The alkynyl groups may be unsubstituted or substituted (e.g., optionally substituted alkynyl) as defined for alkyl.

The term "5-alkynyluridine," as used herein, represents a nucleoside, in which the nucleobase is 5-alkynyluracil of the following structure:

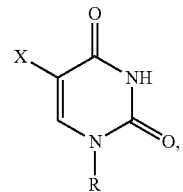

where R is a bond to the anomeric carbon of the pentafuranose of the nucleoside, and X is alkynyl. In some embodiments, X is ethynyl or propynyl (e.g., X is ethynyl).

The term "alkynylene," as used herein, refers to a straight-chain or branched-chain divalent substituent including one or two carbon-carbon triple bonds and containing only C and H when unsubstituted. Non-limiting examples of the alkynylene groups include ethyn-1,2-diyl; prop-1-yn-1,3-diyl; prop-2-yn-1,1-diyl; but-1-yn-1,3-diyl; but-1-yn-1,4-diyl; but-2-yn-1,1-diyl; but-2-yn-1,4-diyl; but-3-yn-1,1-diyl; but-3-yn-1,2-diyl; but-3-yn-2,2-diyl; and buta-1,3-diyn-1,4-diyl. The alkynylene group may be unsubstituted or substituted (e.g., optionally substituted alkynylene) as described for alkynyl groups.

The term "amino," as used herein, represents —N($R^{N1}$)$_2$, where, if amino is unsubstituted, both $R^{N1}$ are H; or, if amino is substituted, each $R^{N1}$ is independently H, —OH, —NO$_2$, —N($R^{N2}$)$_2$, —SO$_2$O$R^{N2}$, —SO$_2$$R^{N2}$, —SO$R^{N2}$, —COO$R^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one $R^{N1}$ is not H, and where each $R^{N2}$ is independently H, alkyl, or aryl. Each of the substituents may itself be unsubstituted or substituted with unsubstituted substituent(s) defined herein for each respective group. In some embodiments, amino is unsubstituted amino (i.e., —NH$_2$) or substituted amino (e.g., —NHR$^{N1}$), where $R^{N1}$ is independently —OH, —SO$_2$O$R^{N2}$, —SO$_2$$R^{N2}$, —SO$R^{N2}$, —COO$R^{N2}$, optionally substituted alkyl, or optionally substituted aryl, and each $R^{N2}$ can be optionally substituted alkyl or optionally substituted aryl. In some embodiments, substituted amino may be alkylamino, in which the alkyl groups are optionally substituted as described herein for alkyl. In certain embodiments, an amino group is —NHR$^{N1}$, in which $R^{N1}$ is optionally substituted alkyl. Non-limiting examples of —NHR$^{N1}$, in which $R^{N1}$ is optionally substituted alkyl, include: optionally substituted alkylamino, a proteinogenic amino acid, a non-proteinogenic amino acid, a C$_{1-6}$ alkyl ester of a proteinogenic amino acid, and a C$_{1-6}$ alkyl ester of a non-proteinogenic amino acid.

The term "aminoalkyl," as used herein, represents an alkyl substituted with one, two, or three amino groups, as defined herein. Aminoalkyl may be further optionally substituted as described for alkyl groups.

The term "arene-tetrayl," as used herein, represents a tetravalent group that is an aryl group, in which three hydrogen atoms are replaced with valencies. Arene-tetrayl can be optionally substituted as described herein for aryl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. The aryl and alkyl portions may be optionally substituted as the individual groups as described herein.

The term "aryl alkylene," as used herein, represents an aryl alkyl group, in which one hydrogen atom is replaced with a valency. Aryl alkylene may be optionally substituted as described herein for aryl alkyl.

The term "arylene," as used herein, represents an aryl group, in which one hydrogen atom is replaced with a valency. Arylene may be optionally substituted as described herein for aryl.

The term "aryloxy," as used herein, represents a chemical substituent of formula —OR, where R is an aryl group, unless otherwise specified. In optionally substituted aryloxy, the aryl group is optionally substituted as described herein for aryl.

The term "auxiliary moiety," as used herein, represents a monovalent group containing a hydrophilic polymer, a positively charged polymer, or a sugar alcohol.

The term "optionally substituted N," as used herein, represents a divalent —N($R^{N1}$)— group or a trivalent —N= group. The aza group may be unsubstituted, where $R^{N1}$ is H or absent, or substituted, where $R^{N1}$ is as defined for "amino," except $R^{N1}$ is not H. Two aza groups may be connected to form "diaza."

The term "optionally substituted N-protected amino," as used herein, represents substituted amino, as defined herein, in which at least one substituent is an N-protecting group and the other substituent is H, if N-protected amino is unsubstituted, or a substituent other than H, if N-protected amino is substituted.

The term "azido," as used herein, represents an —$N_3$ group.

The term "bulky group," as used herein, represents any substituent or group of substituents as defined herein, in which the radical bonding to disulfide is a carbon atom that bears one hydrogen atom or fewer if the radical is $sp^3$-hybridized carbon or bears no hydrogen atoms if the radical is $sp^2$-hybridized carbon. The radical is not sp-hybridized carbon. The bulky group bonds to disulfide only through a carbon atom.

The term "5'-5' cap," as used herein, represents a group of formula R'-$Nuc^1$-O-($L^P$)$_n$-, where R' is phosphate, phosphorothioate, phosphorodithioate, phosphotriester, phosphodiester, hydroxyl, or hydrogen; $Nuc^1$ is a nucleoside; each $L^P$ is independently —P(=$X^{E1}$)(—$X^{E2}$—$R^{E2A}$)—O—; and n is 1, 2, or 3;
    where each $X^{E1}$ and each $X^{E2}$ is independently O or S, and each $R^{E2A}$ is independently hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties; and where R' is bonded to the 3'-carbon of the nucleoside, and —O— is bonded to the 5'-carbon of the nucleoside.

The term "capping group," as used herein represents a monovalent or a divalent group situated at the 5'- or 3'-terminus of a polynucleotide. The capping group is a terminal phosphoester; diphosphate; triphosphate; an auxiliary moiety; a bioreversible group; a non-bioreversible group; 5' cap (e.g., 5'-5' cap); solid support; a linker bonded to a targeting moiety and optionally to one or more (e.g., 1 to 6) auxiliary moieties; or a group —OR', where R' is selected from the group consisting of hydrogen, a bioreversible group, non-bioreversible group, solid support, and O-protecting group. Group —OR', diphosphate, triphosphate, bioreversible group, non-bioreversible group, solid support, and auxiliaty moiety are examples of monovalent capping groups. A terminal phosphoester is an example of a capping group that can be either monovalent, if the terminal phosphoester does not include a linker to a targeting moiety, or divalent, if the terminal phosphoester includes a linker to a targeting moiety. A linker bonded to a targeting moiety (with our without auxiliary moieties) is an example of a divalent capping group.

The term "carbocyclic," as used herein, represents an optionally substituted $C_{3-16}$ monocyclic, bicyclic, or tricyclic structure in which the rings, which may be aromatic or non-aromatic, are formed by carbon atoms. Carbocyclic structures include cycloalkyl, cycloalkenyl, cycloalkynyl, and certain aryl groups.

The term "carbonyl," as used herein, represents a —C(O)— group.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "cyano," as used herein, represents —CN group.

The term "cycloaddition reaction" as used herein, represents reaction of two components in which a total of [4n+2] π electrons are involved in bond formation when there is either no activation, activation by a chemical catalyst, or activation using thermal energy, and n is 1, 2, or 3. A cycloaddition reaction is also a reaction of two components in which [4n] π electrons are involved, there is photochemical activation, and n is 1, 2, or 3. Desirably, [4n+2] π electrons are involved in bond formation, and n=1. Representative cycloaddition reactions include the reaction of an alkene with a 1,3-diene (Diels-Alder reaction), the reaction of an alkene with an α,β-unsaturated carbonyl (hetero Diels-Alder reaction), and the reaction of an alkyne with an azido compound (e.g., Hüisgen cycloaddition).

The term "cycloalkenyl," as used herein, refers to a non-aromatic carbocyclic group having at least one double bond in the ring and from three to ten carbons (e.g., a $C_3$-$C_{10}$ cycloalkenyl), unless otherwise specified. Non-limiting examples of cycloalkenyl include cycloprop-1-enyl, cycloprop-2-enyl, cyclobut-1-enyl, cyclobut-1-enyl, cyclobut-2-enyl, cyclopent-1-enyl, cyclopent-2-enyl, cyclopent-3-enyl, norbornen-1-yl, norbornen-2-yl, norbornen-5-yl, and norbornen-7-yl. The cycloalkenyl group may be unsubstituted or substituted (e.g., optionally substituted cycloalkenyl) as described for cycloalkyl.

The term "cycloalkenyl alkyl," as used herein, represents an alkyl group substituted with a cycloalkenyl group, each as defined herein. The cycloalkenyl and alkyl portions may be substituted as the individual groups defined herein.

The term "cycloalkenylene," as used herein, represents a divalent group that is a cycloalkenyl group, in which one hydrogen atom is replaced with a valency. Cycloalkenylene may be optionally substituted as described herein for cycloalkyl. A non-limiting example of cycloalkenylene is cycloalken-1,3-diyl.

The term "cycloalkoxy," as used herein, represents a chemical substituent of formula —OR, where R is cycloalkyl group, unless otherwise specified. In some embodiments, the cycloalkyl group can be further substituted as defined herein.

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1,]heptyl, 2-bicyclo[2.2.1,]heptyl, 5-bicyclo[2.2.1,]heptyl, 7-bicyclo[2.2.1,]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "cycloalkyl alkyl," as used herein, represents an alkyl group substituted with a cycloalkyl group, each as defined herein. The cycloalkyl and alkyl portions may be optionally substituted as the individual groups described herein.

The term "cycloalkylene," as used herein, represents a divalent group that is a cycloalkyl group, in which one hydrogen atom is replaced with a valency. A non-limiting example of cycloalkylene is cycloalkane-1,3-diyl. Cycloalkylene may be optionally substituted as described herein for cycloalkyl.

The term "cycloalkynyl," as used herein, refers to a monovalent carbocyclic group having one or two carbon-carbon triple bonds and having from eight to twelve carbons, unless otherwise specified. Cycloalkynyl may include one transannular bond or bridge. Non-limiting examples of cycloalkynyl include cyclooctynyl, cyclononynyl, cyclodecynyl, and cyclodecadiynyl. The cycloalkynyl group may be unsubstituted or substituted (e.g., optionally substituted cycloalkynyl) as defined for cycloalkyl.

The term "dihydropyridazine group," as used herein represents a divalent group obtainable through cycloaddition between 1,2,4,5-tetrazine group and a strained cycloalkenyl.

The term "halo," as used herein, represents a halogen selected from bromine, chlorine, iodine, and fluorine.

The term "5-halouridine," as used herein, represents a nucleoside, in which the nucleobase is 5-halouracil of the following structure:

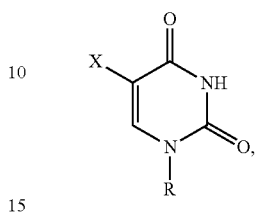

where R is a bond to the anomeric carbon of the pentafuranose of the nucleoside, and X is fluoro, chloro, bromo, iodo. In some embodiments, X is bromo or iodo.

The term "heteroalkane-tetrayl," as used herein refers to an alkane-tetrayl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkane-tetrayl contains from X to Y carbon atoms as well as the heteroatoms as defined herein. The heteroalkane-tetrayl group may be unsubstituted or substituted (e.g., optionally substituted heteroalkane-tetrayl), as described for heteroalkyl.

The term "heteroalkane-triyl," as used herein refers to an alkane-triyl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted CX Y heteroalkane-triyl contains from X to Y carbon atoms as well as the heteroatoms as defined herein. The heteroalkane-triyl group may be unsubstituted or substituted (e.g., optionally substituted heteroalkane-triyl), as described for heteroalkyl.

The term "heteroalkyl," as used herein refers to an alkyl, alkenyl, or alkynyl group interrupted once by one or two heteroatoms; twice, each time, independently, by one or two heteroatoms; three times, each time, independently, by one or two heteroatoms; or four times, each time, independently, by one or two heteroatoms. Each heteroatom is, independently, O, N, or S. In some embodiments, the heteroatom is O or N. None of the heteroalkyl groups includes two contiguous oxygen or sulfur atoms. The heteroalkyl group may be unsubstituted or substituted (e.g., optionally substituted heteroalkyl). When heteroalkyl is substituted and the substituent is bonded to the heteroatom, the substituent is selected according to the nature and valency of the heteroatom. Thus, the substituent bonded to the heteroatom, valency permitting, is selected from the group consisting of =O, —N($R^{N2}$)$_2$, —SO$_2$OR$^{N3}$, —SO$_2$R$^{N2}$, —SOR$^{N3}$, —CO-OR$^{N3}$, an N-protecting group, alkyl, alkenyl, alkynyl, aryl, cycloalkyl, cycloalkenyl, cycloalkynyl, heterocyclyl, orcyano, where each $R^{N2}$ is independently H, alkyl, cycloalkyl, cycloalkenyl, cycloalkynyl, aryl, or heterocyclyl, and each $R^{N3}$ is independently alkyl, cycloalkyl, cycloalkenyl, cycloalkynyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not Cl, Br, or I. It is understood that carbon atoms are found at the termini of a heteroalkyl group.

The term "heteroaryloxy," as used herein, refers to a structure —OR, in which R is heteroaryl. Heteroaryloxy can be optionally substituted as defined for heterocyclyl.

The term "heterocyclyl," as used herein, represents a monocyclic, bicyclic, tricyclic, or tetracyclic ring system having fused or bridging 5-, 6-, 7-, or 8-membered rings, unless otherwise specified, containing one, two, three, or four heteroatoms independently selected from the group consisting of nitrogen, oxygen, and sulfur. Heterocyclyl can be aromatic or non-aromatic. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups include from 1 to 16 carbon atoms unless otherwise specified. Certain heterocyclyl groups may include up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, etc. If the heterocyclic ring system has at least one aromatic resonance structure or at least one aromatic tautomer, such structure is an aromatic heterocyclyl (i.e., heteroaryl). Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "heterocyclyl alkyl," as used herein, represents an alkyl group substituted with a heterocyclyl group, each as defined herein. The heterocyclyl and alkyl portions may be optionally substituted as the individual groups described herein.

The term "(heterocyclyl)aza," as used herein, represents a chemical substituent of formula —N($R^{N1}$)($R^{N2}$), where $R^{N1}$ is a heterocyclyl group, and $R^{N2}$ is H, —OH, —NO$_2$, —N($R^{N2}$)$_2$, —SO$_2$O$R^{N2}$, —SO$_2$$R^{N2}$, —SO$R^{N2}$, —CO-O$R^{N2}$, an N-protecting group, alkyl, alkenyl, alkynyl, alkoxy, aryl, arylalkyl, aryloxy, cycloalkyl, cycloalkenyl, heteroalkyl, or heterocyclyl. Preferably, $R^{N2}$ is H.

The term "heterocyclylene," as used herein, represted a heterocyclyl group, in which one hydrogen atom is replaced with a valency. The heterocyclylene may be optionally substituted in a manner described for heterocyclyl. A non-limiting example of heterocyclylene is heterocycle-1,3-diyl.

The term "(heterocyclyl)oxy," as used herein, represents a chemical substituent of formula —OR, where R is a heterocyclyl group, unless otherwise specified. (Heterocyclyl)oxy can be optionally substituted in a manner described for heterocyclyl.

The terms "hydroxyl" and "hydroxy," as used interchangeably herein, represent an —OH group.

The term "immunomodulating polynucleotide" as used herein, represents a polynucleotide construct containing a total of from 6 to 50 contiguous nucleosides covalently bound together by internucleoside bridging groups independently selected from the group consisting of internucleoside phosphoesters and optionally internucleoside abasic spacers. The immunomodulating polynucleotides are capped at 5'- and 3'-termini with 5'- and 3'-capping groups, respectively. The immunomodulating polynucleotides are capable of modulating an innate immune response, as determined by, e.g., a change in the activation of NFκB or a change in the secretion of at least one inflammatory cytokine or at least one type I interferon in an antigen-presenting cell to which an immunomodulating polynucleotide was delivered (e.g., in comparison to another antigen-presenting cell to which an immunomodulating polynucleotide was not delivered). The immunomodulating polynucleotide may contain a conjugating group or, if the immunomodulating polynucleotide is part of a conjugate, a linker bonded to a targeting moiety and optionally to one or more (e.g., 1 to 6) auxiliary moieties (e.g., polyethylene glycols). The conjugating group or the linker may be part of the phosphotriester or the terminal capping group.

The term "immunostimulating polynucleotide" as used herein, represents an immunomodulating polynucleotide capable of activating an innate immune response, as determined by, e.g., an increase in the activation of NFκB or an increase in the secretion of at least one inflammatory cytokine or at least one type I interferon in an antigen-presenting cell to which an immunostimulating polynucleotide was delivered (e.g., in comparison to another antigen-presenting cell to which an immunostimulating polynucleotide was not delivered). In some embodiments, the immunostimulating polynucleotide contains at least one cytidine-p-guanosine (CpG) sequence, in which p is an internucleoside phosphodiester (e.g., phosphate or phosphorothioate) or an internucleoside phosphotriester or phosphothiotriester. As used herein, the CpG-containing immunostimulating polynucleotide can be naturally existing, such as CpG ODNs of bacterial or viral origins, or synthetic. For example, in some embodiments, the CpG sequence in the immunostimulating polynucleotide contains 2'-deoxyribose. In some embodiments, the CpG sequence in the immunostimulating polynucleotide is unmethylated. In some embodiments, the immunostimulating polynucleotide is an oligonucleotide of Formula (A) as provided herein. In some embodiments, the immunostimulating polynucleotide is compound of Formula (B) as provided herein.

The term "immunosuppressive polynucleotide" as used herein, represents an immunomodulating polynucleotide capable of antagonizing an innate immune response, as determined by e.g., a reduction in the activation of NFκB or a reduction in the secretion of at least one inflammatory cytokine or at least one type I interferon in an antigen-presenting cell to which an immunosuppressive polynucleotide was delivered (e.g., in comparison to another antigen-presenting cell to which an immunosuppressive polynucleotide was not delivered).

The term "internucleoside bridging group," as used herein, represents an internucleoside phosphoester or an internucleoside abasic spacer.

The term "5-modified cytidine," as used herein represents a nucleoside, in which the nucleobase is of the following structure:

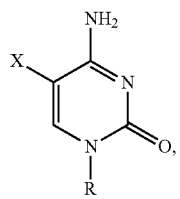

where R is a bond to the anomeric carbon of the pentafuranose of the nucleoside, and X is halogen, alkynyl, alkenyl, alkyl, cycloalkyl, heterocyclyl, or aryl. In some embodiments, 5-modified cytidine is 5-halo cytidine (e.g., 5-iodo cytidine or 5-bromo cytidine). In other embodiments, 5-modified cytidine is 5-alkynyl cytidine.

The term "5-modified uridine," as used herein represents a nucleoside, in which the nucleobase is of the following structure:

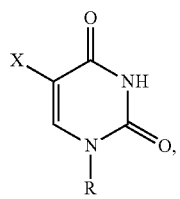

where R is a bond to the anomeric carbon of the pentafuranose of the nucleoside, and X is halogen, alkyl, alkenyl, alkynyl, cycloalkyl, heterocyclyl, or aryl, provided that the 5-modified uridine is not thymidine. In some embodiments, 5-modified uridine is 5-halouridine (e.g., 5-iodouridine or 5-bromouridine). In other embodiments, 5-modified uridine is 5-alkynyl uridine. In some embodiments, 5-modified uridine is a nucleoside containing 2-deoxyribose.

The term "nitro," as used herein, represents an —NO$_2$ group.

The term "non-bioreversible," as used herein, refers to a chemical group that is resistant to degradation under conditions existing inside an endosome. Non-bioreversible groups do not contain thioesters and/or disulfides.

The term "nucleobase," as used herein, represents a nitrogen-containing heterocyclic ring bound to the V position of the sugar moiety of a nucleotide or nucleoside. Nucleobases can be unmodified or modified. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-iodo, 5-bromo, 5-trifluoromethyl and other 5-substituted uracils and cytosines, 5-alkynyl (e.g., 5-ethynyl) uracil, 5-acetamido-uracil, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; those disclosed in The Concise Encyclopedia Of Polymer Science And Engineering, pages 858-859, Kroschwitz, J. I., ed. John Wiley & Sons, 1990; those disclosed by Englisch et al., *Angewandte Chemie, International Edition*, 1991, 30, 613; and those disclosed by Sanghvi, Y. S., Chapter 15, Antisense Research and Applications, pages 289 302, (Crooke et al., ed., CRC Press, 1993). Certain nucleobases are particularly useful for increasing the binding affinity of the hybridized polynucleotides of the invention, including 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,594,121; 5,596,091; 5,614,617; and 5,681,941. For the purposes of this disclosure, "modified nucleobases," as used herein, further represents nucleobases, natural or non-natural, which include one or more protecting groups as described herein.

The term "nucleoside," as used herein, represents a pentafuranose-nucleobase combination. The pentafuranose is 2-deoxyribose or a modified version thereof, in which position 2 is substituted with OR, R, halo (e.g., F), SH, SR, NH$_2$, NHR, NR$_2$, or CN, where R is an optionally substituted C$_{1-6}$ alkyl (e.g., C$_{1-6}$ alkyl or (C$_{1-6}$ alkoxy)-C$_{1-6}$-alkyl) or optionally substituted (C$_{6-14}$ aryl)-C$_{1-4}$-alkyl. In certain embodiments, position 2 is substituted with OR or F, where R is C$_{1-6}$ alkyl or (C$_{1-6}$-alkoxy)-C$_{1-6}$-alkyl. The pentafuranose is bonded to a nucleobase at the anomeric carbon. In some embodiments, the term "nucleoside" refers to a divalent group having the following structure:

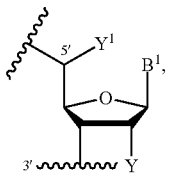

in which $B^1$ is a nucleobase; Y is H, halogen (e.g., F), hydroxyl, optionally substituted $C_{1-6}$ alkoxy (e.g., methoxy or methoxyethoxy), or a protected hydroxyl group; $Y^1$ is H or $C_{1-6}$ alkyl (e.g., methyl); and each of 3' and 5' indicate the position of a bond to another group.

The term "nucleotide," as used herein, refers to a nucleoside that is bonded to a phosphate, phosphorothioate, or phosphorodithioate.

The term "oxo," as used herein, represents a divalent oxygen atom (e.g., the structure of oxo may be shown as =O).

The term "patient," as used herein, represents a human or non-human animal (e.g., a mammal). In some embodiments, the subject may be suffering from a tumor (e.g., a liquid tumor or a solid tumor), as determined by a qualified professional (e.g., a doctor or a nurse practitioner) with or without known in the art laboratory test(s) of sample(s) from the patient.

The term "Ph," as used herein, represents phenyl.

The term "phosphoester," as used herein, represents a group containing a phosphate, phosphorothioate, or phosphorodithioate, in which, at least one valency is covalently bonded to a non-hydrogen substituent, provided that at least one non-hydrogen substituent is a group containing at least one nucleoside. A phosphoester, in which one and only one valency is covalently bonded to a group containing a nucleoside, is a terminal phosphoester. A phosphoester, in which two valencies are covalently bonded to nucleoside-containing groups, is an internucleoside phosphoester. A phosphoester may be a group of the following structure:

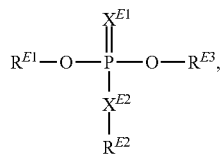

where
each of $X^{E1}$ and $X^{E2}$ is independently O or S;
each or $R^{E1}$ and $R^{E3}$ is independently hydrogen or a bond to a nucleoside; a sugar analogue of an abasic spacer; a bioreversible group; a non-bioreversible group; an auxiliary moiety; a conjugating group; a linker bonded to a targeting moiety; a linker bonded to a targeting moiety and one or more (e.g., 1 to 6) auxiliary moieties; or the phosphorus atom in a group of formula —P(=$X^{E1}$)(—$X^{E2}$—$R^{E2A}$)—O—,
where $R^{E2A}$ is hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties; and
$R^{E2}$ is hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties;
provided that at least one of $R^{E1}$ and $R^{E3}$ is a bond to a group containing at least one nucleoside. If each of $R^{E1}$ and $R^{E3}$ is independently a bond to a group containing at least one nucleoside, the phosphoester is an internucleoside phosphoester. If one of $R^{E1}$ and $R^{E3}$ is a bond to a group that does not contain a nucleoside, the phosphoester is a terminal phosphoester.

The term "phosphodiester," as used herein, refers to a phosphoester, in which, two of the three valencies are substituted with non-hydrogen substituents, while the remaining valency is substituted with hydrogen. The phosphodiester consists of phosphate, phosphorothioate, or phosphorodithioate; one or two bonds to nucleoside(s), abasic spacer(s), and/or phosphoryl group(s); and, if the phosphodiester contains only one bond to a nucleoside, an abasic spacer, or a phosphoryl group, one group independently selected from the group consisting of a bioreversible group; a non-bioreversible group; an auxiliary moiety; a conjugating group; a linker bonded to a targeting moiety; and a linker bonded to a targeting moiety and one or more (e.g., 1 to 6) auxiliary moieties. A terminal phosphodiester includes one bond to a group containing a nucleoside, and one group selected from the group consisting of a bioreversible group; a non-bioreversible group; an auxiliary moiety; a conjugating group; a phosphoryl group; and a linker bonded to a targeting moiety and optionally to one or more (e.g., 1 to 6) auxiliary moieties. An internucleoside phosphodiester includes two bonds to nucleoside-containing groups. A phosphodiester may be a group of the following structure:

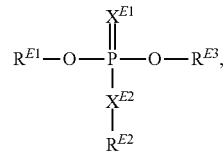

where
each of $X^{E1}$ and $X^{E2}$ is independently O or S;
each or $R^{E1}$ and $R^{E3}$ is independently hydrogen or a bond to a nucleoside; a sugar analogue of an abasic spacer; a bioreversible group; a non-bioreversible group; an auxiliary moiety; a conjugating group; a linker bonded to a targeting moiety; a linker bonded to a targeting moiety and one or more (e.g., 1 to 6) auxiliary moieties; or the phosphorus atom in a group of formula —P(=$X^{E1}$)(—$X^{E2}$—$R^{E2A}$)—O—,
where $R^{E2A}$ is hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties; and
$R^{E2}$ is hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties;
provided that one and only one of $R^{E1}$, $R^{E2}$, and $R^{E3}$ is hydrogen; and
provided that at least one of $R^{E1}$ and $R^{E3}$ is a bond to a group containing at least one nucleoside.

If both $R^{E1}$ and $R^{E3}$ are bonds to groups containing at least one nucleoside, the phosphodiester is an internucleoside phosphodiester. If one and only one of $R^{E1}$ and $R^{E3}$ is a bond to a group containing a nucleoside, the phosphodiester is a terminal phosphodiester.

The term "phosphoryl," as used herein, refers to a substituent of formula

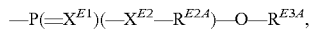

where each of $X^{E1}$ and $X^{E2}$ is independently O or S;

$R^{E2A}$ is hydrogen, a bioreversible group, a non-bioreversible group, an auxiliary moiety, a conjugating group, a linker bonded to a targeting moiety, or a linker bonded to a targeting moiety and one or more (e.g., 1 to 6) auxiliary moieties; and $R^{E3A}$ is hydrogen or an open valency.

When a group is identified as being bonded to a phosphoryl, the group is bonded to the phosphorus atom of the phosphoryl.

The term "phosphotriester," as used herein, refers to a phosphoester, in which all three valences are substituted with non-hydrogen substituents. The phosphotriester consists of phosphate, phosphorothioate, or phosphorodithioate; one or two bonds to nucleoside(s), or abasic spacer(s), and/or phosphoryl group(s); and one or two groups independently selected from the group consisting of a bioreversible group; a non-bioreversible group; an auxiliary moiety; a conjugating group; and a linker bonded to a targeting moiety and optionally to one or more (e.g., 1 to 6) auxiliary moieties. A terminal phosphotriester includes one bond to a group containing a nucleoside and two groups independently selected from the group consisting of a bioreversible group; a non-bioreversible group; an auxiliary moiety; a conjugating group; a phosphoryl group; and a linker bonded to a targeting moiety and optionally to one or more (e.g., 1 to 6) auxiliary moieties. In some embodiments, a terminal phosphotriester contains 1 or 0 linkers bonded to a targeting moiety and optionally to one or more (e.g., 1 to 6) auxiliary moieties. An internucleoside phosphotriester includes two bonds to nucleoside-containing groups. A phosphotriester may be a group of the following structure:

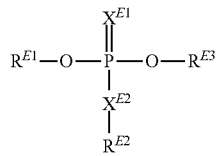

where each of $X^{E1}$ and $X^{E2}$ is independently O or S;

each or $R^{E1}$ and $R^{E3}$ is independently a bond to a nucleoside; a sugar analogue of an abasic spacer; a bioreversible group; a non-bioreversible group; an auxiliary moiety; a conjugating group; a linker bonded to a targeting moiety; a linker bonded to a targeting moiety and one or more (e.g., 1 to 6) auxiliary moieties; or the phosphorus atom in a group of formula —P(=$X^{E1}$)(—$X^{E2}$—$R^{E2A}$)—O— where $R^{E2A}$ is hydrogen; a bioreversible group; a non-bioreversible group; an auxiliary moiety; a conjugating group; a linker bonded to a targeting moiety; or a linker bonded to a targeting moiety and one or more (e.g., 1 to 6) auxiliary moieties; and $R^{E2}$ is a bioreversible group; a non-bioreversible group; an auxiliary moiety; a conjugating group; a linker bonded to a targeting moiety; or a linker bonded to a targeting moiety and one or more (e.g., 1 to 6) auxiliary moieties;

provided that at least one of $R^{E1}$ and $R^{E3}$ is a bond to a group containing at least one nucleoside. If both $R^{E1}$ and $R^{E3}$ are bonds to groups containing at least one nucleoside, the phosphotriester is an internucleoside phosphotriester. If one and only one of $R^{E1}$ and $R^{E3}$ is a bond to a group containing a nucleoside, the phosphotriester is a terminal phosphotriester.

The term "physiological conditions," as used herein, refer to the conditions that may exist inside a living, mammalian, professional antigen-presenting cell. The physiological conditions include temperatures from about 35° C. to about 42° C. and aqueous pH from about 6 to about 8.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3$^{rd}$ Edition (John Wiley & Sons, New York, 1999), which is incorporated herein by reference. Exemplary O- and N-protecting groups include alkanoyl, aryloyl, orcarbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "pyrid-2-yl hydrazone," as used herein, represents a group of the structure:

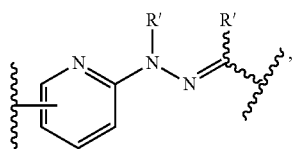

where each R' is independently H or optionally substituted $C_{1-6}$ alkyl. Pyrid-2-yl hydrazone may be unsubstituted (i.e., each R' is H).

The term "stereochemically enriched," as used herein, refers to a local stereochemical preference for one stereoisomeric configuration of the recited group over the opposite stereoisomeric configuration of the same group. Thus, a polynucleotide containing a stereochemically enriched phosphorothioate is a strand, in which a phosphorothioate of predetermined stereochemistry is present in preference to a phosphorothioate of the opposite stereochemistry. This preference can be expressed numerically using a diastereomeric ratio for the phosphorothioate of the predetermined stereochemistry. The diastereomeric ratio for the phosphorothioate of the predetermined stereochemistry is the molar ratio of the diastereomers having the identified phosphorothioate with the predetermined stereochemistry relative to the diastereomers having the identified phosphorothioate with the opposite stereochemistry. The diastereomeric ratio for the phosphorothioate of the predetermined stereochemistry may be greater than or equal to 1.1 (e.g., greater than or equal to 4, greater than or equal to 9, greater than or equal to 19, or greater than or equal to 39).

The term "Q-tag," as used herein, refers to a portion of a polypeptide containing glutamine residue that, upon transglutaminase-mediated reaction with a compound containing —NH$_2$ amine, provides a conjugate containing the portion of polypeptide, in which the glutamine residue includes a side chain modified to include the amide bonded to the compound. Q-tags are known in the art. Non-limiting examples of Q-tags are LLQGG and GGGLLQGG.

The term "strained cycloalkenyl," as used herein, refers to a cycloalkenyl group that, if the open valency were substituted with H, has a ring strain energy of at least 16 kcal/mol.

The term "sugar analogue," as used herein, represents a divalent or trivalent group that is a $C_{3-6}$ monosaccharide or $C_{3-6}$ alditol (e.g., glycerol), which is modified to replace two hydroxyl groups with bonds to the oxygen atoms in phosphate, phosphorothioate, or phosphorodithioate, or a capping group. A sugar analogue does not contain a nucleobase capable of engaging in hydrogen bonding with a nucleobase in a complementary strand. A sugar analogue is cyclic or acyclic. Further optional modifications included in a sugar analogue are: a replacement of one, two, or three of the remaining hydroxyl groups or carbon-bonded hydrogen atoms with H; optionally substituted $C_{1-6}$ alkyl; -LinkA(-T)$_p$, as defined herein; a conjugating group; —(CH$_2$)$_{t1}$—OR$^Z$, where t1 is an integer from 1 to 6, and R$^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl; introduction of one or two unsaturation(s) (e.g., one or two double bonds); and replacement of one, two, or three hydrogens or hydroxyl groups with substituents as defined for alkyl, alkenyl, cycloalkyl, cycloalkenyl, or heterocyclyl. Non-limiting examples of sugar analogues are optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted ($C_{1-4}$ alkyl)-($C_{3-8}$ cycloalkylene) (e.g., optionally substituted ($C_1$ alkyl)-($C_3$ cycloalkylene)).

The term "sulfide," as used herein, represents a divalent —S— or =S group. Disulfide is —S—S—.

The term "targeting moiety," as used herein, represents a moiety (e.g., a small molecule, e.g., a carbohydrate) that specifically binds or reactively associates or complexes with a receptor or other receptive moiety associated with a given target cell population (e.g., an antigen-presenting cell (APC; e.g., a professional APC (e.g., B-cell, pDC, or macrophage))). A conjugate of the invention contains a targeting moiety. The targeting moiety can be an antibody or an antigen-binding fragment or an engineered derivative thereof (e.g., Fcab or a fusion protein (e.g., scFv)). The targeting moiety can be a polypeptide. Alternatively, the targeting moiety can be a small molecule (e.g., mannose) or a cluster of small molecules (e.g., a cluster of mannoses). A conjugate of the invention that includes the targeting moiety may exhibit $K_d$ of less than 100 nM for the target, to which the targeting moiety bind. $K_d$ is measured using methods known in the art, e.g., using surface plasmon resonance (SPR), e.g., using BIACORE™ system (GE Healthcare, Little Chalfont, the United Kingdom).

The term "1,2,4,5-tetrazine group," as used herein, represents a group of the following formula

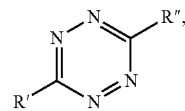

where R' is optionally substituted alkyl, optionally substituted aryl, optionally substituted cycloalkyl, optionally substituted heterocyclyl; and R" is optionally substituted alkylene, optionally substituted heteroalkylene, optionally substituted arylene, optionally substituted cycloalkylene, optionally substituted heterocyclylene, or a group —R$^a$—R$^b$—, in which each of R$^a$ and R$^b$ is independently optionally substituted alkylene, optionally substituted heteroalkylene, optionally substituted arylene, optionally substituted cycloalkylene, or optionally substituted heterocyclylene.

The term "therapeutic effect" refers to a local or systemic effect in a subject, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The term "therapeutically effective amount" or "therapeutically effective dose," as used herein, represents the quantity of an immunomodulating polynucleotide or a conjugate necessary to ameliorate, treat, or at least partially arrest the symptoms of a disease to be treated. Amounts effective for this use depend on the severity of the disease and the weight and general state of the subject. Typically, dosages used in vitro may provide useful guidance in the amounts useful for in vivo administration of the pharmaceutical composition, and animal models may be used to determine effective dosages for treatment of a particular disease.

The term "thiocarbonyl," as used herein, represents a C(=S) group.

The term "thioheterocyclylene," as used herein, represents a group —S—R—, where R is heterocyclylene. Thioheterocyclylene may be optionally substituted in a manner described for heterocyclyl.

The term "thiol," as used herein, represents an —SH group.

The term "treating" as used in reference to a disease or a condition in a patient, is intended to refer to obtaining beneficial or desired results, e.g., clinical results, in a patient by administering the polynucleotide or conjugate of the invention to the patient. Beneficial or desired results may include alleviation or amelioration of one or more symptoms of a disease or condition; diminishment of extent of a disease or condition; stabilization (i.e., not worsening) of a disease or condition; prevention of the spread of a disease or condition; delay or slowing the progress of a disease or condition; palliation of a disease or condition; and remission (whether partial or total). "Palliating" a disease or condition means that the extent and/or undesirable clinical manifestations of the disease or condition are lessened and/or time course of the progression is slowed, as compared to the extent or time course in the absence of the treatment with the polynucleotide or conjugate of the invention.

The term "triazolocycloalkenylene," as used herein, refers to the heterocyclylenes containing a 1,2,3-triazole ring fused to an 8-membered ring, all of the endocyclic atoms of which are carbon atoms, and bridgehead atoms are sp$^2$-hybridized carbon atoms. Triazocycloalkenylenes can be optionally substituted in a manner described for heterocyclyl.

The term "triazoloheterocyclylene," as used herein, refers to the heterocyclylenes containing a 1,2,3-triazole ring fused to an 8-membered ring containing at least one heteroatom. The bridgehead atoms in triazoloheterocyclylene are carbon atoms. Triazoloheterocyclylenes can be optionally substituted in a manner described for heterocyclyl.

It is to be understood that the terms "immunomodulating polynucleotide," "immunostimulating polynucleotide," "immunosuppressive polynucleotide," and "conjugate" encompass salts of the immunomodulating polynucleotide, immunostimulating polynucleotide, immunosuppressive polynucleotide and conjugate, respectively. For example, the terms "immunomodulating polynucleotide," "immunostimulating polynucleotide," "immunosuppressive polynucleotide," and "conjugate" encompasses both the protonated, neutral form (P—XH moiety, where X is O or S) of a phosphate, phosphorothioate, or phosphorodithioate and the deprotonated, ionic form (P—X$^-$ moiety, where X is O or S) of a phosphate, phosphorothioate, or phosphorodithioate. Accordingly, it is to be understood that the phosphoesters and phosphodiesters described as having one or more of $R^{E1}$, $R^{E2}$, and $R^{E3}$ as hydrogen encompass salts, in which the phosphate, phosphorothioate, or phosphorodithioate is present in a deprotonated, ionic form.

The terms "innate immune response" and "innate immunity" are recognized in the art, and refer to non-specific defense mechanism a body's immune system initiates upon recognition of pathogen-associated molecular patterns, which involves different forms of cellular activities, including cytokine production and cell death through various pathways. As used herein, innate immune responses include cellular responses to a CpG-containing immunostimulating polynucleotide mediated by toll-like receptor 9 (TLR9), which include, without limitation, increased production of inflammation cytokines (e.g., type I interferon or IL-10 production), activation of the NFκB pathway, increased proliferation, maturation, differentiation and/or survival of immune cells, and in some cases, induction of cell apoptosis. Activation of the innate immunity can be detected using methods known in the art, such as measuring the (NF)-κB activation.

The terms "adaptive immune response" and "adaptive immunity" are recognized in the art, and refer to antigen-specific defense mechanism a body's immune system initiates upon recognition of a specific antigen, which include both humoral response and cell-mediated responses. As used herein, adaptive immune responses include cellular responses that is triggered and/or augmented by a CpG-containing immunostimulating polynucleotide. In some embodiments, the immunostimulating polynucleotide or a portion thereof is the antigen target of the antigen-specific adaptive immune response. In other embodiments, the immunostimulating polynucleotide is not the antigen target of the antigen-specific adaptive immune response, but nevertheless augments the adaptive immune response. Activation of an adaptive immune response can be detected using methods known in the art, such as measuring the antigen-specific antibody production, or the level of antigen-specific cell-mediated cytotoxicity.

The term "Toll-like receptor" (or "TLR") is recognized in the art, and refers to a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce an innate immune response and/or adaptive immune response. As used herein, the term "toll-like receptor" or "TLR" also refers to a functional fragment of a toll-like receptor protein expressed by a cell. In humans, ten TLRs have been identified, including TLR-1, -2, -3, -4, -5, -6, -7/8, and -9. D'Arpa and Leung, *Adv. Wound Care*, 6:330-343 (2017), the content of which is incorporated herein by reference in its entirety. Human genes encoding TLRs are known.

Toll-like receptor 9 (TLR9), also designated as CD289 (cluster of differentiation 289), is a member of the toll-like receptor (TLR) family. Du et al., *Eur. Cytokine Netw.*, 11:362-371 (2000), the content of which is incorporated herein by reference in its entirety. TLR9 is an important receptor expressed in immune system cells including dendritic cells (DCs), B lymphocytes, macrophages, natural killer cells, and other antigen presenting cells. TLR9 activation triggers signaling cascades that bridges the innate and adaptive immunity. Martinez-Campos et al. *Viral Immunol.*, 30:98-105 (2016); Notley et al., *Sci. Rep.*, 7:42204 (2017); the content of each of which is incorporated herein by reference in its entirety. Natural TLR-9 agonists include unmethylated cytosine-guanine dinucleotide (CpG)-containing oligodeoxynucleotides (CpG ODNs). TLR-9 ligand finding use in the present disclosure include, but are not limited to, naturally existing or synthetic CpG ODNs, and other CpG-containing immunostimulating polynucleotide and/or immunoconjugates as provided herein. Activation of the TLR9 signaling pathway can be detected using methods known in the art, such as measuring recruitment of myeloid differentiation antigen 88 (MyD88), activation of nuclear factor (NF)-κB, c-Jun N-terminal kinase (JNK), and p38 mitogen-activated protein kinase (MAPK) signaling pathways, activation of interferon regulatory factor-7, expression level of one or more of cytokines such as type I interferons (IFNs), interleukin (IL)-6, IL-10, and IL-12, activation of one or more immune cell populations such as NK cells, natural killer T cells, monocytes, and level of cytotoxic lymphocyte (CTL) and T helper-1 (Th1) responses, and the level of immunoglobulin secretion.

The term "TLR-expressing cell" as used herein refers to a cell that expresses a toll-like receptor and is capable of activating the toll-like receptor signaling pathway upon binding of the toll-like receptor to an agonist. The toll-like receptor may be expressed on the cell surface, and/or on the membrane of one or more intracellular compartments of the cell, such as the endosome or phagosome. A TLR-expressing cell may further express one or more cell surface antigens other than the toll-like receptor. Certain immune cells express TLRs, and activation of the TLR signaling pathway in the immune cells elicits an innate immune response, and/or an adaptive immune response. Immune cells activated by the TLR signaling pathway can help eliminate other diseased cells from the body. Certain diseased cells (e.g., cancer cells or viral-infected cells) express TLRs, and activation of the TLR signaling pathway in the diseased cells can results in death of the diseased cell, such as via induced apoptosis. Examples of TLR9-expressing cells include but are not limited to dendritic cells (DCs), B cells, T cells, Langerhans cells, keratinocytes, mast cells, endothelial cells, myofibroblast cells, and primary fibroblast. Determining whether a cell expresses any toll-like receptor (e.g., TLR9) can be performed using methods known in the art, such as detecting mRNA of the toll-like receptor in a cell.

The term "immune cell" is recognized in the art, as used herein refers to any cell involved in a host defense mechanism, such as cells that produces pro-inflammatory cytokines, and cells that participate in tissue damage and/or disease pathogenesis. Examples of immune cells include, but are not limited to, T cells, B cells, natural killer cells, neutrophils, mast cells, macrophages, antigen-presenting cells (APC), basophils, and eosinophils.

The term "antigen presenting cell" or "APC" is recognized in the art, and refers to a heterogeneous group of immune cells that mediate the cellular immune response by processing and presenting antigens for recognition by certain lymphocytes such as T cells. Exemplary types of antigen presenting cells include, but are not limited to, professional antigen presenting cells including, for example, B cells, monocytes, dendritic cells, and Langerhans cells, as well as other antigen presenting cells including, for example, keratinocytes, endothelial cells, astrocytes, fibroblasts, and oligodendrocytes. As used herein, the term "antigen presenting cell" includes antigen presenting cells found in vivo and those found in in vitro cell cultures derived from the in vivo cells. As used herein, antigen presenting cells also include a APC that is artificially modified, such as genetically modified to express a toll-like receptor (e.g., TLR9) or to modulate expression level of a toll-like receptor (e.g., TLR9).

The term "dendritic cells" or "DC" is recognized in the art, and refers to a heterogeneous group of specialized antigen-sensing and antigen-presenting cells (APCs). Human DC are divided into three major subsets: plasmacytoid DC (pDC), myeloid DC (mDC) and monocyte-derived DC (MDDC). Schraml et al., *Curr. Opin. Immunol.*, 32:13-20 (2015); the content of which is incorporated herein by reference in its entirety. Subsets of DCs can be identified on the basis of distinct TLR expression patterns. By way of an example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. The plasmacytoid subset of DC (pDC) expresses TLR7 and TLR9 upon activation, with a resulting activation of NK cells as well as T-cells.

The term "antigen" as used herein, refers to a molecule or an antigenic fragment thereof capable of eliciting an immune response, including both an innate immune response and an adaptive immune response. As used herein, antigens can be proteins, peptides, polysaccharides, lipids, nucleic acids, especially RNA and DNA, nucleotides, and other biological or biochemical substances. The term "elicit an immune response" refers to the stimulation of immune cells in vivo in response to a stimulus, such as an antigen. The immune response consists of both cellular immune response, e.g., T cell and macrophage stimulation, and humoral immune response, e.g., B cell and complement stimulation and antibody production. Immune response may be measured using techniques well-known in the art, including, but not limited to, antibody immunoassays, proliferation assays, and others.

The terms "antigenic fragment" and "antibody binding fragment" are used interchangeably herein. An antigenic fragment as used herein is able to complex with an antigen binding molecule, e.g., an antibody, in a specific reaction. The specific reaction referred to herein indicates that the antigen or antigenic fragment will react, in a highly selective manner, with its corresponding antibody and not with the multitude of other antibodies which may be evoked by other antigens. The specificity of such reaction is determined by the presence of one or more epitopes (immunogenic determinants) in the antigen. As used herein, an antigen or antigenic fragment thereof may have one epitope, or have more than one epitopes.

The term "T cell epitope" as used herein, refers to any epitopes of antigens produced by a T cell.

The term "tumor associated antigen" or "TAA", as used herein, refers to an antigen expressed by a cancer cell or in the stroma of a solid tumor in a cancer patient receiving the treatment or preventive care as provided herein (e.g., receiving a therapeutic dose of an immunostimulating polynucleotide or a CpG-Ab immunoconjugate). The TAA may or may not be targeted in the treatment or the preventive care provided herein. The TAA does not have to be overexpressed, mutated or misregulated on cancer cell but can have same features as the TAA would have in a normal cell. In some embodiments, the TAA can be overexpressed, mutated or misregulated in cancer cell. The TAA can be a protein, nucleic acid, lipid or other antigen. The TAA can be a cell-surface expressed TAA, an intracellular TAA or an intranuclear TAA. In the context of a solid tumor, the TAA can be expressed in the stroma of a solid tumor mass. The term "stroma" as used herein refers to components in a solid tumor mass other than a cancer cell. For example, the stroma can include fibroblasts, epithelial cells, other blood vessel components or extracellular matrix components. As used herein, the term "stroma" does not include components of the immune system, such as immune cells (e.g., B-cells, T-cells, dendritic cells, macrophages, natural killer cells, and the like)). Various TAAs are known in the art. Identifying TAA can be performed using methods known in the art, such as disclosed in Zhang et al. *Methods Mol. Biol.*, 520:1-10 (2009); the content of which is enclosed herein by reference.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hyper variability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, antibodies include, but are not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

As used herein, depending on the context, the term "antibody" may also refer to an antigen binding fragment of an antibody molecule. The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al. *Nature,* 341:544-546 (1989)), which consists of a VH or VL domain; a single domain antibody (VHH), and an isolated complementarity determining region (CDR), or other epitope-binding fragments of an antibody.

The term "specifically binds," "selectively binds" or the like refers to a chemical interaction between two molecules, compounds, cells and/or particles wherein the first entity binds to the second, target entity with greater specificity and affinity than it binds to a third entity which is a non-target. In some embodiments, "specific binding" can refer to an affinity of the first entity for the second target entity which is at least 10 times, at least 50 times, at least 100 times, at least 500 times, at least 1000 times or greater than the affinity for the third non-target entity. In some embodiments, "specific binding" is used in the context of describing the interaction between an antigen (or an antigenic fragment thereof) and an antibody (or antigen-binding fragment thereof). In particular embodiments, "specific binding" refers to binding of the antibody to a predetermined antigen with a disassociation constant (KD) of $10^{-5}$ M or less, $10^{-6}$ M or less, or $10^{-7}$ M or less, or binding of an antibody to a predetermined antigen with a KD that is at least twofold less than its KD for binding to a nonspecific antigen other than the predetermined antigen. In some embodiments, specific binding can be used to determine the presence of the predetermined antigen in a heterogeneous population of proteins and other biologies, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least two, three, four, five, six, seven, eight, nine or ten times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

The term "cancer" or "tumor" refers to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of immune checkpoint inhibitors, such as PD-1, PD-L1, and/or CTLA-4. Cancer cells are often in the form of a solid tumor, which is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient. In some embodiments, a solid tumor does not need to have measurable dimensions. Cancer cells may also in the form of a liquid tumor, which cancer cells may exist alone or disseminated within an animal. As used herein, the terms "disseminated tumor" and "liquid tumor" are used interchangeably, and include, without limitation, leukemia and lymphoma and other blood cell cancers.

The term "leukemia" refers to a type of cancer of the blood or bone marrow characterized by an abnormal increase of immature white blood cells called "blasts." Leukemia is a broad term covering a spectrum of diseases. In turn, it is part of the even broader group of diseases affecting the blood, bone marrow, and lymphoid system, which are all known as hematological neoplasms. Leukemias can be divided into four major classifications, acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML). Further types of leukemia include Hairy cell leukemia (HCL), T-cell prolymphocytic leukemia (T-PLL), large granular lymphocytic leukemia, and adult T-cell leukemia.

The term "lymphoma" refers to a group of blood cell tumors that develop from lymphatic cells. The two main categories of lymphomas are Hodgkin lymphomas (HL) and non-Hodgkin lymphomas (NHL) Lymphomas include any neoplasms of the lymphatic tissues. The main classes are cancers of the lymphocytes, a type of white blood cell that belongs to both the lymph and the blood and pervades both.

As used herein, the term "cancer" includes premalignant as well as malignant cancers, and also includes primary tumors (e.g., those whose cells have not migrated to sites in the subject's body other than the site of the original tumor) and secondary tumors (e.g., those arising from metastasis, the migration of tumor cells to secondary sites that are different from the site of the original tumor), recurrent cancer and refractory cancer.

The terms "cancer recurrence" and "cancer relapse" are used interchangeably and refer to the return of a sign, symptom or disease after a remission. The recurrent cancer cells may re-appear in the same site of the primary tumor or in another location, such as in secondary cancer. The cancer cells may re-appear in the same diseased form as the primary cancer or a different diseased form. For example, in some embodiments, a primary cancer is a solid tumor, and the recurrent cancer is a liquid tumor. In other embodiments, a primary cancer is a liquid tumor, and the recurrent cancer is a solid tumor. In yet other embodiments, the primary cancer and the recurrent cancer are both solid tumors, or both liquid tumors. In some embodiments, the recurrent tumor expresses at least one tumor associated antigen that is also expressed by the primary tumor.

The term "refractory cancer" as used herein refers to a cancer that does not respond to a treatment, for example, a cancer that is resistant at the beginning of treatment (e.g., treatment with an immunotherapy) or a cancer that may become resistant during treatment. The terms "respond," "response" or "responsiveness" refer to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

As used herein, cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal qammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, sominoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "cancer therapy" or "cancer therapeutic agent" as used herein, refers to those therapies or agents that can exert anti-tumor effect or have an anti-tumor activity. Such anti-tumor effect or anti-tumor activity can be exhibited as a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

As used herein, the term "prevent", "preventing" or "prevention" of any disease or disorder means the prevention of the onset, recurrence or spread, in whole or in part, of the disease or condition as described herein, or a symptom thereof.

As used herein, a subject is "in need of" a treatment if such subject would benefit biologically, medically or in quality of life from such treatment.

The term "therapeutic agent" is art-re cognized and refers to any substance that, upon administration to a subject in need thereof, is biologically, physiologically, or pharmacologically active, and acts locally or systemically to exert a beneficial therapeutic effect to the subject.

The term "immunoconjugate" or "antibody-drug-conjugate (ADC)" as used herein refers to the linkage of an antigen binding moiety (e.g., an antibody or an antigen binding fragment thereof) with an immunomodulatory polynucleotide as described herein. The linkage can be covalent bonds, or non-covalent interactions, and can include chelation. Various linkers, known in the art or provided herein, can be employed in order to form the immunoconjugate. In some embodiments, the immunoconjugate is a conjugate of Formula (C) as provided herein.

The term "antigen binding moiety" as used herein refers to a moiety capable of binding specifically to an antigen, and includes but is not limited to antibodies and antigen binding fragments.

The term "CpG-Ab immunoconjugate" or "CpG-Ab" as used herein refers to the linkage of an antibody (Ab) or an antigen binding fragment thereof with a CpG-containing immunostimulating polynucleotide as described herein.

The term "T-cell agonist" as used herein refers to any agent that selectively stimulates the proliferation, differentiation, and/or survival of T cells from a mixed starting population of cells. Thus, the resulting cell population is enriched with an increased number of T cells compared with the starting population of cells. T cell agonists finding use in the present disclosure include but are not limited to antigen molecules specifically binding to T cell receptors (TCRs), as well as T cell co-stimulatory molecules. Examples of T cell co-stimulatory molecules includes but are not limited to OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand. In particular embodiments, the T-cell agonist is an antibody against a T cell co-stimulatory molecule. In particular embodiments, the T cell agonist is a tumor associated antigen (TAA). In particular embodiments, the T cell agonist is a pathogenic antigen.

As used herein, an "immune checkpoint" or "immune checkpoint molecule" is a molecule in the immune system that modulates a signal. An immune checkpoint molecule can be a stimulatory checkpoint molecule, i.e., turn up a signal, or inhibitory checkpoint molecule, i.e., turn down a signal. In specific embodiments, immune checkpoint is a protein expressed either by T cells or by antigen presenting cells (APC). Certain types of cancer cells express immune checkpoint proteins to evade immune clearance. Use of immune checkpoint modulators to inhibit the interaction between the immune checkpoint protein expressed by cancer cells and the immune checkpoint protein expressed by T cells has proved effective in certain cancer treatment.

As used herein, an "immune checkpoint modulator" is an agent capable of altering the activity of an immune checkpoint in a subject. In certain embodiments, an immune checkpoint modulator alters the function of one or more immune checkpoint molecules including, but not limited to, PD-1, PD-L1, PD-L2, TIM-3, LAG-3, CEACAM-1, CEACAM-5, VISTA, BTLA, TIGIT, LAIR1, CD160, CD47, 2B4 and TGFR. The immune checkpoint modulator may be an agonist or an antagonist of the immune checkpoint. In some embodiments, the immune checkpoint modulator is an immune checkpoint binding protein (e.g., an antibody, antibody Fab fragment, divalent antibody, antibody drug conjugate, scFv, fusion protein, bivalent antibody, or tetravalent antibody). In other embodiments, the immune checkpoint modulator is a small molecule. In a particular embodiment, the immune checkpoint modulator is an anti-PDI or an anti-PD-LI antibody.

The term "targeted delivery" or the verb form "target" as used herein refers to the process that promotes the arrival of a delivered agent (such as an immunostimulating polynucleotide) at a specific organ, tissue, cell and/or intracellular compartment (referred to as the targeted location) more than any other organ, tissue, cell or intracellular compartment (referred to as the non-target location). Targeted delivery can be detected using methods known in the art, for example, by comparing the concentration of the delivered agent in a targeted cell population with the concentration of the delivered agent at a non-target cell population after systemic administration. As provided herein, targeted delivery results in at least 2 fold higher concentration at a targeted location as compared to a non-target location. Targeted delivery may be achieved by specific binding of the targeting moiety to an receiving moiety associated with a targeted cell. As used herein, an receiving moiety associated with a targeted cell may be located on the surface or within the cytosol of the targeted cell. In some embodiments, the receiving moiety is an antigen associated with the targeted cell.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type. In some embodiments, an abnormal cell is a cancer cell.

The term "combination therapy" refers to the administration of two or more therapeutic agents to treat a condition or disorder (e.g., cancer) described in the present disclosure. Such administration encompasses co-administration of these therapeutic agents in a substantially simultaneous manner, such as administering a single formulation having a fixed ratio of therapeutic agents or in separate formulations (e.g., capsules and/or intravenous formulations) for each therapeutic agent. In addition, such administration also encompasses use of each type of therapeutic agent in a sequential or separate manner, either at approximately the same time or at different times. Such administration also encompasses each component being formulated as a separate formulation that can be administered at different times and/or through different administration routes. In any case, the treatment regimen of the combination therapy will provide beneficial therapeutic effects in treating the conditions or disorders described herein.

As used herein, the term "co-administering," or "co-administration," and the like refers to the act of administering two or more therapeutic agents (e.g., an immunoconjugate and an immune checkpoint modulator), compounds, therapies, or the like, at or about the same time. Co-administering may refer to simultaneous administration, where the different therapeutic agents of the present disclosure, e.g., an immunoconjugate, T cell agonists, immune checkpoint modulators, or other chemotherapeutics, may be combined into the same formulation, or formulated separately for simultaneous administration to a subject. Co-administering may also refer to sequential administration. The order or sequence of administering the different therapeutic agents of the invention, e.g., an immunoconjugate, T cell agonists, immune checkpoint modulators, or other chemotherapeutics may vary and is not confined to any particular sequence. Co-administering may also refer to the situation where two or more agents are administered to different regions of the body or via different delivery schemes, e.g., where a first agent is administered systemically and a second agent is administered intratumorally, or where a first agent is administered intratumorally and a second agent is administering systemically into the blood or proximally to the tumor. Co-administering may also refer to two or more agents administered via the same delivery scheme, e.g., where a first agent is administered intratumorally and a second agent is administered intratumorally.

"Intratumoral injection" refers to administration of an agent as provided herein directly into the tumor cellular mass and/or the tumor microenvironment. As used herein, tumor microenvironment includes the neoplasia milieu that creates a structural and/or functional environment for the neoplastic process to survive, expand, or spread. A tumor microenvironment is constituted by the cells, molecules, fibroblasts, extracellular matrix and blood vessels that surround and feed one or more neoplastic cells forming the tumor. Examples of cells or tissues in the tumor microenvironment include, but are not limited to, tumor vasculature, tumor infiltrating lymphocytes, fibroblast reticular cells, endothelial progenitor cells (EPC), cancer-associated fibroblasts, pericytes, other stromal cells, components of the extracellular matrix (ECM), dendritic cells, antigen presenting cells, T-cells, regulatory T-cells, macrophages, neutrophils, and other immune cells located proximal to a tumor. Examples of cellular functions affecting the tumor microenvironment include, but are not limited to, production of cytokines and/or chemokines, response to cytokines, antigen processing and presentation of peptide antigen, regulation of leukocyte chemotaxis and migration, regulation of gene expression, complement activation, regulation of signaling pathways, cell-mediated cytotoxicity, cell-mediated immunity, humoral immune responses, and other innate or adaptive immune responses. Measuring the effect of modulating of these cellular functions The terms "subject," "patient," "individual" and the like are used interchangeably herein, and refer to any animal or cells thereof whether in vitro or in vivo, amendable to the methods provided herein. In certain non-limiting embodiments, the patient, subject or individual is a mammal, such as a human, or other animals, such as wild animals (such as herons, storks, cranes, etc.), livestock (such as ducks, geese, etc.) or experimental animals (such as orangutans, monkeys, rats, mice, rabbits, guinea pigs, marmots, ground squirrels, etc.).

The term "survival" as used in the context of cancer includes any of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The invention provides immunomodulating (e.g., immunostimulating) polynucleotides and conjugates containing a targeting moiety and one or more immunomodulating (e.g., immunostimulating) polynucleotides. The immunomodulating polynucleotides may contain a 5-modified uridine or 5-modified cytidine. The inclusion of 5-modified uridine (e.g., 5-ethynyl-uridine) at the 5'-terminus of the immunomodulating polynucleotides (e.g., among the two 5'-terminal nucleosides) may enhance the immunomodulating properties of the polynucleotides. The immunomodulating polynucleotides may be shorter (e.g., contain a total of from 6 to 16 nucleotides or from 12 to 14 nucleotides) than typical CpG ODNs, which are 18 to 28 nucleotides in length. The shorter immunomodulating polynucleotides of the invention (e.g., those containing a total of from 6 to 16 nucleotides or from 12 to 14 nucleotides) may retain immunomodulating activity of the longer, typical CpG ODNs and may exhibit higher immunomodulating activity (e.g., as measured by NFκB activation or by the changes in the expression levels of at least one cytokine (e.g., IL-6 or IL-10), as compared to longer CpG ODNs. Advantageously, the shorter immunomodulating polynucleotides are easier and more economical to prepare, as their synthesis would involve fewer polynucleotide synthesis steps than the synthesis of a full length, typical CpG ODN. The immunomodulating polynucleotides may contain one or more abasic spacers and/or internucleoside phosphotriesters.

The immunomodulating polynucleotides of the invention may exhibit stability (e.g., stability against nucleases) that is superior to that of CpG ODNs containing mostly internucleoside phosphate (e.g., more than 50% of internucleoside phosphates) without substantially sacrificing their immunostimulating activity. This effect can be achieved, e.g., by incorporating at least 50% (e.g., at least 70%) internucleoside phosphorothioates or phosphorodithioates or through the inclusion of internucleoside phosphotriesters and/or internucleoside abasic spacers. Phosphotriesters and abasic spacers are also convenient for conjugation to a targeting moiety. Phosphate-based phosphotriesters and abasic spacers may also be used for reduction of off-target activity, relative to polynucleotides with fully phosphorothioate backbones. Without wishing to be bound by theory, this effect may be achieved by reducing self-delivery without disrupting targeting moiety-mediated delivery to target cells. Accordingly, a polynucleotide of the invention can include 15 or fewer contiguous internucleoside phosphorothioates (e.g., 14 or fewer, 13 or fewer, 12 or fewer, 11 or fewer, or 10 or fewer contiguous internucleoside phosphorothioates). For example, an immunostimulating polynucleotide containing a total of from 12 to 16 nucleosides may contain 10 or fewer contiguous internucleoside phosphorothioates.

The immunostimulating polynucleotide of the invention can contain a total of 50 or fewer nucleosides (e.g., 30 or fewer, 28 or fewer, or 16 or fewer nucleosides). The immunostimulating polynucleotide of the invention can contain a total of at least 6 nucleosides (e.g., 10 or more or 12 or more nucleosides). For example, the immunostimulating polynucleotide of the invention can contain a total of from 6 to 30 nucleosides (e.g., a total of from 6 to 28 nucleosides, a total of from 6 to 20 nucleosides, a total of from 6 to 16 nucleosides, a total of from 10 to 20 nucleosides, a total of from 10 to 16 nucleosides, a total of from 12 to 28 nucleosides, a total of from 12 to 20 nucleosides, or a total of from 12 to 16 nucleosides).

The immunostimulating polynucleotide the invention can include one or more phosphotriesters (e.g., internucleoside phosphotriesters) and/or phosphorothioates (e.g., from 1 to 6 or from 1 to 4), e.g., at one or both termini (e.g., within the six 5'-terminal nucleosides or the six 3'-terminal nucleosides). The inclusion of one or more internucleoside phosphotriesters and/or phosphorothioates can enhance the stability of the polynucleotide by reducing the rate of exonuclease-mediated degradation.

In certain embodiments, the immunostimulating polynucleotide of the invention contains a phosphotriester or a terminal phosphodiester, where the phosphotriester or the terminal phosphodiester includes a linker bonded to a targeting moiety or a conjugating group and optionally to one or more (e.g., 1 to 6) auxiliary moieties. In particular embodiments, the immunostimulating polynucleotide contains only one linker. In some embodiments, the immunostimulating polynucleotide contains only one conjugating group.

The polynucleotide of the invention (e.g., immunostimulating polynucleotide) can be a hybridized polynucleotide including a strand and its partial or whole complement. The hybridized polynucleotides can have at least 6 complementary base pairings (e.g., 6, 7, 8, 9, 10, 11, 12, 13, 14, 15, 16, 17, 18, 19, 20, 21, 22, or 23), up to the total number of the nucleotides present in the included shorter strand. For example, the hybridized portion of the hybridized polynucleotide may contain 6, 7, 8, 9, 10, 11, 12, 13, 14, 15, 16, 17, 18, 19, 20, 21, 22, or 23 base pairs.

Conjugates of the invention contain a targeting moiety and one or more immunomodulating (e.g., immunostimulating) polynucleotides (e.g., from 1 to 6 or from 1 to 4 (e.g., 1 or 2) immunomodulating (e.g., immunostimulating) polynucleotides). In the conjugates, each of the immunomodulating polynucleotides includes independently a linker. A targeting moiety is covalently bonded to the linker. The linker may be bonded to a nucleobase, abasic spacer, phosphate, phosphorothioate, or phosphorodithioate in the immunomodulating polynucleotide. The cells targeted by the conjugates of the invention are professional APCs (e.g., B cells, pDCs, or macrophages). The targeting moiety can be an antigen-binding moiety (e.g., an antibody or antigen-binding fragment thereof), a polypeptide, an aptamer, or a group including one or more small molecules (e.g., mannose). In the conjugates of the invention, a targeting moiety may be an antibody or antibody fragment. A conjugate of the invention can contain an antibody or an antibody fragment and one or more immunomodulating polynucleotides covalently linked to a Q-tag in the antibody or the antibody fragment. The Q-tag may be N-terminal or C-terminal. The Q-tag may be disposed in the heavy or light chain of the antibody or the antibody fragment. The use of targeting moiety-based delivery of the immunomodulating polynucleotides of the invention to specifically targeted tissues and cells may overcome the disadvantages of the typically uneven distribution of immunomodulating polynucleotides in vivo. Further, the targeting moiety-based delivery of the immunomodulating polynucleotides of the invention may be advantageous to systemic administration or to administration to a target tissue of immunomodulating polynucleotides, as systemic administration and the administration to a target tissue may produce an undesirable distribution of the immunomodulating polynucleotides through blood circulation in vivo, whereas a conjugate of the invention may undergo the intracellular delivery predominantly at the target tissue or cells, even when systemically administered. The distribution-related advantages may be particularly pronounced in conjugates containing short immunomodulating polynucleotide(s) (e.g., immunomodulating polynucleotides containing a total of 6 to 16 nucleosides (e.g., a total of 10 to 16 or 12 to 16 nucleosides)).

The conjugates of the invention may further contain one or more (e.g., from 1 to 6) auxiliary moieties (e.g., polyethylene glycols (PEGs)). The auxiliary moiety may be a part of a capping group, bioreversible group, or non-bioreversible group. The auxiliary moieties may be bonded to the linkers (e.g., to the linkers bonded to phosphates, phosphorothioates, or phosphorodithioates in the immunomodulating (e.g., immunostimulating) polynucleotides). Inclusion of the auxiliary moieties (e.g., PEGs) in the conjugates of the invention may improve pharmacokinetic and/or biodistribution properties of the conjugates relative to a reference conjugate lacking such auxiliary moieties.

One or more of the immunomodulating polynucleotides of the invention can be conjugated to a targeting moiety (e.g., an antigen-binding moiety) that targets an antigen-presenting cell (APC; e.g., a professional APC (e.g., B-cell, pDC, or macrophage)). Delivery of the immunomodulating polynucleotides of the invention or conjugates of the invention to a cell (e.g., an antigen-presenting cell (APC; e.g., a professional APC (e.g., B-cell, pDC, or macrophage))) containing an endosomal toll-like receptor (e.g., TLR9) may be used to agonize (for immunostimulating polynucleotides) or antagonize (for immune suppressive polynucleotides) the endosomal toll-like receptor in the cell. Without being bound by theory, activation of an endosomal toll-like receptor can induce proinflammatory cytokines (e.g., IL-6, IL-10, and/or type I interferon); this activity is believed to be useful for the treatment of various tumors (e.g., solid and liquid tumors in a patient).

In one embodiment, provided herein is an oligonucleotide of Formula (A):

$$X^{5'}-(X^N)_b-Y^P-(X^N)_c-X^{3'} \qquad (A)$$

or a stereoisomer, a mixture of two or more diastereomers, a tautomer, or a mixture of two or more tautomers thereof; or a pharmaceutically acceptable salt, solvate, or hydrate thereof; wherein:
each $X^N$ is independently a nucleotide;
$X^{3'}$ is a 3' terminal nucleotide;
$X^{5'}$ is a 5' terminal nucleotide;
$Y^P$ is an internucleoside phosphotriester; and
b and c are each an integer ranging from about 0 to about 25; with the proviso that their sum is no less than 5;

wherein the oligonucleotide comprises a nucleotide with a modified nucleobase.

In certain embodiments, b is an integer ranging from about 1 to about 15. In certain embodiments, b is an integer of about 1, about 2, about 3, about 4, about 5, about 6, about 7, about 8, about 9, about 10, about 11, about 12, about 13, about 14, or about 15. In certain embodiments, b is an integer of about 3, about 4, about 11, or about 14. In certain embodiments, b is an integer of about 3. In certain embodiments, b is an integer of about 4. In certain embodiments, b is an integer of about 11. In certain embodiments, b is an integer of about 14.

In certain embodiments, c is an integer ranging from about 0 to about 10. In certain embodiments, c is an integer of about 0, about 1, about 2, about 3, about 4, about 5, about 6, about 7, about 8, about 9, or about 10. In certain embodiments, c is an integer of about 0 or about 8. In certain embodiments, c is an integer of about 0. In certain embodiments, c is an integer of about 8.

In certain embodiments, b is an integer of about 3 and c is an integer of about 8. In certain embodiments, b is an integer of about 4 and c is an integer of about 8. In certain embodiments, b is an integer of about 11 and c is an integer of about 0. In certain embodiments, b is an integer of about 14 and c is an integer of about 0.

In certain embodiments, b and c together in total are ranging from about 5 to about 20. In certain embodiments, b and c together in total ranging from about 5 to about 15. In certain embodiments, b and c together in total are about 5, about 6, about 7, about 8, about 9, about 10, about 11, about 12, about 13, about 14, or about 15. In certain embodiments, b and c together in total are about 8, about 9, about 10, about 11, about 12, about 13, or about 14. In certain embodiments, b and c together in total are about 11. In certain embodiments, b and c together in total are about 12. In certain embodiments, b and c together in total are about 14.

In certain embodiments, each $X^N$ is independently a 2'-deoxyribonucleotide or a 23-modified ribonucleotide. In certain embodiments, each $X^N$ is independently 2'-deoxyadenosine (A), 23-deoxyguanosine (G), 2'-deoxycytidine (C), a 5-halo-2'-deoxycytidine, 2'-deoxythymidine (T), 23-deoxyuridine (U), a 5-halo-2'-deoxyuridine, a 2'-fluororibonucleotide, a 2'-methoxyribonucleotide, or a 23-(2-methoxyethoxy)ribonucleotide. In certain embodiments, each $X^N$ is independently a 23-deoxyribonucleotide. In certain embodiments, each $X^N$ is independently 2'-deoxyadenosine, 23-deoxyguanosine, 2'-deoxycytidine, a 5-halo-2'-deoxycytidine, 2'-deoxythymidine, 2'-deoxyuridine, or a 5-halo-2'-deoxyuridine. In certain embodiments, each $X^N$ is each $X^N$ is independently 2'-deoxyadenosine, 2'-deoxyguanosine, 2'-deoxycytidine, 2'-deoxythymidine, 5-bromo-2'-deoxyuridine, or 5-iodo-2'-deoxyuridine.

In certain embodiments, $X^{3'}$ is a 2'-deoxyribonucleotide or a 2'-modified ribonucleotide. In certain embodiments, $X^{3'}$ is a 2'-deoxyribonucleotide. In certain embodiments, $X^{3'}$ is 2'-deoxyadenosine, 2'-deoxyguanosine, 2'-deoxycytidine, a 5-halo-2'-deoxycytidine, 2'-deoxythymidine, 2'-deoxyuridine, a 5-halo-2'-deoxyuridine, a 2'-fluororibonucleotide, a 2'-methoxyribonucleotide, or a 2'-(2-methoxyethoxy)ribonucleotide. In certain embodiments, $X^{3'}$ is 2'-deoxyadenosine, 2'-deoxyguanosine, 23-deoxycytidine, a 5-halo-2'-deoxycytidine, 2'-deoxythymidine, 2'-deoxyuridine, or a 5-halo-2'-deoxyuridine. In certain embodiments, $X^{3'}$ is 2'-deoxythymidine. In certain embodiments, $X^{3'}$ is a 2'-deoxyribonucleotide with a substituted pyrimidine base. In certain embodiments, $X^{3'}$ is a 2'-deoxyribonucleotide with a 5-substituted pyrimidine base. In certain embodiments, $X^{3'}$ is 2'-deoxythymidine, a 5-halo-2'-deoxycytidine, or a 5-halo-2'-deoxyuridine. In certain embodiments, $X^{3'}$ is 2'-deoxythymidine, 5-bromo-2'-deoxycytidine, 5-iodo-2'-deoxycytidine, 5-bromo-2'-deoxyuridine, or 5-iodo-2'-deoxyuridine. In certain embodiments, $X^{3'}$ is 2'-deoxythymidine, 5-bromo-2'-deoxyuridine, or 5-iodo-2'-deoxyuridine. In certain embodiments, $X^{3'}$ is a terminal nucleotide comprising a 3' capping group. In certain embodiments, the 3' capping group is a terminal phosphoester. In certain embodiments, the 3' capping group is 3-hydroxyl-propylphosphoryl (i.e., $-P(O_2)-CH_2CH_2CH_2OH$).

In certain embodiments, $X^{5'}$ is a 2'-deoxyribonucleotide or a 2'-modified ribonucleotide. In certain embodiments, $X^{5'}$ is a 2'-deoxyribonucleotide. In certain embodiments, $X^{5'}$ is 2'-deoxyadenosine, 2'-deoxyguanosine, 2'-deoxycytidine, a 5-halo-2'-deoxycytidine, 2'-deoxythymidine, 2'-deoxyuridine, a 5-halo-2'-deoxyuridine, a 2'-fluororibonucleotide, a 2'-methoxyribonucleotide, or a 2'-(2-methoxyethoxy)ribonucleotide. In certain embodiments, $X^{5'}$ is 2'-deoxyadenosine, 2'-deoxyguanosine, 23-deoxycytidine, a 5-halo-2'-deoxycytidine, 2'-deoxythymidine, 2'-deoxyuridine, or a 5-halo-2'-deoxyuridine. In certain embodiments, $X^{5'}$ is a 2'-deoxyribonucleotide with a substituted pyrimidine base. In certain embodiments, $X^{5'}$ is a 2'-deoxyribonucleotide with a 5-substituted pyrimidine base. In certain embodiments, $X^{5'}$ is 2'-deoxythymidine, a 5-halo-2'-deoxycytidine, or a 5-halo-2'-deoxyuridine. In certain embodiments, $X^{5'}$ is a 5-halo-2'-deoxycytidine. In certain embodiments, $X^{5'}$ is a 5-halo-2'-deoxyuridine. In certain embodiments, $X^{5'}$ is 2'-deoxythymidine, 5-bromo-2'-deoxycytidine, 5-iodo-2'-deoxycytidine, 5-bromo-2'-deoxyuridine, or 5-iodo-2'-deoxyuridine. In certain embodiments, $X^{5'}$ is 2'-deoxythymidine, 5-bromo-2'-deoxyuridine, or 5-iodo-2'-deoxyuridine. In certain embodiments, $X^{5'}$ is 5-bromo-2'-deoxyuridine. In certain embodiments, $X^{5'}$ is 5-iodo-2'-deoxyuridine. In certain embodiments, $X^{5'}$ has a 3'-phosphorothoate group. In certain embodiments, $X^{5'}$ has a 3'-phosphorothoate group with a chirality of Rp. In certain embodiments, $X^{5'}$ has a 3'-phosphorothoate group with a chirality of Sp.

In certain embodiments, $Y^P$ is an internucleoside phosphothiotriester.

In certain embodiments, $Y^P$ is:

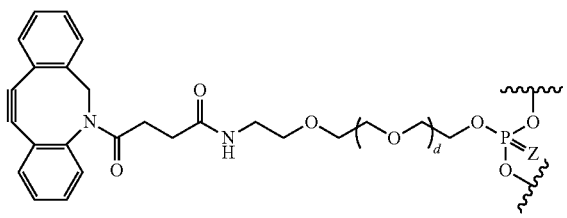

wherein Z is O or S; and d is an integer ranging from about 0 to about 50. In certain embodiments, Z is O. In certain embodiments, Z is S. In certain embodiments, d is an integer ranging from about 0 to about 10. In certain embodiments, d is an integer ranging from about 0 to about 5. In certain embodiments, d is an integer of about 0, about 1, about 2, about 3, about 4, or about 5. In certain embodiments, d is an integer of about 0, about 1, or about 3.

In certain embodiments, $Y^P$ is:

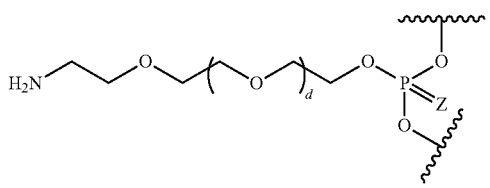

wherein Z is O or S; and d is an integer ranging from about 0 to about 50. In certain embodiments, Z is O. In certain embodiments, Z is S. In certain embodiments, d is an integer ranging from about 0 to about 10. In certain embodiments, d is an integer ranging from about 0 to about 5. In certain embodiments, d is an integer of about 0, about 1, about 2, about 3, about 4, or about 5. In certain embodiments, d is an integer of about 0, about 1, or about 3.

In certain embodiments, the oligonucleotide of Formula (A) comprises one additional internucleoside phosphotriester. In one embodiment, the additional internucleoside phosphotriester is a $C_{1-6}$ alkylphosphotriester. In another embodiment, the additional internucleoside phosphotriester is ethylphosphotriester.

In certain embodiments, the oligonucleotide of Formula (A) comprises one 5-halo-2'-deoxyuridine. In one embodiment, the 5-halo-2'-deoxyuridine is 5-fluoro-2'-deoxyuridine, 5-bromo-2'-deoxyuridine, or 5-iodo-2'-deoxyuridine. In another embodiment, the 5-halo-2'-deoxyuridine is 5-bromo-2'-deoxyuridine or 5-iodo-2'-deoxyuridine. In yet another embodiment, the 5-halo-2'-deoxyuridine is 5-fluoro-2'-deoxyuridine. In yet another embodiment, the 5-halo-2'-deoxyuridine is 5-bromo-2'-deoxyuridine. In still another embodiment, the 5-halo-2'-deoxyuridine is 5-iodo-2'-deoxyuridine.

In certain embodiments, the oligonucleotide of Formula (A) comprises three or more 2'-deoxycytidines. In certain embodiments, the oligonucleotide of Formula (A) comprises three 23-deoxycytidines.

In certain embodiments, the oligonucleotide of Formula (A) comprises four or more 2'-deoxyguanosines. In certain embodiments, the oligonucleotide of Formula (A) comprises four 2'-deoxyguanosines.

In certain embodiments, the oligonucleotide of Formula (A) comprises three 2'-deoxycytidines and four 2'-deoxyguanosines. In certain embodiments, the oligonucleotide of Formula (A) comprises one, two, or three CG dinucleotides. In certain embodiments, the oligonucleotide of Formula (A) comprises three CG dinucleotides.

In certain embodiments, the oligonucleotide of Formula (A) comprises three or more 2'-deoxythymidines. In certain embodiments, the oligonucleotide of Formula (A) comprises three, four, five, six, seven, or eight 2'-deoxythymidines. In certain embodiments, the oligonucleotide of Formula (A) comprises three, four, five, or eight 2'-deoxythymidines.

In certain embodiments, the oligonucleotide of Formula (A) does not comprise a 23-deoxyadenosine. In certain embodiments, the oligonucleotide of Formula (A) comprises one or two 23-deoxyadenosines.

In certain embodiments, the oligonucleotide of Formula (A) has a length ranging from about 5 to about 20 or from about 6 to about 15 nucleotides. In certain embodiments, the oligonucleotide of Formula (A) has a length of about 6, about 7, about 8, about 9, about 10, about 11, about 12, about 13, about 14, or about 15. In certain embodiments, the oligonucleotide of Formula (A) has a length of about 10, about 11, about 12, about 13, about 14, or about 15.

In certain embodiments, the oligonucleotide of Formula (A) comprises one or more internucleoside phosphorothioates. In certain embodiments, all the internucleoside phosphoesters in the oligonucleotide of Formula (A) are internucleoside phosphorothioates. In certain embodiments, the oligonucleotide of Formula (A) comprises one or more chiral internucleoside phosphorothioates.

In certain embodiments, the oligonucleotide of Formula (A) is p275, p276, p313, or p347. In certain embodiments, the oligonucleotide of Formula (A) is p236, p238, p243, p246, p308, p361, p362, or p425. In certain embodiments, the oligonucleotide of Formula (A) is p236, p238, p243, p246, p275, p276, p308, p313, p347, p361, p362, p425, p433, p434, p435, p436, p437, p438, p477, p478, p479, p480, p481, p482, p483, p484, p485, p486, p487, p488, or p489.

In certain embodiments, the oligonucleotide of Formula (A) is an immunomodulating oligonucleotide.

In one embodiment, provided herein is an oligonucleotide having a sequence of $N^1N^2CGN^3CG(T)_xGN^4CGN^5T$(SEQ ID NO: 497), or a stereoisomer, a mixture of two or more diastereomers, a tautomer, or a mixture of two or more tautomers thereof; or a pharmaceutically acceptable salt, solvate, or hydrate thereof; wherein:

x is an integer ranging from 1 to 4;

$N^1$ is absent or 2'-deoxythymidine;

$N^2$ is a 2'-deoxyribonucleotide with a modified nucleobase;

$N^3$ is 2'-deoxyadenosine or 2'-deoxythymidine, each optionally comprising a 3'-phosphotriester;

$N^4$ is 2'-deoxyadenosine or 2'-deoxythymidine;

$N^5$ is 2'-deoxythymidine optionally comprising a 3'-phosphotriester; and

C is 2'-deoxycytidine and G is 2'-deoxyguanosine.

In certain embodiments, in $N^1N^2CGN^3CG(T)_xGN^4CGN^5T$(SEQ ID NO: 497), x is an integer of 1, 2, 3, or 4. In certain embodiments, in $N^1N^2CGN^3CG(T)_xGN^4CGN^5T$(SEQ ID NO: 497), x is an integer of 1. In certain embodiments, in $N^1N^2CGN^3CG(T)_xGN^4CGN^5T$(SEQ ID NO: 497), x is an integer of 4.

In certain embodiments, in $N^1N^2CGN^3CG(T)_xGN^4CGN^5T$(SEQ ID NO: 497), $N^1$ is absent. In certain embodiments, in $N^1N^2CGN^3CG(T)_xGN^4CGN^5T$(SEQ ID NO: 497), $N^1$ is 2'-deoxythymidine.

In certain embodiments, in $N^1N^2CGN^3CG(T)_xGN^4CGN^5T$(SEQ ID NO: 497), $N^2$ is a 2'-deoxyribonucleotide with a substituted pyrimidine base. In certain embodiments, in $N^1N^2CGN^3CG(T)_xGN^4CGN^5T$(SEQ ID NO: 497), $N^2$ is a 2'-deoxyribonucleotide with a 5-substituted pyrimidine base. In certain embodiments, in $N^1N^2CGN^3CG(T)_xGN^4CGN^5T$(SEQ ID NO: 497), $N^2$ is a 5-halo-2'-deoxycytidine or a 5-halo-2'-deoxyuridine. In certain embodiments, in $N^1N^2CGN^3CG(T)_xGN^4CGN^5T$(SEQ ID NO: 497), $N^2$ is 5-bromo-2'-deoxyuridine or 5-iodo-2'-deoxyuridine.

In certain embodiments, in $N^1N^2CGN^3CG(T)_xGN^4CGN^5T$(SEQ ID NO: 497), $N^3$ is 2'-deoxyadenosine comprising a 3'-phosphotriester. In certain embodiments, in $N^1N^2CGN^3CG(T)_xGN^4CGN^5T$(SEQ ID NO: 497), $N^3$ is 2'-deoxythymidine. In certain embodiments, in $N^1N^2CGN^3CG(T)_xGN^4CGN^5T$(SEQ ID NO: 497), $N^3$ is 2'-deoxythymidine comprising a 3'-phosphotriester.

In certain embodiments, in $N^1N^2CGN^3CG(T)_xGN^4CGN^5T$(SEQ ID NO: 497), $N^4$ is 2'-deoxyadenosine. In certain embodiments, in N¹N²CGN³CG(T)$_x$GN⁴CGN⁵T(SEQ ID NO: 497), N⁴ is 2'-deoxythymidine.

In certain embodiments, in N¹N²CGN³CG(T)$_x$GN⁴CGN⁵T(SEQ ID NO: 497), N⁵ is 2'-deoxythymidine. In certain embodiments, in N¹N²CGN³CG(T)$_x$GN⁴CGN⁵T(SEQ ID NO: 497), N⁵ is 2'-deoxythymidine comprising a 3'-phosphotriester.

In certain embodiments, the oligonucleotide of N¹N²CGN³CG(T)$_x$GN⁴CGN⁵T comprises one or more internucleoside phosphorothioates. In certain embodiments, the oligonucleotide of N¹N²CGN³CG(T)$_x$GN⁴CGN⁵T(SEQ ID NO: 497) comprises at least one chiral internucleoside phosphorothioates.

In certain embodiments, the oligonucleotide of N¹N²CGN³CG(T)$_x$GN⁴CGN⁵T(SEQ ID NO: 497) is p275, p276, or p313. In certain embodiments, the oligonucleotide of N¹N²CGN³CG(T)$_x$GN⁴CGN⁵T(SEQ ID NO: 497) is p236, p238, p243, p246, p308, p361, p362, or p425. In certain embodiments, the oligonucleotide of N¹N²CGN³CG(T)$_x$GN⁴CGN⁵T(SEQ ID NO: 497) is p236, p238, p243, p246, p275, p276, p308, p313, p347, p361, p362, p425, p433, p434, p435, p436, p437, p438, p477, p478, p479, p480, p481, p482, p483, p484, p485, p486, p487, p488, or p489.

Immunostimulating Polynucleotides

Immunostimulating polynucleotides of the invention can function as PAMPs and can activate innate immune response or stimulate adaptive immune response by triggering TLR9 signaling (e.g., as TLR9 agonists). The sequences that may be used in the immunostimulating polynucleotides of the invention are those known in the art for class B CpG polynucleotides, or their modifications including 5-halouridine or 5-alkynyluridine, or truncated versions thereof (e.g., those containing a total of 6 to 16 nucleosides). The truncated immunostimulating polynucleotides of the invention (e.g., those containing a total of from 6 to 16 nucleosides) may contain a truncated class B CpG polynucleotide sequence (e.g., a class B CpG polynucleotide sequence, from which one or more 3'-terminal nucleotides are eliminated or one or more of the intra-sequence nucleotides excised).

The immunostimulating polynucleotide of the invention contains at least one immunostimulating sequence (ISS). For example, an immunostimulating polynucleotide of the invention can contain 1, 2, 3 or 4 ISS. The ISS in immunostimulating polynucleotides is dependent on the targeted organism. The common feature of the ISS used in the immunostimulating polynucleotides of the invention is the cytidine-p-guanosine sequence, in which p is an internucleoside phosphodiester (e.g., phosphate or phosphorothioate) or an internucleoside phosphotriester. Preferably, cytidine and guanosine in the ISS contain 2'-deoxyribose. In some embodiments, the immunostimulating polynucleotide of the invention contains 1, 2, or 3 human ISSs. For example, the human ISS can be CG or NCG, where N is uridine, cytidine, or thymidine, or a modified version of uridine or cytidine, as disclosed herein (e.g., a 5-halouridine (e.g., 5-iodouridine or 5-bromouridine), a 5-alkynyluridine (e.g., 5-ethynyluridine or 5-propynyluridine), 5-heteroaryluridine, or 5-halocytidine); and G is guanosine or a modified version thereof, as disclosed herein (e.g., 7-deazaguanosine). Preferably, the human ISS is NCG (e.g., where N is 5-halouridine). In some embodiments, the human ISS is UCG (e.g., where U is 5-alkynyluridine (e.g., 5-ethynyluridine)). Preferably, an immunostimulating polynucleotide of the invention targeting humans contains an ISS within four contiguous nucleotides that include a 5'-terminal nucleotide (e.g., an immunostimulating polynucleotide of the invention contains a 5'-terminal ISS). Murine ISS is a hexameric nucleotide sequence: Pu-Pu-CG-Py-Py, where each Pu is independently a purine nucleotide, and each Py is independently a pyrimidine nucleotide.

In some embodiments, the 5'-flanking nucleotides relative to CpG in the immunostimulating polynucleotides of the invention does not contain 2'-alkoxyriboses. Preferably, the 5'-flanking nucleotides relative to CpG in the immunostimulating polynucleotides of the invention contains only 2'-deoxyriboses as sugars.

The structural features of the immunostimulating polynucleotides of the invention may include: (1) high content of phosphorothioates (e.g., at least 50%, at least 60%, at least 70%, or at least 80% of nucleosides may be linked by phosphorothioates), (2) absence of poly-G tails, (3) nucleosides in the immunostimulating polynucleotides may contain 2'-deoxyriboses or 2'-modified riboses (e.g., 2'-halo (e.g., 2'-fluoro) or optionally substituted 2'-alkoxy (e.g., 2'-methoxy)), and/or (4) the inclusion of 5'-terminal ISS that is NCG, in which N is uridine, cytidine, or thymidine, or a modified version of uridine or cytidine, as disclosed herein (e.g., a 5-halouridine (e.g., 5-iodouridine or 5-bromouridine), a 5-alkynyluridine (e.g., 5-ethynyluridine or 5-propynyluridine), 5-heteroaryluridine, or 5-halocytidine); and G is guanosine or a modified version thereof, as disclosed herein (e.g., 7-deazaguanosine).

In some embodiments, the conjugate contains one targeting moiety (e.g., an antibody or antigen-binding fragment thereof) and one immunomodulating polynucleotide covalently linked to the targeting moiety.

Immunosuppressive Polynucleotides

A polynucleotide of the invention can suppress adaptive immune response by reducing activation of TLR9 signaling (e.g., through TLR9 antagonism). In some embodiments, immunosuppressive polynucleotides of the invention include at least two 2'-alkoxynucleotides that are 5'-flanking relative to CpG, as described by the following formula: N¹—N²—CG, where each of N¹ and N² is independently a nucleotide containing 2'-alkoxyribose (e.g., 2'-methoxyribose).

Structural Features of the Polynucleotides

Abasic Spacers

The immunomodulating polynucleotides disclosed herein may include one or more (e.g., one or two) abasic spacers (e.g., internucleoside abasic spacers and/or terminal abasic spacers). When the immunomodulating polynucleotide includes two or more of the abasic spacers, the structures of the abasic spacers may be same or different.

An abasic spacer is of formula (I):

$$R^1\text{-}L^1\text{-}[\text{-}L^2\text{-}(L^1)_{n1}\text{-}]_{n2}\text{-}R^2, \qquad (I)$$

where n1 is 0 or 1, n2 is an integer from 1 to 6,

R¹ is a bond to a nucleoside in the immunomodulating polynucleotide,

R² is a bond to a nucleoside in the immunomodulating polynucleotide or to a capping group, each L¹ is independently a phosphodiester or a phosphotriester, and each L² is a sugar analogue.

In particular embodiments, if the abasic spacer is an internucleoside, abasic spacer, n1 is 1, and R² is a bond to a nucleoside, and if the abasic spacer is a terminal, abasic spacer, n1 is 0 or 1, and R² is a bond to a capping group.

In some embodiments, the abasic spacer is an internucleoside, abasic spacer or a 3'-terminal, abasic spacer. In certain embodiments, each two contiguous $L^2$ groups are separated by $L^1$ groups (e.g., n1 is 1 for $L^1$ disposed between two contiguous $L^2$ groups).

In certain embodiments, the immunostimulating polynucleotide contains an ISS disposed within four contiguous nucleotides that include a 5'-terminal nucleotide of the immunostimulating polynucleotide, where the ISS is NCG, where N is uridine, cytidine, or thymidine, or a modified version of uridine orcytidine, as disclosed herein (e.g., a 5-halouridine (e.g., 5-iodouridine or 5-bromouridine), a 5-alkynyluridine (e.g., 5-ethynyluridine or 5-propynyluridine), 5-heteroaryluridine, or 5-halocytidine), and where N and C are linked to each other through a phosphodiester or phosphotriester.

Sugar Analogues

A sugar analogue is a divalent or trivalent group that is a $C_{3-6}$ monosaccharide or $C_{3-6}$ alditol (e.g., glycerol), which is modified to replace two hydroxyl groups with bonds (i) to an oxygen atom in one phosphoester and (ii) to an oxygen atom in another phosphoester or to a capping group. A sugar analogue is cyclic or acyclic. Further optional modifications included in a sugar analogue are: a replacement of one, two, or three of the remaining hydroxyl groups or carbon-bonded hydrogen atoms with H; optionally substituted $C_{1-6}$ alkyl; -LinkA(-T)$_P$, as defined herein; a conjugating group; —(CH$_2$)$_{t1}$—OR$^Z$, where t1 is an integer from 1 to 6, and R$^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl; introduction of one or two unsaturation(s) (e.g., one or two double bonds); and replacement of one, two, or three hydrogens or hydroxyl groups with substituents as defined for alkyl, alkenyl, cycloalkyl, cycloalkenyl, or heterocyclyl. In some embodiments, R$^Z$ is optionally substituted $C_{1-6}$ aminoalkyl (e.g., optionally substituted $C_{1-6}$ amino alkyl containing —NH$_2$).

Non-limiting examples of sugar analogues are optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted ($C_{1-4}$ alkyl)-($C_{3-8}$ cycloalkylene) (e.g., optionally substituted ($C_1$ alkyl)-($C_3$ cycloalkylene)). Non-limiting examples of sugar analogues are:

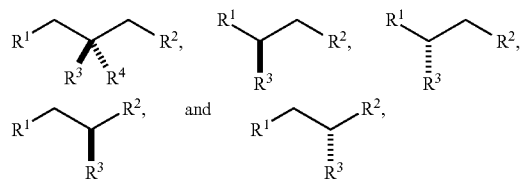

where
each of $R^1$ and $R^2$ is independently a bond to an oxygen atom in a phosphoester;

each of $R^3$ and $R^4$ is independently H; optionally substituted $C_{1-6}$ alkyl; —(CH$_2$)$_{t1}$—OR$^Z$; or -LinkA-R$^T$;

where t1 is an integer from 1 to 6;

$R^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl;

LinkA is linker; and $R^T$ is a bond to a targeting moiety; a conjugation moiety; optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl.

In certain embodiments, R$^Z$ is optionally substituted $C_{1-6}$ aminoalkyl (e.g., optionally substituted $C_{1-6}$ amino alkyl containing —NH$_2$).

Phosphoesters

The immunomodulating polynucleotides of the invention may contain one or more internucleoside phosphotriesters and/or one or two terminal phosphodiesters and/or phosphotriesters. A phosphotriester may contain a phosphate, phosphorothioate, or phosphorodithioate, in which one or two valencies are substituted with nucleosides and/or abasic spacers, and the remaining valencies are bonded to a bioreversible group, a non-bioreversible group, a linker bonded to a targeting moiety, or a conjugating group. An internucleoside phosphotriester is bonded to two nucleosides and/or abasic spacers, and the remaining valency is bonded to a bioreversible group, a non-bioreversible group, a linker bonded to a targeting moiety, or a conjugating group. An internucleoside phosphodiester is bonded to two nucleosides and/or abasic spacers. A terminal phosphodiester contains a phosphate, phosphorothioate, or phosphorodithioate at the 5'- or 3'-terminus of the immunomodulating polynucleotide, where one of the two remaining valencies is bonded to a bioreversible group, a non-bioreversible group, a linker bonded to a targeting moiety, or a conjugating group.

Linkers and Conjugation Moieties

The immunomodulating polynucleotides of the invention may contain a linker bonded to a targeting moiety and optionally one or more auxiliary moieties. The linker has a molecular weight of from 43 Da to 10 kDa (e.g., from 100 Da to 8 kDa, from 100 Da to 7 kDa, or from 100 Da to 3 kDa). The linker may be represented herein as LinkA. The linker may be a multivalent group, in which the first valency is bonded to an internucleoside or terminal phosphate, an internucleoside or terminal phosphorothioate, an internucleoside or terminal phosphorodithioate, an abasic spacer, a capping group, or a nucleobase, and a second valency is bonded to a targeting moiety. The linker may further include one or more valencies, each of which is independently bonded to an auxiliary moiety. In some embodiments (e.g., when the targeting moiety is a small molecule), the immunomodulating polynucleotide contains multiple linkers to multiple targeting moieties. In other embodiments (e.g., when the targeting moiety is an antibody or an antigen-binding fragment thereof), the immunomodulating polynucleotide may contain one linker to a targeting moiety.

The immunomodulating polynucleotides disclosed herein may include a conjugating group. A conjugating group includes at least one conjugationg moiety which is a functional group that is capable of undergoing a conjugation reaction (e.g., a cycloaddition reaction (e.g., dipolar cycloaddition), amidation reaction, or nucleophilic aromatic substitution) or is rendered capable of undergoing a conjugation reaction, upon deprotection of the functional group. Upon reaction with a complementary reactive group, the conjugating group produces the linker in the immunomodulating polynucleotide of the invention.

In particular embodiments, the linker bonded to a targeting moiety is part of an internucleoside phosphotriester. In certain embodiments, the linker bonded to a targeting moiety is part of an abasic spacer.

In some embodiments, the linker (e.g., LinkA) or a conjugating group is of formula (II):

(II)

where $Z^1$ is a divalent group, a trivalent group, a tetravalent group, or a pentavalent group, in which one of valency is bonded to $Q^{41}$, the second valency is open or, if formula (II) is for the linker, is bonded to $R^T$, and each of the remaining valencies, when present, is independently bonded to an auxiliary moiety;

$Z^2$ is absent, a divalent group, a trivalent group, a tetravalent group, or a pentavalent group, in which one of valency is bonded to $Q^{41}$, the second valency is bonded to $Q^{42}$ or $R^T$, and each of the remaining valencies, when present, is independently bonded to an auxiliary moiety;

$Z^3$ is absent, a divalent group, a trivalent group, a tetravalent group, or a pentavalent group, in which one of valency is bonded to $Q^{42}$, the second valency is bonded to $R^T$, and each of the remaining valencies, when present, is independently bonded to an auxiliary moiety;

$R^T$ is absent or a bond to a targeting moiety;

k is 0 or 1.

If formula (II) is for the linker, $Q^{41}$ and $Q^{42}$ is independently absent, optionally substituted $C_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted $C_{1-12}$ thioheterocyclylene (e.g., 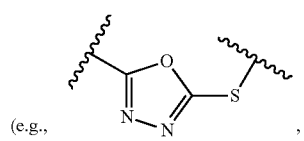,

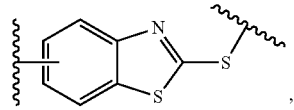 , 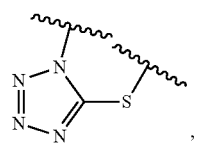 , 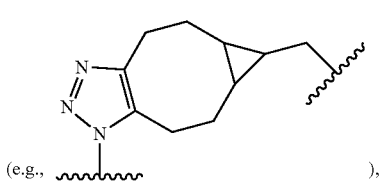), optionally substituted $C_{1-12}$ heterocyclylene (e.g., 1,2,3-triazole-1,4-diyl or

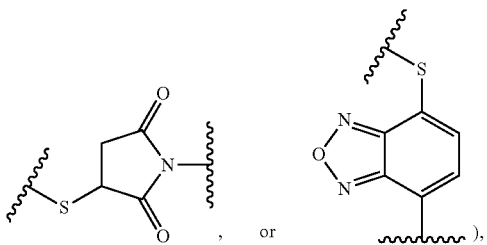), cyclobut-3-ene-1,2-dione-3,4-diyl, pyrid-2-yl hydrazone, optionally substituted $C_{6-16}$ triazoloheterocyclylene (e.g., 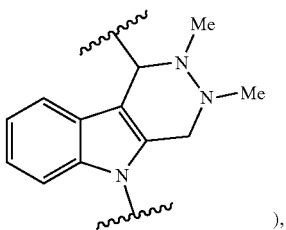 [SMILES: *C1c2c(n(*)c3ccccc23)CN(C)N1C] or

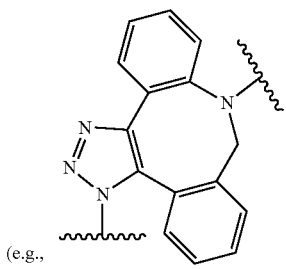), optionally substituted $C_{8-16}$ triazolocycloalkenylene (e.g., 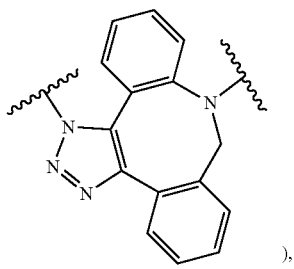), or a dihydropyridazine group

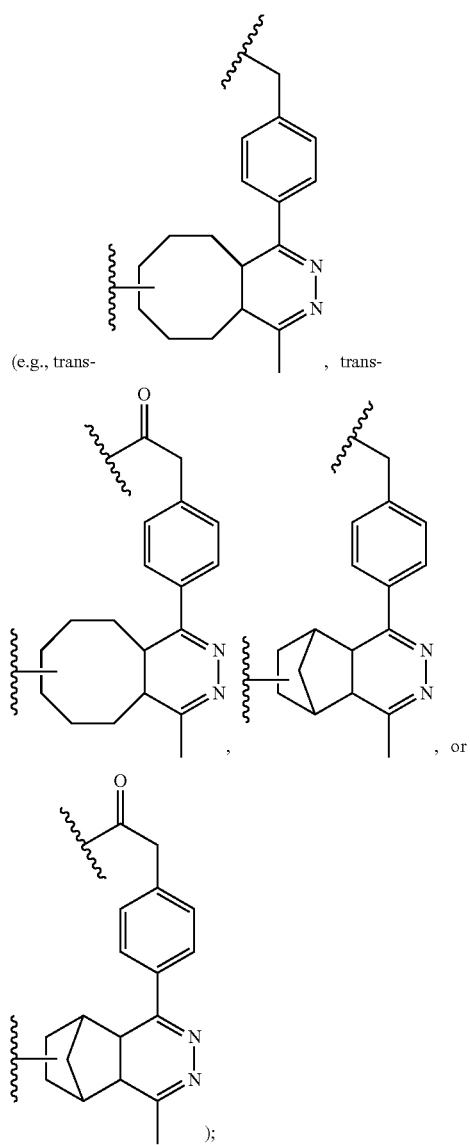

(e.g., trans-           , trans-      , or

);

and
R$^T$ is a bond to a targeting moiety;
provided that at least one of Q$^{41}$ and Q$^{42}$ is present.
If formula (II) is for a conjugating group,
either
(i) Q$^{42}$ is absent, and Q$^{41}$ is a conjugation moiety, e.g., optionally substituted C$_{2-12}$ alkynyl, optionally substituted N-protected amino, azido, N-maleimido, S-protected thiol,

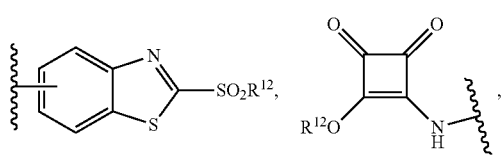

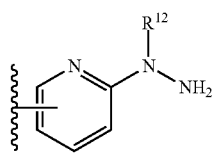

or N-protected version thereof,

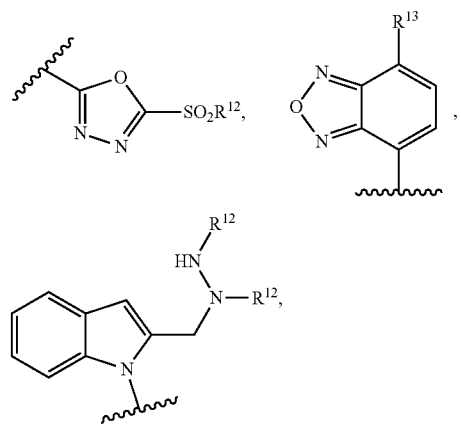

optionally substituted C$_{6-16}$ heterocyclyl containing an endocyclic carbon-carbon triple bond

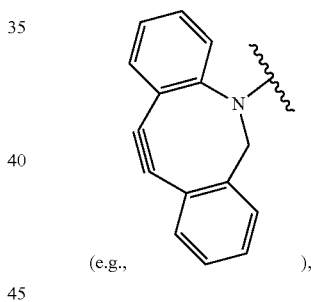

(e.g.,         ), 1,2,4,5-tetrazine group (e.g.,

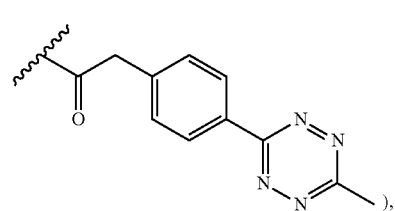

(e.g.,         or         ), or optionally substituted $C_{8-16}$ cycloalkynyl

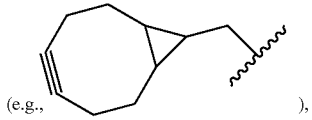 [SMILES: *CC1C2CCC#CCCC12]
(e.g., ),

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO; and k is 0;

or (ii) $Q^{41}$ is as defined for the linker, and $Q^{42}$ is a conjugation moiety, e.g., optionally substituted $C_{2-12}$ alkynyl, optionally substituted N-protected amino, azido, N-maleimido, S-protected thiol,

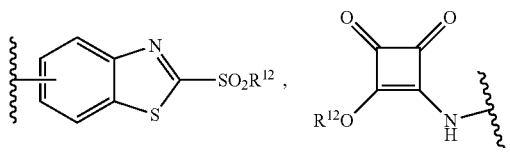

or N-protected version thereof,

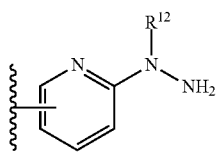

optionally substituted $C_{6-16}$ heterocyclyl containing an endocyclic carbon-carbon triple bond

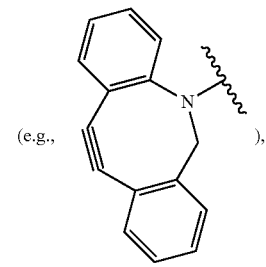 [SMILES: *N1Cc2ccccc2C#Cc2ccccc21]
(e.g., ), 1,2,4,5-tetrazine group

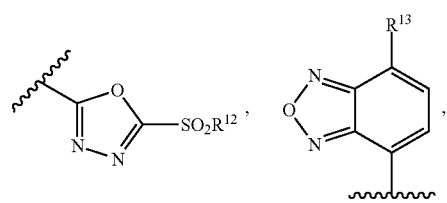

or optionally substituted $C_{8-16}$ cycloalkynyl

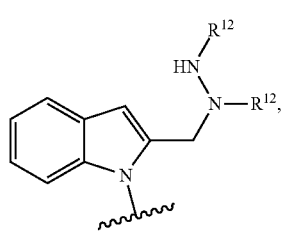
(e.g., ),

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO; and k is 1;

where

R$^{N1}$ is H, N-protecting group, or optionally substituted $C_{1-6}$ alkyl;

each R$^{12}$ is independently H or optionally substituted $C_{1-6}$ alkyl;

R$^{13}$ is halogen (e.g., F);

$Z^3$ and R$^T$ are absent.

In certain embodiments, $Z^1$ has a branching group and two divalent segments, where the branching group is bonded to each of the two divalent segments, where one of the divalent segments is bonded to an internucleoside or terminal phosphate, an internucleoside or terminal phosphorothioate, an internucleoside or terminal phosphorodithioate, an abasic spacer, or a nucleobase, and the remaining divalent segment is bonded to $Q^{41}$;

the branching group is optionally substituted $C_{1-12}$ alkane-triyl or optionally substituted $C_{2-12}$ heteroalkane-triyl, in which two valencies are substituted with the divalent segments, and the remaining valency is substituted with

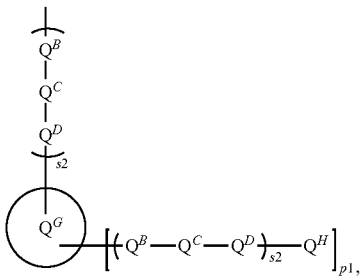

where
p1 is 1, 2, or 3;
each s2 is independently an integer from 0 to 10;
each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and
each $Q^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{1-9}$ heterocyclylene, or —P(Z)(OH)—, where Z is O or S;
each $Q^G$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl; and
each $Q^H$ is independently $R^{M1}$ or -$Q^G$[(-$Q^B$-$Q^C$-$Q^D$)$_{s2}$-$R^{M1}$]$_{p1}$, where each $R^{M1}$ is independently a bond to an auxiliary moiety.

In certain embodiments, $Z^2$ has a branching group and two divalent segments, where the branching group is bonded to each of the two divalent segments,
where
one of the divalent segments is bonded to a targeting moiety or $Q^{A2}$, and the remaining divalent segment is bonded to $Q^{A1}$;
the branching group is optionally substituted $C_{1-12}$ alkane-triyl or optionally substituted $C_{2-12}$ heteroalkane-triyl, in which two valencies are substituted with the divalent segments, and the remaining valency is substituted with

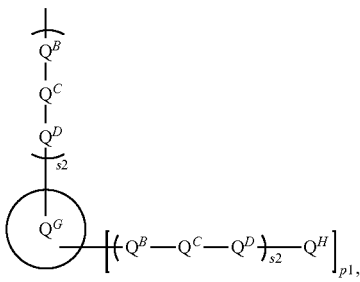

where
p1 is 1, 2, or 3;
each s2 is independently an integer from 0 to 10;
each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and
each $Q^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{1-9}$ heterocyclylene, or —P(Z)(OH)—, where Z is O or S;
each $Q^G$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl; and
each $Q^H$ is independently $R^{M1}$ or -$Q^G$[(-$Q^B$-$Q^C$-$Q^D$)$_{s2}$-$R^{M1}$]$_{p1}$, where each $R^{M1}$ is independently a bond to an auxiliary moiety.

In certain embodiments, $Z^3$ has a branching group and two divalent segments, where the branching group is bonded to each of the two divalent segments,
where
one of the divalent segments is bonded to a targeting moiety, and the remaining divalent segment is bonded to $Q^{A2}$;
the branching group is optionally substituted $C_{1-12}$ alkane-triyl or optionally substituted $C_{2-12}$ heteroalkane-triyl, in which two valencies are substituted with the divalent segments, and the remaining valency is substituted with

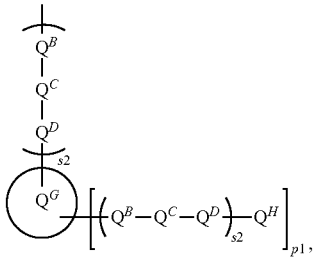

where
p1 is 1, 2, or 3;
each s2 is independently an integer from 0 to 10;
each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and
each $Q^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{1-9}$ heterocyclylene, or —P(Z)(OH)—, where Z is O or S;
each $Q^G$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl; and
each $Q^H$ is independently $R^{M1}$ or -$Q^G$[(-$Q^B$-$Q^C$-$Q^D$)$_{s2}$-$R^{M1}$]$_{p1}$, where each $R^{M1}$ is independently a bond to an auxiliary moiety.

The divalent segment in $Z^1$, $Z^2$, or $Z^3$ may be -(-$Q^B$-$Q^C$-$Q^D$-)$_{s1}$-,
where
each s1 is independently an integer from 1 to 50 (e.g., from 1 to 30);
each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and each $Q^C$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene;

provided that at least one of $Q^B$, $Q^C$, and $Q^D$ is present.

In certain embodiments, at least one $Q^C$ is present in the divalent segment. In particular embodiments, $Q^C$ is present in each monomeric unit of the divalent segment. In some embodiments, $Z^1$ is bonded through a $Q^C$ that is present. In further embodiments, at least one of $Q^B$ and $Q^D$ is present in each monomeric unit of $Z^1$. In yet further embodiments, at least one of $Q^B$ and $Q^D$ is present in each monomeric unit of $Z^2$. In particular embodiments, only one of $Z^1$, $Z^2$, and $Z^3$, when present, contains a branching group.

In yet further embodiments, one, two, or three of $Z^1$, $Z^2$, and $Z^3$ are independently

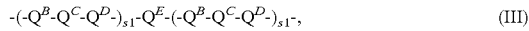
-(-$Q^B$-$Q^C$-$Q^D$-)$_{s1}$-$Q^E$-(-$Q^B$-$Q^C$-$Q^D$-)$_{s1}$-,    (III)

where each s1 is independently an integer from 1 to 50 (e.g., from 1 to 30);

each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and each $Q^C$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, optionally substituted C$_{1-9}$ heterocyclylene, or —P(Z)(OH)—, where Z is O or S; and $Q^E$ is absent or a branching group of formula (IV):

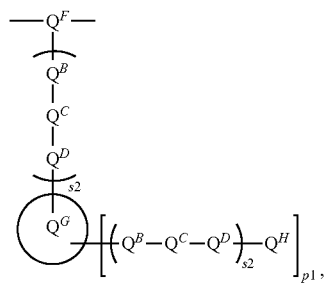
(IV)

where p1 is 1, 2, or 3;

each s2 is independently an integer from 0 to 10;

$Q^F$ is optionally substituted C$_{1-12}$ alkane-triyl or optionally substituted C$_{2-12}$ heteroalkane-triyl; and each $Q^G$ is independently optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl; and each $Q^H$ is independently $R^{M1}$ or -$Q^G$[(-$Q^B$-$Q^C$-$Q^D$)$_{s2}$-$R^{M1}$]$_{p1}$, where each $R^{M1}$ is independently a bond to an auxiliary moiety.

In formula (IV), $Q^G$ is absent, if p1 is 1; and at least one $Q^G$ is present, if p1 is 2 or 3.

In particular embodiments, $Z^1$ is bonded to an internucleoside or terminal phosphate, an internucleoside or terminal phosphorothioate, an internucleoside or terminal phosphorodithioate, an abasic spacer, a capping group, or a nucleobase through a $Q^C$ that is present.

In particular embodiments, at least one of $Q^B$, $Q^C$, $Q^D$, and $Q^E$ is present (e.g., at least one $Q^C$ is present, $Q^E$ is present, or $Q^E$ is absent) in the divalent segment. In certain embodiments, each $Q^B$ and each $Q^D$ is independently absent, —CO—, —NH—, —O—, —S—, —SO$_2$—, —NHC(O)—, —C(O)NH—, —CH$_2$—, —CH$_2$NH—, —NHCH$_2$—, —CH$_2$O—, or —OCH$_2$—.

In some embodiments, -(-$Q^B$-$Q^C$-$Q^D$-)$_{s1}$- combine to form a group:

-$Q^B$-(CH$_2$)$_{g1}$—(CH$_2$OCH$_2$)$_{g2}$—(CH$_2$)$_{g3}$-$Q^D$-, where (i) g2 is an integer from 1 to 50;

(ii) g1 is 1 and $Q^B$ is —NHCO—, —CONH—, or —O—; or g1 is 0 and $Q^D$ is —NHCO—; and (iii) g3 is 1 and $Q^B$ is —NHCO—, —CONH—, or —O—; or g3 is 0 and $Q^D$ is —CONH—.

The conjugation moiety may be protected until an auxiliary moiety is conjugated to the polynucleotide. For example, a conjugation moiety that is protected may include —COOR$^{PGO}$ or —NHR$^{PGN}$, where R$^{PGO}$ is an O-protecting group (e.g., a carboxyl protecting group), and R$^{PGN}$ is an N-protecting group.

In further embodiments, Link A is

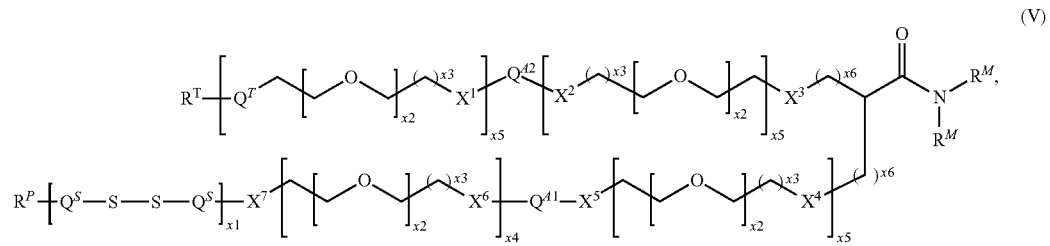
(V)

where each of $Q^{A1}$ and $Q^{A2}$ is absent, independently optionally substituted $C_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted $C_{1-12}$ thioheterocyclylene (e.g., 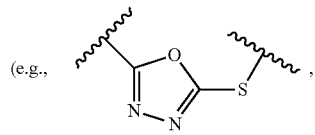,

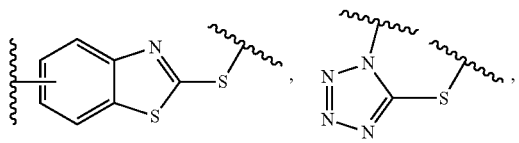

optionally substituted $C_{1-12}$ heterocyclylene (e.g., 1,2,3-triazole-1,4-diyl or

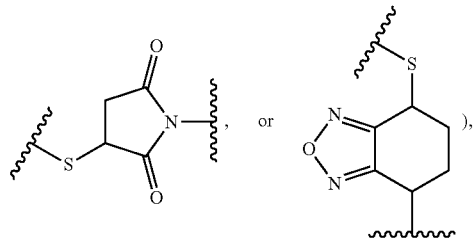

cyclobut-3-ene-1,2-dione-3,4-diyl, pyrid-2-yl hydrazone, optionally substituted $C_{6-16}$ triazoloheterocyclylene (e.g., 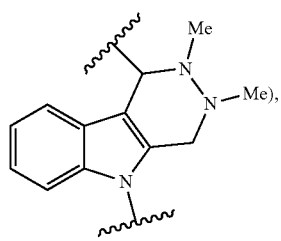 or

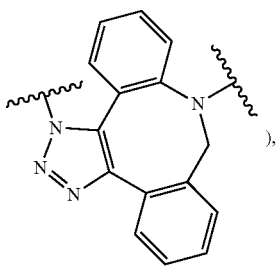), optionally substituted $C_{8-16}$ triazolocycloalkenylene (e.g., 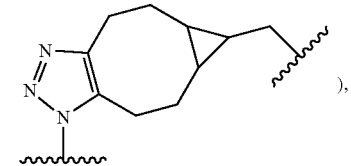), or a dihydropyridazine group (e.g., trans- 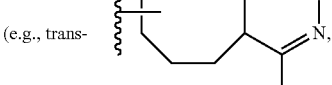

trans- 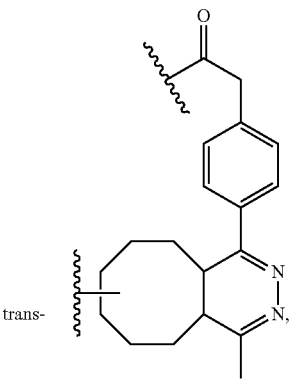

-continued

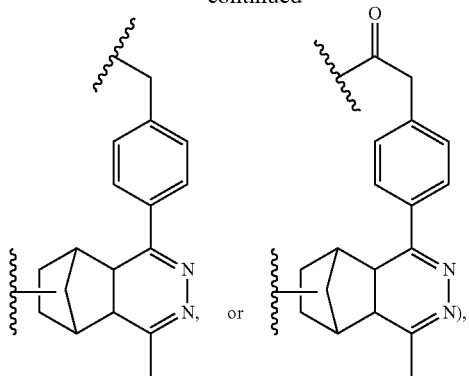

provided that at least one of $Q^{41}$ and $Q^{42}$ is present;

$R^T$ is a bond to a targeting moiety;

$R^P$ is a bond to an internucleoside bridging group, a nucleobase, a capping group, or an abasic spacer;

$Q^T$ is —CO—, —NH—, —NH—CH$_2$—, or —CO—CH$_2$—;

each $Q^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene;

each $R^M$ is independently H, auxiliary moiety, —(CH$_2$)$_{q7}$—CO—N(R$^{M1}$)$_2$, or —C[—CH$_2$O—(CH$_2$)$_{q7}$—CO—N(R$^{M1}$)$_2$]$_3$, where each q7 is independently an integer from 1 to 5, and each R$^{M1}$ is independently H or an auxiliary moiety;

each of $X^1$, $X^3$, and $X^5$ is independently absent, —O—, —NH—, —CH$_2$—NH—, —C(O)—, —C(O)—NH—, —NH—C(O)—, —NH—C(O)—NH—, —O—C(O)—NH—, —NH—C(O)—O—, —CH$_2$—NH—C(O)—NH—, —CH$_2$—O—C(O)—NH—, or —CH$_2$—NH—C(O)—O—;

$X^7$ is absent, —O—, —O—P(O)(OH)—O—, —O—P(S)(OH)—O—, —NH—, —CH$_2$—NH—, —C(O)—, —C(O)—NH—, —NH—C(O)—, —NH—C(O)—NH—, —O—C(O)—NH—, —NH—C(O)—O—, —CH$_2$—NH—C(O)—NH—, —CH$_2$—O—C(O)—NH—, or —CH$_2$—NH—C(O)—O—;

each of $X^2$, $X^4$, and $X^6$ is independently absent, —O—, —NH—, —C(O)—, —C(O)—NH—, —NH—C(O)—, —NH—C(O)—NH—, —O—C(O)—NH—, or —NH—C(O)—O—;

x1 and each x5 are independently 0 or 1;

each x2 is independently an integer from 0 to 50 (e.g., from 1 to 40 or from 1 to 30); each x3 is independently an integer from 1 to 11;

x4 is 0, 1, or 2; and each x6 is independently an integer from 0 to 10 (e.g., from 1 to 6), provided that the sum of both x6 is 12 or less.

In yet further embodiments, LinkA is (VI)

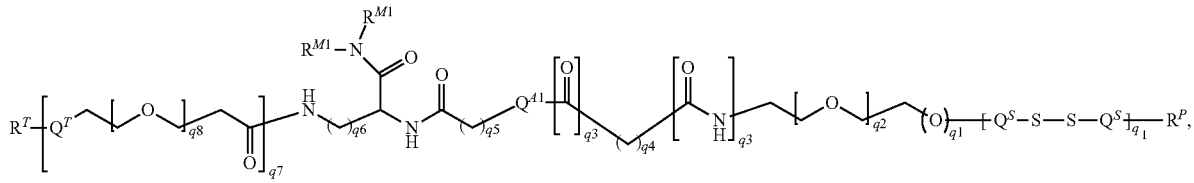

(VII)

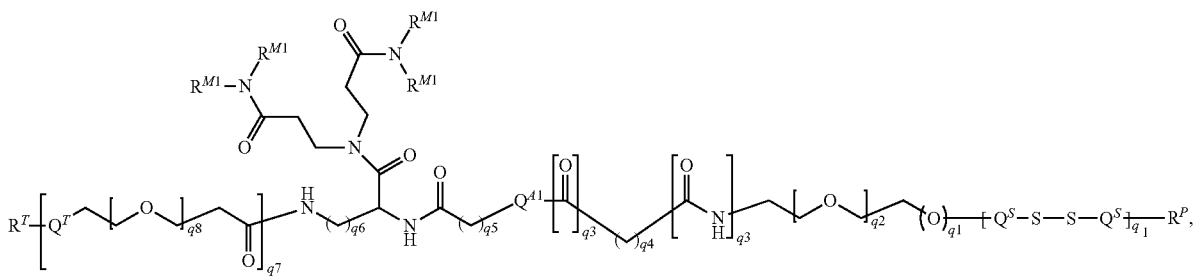

(VIII)

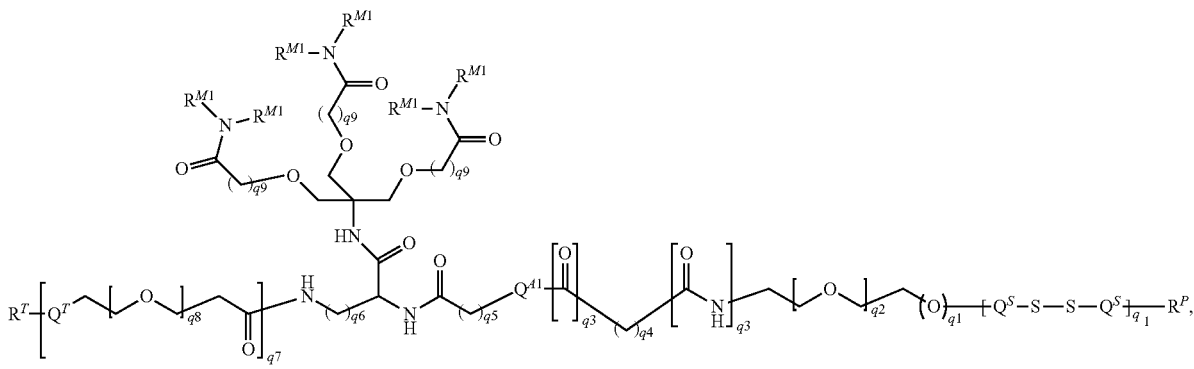

-continued (IX)
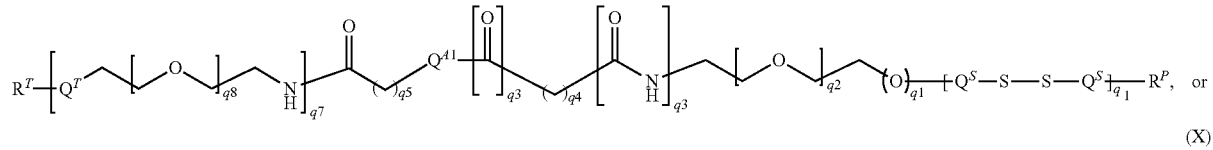

or (X)
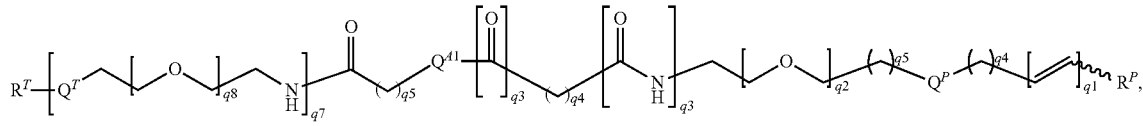

where $Q^{A1}$ is optionally substituted $C_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted $C_{1-12}$ thioheterocyclylene

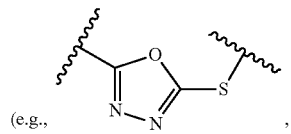

(e.g.,

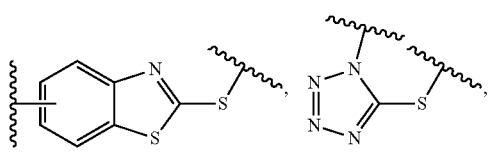, 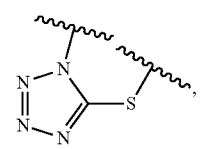

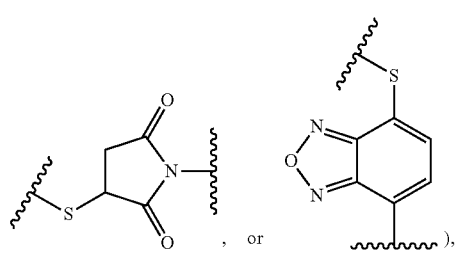, or 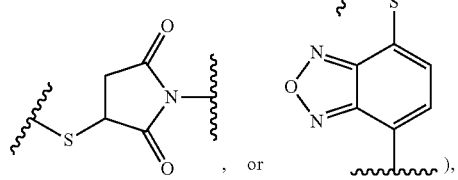), optionally substituted $C_{1-12}$ heterocyclylene (e.g., 1,2,3-triazole-1,4-diyl or

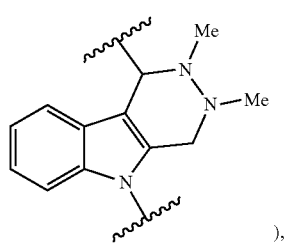 [SMILES: *C1c2c(n(*)c3ccccc23)CN(C)N1C]), cyclobut-3-ene-1,2-dione-3,4-diyl, or pyrid-2-yl hydrazone), optionally substituted $C_{6-16}$ triazoloheterocyclylene

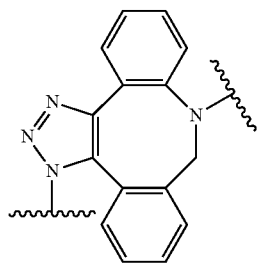

(e.g., or

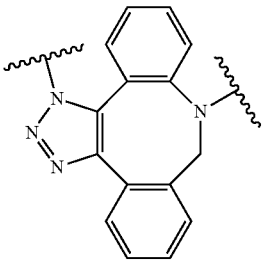), optionally substituted $C_{8-16}$ triazolocycloalkenylene (e.g., 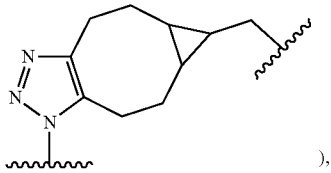), or a dihydropyridazine group

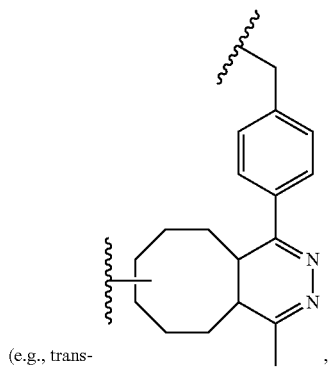

(e.g., trans-

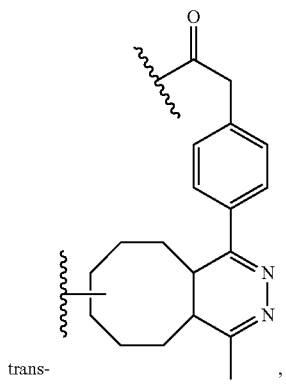

trans-

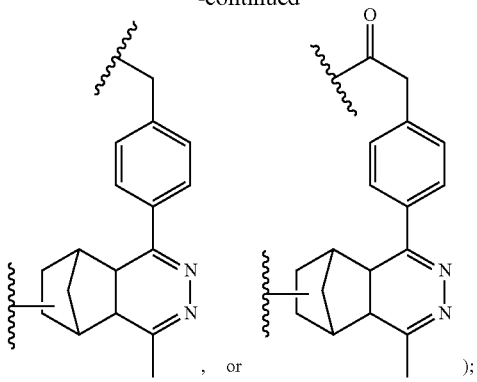

, or each $R^{M1}$ is independently H or an auxiliary moiety;

$R^T$ is a bond to a targeting moiety;

$R^P$ is a bond to an internucleoside bridging group, a nucleobase, a capping group, or an abasic spacer;

$Q^T$ is —CO—, —NH—, —NH—CH$_2$—, or —CO—CH$_2$—;

$Q^P$ is —C(O)—N(H)—, —N(H)—C(O)—, —S(O)$_2$—N(H)—, or —N(H)—S(O)$_2$—;

each $Q^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene; each of q1, q3, and q7 is independently 0 or 1;

each of q2 and q8 is an integer from 0 to 50 (e.g., from 1 to 40 or from 1 to 30);

q4 is an integer from 0 to 10;

each of q5 and q6 is independently an integer from 1 to 10 (e.g., from 1 to 6); and q9 is an integer from 1 to 10.

In still further embodiments, LinkA is

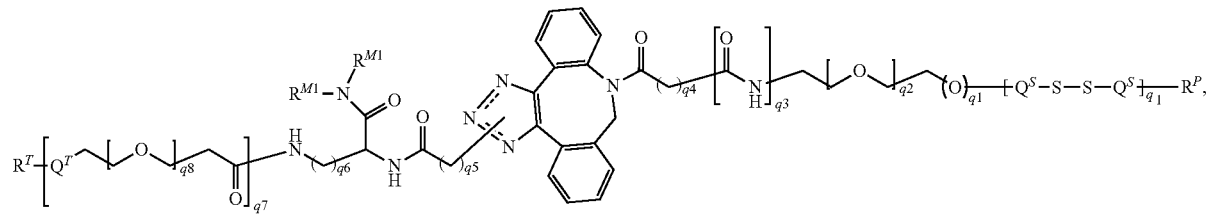

(XI)

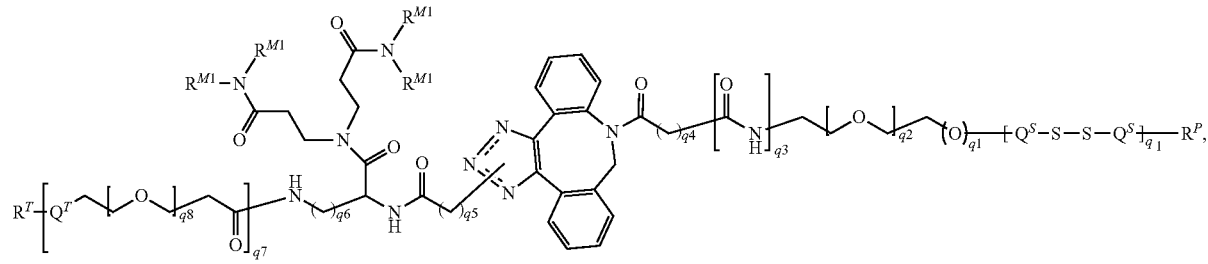

(XII)

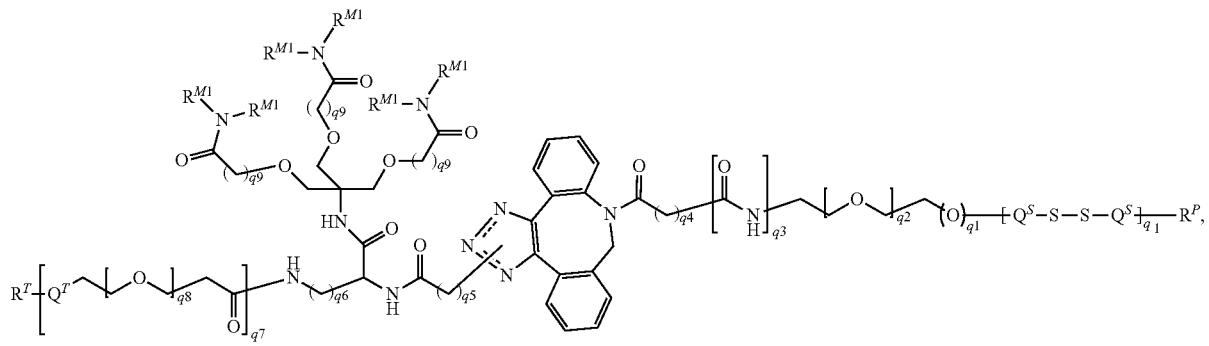

(XIII)

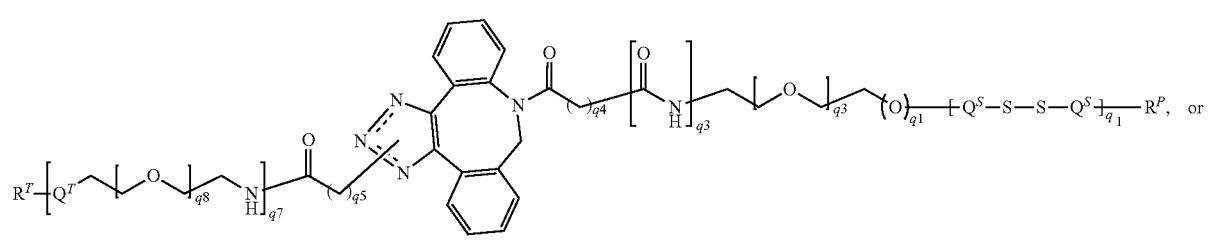

(XIV)

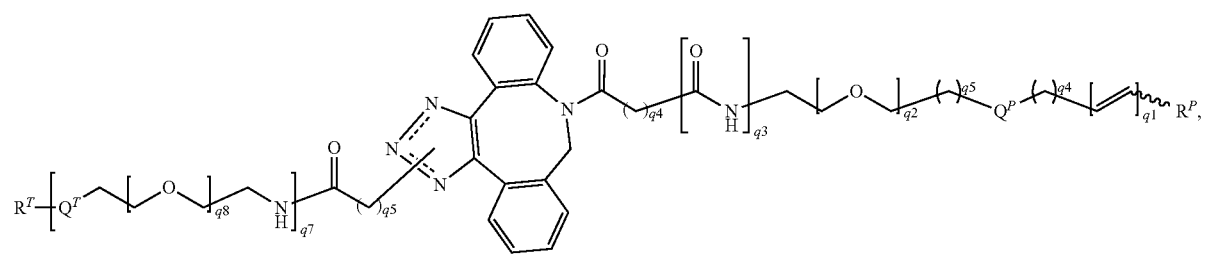

(XV)

where in each structural formula, one ---- represents a single bond, and the other ---- represents a double bond;

each $R^{M1}$ is independently H or an auxiliary moiety;

$R^T$ is a bond to a targeting moiety;

$R^P$ is a bond to an internucleoside bridging group, a nucleobase, a capping group, or an abasic spacer;

$Q^T$ is —CO—, —CO—CH$_2$—, —NH—, or —NH—CH$_2$—;

$Q^P$ is —C(O)—N(H)—, —N(H)—C(O)—, —S(O)$_2$—N(H)—, or —N(H)—S(O)$_2$—;

each $Q^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene;

each of q1, q3, and q7 is independently 0 or 1;

each of q2 and q8 is an integer from 0 to 50 (e.g., from 1 to 40 or from 1 to 30);

q4 is an integer from 0 to 10;

each of q5 and q6 is independently an integer from 1 to 10 (e.g., from 1 to 6); and q9 is an integer from 1 to 10.

In some embodiments, q5 is 0. In other embodiments q5 is an integer from 2 to 6.

In particular embodiments, a conjugating group is:

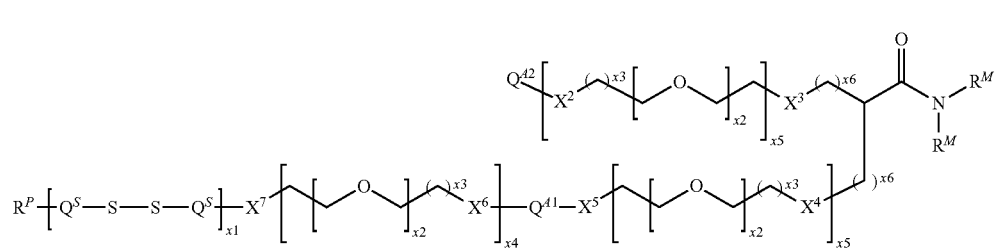

(XVI)

where

Q$^{A1}$ is independently optionally substituted C$_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted C$_{1-12}$ thioheterocyclylene (e.g., 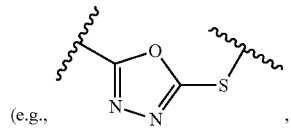,

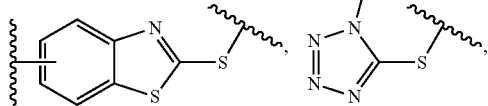

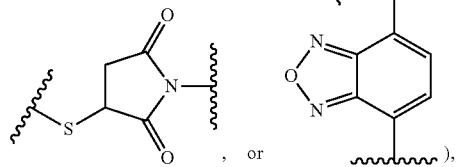, or ), optionally substituted C$_{1-12}$ heterocyclylene (e.g., 1,2,3-triazole-1,4-diyl or

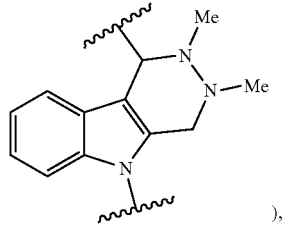 [SMILES: *C1c2c(n(*)c3ccccc23)CN(C)N1C]), cyclobut-3-ene-1,2-dione-3,4-diyl, pyrid-2-yl hydrazone, optionally substituted C$_{6-16}$ triazoloheterocyclyene (e.g., 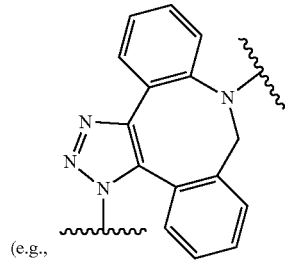 or

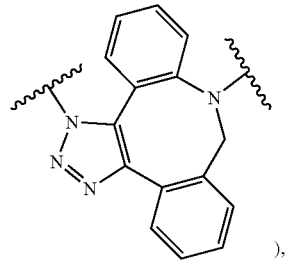), optionally substituted C$_{8-16}$ triazolocycloalkenylene (e.g., 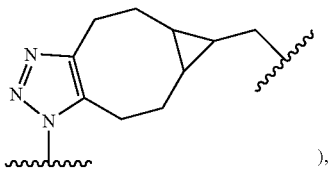), or a dihydropyridazine group

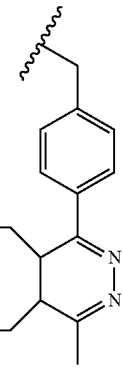

(e.g., trans- , trans-

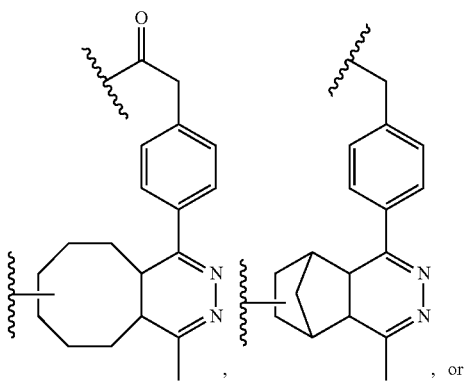, , or

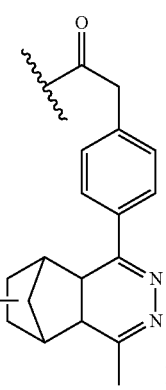);

Q$^{A2}$ is optionally substituted C$_{2-12}$ alkynyl, optionally substituted N-protected amino, azido, N-maleimido, S-protected thiol,

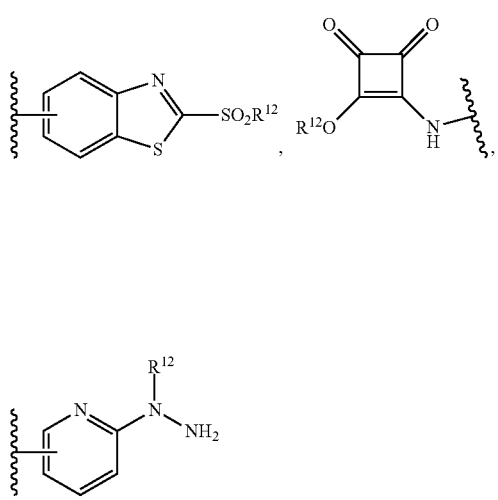
, or N-protected version thereof,

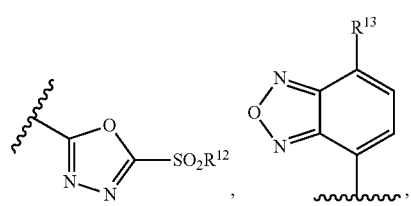
,

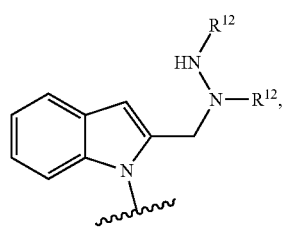
, optionally substituted $C_{6-16}$ heterocyclyl containing an endocyclic carbon-carbon triple bond

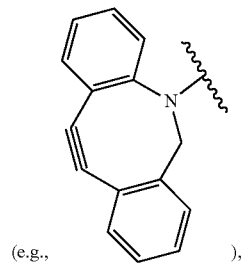 [SMILES: *N1Cc2ccccc2C#Cc2ccccc21]
(e.g., ), 1,2,4,5-tetrazine group

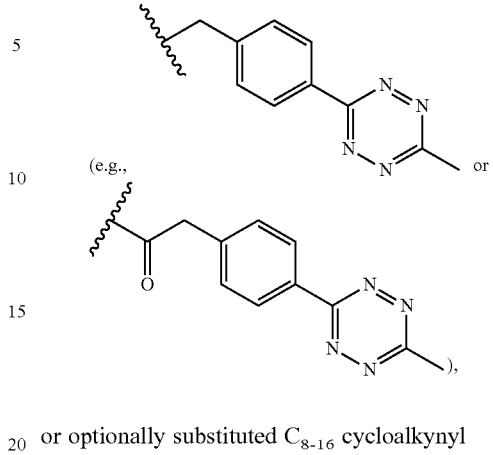

or optionally substituted $C_{8-16}$ cycloalkynyl (e.g., ),

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO;

R$^{N1}$ is H, N-protecting group, or optionally substituted $C_{1-6}$ alkyl;

each R$^{12}$ is independently H or optionally substituted $C_{1-6}$ alkyl;

R$^{13}$ is halogen (e.g., F);

R$^P$ is a bond to an internucleoside bridging group, a nucleobase, a capping group, or an abasic spacer;

each Q$^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene;

each R$^M$ is independently H, auxiliary moiety, —(CH$_2$)$_{q7}$—CO—N(R$^{M1}$)$_2$, or —C[—CH$_2$O—(CH$_2$)$_{q7}$—CO—N(R$^{M1}$)$_2$]$_3$, where each q7 is independently an integer from 1 to 5, and each R$^{M1}$ is independently H or auxiliary moiety;

each of X$^3$ and X$^5$ is independently absent, —O—, —NH—, —CH$_2$—NH—, —C(O)—, —C(O)—NH—, —NH—C(O)—, —NH—C(O)—NH—, —O—C(O)—NH—, —NH—C(O)—O—, —CH$_2$—NH—C(O)—NH—, —CH$_2$—O—C(O)—NH—, or —CH$_2$—NH—C(O)—O—;

X$^7$ is absent, —O—, —O—P(O)(OH)—O—, —O—P(S)(OH)—O—, —NH—CH$_2$—NH—, —C(O)—, —C(O)—NH—, —NH—C(O)—, —NH—C(O)—NH—, —O—C(O)—NH—, —NH—C(O)—O—, —CH$_2$—NH—C(O)—NH—, —CH$_2$—O—C(O)—NH—, or —CH$_2$—NH—C(O)—O—;

each of X$^2$, X$^4$, and X$^6$ is independently absent, —O—, —NH—, —O—, —C(O)—, —C(O)—NH—, —NH—C(O)—, —NH—C(O)—NH—, —O—C(O)—NH—, or —NH—C(O)—O—;

x1 and each x5 are independently 0 or 1;

each x2 is independently an integer from 0 to 50 (e.g., from 1 to 40 or from 1 to 30);

each x3 is independently an integer from 1 to 11;

x4 is 0, 1, or 2; and each x6 is independently an integer from 0 to 10 (e.g., from 1 to 6), provided that the sum of both x6 is 12 or less.

In some embodiments, a conjugating group is:

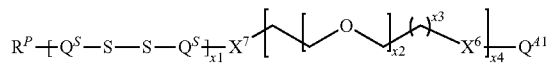
(XVII)

where $Q^{41}$ is optionally substituted $C_{2-12}$ alkynyl, optionally substituted N-protected amino, azido, N-maleimido, S-protected thiol

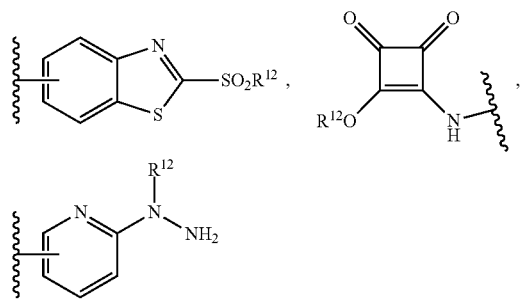

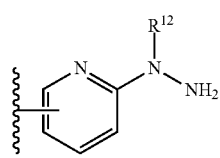

or N-protected version thereof, optionally substituted $C_{6-16}$ heterocyclyl containing an endocyclic carbon-carbon triple bond

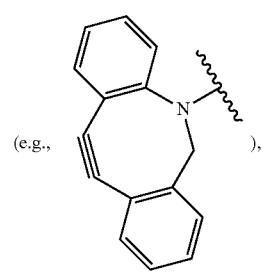

1,2,4,5-tetrazine group (e.g., 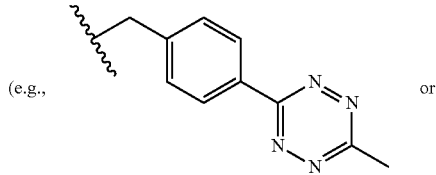 or

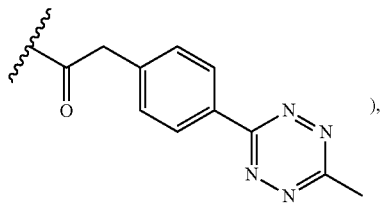), or optionally substituted $C_{8-16}$ cycloalkynyl (e.g., ), —$NHR^{N1}$, optionally substituted $C_{4-8}$ strained cycloalkenyl (e.g., trans-cyclooctenyl or norbornenyl), or optionally substituted $C_{1-16}$ alkyl containing —$COOR^{12}$ or —CHO;

$R^{N1}$ is H, N-protecting group, or optionally substituted $C_{1-6}$ alkyl;

each $R^{12}$ is independently H or optionally substituted $C_{1-6}$ alkyl;

$R^{13}$ is halogen (e.g., F);

$R^P$ is a bond to an internucleoside bridging group, a nucleobase, a capping group, or an abasic spacer;

each $Q^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene;

$X^7$ is absent, —O—, —NH—, —O—P(O)(OH)—O—, —O—P(S)(OH)—O—, —CH$_2$—NH—, —C(O)—, —C(O)—NH—, —NH—C(O)—, —NH—C(O)—NH—, —O—C(O)—NH—, —NH—C(O)—O—, —CH$_2$—NH—C(O)—NH—, —CH$_2$—O—C(O)—NH—, or —CH$_2$—NH—C(O)—O—;

$X^6$ is absent, —O—, —NH—, —O—, —C(O)—, —C(O)—NH—, —NH—C(O)—, —NH—C(O)—NH—, —O—C(O)—NH—, or —NH—C(O)—O—;

x1 is independently 0 or 1;

each x2 is independently an integer from 0 to 50 (e.g., from 1 to 40 or from 1 to 30);

each x3 is independently an integer from 1 to 11; and x4 is 0, 1, or 2.

In certain embodiments, a conjugating group is:

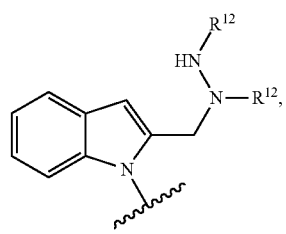

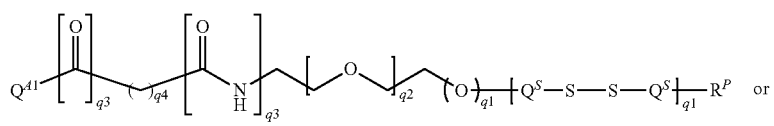

(XVIII)

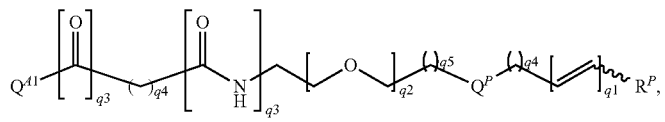

(XIX)

where $Q^{41}$ is optionally substituted $C_{2-12}$ alkynyl, optionally substituted N-protected amino, azido, N-maleimido, S-protected thiol,

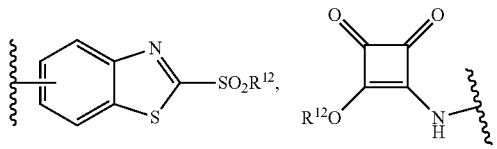

optionally substituted $C_{6-16}$ heterocyclyl containing an endocyclic carbon-carbon triple bond

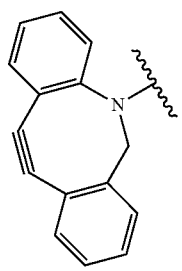

(e.g., ), 1,2,4,5-tetrazine group

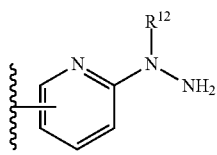

or N-protected version thereof,

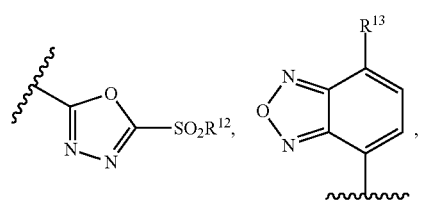

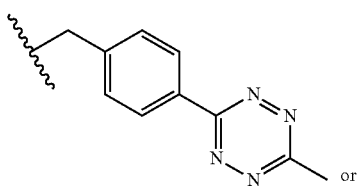

(e.g., or

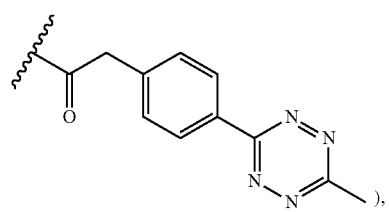

), or optionally substituted $C_{8-16}$ cycloalkynyl (e.g., 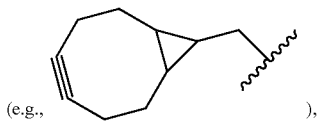 [SMILES: *CC1C2CCC#CCCC12]),

—$NHR^{N1}$, optionally substituted $C_{4-8}$ strained cycloalkenyl (e.g., trans-cyclooctenyl or norbornenyl), or optionally substituted $C_{1-16}$ alkyl containing —$COOR^{12}$ or —CHO;

$R^{N1}$ is H, N-protecting group, or optionally substituted $C_{1-6}$ alkyl;

each $R^{12}$ is independently H or optionally substituted $C_{1-6}$ alkyl;

$R^{13}$ is halogen (e.g., F);

$R^P$ is a bond to an internucleoside bridging group, a nucleobase, a capping group, or an abasic spacer;

$Q^P$ is —C(O)—N(H)—, —N(H)—C(O)—, —S(O)$_2$—N(H)—, or —N(H)—S(O)$_2$—;

each $Q^S$ is independently optionally substituted $C_{2-12}$ alkylene, optionally substituted $C_{2-12}$ alkenylene, optionally substituted $C_{2-12}$ alkynylene, or optionally substituted ($C_{6-10}$ aryl)-$C_{1-6}$-alkylene;

each of q1 and q3 is independently 0 or 1;

q2 is an integer from 0 to 50 (e.g., from 1 to 40 or from 1 to 30);

q4 is an integer from 0 to 10; and q5 is an integer from 1 to 10 (e.g., from 1 to 6).

In yet further embodiments, the conjugating group is:

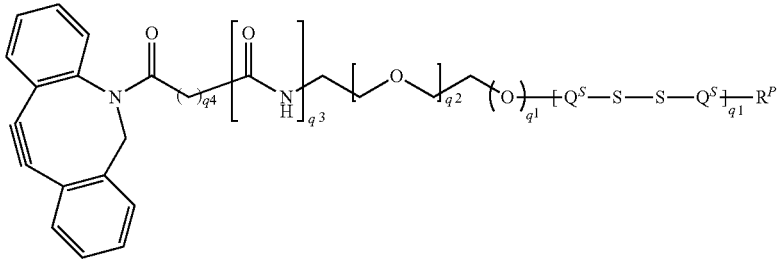

(XX)

or

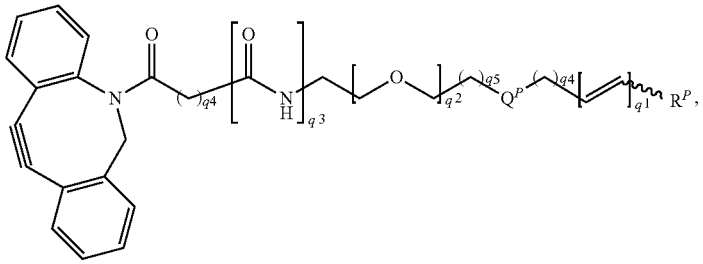

(XXI)

where
R$^P$ is a bond to an internucleoside bridging group, a nucleobase, a capping group, or an abasic spacer;

Q$^P$ is —C(O)—N(H)—, —N(H)—C(O)—, —S(O)$_2$—N(H)—, or —N(H)—S(O)$_2$—;

each Q$^S$ is independently optionally substituted C$_{2-12}$ alkylene, optionally substituted C$_{2-12}$ alkenylene, optionally substituted C$_{2-12}$ alkynylene, or optionally substituted (C$_{6-10}$ aryl)-C$_{1-6}$-alkylene;

each of q1 and q3 is independently 0 or 1;

q2 is an integer from 0 to 50 (e.g., from 1 to 40 or from 1 to 30);

q4 is an integer from 0 to 10; and q5 is an integer from 1 to 10 (e.g., from 1 to 6).

In certain exemplary embodiments, a conjugating group is:

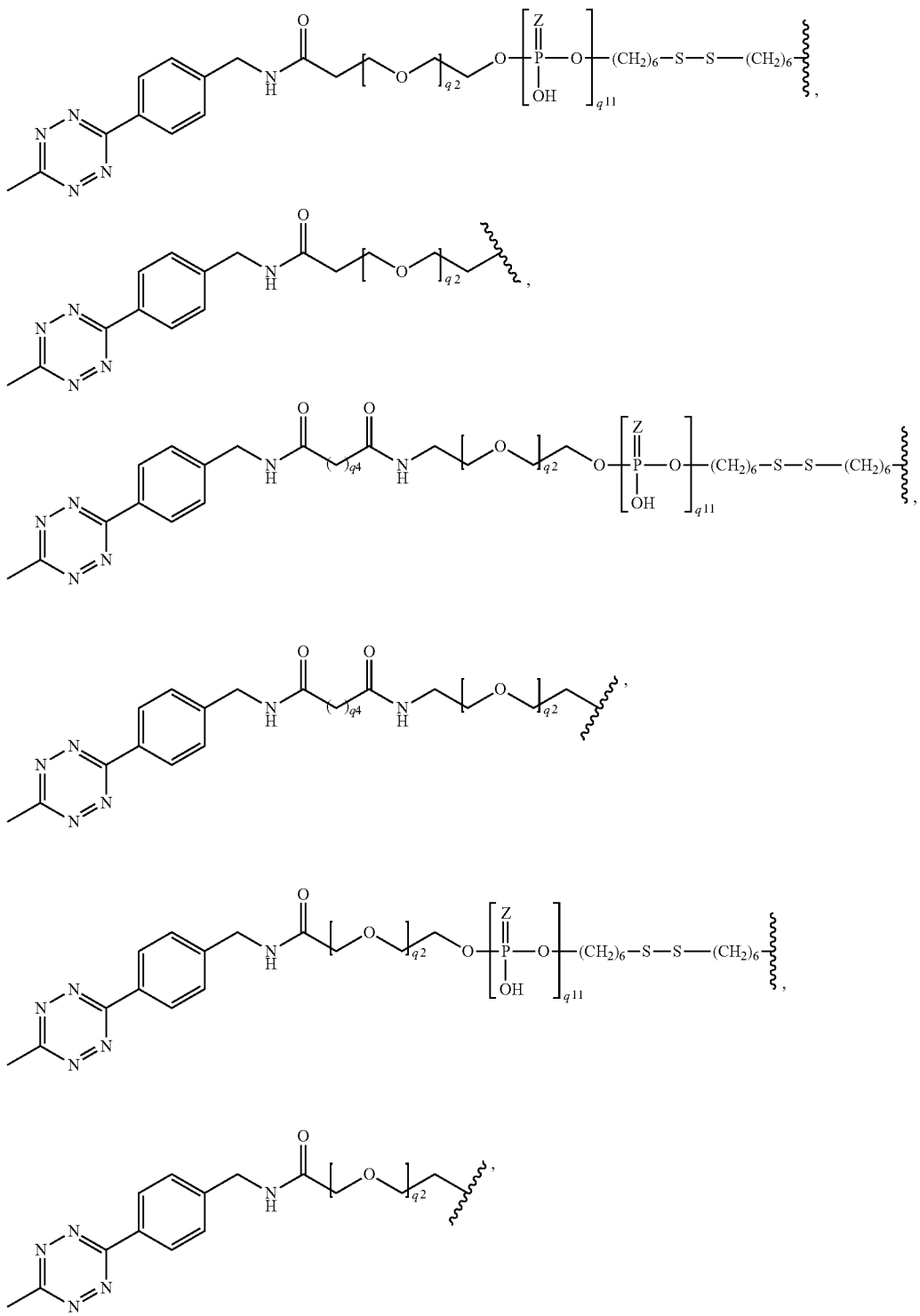

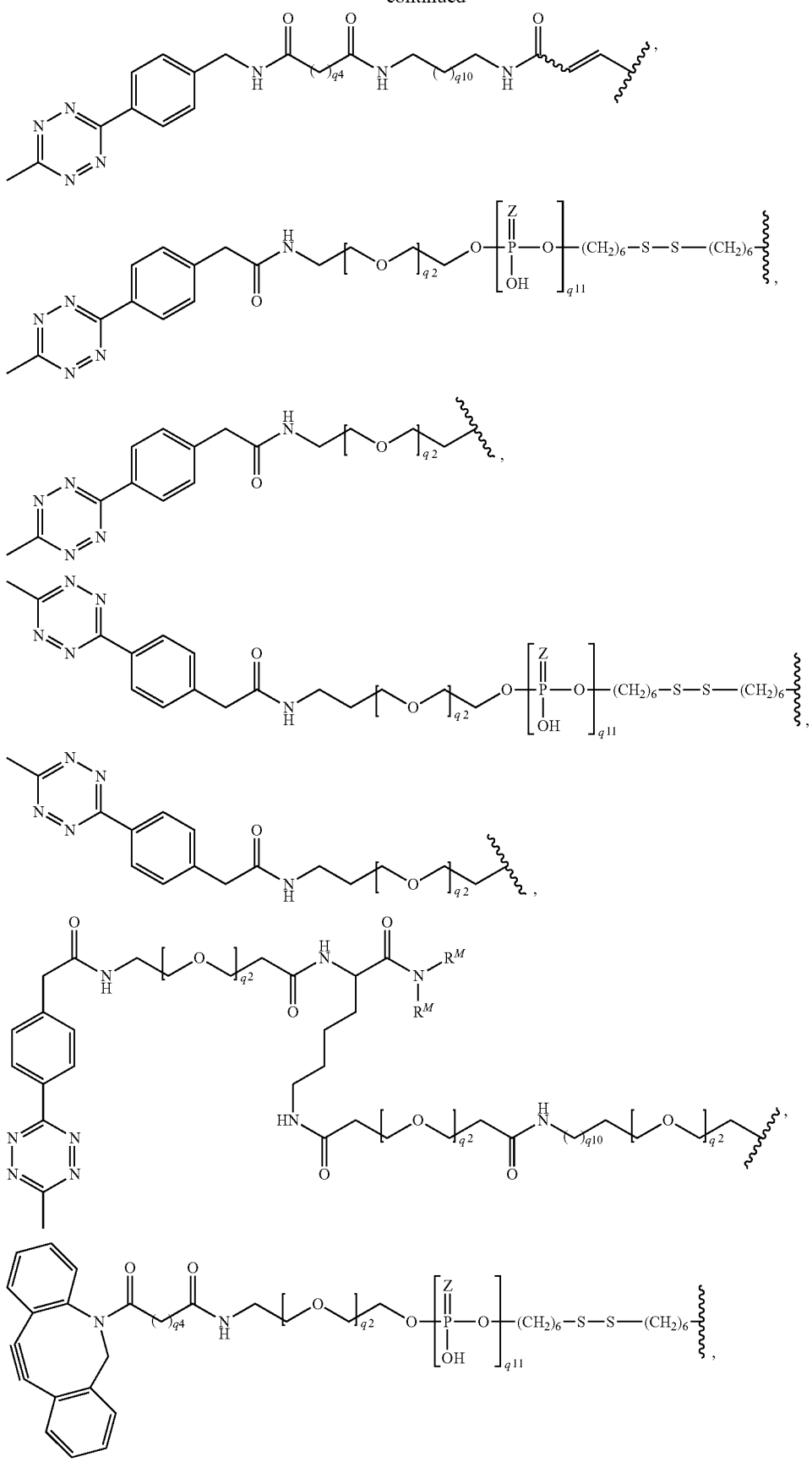

-continued
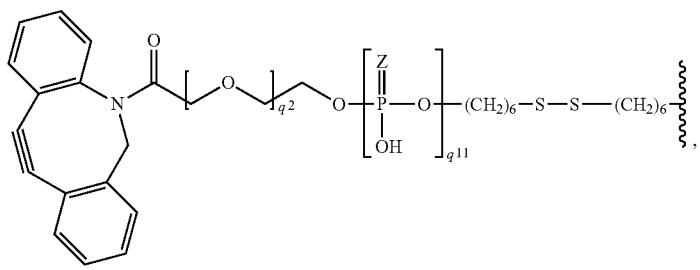
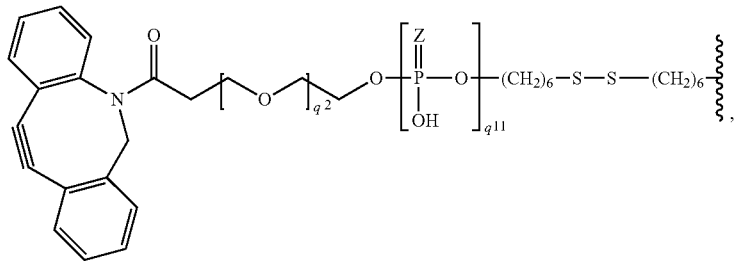
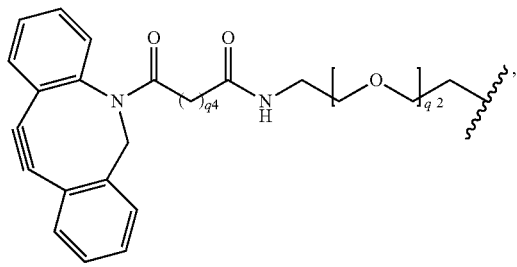, 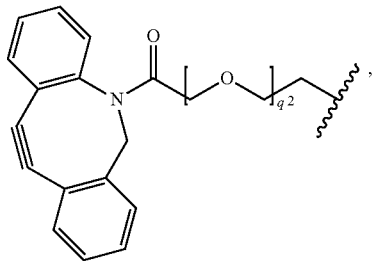
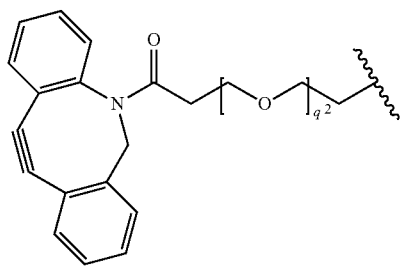, 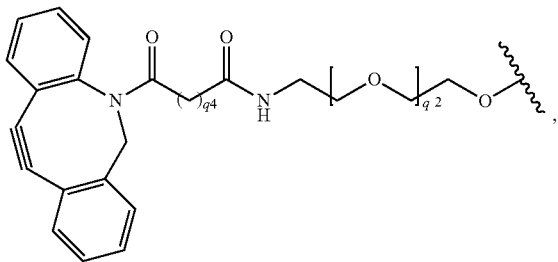
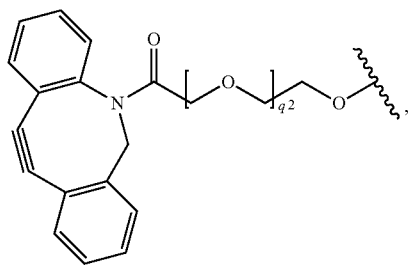, 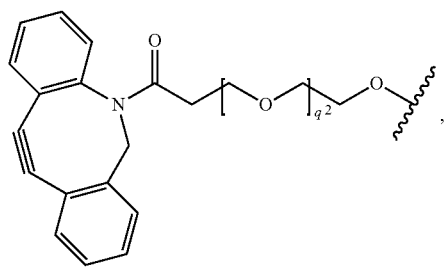
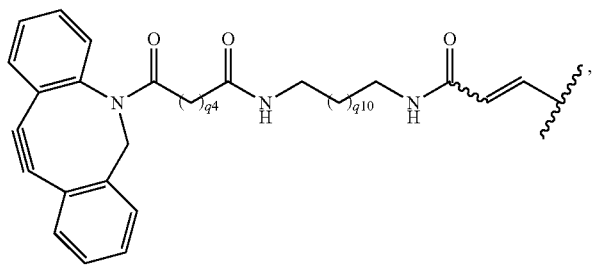, 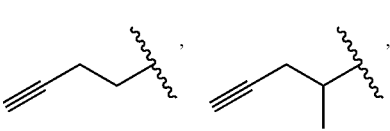

-continued

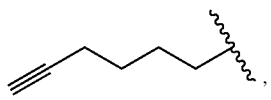 , 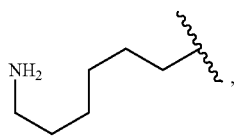 , 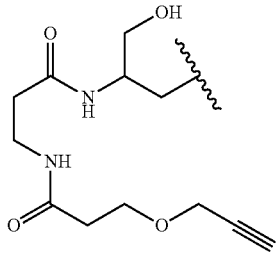 ,

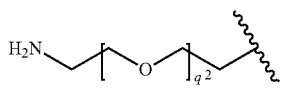 , or 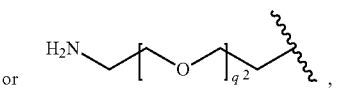 , where q2 is an integer from 1 to 50 (e.g., an integer from 1 to 24 or from 1 to 8 (e.g., 2 or 3)), q4 is an integer from 0 to 10 (e.g., 0, 1, 2, 3, 4, 5, 6, 7, or 8), q10 is an integer from 0 to 8 (e.g., 1, 2, 3, 4, 5, or 6), q11 is 0 or 1, Z is O or S, and each $R^M$ is independently H, auxiliary moiety, —$(CH_2)_{q7}$—CO—N$(R^{M1})_2$, or —C[—CH$_2$O—$(CH_2)_{q7}$—CO—N$(R^{M1})_2]_3$, where each q7 is independently an integer from 1 to 5, and each $R^{M1}$ is independently H or auxiliary moiety.

The following exemplary conjugating groups can be used for conjugation to a targeting moiety through a metal-catalyzed cycloaddition:

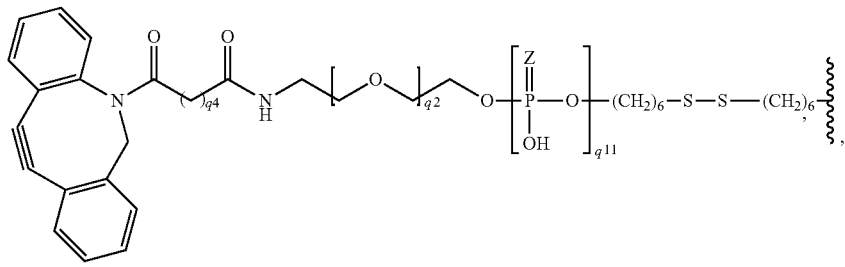

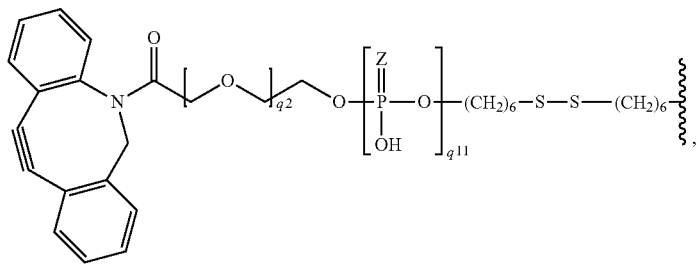

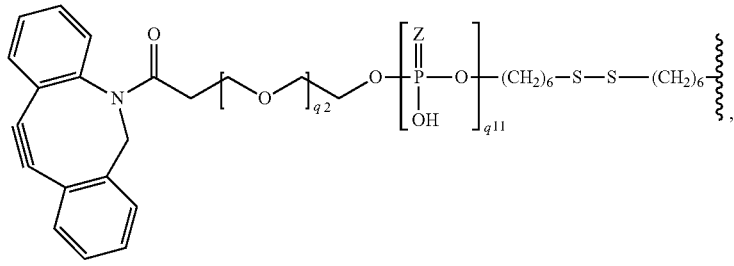

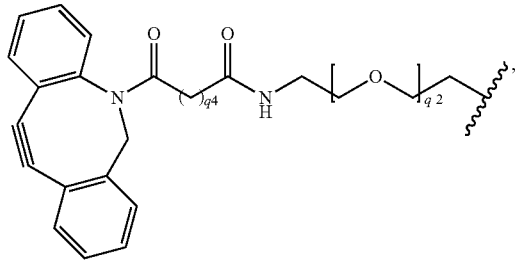 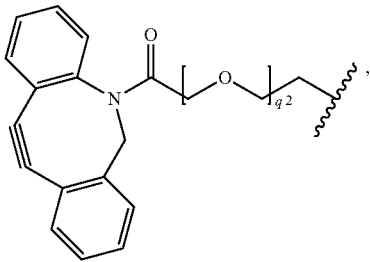

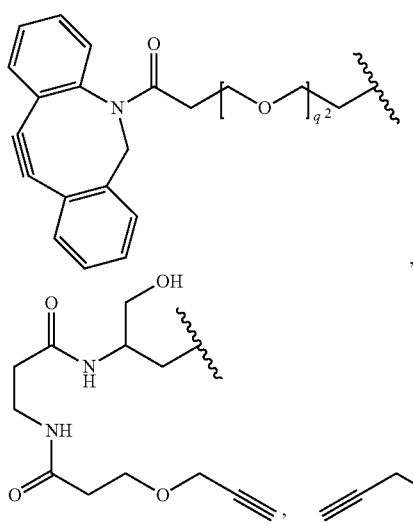
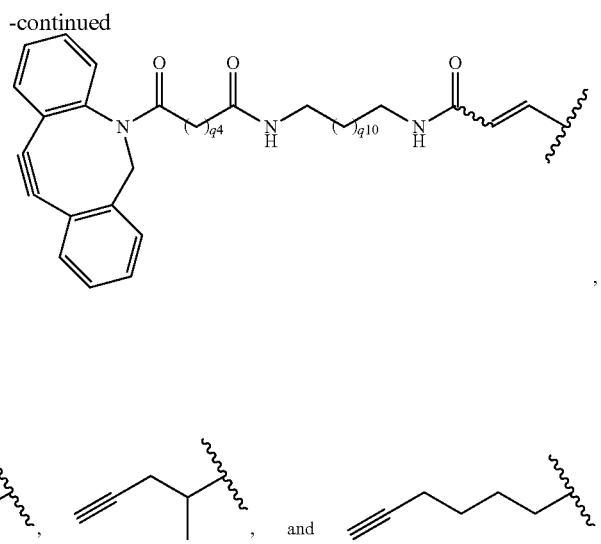
where q2 is an integer from 1 to 50 (e.g., an integer from 1 to 24 or from 1 to 8 (e.g., 2 or 3)), q4 is an integer from 0 to 10 (e.g., 0, 1, 2, 3, 4, 5, 6, 7, or 8), q10 is an integer from 0 to 8 (e.g., 1, 2, 3, 4, 5, or 6), q11 is 0 or 1, and Z is O or S.
The following exemplary conjugating groups can be used for conjugation to a targeting moiety through a metal-free cycloaddition:
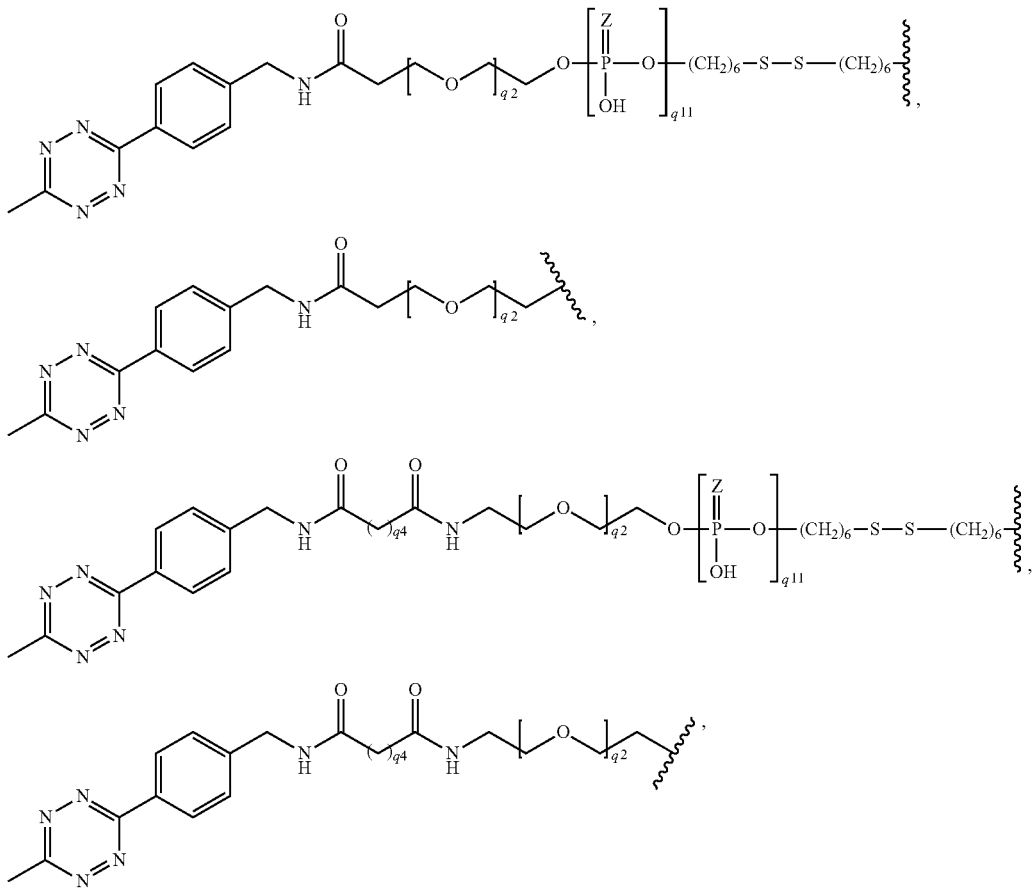

-continued
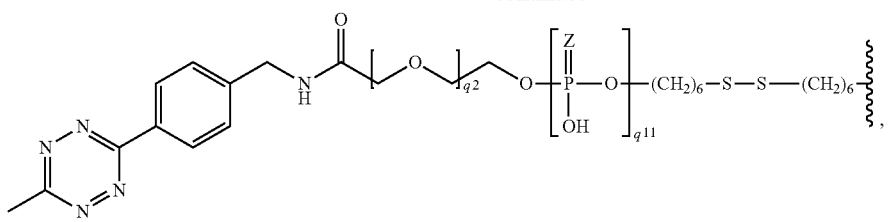
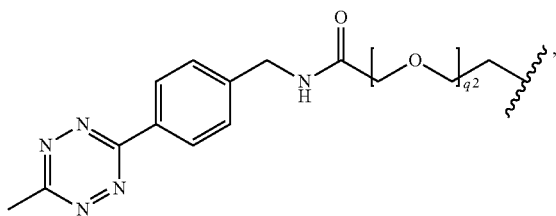
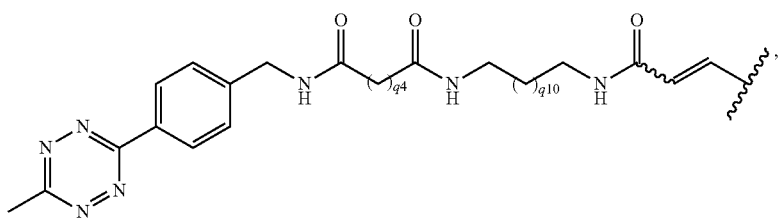
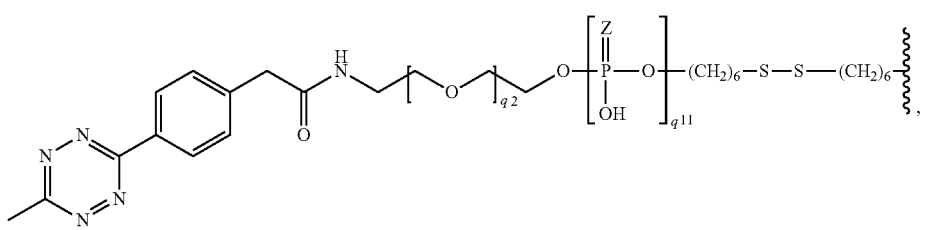
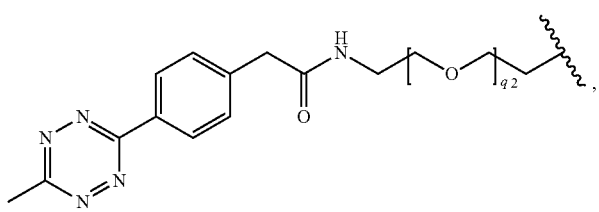
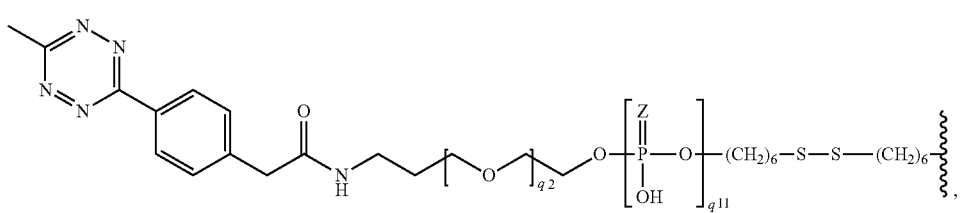
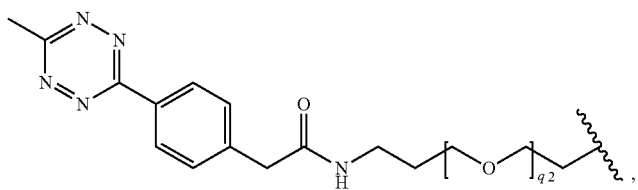

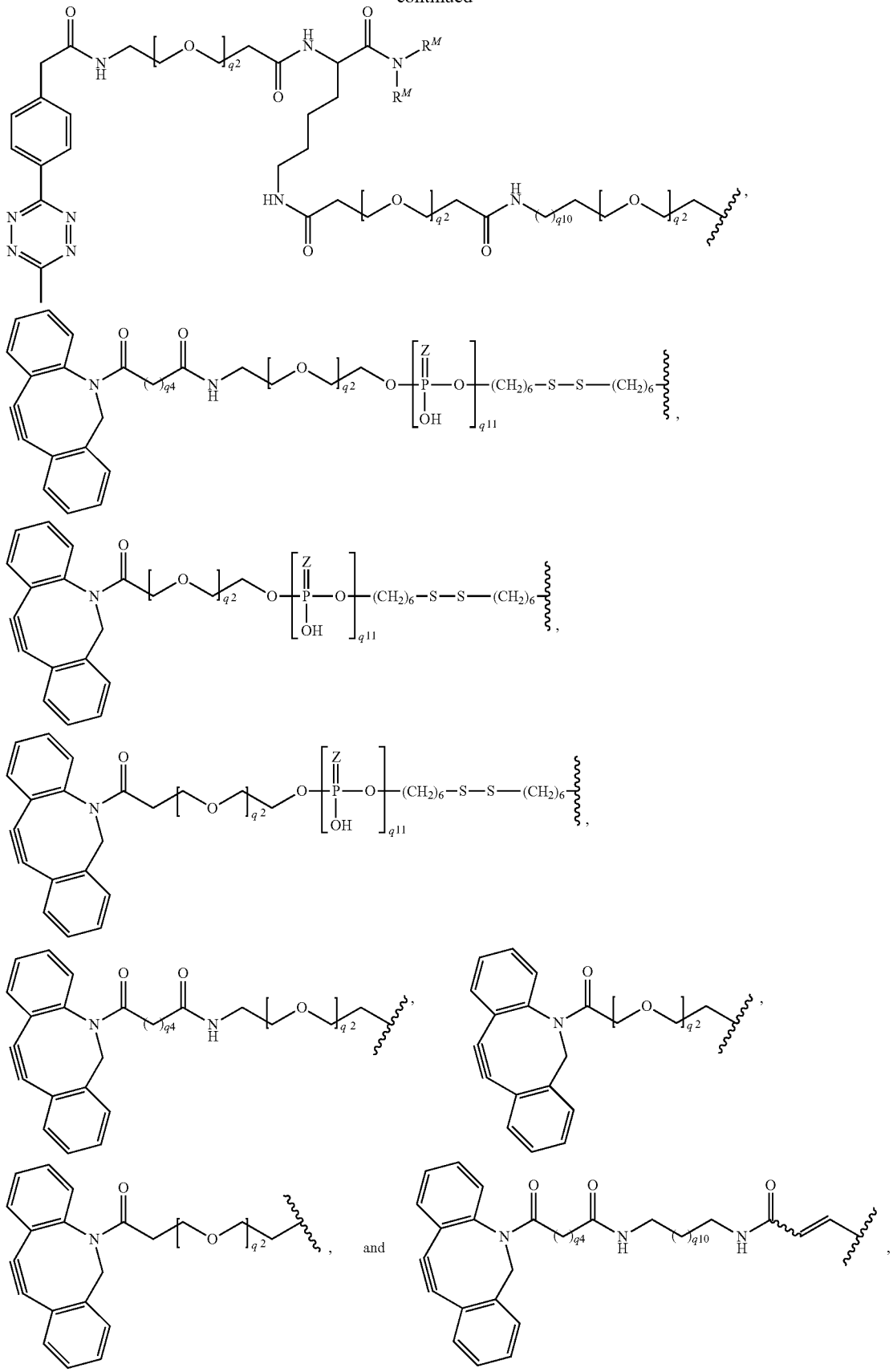

where q2 is an integer from 1 to 50 (e.g., an integer from 1 to 24 or from 1 to 8 (e.g., 2 or 3)), q4 is an integer from 0 to 10 (e.g., 0, 1, 2, 3, 4, 5, 6, 7, or 8), q10 is an integer from 0 to 8 (e.g., 1, 2, 3, 4, 5, or 6), q11 is 0 or 1, Z is O or S, and each $R^M$ is independently H, an auxiliary moiety, —(CH$_2$)$_{q7}$—CO—N(R$^{M1}$)$_2$, or —C[—CH$_2$O—(CH$_2$)$_{q7}$—CO—N(R$^{M1}$)$_2$]$_3$, where each q7 is independently an integer from 1 to 5, and each $R^{M1}$ is independently H or auxiliary moiety.

The following exemplary conjugating groups can be used for conjugation to a targeting moiety through amide formation:

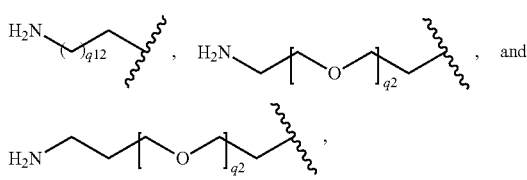

where q2 is an integer from 0 to 50 (e.g., an integer from 1 to 8 (e.g., 2 or 3)), and q12 is an integer from 1 to 11 (e.g., an integer from 1 to 5 (e.g., 1, 2, 3, 4, or 5).

Bioreversible Groups

A bioreversible group is a monovalent substituent having a molecular weight of from 135 Da to 10 kDa (e.g., from 135 Da to 5 kDa, from 200 Da to 5 kDa, or from 200 Da to 2 kDa) and containing disulfide (—S—S—). In a bioreversible group, the shortest chain of atoms covalently linking the disulfide and the valency of the bioreversible group may be from 2 to 10 atoms (e.g., from 2 to 6 atoms or from 4 to 6 atoms (e.g., 4 or 5 atoms)). The bioreversible group may be cleavable intracellularly under physiological conditions.

A bioreversible group may be included in phosphoesters, e.g., to reduce the overall negative charge of an immunomodulating polynucleotide of the invention. The reduction in the overall negative charge of an immunomodulating polynucleotide may enhance cellular uptake of an immunomodulating polynucleotide and/or conjugate of the invention. Immunomodulating polynucleotides of the invention may include one or more bioreversible groups in phosphoesters and/or abasic spacers. In some embodiments, an immunomodulating polynucleotide of the invention may include from 1 to 6 bioreversible groups (e.g., from 1 to 4 bioreversible groups (e.g., 1, 2, or 3 bioreversible groups)).

A bioreversible group can be of formula (XXII):

$$R^5—S—S-(LinkB)-, \quad (XXII)$$

where
LinkB is a divalent group containing an sp$^3$-hybridized carbon atom bonded to phosphate, phosphorothioate, or phosphorodithioate, and a carbon atom bonded to —S—S—, and $R^5$ is optionally substituted C$_{1-6}$ alkyl, optionally substituted C$_{6-10}$ aryl, or -LinkC(-R$^M$)$_r$, or LinkB is a trivalent linker containing an sp$^3$-hybridized carbon atom bonded to phosphate, phosphorothioate, or phosphorodithioate, and a carbon atom bonded to —S—S—, in which the third valency of LinkB combines with —S—S— and R$^5$ to form optionally substituted C$_{3-9}$ heterocyclylene;
LinkC is a multivalent group;
each R$^M$ is independently H, an auxiliary moiety, or -Q$^G$[(-Q$^B$-Q$^C$-Q$^D$)$_{s2}$-R$^{M1}$]$_{p1}$, where
each R$^{M1}$ is independently H or an auxiliary moiety,
each Q$^B$ and each Q$^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—,
each Q$^C$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene,
each Q$^G$ is independently optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl,
each s2 is independently an integer from 0 to 10, and p1 is 2 or 3;
and
r is an integer from 1 to 6 (e.g., 1, 2, or 3).

In certain embodiments, LinkB and/or R$^5$ includes a bulky group attached to —S—S—. The inclusion of a bulky group attached to —S—S— may enhance the stability of the sulfur-sulfur bond, e.g., during the polynucleotide synthesis.

In further embodiments, LinkB consists of 1, 2, or 3 groups, each of the groups being independently selected from the group consisting of optionally substituted C$_{1-12}$ alkylene, optionally substituted C$_{2-12}$ alkenylene, optionally substituted C$_{2-12}$ alkynylene, optionally substituted C$_{6-10}$ arylene, optionally substituted C$_{2-12}$ heteroalkylene, and optionally substituted C$_{1-9}$ heterocyclylene.

In particular embodiments, LinkB and —S—S— combine to form a structure selected from the group consisting of:

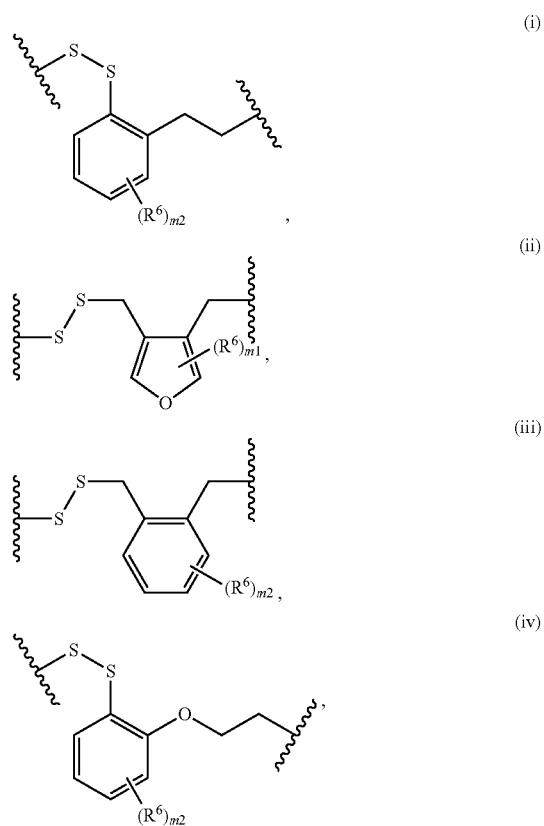

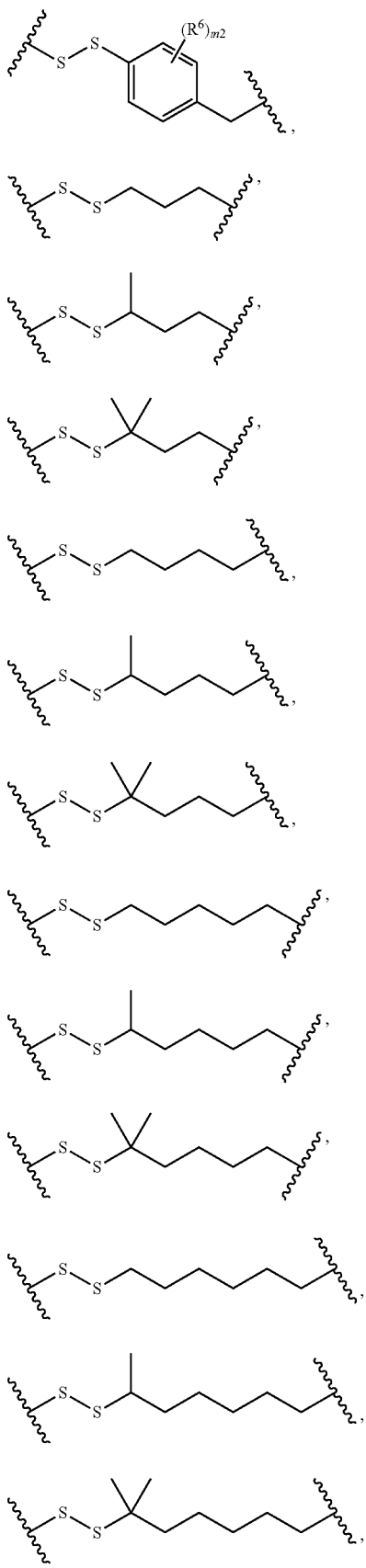

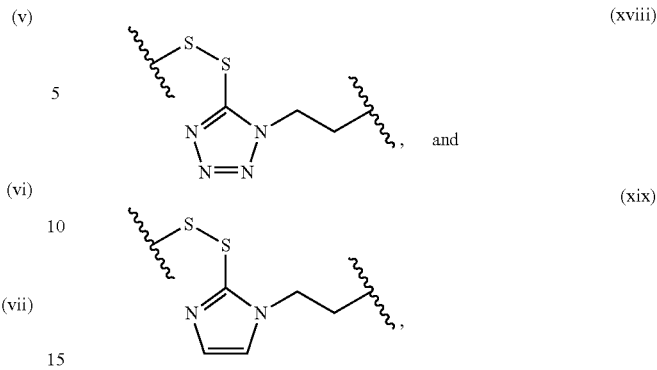

where
each $R^6$ is independently $C_{2-7}$ alkanoyl; $C_{1-6}$ alkyl; $C_{2-6}$ alkenyl; $C_{2-6}$ alkynyl; $C_{1-6}$ alkylsulfinyl; $C_{6-10}$ aryl; amino; $(C_{6-10}$ aryl$)$-$C_{1-4}$-alkyl; $C_{3-8}$ cycloalkyl; $(C_{3-8}$ cycloalkyl$)$-$C_{1-4}$-alkyl; $C_{3-8}$ cycloalkenyl; $(C_{3-8}$ cycloalkenyl$)$-$C_{1-4}$-alkyl; halo; $C_{1-9}$ heterocyclyl; $C_{1-9}$ heteroaryl; $(C_{1-9}$ heterocyclyl$)$oxy; $(C_{1-9}$ heterocyclyl$)$aza; hydroxy; $C_{1-6}$ thioalkoxy; —$(CH_2)_q CO_2 R^A$, where q is an integer from zero to four, and $R^A$ is selected from the group consisting of $C_{1-6}$ alkyl, $C_{6-10}$ aryl, and $(C_{6-10}$ aryl$)$-$C_{1-4}$-alkyl; —$(CH_2)_q CONR^B R^C$, where q is an integer from zero to four and where $R^B$ and $R^C$ are independently selected from the group consisting of hydrogen, $C_{1-6}$ alkyl, $C_{6-10}$ aryl, and $(C_{6-10}$ aryl$)$-$C_{1-4}$-alkyl; —$(CH_2)_q SO_2 R^D$, where q is an integer from zero to four and where $R^D$ is selected from the group consisting of $C_{1-6}$ alkyl, $C_{6-10}$ aryl, and $(C_{6-10}$ aryl$)$-$C_{1-4}$-alkyl; —$(CH_2)_q SO_2 NR^E R^F$, where q is an integer from zero to four and where each of $R^E$ and $R^F$ is, independently, selected from the group consisting of hydrogen, alkyl, aryl, and $(C_{6-10}$ aryl$)$-$C_{1-4}$-alkyl; thiol; aryloxy; cycloalkoxy; arylalkoxy; $(C_{1-9}$ heterocyclyl$)$-$C_{1-4}$-alkyl; $(C_{1-9}$ heteroaryl$)$-$C_{1-4}$-alkyl; $C_{3-12}$ silyl; cyano; or —$S(O)R^H$ where $R^H$ is selected from the group consisting of hydrogen, $C_1$-$C_6$ alkyl, $C_{6-10}$ aryl, and $(C_{6-10}$ aryl$)$-$C_{1-4}$-alkyl; or two adjacent $R^6$ groups, together with the atoms to which each of the $R^6$ groups is attached combine to form a cyclic group selected from the group consisting of $C_6$ aryl, $C_{2-5}$ heterocyclyl, or $C_{2-5}$ heteroaryl, wherein the cyclic group is optionally substituted with 1, 2, or 3 substituents selected from the group consisting of $C_{2-7}$ alkanoyl; $C_{1-6}$ alkyl; $C_{2-6}$ alkenyl; $C_{2-6}$ alkynyl; $C_{1-6}$ alkylsulfinyl; $C_{6-10}$ aryl; amino; $(C_{6-10}$ aryl$)$-$C_{1-4}$-alkyl; $C_{3-8}$ cycloalkyl; $(C_{3-8}$ cycloalkyl$)$-$C_{1-4}$-alkyl; $C_{3-8}$ cycloalkenyl; $(C_{3-8}$ cycloalkenyl$)$-$C_{1-4}$-alkyl; halo; $C_{1-9}$ heterocyclyl; $C_{1-9}$ heteroaryl; $(C_{1-9}$ heterocyclyl$)$oxy; $(C_{1-9}$ heterocyclyl$)$aza; hydroxy; $C_{1-6}$ thioalkoxy; —$(CH_2)_q CO_2 R^A$, where q is an integer from zero to four, and $R^A$ is selected from the group consisting of $C_{1-6}$ alkyl, $C_{6-10}$ aryl, and $(C_{6-10}$ aryl$)$-$C_{1-4}$-alkyl; —$(CH_2)_q CONR^B R^C$, where q is an integer from zero to four and where $R^B$ and $R^C$ are independently selected from the group consisting of hydrogen, $C_{1-6}$ alkyl, $C_{6-10}$ aryl, and $(C_{6-10}$ aryl$)$-$C_{1-4}$-alkyl; —$(CH_2)_q SO_2 R^D$, where q is an integer from zero to four and where $R^D$ is selected from the group consisting of $C_{1-6}$ alkyl, $C_{6-10}$ aryl, and $(C_{6-10}$ aryl$)$-$C_{1-4}$-alkyl; —$(CH_2)_q SO_2 NR^E R^F$, where q is an integer from zero to four and where each of $R^E$ and $R^F$ is, independently, selected from the group consisting of hydrogen, alkyl, aryl, and $(C_{6-10}$ aryl$)$-$C_{1-4}$-alkyl; thiol; aryloxy; cycloalkoxy; arylalkoxy; $(C_{1-9}$ heterocyclyl$)$-$C_{1-4}$-alkyl; $(C_{1-9}$ heteroaryl$)$-$C_{1-4}$-alkyl; $C_{3-12}$ silyl; cyano; and —$S(O)R^H$ where $R^H$ is selected from the group consisting of hydrogen, $C_1$-$C_6$ alkyl, $C_{6-10}$ aryl, and $(C_{6-10}$ aryl$)$-$C_{1-4}$-alkyl;

m1 is 0, 1, or 2; and
m2 is 0, 1, 2, 3, or 4;
or LinkB, —S—S—, and $R^5$ combine to form a group containing

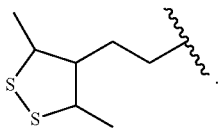

(XX)

In yet further embodiments, LinkC can include from 0 to 3 multivalent monomers (e.g., optionally substituted $C_{1-6}$ alkane-triyl, optionally substituted $C_{1-6}$ alkane-tetrayl, ortrivalent nitrogen atom) and one or more divalent monomers (e.g., from 1 to 40), where each divalent monomer is independently optionally substituted $C_{1-6}$ alkylene; optionally substituted $C_{2-6}$ alkenylene; optionally substituted $C_{2-6}$ alkynylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; imino; optionally substituted N; O; or $S(O)_m$, wherein m is 0, 1, or 2. In some embodiments, each monomer is independently optionally substituted $C_{1-6}$ alkylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; imino; optionally substituted N; O; or $S(O)_m$, where m is 0, 1, or 2 (e.g., m is 2). In certain embodiments, each monomer is independently optionally substituted $C_{1-6}$ alkylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; optionally substituted N; O; or $S(O)_m$, where m is 0, 1, or 2 (e.g., m is 2). The non-bioreversible linker connecting the auxiliary moiety to the conjugation moiety or to the reaction product thereof can include from 2 to 500 (e.g., 2 to 300, 2 to 200, 2 to 100, or 2 to 50) of such monomers. LinkC may include one or more polyethylene glycols (e.g., the polyethylene glycols may have a molecular weight of from 88 Da to 1 kDa (e.g., from 88 Da to 500 Da).

Compounds that may be used in the preparation of group -LinkC(-$R^M$)$_r$ in formula (IIa) are described herein as well as in WO 2015/188197. Non-limiting examples of -LinkC(-$R^M$)$_r$ include:

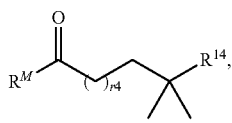

(xxi)

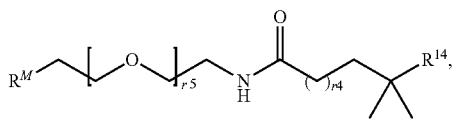

(xxii)

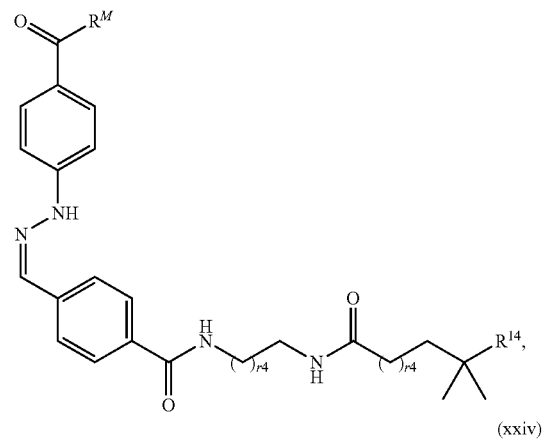

(xxiii)

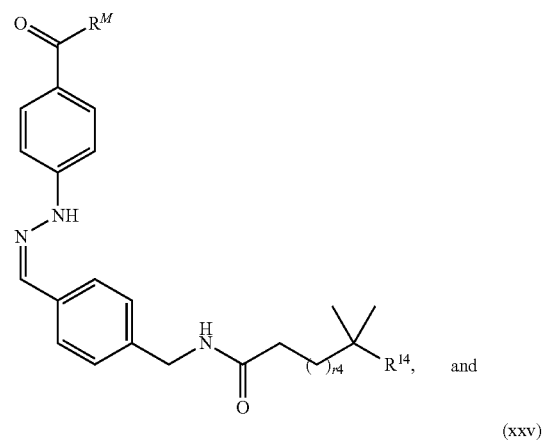

(xxiv)

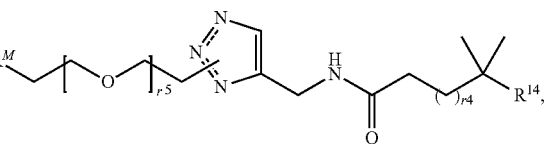

(xxv)

where
$R^{14}$ is a bond to —S—S—,
$R^M$ is an auxiliary moiety or -$Q^G$[(-$Q^B$-$Q^C$-$Q^D$)$_{s2}$-$R^{M1}$]$_{p1}$,
where
each $R^{M1}$ is independently H or an auxiliary moiety,
each $Q^B$ and each $Q^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—,
each $Q^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;
each $Q^G$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl,
each s2 is independently an integer from 0 to 10, and
p1 is 2 or 3;
each r4 is independently an integer from 1 to 6; and
each r5 is independently an integer from 0 to 10.

In certain embodiments, $R^M$ is an auxiliary moiety. In some embodiments, at least one $R^{M1}$ is an auxiliary moiety.

In certain embodiments, the bioreversible linker group is

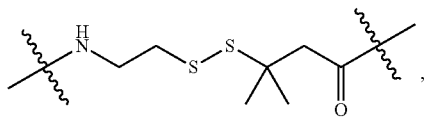 [SMILES: *NCCSSC(C)(C)CC(*)=O]

wherein one end of the group is connected to a polynucleotide and the other end is connected to a target moiety (in one embodiment, an antibody).

Non-Bioreversible Groups

A non-bioreversible group is a monovalent substituent that does not contain bonds cleavable under physiologic conditions in serum or in an endosome (e.g., esters, thioesters, or disulfides). The non-bioreversible group may be optionally substituted $C_{2-16}$ alkyl; optionally substituted $C_{3-16}$ alkenyl; optionally substituted $C_{3-16}$ alkynyl; optionally substituted $C_{3-8}$ cycloalkyl; optionally substituted $C_{3-8}$ cycloalkenyl; optionally substituted ($C_{3-8}$ cycloalkyl)-$C_{1-4}$-alkyl; optionally substituted ($C_{3-8}$ cycloalkenyl)-$C_{1-4}$-alkyl; optionally substituted $C_{6-14}$ aryl; optionally substituted ($C_{6-14}$ aryl)-$C_{1-4}$-alkyl; optionally substituted $C_{1-9}$ heteroaryl having 1 to 4 heteroatoms selected from N, O, and S; optionally substituted ($C_{1-9}$ heteroaryl)-$C_{1-4}$-alkyl having 1 to 4 heteroatoms selected from N, O, and S; optionally substituted $C_{2-9}$ heterocyclyl having 1 to 4 heteroatoms selected from N, O, and S, where the heterocyclyl does not contain an S—S bond; optionally substituted ($C_{2-9}$ heterocyclyl)-$C_{1-4}$-alkyl having 1 to 4 heteroatoms selected from N, O, and S, where the heterocyclyl does not contain an S—S bond; or a group of formula (XXIII):

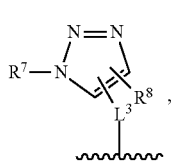

(XXIII)

where $L^3$ is $C_{2-6}$ alkylene;

$R^7$ is optionally substituted $C_{2-6}$ alkyl; optionally substituted $C_{6-14}$ aryl; optionally substituted ($C_{6-14}$ aryl)-$C_{1-4}$-alkyl; optionally substituted $C_{3-8}$ cycloalkyl; optionally substituted ($C_{3-8}$ cycloalkyl)-$C_{1-4}$-alkyl; optionally substituted $C_{1-9}$ heteroaryl having 1 to 4 heteroatoms selected from the group consisting of N, O, and S; optionally substituted ($C_{1-9}$ heteroaryl)-$C_{1-4}$-alkyl having 1 to 4 heteroatoms selected from the group consisting of N, O, and S; optionally substituted $C_{2-9}$ heterocyclyl having 1 to 4 heteroatoms selected from the group consisting of N, O, and S, wherein the heterocyclyl does not contain an S—S bond; optionally substituted ($C_{2-9}$ heterocyclyl)-$C_{1-4}$-alkyl having 1 to 4 heteroatoms selected from N, O, and S, wherein the heterocyclyl does not contain an S—S bond; and a polyethylene glycol) terminated with —OH, $C_{1-6}$ alkoxy, or —COOH; and $R^8$ is H or $C_{1-6}$ alkyl.

A non-bioreversible phosphotriester may be a phosphate or a phosphorothioate substituted with a substituent that is a conjugating group, $C_{2-6}$ alkyl,

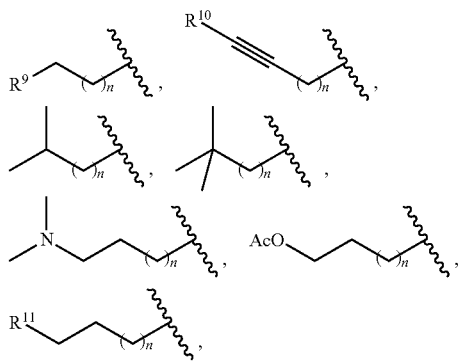

or a group formed by cycloaddition reaction of

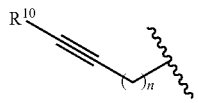

with an azido-containing substrate, where n is an integer from 1 to 6;

$R^9$ is optionally substituted $C_6$ aryl; optionally substituted $C_{4-5}$ heteroaryl that is a six member ring containing 1 or 2 nitrogen atoms; or optionally substituted $C_{4-5}$ heterocyclyl that is a six member ring containing 1 or 2 nitrogen atoms;

$R^{10}$ is H or $C_{1-6}$ alkyl;

$R^{11}$ is a halogen, —COOR$^{11A}$, or —CON(R$^{11B}$)$_2$, where each of $R^{11A}$ and $R^{11B}$ is independently H, optionally substituted $C_{1-6}$ alkyl, optionally substituted $C_{6-14}$ aryl, optionally substituted $C_{1-9}$ heteroaryl, or optionally substituted $C_{2-9}$ heterocyclyl; and the azido-containing substrate is

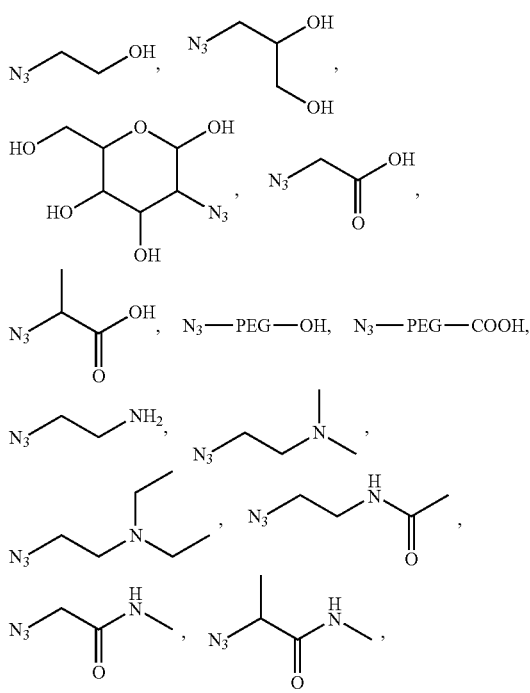

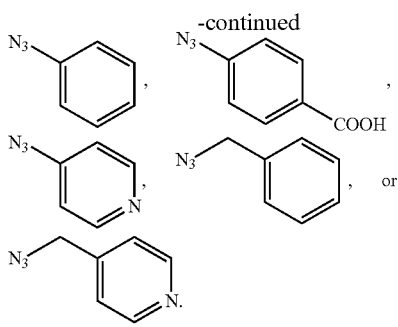

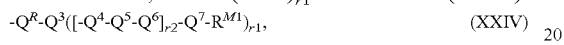

In some embodiments, a non-bioreversible group is -LinkD(-R$^{M1}$)$_{r1}$, where LinkD is a multivalent linker, each R$^{M1}$ is independently H or an auxiliary moiety, and r1 is an integer from 1 to 6.

In some instances, -LinkD(-R$^{M1}$)$_{r1}$ is of formula (XXIV):

$$-Q^R-Q^3([-Q^4-Q^5-Q^6]_{r2}-Q^7-R^{M1})_{r1}, \quad (XXIV)$$

where
r1 is an integer from 1 to 6;
each r2 is independently an integer from 0 to 50 (e.g., from 0 to 30), where the repeating units are same or different;
Q$^R$ is [-Q$^4$-Q$^5$-Q$^6$]$_{r2}$-Q$^L$-, where Q$^L$ is optionally substituted C$_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted C$_{1-12}$ thioheterocyclylene (e.g., 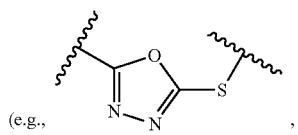,

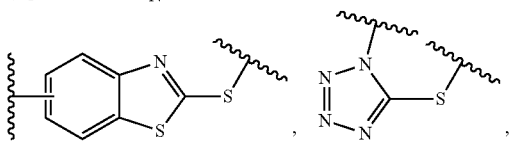,

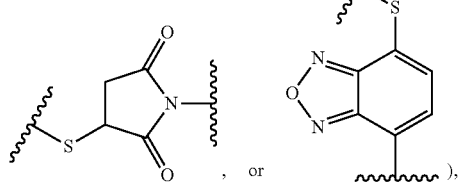, or 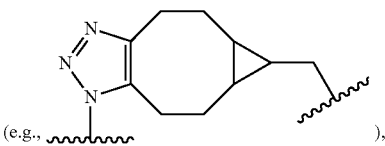), optionally substituted C$_{1-12}$ heterocyclylene (e.g., 1,2,3-triazole-1,4-diyl or

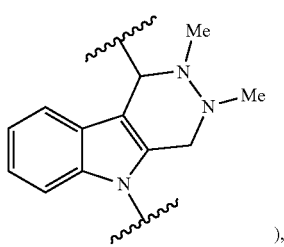 [SMILES: *C1c2c(n(*)c3ccccc23)CN(C)N1C]), cyclobut-3-ene-1,2-dione-3,4-diyl, pyrid-2-yl hydrazone, optionally substituted C$_{6-16}$ triazoloheterocyclylene (e.g., 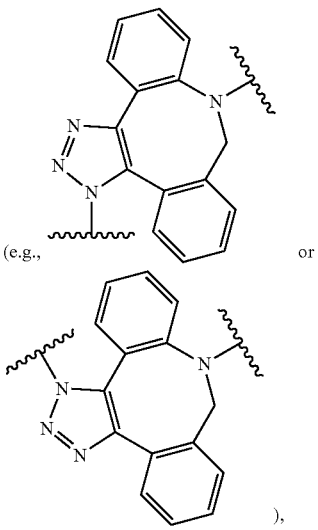 or

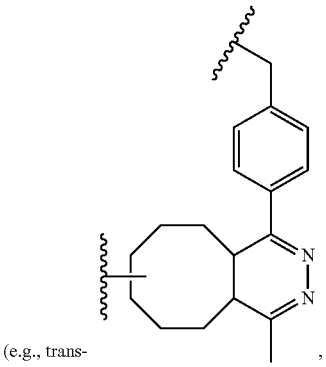), optionally substituted C$_{8-16}$ triazolocycloalkenylene (e.g., ), (e.g., A), or a dihydropyridazine group

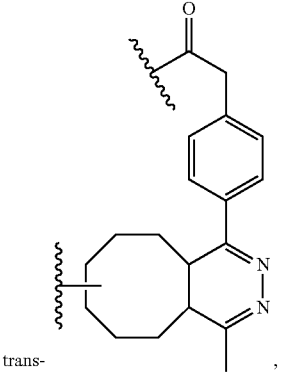

(e.g., trans- , trans-

-continued

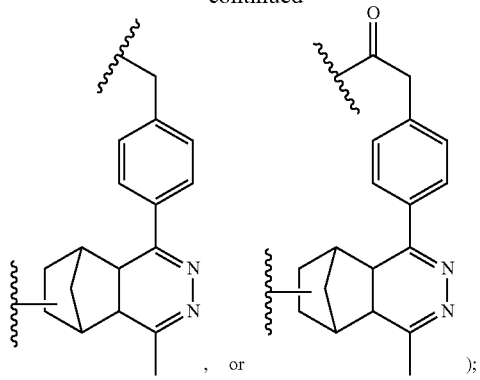

, or );

Q³ is a linear group (e.g., [-Q⁴-Q⁵-Q⁶]$_{r2}$-), if r1 is 1, or a branched group (e.g., [-Q⁴-Q⁵-Q⁶]$_s$-Q⁸([-Q⁴-Q⁵-Q⁶]$_{r2}$-(Q⁸)$_{r3}$)$_{r4}$, where r3 is 0 or 1, r4 is 0, 1, 2, or 3, if r1 is an integer from 2 to 6; each r2 is independently an integer from 0 to 50 (e.g., from 0 to 30), where the repeating units are the same or different;

each Q⁴ and each Q⁶ is independently absent —CO—, —NH—, —O—, —S—, —SO₂—, —OC(O)—, —COO—, —NHC(O)—, —C(O)NH—, —CH₂—, —CH₂NH—, —NHCH₂—, —CH₂O—, or —OCH₂—; each Q⁵ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene;

each Q⁷ is independently absent, —CO—, —NH—, —O—, —S—, —SO₂—, —CH₂—, —C(O)O—, —OC(O)—, —C(O)NH—, —NH—C(O)—, —NH—CH(R$^a$)—C(O)—, or —C(O)—CH(R$^a$)—NH—;

each Q⁸ is independently optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl; and each R$^a$ is independently H or an amino acid side chain; and each R$^{M1}$ is independently H or an auxiliary moiety.

In formula (XXIV), at least one of Q⁴, Q⁵, and Q⁶ is present. In formula (XXIV), LinkD may include a single branching point, if each r3 is 0, or multiple branching points, if at least one r3 is 1. In formula (XXIV), Q$^R$ may be -Q⁵-Q⁴-Q$^L$-, where Q⁵ is optionally substituted C$_{2-12}$ heteroalkylene or optionally substituted C$_{1-12}$ alkylene, and Q⁴ is —CO—, —NH—, or —O—. In formula (XXIV), Q$^L$ may be:

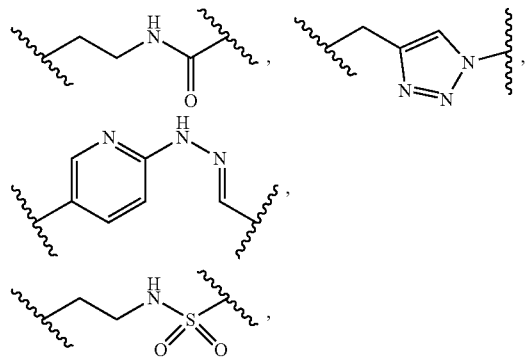

trans-

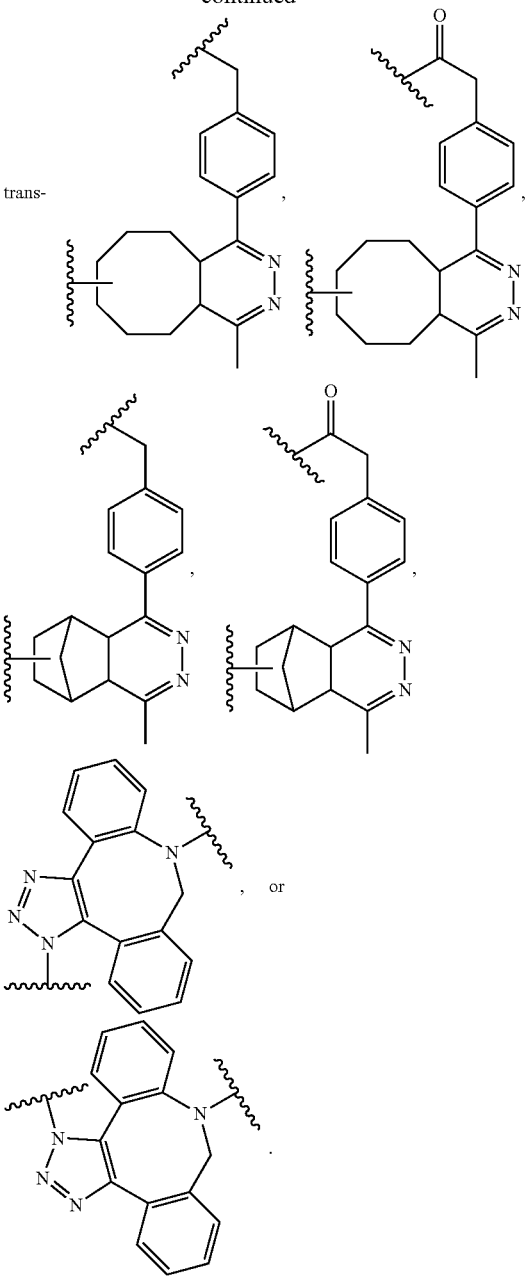

In formula (XXIV), Q³ may be a linear group of formula [-Q⁴-Q⁵-Q⁶]$_{r2}$-, where Q⁴, Q⁵, and Q⁶ are as defined for formula (XXIV). Alternatively, Q³ may be a branched group [-Q⁴-Q⁵-Q⁶]$_{r2}$-Q⁸([-Q⁴-Q⁵-Q⁶]$_{r2}$-(Q⁸)$_{r3}$)$_{r4}$, where each Q⁸ is independently optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl;

where each r2 is independently an integer from 0 to 50 (e.g., from 0 to 30), where the repeating units are the same or different;

r3 is 0 or 1;

r4 is 0, 1, 2, or 3;

where, when r3 is 0, LinkD is a trivalent or tetravalent group, and, when r3 is 1, LinkD is a tetravalent, pentavalent, or hexavalent group.

In certain embodiments, r3 is 0.

In some embodiments, $Q^8$ is:

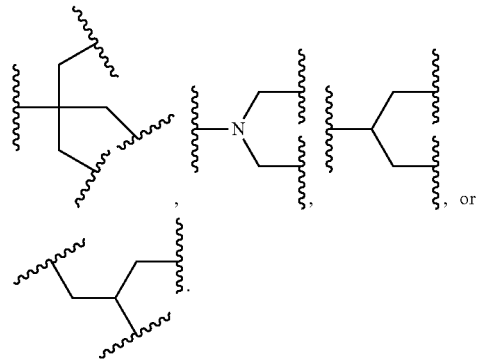

, or

Compounds that may be used in the preparation of group -LinkD(-$R^{M1}$)$_p$ in formula (I) are described herein as well as in WO 2015/188197.

In certain embodiments, the non-bioreversible linker group is

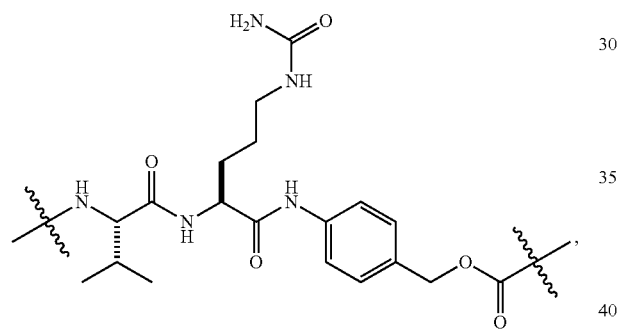

wherein one end of the group is connected to a polynucleotide and the other end is connected to a target moiety (in one embodiment, an antibody).

Auxiliary Moieties

An auxiliary moiety is a monovalent group containing a dye or a hydrophilic group or a combination thereof (e.g., a hydrophilic polymer (e.g., polyethylene glycol) (PEG)), a positively charged polymer (e.g., polyethylene imine)), or a sugar alcohol (e.g., glucitol)). An auxiliary moiety may have a theoretical molecular weight of from 100 Da to 2.5 kDa (e.g., from 350 Da to 2.5 kDa, from 100 Da to 1,200 Da, or from 1 kDa to 2.5 kDa).

Dyes may be included in the phosphoester groups for the purpose of visualization of uptake or monitoring the movement of the conjugates of the invention inside a cell (e.g., using Fluorescence Recovery After Photobleaching (FRAP)). Dyes known in the art may be included as an auxiliary moiety linked to the polynucleotide via a phosphate or phosphorothioate at the 5'- or 3'-terminus or via a phosphate or phosphorothioate bonding two consecutive nucleosides together. Non-limiting examples of useful structures that can be used as dyes include FITC, RD1, allophycocyanin (APC), aCF™ dye (Biotium, Hayward, Calif.), BODIPY (Invitrogen™ 10 of Life Technologies, Carlsbad, Calif.), AlexaFluor® (Invitrogen™ of Life Technologies, Carlsbad, Calif.), DyLight Fluor (Thermo Scientific Pierce Protein Biology Products, Rockford, Ill.), ATTO (ATTO-TEC GmbH, Siegen, Germany), FluoProbe (Interchim SA, Motlugon, France), and Abberior Probes (Abberior GmbH, Gottingen, Germany).

Hydrophilic polymers and positively charged polymers that may be used as auxiliary moieties in the immunomodulating polynucleotides of the invention and in the conjugates of the invention are known in the art. A non-limiting example of a hydrophilic polymer is polyethylene glycol). A non-limiting example of a positively charged polymer is polyethylene imine).

A sugar alcohol-based auxiliary moiety may be, e.g., amino-terminated glucitol or a glucitol cluster. The amino-terminated glucitol auxiliary moiety is:

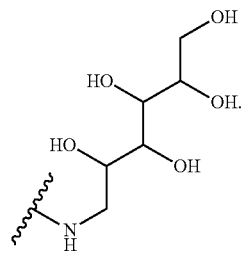 [SMILES: *NCC(O)C(O)C(O)C(O)CO]

Non-limiting examples of glucitol clusters are:

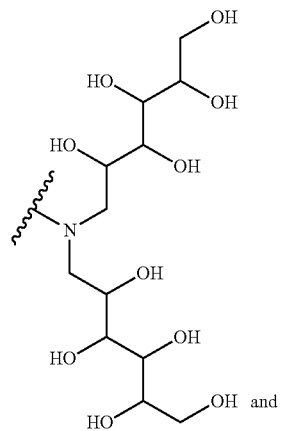

and

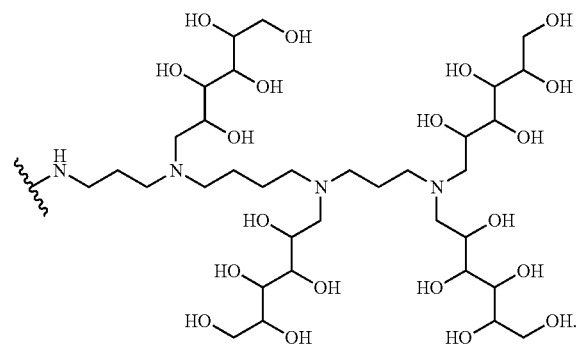

In one embodiment, provided herein is a compound of Formula (B):

or a stereoisomer, a mixture of two or more diastereomers, a tautomer, or a mixture of two or more tautomers; or a pharmaceutically acceptable salt, solvate, or hydrate thereof; wherein:

$R^x$ is a conjugating group;
$L^N$ is a linker;
each Q is independently an oligonucleotide comprising a phosphotriester; and
e is an integer of 1, 2, 3, or 4.

In certain embodiments, in Formula (B), $R^x$ is

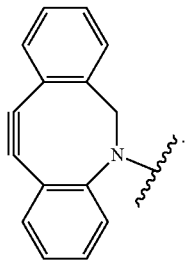 [SMILES: *N1Cc2ccccc2C#Cc2ccccc21]

In certain embodiments, in Formula (B), $L^N$ is a linker comprising a polyethylene glycol.

In certain embodiments, in Formula (B), $L^N$ is

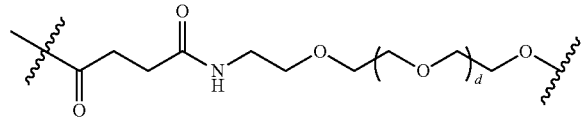

wherein d is an integer ranging from about 0 to about 50. In certain embodiments, d is an integer ranging from about 0 to about 10. In certain embodiments, d is an integer ranging from about 0 to about 5. In certain embodiments, d is an integer of about 0, about 1, or about 3.

In certain embodiments, in Formula (B), e is an integer of 1.

In certain embodiments, in Formula (B), each Q independently has the structure of Formula (D):

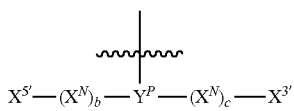

wherein $X^N$, $X^{3'}$, $X^{5'}$, $Y^P$, b, and c are each as defined herein.

Targeting Moieties

The targeting moieties used in the conjugates of the invention can be used to target specific cells and tissues in a body for targeted delivery of the conjugated payload polynucleotide. The cells targeted by the conjugates of the invention are professional APCs (e.g., B cells, pDCs, or macrophages). The targeting moiety can be an antigen-binding moiety (e.g., an antibody or antigen-binding fragment thereof), a polypeptide, an aptamer, or a group including one or more small molecules (e.g., mannose). The targeting moieties in the conjugates of the invention can be effective in addressing the problem of the uneven tissue distribution of of immunomodulating polynucleotides in vivo.

Antigen-Binding Moieties

An antigen-binding moiety in the conjugate of the invention can be an antibody or an antigen-binding fragment thereof (e.g., $F(ab)_2$ or Fab) or an engineered derivative thereof (e.g., Fcab or a fusion protein (e.g., scFv)). A human or chimeric (e.g., humanized) antibody can be used as an antibody in the conjugate of the invention.

The antigen-binding moiety targets the cells having the surface antigen that is recognized by the antigen-binding moiety. In particular, APCs can be targeted by the antigen-binding moieties in the conjugates of the invention. B cells can be targeted by anti-CD38, anti-CD79b, anti-CD30, anti-CD22, or anti-CD20, anti-CD19 antibodies or antigen-binding fragments thereof or engineered derivatives thereof. Plasmacytoid dendritic cells (pDCs) can be targeted by anti-DEC205, anti-CD304, anti-CD303, anti-CD40, anti-CD74, anti-BDCA2, or anti-CD123 antibodies or antigen-binding fragments thereof or engineered derivatives thereof. Macrophages can be targeted by anti-CD163, anti-CD40, anti-CD74, anti-CD206, or anti-CD123 antibodies or antigen-binding fragments thereof or engineered derivatives thereof.

Non-limiting examples of anti-CD38 antibodies are daratumumab, SAR650984, MOR202, or any one of antibodies Ab79, Ab19, Ab43, Ab72, and Ab110 disclosed in WO 2012/092616, the disclosure of these antibodies is incorporated herein by reference. A non-limiting example of an anti-CD79b antibody is huMA79b v28 disclosed in WO 2014/011521. A non-limiting example of an anti-CD22 antibody is 10F4 disclosed in US 2014/0127197. A non-limiting example of an anti-CD20 antibody is rituximab. A non-limiting example of an anti-DEC205 antibody is provided in US 2010/0098704, the antibodies of which are incorporated herein by reference. Non-limiting examples of anti-CD40 antibodies are lucatumumab and dacetuzumab. A non-limiting example of of an anti-CD304 antibody is vesencumab.

Polypeptides

The targeting moiety can be a polypeptide having an affinity for cells (e.g., having an affinity for a cell type, e.g., a plasmacytoid cell). Non-limiting examples of polypeptides are RGD peptide, rabies virus glycoprotein (RVG), and a DC3 peptide.

Small Molecules

The targeting moiety can be a small molecule capable of complexing a receptor expressed on the surface of the targeted cell. Non-limiting examples of small molecules that may be used as targeting moieties in the conjugates of the invention are folate, mannose, PSMA ligand, and mannose clusters.

Folate may be used as a targeting moiety. In the conjugates of the invention, folate may be of the following structure:

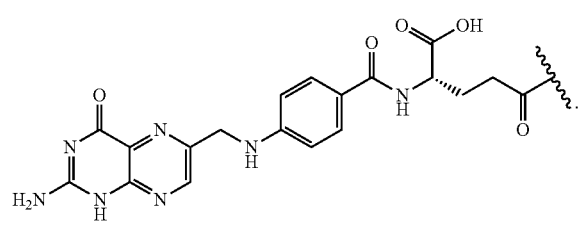 [SMILES: *C(=O)CC[C@H](NC(=O)c1ccc(NCc2cnc3[nH]c(N)nc(=O)c3n2)cc1)C(=O)O]

Mannose or a mannose cluster can be used to target the conjugates of the invention to plasmacytoid dendritic cells and macrophages, as these cells express mannose receptor on their surface.

Mannose clusters are known in the art. The mannose auxiliary moiety (e.g., a mannose cluster) may be of formula (XXV):

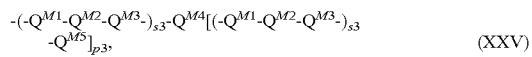
(XXV)

where p3 is 1, 2, or 3;

each s3 is independently an integer from 0 to 50 (e.g., from 0 to 30);

each $Q^{M1}$ and each $Q^{M3}$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and each $Q^{M2}$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;

$Q^{M4}$ is absent (if p3 is 1), optionally substituted $C_{1-6}$ alkane-triyl (if p3 is 2), optionally substituted $C_{1-6}$ alkane-tetrayl (if p3 is 3), optionally substituted $C_{2-6}$ heteroalkane-triyl (if p3 is 2), or optionally substituted $C_{2-6}$ heteroalkane-tetrayl (if p3 is 3);

each $Q^{M5}$ is independently mannose or -$Q^{M6}$[(-$Q^{M1}$-$Q^{M2}$-$Q^{M3}$)$_{s2}$-$R^{M2}$]$_{p1}$, where each $R^{M2}$ is independently mannose; and each $Q^{M6}$, if present, is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl.

Non-limiting examples of mannose clusters are:

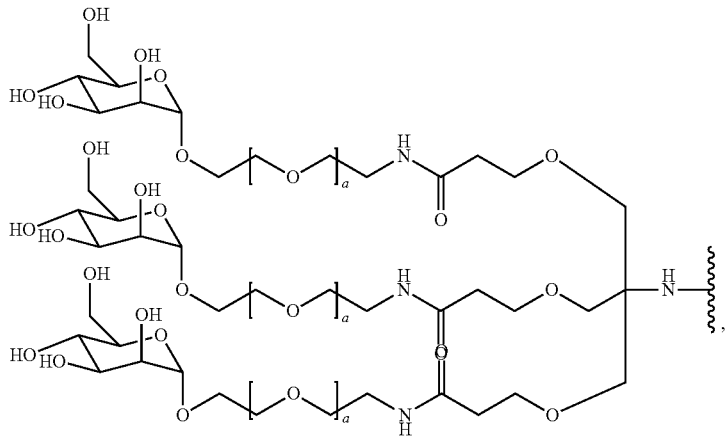
(XXVI)

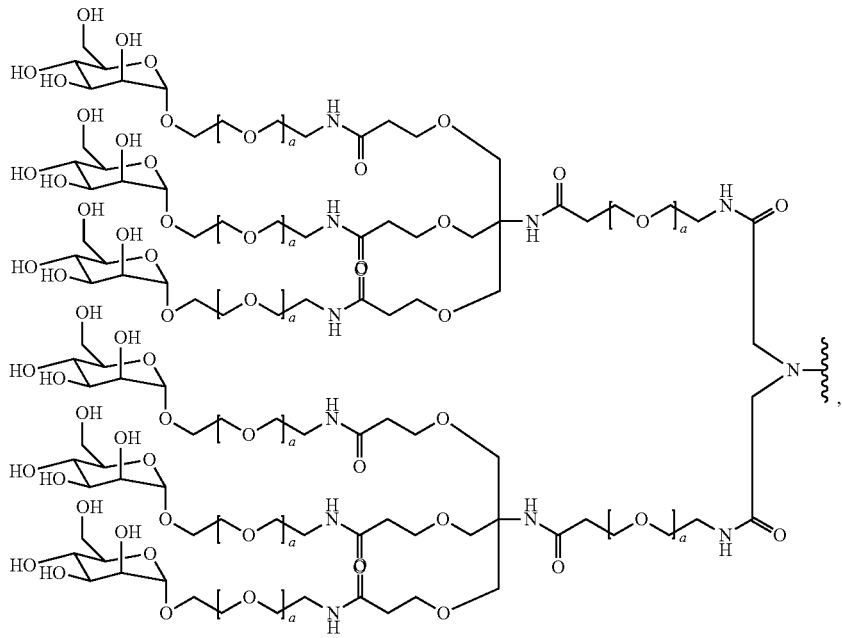
(XXVII)

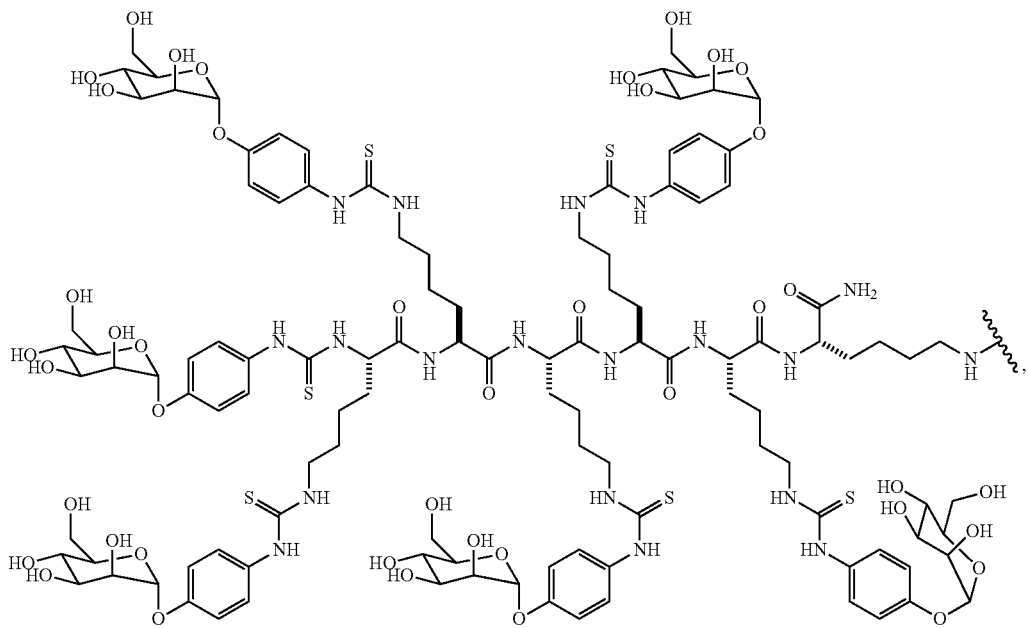

(XXVIII)

where each a is independently an integer from 0to 10.

Conjugates

In one embodiment, provided herein is a conjugate of Formula (C):

or a stereoisomer, a mixture of two or more diastereomers, a tautomer, or a mixture of two or more tautomers thereof; or a pharmaceutically acceptable salt, solvate, or hydrate thereof; wherein Ab is a targeting moiety; f is an integer of 1, 2, 3, or 4; and $L^N$, Q, and e are each as defined herein.

In certain embodiments, in Formula (C), Ab is an antibody. In certain embodiments, in Formula (C), Ab is a monoclonal antibody.

In certain embodiments, in Formula (C), f is an integer of 1 or 2. In certain embodiments, in Formula (C), f is an integer of 1.

In certain embodiments, in Formula (C), both e and f are each an integer of 1. The term "DAR" refers to a drug-antibody ratio of a CpG antibody conjugate, more specifically a polynucleotide-antibody ratio. In one embodiment, the CpG antibody conjugate has a DAR ranging from about 1 to about of about 20, from about 1 to about 10, from about 1 to about 8, from about 1 to about 4, or from about 1 to about 2. In another embodiment, the CpG antibody conjugate has a DAR of about 1, about 2, about 3, about 4, about 5, about 6, about 7, or about 8.

Preparation of Conjugates

Conjugation

Reactions useful for conjugating a targeting moiety to one or more immunomodulating polynucleotides are described herein and are known in the art (e.g., bioorthogonal reactions). Exemplary reactions that can be used to form this bond include Hüisgen cycloaddition (metal-catalyzed or metal-free) between an azido and an alkyne-based conjugating group (e.g., optionally substituted $C_{6-16}$ heterocyclylene containing an endocyclic carbon-carbon triple bond or optionally substituted $C_{8-16}$ cycloalkynyl) to form a triazole moiety; the Diels-Alder reaction between a dienophile and a diene/hetero-diene; bond formation via other pericyclic reactions such as the ene reaction; amide orthioamide bond formation; sulfonamide bond formation (e.g., with azido compounds); alcohol or phenol alkylation (e.g., Williamson alkylation), condensation reactions to form oxime, hydrazone, or semicarbazide group; conjugate addition reactions by nucleophiles (e.g., amines and thiols); disulfide bond formation; and nucleophilic substitution (e.g., by an amine, thiol, or hydroxyl nucleophile) at a carbonyl (e.g., at an activated carboxylic acid ester, such as pentafluorophenyl (PFP) ester or tetrafluorophenyl (TFP) ester) or at an electrophilic arene (e.g., SnAr at an oligofluorinated arene, a fluorobenzonitrile group, or fluoronitrobenzene group). In some embodiments, the conjugation reaction is a dipolar cycloaddition, and the conjugation moiety includes azido, optionally substituted $C_{6-16}$ heterocyclylene containing an endocyclic carbon-carbon triple bond, or optionally substituted $C_{8-16}$ cycloalkynyl. The complementary reactive group and the conjugating group are selected for their mutual complementarity. For example, an azide may be used in one of the conjugating group and the complementary reactive group, while an alkyne may be used in the other of the conjugating group and the complementary reactive group.

Nucleophile/Electrophile Reactions

Nucleophiles and electrophiles can engage in bond forming reactions selected from, without limitation, insertion by an electrophile into a C—H bond, insertion by an electrophile into an O—H bond, insertion by an electrophile into an N—H bond, addition of the electrophile across an alkene, addition of the electrophile across an alkyne, addition to electrophilic carbonyl centers, substitution at electrophilic carbonyl centers, addition to ketenes, nucleophilic addition to isocyanates, nucleophilic addition to isothiocyanates, nucleophilic substitution in electrophilic silyl groups, nucleophilic displacement of a leaving group (e.g., a halide or a pseudohalide) in an alkyl halide or pseudohalide; nucleophilic addition/elimination at a carbonyl of an activated carboxylic acid ester (e.g., PFP ester or TFP ester), thioester, anhydride, or acyl halide; 1,4-conjugate addition of a nucleophile to an α, β-unsaturated carbonyl groups, nucleophilic ring opening of an epoxide, nucleophilic aromatic substitution of an electron deficient aromatic compound, a nucleophilic addition to activated phosphorus centers, nucleophilic substitution at activated phosphorous centers, nucleophilic addition to activated sulfur centers, and nucleophilic substitution at activated sulfur centers.

A nucleophilic conjugating group can be optionally substituted alkene, optionally substituted alkyne, optionally substituted aryl, optionally substituted heterocyclyl, hydroxyl, amino, alkylamino, anilido, orthio.

An electrophilic conjugating group can be azide, activated carbonyl (e.g., activated carboxylic acid ester (e.g., succinimidyl ester or sulfosuccinimidyl ester), thioester, anhydride, or acyl halide), isocyanate, thioisocyanate, Michael acceptor (e.g., maleimide), alkyl halide or pseudohalide, epoxide, episulfide, aziridine, or electron-deficient aryl.

For example, conjugation can occur via a condensation reaction to form a linkage that is a hydrazone bond.

Conjugation can involve the formation of an amide bond, e.g., by activation of a carboxyl-based conjugating group (e.g., carboxylic acid, ester, or —$CONH_2$) and subsequent reaction with a primary amine in a conjugating group. Activating agents can be various carbodiimides like: EDC (1-Ethyl-3-(3-dimethylaminopropyl)carbodiimide hydrochloride), EDAC (1-ethyl-3(3-dimethylaminopropyl)carbodiimide hydrochloride), DCC (dicyclohexyl carbodiimide), CMC (1-Cyclohexyl-3-(2-morpholinoethyl) carbodiimide), DIC (diisopropyl carbodiimide) or Woodward's reagent K (N-ethyl-3-phenylisoxazolium-3'-sulfonate). Activation of the carboxyl-based conjugating group that is —$CONH_2$ can be achieved using a transglutaminase. Reaction of an activated NHS-Ester-based conjugating group with a primary amine-based conjugating group also results in formation of an amide bond.

The polynucleotide may contain a carbonyl-based conjugating group. Conjugation with concomitant formation of a secondary amine can be achieved through reductive amination (i.e., by reacting an amine-based conjugating group with an aldehyde-based conjugating group, followed by a reduction with a hydride donor (e.g., sodium cyanoborohydride or sodium triacetoxyborohydride)).

Ether formation can also be used to conjugate a targeting moiety to one or more polynucleotides to form a conjugate of the invention. Ether linkage formation can involve a reaction between an epoxide-based conjugating group with a hydroxy-based conjugating group.

Thiols can also be used as conjugating groups. For example, conjugation via the formation of disulfide bonds can be accomplished by pyridyldisulfide mediated thiol-disulfide exchange. Introduction of sulfhydryl-based conjugating groups is mediated for instance by Traut's Reagent (2-iminothiolane) SATA (N-succinimidyl S-acetylthioacetate, SATP (succinimidyl acetylthiopropionate), SPDP (N-succinimidyl 3-(2-pyridyldithio)propionate, SMPT (succinimidyloxycarbonyl-α-methyl-α-(2-pyridyldithio)toluene), N-acetylhomocysteinethiolactone, SAMSA (S-acetylmercaptosuccinic anhydride), AMBH (2-Acedamido-4-mercaptobuturic acid hydrazide), and cystamine (2,2'-dithiobis(ethylamine).

Thioether linkage formation can be performed by reacting a sulfhydryl based conjugating groups with maleimide- or iodoacetyl-based conjugating groups or by reacting with epoxide-based conjugating groups.

Maleimide-based conjugating groups can be introduced by SMCC (succinimidyl-4-(N-maleimidomethyl)cyclohexane-1-carboxylate), sulfo-SMCC (sulfosuccinimidyl 4-(N-maleidomethyl)-cyclohexane-1-carboxylate), MBS (m-Maleimidobenzoyl-N-hydroxysuccinimide ester), sulfo-MBS (m-Maleimidobenzoyl-N-sulfohydroxy succinimide ester), SMPB (Succinimidyl-4-(p-maleidophenyl)butyrate), sulfo-SMPB (sulfosuccinimidyl 4-(p-maleimidophenyl)butyrate), GMBS (N-α-maleimidobuturyl-oxysuccinimide ester), sulfo GMBS (N-α-maleimidobuturyl-oxysulfosuccinimide ester).

Conjugation via the formation of a carbamate linkage can be performed by reaction of a hydroxy-based conjugating groups with CDI (N,N'-carbonyldiimidazole) or DSC (N,N'-disuccinimidyl carbonate) or N-hydroxysuccinimidylchloroformate and subsequent reaction with an amine-based conjugating group.

Cycloaddition Reactions

Cycloaddition reactions can be used to form the desired covalent bond. Representative cycloaddition reactions include, but are not limited to, the reaction of an alkene-based conjugating group with a 1,3-diene-based conjugating group (Diels-Alder reaction), the reaction of an alkene-based conjugating group with an α,β-unsaturated carbonyl-based conjugating group (hetero Diels-Alder reaction), and the reaction of an alkyne-based conjugating group with an azido-based conjugating group (Hüisgen cycloaddition, including metal-catalyzed and metal-free variants thereof) to afford a triazole moiety. Selected, non-limiting examples of conjugating groups that include reactants for cycloaddition reactions are: alkenes, alkynes, 1,3-dienes, α,β-unsaturated carbonyls, and azides. For example, the Hüisgen cycloaddition (click reaction) between azides and alkynes has been used for the functionalization of diverse biological entities.

Strained alkyne-based conjugating group is a carbocyclic or heterocyclic ring system including one endocyclic carbon-carbon triple bond (e.g., optionally substituted $C_{6-16}$ heterocyclylene containing an endocyclic carbon-carbon triple bond or optionally substituted $C_{8-16}$ cycloalkynyl). Strained alkyne-based conjugating groups can be useful for conjugating a targeting moiety to a polynucleotide through metal-free dipolar cycloadditions with an azido conjugating group.

Coupling Reactions

Conjugating groups can include, but are not limited to, reactants for hydrosilylation, olefin cross-metathesis, conjugate addition, Stille coupling, Suzuki coupling, Sonogashira coupling, Hiyama coupling, and Heck reaction. Conjugation moieties for these reactions include hydridosilanes, alkenes (e.g., activated alkenes, such as enones orenoates), alkynes, aryl halides, aryl pseudohalides (e.g., triflates or nonaflates), alkyl halides, and alkyl pseudohalides (e.g., triflates, nonaflates, and phosphates). Catalysts for cross-coupling reactions are well-known in the art. Such catalysts may be organometallic complexes or metal salts (e.g., Pd(0), Pd(II), Pt(0), Pt(II), Pt(IV), Cu(I), or Ru(II)). Additives, such as ligands (e.g., PPtb, PCy3, BINAP, dppe, dppf, SIMes, or SIPr) and metal salts (e.g., LiCl), may be added to facilitate cross-coupling reactions.

Preparation of Immunomodulating Polynucleotides

The immunomodulating polynucleotides can be prepared according to methods known in the art of chemical synthesis of polynucleotides, e.g., from nucleoside phosphoramidites. Non-limiting examples of the syntheses of nucleoside phosphoramidites and immunomodulating polynucleotides are provided in the Examples. The phosphoramidite can include a conjugating group covalently linked to the P atom of the phosphoramidite.

Preparation of a Targeting Moiety Portion

A targeting moiety can be conjugated to one or more polynucleotides by forming a bond between a conjugating group in the immunomodulating polynucleotide and a complementary reactive group bonded to the targeting moiety. The targeting moiety may intrinsically possess the complementary reactive group (e.g., a Q-tag (e.g., LLQGG, GGGLLQGG, or another Q-tag sequence known in the art) in an antibody or antigen-binding fragment or an engineered derivative thereof), or it may be modified to include a complementary reactive group (e.g., by attaching the complementary reactive group to the Q-tag). Methods of introducing such complementary reactive groups into a targeting moiety is known in the art.

The complementary reactive group may include optionally substituted $C_{2-12}$ alkynyl, optionally substituted N-protected amino, azido, N-maleimido, S-protected thiol,

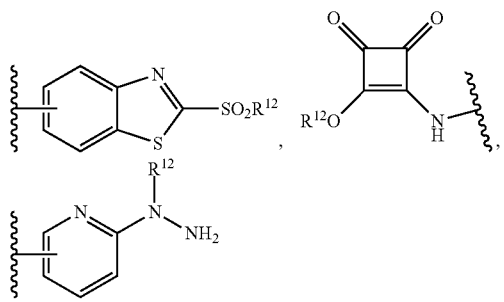

or N-protected version thereof,

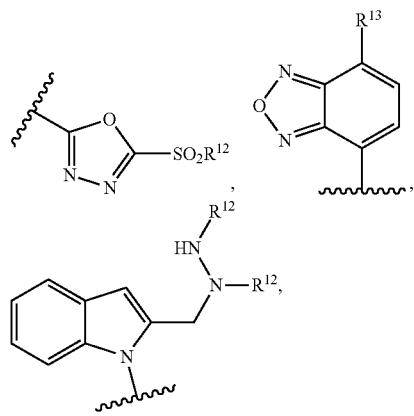

optionally substituted $C_{6-16}$ heterocyclyl containing an endocyclic carbon-carbon triple bond

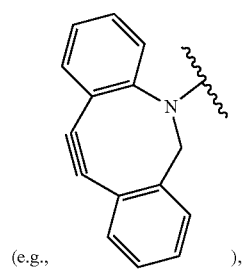 [SMILES: *N1Cc2ccccc2C#Cc2ccccc21]

(e.g., ), 1,2,4,5-tetrazine group

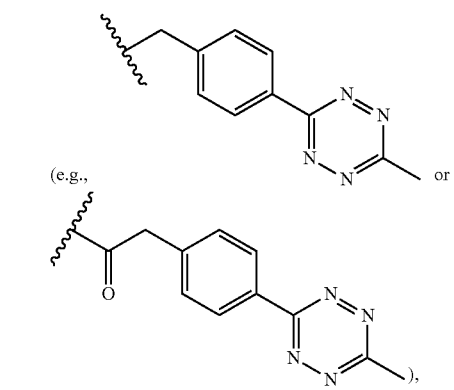

optionally substituted $C_{8-16}$ cycloalkynyl

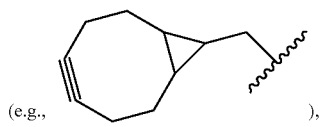 [SMILES: *CC1C2CCC#CCCC12]

(e.g., ),

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO;

where

R$^{N1}$ is H, N-protecting group, or optionally substituted $C_{1-6}$ alkyl;

each R$^{12}$ is independently H, optionally substituted $C_{1-6}$ alkyl, or O-protecting group (e.g., a carboxyl protecting group); and R$^{13}$ is halogen (e.g., F).

The complementary reactive group may be protected until the conjugation reaction. For example, a complementary reactive group that is protected may include —COOR$^{PGO}$ or —NHR$^{PGN}$, where R$^{PGO}$ is an o-protecting group (e.g., a carboxyl protecting group), and R$^{PGN}$ is an N-protecting group.

In some embodiments, a complementary reactive group is a group —Z$^3$-Q$^{43}$, where Z$^3$ is a divalent, trivalent, tetravalent, or pentavalent group, in which one of the valencies is substituted with Q$^{43}$, one of the valencies is open, and each of the remaining valencies, if present, is independently substituted with an auxiliary moiety;

Q$^{43}$ is optionally substituted $C_{2-12}$ alkynyl, optionally substituted N-protected amino, azido, N-maleimido, S-protected thiol,

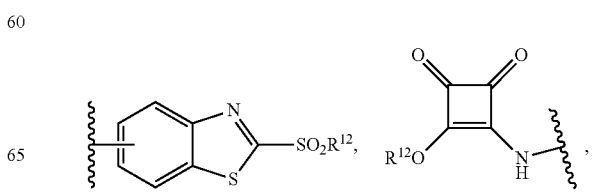

-continued

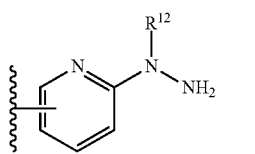

or N-protected version thereof,

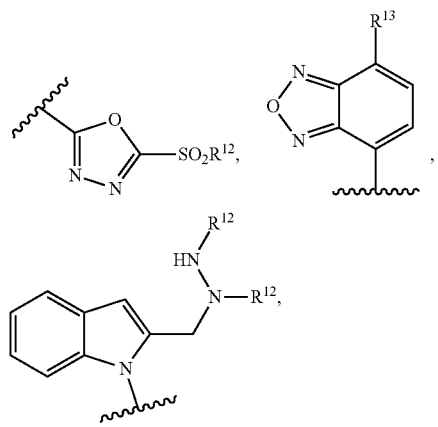

optionally substituted $C_{6-16}$ heterocyclyl containing an endocyclic carbon-carbon triple bond

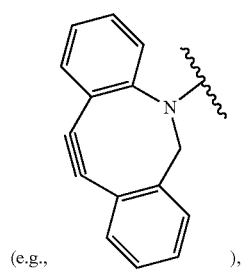 [SMILES: *N1Cc2ccccc2C#Cc2ccccc21]

1,2,4,5-tetrazine group

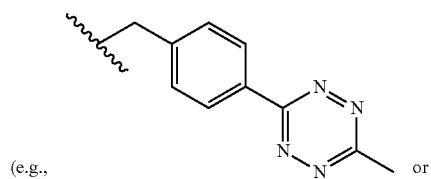

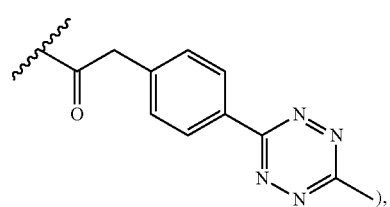

optionally substituted $C_{8-16}$ cycloalkynyl

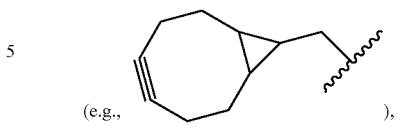

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO;
where
  R$^{N1}$ is H, N-protecting group, or optionally substituted $C_{1-6}$ alkyl;
  each R$^{12}$ is independently H, optionally substituted $C_{1-6}$ alkyl, or O-protecting group (e.g., a carboxyl protecting group); and
  R$^{13}$ is halogen (e.g., F).

In certain embodiments, $Z^3$ consists of a branching group and two divalent segments, where the branching group is bonded to each of the two divalent segments,
where
  one of the divalent segments has an open valency, and the remaining divalent segment is bonded to $Q^{43}$; and
  the branching group consists of one or two monomers independently selected from the group consisting of optionally substituted $C_{1-12}$ alkane-triyl, optionally substituted $C_{1-12}$ alkane-tetrayl, optionally substituted $C_{2-12}$ heteroalkane-triyl, and optionally substituted $C_{2-12}$ heteroalkane-tetrayl, where two valencies of the branching group are bonded to the two divalent segments, and each of the remaining valencies is independently substituted with an auxiliary moiety.

The divalent segment in $Z^3$ may be -(-Q$^B$-Q$^C$-Q$^D$-)$_{s1}$-,
where
  each s1 is independently an integer from 1 to 50 (e.g., from 1 to 30);
  each Q$^B$ and each Q$^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and
  each Q$^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene.

In further embodiments, at least one of Q$^B$ and Q$^D$ is present in each monomeric unit of $Z^3$.

In yet further embodiments, —Z$^3$-Q$^{43}$ is $$-(-Q^B-Q^C-Q^D-)_{s1}-Q^E-(-Q^B-Q^C-Q^D-)_{s1}-Q^{43}, \qquad (Vb)$$

where
  each s1 is independently an integer from 1 to 50 (e.g., from 1 to 30);
  $Q^{43}$ is as described herein;
  each Q$^B$ and each Q$^D$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—; and
  each Q$^C$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene; and
  $Q^E$ is absent or a branching group of formula (IV), as described herein.

In certain embodiments, each $Q^B$ and each $Q^D$ is independently absent, —CO—, —NH—, —O—, —S—, —SO$_2$—, —NHC(O)—, —C(O)NH—, —CH$_2$—, —CH$_2$NH—, —NHCH$_2$—, —CH$_2$O—, or —OCH$_2$—.

In some embodiments, -(-$Q^B$-$Q^C$-$Q^D$-)$_{s1}$- combine to form a group:

where
(i) g2 is an integer from 1 to 50 (e.g., from 1 to 40 or from 1 to 30);
(ii) g1 is 1 and $Q^B$ is —NHCO—, —CONH—, or —O—; or g1 is 0 and $Q^D$ is —NHCO—; and
(iii) g3 is 1 and $Q^B$ is —NHCO—, —CONH—, or —O—; or g3 is 0 and $Q^D$ is —CONH—.

In further embodiments, the complementary reactive group is:

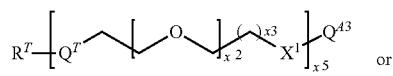

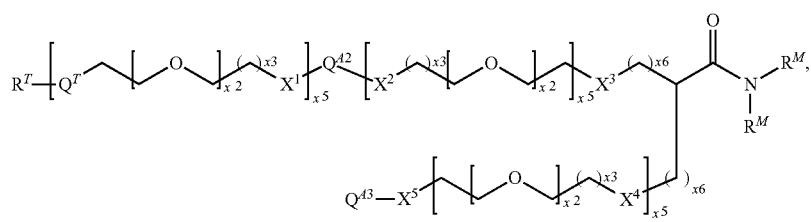

where
$Q^{42}$ is absent, independently optionally substituted $C_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted $C_{1-12}$ thioheterocyclylene

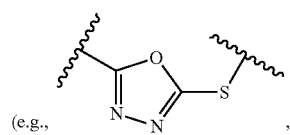

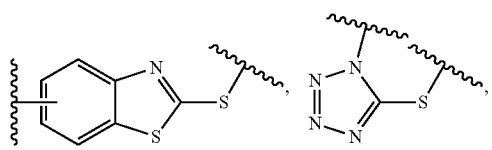

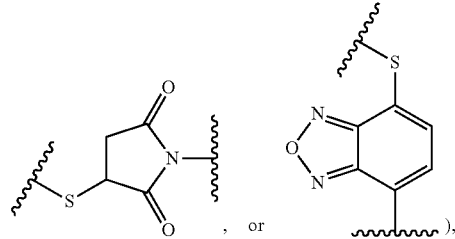

optionally substituted $C_{1-12}$ heterocyclylene (e.g., 1,2,3-triazole-1,4-diyl or

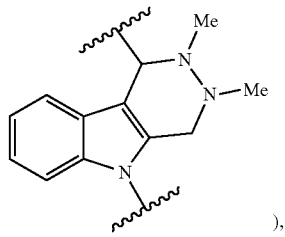 [SMILES: *C1c2c(n(*)c3ccccc23)CN(C)N1C]

(XXIX)

(XXX)

cyclobut-3-ene-1,2-dione-3,4-diyl, pyrid-2-yl hydrazone, optionally substituted $C_{6-16}$ triazoloheterocyclyene

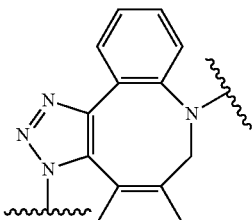

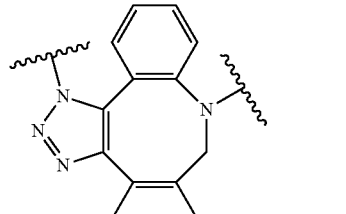

optionally substituted $C_{8-16}$ triazolocycloalkenylene

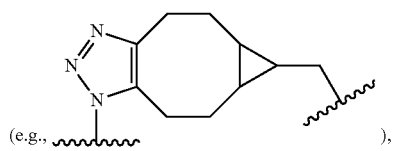

or a dihydropyridazine group

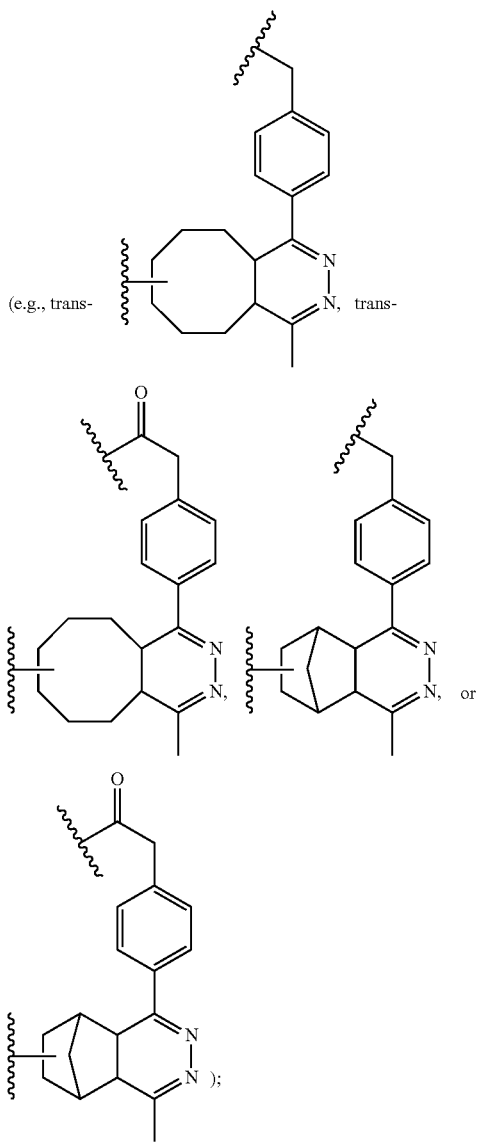

(e.g., trans- ... trans-

Q^43 is optionally substituted $C_{2-12}$ alkynyl, optionally substituted N-protected amino, azido, N-maleimido, S-protected thiol,

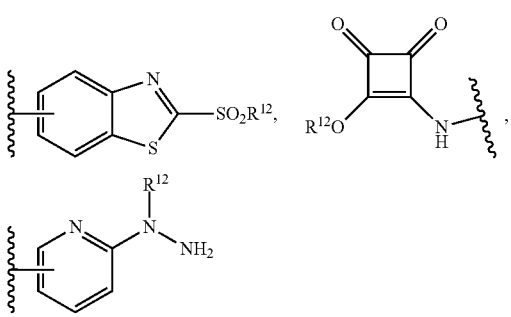

or N-protected version thereof,

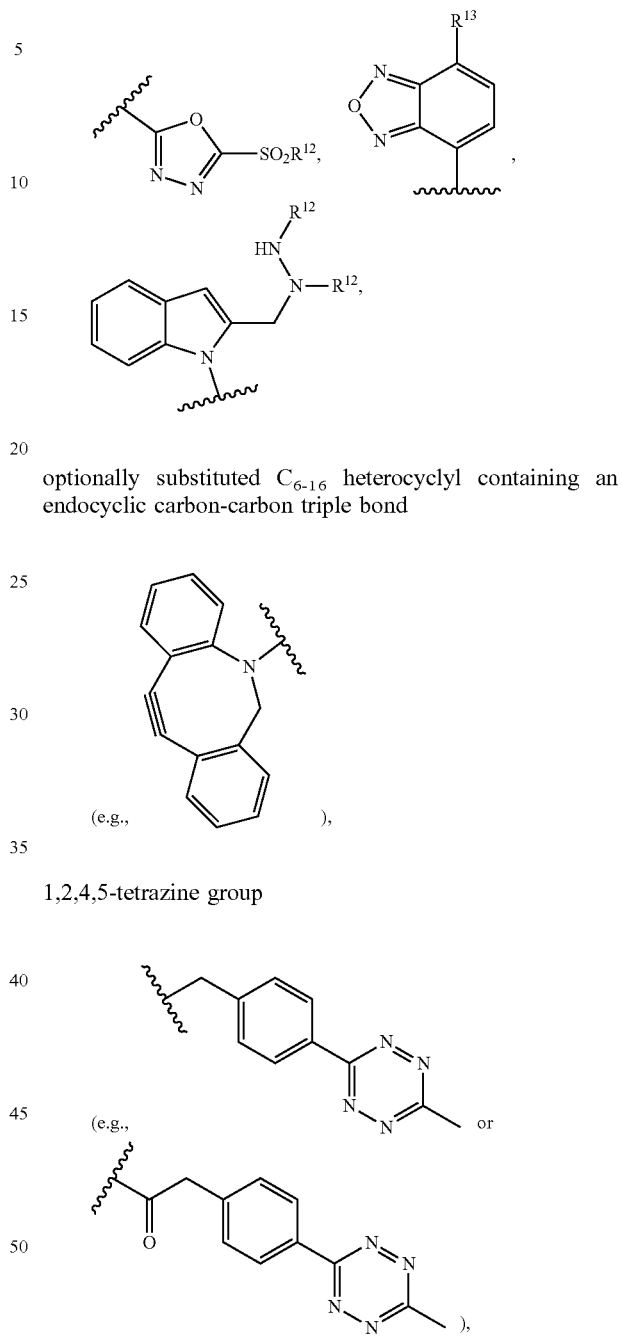

optionally substituted $C_{6-16}$ heterocyclyl containing an endocyclic carbon-carbon triple bond (e.g., ), 1,2,4,5-tetrazine group (e.g., or ), or optionally substituted $C_{8-16}$ cycloalkynyl

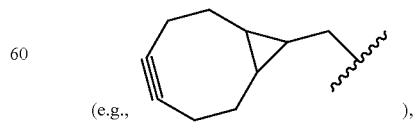

(e.g., ),

—NHR$^{N1}$, optionally substituted $C_{4-8}$ strained cycloalkenyl (e.g., trans-cyclooctenyl or norbornenyl), or optionally substituted $C_{1-16}$ alkyl containing —COOR$^{12}$ or —CHO;

$R^{N1}$ is H, N-protecting group, or optionally substituted $C_{1-6}$ alkyl;

each $R^{12}$ is independently H or optionally substituted $C_{1-6}$ alkyl;

$R^{13}$ is halogen (e.g., F);

$R^T$ is a bond to a targeting moiety;

$Q^T$ is —CO—, —NH—, —NH—$CH_2$—, or —CO—$CH_2$—;

each of $X^1$, $X^3$, and $X^5$ is independently absent, —O—, —NH—, —$CH_2$—NH—, —C(O)—, —C(O)—NH—, —NH—C(O)—, —NH—C(O)—NH—, —O—C(O)—NH—, —NH—C(O)—O—, —$CH_2$—NH—C(O)—NH—, —$CH_2$—O—C(O)—NH—, or —$CH_2$—NH—C(O)—O—;

each of $X^2$ and $X^4$ is independently absent, —O—, —NH—, —C(O)—, —C(O)—NH—, —NH—C(O)—, —NH—C(O)—NH—, —O—C(O)—NH—, or —NH—C(O)—O—;

x2 is an integer from 0 to 50 (e.g., from 1 to 40 or from 1 to 30);

x3 is an integer from 1 to 11; and each x5 is independently 0 or 1; and each x6 is independently an integer from 0 to 10 (e.g., from 1 to 6), provided that the sum of both x6 is 12 or less.

In yet further embodiments, the complementary reactive group is:

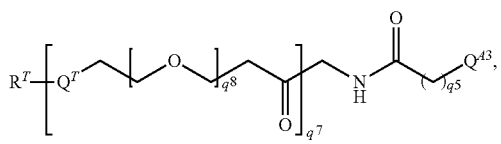

(XXXI)

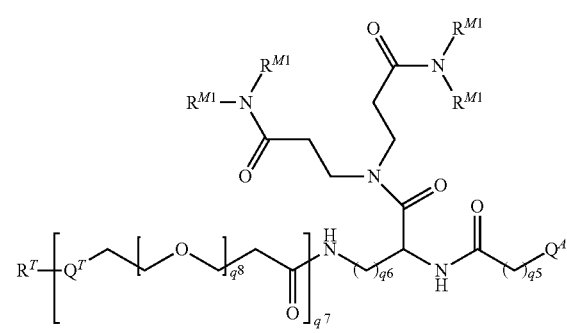

(XXXII)

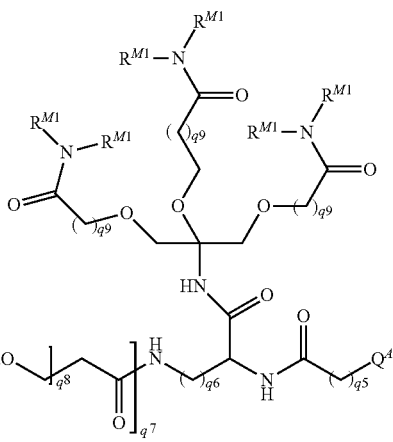

(XXXIII)

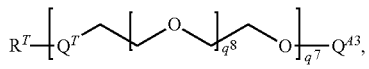

(XXXIV)

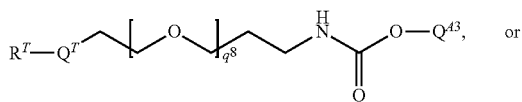

(XXXV)

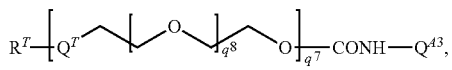

(XXXVI)

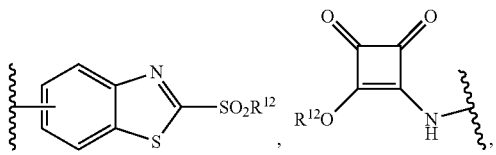

or (XXXVII)

where $Q^{43}$ is optionally substituted $C_{2-12}$ alkynyl, optionally substituted N-protected amino, azido, N-maleimido, S-protected thiol,

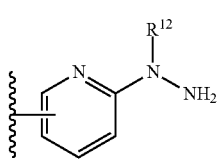

or N-protected version thereof,

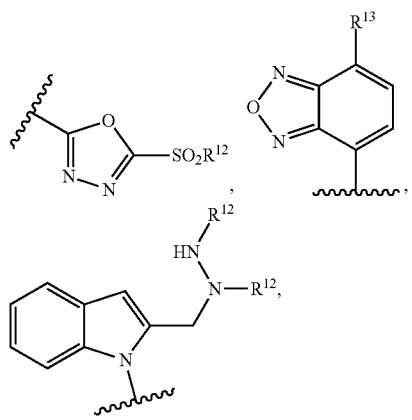

optionally substituted $C_{6-16}$ heterocyclyl containing an endocyclic carbon-carbon triple bond

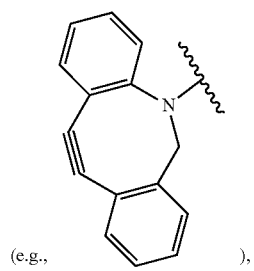 [SMILES: *N1Cc2ccccc2C#Cc2ccccc21]

(e.g., ), 1,2,4,5-tetrazine group

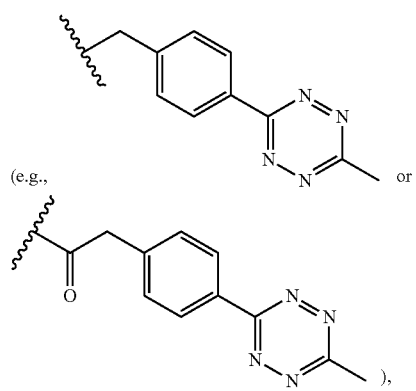

or optionally substituted $C_{8-16}$ cycloalkynyl

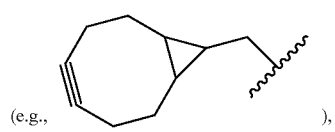 [SMILES: *CC1C2CCC#CCCC12]

(e.g., ),

—$NHR^{N1}$, optionally substituted $C_{4-8}$ strained cycloalkenyl (e.g., trans-cyclooctenyl or norbornenyl), or optionally substituted $C_{1-16}$ alkyl containing —$COOR^{12}$ or —CHO;

each $R^{M1}$ is independently H or an auxiliary moiety;
$R^{N1}$ is H, N-protecting group, or optionally substituted $C_{1-6}$ alkyl;
each $R^{12}$ is independently H or optionally substituted $C_{1-6}$ alkyl;
$R^{13}$ is halogen (e.g., F);
$Q^T$ is —CO—, —NH—, —NH—$CH_2$—, or —CO—$CH_2$—;
$R^T$ is a bond to a targeting moiety;
each of q5 and q6 is independently an integer from 1 to 10 (e.g., from 1 to 6);
q7 is 0 or 1;
q8 is an integer from 0 to 50 (e.g., from 1 to 40 or from 1 to 30); and
q9 is an integer from 1 to 10.

In yet further embodiments, the complementary reactive group is:

(XXXVIII)

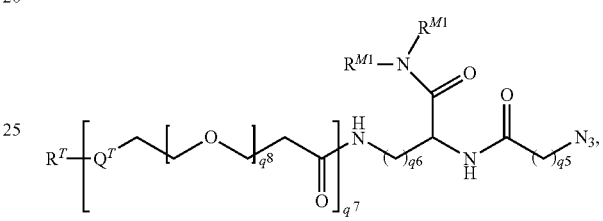

(XXXIX)

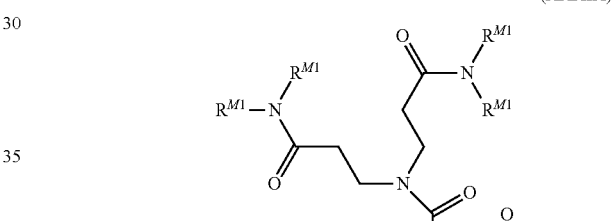

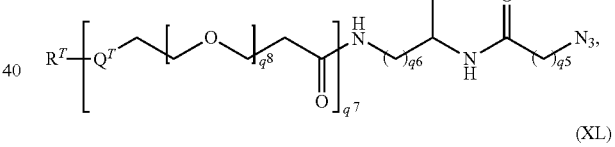

(XL)

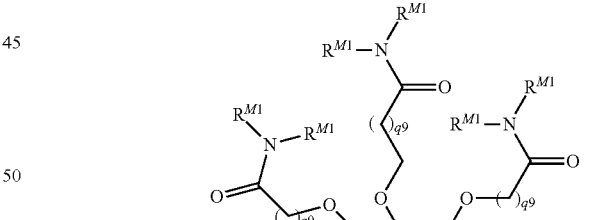

(XLI)

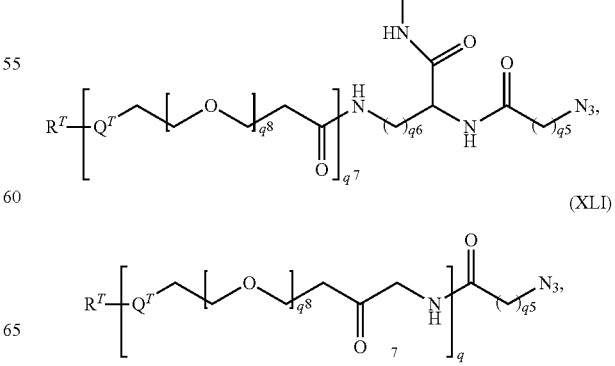

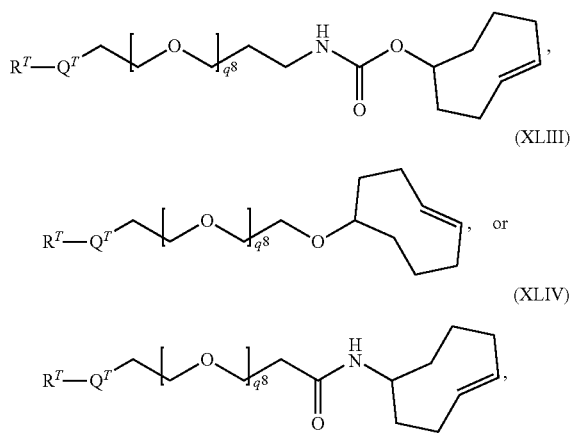

where
each $R^{M1}$ is independently H or an auxiliary moiety;
$Q^T$ is —CO—, —NH—, —NH—CH$_2$—, or —CO—CH$_2$—;
$R^T$ is a bond to a targeting moiety;
each of q5 and q6 is independently an integer from 1 to 10 (e.g., from 1 to 6);
q7 is 0 or 1;
q8 is an integer from 0 to 50 (e.g., from 1 to 40 or from 1 to 30); and
q9 is an integer from 1 to 10.

Solid Support

The immunomodulating polynucleotides disclosed herein may be bonded to solid support. Cleavable solid supports that may be used with the polynucleotides are known in the art. Non-limiting examples of the solid support include, e.g., controlled pore glass or macroporous polystyrene bonded to a strand through a cleavable linker (e.g., succinate-based linker) known in the art (e.g., UNYLINKER™).

Methods

Conjugates of the invention can be used for selective delivery of an immunomodulating polynucleotide to a professional APC (e.g., a B cell, a pDC, or a macrophage) by using a targeting moiety that recognizes a surface receptor for the APC type. Without being bound by theory, it is thought that the conjugate of the invention can be transported (e.g., through active transport) into an endosome of a professional APC (e.g., a B cell, a pDC, or a macrophage), which expresses one or more endosomal toll-like receptors (e.g., TLR9). Thus, an immunostimulating polynucleotide delivered to the endosome can agonize the endosomal toll-like receptor (e.g., TLR9). Similarly, an immunosuppressive polynucleotide delivered to the endosome can antagonize the endosomal toll-like receptor (e.g., TLR9).

Cytokine Induction

Endosomal toll-like receptors can be agonized using an immunostimulating polynucleotide of the invention (e.g., provided in a conjugate of the invention) to induce cytokines in APCs. For example, agonizing TLR9 in a B cell can lead to the activation of NFκB-mediated secretion of inflammatory cytokines (e.g., IL-6 and IL-10), whereas agonizing TLR9 in a pDC or a macrophage can induce type I interferons (e.g., IFNα or IFNβ). Induction of a cytokine in an APC can be determined using methods known in the art. For example, a level of an induced cytokine in the APC can be higher (e.g., at least 1%, at least 10%, at least 20%, at least 30%, at least 40%, or at least 50% higher) after contacting the cell with an immunostimulating polynucleotide or conjugate of the invention (e.g., when compared to a reference cell, such as a reference cell that differs from the tested cell in that the the immunostimulating polynucleotide or conjugate of the invention was not delivered to the reference cell).

Treatment of Liquid (Hematologic) and Solid Tumors

An immunostimulating polynucleotide and/or conjugate of the invention may be used in a method of treating a liquid (e.g., hematologic) or solid tumor. Without wishing to be bound by theory, it is thought that agonizing TLR9 and inducing cytokines, as described herein, may stimulate an innate or adaptive immune response against a liquid or solid tumor. Typically, agonizing TLR9 has a pro-proliferative effect on healthy B cells. In contrast, TLR9 agonist immunostimulating polynucleotides exhibit anti-proliferative effect on B lymphoma cells. The anti-proliferative effect of TLR9 agonist immunostimulating polynucleotides does not require delivery to the B lymphoma cell. Instead, anti-proliferative effect on B lymphoma cells can be induced by delivering an immunostimulating polynucleotide to another APC (e.g., a healthy APC). Without wishing to be bound by theory, it is thought that immunostimulating polynucleotides of the invention can induce one or more cytokines in an APC (e.g., a healthy APC), and one or more induced cytokines can be transported to the B lymphoma cells to induce an anti-proliferative effect. Thus, the conjugates of the invention targeting B cells and immunostimulating polynucleotides of the invention may be useful in the treatment of liquid tumors, e.g., non-Hodgkin B-cell lymphomas. Non-limiting examples of lymphomas that may be treated using immunostimulating polynucleotides of the invention and their conjugates are mantle cell lymphoma, diffuse large B cell lymphoma, follicular lymphoma, chronic lymphocytic leukemia, and multiple myeloma. Agonizing TLR9 in pDCs and macrophages can induce type I interferon (e.g., IFNα or IFNβ) and activate NK cells, which can kill tumor cells (e.g., solid tumor cells). Thus, innate immune response stimulated by an immunostimulating polynucleotide or conjugate of the invention can result in degradation of tumor cells. The tumor cell degradation products, i.e., tumor-associated antigens, can then be recruited by pDCs to prime CD8$^+$ T cells against the remaining tumor cells, thereby stimulating an adaptive immune response against the solid tumor.

Conjugates of the invention may address the problem of the uneven tissue distribution of immunostimulating polynucleotides in vivo. Accordingly, a conjugate of the invention may be administered to a patient systemically or at a site that is remote from the targeted site of action.

Toll-like receptor (TLR) signaling works as a bridge between innate and adaptive immunity. Toll-like receptor agonists are able to induce immune responses against diseased cells, (such as cancer cells or pathogen infected cells), and thus can serve as a therapeutic agent for preventing or treating such diseases. Accordingly, in certain aspects, provided herein are methods of preventing or treating a disease using a toll-like receptor (TLR) agonist. Such methods comprises administering to a subject in need thereof an therapeutic agent capable of activating a TLR, wherein upon administering of the TLR agonist, an immune response against the disease being treated is induced in the subject. In certain embodiments, the disease is selected from a neoplastic disease, such as cancer, and an infectious disease, such as a viral infection.

In some embodiments, provided herein are methods of treating cancer in a subject having cancer, comprising administering to the subject a therapeutically effective amount of a TLR agonist. As described herein, in various embodiments, the types of cancer that can be successfully treated with the present method include primary cancer, secondary cancer, recurrent cancer and refractory cancer. Further as described herein, in various embodiments, the types of cancer that can be successfully treated with the present method include solid tumor and liquid tumor. Successful treatment of a cancer can be determined by the responsible practitioner based on clinical standards, such as shown by cancer survival, cancer regress (e.g., shrinkage of tumor size), partial or complete cancer remission, including a cancer-free phenotype (i.e. no detectable cancer cell in a patient) resulted from the treatment.

Accordingly, in some embodiments, the method for preventing or treating cancer comprises administering to a subject in need thereof an therapeutically effective amount of one or more TLR agonist(s) selected from TLR1 agonists, TLR2 agonists, TLR3 agonists, TLR4 agonists, TLR5 agonists, TLR6 agonists, TLR7 agonists, TLR8 agonists, TLR9 agonists, and TLR10 agonists. Non-limiting examples of TLR agonists finding use in the present disclosure include but are not limited to Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyribosinic:polyribocytidic acid (Poly I:C), a TLR3 agonist; polyadenosine-polyuridylic acid (polyAU), a TLR3 agonist; Polyinosinic-Polycytidylic acid stabilized with poly-L-lysine and carboxymethylcellulose (Hiltonol), a TLR3 agonist; bacterial LPS a TLR4 agonist, bacterial flagellin a TLR5 agonist; imiquimod, a TLR7 agonist; resiquimod, a TLR7/8 agonist; loxoribine, a TLR7/8 agonist; and unmethylated CpG ODN, a TLR9 agonist. Additional TLR agonists known in the art and finding use in the present disclosure further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals.

Additional TLR agonists known in the art and finding use in the present disclosure further include other pathogen-associated molecular patterns (PAMPs) and damage-associated molecular patterns (DAMPs). (P. D'Arpa and K. Leung, Supra.) Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. rt.-Galactosylceramide (rt.-GalCer) is an activator of natural killer T (NKT) cells. Muramyl dipeptide is a bioactive peptidoglycan motif common to all bacteria. Examples of DAMPs include proteins secreted through a nonclassical secretion mechanism involving secretory lysosomes, e.g., high mobility group box (HMGB)1 and galectin-3; and molecules released by necrotic cells, e.g., S100 proteins, HMGB1, IL-1a, galectin-3, HSP60, HSP70, HSP72, histones, and nucleic acids; and extracellular matrix molecules, e.g., hyaluronan, heparin sulfate, fibronectin, and degraded matrix constituents.

Oligodeoxynucleotides (ODNs) containing CpG are agonists for TLR9 and activate both innate and adaptive immunity against tumor. As described herein, immunostimulating polynucleotides, including both naturally existing CpG ODNs and synthetic CpG-containing polynucleotides, are contemplated as therapeutic agents for preventing or treating cancer.

Accordingly, in some embodiments, provided herein are methods for treating cancer in a subject having cancer, comprising administering a therapeutically effective amount of a CpG-containing immunostimulating polynucleotide to the subject. In some embodiments, the CpG-containing immunostimulating polynucleotide administered in above methods for treating cancer is capable of activating a TLR-medicated signaling pathway upon administration. In some embodiments, the CpG-containing immunostimulating polynucleotide is naturally exiting. Examples of naturally existing CpG-containing immunostimulating polynucleotides include, without limitation, CpG ODNs of bacterial or viral origins. In some embodiments, the CpG-containing immunostimulating polynucleotide is artificially synthesized. In some embodiments, the synthetic CpG-containing immunostimulating polynucleotide has the same sequence as its natural counterpart. In some embodiments, the sequence of a synthetic CpG-containing immunostimulating polynucleotide is different from a naturally existing CpG-containing immunostimulating polynucleotide. In some embodiments, a CpG-containing immunostimulating polynucleotide is chemically modified to contain one or more chemical entities that are not normally found in nucleic acids.

In some embodiments, the CpG-containing immunostimulating polynucleotide is one of the immunostimulating polypeptides listed in Table 2 of the present disclosure. In some embodiments, the CpG-containing polynucleotide is selected from p236, p238, p243, p246, p275, p276, p308, p313, p347, p361, p362, p425, p433, p434, p435, p436, p437, p438, p477, p478, p479, p480, p481, p482, p483, p484, p485, p486, p487, p488 and p489. In some embodiments, the CpG-containing immunostimulating polynucleotide is p236. In some embodiments, the CpG-containing immunostimulating polynucleotide is p238. In some embodiments, the CpG-containing immunostimulating polynucleotide is p238. In some embodiments, the CpG-containing immunostimulating polynucleotide is p243. In some embodiments, the CpG-containing immunostimulating polynucleotide is p246. In some embodiments, the CpG-containing immunostimulating polynucleotide is p275. In some embodiments, the CpG-containing immunostimulating polynucleotide is p276. In some embodiments, the CpG-containing immunostimulating polynucleotide is p308. In some embodiments, the CpG-containing immunostimulating polynucleotide is 313. In some embodiments, the CpG-containing immunostimulating polynucleotide is p347. In some embodiments, the CpG-containing immunostimulating polynucleotide is p361. In some embodiments, the CpG-containing immunostimulating polynucleotide is p362. In some embodiments, the CpG-containing immunostimulating polynucleotide is p425. In some embodiments, the CpG-containing immunostimulating polynucleotide is p433. In some embodiments, the CpG-containing immunostimulating polynucleotide is p434. In some embodiments, the CpG-containing immunostimulating polynucleotide is p435. In some embodiments, the CpG-containing immunostimulating polynucleotide is p436. In some embodiments, the CpG-containing immunostimulating polynucleotide is p437. In some embodiments, the CpG-containing immunostimulating polynucleotide is p438. In some embodiments, the CpG-containing immunostimulating polynucleotide is p477. In some embodiments, the CpG-containing immunostimulating polynucleotide is p478. In some embodiments, the CpG-containing immunostimulating polynucleotide is p479. In some embodiments, the CpG-containing immunostimulating polynucleotide is p480. In some embodiments, the CpG-containing immunostimulating polynucleotide is p481. In some embodiments, the CpG-containing immunostimulating polynucleotide is p482. In some embodiments, the CpG-containing immunostimulating polynucleotide is p483. In some embodiments, the CpG-containing immunostimulating polynucleotide is p484. In some embodiments, the CpG-containing immunostimulating polynucleotide is p485. In some embodiments, the CpG-containing immunostimulating polynucleotide is p486. In some embodiments, the CpG-containing immunostimulating polynucleotide is p487. In some embodiments, the CpG-containing immunostimulating polynucleotide is p488. In some embodiments, the CpG-containing immunostimulating polynucleotide is p489.

As provided herein, the CpG-containing immunostimulating polynucleotide can be free-standing or form a part of a larger molecule or complex. In some embodiments, the CpG-containing immunostimulating polynucleotide is not conjugated, covalently or non-covalently, to an antigen or an antigenic fragment thereof. In some embodiments, the CpG-containing immunostimulating polynucleotide is not conjugated to an antigen encoded and expressed by a normal immune cell or an antigenic fragment thereof. In some embodiments, the CpG-containing immunostimulating polynucleotide is not conjugated to a T cell antigen or an epitope thereof. In some embodiments, the CpG-containing immunostimulating polynucleotide is not conjugated to ovalbumin (OVA) or an epitope thereof. In some embodiments, the CpG-containing immunostimulating polynucleotide is not conjugated to the Japanese cedar pollen allergen Cryj2 T-cell epitope peptide. In some embodiments, the CpG-containing immunostimulating polynucleotide is not conjugated to a tumor associated antigen.

In particular embodiments, the CpG-containing immunostimulating polynucleotide is conjugated to a targeting moiety for targeted delivery to a specific organ, tissue, cell and/or cellular compartment upon administering to the subject. In some embodiments, the targeting moiety is an antibody or an antigen-binding fragment thereof. In some embodiments, the targeting moiety comprises a chemical moiety as described herein.

In some embodiments, the targeting moiety specifically promotes the arrival of the CpG-containing immunostimulating polynucleotide at a targeted cell or cell population more than other non-targeted cells. The targeted delivery can be detected using methods known in the art, such as measuring the cellular concentration of the CpG-containing immunostimulating polynucleotide in a targeted cell or cell population and comparing it to the cellular concentration of the CpG-containing immunostimulating polynucleotide in a non-targeted cell or cell population. For example, cell markers can be used identify and purify a particular cell population. Other methods for detecting and measuring targeted delivery of the CpG-containing immunostimulating polynucleotides are known to those skilled in the art, and fall within the scope of the present disclosure.

In some embodiments, the targeting moiety delivers more CpG-containing immunostimulating polynucleotide to the targeted cell or cell population than a non-targeted cell or cell population by at least 2 folds. In some embodiments, the targeting moiety delivers more CpG-containing immunostimulating polynucleotide to the targeted cell or cell population than to a non-targeted cell or cell population by at least 5 folds. In some embodiments, the targeting moiety delivers more CpG-containing immunostimulating polynucleotide to the targeted cell or cell population than to a non-targeted cell or cell population by at least 10 folds. In some embodiments, the targeting moiety delivers more CpG-containing immunostimulating polynucleotide to the targeted cell or cell population than to a non-targeted cell or cell population by at least 20 folds. In some embodiments, the targeting moiety delivers more CpG-containing immunostimulating polynucleotide to the targeted cell or cell population than to a non-targeted cell or cell population by at least 30 folds. In some embodiments, the targeting moiety delivers more CpG-containing immunostimulating polynucleotide to the targeted cell or cell population than to a non-targeted cell or cell population by at least 40 folds. In some embodiments, the targeting moiety delivers more CpG-containing immunostimulating polynucleotide to the targeted cell or cell population than to a non-targeted cell or cell population by at least 50 folds. In some embodiments, the targeting moiety delivers more CpG-containing immunostimulating polynucleotide to the targeted cell or cell population than to a non-targeted cell or cell population by at least 100 folds. In some embodiments, the targeting moiety delivers more CpG-containing immunostimulating polynucleotide to the targeted cell or cell population than to a non-targeted cell or cell population by more than 100 folds.

In some embodiments, the targeting moiety delivers the CpG-containing immunostimulating polynucleotide to a targeted cell by specifically binding to a receiving moiety located near, on and/or inside the targeted cell. In some embodiments, the targeting moiety is an antibody or an antigen-binding fragment thereof, and the receiving moiety is an antigen produced by the targeted cell or an antigen fragment thereof. In some embodiments, the receiving moiety is a cell surface antigen. In some embodiments, the receiving moiety is located within the cytosol of the targeted cell. In some embodiments, the receiving moiety is associated with an intracellular organelle of the targeted cell, such as the endosome or phagosome. In some embodiments, upon binding of the targeting moiety, the targeted cell internalizes the CpG-containing immunostimulating polynucleotide. In some embodiments, the receiving moiety facilitates internalization of the CpG-containing immunostimulating polynucleotide. In some embodiments, the targeted cell further transports the internalized CpG-containing immunostimulating polynucleotide to an intracellular compartment, such as the endosome or phagosome. In some embodiments, the receiving moiety facilitates transportation of the CpG-containing immunostimulating polynucleotide.

In some embodiments of the method of treating cancer, the targeted cell expresses at least one toll-like receptor, such as TLR 7 and/or TLR9. In some embodiments, the targeted cell is a normal immune cell, such as an antigen presenting cell (APC). In some embodiments, the targeted cell is a cancer cell, such as a B cell lymphoma cell. In some embodiments, the receiving moiety is located on the same cellular membrane as the toll-like receptor. In some embodiments, both the receiving moiety and the toll-like receptor are located on the cell membrane of the targeted cell. In some embodiments, both the receiving moiety and the toll-like receptor are located on the endosomal membrane or phagosomal membrane of the targeted cell. In some embodiments, binding of the targeting moiety to the receiving moiety facilitates binding of the CpG-containing immunostimulating polynucleotide to the TLR9 receptor expressed by the targeted cell.

In some embodiments, the CpG-containing immunostimulating polynucleotide is conjugated to an antibody or antigen binding fragment thereof to form a CpG-Ab immunoconjugate. In some embodiments, the conjugation is through covalent linkage, such as through a chemical linker molecule as provided herein. In other embodiments, the conjugation is through non-covalent linkage, such as through binding interaction between a ligand and its receptor. Other examples of non-covalent linkage that can be used in connection with the present disclosure include but are not limited to electrostatic interactions (e.g., TAT or Spermine or Protamine complexes) and biotin-avidin/streptavidin interactions.

In some embodiments, the antibody is selected from an anti-CD20 antibody, anti-CD22 antibody, anti-CD30 antibody, anti CD37 antibody, anti-CD38 antibody, anti-CD40 antibody, anti-CD74 antibody, anti-CD79b antibody, anti-CD205 antibody, anti-CD274 antibody, anti-CD303 antibody, anti-CD304 antibody, anti-CD19 antibody, anti-CD1 antibody, anti-CD2 antibody, anti-CD3 antibody, anti-CD5 antibody, anti-CD6 antibody, anti-CD9 antibody, anti-CD11 antibody, anti-CD18 antibody, anti-CD21 antibody, anti-CD23 antibody, anti-CD24 antibody, anti-CD25 antibody, anti-CD26 antibody, anti-CD44 antibody, anti-CD45R antibody, anti-CD49 antibody, anti-CD66 (Carcinoembrionic antigen, CEA) antibody, anti-CD93 antibody, anti-CD52 antibody, anti-CD56 antibody, anti-CD123 antibody, anti-CD138 antibody, anti-CD163 antibody, anti-CD206 antibody. In some embodiments, the antibody is an anti-CD20 antibody. In some embodiments, the antibody is an anti-CD22 antibody. In some embodiments, the antibody is an anti-CD30 antibody. In some embodiments, the antibody is an anti-CD38 antibody. In some embodiments, the antibody is an anti-CD40 antibody. In some embodiments, the antibody is an anti-CD74 antibody. In some embodiments, the antibody is an anti-CD76b antibody. In some embodiments, the antibody is an anti-CD205 antibody. In some embodiments, the antibody is an anti-CD274 antibody. In some embodiments, the antibody is an anti-CD303 antibody. In some embodiments, the antibody is an anti-CD304 antibody. In some embodiments, the antibody is an anti-CD19 antibody. In some embodiments, the antibody is an anti-CD1 antibody. In some embodiments, the antibody is an anti-CD2 antibody. In some embodiments, the antibody is an anti-CD3 antibody. In some embodiments, the antibody is an anti-CD5 antibody. In some embodiments, the antibody is an anti-CD6 antibody. In some embodiments, the antibody is an anti-CD9 antibody. In some embodiments, the antibody is an anti-CD11 antibody. In some embodiments, the antibody is an anti-CD18 antibody. In some embodiments, the antibody is an anti-CD21 antibody. In some embodiments, the antibody is an anti-CD23 antibody. In some embodiments, the antibody is an anti-CD24 antibody. In some embodiments, the antibody is an anti-CD25 antibody. In some embodiments, the antibody is an anti-CD26 antibody. In some embodiments, the antibody is an anti-304 antibody. In some embodiments, the antibody is an anti-CD44 antibody. In some embodiments, the antibody is an anti-CD45R antibody. In some embodiments, the antibody is an anti-CD49 antibody. In some embodiments, the antibody is an anti-CD66 (Carcinoembrionic antigen, CEA) antibody. In some embodiments, the antibody is an anti-CD93 antibody. In some embodiments, the antibody is an anti-CD52 antibody. In some embodiments, the antibody is an anti-CD56 antibody. In some embodiments, the antibody is an anti-CD123 antibody. In some embodiments, the antibody is an anti-CD138 antibody. In some embodiments, the antibody is an anti-CD163 antibody. In some embodiments, the antibody is an anti-CD206 antibody.

In some embodiments, the antibody is a monoclonal antibody. In some embodiments, the antibody is a human antibody. In some embodiments, the antibody is a humanized antibody.

In some embodiments, the CpG-Ab conjugate is one of the immunoconjugates listed in Table 6-A or 6-B of the present disclosure. In some embodiments, the CpG-Ab conjugate is selected from SB-342, SB-343, SB-341, SB-340, SB-179, SB-181, SB-186, SB-189, SB-228, SB-229, SB-242, SB-263, SB-337, SB-267, SB-284, SB-312, SB-313, SB-347, SB-373, SB-382, SB-388, SB-389, SB-408, SB-416, SB-419, SB-421, SB-423, SB-426, SB-427, SB-428, SB-429, and SB-430 as shown in Tables 6-A and 6-B.

The CpG-Ab immunoconjugate can comprise one or more CpG-containing immunostimulating polynucleotide and one or more antibody or antigen binding fragment thereof. The molecular ratios between the antibody or antigen binding fragment thereof and the CpG-containing immunostimulating polynucleotide (Ab:CpG ratio) in the immunoconjugate can range from 1:1 through 1:100. In some embodiments, the Ab:CpG ratio of the CpG-Ab immunoconjugate is 1:1. In some embodiments, the Ab:CpG ratio of the CpG-Ab immunoconjugate is 1:2. In some embodiments, the Ab:CpG ratio of the CpG-Ab immunoconjugate is 1:3. In some embodiments, the Ab:CpG ratio of the CpG-Ab immunoconjugate is 1:4. In some embodiments, the Ab:CpG ratio of the CpG-Ab immunoconjugate is 1:5. In some embodiments, the Ab:CpG ratio of the CpG-Ab immunoconjugate is 1:6. In some embodiments, the Ab:CpG ratio of the CpG-Ab immunoconjugate is 1:7. In some embodiments, the Ab:CpG ratio of the CpG-Ab immunoconjugate is 1:8. In some embodiments, the Ab:CpG ratio of the CpG-Ab immunoconjugate is 1:9. In some embodiments, the Ab:CpG ratio of the CpG-Ab immunoconjugate is 1:10. In some embodiments, the Ab:CpG ratio of the CpG-Ab immunoconjugate is 1:15. In some embodiments, the Ab:CpG ratio of the CpG-Ab immunoconjugate is 1:20. In some embodiments, the Ab:CpG ratio of the CpG-Ab immunoconjugate is 1:30. In some embodiments, the Ab:CpG ratio of the CpG-Ab immunoconjugate is 1:40. In some embodiments, the Ab:CpG ratio of the CpG-Ab immunoconjugate is 1:50. In some embodiments, the Ab:CpG ratio of the CpG-Ab immunoconjugate is 1:60. In some embodiments, the Ab:CpG ratio of the CpG-Ab immunoconjugate is 1:70. In some embodiments, the Ab:CpG ratio of the CpG-Ab immunoconjugate is 1:80. In some embodiments, the Ab:CpG ratio of the CpG-Ab immunoconjugate is 1:90. In some embodiments, the Ab:CpG ratio of the CpG-Ab immunoconjugate is 1:100.

In some embodiments, the method for treating cancer comprises administering to a subject having cancer a therapeutic effective amount of a CpG-Ab immunoconjugate, wherein upon administering to the subject, the CpG-Ab immunoconjugate targets a normal immune cell. In some embodiments, the CpG-Ab immunoconjugates target one or more type(s) of normal cell selected from T cells, B cells, natural killer cells, neutrophils, mast cells, macrophages, antigen-presenting cells (APC), basophils, and eosinophils. In some embodiments, the CpG-Ab immunoconjugate targets a normal APC. In some embodiments, the CpG-Ab immunoconjugates target one or more type(s) of normal APC selected from B cells, monocytes, dendritic cells, Langerhans cells, keratinocytes, endothelial cells, astrocytes, fibroblasts, and oligodendrocytes. In some embodiments, the CpG-Ab immunoconjugate targets a normal B cell. In some embodiments, the CpG-Ab immunoconjugate targets a normal dendritic cell. In some embodiments, the CpG-Ab immunoconjugate targets a normal macrophage. In some embodiments the CpG-Ab immunoconjugates targeting one or more type(s) of normal cells do not target an abnormal cell, such as a cancer cell.

In some embodiments, the method for treating cancer comprises administering to a subject having cancer a therapeutic effective amount of a CpG-Ab immunoconjugate, wherein upon administering to the subject, the CpG-Ab immunoconjugate targets a cell that expresses at least one toll-like receptor. In some embodiments, the CpG-Ab immunoconjugate targets a cell that expresses TLR9. In some embodiments, the CpG-immunoconjugate targets a cell that expresses TLR7. In some embodiments, the CpG-Ab immunoconjugate targets a TLR-expressing cell selected from dendritic cells (DCs), B cells, T cells, Langerhans cells, keratinocytes, mast cells, endothelial cells, myofibroblast cells, and primary fibroblast.

In some embodiments, the method for treating cancer comprises administering to a subject having cancer a therapeutic effective amount of a CpG-Ab immunoconjugate, wherein the CpG-Ab immunoconjugate targets an abnormal cell of the cancer being treated. In some embodiments, such abnormal cell is a cancer cell. In some embodiments, such abnormal cell is a stromal cell of the tumor being treated. In some embodiments, the CpG-Ab immunoconjugate targets one or more type(s) of cancer cells selected from B cell cancer, e.g., multiple myeloma, Waldenstrom's macroglobulinemia, the heavy chain diseases, such as, for example, alpha chain disease, gamma chain disease, and mu chain disease, benign monoclonal qammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, sominoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, the method for treating cancer comprises administering to a subject having cancer a therapeutic effective amount of a CpG-Ab immunoconjugate, wherein the CpG-Ab immunoconjugate targets an abnormal cell of the cancer being treated and also targets a normal immune cell selected from T cells, B cells, natural killer cells, neutrophils, mast cells, macrophages, antigen-presenting cells (APC), basophils, and eosinophils. In some embodiments, the CpG-Ab immunoconjugate targeting an abnormal cell of the cancer being treated also targets a normal APC selected from B cells, monocytes, dendritic cells, Langerhans cells, keratinocytes, endothelial cells, astrocytes, fibroblasts, and oligodendrocytes. In some embodiments, the CpG-Ab immunoconjugate targeting an abnormal cell of the cancer being treated also targets a cell expressing a TLR receptor selected from dendritic cells (DCs), B cells, T cells, Langerhans cells, keratinocytes, mast cells, endothelial cells, myofibroblast cells, and primary fibroblast. In particular embodiments, such abnormal cell is a cancerous immune cell. In particular embodiments, such abnormal cell is a lymphoma cell or a leukemia cell. In particular embodiments, such abnormal cell is a B cell lymphoma cell, and the CpG-Ab immunoconjugates target both the B cell lymphoma cell and normal B cells in the subject.

In some embodiments, the method for treating cancer comprises administering to a subject having cancer a therapeutic effective amount of a CpG-Ab immunoconjugate, wherein the CpG-containing immunostimulating polynucleotide activates a TLR9 mediated signaling pathway upon arrival at the targeted cell. Such activation can be through binding of the CpG-containing immunostimulating polynucleotide with the TLR9 receptor expressed on the surface or within the cytosol of the targeted cell. In some embodiments, the cell targeted by the CpG-Ab immunoconjugate is capable of internalizing the CpG-Ab immunoconjugate. In some embodiments, the cell targeted by the CpG-Ab immunoconjugate is capable of internalizing the CpG-containing immunostimulating polynucleotide portion of the immunoconjugate. In some embodiments, the cell targeted by the CpG-Ab immunoconjugate is capable of transporting the internalized CpG-Ab immunoconjugate or the CpG-containing immunostimulating polynucleotide portion thereof to a intracellular organelle that expressed a TLR receptor. In some embodiments, the cell targeted by the CpG-Ab immunoconjugate is capable of transporting the internalized CpG-Ab immunoconjugate or the CpG-containing immunostimulating polynucleotide portion thereof to the endosome or phagosome of the cell.

In some embodiments, the method for treating cancer comprises administering to a subject having cancer a therapeutic effective amount of a CpG-Ab immunoconjugate, wherein the CpG-Ab immunoconjugate specifically binds to an antigen associated with a targeted cell. As described herein, an antigen associated with a targeted cell may be found on the surface and/or or within the cytosol of the target cell. In some embodiments, the CpG-Ab immunoconjugate specifically binds to an antigen present on the surface of a targeted cell. In some embodiments, CpG-Ab immunoconjugate specifically binds to an antigen present within the cytosol of a targeted cell. In some embodiments, CpG-Ab immunoconjugate specifically binds to an antigen present on the membrane of an intracellular compartment or organelle of a targeted cell. In some embodiments, CpG-Ab immunoconjugate specifically binds to an antigen reside on the endosomal or phagosomal membrane of the targeted cell. In some embodiments, upon binding by the CpG-Ab immunoconjugate, the target antigen facilitates internalization of the CpG-Ab immunoconjugate or the CpG-containing immunostimulating polynucleotide into the targeted cell. In some embodiments, upon binding by the CpG-Ab immunoconjugate, the target antigen facilitates transportation of the CpG-Ab immunoconjugate or the CpG-containing immunostimulating polynucleotide to the endosome of the targeted cell. In some embodiments, upon binding by the CpG-Ab immunoconjugate, the target antigen facilitates binding of the CpG-containing immunostimulating polynucleotide to TLR9 expressed by the targeted cell.

In some embodiments, an antigen associated with a targeted cell is a protein encoded and expressed by the targeted cell. In those embodiments, the protein antigen can be encoded by an endogenous gene (e.g., encoded by the targeted cell genome) or exogenous gene (e.g., encoded by a gene artificially introduced to the targeted cell) of the targeted cell. In other embodiments, the target antigen of the CpG-Ab immunoconjugate is not encoded or expressed by the targeted cell. In some embodiments, an antigen associated with a targeted cell is an exogenous antigen uptaken by the targeted cell (e.g., an antigen endocytosed and processed by an APC).

As non-limiting examples, in some embodiments, for targeting a normal immune cell, the target antigen of the CpG-Ab immunoconjugate is encoded and expressed by the normal immune cell (e.g., a B cell antigen). In some embodiments, the target antigen of the CpG-Ab immunoconjugate is encoded by an endogenous gene of the normal immune cell. In some embodiments, the target antigen of the CpG-Ab immunoconjugate is encoded by an exogenous gene introduced into the normal immune cell (e.g., a reporter gene). In some embodiments, the target antigen of the CpG-Ab immunoconjugate is a disease antigen taken up and processed by the immune cell (e.g., a tumor associated antigen or a viral antigen).

As non-limiting examples, in some embodiments, for targeting an abnormal cell (e.g., a cancer cell or a pathogen infected cell), the target antigen of the CpG-Ab immunoconjugate may be a protein encoded by an endogenous gene of the abnormal cell. In various embodiments, the target antigen of the CpG-Ab immunoconjugate is overexpressed, mutated or misregulated in the targeted cell. In other embodiments, the target antigen of the CpG-Ab immunoconjugate has the same features as the antigen would have in a normal cell. In other embodiments, the target antigen of the CpG-immunoconjugate is encoded by an exogenous gene introduced into the abnormal cell (e.g., through pathogen infection).

In some embodiments, the CpG-Ab immunoconjugate specifically binds to an antigen encoded and expressed by a normal immune cell selected from T cells, B cells, natural killer cells, neutrophils, mast cells, macrophages, antigen-presenting cells (APC), basophils, and eosinophils. In some embodiments, the CpG-Ab immunoconjugate specifically binds to an antigen encoded and expressed by a normal antigen-presenting cells (APC) selected from B cells, monocytes, dendritic cells, Langerhans cells, keratinocytes, endothelial cells, astrocytes, fibroblasts, and oligodendrocytes. In some embodiments, the CpG-Ab immunoconjugate specifically binds to an antigen encoded and expressed by a normal B cell. In some embodiments, the CpG-Ab immunoconjugate specifically binds to an antigen encoded and expressed by a normal dendritic cell. In some embodiments, the CpG-Ab immunoconjugate specifically binds to an antigen encoded and expressed by a macrophage cell.

In some embodiments, the CpG-Ab immunoconjugate specifically binds to an antigen encoded and expressed by a normal immune cell selected from immune checkpoint molecules, T cell costimulatory molecules, MHC proteins (including MHC class I and II molecules), and other immune cell specific antigens.

In particular embodiments, immune checkpoint molecules finding use in the present disclosure include but are not limited to PD-1, PD-L1, PD-L2, TIM-3, LAG-3, CEACAM-1, CEACAM-5, CLTA-4, VISTA, BTLA, TIGIT, LAIR1, CD47, CD160, 2B4 and TGFR.

In particular embodiments, T cell costimulatory molecules finding use in the present disclosure include but are not limited to OX40, CD2, CD27, CDS, ICAM-1, LFA-1/CD11a/CD18, ICOS/CD278, 4-1 BB/CD137, GITR, CD30, CD40, BAFFR, HVEM, CD7, LIGHT, NKG2C, SLAMF7, NKp80, CD160, B7-H3, and CD83.

In particular embodiments, B cell specific antigens finding use in the present disclosure include but are not limited to B220/CD45R, B7-1/CD80, B7-2/CD86, BCMA/TNFRSF17, BLIMP1/PRDM1, Clq R1/CD93, CD117/c-kit, CD11b/Integrin alpha M, CD19, CD1c/BDCA-1, CD1d, CD20, CD21, CD23/Fc epsilon RII, CD24, CD25/IL-2R alpha, CD27/TNFRSF7, CD34, CD37, CD38, CD40/TNFRSF5, CD43, CD5, CD69, CD72, CD83, CXCR4, CXCR5, DEP-1/CD148, EMMPRIN/CD147, FCRL3/FcRH3, Flt-3/Flk-2, HLA-DR, IgM, IL-10, IL-12 R beta 2, IL-12/IL-35 p35, IL-21, IL-21 R, IL-27 R alpha/WSX-1/TCCR, IL-27/IL-35 EB13 Subunit, IL-3 R alpha/CD123, IL-4 R alpha, IL-7 R alpha/CD127, IRF4, MHC class II (I-A/I-E), Neprilysin/CD10, Pax5/BSAP, Sca-1/Ly6, Siglec-2/CD22, STAT1, STAT3, Syndecan-1/CD138, TACI/TNFRSF13B, TGF-beta, TIM-1/KIM-1/HAVCR, TLR4. In particular embodiments, B cell specific antigens are selected from CD1, CD2, CD5, CD9, CD11, CD17, CD18, CD19, CD20, CD21/CD35, CD22, CD23, CD24, CD25, CD27, CD30, CD38, CD40, CD45R/B220, CD69, CD70, CD78, CD79a (Iga), CD79b (Igp), CD80, CD86, CD93 (C1Rqp), CD137/4-1 BB, CD138, CD252/OX40L, CD267, CD268/BAFF-R, CD279/PD1, CD319, PDL-2, Pax-5, IgD, IgM, Notch 2, and TLR4.

In particular embodiments, dendritic cell specific antigens finding use in the present disclosure include but are not limited to B220/CD45R, BATF3, BST-2/Tetherin, CD11b/Integrin alpha M, CD11c, CD14, CD163, CD19, CD1c/BDCA-1, CiD1d, CD20, CD3, CD4, CD8, CLEC9a, CX3CR1, DC-SIGN/CD209, DEC-205/CD205, DLEC/CLEC4C/BDCA-2, E-Cadherin, EpCAM/TROP1, F4/80, Fc epsilon RI alpha, Fc gamma RI/CD64, Fc gamma RIA/CD64, Fc gamma RIB/CD64, Fc gamma RIII (CD16), Fc gamma RIIIA/CD16a, Fcgamma RIIIB/CD16b, GFI-1, HLA-DR, IFN-alpha, IFN-beta, IFN-gamma, IGSF4A/Syn- CAM1, Ikaros, IL-1 beta/IL-1F2, IL-10, IL-12, IL-2, IL-23, IL-3 R alpha/CD123, IL-6, iNOS, Integrin alpha E/CD103, IRF4, IRF8, Langerin/CD207, Ly-6G (Gr-1), Ly-6G/Ly-6C (Gr-1), MHC class II (I-A/I-E), MMR/CD206, NCAM-1/CD56, Neuropilin-1, NFIL3/E4BP4, Nitric Oxide, PU.1/Spi-1, SIRP alpha/CD172a, Spi-B, Thrombomodulin/BDCA-3, TLR7, TLR9, TNF-alpha, and XCR1. Additional dendritic cell antigens and antibodies specifically binding to dendritic cell antigens are known in the art, such as those described in Rafael Nuñez Current Protocols in Cytometry (2001) 9.17.1-9.17.15; Hock et al., Immunology 1994, 83:573-581; Jiang et al., Nature 1995, 375:151-155; Bender et al., J. Immunol. Methods 1996, 196:121-135; and Colli et al., Immunology 2013, 140:22-30; the content of each of which is incorporated herein by reference in its entirety. In particular embodiments, dendritic cell specific antigens are selected from CD1a, CD1b/c, CD4, CD8, CD11b, CD11c, CD40, CD45R/B220, CD49d, CD80, CD83, CD85a, CD85f, CD85g/ILT7, CD85i, CD85j, CD86, CD123, CD197/CCR7, CD205, CD206, CD207, CD208, CD209, CD273/B7-DC/PD-L2, CD303/BDCA-2, CD304/neuropilin-1, DC marker/33D1, F4/80, MHC class I, fascin, HLA-DR and Siglec H. In particular embodiments, dendritic cell specific antigens are plasmacytoid dendritic cell antigens selected from CD1a, CD1 b, CD1c, CD4, CD8, CD11 b, CD11c, CD40, CD45R/B220, CD49d, CD80, CD83, CD85g/ILT7, CD86, CD123, CD197 (CCR7), CD273 (B7-DC, PD-L2), CD303 (BDCA-2), CD304 (Neuropilin-1), DC Marker (33D1), F4/80, HLA-DR, MHC Class II, Siglec H.

In particular embodiments, macrophage surface antigens finding use in the present disclosure include but are not limited to Activin A, AIF-1/Iba1, Arginase 1/ARG1, B7-1/CD80, B7-2/CD86, Calcitonin R, CCL1/I-309/TCA-3, CCL11/Eotaxin, CCL14/HCC-1/HCC-3, CCL15/MIP-1 delta, CCL16/HCC-4, CCL17/TARC, CCL18/PARC, CCL19/MIP-3 beta, CCL2/JE/MCP-1, CCL20/MIP-3 alpha, CCL22/MDC, CCL23/Ck beta 8-1, CCL23/MPIF-1, CCL24/Eotaxin-2/MPIF-2, CCL26/Eotaxin-3, CCL3/CCL4, CCL3/MIP-1 alpha, CCL4/MIP-1 beta, CCL5/RANTES, CCL8/MCP-2, CCR2, CCR5, CD11b/Integrin alpha M, CD11c, CD15/Lewis X, CD163, CD200 R1, CD200R1L, CD36/SR-B3, CD43, CD45, CD68/SR-D1, CLEC10A/CD301, COX-2, CX3CL1/Fractalkine, CX3CR1, CXCL1/GRO alpha/KC/CINC-1, CXCL10/IP-10/CRG-2, CXCL11/I-TAC, CXCL13/BLC/BCA-1, CXCL16, CXCL2/GRO beta/MIP-2/CINC-3, CXCL3/GRO gamma/CINC-2/DCIP-1, CXCL5/ENA-70, CXCL5/ENA-74, CXCL5/ENA-78, CXCL9/MIG, CXCR1/IL-8 RA, CXCR2/IL-8 RB, DC-SIGN/CD209, DEC-205/CD205, Dectin-1/CLEC7A, Dectin-2/CLEC6A, EMR1, F4/80, Fc epsilon RI alpha, Fc gamma RI/CD64, Fc gamma RIA/CD64, Fc gamma RIB/CD64, Fc gamma RII/CD32, Fc gamma RIII (CD16), FIZZ1/RELM alpha, Galectin-3, GATA-6, G-CSF, GITR Ligand/TNFSF18, GM-CSF, HLA-DR, ID2, IFN-gamma, IFN-gamma R1/CD119, IL-1 beta/IL-1F2, IL-1 RII, IL-10, IL-15, IL-17/IL-17A, IL-18/IL-1F4, IL-1ra/IL-1F3, IL-23, IL-4 R alpha, IL-6, IL-8/CXCL8, iNOS, Integrin alpha L/CD11a, IRF4, IRF5, LAMP-2/CD107b, Langerin/CD207, LILRB4/CD85k/ILT3, L-Selectin/CD62L, LXR alpha/NR1H3, Ly-6G (Gr-1), Ly-6G/Ly-6C (Gr-1), MARCO, M-CSF R/CD115, Mer, MFG-E8, MHC class II (I-A/I-E), MMR/CD206, NFATC1, NGFI-B alpha/Nur77/NR4A1, PPAR delta/NR1C2, PPAR gamma/NR1C3, RANK/TNFRSF11A, RUNX3/CBFA3, Siglec-1/CD169, Siglec-3/CD33, Siglec-F, SIGNR1/CD209b, SIRP alpha/CD172a, SLAM/CD150, SOCS-3, Sphingosine Kinase 1/SPHK1, Sphingosine Kinase 2/SPHK2, SR-AI/MSR, SR-BI, STAT1, STAT6, TGF-beta, TIM-4, TLR1, TLR2, TLR4, TLR8, TNF-alpha, TRACP/PAP/ACP5, VCAM-1/CD106, VEGF, and YM1/Chitinase 3-like 3. In particular embodiments, macrophage specific antigens are selected from CD11a, CD11b, CD11c, CD14, CD15 (SSEA-1), CD16/32, CD33, CD64, CD68, CD80, CD85k (ILT3), CD86, CD105 (Endoglin), CD107b, CD115, CD163, CD195 (CCR5), CD282 (TLR2), CD284 (TLR4), F4/80, GITRL, HLA-DR, Mac-2 (Galectin-3), MHC Class II.

In particular embodiments, T cell specific antigens finding use in the present disclosure include but are not limited to CD3, CD4, CD8, CD25, CD127, and CD196/CCR6, CD197/CCR7, CD62L, CD69, and CD45RO.

In particular embodiments, T Follicular helper cell specific antigens finding use in the present disclosure include but are not limited to BCL-6, Stat-3, CD3, CD4, CD84, CD126/IL-6Rα, CD150/SLAM), CD154/CD40L, CD185/CXCR5, CD252/OX40L, CD278/ICOS, CD279/PD1, and TCR α/β. In particular embodiments, Th1 cell specific antigens finding use in the present disclosure include but are not limited to GM-CSF, IFN-γ, IL-2, T-bet, Extracellular Markers, CD4, CD26, CD94, CD119, CD183, CD191 (CCR1), CD195 (CCR5), CD254 (TRANCE, RANKL), CD366 (Tim-3), IL-18R, Lymphotoxin beta receptor (LTPR), TNF-α, and TNF-β. In particular embodiments, Th2 cell specific antigens finding use in the present disclosure include but are not limited to c-MAF, GATA3, GM-CSF, IL-4, IL-5, IL-6, IL-10, IL-13, Extracellular Markers, CCR8, CD4, CD184 (CXCR4), CD193 (CCR3), CD194 (CCR4), CD197 (CCR7), CD278 (ICOS), CD294 (CRTH2), CD365 (Tim-1), and IL-1R. In particular embodiments, Th9 cell specific antigens finding use in the present disclosure include but are not limited to GATA3, IRF4, Stat-6, CD3, CD4, and TCR α/β. In particular embodiments, Th17 cell specific antigens finding use in the present disclosure include but are not limited to IL-17A, IL-17F, IL-21, IL-22, RORα, RORγt, Stat-3, CD3, CD4, CD38, CD161/NK-1.1, CD194/CCR4, CD196/CCR6, IL-1R and TGF-β. In particular embodiments, Th22 cell specific antigens finding use in the present disclosure include but are not limited to AHR, CCR10, CD3, CD$, CD194/CCR4, CD196/CCR6, and TCR α/β. In particular embodiments, Treg cell specific antigens finding use in the present disclosure include but are not limited to FOXP3, Helios, Extracellular Markers, CD4, CD25, CD39, CD62L, CD73, CD103, CD134, CD152/CTLA-4, CD194/CCR4, CD223, FR4, GARP, GITR, and TGF-β.

In particular embodiments, natural killer cell specific antigens finding use in the present disclosure include but are not limited to CD11b, CD11c, CD16/32, CD49b, CD56 (NCAM), CD57, CD69, CD94, CD122, CD158 (Kir), CD161 (NK-1.1), CD244 (2B4), CD314 (NKG2D), CD319 (CRACC), CD328 (Siglec-7), CD335 (NKp46), Ly49, Ly108, Vα24-Jα18 TCR (iNKT), Granulysin, Granzyme, and Perforin.

In particular embodiments, endothelial cell specific antigens finding use in the present disclosure include but are not limited to CD31, CD34, CD54, CD61, CD62E/E-Selectin, CD105/Endoglin, CD106/VCAM-1, CD144/VE-Cadherin, CD146/MUC18, Mel-CAM, CD201/EPCR, CD202b/Tie2/Tek, CD309/VEGFR2-Flk-1, Podoplanin, and VEGFR3. In particular embodiments, basophil cell specific antigens finding use in the present disclosure include but are not limited to Pro-Major Basic Protein 1, CD13, CD44, CD54, CD63, CD69, CD107a, CD123, CD193/CCR3, CD203c, FcεRIα, IgE, and TLR4. In particular embodiments, astrocyte cell specific antigens finding use in the present disclosure include but are not limited to S100B, CD40, CD80, CD86, CD88, and GFAP. In particular embodiments, eosinophil cell specific antigens finding use in the present disclosure include but are not limited to C3AR, CD15 (SSEA-1), CD23, CD49d, CD52, CD53, CD88, CD129, CD183, CD191, CD193, CD244 (2B4), CD294, CD305, FcεRIα, Galectin-9, MRP-14, Siglec-8, and Siglec-10. In particular embodiments, mast cell specific antigens finding use in the present disclosure include but are not limited to CD117/C-kit, CD203c and FcεRIα. In particular embodiments, fibroblast cell specific antigens finding use in the present disclosure include but are not limited to CD10, CD29, CD47, CD81, CD91, CD121a.

In particular embodiments, the CpG-Ab immunoconjugate specifically binding to an target antigen associated with a normal immune cell that is selected from CD19, CD20, CD22, CD30, CD38, CD40, CD74, CD79b, CD205, CD274, CD303, and CD304. In particular embodiments, the CpG-Ab immunoconjugate specifically binding to an target antigen selected from CD19, CD20, CD22, CD30, CD38, CD40, CD74, CD79b, CD205, CD274, CD303, and CD304.

In some embodiments, the CpG-Ab immunoconjugate specifically binding to an antigen associated with a normal immune cell (e.g., an APC) does not target an abnormal cell. In some embodiments, the CpG-Ab immunoconjugate specifically binding to an antigen associated with a normal immune cell (e.g., an APC) does not bind to an antigen associated with an abnormal cell. In some embodiments, the CpG-Ab immunoconjugate specifically binding to an antigen associated with a normal immune cell (e.g., an APC) does not bind to a tumor associated antigen of the cancer being treated with the method provided herein.

In some embodiments, the CpG-Ab immunoconjugate specifically binds to an antigen associated with a TLR-expressing cell selected from keratinocytes, Langerhans cells, T cells, B cells, mast cells, endothelial cells, myofibroblast cells, and primary fibroblast cells. In some embodiments, the CpG-Ab immunoconjugate specifically binding to an antigen associated with a TLR-expressing cell does not target an abnormal cell. In some embodiments, the CpG-Ab immunoconjugate specifically binding to an antigen associated with a TLR-expressing cell does not bind to an antigen associated with an abnormal cell. In some embodiments, the CpG-Ab immunoconjugate specifically binding to an antigen associated with a TLR-expressing cell does not bind to tumor associated antigen of the cancer being treated with the method provided herein.

In some embodiments, the CpG-Ab immunoconjugate specifically binds to a tumor associated antigen of the cancer being treated by the present method. Examples of tumor associated antigens (TAAs) that can be targeted by the CpG-Ab immunoconjugate of the present disclosure include, but are not limited to, sequences comprising all or part of the sequences of EGFR, EGFRvIII, gp100 or Pmel17, HER2/neu, mesothelin, CEA, MART-1/Melan-A, MAGE-A1, MAGE-A2, MAGE-A3, MAGE-A4, MUC-1, GPNMB, HMW-MAA, TIM1, ROR1, CD19, gp100, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family (e.g. MUC1, MUC16, etc; see e.g. U.S. Pat. No. 6,054,438; WO98/04727; or WO98/37095), p21ras, RCAS1, alpha-fetoprotein, E-cadherin, alpha-catenin, beta-catenin and gamma-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, Smad family of tumor antigens brain glycogen phosphorylase, SSX-1, SSX-2 (HOM-MEL-40), SSX-1, SSX-4, SSX-5, SCP-1 and CT-7, and c-erbB-2 and viral antigens such as the HPV-16 and HPV-18 E6 and E7 antigens and the EBV-encoded nuclear antigen (EBNA)-1 as well as markers (beta-galactosidase, luciferase . . . ), βhCG, WT1, TRP-2, NY-BR-1, NY-CO-58, MN (gp250), Telomerase, and germ cell derived tumor antigens. Tumor associated antigens also include the blood group antigens, for example, Lea, Leb, LeX, LeY, H-2, B-1, B-2 antigens. Tumor associated antigen can be identified using methods known in the art, such as disclosed in Zhang et al. Supra.

Particularly, in some embodiments, the CpG-Ab immunoconjugate specifically binds to a tumor associated antigen selected from CD19, CD20, CD22, CD25, CD30, CD33, CD38, CD40, CD44, CD45R (B220), CD49, CD52, CD56, CD70, CD74, CD79a, CD79b, CD93, CD123, CD138, CD163, CD205, CD206, CD274, CD303, and CD304, folate receptor alpha, folate receptor beta, mesothelin, PSMA, Her-2, EGFR, transferrin receptor, integrin, cripto, EphA2, AGS-5, AGS-16, CanAg, EpCAM, IL4 receptor, IL2 receptor, Lewis Y, GPNMB.

In other embodiments, the CpG-Ab immunoconjugate does not bind to a tumor associated antigen selected from CD19, CD20, CD22portin 7, Her2, Src, EGFR, CD52, CXCR-4, Muc-1 and DNA.

In some embodiments, the tumor associated antigen is associated with one or more normal immune cells. In some embodiments, the tumor associated antigen is also associated with one or more TLR-expressing cells. In particular embodiments, the tumor associated antigen is a protein encoded and expressed by a normal immune cell. In particular embodiments, the normal immune cell has been artificially engineered to contain or express the tumor associated antigen. In particular embodiments, the tumor associated antigen is an exogenous antigen taken up and processed by an APC. In particular embodiments, the cancer is an immune cell cancer, and the CpG-Ab immunoconjugates targets both cancerous immune cells and normal immune cells by specifically binding to the tumor associated antigen. In particular embodiments, the cancer is lymphoma or leukemia. In particular embodiments, the cancer is B cell lymphoma.

In some embodiments of the methods of treating cancer as described herein, the cancer being treated with the methods disclosed herein is a solid tumor. In some embodiments, the cancer being treated with the methods disclosed herein is a liquid tumor. In particular embodiments, the cancer being treated with the methods disclosed herein is a lymphoma or a leukemia. In particular embodiments, the cancer being treated with the methods disclosed herein is selected from the list consisting of mantle cell cymphoma (MCL), diffuse large B-cell lymphoma (DLBCL), Burkitts lymphoma, multiple melanoma (MM), chronic lymphocytic leukemia (CLL), acute myeloid leukemia (AML), small lymphocytic lymphoma (SLL), hairy cell leukemia (HCL), lymphoplasmacytic lymphoma (LPL), skeletal muscle lymphoma (SML), splenic marginal zone lymphoma (SMZL), follicle center lymphoma (FCL), colorectal cancer, non-small cell lung cancer (NSCLC), head and neck cancer, breast cancer, pancreatic cancer, glioblastoma (GBM), prostate cancer, esophageal cancer, renal cell carcinoma, hepatic carcinoma, bladder cancer and gastric carcinoma.

In some embodiments, the cancer being treated with the methods disclosed herein is resistant to at least one immunotherapy. In some embodiments, the method of treating cancer comprises co-administering to a subject having cancer (i) a therapeutic effective amount of the CpG-containing immunostimulating polynucleotide or the CpG-Ab immunoconjugate; and (ii) the immunotherapeutic agent which the cancer being treated has shown to resist or not to respond, when the cancer is treated with the immunotherapeutic agent alone.

In particular embodiments, the cancer being treated with the methods provided herein has been shown to not to respond to a treatment with an immune checkpoint modulator. In particular embodiments, the immune checkpoint modulator is an inhibitor of PD-1. In particular embodiments, the immune checkpoint modulator is an inhibitor of PD-L1. In some embodiments, the method of treating cancer comprises co-administering to a subject having cancer (i) a therapeutic effective amount of the CpG-containing immunostimulating polynucleotide or the CpG-Ab immunoconjugate; and (ii) a therapeutic effective amount of the inhibitor of PD-1. In some embodiments, the method of treating cancer comprises co-administering to a subject having cancer (i) a therapeutic effective amount of the CpG-containing immunostimulating polynucleotide or the CpG-Ab immunoconjugate; and (ii) a therapeutic effective amount of the inhibitor of PD-L1. In particular, in some embodiments, the inhibitor of PD-1 is an anti-PD-1 antibody or an antigen binding fragment thereof. In some embodiments, the inhibitor of PD-L1 is an anti-PD-L1 antibody or an antigen binding fragment thereof.

In certain aspects, provided herein are methods of preventing cancer in a subject susceptible of developing cancer, comprising administering to the subject a therapeutic effective amount of a TLR agonist as described herein. In some embodiments, the method comprising administering to the subject an therapeutic effective amount of a CpG-containing immunostimulating polynucleotide or a CpG-Ab immunoconjugate described herein. In particular embodiments, the CpG-Ab immunoconjugate targets a normal immune cell as described herein. In particular embodiments, the CpG-Ab immunoconjugate targets a TLR-expressing cell as described herein. In particular embodiments, the CpG-Ab immunoconjugate specifically binds to an antigen associated with a normal immune cell as described herein. In particular embodiments, the CpG-Ab immunoconjugate specifically binds to an antigen associated with a normal immune cell does not bind to a tumor associated antigen of the cancer being prevented. In particular embodiments, the CpG-Ab immunoconjugate specifically binds to an antigen associated with a TLR-expressing cell as described herein. In particular embodiments, the CpG-Ab immunoconjugate specifically binds to an antigen associated with a TLR-expressing cell does not bind to a tumor associated antigen of the cancer being prevented. In particular embodiments, the CpG-Ab immunoconjugate specifically binds to a tumor associated antigen of the cancer being prevented as described herein. In particular embodiments, a tumor associated antigen of the cancer being prevented is also associated with a normal immune cell or a TLR-expressing cell. In particular embodiments, the CpG-Ab immunoconjugate does not specifically bind to an antigen selected from CD19, CD20, CD22, STAT3, exportin 7, Her2, Src, EGFR, CD52, CXCR-4, Muc-1 and DNA.

In some embodiments, the methods of preventing cancer further comprises administering to a subject susceptible to developing cancer (i) a therapeutic effective amount of a CpG-Ab immunoconjugate and (ii) a tumor associated antigen of the cancer being prevented. In some embodiments, the tumor associated antigen is not conjugated to the CpG-Ab immunoconjugate. In particular embodiments, the tumor associated antigen is formulated as a cancer vaccine. In particular embodiments, the CpG-Ab immunoconjugate is formulated as an adjuvant of the cancer vaccine.

In some embodiments, the cancer being prevented or treated using the methods provided herein is an episode of cancer recurrence in a subject who is in partial or complete remission of a prior cancer. In particular embodiments, the prior cancer is a liquid cancer and the recurrent cancer being prevented or treated is a liquid cancer. In particular embodiments, the prior cancer is a solid cancer and the recurrent cancer being prevented or treated is a solid cancer. In particular embodiments, the prior cancer is a liquid cancer and the recurrent cancer being prevented or treated is a solid cancer. In particular embodiments, the prior cancer is a solid cancer and the recurrent cancer being prevented or treated is a liquid cancer.

In some embodiments, the cancer being prevented or treated using the methods provided herein is first episode of cancer recurrence in the subject after the subject showed partial or complete remission. In some embodiments, the cancer being prevented or treated using the methods provided herein is second episode of cancer recurrence in the subject after the subject showed partial or complete remission. In some embodiments, the cancer being prevented or treated using the methods provided herein is third episode of cancer recurrence in the subject after the subject showed partial or complete remission. In some embodiments, the cancer being prevented or treated using the methods provided herein is an episode of cancer recurrence subsequent to the third episode of cancer recurrence in the subject after the subject showed partial or complete remission.

In certain aspects, provided herein are methods of inducing an adaptive immune response in a subject in need thereof, wherein method comprises administering to the subject an therapeutic effective amount of a TLR agonist as described herein. In particular embodiments, the method of inducing an adaptive immune response comprises administering to the subject in need thereof an therapeutic effective amount of a CpG-containing immunostimulating polynucleotide or a CpG-Ab immunoconjugate described herein. In particular embodiments, the CpG-Ab immunoconjugate targets a normal immune cell as described herein. In particular embodiments, the CpG-Ab immunoconjugate targets a TLR-expressing cell as described herein. In particular embodiments, the CpG-Ab immunoconjugate targets a diseased cell selected from a cancer cell or a pathogen infected cell. In particular embodiments, the CpG-Ab immunoconjugate specifically binds to an antigen associated with a normal immune cell as described herein. In particular embodiments, the CpG-Ab immunoconjugate specifically binds to an antigen associated with a normal immune cell does not bind to a disease antigen. In particular embodiments, the CpG-Ab immunoconjugate specifically binds to an antigen associated with a TLR-expressing cell as described herein. In particular embodiments, the CpG-Ab immunoconjugate specifically binds to an antigen associated with a TLR-expressing cell does not bind to a disease antigen. In particular embodiments, the CpG-Ab immunoconjugate specifically binds to a disease antigen as described herein. In particular embodiments, the diseased antigen is also associated with a normal immune cell or a TLR-expressing cell. In particular embodiments, the diseased antigen is a tumor associated antigen or a pathogenic antigen. In particular embodiments, the CpG-Ab immunoconjugate does not specifically bind to an antigen selected from CD19, CD20, CD22, STAT3, exportin 7, Her2, Src, EGFR, CD52, CXCR-4, Muc-1 and DNA.

In some embodiments of the methods and uses described herein, the CpG-containing immunostimulating polynucleotide is administered to a subject in need thereof at a dosage that is sufficient for activating the TLR9-mediated signaling pathway in the subject. In some embodiments, the CpG-Ab immunoconjugate is administered to a subject in need thereof at a dosage that is sufficient for activating the TLR9 mediated signaling pathway in a cell population targeted by the CpG-Ab immunoconjugate. As described herein, in some embodiments, the cell population targeted by the CpG-Ab immunoconjugate expresses TLR9. In some embodiments, the cell population targeted by the CpG-Ab immunoconjugate can express the TLR9 on the cell surface of the targeted cell, on the endosomal membrane of the targeted cell, or both on the cell surface and on the endosomal membrane of the targeted cell.

Particularly, in some embodiments of the methods and uses described herein, the CpG-containing immunostimulating polynucleotide is administered to a subject in need thereof at a dosage that is effective for inducing one or more of effects selected from (a) specifically binding to a TLR9 receptor by the CpG-containing immunostimulating polynucleotide on a targeted cell; (b) efficient internalization of the CpG-Ab immunoconjugate or the CpG-containing immunostimulating polynucleotide portion thereof by a targeted cell; (c) activating one or more signaling pathways in the targeted cell; (d) inducing secretion of one or more inflammatory cytokines by the targeted cell; (e) suppressing secretion of one or more inflammatory cytokines by the targeted cell; (f) upregulating expression of one or more genes of the targeted cell; (g) supressing expression of one or more genes of the targeted cell; (h) activating targeted normal immune cells, and (i) inducing apoptosis of a targeted cancer cell, ( ) inducing necrosis of targeted cancer cell.

Particularly, in some embodiments of the methods and uses described herein, wherein upon administration of the CpG-Ab immunoconjugate, the CpG-containing immunostimulating polynucleotide specifically binds to a TLR9 receptor of the targeted cell. Particularly, in some embodiments, binding of CpG-Ab immunoconjugate to an antigen associated with a targeted cell facilitates specific binding of the CpG-containing immunostimulating polynucleotide to a TLR9 receptor. In some embodiments, the target antigen of the CpG-Ab immunoconjugate is located near the TLR9 receptor. In particular embodiments, both the target antigen and the TLR9 receptor locate on the cell membrane of the targeted cell. In particular embodiments, both the target antigen and the TLR9 receptor locate on an intracellular membrane of the targeted cell. In particular embodiments, both the target antigen and the TLR9 receptor locate on the endosomal or phagosomal membrane of the targeted cell. In some embodiments, the target antigen locates on the cell membrane and facilitates internalization of the CpG-Ab immunoconjugate into the cytosol upon binding to the CpG-Ab immunoconjugate.

Particularly, in some embodiments of the methods and uses described herein, the method comprises administering to a subject in need thereof a therapeutic effective amount of a CpG-Ab immunoconjugate targeting a normal immune cell, wherein upon administration of the CpG-Ab immunoconjugate, one or more immunogenic signaling pathways in the targeted cell are activated. In particular embodiments, the activated signaling pathways are one or more selected from the nuclear factor (NF)-κB signaling pathway, the c-Jun N-terminal kinase (JNK) signaling pathway, the AP1 signaling pathway, the IRF3/7 pathway, and the p38 mitogen-activated protein kinase (MAPK) signaling pathway. The activation of a cellular signaling pathway can be detected using methods known in the art, such as but not limited to, detecting the presence of a molecular marker of which the expression is specifically induced upon activation of the signaling pathway of interest.

Particularly, in some embodiments of the methods and uses described herein, the method comprises administering to a subject in need thereof a therapeutic effective amount of a CpG-Ab immunoconjugate targeting a normal immune cell, wherein upon administration of the CpG-Ab immunoconjugate, secretion of one or more inflammatory cytokines is induced. In particular embodiments, the one or more inflammatory cytokines are selected from type I interferon (IFN), interleukin (IL)-6, IL10, IL-12, IL-18, and tumor necrosis factor (TNF).

Particularly, in some embodiments of the methods and uses described herein, the method comprises administering to a subject in need thereof a therapeutic effective amount of a CpG-Ab immunoconjugate targeting a normal immune cell, wherein upon administration of the CpG-Ab immunoconjugate, expression of one or more additional proteins are upregulated. In particular embodiments, the upregulated proteins are one or more selected from antigen presenting molecules (e.g., MHC class I and II), cytokine receptors (e.g., IL-6 receptors, IL-10 receptors, IL-12 receptors, TNF-α receptor, TNF-β receptor, IFN-α receptor, IFN-β receptor, IFN-γ), chemokine receptors (e.g., chemokine receptor 7), T cell costimulatory molecules (e.g., CD3, CD28, CD27, CD30, CD40, CD80/B7-1, CD86/B7-2, CD134/OX-40, OX-40L, CD137/4-1 BB, 4-1 BBL, CD278/ICOS, B7-H3, B7h/B7RP-1, LIGHT etc.), and T cell maturation regulatory proteins (e.g., indoleamine 2,3-dioxygenase).

Particularly, in some embodiments of the methods and uses described herein, the method comprises administering to a subject in need thereof a therapeutic effective amount of a CpG-Ab immunoconjugate targeting a normal immune cell, wherein upon administration of the CpG-Ab immunoconjugate, proliferation, differentiation, maturation and/or survival of one or more populations of normal immune cells are increased. In particular embodiments, the one or more increased populations of normal immune cells are selected from CD4+ T cells, CD8+ T cells, natural killer cells, T helper cells, B cells, and APCs (including mDCs). in some embodiments of the methods and uses described herein, the method comprises administering to a subject in need thereof a therapeutic effective amount of a CpG-Ab immunoconjugate targeting a normal immune cell, wherein upon administration of the CpG-Ab immunoconjugate, proliferation, differentiation, maturation and/or survival of one or more populations of normal immune cells are reduced. In particular embodiments, the one or more reduced populations of normal immune cells is selected from B-reg cells and T-reg cells.

In particular embodiments, upon administration of the CpG-Ab immunoconjugate, antigen presentation activities are increased in APCs in the subject. In some embodiments, the APC is selected from B cells, monocytes, dendritic cells, and Langerhans cells, keratinocytes, endothelial cells, astrocytes, fibroblasts, and oligodendrocytes. In particular embodiments, the APC is B cells. In particular embodiments, the APC is dendritic cells. In particular embodiments, the APC is macrophage. In some embodiments, the dendritic cell is pDC. In particular embodiments, the increased antigen presentation activities lead to more efficient presentation of a tumor associated antigen by the activated APCs.

In particular embodiments, upon administration of the CpG-Ab immunoconjugate, antigen-specific CD4+ T cell mediated immunity against one or more tumor associated antigen of the cancer being treated or prevented is increased. In particular embodiments, upon administration of the CpG-Ab immunoconjugate, tumor infiltration by CD4+ T cell is increased. In particular embodiments, upon administration of the CpG-Ab immunoconjugate, antigen-specific CD8+ T cell mediated immunity against one or more tumor associated antigen of the cancer being treated or prevented is increased is increased. In particular embodiments, upon administration of the CpG-Ab immunoconjugate, tumor infiltration by CD8+ T cell is increased. In particular embodiments, upon administration of the CpG-Ab immunoconjugate, B cell secretion of immunoglobulin specifically against one or more tumor associated antigen of the cancer being treated or prevented is increased is increased.

Particularly, in some embodiments of the methods and uses described herein, the method comprises administering to a subject in need thereof, a therapeutic effective amount of a CpG-Ab immunoconjugate targeting a diseased cell, wherein upon administration of the CpG-Ab immunoconjugate, one or more apoptotic signaling pathways are induced trigger apoptosis of the targeted diseased cell. In some embodiments, the diseased cell is a cancer cell.

In some embodiments of the methods and uses described herein, the CpG-Ab immunoconjugate is administered to a subject in need thereof in an amount that is not effective for activating the complement system in the subject. In some embodiments, the CpG-containing immunostimulating polynucleotide is administered to a subject in need thereof in an amount that is not effective to activate complement C1 in the subject. In some embodiments, the CpG-containing immunostimulating polynucleotide is administered to a subject in need thereof in an amount that is not effective to activate complement C3 in the subject. Complement activation can be detected using methods known in the art. In some embodiments, the CpG-Ab immunoconjugate is administered to a subject in need thereof in an amount that is not effective for the antibody portion of the CpG-Ab immunoconjugate to induce antibody-dependent cell-mediated cytotoxicity in the subject.

As described herein, therapeutic agents, conjugates or compositions comprising the CpG-containing polynucleotides can be used in combination with at least one additional therapeutic agents for preventing or treating cancer. In some embodiments, such combination therapy exhibits a synergistic therapeutic effect that is better than the separate effect of either therapeutic agent alone. In some embodiments, such combination therapies exhibits a synergistic therapeutic effect that is better than the sum of the separate effects of the therapeutic agents alone.

Accordingly, in certain aspects, provided herein are methods for preventing or treating cancer using the CpG-containing immunostimulating polynucleotide in combination with at least one additional cancer therapeutic agent. Such methods comprising administering to a subject in need thereof (i) a therapeutically effective amount of the CpG-containing immunostimulating polynucleotide, and (ii) a therapeutically effective amount of at least one additional cancer therapeutic agents. In particular embodiments, the CpG-containing immunostimulating polynucleotide is administered as a free-standing polynucleotide. In particular embodiments, the CpG-containing immunostimulating polynucleotide is administered as a CpG-Ab immunoconjugate. In particular embodiments, the CpG-containing immunostimulating polynucleotide and the additional therapeutic agents are formulated in the same composition. In other embodiments, CpG-containing immunostimulating polynucleotide and the additional therapeutic agents are formulated in the separate compositions.

In some embodiments, the at least one additional cancer therapeutic agent is selected from T cell agonists, immune checkpoint modulators, STING agonists, RIG-I agonists, other toll-like receptor agonists.

In some embodiments, the additional cancer therapeutic agent is a T cell costimulatory molecule. In some embodiments, the T cell costimulatory molecule is selected from OX40, CD2, CD27, CDS, ICAM-1, LFA-1/CD11a/CD18, ICOS/CD278, 4-1 BB/CD137, GITR, CD30, CD40, BAFFR, HVEM, CD7, LIGHT, NKG2C, SLAMF7, NKp80, CD160, B7-H3, and CD83, or a ligand thereof. In some embodiments, a ligand of a costimulatory molecule is an antibody specifically binding to the costimulatory molecule. In particular embodiments, the additional cancer therapeutic agent is selected from an anti-OX40 antibody, an anti-OX40L antibody, an anti-ICOS antibody, an anti-CTLA4 antibody, an anti-CD40L antibody, an anti-CD28 antibody, an anti-LFA1 antibody, an anti-TIM1/TIM3 antibody, an anti-PD1 antibody, an anti-PDL1 antibody, an anti-CD27 antibody and an anti-4-1 BB antibody.

In some embodiments, the additional cancer therapeutic agent is a tumor associated antigen produced by the cancer that is being prevented or treated with the method. In some embodiments, the cancer being prevented or treated is leukemia, lymphoma, melanoma, colorectal, breast, prostate, renal, pancreatic, head and neck, skin, and brain cancer, lung cancer, and the tumor associated antigen is selected from CD19, CD20, CD22, CD38, CD138, CD30, CD52, CD56, CD79, CD123, CD206, CD303, CD304, EGFR, folate receptor alpha, folate receptor beta, mesothelin, Her2, transferrin receptor, and PSMA. In some embodiments, the additional cancer therapeutic agent is an immune checkpoint modulator selected from inhibitors of PD-1, PD-L1, PD-L2, TIM-3, LAG-3, CEACAM-1, CEACAM-5, CLTA-4, VISTA, BTLA, TIGIT, LAIR1, CD47, CD160, 2B4, CD172a, and TGFR. In particular embodiments, the additional cancer therapeutic agent is an PD-1 inhibitor. In particular embodiments, the additional cancer therapeutic agent is an PD-L1 inhibitor. In particular embodiments, the additional cancer therapeutic agent is an CD47 inhibitor. In some embodiments, the additional cancer therapeutic agent is an antibody specifically binding to the immune checkpoint modulator. In some embodiments, In particular embodiments, the additional cancer therapeutic agent is an anti-PD-1 antibody or an antigen binding fragment thereof. In particular embodiments, the additional cancer therapeutic agent is an anti-PD-L1 antibody or an antigen binding fragment thereof. In particular embodiments, the additional cancer therapeutic agent is an anti-CD47 antibody or an antigen binding fragment thereof. In particular embodiments, the additional cancer therapeutic agent is an anti-CD172a antibody or an antigen binding fragment thereof, In particular embodiments, the additional cancer therapeutic agent is an anti-OX40 antibody or an antigen binding fragment thereof, In particular embodiments, the additional cancer therapeutic agent is an anti-TIM3 antibody or an antigen binding fragment thereof, In particular embodiments, the additional cancer therapeutic agent is an anti-LAG3 antibody or an antigen binding fragment thereof. Anti-PD-1 and anti-PD-L1 antibodies and their uses are described in, for example, US20180030137, U.S. Pat. No. 9,815,898, US20170313776, US20170313774, US20170267762, WO2017019846, WO2018013017, US20180022809, US20180002423, WO2017220990, WO2017218435, WO2017215590, U.S. Pat. No. 9,828,434, and WO2017196867. Anti-CD47 antibodies and their uses are described in, for example U.S. Pat. Nos. 9,663,575, 9,803,016, US20170283498, US20170369572, WO2017215585, WO2017196793, and WO2017049251.

In some embodiments, the additional cancer therapeutic agent is a STING pathway agonist. STING (stimulator of interferon genes, also known as TMEM173, MITA, ERIS, and MPYS) is a transmembrane protein localized to the ER that undergoes a conformational change in response to direct binding of cyclic dinucleotides (CDNs), resulting in a downstream signaling cascade involving TBK1 activation, IRF-3 phosphorylation, and production of IFN-β and other cytokines. The STING pathway in tumor-resident host antigen presenting cells is involved in the induction of a spontaneous CD8+ T cell response against tumor associated antigens. Activation of this pathway and the subsequent production of IFN-β also contributes to the anti-tumor effect. In some embodiments, the STING pathway agonist is ADU-S100. Additional STING agonists and their uses are described in, for example, US20180028553, US20170319680, US20170298139, US20060040887, US20080286296, US20120041057, US20140205653, WO2014179335, WO 2014179760, US20150056224, WO 2016096174, WO 2017011444, WO 2017027645, and WO 2017027646.

In some embodiments, the additional cancer therapeutic agent is a RIG-1 pathway agonist. RIG-1 (retinoic acid-inducible gene-I) is a member of pattern-recognition receptors that initiates a host's innate immune system to defend against pathogenic microbes in early phases of infection. There are three members of the (RIG-I)-like receptors family: RIG-I, MDA5 (melanoma differentiation factor 5), and LGP2 (laboratory of genetics and physiology 2), which are expressed in most cell and tissue types. RIG-1 functions as a cytoplasmic sensor for the recognition of a variety of RNA viruses and subsequent activation of downstream signaling to drive type I IFN production and antiviral gene expressions. Activated RIG-1 recruits its downstream adaptor molecule MAVS (also known as IPS-1, CARDIF, and VISA) through CARD-CARD-mediated interactions. The oligomeric RIG-1 CARD assembly and the polymeric formation of MAVS, together serve as a signaling platform for protein complexes that mediate the bifurcation of signaling into two branches. One branch recruits tumor necrosis factor receptor-associated factors (TRAF)-2/6 and the receptor-interacting protein 1 to subsequently activate the IKK complex, resulting in NF-κB activation. The other branch signals through TRAF3 and activates the TANK/IKKγ/IKKε/TBK1 complex, leading to the phosphorylation and dimerization of interferon regulator factors (IRF)-3 and -7. Liu et al., *Front Immunol*. 2017, 7:662. Activation of this pathway contributes to the anti-tumor effect. In some embodiments, the RIG-I pathway agonist is RGT100. RIG-I agonists and their uses are described in, for example, US20170057978, US20170258897, U.S. Pat. Nos. 9,381,208, 9,738,680, 9,650,427, WO2017173427, and WO2017011622.

In some embodiments, the additional cancer therapeutic agent is a toll-like receptor agonist selected from TLR1 agonist, TLR2 agonist, TLR3 agonist, TLR4 agonist, TLR5 agonist, TLR6 agonist, TLR7 agonist, TLR8 agonist, and TLR10 agonist.

In further embodiments, in relation to a method of treating cancer, the CpG-containing immunostimulating polynucleotide is administered (either in the free-standing form or as a CpG-Ab immunoconjugate) in combination with one or more additional therapeutic agents or procedures, for example wherein the additional therapeutic agent or procedure is selected from the group consisting of chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, a cellular immunotherapy, and an oncolytic virus therapy.

As provided herein, the CpG-containing polynucleotide (either in a free-standing form or as a CpG-Ab conjugate) may be administered, for example, by non-parenteral or parenteral administration. Parenteral administration may include intramuscular, intravenous, intraarterial, intracranial, subcutaneous, intraorbital, intraventricular, intraspinal, intrathecal, intraperitoneal, rectal, and topical routes of administration. Topical route of administration may include transdermal, intradermal, buccal, and sublingual routes of administration. The pharmaceutical compositions are formulated according to the selected route of administration. Parenteral administration may be by continuous infusion over a selected period of time. In particular embodiments, the administration is subcutaneous, intramuscular, intradermal, mucosal, vaginal, cervical, peri-tumoral, intra-tumoral, or directly into the tumor-draining lymph node(s). The polynucleotides and/or conjugates desirably are administered with a pharmaceutically acceptable carrier. Pharmaceutical formulations of the polynucleotides and/or conjugates described herein formulated for treatment of the disorders described herein are also part of the present invention.

The actual dosage amount of the CpG-containing immunostimulating polynucleotide (either in a free-standing form or as a CpG-Ab conjugate) administered to a subject can be determined by physical and physiological factors such as body weight, severity of condition, the type of disease being treated, previous or concurrent therapeutic interventions, idiopathy of the patient and on the route of administration. The actual dosage amount of the CpG-containing immunostimulating polynucleotide (either in a free-standing form or as a CpG-Ab conjugate) can be administered in a single dose or in a series of sequential doses. Depending upon the dosage and the route of administration, the number of administrations of a preferred dosage and/or an effective amount may vary according to the response of the subject. The practitioner responsible for administration will, in any event, determine the concentration of active ingredient(s) in a composition, appropriate dose(s) and schedule(s) for the individual subject.

In certain embodiments, the CpG-containing immunostimulating polynucleotide is administered in a free-standing form at a dosage that ranges from 0.01 milligram/kg body weight to 1000 milligram/kg body weight, including the end points. In other non-limiting examples, a dose may also comprise from about 0.01 milligram/kg bodyweight to about 0.05 milligram/kg bodyweight. In other non-limiting examples, a dose may also comprise from about 0.01 milligram/kg bodyweight, about 0.05 milligram/kg bodyweight, about 0.1 milligram/kg bodyweight, about 0.2 milligram/kg bodyweight, about 0.3 milligram/kg bodyweight, about 0.4 milligram/kg bodyweight, about 0.5 milligram/kg bodyweight, about 0.6 milligram/kg bodyweight, about 0.7 milligram/kg bodyweight, about 0.8 milligram/kg bodyweight, about 0.9 milligram/kg bodyweight, about 1 milligram/kg bodyweight, about 2 milligram/kg bodyweight, about 3 milligram/kg bodyweight, about 4 milligram/kg bodyweight, about 5 milligram/kg bodyweight, about 6 milligram/kg bodyweight, about 7 milligram/kg bodyweight, about 8 milligram/kg bodyweight, about 9 milligram/kg bodyweight, about 10 milligram/kg bodyweight, about 20 milligram/kg bodyweight, about 30 milligram/kg bodyweight, about 40 milligram/kg bodyweight, about 50 milligram/kg bodyweight, about 60 milligram/kg bodyweight, about 70 milligram/kg bodyweight, about 80 milligram/kg bodyweight, about 90 milligram/kg bodyweight, about 100 milligram/kg bodyweight, about 200 milligram/kg bodyweight, about 300 milligram/kg bodyweight, about 400 milligram/kg bodyweight, about 500 milligram/kg bodyweight, about 600 milligram/kg bodyweight, about 700 milligram/kg bodyweight, about 800 milligram/kg bodyweight, about 900 milligram/kg bodyweight, about 1000 milligram/kg bodyweight, or more per administration, and any range derivable therein.

In certain embodiments, the CpG-Ab immunoconjugate is administered at a dosage that ranges from about 1 microgram/kg body weight to about 500 milligram/kg body weight, including the end points. In other non-limiting examples, a dose may also comprise from about 1 microgram kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, about 1000 mg/kg body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments, the CpG-Ab conjugate is administered in three sequential doses, each dose of about 3 milligram/kg/body weight per administration. In particular embodiments, the CpG-Ab conjugate is administered in three sequential doses, each dose of about 10 milligram/kg/body weight per administration. In particular embodiments, the sequential doses are performed at 48-hour intervals.

As provided herein, the combination therapy involves the administration of two or more therapeutic agents. Such administration encompasses co-administration of these therapeutic agents in a substantially simultaneous manner, such as in a single formulation having a fixed ratio of active ingredients or in separate formulations (e.g., capsules and/or intravenous formulations) for each therapeutic agent. In addition, such administration also encompasses administration of each type of therapeutic agent simultaneously or sequentially. Such administration also encompasses each component being formulated as a separate formulation that can be administered at different locations or through different administration routes (e.g., intratumorally and/or systemically). In any case, the treatment regimen of the combination therapy can be determined by the responsible practitioner to provide beneficial effects in treating the conditions or disorders described herein.

In certain embodiments, the CpG-containing immunostimulating polynucleotide or CpG-Ab immunoconjugate is administered at about the same time as administration of the at least one additional cancer therapeutic agent. As non-limiting examples, administration of the CpG-containing immunostimulating polynucleotide or CpG-Ab immunoconjugate and the at least one additional cancer therapeutic agent can be simultaneous, such as within 30 minutes of one another, within 25 minutes of one another, within 20 minutes of one another, within 15 minutes of one another, within 10 minutes of one another, within 5 minutes of one another, or within 1 minute of one another.

In certain embodiments, the CpG-containing immunostimulating polynucleotide or CpG-Ab immunoconjugate is administered sequentially with the at least one additional cancer therapeutic agent. In some embodiments, the CpG-containing immunostimulating polynucleotide or CpG-Ab immunoconjugate is administered prior to the administration of the at least one additional cancer therapeutic agent. In some embodiments, the CpG-containing immunostimulating polynucleotide or CpG-Ab immunoconjugate is administered after the administration of the at least one additional cancer therapeutic agent. As non-limiting examples, administration of the CpG-containing immunostimulating polynucleotide or CpG-Ab immunoconjugate and the at least one additional cancer therapeutic agent can be separated for at least 30 minutes from one another, at least 1 hour from one another, at least 6 hours from one another, at least 12 hours from one another, at least 24 hours from one another, at least 36 hours from one another, at least 48 hours from one another, at least 3 days from one another, at least 1 week from one another, at least 2 weeks from one another, or at least 1 month from one another.

In certain embodiments, the CpG-containing immunostimulating polynucleotide is administered prior to administration of the immune checkpoint modulator. In such methods, the immune checkpoint modulator can be administered within 48 hours of administration of the CpG-containing immunostimulating polynucleotide, such as within at least or at least about or about or 5 minutes, 15 minutes, 30 minutes, 1 hour, 2 hours, 3 hours, 4 hours, 6 hours, 8 hours, 12 hours, 16 hours, 18 hours, 20 hours, 22 hours, 24 hours, 30 hours, 36 hours, 40 hours or 48 hours of administration of the CpG-containing immunostimulating polynucleotide. In some methods and uses, the CpG-containing immunostimulating polynucleotide is administered 6 hours to 30 hours or 12 hours to 24 hours, each inclusive, prior to administration of the immune checkpoint modulator. In certain embodiments, the immune checkpoint modulator can be administered within 3 days, 4 days, 5 days, 7 days, 2 weeks, 3 weeks, or 4 weeks of administration of the CpG-containing immunostimulating polynucleotide. The timing and order of administration can be empirically determined, if necessary, for particular immune checkpoint modulators. In these embodiments, the CpG-containing immunostimulating polynucleotide can be administered either in the free-standing form or as a CpG-Ab immunoconjugate.

In certain embodiments, both the CpG-containing immunostimulating polynucleotide and the immune checkpoint modulator are administered through a series of sequential doses. In particular embodiments, the first dose of the CpG-containing immunostimulating polynucleotide and the first dose of the immune checkpoint modulator are administered simultaneously, and the subsequent dose(s) of the CpG-containing immunostimulating polynucleotide and subsequent dose(s) of the immune checkpoint modulator are administered sequentially. In these embodiments, the CpG-containing immunostimulating polynucleotide can be administered either in the free-standing form or as a CpG-Ab immunoconjugate.

In certain embodiments, the CpG-containing immunostimulating polynucleotide is administered prior to administration of a T cell agonist. In such methods, the T cell agonist can be administered within 48 hours of administration of the CpG-containing immunostimulating polynucleotide, such as within at least or at least about or about or 5 minutes, 15 minutes, 30 minutes, 1 hour, 2 hours, 3 hours, 4 hours, 6 hours, 8 hours, 12 hours, 16 hours, 18 hours, 20 hours, 22 hours, 24 hours, 30 hours, 36 hours, 40 hours or 48 hours of administration of the CpG-containing immunostimulating polynucleotide. In some methods and uses, the CpG-containing immunostimulating polynucleotide is administered 6 hours to 30 hours or 12 hours to 24 hours, each inclusive, prior to administration of the T cell agonist. In certain embodiments, the T cell agonist can be administered within 3 days, 4 days, 5 days, 7 days, 2 weeks, 3 weeks, or 4 weeks of administration of the CpG-containing immunostimulating polynucleotide. The timing and order of administration can be empirically determined, if necessary, for particular T cell agonists. In these embodiments, the CpG-containing immunostimulating polynucleotide can be administered either in the free-standing form or as a CpG-Ab immunoconjugate.

In certain embodiments, both the CpG-containing immunostimulating polynucleotide and the T cell agonist are administered through a series of sequential doses. In particular embodiments, the first dose of the CpG-containing immunostimulating polynucleotide and the first dose of the T cell agonist are administered simultaneously, and the subsequent dose(s) of the CpG-containing immunostimulating polynucleotide and the subsequent dose(s) of the T cell agonist are administered sequentially. In these embodiments, the CpG-containing immunostimulating polynucleotide can be administered either in the free-standing form or as a CpG-Ab immunoconjugate.

Treatment of Autoimmune Diseases

Antagonizing TLR9 can help reducing the secretion of pro-inflammatory cytokines. Accordingly, immunosuppressive polynucleotides of the invention and their conjugates may be useful in the treatment of diseases characterized by the overexpression of pro-inflammatory cytokines (e.g., autoimmune diseases). Non-limiting examples of autoimmune disease are: psoriasis, rheumatoid arthritis, lupus, Guillain-Barre syndrome, vasculitis, myasthenia gravis, ankylosing spondylitis, hemolytic anemia, polyarteritis nodosa, idiopathic thrombocytopenic purpura, antiphospholipid antibody syndrome, primary biliary cirrhosis, Crohn's disease, ulcerative colitis, autoimmune hepatitis, scleroderma, dermatomyositis, and alopecia areata.

Pharmaceutical Compositions

Delivery of an immunomodulating polynucleotide can be achieved by contacting a cell with the immunomodulating polynucleotide or the conjugate using a variety of methods known to those of skill in the art. In particular embodiments, the immunomodulating polynucleotide or the conjugate of the invention may be formulated as a pharmaceutical composition including a pharmaceutically acceptable excipient and/or a pharmaceutically acceptable carrier. The pharmaceutical composition can be in a liquid or solid (e.g., lyophilized) form.

For human use, the immunomodulating polynucleotide or the conjugate of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers, excipients, and auxiliaries that facilitate processing the conjugate of the invention into preparations which can be used pharmaceutically.

Frequently used carriers or excipients include sugars (e.g., lactose, mannitol), milk protein, gelatin, starch, vitamins, cellulose and its derivatives, poly(ethylene glycol)s and solvents, such as sterile water, alcohols, glycerol, and polyhydric alcohols. Intravenous vehicles can include fluid and nutrient replenishers. Other pharmaceutically acceptable carriers include aqueous solutions, non-toxic excipients, including salts, preservatives, buffers and the like, as described, for instance, in *Remington: The Science and Practice of Pharmacy*, 21$^{st}$ Ed., Gennaro, Ed., Lippencott Williams & Wilkins (2005), and The United States Pharmacopeia: The National Formulary (USP 36 NF31), published in 2013. The pH and exact concentration of the various components of the pharmaceutical composition can be adjusted in accordance with routine practices in the art. See Goodman and Gilman's, the Pharmacological Basis for Therapeutics.

In making the pharmaceutical compositions of the invention, the active ingredient is typically mixed with an excipient (e.g., in lyophilized formulations) or diluted by an excipient. When the excipient serves as a diluent, it can be a solid, semisolid, or liquid material (e.g., phosphate-buffered saline), which acts as a vehicle, carrier, or medium for the active ingredient. Thus, the compositions can be in the form of tablets, powders, elixirs, suspensions, emulsions, solutions, and syrups. As is known in the art, the type of diluent can vary depending upon the intended route of administration. The resulting compositions can include additional agents, e.g., preservatives. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009). Preservatives can include antimicrobial agents, anti-oxidants, chelating agents, and inert gases.

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, 21$^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, a polynucleotide or conjugate can be milled to provide the appropriate particle size prior to combining with the other ingredients.

Route of Administration

The pharmaceutical compositions of the invention may be administered locally or systemically. The therapeutically effective amounts will vary according to factors, such as the extent of the diseases progression in a subject, the age, sex, and weight of the individual. Dosage regimens can be adjusted to provide the optimum therapeutic response. For example, several divided doses can be administered daily or the dose can be proportionally reduced as indicated by the exigencies of the therapeutic situation.

The pharmaceutical compositions of the invention may be administered to a patient in a variety of forms depending on the selected route of administration, as will be understood by those skilled in the art. The polynucleotides and/or conjugates used in the methods described herein may be administered, for example, by parenteral administration. Parenteral administration may include intramuscular, intravenous, intraarterial, intracranial, subcutaneous, intraorbital, intraventricular, intraspinal, intrathecal, intraperitoneal, rectal, and topical routes of administration. Topical route of administration may include transdermal, intradermal, buccal, and sublingual routes of administration. The pharmaceutical compositions are formulated according to the selected route of administration. Parenteral administration may be by continuous infusion over a selected period of time. The polynucleotides and/or conjugates desirably are administered with a pharmaceutically acceptable carrier. Pharmaceutical formulations of the polynucleotides and/or conjugates described herein formulated for treatment of the disorders described herein are also part of the present invention.

Formulations for Parenteral Administration

An immunomodulating (e.g., immunostimulating) polynucleotide and/or conjugate of the invention described herein can be administered to a patient in need thereof in a pharmaceutically acceptable parenteral (e.g., intravenous, intramuscular, or subcutaneous) formulation as described herein. The pharmaceutical formulation may also be administered parenterally (e.g., intravenously, intramuscularly, or subcutaneously) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the patient; and aqueous and non-aqueous sterile suspensions which may include suspending agents and thickening agents. For example, to prepare such a composition, an immunomodulating polynucleotide or conjugate of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer (e.g., phosphate buffered saline), 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation of the conjugate of the invention can be any one of the four general types of preparations identified by the USP-NF as suitable for parenteral administration:

(1) "Drug for Injection": the drug substance (e.g., the conjugate of the invention) as a dry (e.g., lyophilized) solid that will be combined with the appropriate sterile vehicle for parenteral administration as a drug injection;

(2) "Drug Injectable Emulsion": a liquid preparation of the drug substance (e.g., the conjugate of the invention) that is dissolved or dispersed in a suitable emulsion medium;

(3) "Drug Injectable Suspension": a liquid preparation of the drug substance (e.g., the conjugate of the invention) suspended in a suitable liquid medium; and (4) "Drug for Injectable Suspension": the drug substance (e.g the conjugate of the invention) as a dry solid that will be combined with the appropriate sterile vehicle for parenteral administration as a drug injectable suspension.

Exemplary formulations for parenteral administration include solutions of the polynucleotides and/or conjugates prepared in water suitably mixed with a surfactant, e.g., hydroxypropylcellulose. Dispersions can also be prepared in glycerol, liquid poly(ethylene glycol)s, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, $21^{st}$ Ed., Gennaro, Ed., Lippencott Williams & Wilkins (2005) and in The United States Pharmacopeia: The National Formulary (USP 36 NF31), published in 2013.

Biocompatible, biodegradable lactide polymer, lactide/glycolide copolymer, or polyoxyethylene-polyoxypropylene copolymers may be used to control the release of the polynucleotide and/or conjugate. Other potentially useful parenteral delivery systems for polynucleotides and/or conjugates include ethylene-vinyl acetate copolymer particles, osmotic pumps or implantable infusion systems. The parenteral formulation can be formulated for prompt release or for sustained/extended release of the polynucleotides and/or conjugates. Exemplary formulations for parenteral release of a polynucleotide or conjugate include: aqueous solutions, powders for reconstitution, cosolvent solutions, oil/water emulsions, suspensions, microspheres, and polymeric gels.

The following examples are meant to illustrate the invention. They are not meant to limit the invention in any way.

EXAMPLES

Example 1. Synthesis and Purification of the Nucleotides and Polynucleotides

Exemplary syntheses of immunomodulating polynucleotides and precursors therefor are described below.

Precursors

Precursors useful in the preparation of the polynucleotides of the invention are provided in WO 2015/188197 (e.g., phosphoramidites, targeting moieties, and bioreversible groups containing PEG chains).

Phosphoramidites and Other Monomers

Nucleoside-containing intermediates useful in the synthesis of polynucleotides of the invention are disclosed in WO 2015/188197 (e.g., compounds U1-U54, A1-A15, C1-9, and G1-G12 in WO 2015/188197).

Commercially available phosphoramidites were purchased from Glen Research (Sterling, Va.) or ChemGenes (Wilmington, Mass.). When required, other phosphoramidtes were prepared from appropriately protected nucleosides using standard reaction conditions described here are elsewhere. Compound S61B

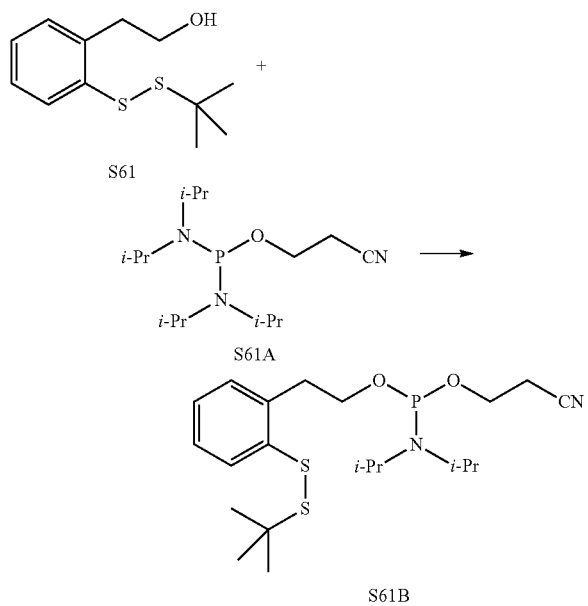

To a solution of S61 (0.48 g, 2.0 mmol) in DCM (5.0 mL) were added S61A (0.60 g, 2.0 mmol) and ETT (0.25 M in acetonitrile, 4.8 mL, 1.2 mmol). The mixture was stirred for 2 h. Evaporation of the volatiles afforded a residue, which was subjected to flash silica gel column purification using ethylacete/hexane (0-30% gradient on Combi Flash Rf instrument) to give compound S61 B as colorless oil (0.49 g, 55%). $^{31}$P NMR (202 MHz, CDCl$_3$; ppm): δ147.83 (s).

Compound S108

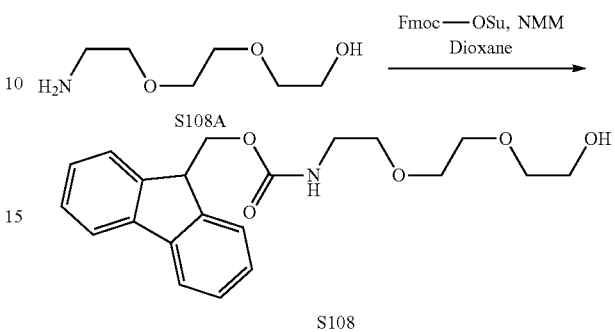

To a stirring mixture of 2-[2-(2-aminoethoxy)ethoxy]ethanol (S108A, 25.0 g, 167 mmol) and N-methyl morpholine (21.0 mL, 191 mmol) in dioxane (100 mL) was added dropwise a solution of Fmoc-OSu (62.2 g, 184 mmol) in dioxane (50 mL). After stirring overnight, the reaction was concentrated in vacuo to afford a light yellow oil. The crude was re-dissolved in EtOAc and washed with sat. NaHCO$_3$ (aq.) and brine. The organic layer was removed in vacuo to afford an oil, which was purified by SiO$_2$ chromatography to provide the FmocNH-PEG2-OH (S108, 55 g, 88% yield). ESI+ m/z calcd 371.4, found 372.2 [M+H]$^+$.

X1 and X2 Abasic Spacer Synthesis—General Scheme:

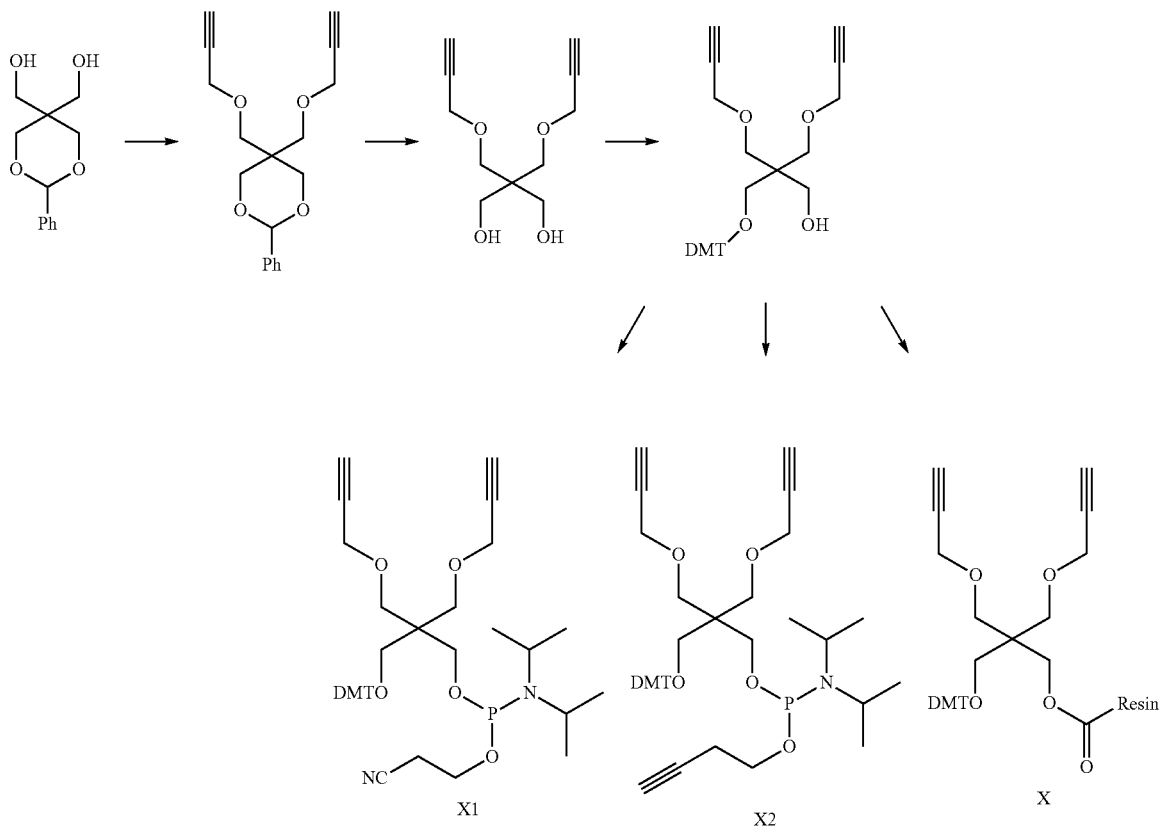

Compound S110

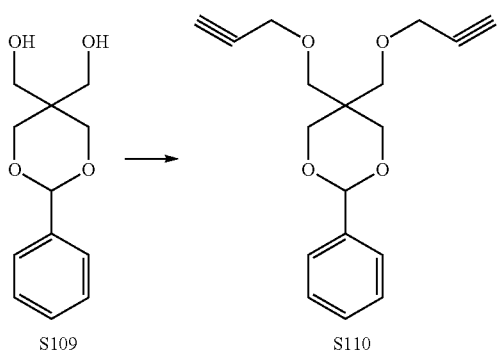 [SMILES: OCC1(CO)COC(c2ccccc2)OC1 ; C#CCOCC1(COCC#C)COC(c2ccccc2)OC1 ; "S109" ; "S110"]

To a suspension of NaH (13.2 g, 60% in mineral oil, 230.0 mmol) in THF (40 mL) under argon at 0° C. was added a solution of diol (S109, 4.92 g, 22.0 mmol) in THF (20 mL) dropwise; the resulting mixture was warmed to room temperature and stirred for 1 h. The reaction mixture was cooled to 0° C., a solution of propargyl bromide (18.6 g, 158.4 mmol) in THF (25 mL) was added slowly, and the resulting mixture was warmed to room temperature and stirred overnight at 40° C. After the product was consumed, as observed by TLC, the reaction was quenched by dropwise addition of water at 0° C., and the resulting mixture was extracted with dichloromethane (50 mL×2). The combined organic layers were washed with brine and dried over anhydrous $Na_2SO_4$, filtered, and evaporated to give a residue, which was purified by flash silica gel column using ISCO companion (hexane/ethyl acetate, 0-30%) to give 5.92 g (89.5%) of compound S110 as an oil. $^1$H NMR (500 MHz, $CDCl_3$, ppm): δ7.49-7.47 (dd, J 8.0, 1.5 Hz, 2H), 7.38-7.34 (m, 3H), 5.43 (s, 1H), 4.21 (d, J 2.5 Hz, 2H), 4.12 (t, J 2.5 Hz, 4H), 4.10 (s, 1H), 3.91 (s, 1H), 3.89 (s, 1H), 3.37 (s, 2H); ESI MS for $C_{18}H_{20}O_4$ calculated 300.34, observed [M+H]$^+$ 301.3.

Compound S111

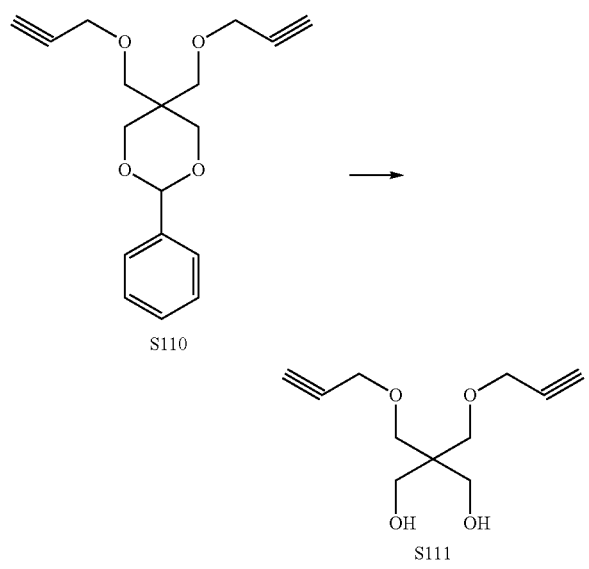

Bis-propargyl compound S110 (5.9 g, 19.64 mmol) was dissolved in acetic acid/water mixture (60 mL, 75:25), and the reaction was continued at 50° C. for 2 h. After completion of the reaction, the solution was evaporated and co-evaporated with toluene (2×20 mL). The residue was purified directly without any workup using the flash silica gel column using ISCO companion (hexane/ethyl acetate, 20-80%) to give 3.02 g (72.5%) of the compound S111 as an oil. $^1$H NMR (500 MHz, $CDCl_3$, ppm): δ4.15 (d, J 2.5 Hz, 4H), 3.68 (s, 4H), 3.59 (s, 4H), 2.44 (t, J 2.5 Hz, 2H), 2.30-2.40 (br, 2H); ESI MS for $C_{11}H_{16}O_4$ calculated 212.24, observed [M+H]$^+$ 213.2.

Compound S112

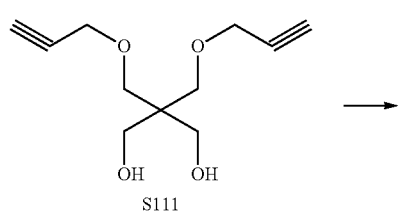

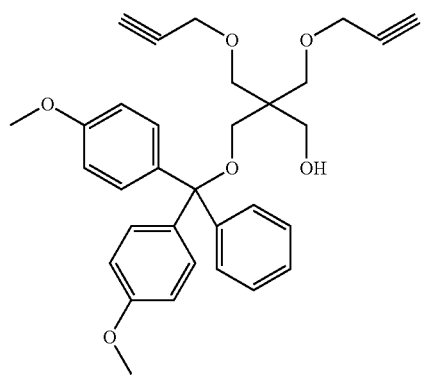

To a solution of diol S111 (3.0 g, 14.2 mmol), N,N-diisopropylethylamine (3.15 mL, 17.0 mmol), and DMAP (0.36 g, 2.83 mmol) in dichloromethane (25 mL) at 0° C. was added dropwise a solution of dimethoxytrityl chloride (4.8 g, 14.2 mmol) in dichloromethane (40 mL), and the reaction continued at room temperature overnight. The mixture was diluted with dichloromethane and washed with water followed by brine, and the organic layers were dried over anhydrous $Na_2SO_4$, filtered, and evaporated. The resulting residue was purified by flash silica gel column using ISCO companion (hexane/ethyl acetate, 0-40%) to give 5.29 g (73%) of the mono DMT protected compound S112 as white solid. $^1$H NMR (500 MHz, $CDCl_3$, ppm): δ7.4-7.42 (m, 2H), 7.32-7.31 (m, 4H), 7.28-7.25 (m, 2H), 6.84-6.81 (m, 4H), 4.09 (d, J 2.5 Hz, 4H), 3.79 (s, 6H), 3.67 (d, J 6.0 Hz, 2H), 3.64-3.56 (m, 4H), 3.13 (s, 2H), 2.39 (t, J 2.5 Hz, 2H); ESI MS for $C_{32}H_{34}O_6$ calculated 514.6, observed [M+Na]$^+$ 537.4, Compound S113

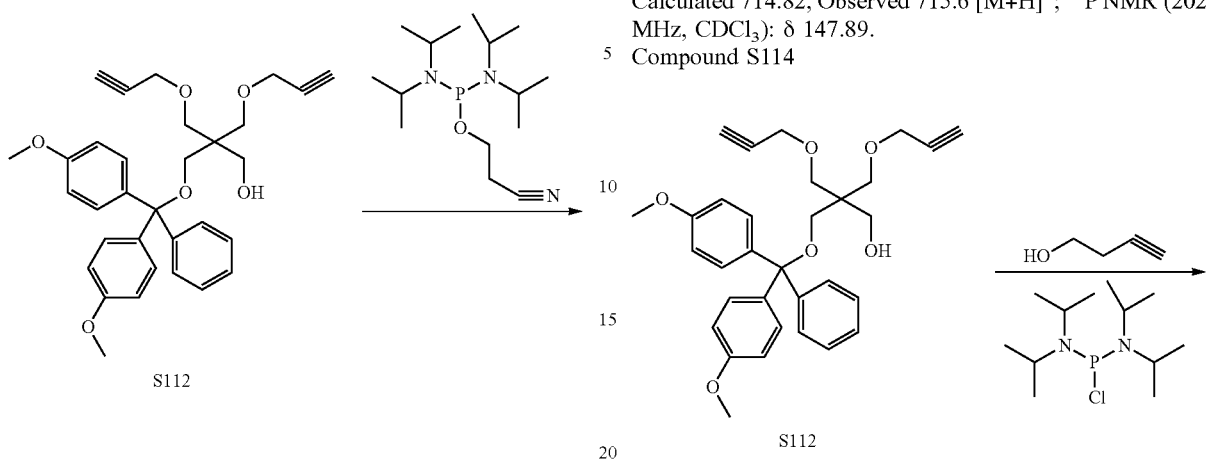

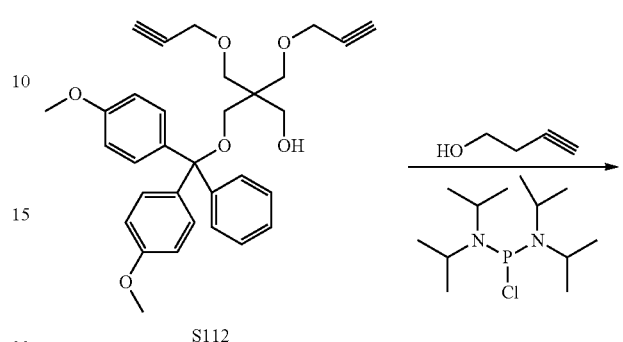

gradient on Combi Flash Rf Instrument) to give 0.53 g of compound S113 (75%) as an oil. ESI MS for $C_{41}H_{51}N_2O_7P$ Calculated 714.82, Observed 715.6 [M+H]+; $^{31}$P NMR (202 MHz, CDCl₃): δ 147.89.

Compound S114

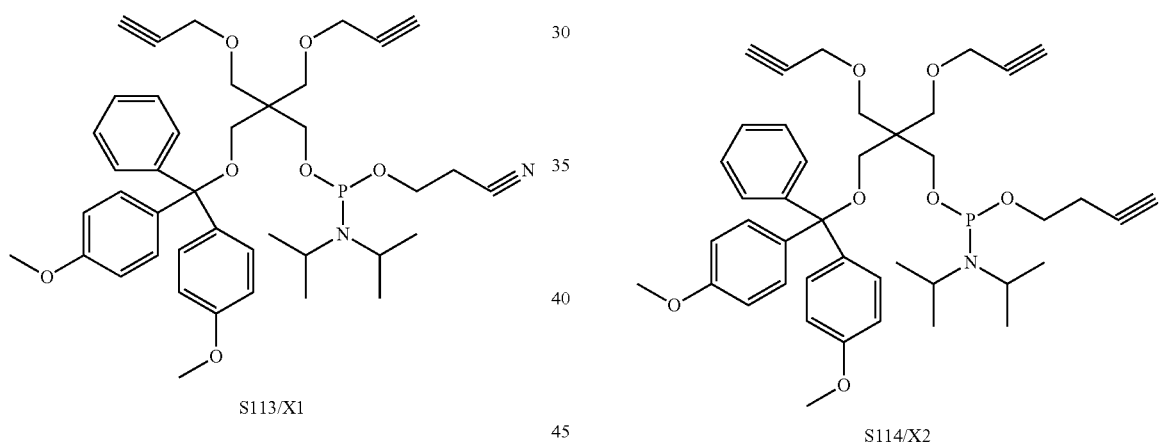

To a solution of DMT-protected compound S112 (0.5 g, 0.98 mmol) in dichloromethane (4 mL) was added dropwise a solution of 2'-cyanoethyl-N,N,N',N'-tetraisopropyl phosphoramidite (0.58 g, 1.95 mmol) in dichloromethane (3 mL) at room temperature followed by 5-benzylthio-1H-tetrazole (BTT; 0.25 M solution in acetonitrile, 0.78 mL, 0.18 mmol) under argon atmosphere. The reaction was continued until the starting material disappeared (2 h), and the crude mixture was diluted with 20 mL of dichloromethane, washed sequentially with saturated NaHCO₃ solution (10 mL) and brine (10 mL), and dried over anhydrous Na₂SO₄. The solvent was evaporated in vacuo, and the crude mixture was purified by silica gel column chromatography using ethyl acetate/hexane having 3% triethylamine as a co-solvent (0-30%

To a −78° C. solution of DMT-protected compound S112 (0.98 g, 1.9 mmol) and N,N-diisopropylethylamine (0.39 mL, 2.09 mmol) in 8.0 mL of dry dichloromethane under argon atmosphere was added dropwise a dichloromethane (4.0 mL) solution of bis-(N,N-diisopropylamino)-chlorophosphine (0.56 g, 2.09 mmol). The reaction mixture was allowed to warm to room temperature while stirring was maintained for 1 h. A solution of 3-butyne-1-ol (0.14 g, 1.9 mmol) in 2.0 mL of dry dichloromethane was added at room temperature; the resulting mixture was stirred for 10 minutes, at which time a 0.25M solution of ETT in acetonitrile (4.6 mL, 1.15 mmol) was added, and stirring continued for an additional 3 h. After completion of the reaction, as observed by the disappearance of the starting material by TLC, the crude mixture was diluted with 20 mL of dichloromethane and washed sequentially with saturated NaHCO$_3$ solution (10 mL) and brine (10 mL) and dried over anhydrous Na$_2$SO$_4$. The volatiles were evaporated in vacuo, and the crude mixture was purified by silica gel column chromatography using ethyl acetate/hexane with 3% triethylamine as solvent system (0-40% gradient on Combi Flash Rf Instrument) to give 0.33 g of compound S114 (25%) as an oil. ESI MS for C$_{42}$H$_{52}$NO$_7$P Calculated 713.83, Observed 714.7 [M+H]$^+$; $^{31}$P NMR (202 MHz, CDCl$_3$): δ146.89.

X3 and X4 Abasic Spacer Synthesis—General Scheme:

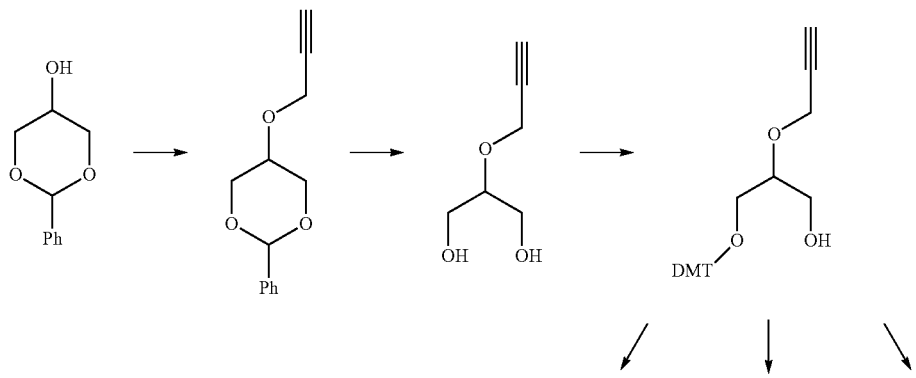

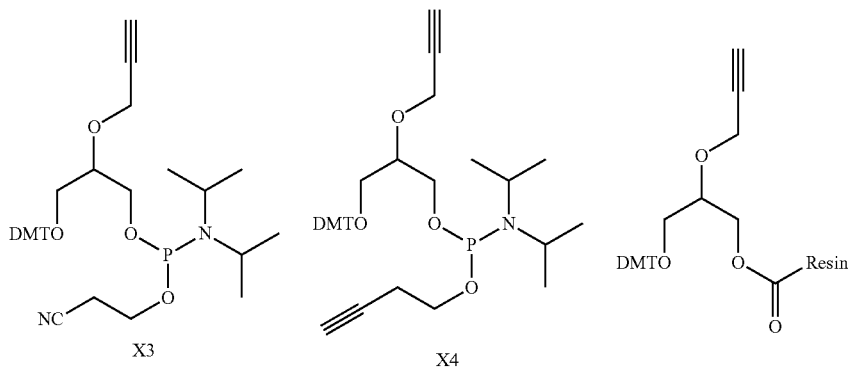

Compound S116

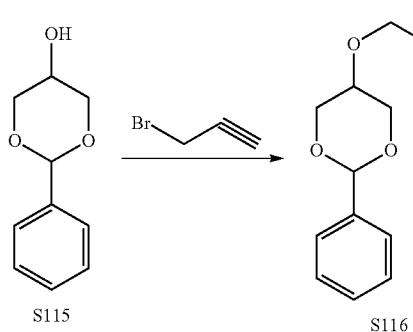

Compound S116 was prepared using the protocol described for compound S110 in 91% yield as oil. $^1$H NMR (500 MHz, CDCl$_3$, ppm): δ7.51 (d, J 7.5 Hz, 2H), 7.37-7.32 (m, 3H), 5.56 (s, 1H), 3.37-3.35 (m, 4H), 4.10-4.07 (dd, J 13.0 Hz, J 2.5 Hz, 2H), 3.65-3.64 (m, 1H), 2.43-2.42 (t, J 6.5 Hz, 1H); ESI MS for C$_{13}$H$_4$O$_3$ calculated 218.24, observed [M+H]$^+$ 219.2.

Compound S117

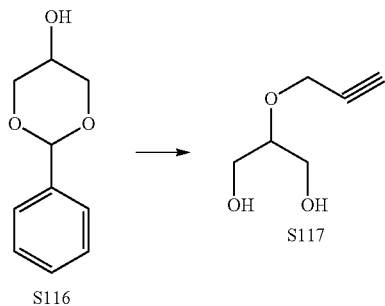

Compound S117 was prepared using the protocol described for compound S111 in 91% yield as oil. $^1$H NMR (500 MHz, CDCl$_3$, ppm): δ4.33 (s, 2H), 3.83-3.70 (m, 5H), 2.48 (s, 1H), 2.04 (br, 2H); ESI MS for C$_6$H$_{10}$O$_3$ calculated 130.14, observed [M+Na]$^+$ 153.0.

Compound S118

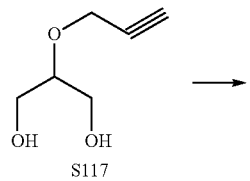

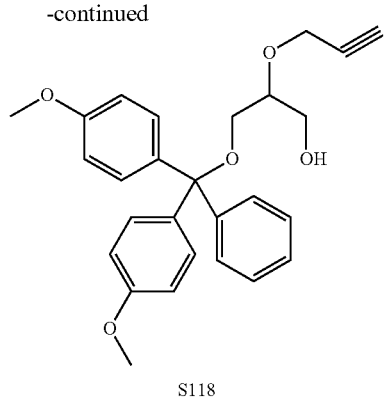

Compound S118 was prepared using the protocol described for compound S112 in 54% yield as a white solid. $^1$H NMR (500 MHz, CDCl$_3$, ppm): δ7.43 (d, J 7.5 Hz, 2H), 7.37-7.27 (m, 5H), 7.23-7.16 (m, 2H), 6.83 (d, J 9.0 Hz, 3H), 6.78-6.76 (dd J 8.5 Hz, 1H), 4.35-4.22 (m, 2H), 3.77 (s, 6H) 3.76-3.72 (m, 2H), 3.71-3.64 (m, 1H), 3.27-3.19 (m, 2H), 2.48 (t, J 4.5 Hz, 1H), 2.03-1.96 (m, 1H); ESI MS for C$_{27}$H$_{28}$O$_5$ calculated 432.50, observed [M+Na]$^+$ 455.4.

Compound S119

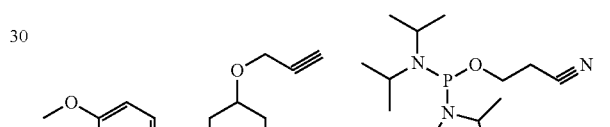

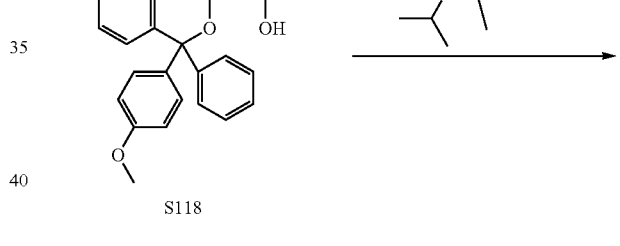

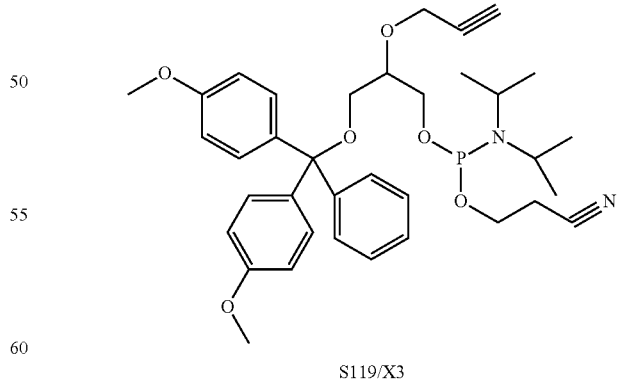

Compound S119 was prepared using the protocol described for compound S113 in 86% yield as oil. ESI MS for C$_{36}$H$_{45}$N$_2$O$_6$P Calculated 432.72, Observed 433.5 [M+H]$^+$; $^{31}$P NMR (202 MHz, CDCl$_3$): δ149.05, 148.96.

Compound S120
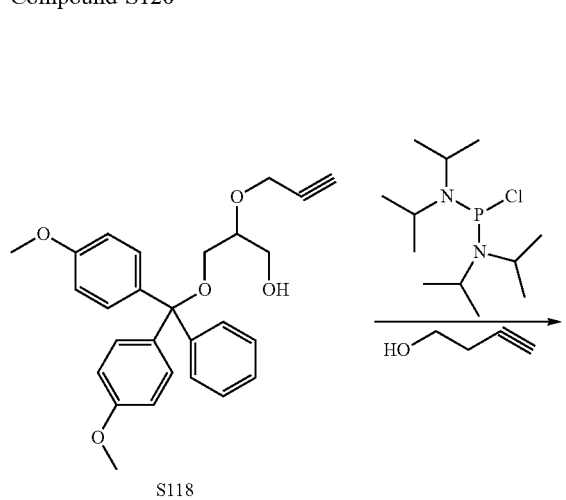
S118
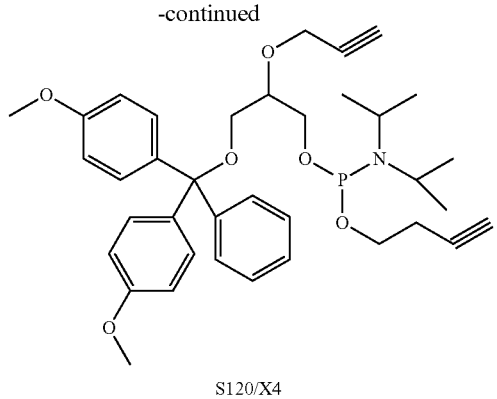
S120/X4
Compound S120 was prepared using the protocol described for compound S114 in 47% yield as oil. ESI MS for $C_{37}H_{46}NO_6P$ Calculated 431.73, Observed 432.5 $[M+H]^+$; $^{31}P$ NMR (202 MHz, $CDCl_3$): $\delta$147.80, 147.71.
X5 and X6 Abasic Spacer Synthesis—General Scheme:
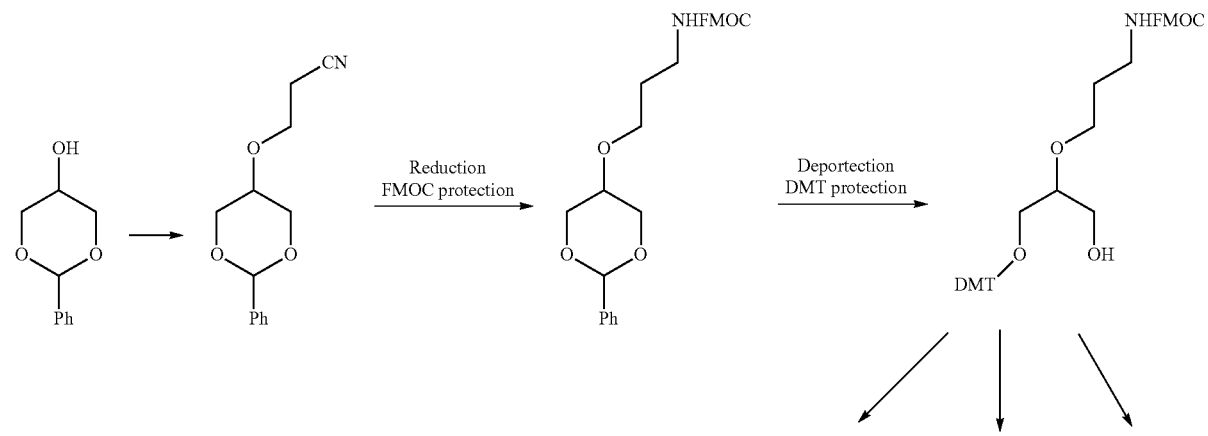
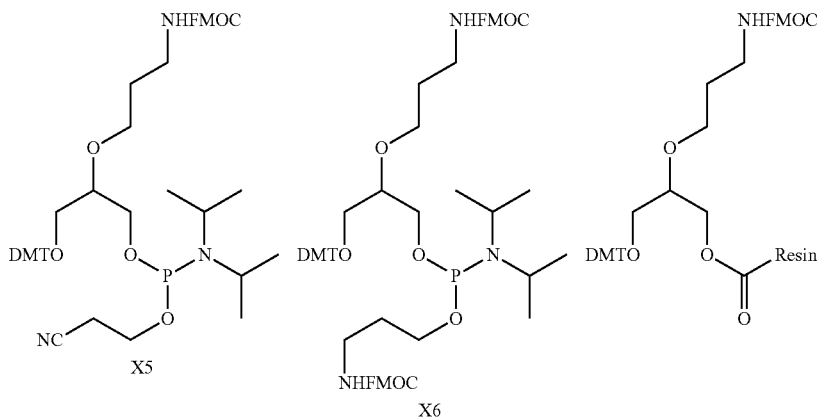

Compound S121

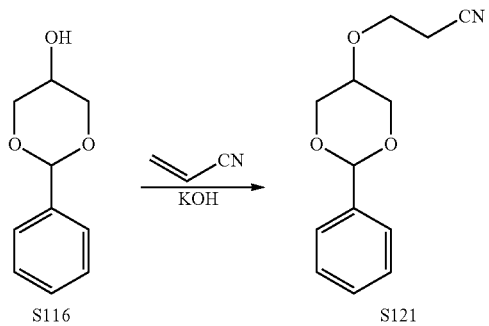

To a solution of S116 (4.0 g, 22.2 mmol) in dioxane (25 mL) was added a solution of KOH (0.12 g, 2.2 mmol) dissolved in minimum amount of water, and the resulting mixture was stirred for at least 30 minutes at room temperature. The mixture was cooled to 0° C., a solution of acrylonitrile (2.35 g, 44.4 mmol) in dioxane (15 mL) was added dropwise, and the resulting mixture was allowed to react at room temperature for overnight. Volatiles were evaporated in vacuo, the residue was diluted with water, and the pH was adjusted to near neutral. The crude product was extracted with ethyl acetate (2×50 mL), and the combined organic layers were washed with brine and dried over anhydrous $Na_2SO_4$, filtered, and evaporated to give a residue, which was purified by flash silica gel column using ISCO companion (dichloromethane/methanol, 0-5%) to give 3.1 g (60%) of the compound S121 as white solid. $^1$H NMR (500 MHz, $CDCl_3$, ppm): δ7.49 (d, J 7.0 Hz, 2H), 7.36-7.34 (m, 3H), 5.56 (s, 1H), 3.36 (d, J 13.0 Hz 2H), 4.10-4.07 (dd, J 13.0 Hz, J 2.0 Hz, 2H), 3.84 (t, J 6.5 Hz, 2H), 3.42 (m, 1H), 3.69 (t, J 6.5 Hz, 2H); ESI MS for $C_{13}H_{15}NO_3$ calculated 233.2, observed [M+Na]$^+$ 256.3.

Compound S122

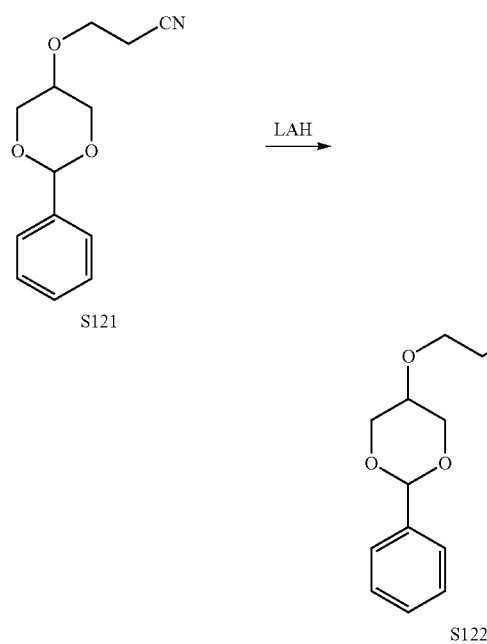

To a suspension of lithium aluminum hydride (0.83 g, 4.0 mmol) in THF (10 mL) at 0° C. was added dropwise a solution of compound S121 (1.28 g, 5.5 mmol) in THF (15 mL), the resulting mixture was warmed to room temperature, and stirring was continued for 3 h. After completion of the reaction, the reaction mixture was cooled to 0° C. and quenched by dropwise addition of water as required (ca. 2-3 mL). Additional ca. 8 mL of water were added, and the crude product was extracted into ethyl acetate (2×25 mL). The combined organic layers were washed with brine, dried over anhydrous $Na_2SO_4$, filtered, and evaporated to give compound S122, which was used in the subsequent step without further purification. $^1$H NMR (500 MHz, $CDCl_3$, ppm): δ7.49 (d, J 7.0 Hz, 2H), 7.40-7.32 (m, 3H), 5.55 (d, J 5.0 Hz, 1H), 4.34 (d, J 13.0 Hz, 1H), 4.20-4.11 (dd, J 12.0 Hz 4H), 4.05-4.03 (d, J 13.0 Hz, J 2.0 Hz, 1H), 3.66-3.62 (m, 2H), 3.27 (m, 1H), 2.86 (t, J 6.5 Hz, 1H), 2.16 (br, 2H); ESI MS for $C_{13}H_{19}NO_3$ calculated 237.2, observed [M+H]$^+$ 238.2.

Compound S123

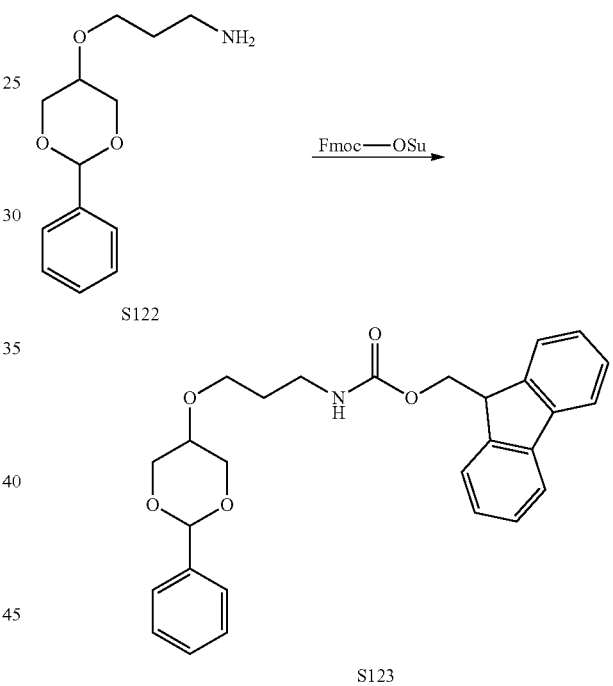

To compound S122 (1.0 g, 4.2 mmol) and N,N-diisopropylethylamine (2.3 mL, 12.6 mmol) in dichloromethane (8 mL) at 0° C. was added dropwise a solution of Fmoc-OSu (1.7 g, 5.0 mmol), and the resulting mixture was allowed to react at room temperature for 3 h. After completion, the reaction mixture was diluted with dichloromethane (10 mL) and washed with water followed by brine. The organic layer was separated, dried over anhydrous $Na_2SO_4$, filtered, and evaporated to give a residue. The residue was purified by flash silica gel column using ISCO companion (hexane/ethyl acetate, 0-50%) to give 0.65 g (35%) of the compound S123 as a white solid. $^1$H NMR (500 MHz, $CDCl_3$, ppm): δ7.75 (d, J 7.5 Hz, 2H), 7.58 (d, J 7.5 Hz, 2H), 7.51 (d, J 7.5 Hz, 2H), 7.37 (t, J 7.5 Hz, 2H), 7.31-7.26 (m, 5H), 5.57 (s, 1H), 5.48 (br, 1H), 4.46-4.32 (m, 4H), 4.15 (d, J 7.0 Hz, 1H), 4.06 (t, J 12.5 Hz 2H), 3.67 (m, 2H), 3.54 (m, 2H), 3.41 (s, 1H), 1.88 (t, J 6.0 Hz, 2H); ESI MS for $C_{28}H_{29}NO_5$ calculated 459.5, observed [M+Na]$^+$ 482.5.

Compound S124

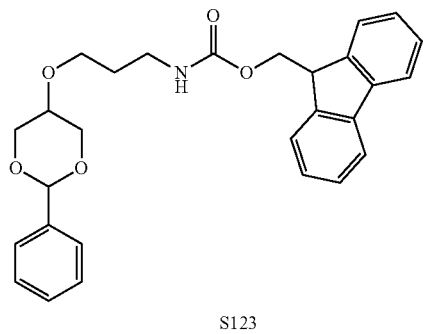

Compound S125

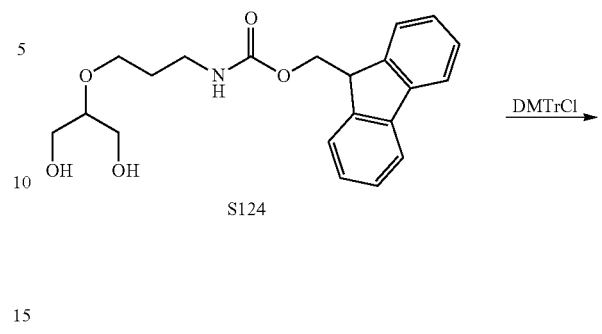

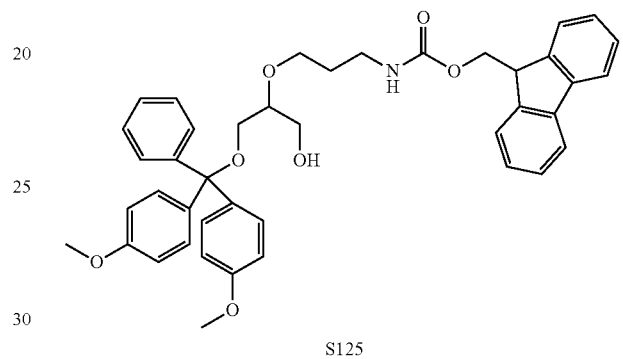

Compound S124 was prepared using the protocol described for compound S111 with quantitative yields as an oil. $^1$H NMR (500 MHz, CDCl$_3$, ppm): δ7.76 (d, J 7.5 Hz, 2H), 7.58 (d, J 7.5 Hz, 2H), 7.39 (t, J 7.5 Hz, 2H), 7.32 (t, J 7.5 Hz, 2H), 5.18 (br, 1H), 4.44 (d, J 6.5 Hz, 2H), 4.21 (t, J 6.5 Hz, 1H), 4.76-4.73 (dd, J 11.5, 3.5 Hz 2H), 3.67-60 (m, 4H), 3.42 (m, 1H), 3.37 (br, 2H), 2.07 (m, 2H), 1.75 (br, 2H); ESI MS for C$_{21}$H$_{25}$NO$_5$ calculated 371.4, observed [M+Na]$^+$ 394.3.

Compound S125 was prepared using the protocol described for compound S112 with 48% of product (S125) yield as a white solid. $^1$H NMR (500 MHz, CDCl$_3$, ppm): δ7.75 (t, J 7.5 Hz, 2H), 7.58 (t, J 7.5 Hz, 2H), 7.40-7.38 (m, 3H), 7.32-27 (m, 7H), 7.18-7.16 (m, 3H), 6.83 (t, J 7.0 Hz, 4H), 5.16 (br, 1H), 4.44 (d, J 6.5 Hz, 2H), 4.20 (m, 1H), 3.80 (s, 3H), 3.79 (m, 1H), 3.76 (s, 3H), 3.74 (m, 2H), 3.66-3.62 (m, 4H), 3.43-3.37 (m, 2H), 2.31 (br, 1H), 1.76 (br, 2H); ESI MS for C$_{42}$H$_{43}$NO$_7$ calculated 673.7, observed [M+Na]$^+$ 696.7.

Compound S126

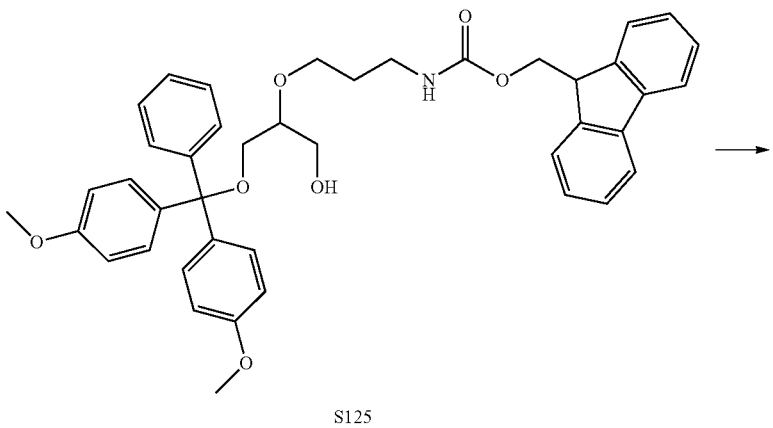

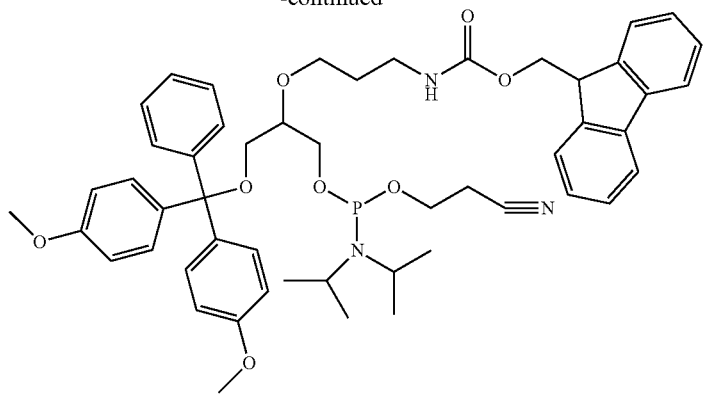
S126/X5
Compound S126 was prepared using the protocol described for compound S113 with 78% of product (S126) yield as an oil. ESI MS for $C_{51}H_{60}N_3O_8P$ Calculated 874.0, Observed 896.9 [M+Na]$^+$, 913.0 [M+K]$^+$; $^{31}$P NMR (202 MHz, CDCl$_3$, ppm): δ148.90, 148.76.
Synthesis of Abasic Spacer S131—General Scheme:
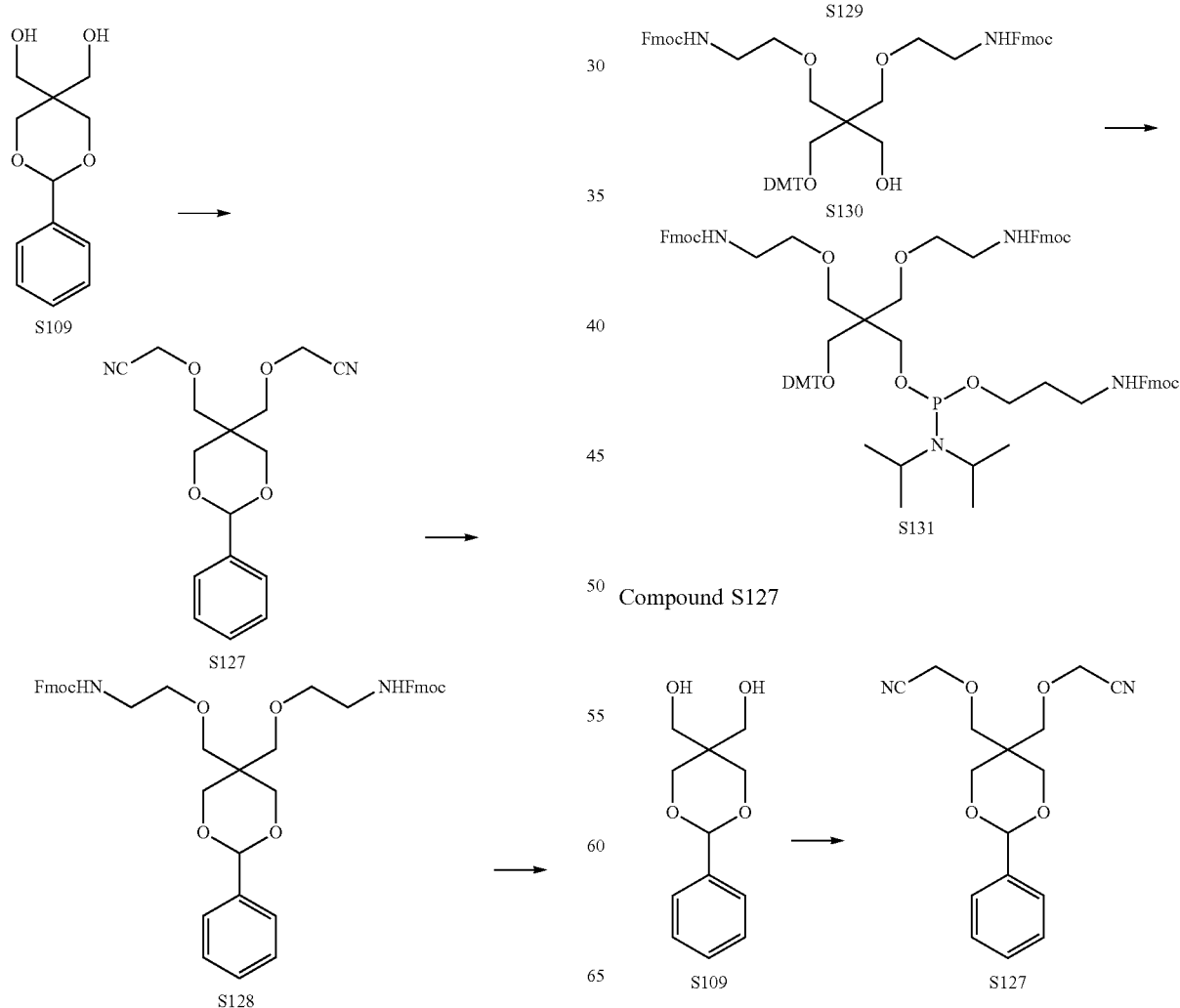
Compound S127

To a solution of S109 (2.56 g, 11.4 mmol) in dichloromethane (50 mL) under argon were added bromoacetonitrile (3.01 g, 25.1 mmol), silver(I) oxide (5.28 g, 22.8 mmol), and tetrabutylammonium iodide (0.84 g, 2.28 mmol), and the resulting mixture was stirred overnight. The mixture was filtered over Celite®, and the filtrate was evaporated to give a black residue, which was subjected to flash silica gel column purification on ISCO companion (hexane/ethyl acetate, 15-90%) to give 1.34 g (39%) of the desired compound S127 as a viscous oil. ESI MS for $C_{16}H_{18}N_2O_4$ calculated 302.3, observed [M+H]$^+$ 303.3.

Compound S128

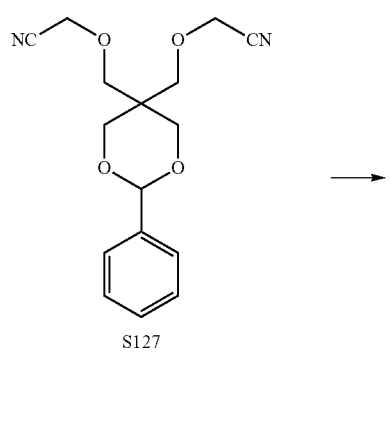

S127

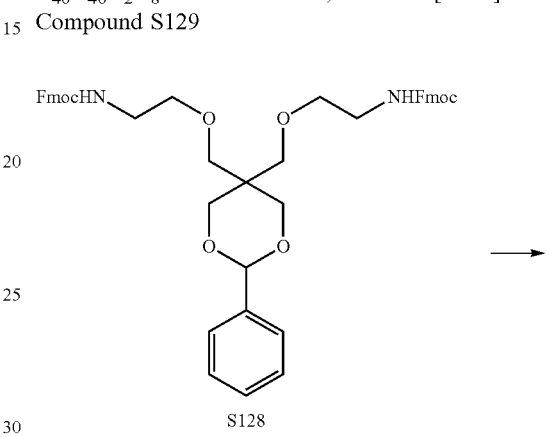

S128

To a solution of compound S127 (1.34 g, 4.43 mmol) in THF (30 mL) was added a solution of LiAlH$_4$ in THF (2M, 8.9 mL, 17.7 mmol) under argon, and the mixture was heated to 55° C. for 4 h. Another portion of LiAlH$_4$ in THF (2M, 4 mL, 8.0 mmol) was added, and the stirring continued for 4 h. After completion of the reaction, the mixture was cooled to room temperature and quenched with Na$_2$SO$_4$·10H$_2$O. The solid was filtered off and washed with ethyl acetate. The filtrate was dried over anhydrous Na$_2$SO$_4$. The mixture was filtered and evaporated to give a residue, which was dissolved in dichloromethane (20 mL). To this solution were added Fmoc-OSu (1.5 g, 4.43 mmol) and DIEA (0.87 mL, 5.0 mmol). The mixture was stirred for 1 h, then evaporated to give a residue, which was subjected to flash silica gel column purification on a ISCO companion (hexane/ethyl acetate, 20-90%) to give 1.04 g (31%) of the compound S128 as a white foam. $^1$H NMR (500 MHz, CDCl$_3$, ppm): δ7.75 (4H, dd, J 7.5, 4.5 Hz), 7.58 (4H, t, J 7.0 Hz), 7.48 (2H, d, J 7.0 Hz), 7.41-7.34 (7H, m), 7.32-7.26 (4H, m), 5.44 (1H, s), 5.15-5.05 (2H, m), 4.44 (2H, d, J 5.5 Hz), 4.38 (2H, d, J 6.0 Hz), 4.25-4.15 (2H, m), 4.10 (2H, d, J 11.5 Hz), 3.82 (2H, d, J 11.5 Hz), 3.78 (2H, s), 3.53 (2H, s), 3.42 (2H, s), 3.36-3.27 (4H, m), 3.25 (2H, s); ESI MS for $C_{46}H_{46}N_2O_8$ calculated 754.9, observed [M+H]$^+$ 755.3.

Compound S129

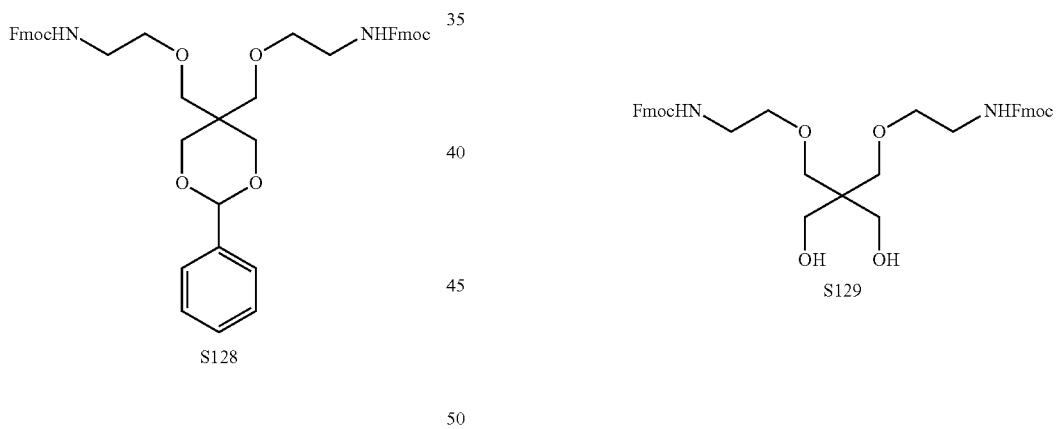

S129

Compound S128 (1.1 g, 1.51 mmol) was dissolved in AcOH/H$_2$O mixture (10 mL, 3:1), and the reaction was continued at 55° C. for 5 h. After completion of the reaction, the volatiles were evaporated and co-evaporated with toluene (2×20 mL), and the residue was subjected to flash silica gel column purification on a ISCO companion (hexane/ethyl acetate, 30-100%) to give 0.54 g (54%) of the compound S129 as white foam. $^1$H NMR (500 MHz, CDCl$_3$, ppm): δ7.75 (4H, d, J 7.5 Hz), 7.58 (4H, d, J 7.5 Hz), 7.39 (4H, t, J 7.5 Hz), 7.30 (4H, t, J 7.5 Hz), 5.20-5.05 (2H, m), 4.41 (4H, d, J 6.5 Hz), 4.21 (4H, t, J 6.5 Hz), 3.64 (4H, s), 3.48 (8H, s), 3.36 (4H, s); ESI MS for $C_{39}H_{42}N_2O_8$ calculated 666.7, observed [M+H]$^+$ 667.3.

Compound S130

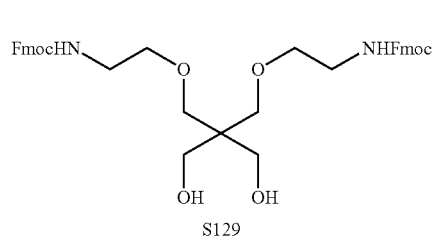

Compound S131

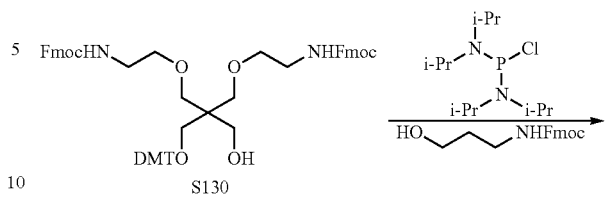

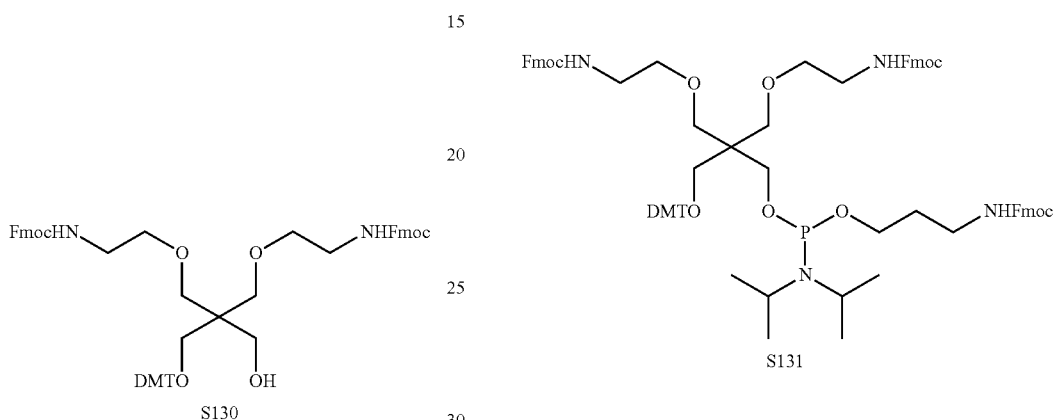

To a solution of diol S129 (0.73 g, 1.1 mmol), DIPEA (0.19 mL, 1.1 mmol) and DMAP (0.013 g, 0.11 mmol) in dichloromethane (6 mL) at 0° C. was added a solution of DMTrCl (0.34 g, 0.99 mmol) in dichloromethane (1 mL) dropwise. The resulting mixture was warmed to room temperature and stirred overnight. the mixture was evaporated to give a residue, which was subjected to flash silica gel column purification on a ISCO (hexane/ethyl acetate, 20-100%) to give 0.47 g (44%) of the mono dimethoxytrityl protected compound S130 as a white foam. $^1$H NMR (500 MHz, CDCl$_3$, ppm): δ7.75 (4H, d, J 7.5 Hz), 7.58 (4H, d, J 7.5 Hz), 7.39 (4H, t, J 7.5 Hz), 7.32-7.25 (8H, m), 7.17 (4H, d, J 6.5 Hz), 6.83 (4H, d, J 6.5 Hz), 5.20-5.05 (2H, m), 4.41 (4H, d, J 6.5 Hz), 4.21 (4H, t, J 6.5 Hz), 3.82 (6H, s), 3.64 (4H, s), 3.48 (8H, s), 3.36 (4H, s); ESI MS for C$_{60}$H$_{60}$N$_2$O$_{10}$ calculated 969.1, observed [M+Na]$^+$ 991.3.

A solution of bis-(N,N-disiopropylamino)-chlorophosphine (0.085 g, 0.32 mmol) in dry CH$_2$Cl$_2$ (1.0 mL) were added dropwise to a solution of 3-Fmoc-amino-propan-1-ol (0.090 g, 0.30 mmol) and N,N-diisopropylethylamine (0.18 mL, 1.05 mmol) in dry CH$_2$Cl$_2$ (3.0 mL) at −78° C. The reaction mixture was warmed to room temperature and stirred for 1.5 h. A solution of compound S130 (0.30 g, 0.30 mmol) in 1.0 mL of dry CH$_2$Cl$_2$ was added, and the resulting mixture was stirred for 10 min. A solution of ETT (0.72 mL, 0.25M in acetonitrile, 0.18 mmol) was added to the reaction mixture, and the resulting mixture was stirred for 3 h. The mixture was diluted with CH$_2$Cl$_2$ (20 mL) and washed with saturated aqueous sodium bicarbonate (20 mL) and brine (20 mL). The organic layer was dried over anhydrous sodium sulfate, and the filtrate was evaporated in vacuum to afford a residue, which was subjected to flash silica gel column purification on a ISCO companion using ethyl acetate/hexane with 3% triethylamine as a co-solvent system (0-30% gradient) to give 0.12 g of product S131 (32%) as a white foam. ESI MS for C$_{84}$H$_{91}$N$_4$O$_{13}$P Calculated 1395.6, Observed 1395.7[M]$^+$; $^{31}$P NMR (202 MHz, CDCl$_3$): δ146.41.

Compound dT4

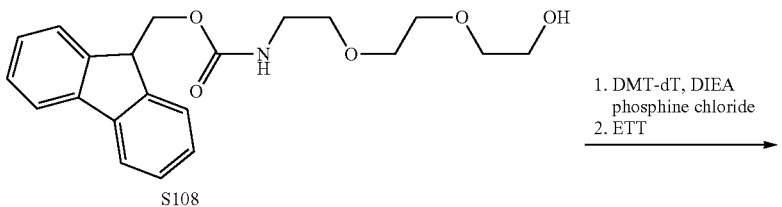

1. DMT-dT, DIEA phosphine chloride
2. ETT

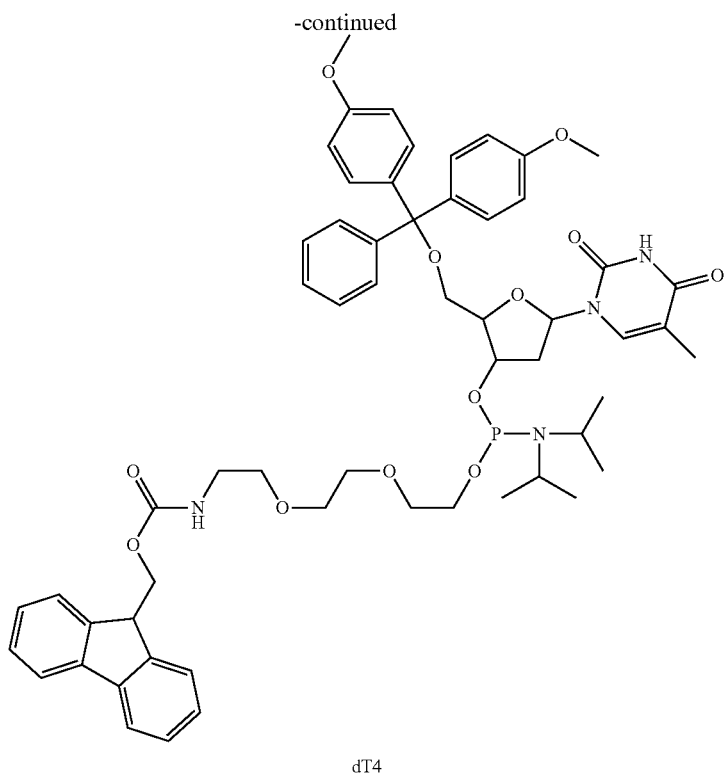

dT4

Synthesis of FmocNH-PEG2-hydroxyl-diisopropylamino-dT(5'-DMT) phosphoramidite (dT4). A stirring suspension of 5'-DMT-deoxythymidine (4.30 g, 7.89 mmol) and DIEA (1.51 mL, 8.68 mmol) in CH₂Cl₂ (40 mL) was cooled to −78° C. under argon. A solution of bis(diisopropylamino)chlorophosphine (2.32 g, 8.68 mmol) in CH₂Cl₂ (10 mL) was added dropwise. The mixture was removed from the cooling bath and stirred for 1 h. FmocNH-Peg2-OH (S108, 2.93 g, 7.89 mmol) in CH₂Cl₂ (15 mL) was added to the reaction mixture followed by a solution of ETT (0.25 M in acetonitrile, 18.9 mL). After stirring overnight, the mixture was concentrated in vacuo, re-dissolved in EtOAc, and washed with sat. NaHCO₃ (aq.) and brine. The organic layer was removed in vacuo to afford a white foam. This crude material was purified by SiO₂ chromatography to provide the title phosphoramidite (dT4, 4.1 g, 50% yield).

Synthetic protocol described above was used for the synthesis of other phosphoramidite precursors of varying triesters.

Compound dU6

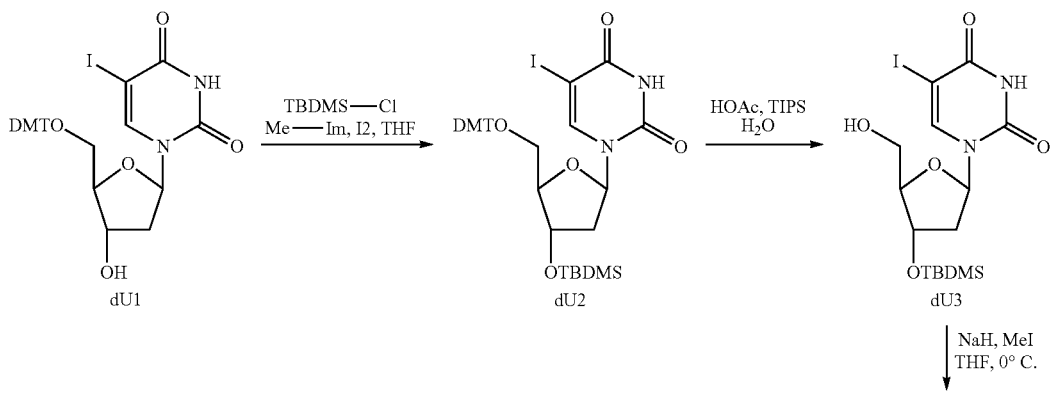

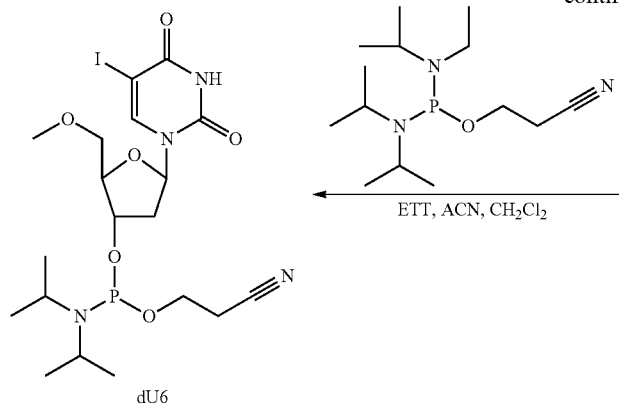

dU6

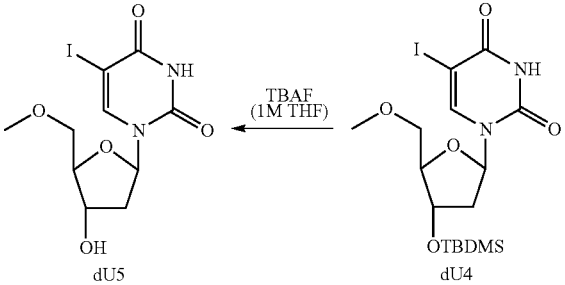

dU5    dU4

To a solution of dU1 (3.3 g, 5.0 mmol), 1-methylimidazole (1.2 mL, 15.0 mmol) and iodine (1.9 g, 15.0 mmol) in THF (10 mL) under Ar (g) at room temperature was added a solution of tert-butyldimethylsilyl chloride (0.8 g, 5.5 mmol) in THF (5 mL) dropwise with stirring. Reaction stirred at room temperature for 1 hour. TLC confirmed the completion of the reaction. Solvent was remove in vacuo, crude was dissolved in ethyl acetate and washed with aq. $Na_2S_2O_3$ (conc). Dried organic phase over $Na_2SO_4$, filtered and evaporated liquor. Crude was purified by flash silica gel column using an ISCO companion (hexanes/ethyl acetate, 0-50%) to give dU2 as a solid in quantitative yield. NMR consistent with published. *Nucleic Acids Research*, 2011, Vol. 39, No. 9, 3962-3971.

A solution of dU2 (3.9 g, 5.0 mmol) dissolved in an 80% aqueous acetic acid solution (40 mL) with triisopropylsilane (1.0 mL, 5.0 mmol) was stirred at room temperature for 1 hour. TLC confirmed the completion of the reaction. Remove solvent in vacuo. Crude was purified by a flash silica gel column using an ISCO companion (hexanes/ethyl acetate, 0-60%) to give 1 g (43%) of the desired compound dU3 as a solid. ESI MS for $C_{15}H_{25}IN_2O_5Si$ calculated 468.4, observed [M+Na]$^+$ 491.0.

To a solution of dU3 (1.0 g, 2.2 mmol) in THF (20 mL) under Ar (g) and cooled to 0° C. in an ice water bath was added sodium hydride (60% dispersion, 0.2 g, 4.7 mmol). The reaction was stirred for 30 minutes at 0° C. Iodomethane (0.7 mL, 10.8 mmol) was added dropwise and the reaction was stirred at 0° C. for 3 hours. RP-HPLC/MS confirmed the completion of the reaction. Reaction was quenched with 20 mL of methanol at 0° C. and warmed to room temperature. Aq. $NaHCO_3$ (sat.) was added and the mixture was extracted with $CH_2Cl_2$. Organic phase was dried over $Na_2SO_4$, filtered and liquor concentrated in vacuo. Purification by silica gel column chromatography (hexanes/ethyl acetate, 0-50%) gave solid dU4 (0.6 g, 58% yield). ESI MS for $C_{16}H_{27}IN_2O_5Si$ calculated 482.4, observed [M+H]$^+$ 483.1.

Tert-butylammonium fluoride (1 M THF, 3 mL, 3.0 mmol) was added dropwise with stirring to a cooled (0° C.) solution of dU4 (0.6 g, 1.3 mmol) dissolved in THF (20 mL) under Ar (g). The cooled solution was stirred for 30 minutes then warmed to room temperature. After 3.5 hours, RP-HPLC/MS confirmed the completion of the reaction. The crude product was purified by silica gel column chromatography (dichloromethane/methanol, 0-10%) to give solid dU5 (0.4 g, 92% yield). ESI MS for $C_{10}H_{13}IN_2O_5$ calculated 368.1, observed [M+H]$^+$ 369.0.

To a solution dU5 (0.4 g, 1.2 mmol) in dichloromethane (5 mL) under Ar (g) at room temperature was added a solution of 2'-cyanoethyl-N, N, N', N'-tetraisopropyl phosphoramidite (0.4 mL, 1.3 mmol) in dichloromethane (5 mL) dropwise with stirring. Reaction stirred for 30 minutes at room temperature. Ethylthiotetrazole (0.25 M solution in ACN, 2.9 mL, 0.7 mmol) was then added and the reaction was continued overnight. TLC confirmed the completion of the reaction. Solvent removed in vacuo and the crude mixture was diluted with 20 mL of dichloromethane, washed sequentially with a saturated $NaHCO_3$ solution (10 mL) and brine (10 mL). Dried organic phase over $Na_2SO_4$, filtered and evaporated liquor. Crude mixture was dissolved in ethyl acetate and purified by silica gel column using an Isco companion (hexanes/ethyl acetate, 0-100%) to give 0.3 g (49.9%) of the desired compound dU6 as a solid. ESI MS for $C_{19}H_{30}N_4O_6P$ Calculated 568.3, Observed 567.3 [M−H]$^-$; $^{31}$P NMR (202 MHz, CDCl$_3$, ppm): δ149.25.

Compound dU9

The title compound was prepared by reacting dU3 under standard reaction conditions shown below. $^{31}$P-NMR (202 mHz, CDCl$_3$, ppm): δ149.42, 149.31; MS ESI− m/z found 667.1 [M−H]. MS ESI+ m/z found 669.2 [M+H], 691.3 [M+Na].

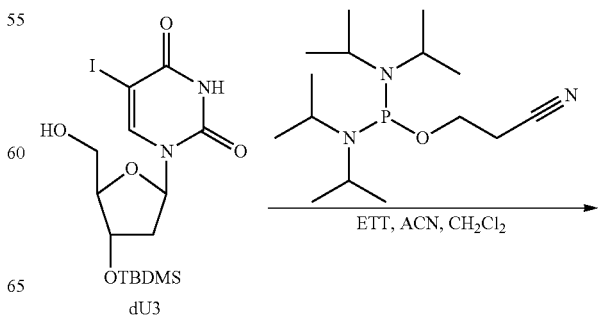

dU3

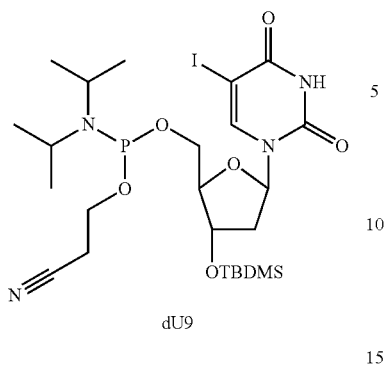

dU9

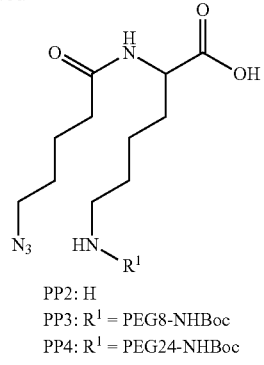

PP2: H
PP3: R¹ = PEG8-NHBoc
PP4: R¹ = PEG24-NHBoc

Preparation of Linkers Bonded to Auxiliary Moieties: Compounds PP2, PP3, and PP4

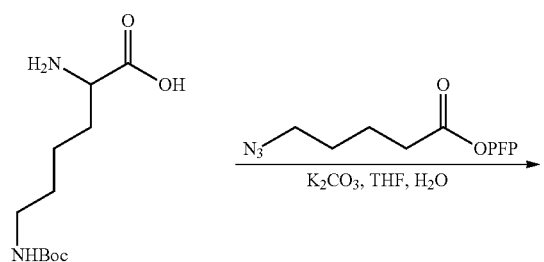

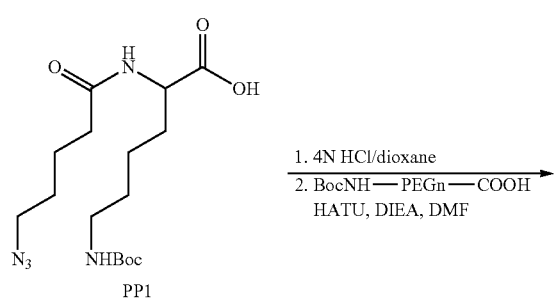

Preparation of (5-Azidovaleryl)-ε-N-Boc lysine (PP1). ε-N-Boc lysine (9.46 g, 38.4 mmol) and $K_2CO_3$ (2.67 g, 19.3 mmol) were dissolved in 1:1 THF:$H_2O$ (60 mL). Pentafluorophenyl-5-azidovalerate (10.8 g, 34.9 mmol) in THF (10 mL) was added, and the reaction stirred overnight at room temperature. The desired product was observed by RP-HPLC-MS, 394.2 [M+Na]. The reaction was acidified to pH 5 by titration with 1 N HCl (aq.), and the product was extracted with EtOAc (3×100 mL). The organic layer was washed sequentially with $H_2O$ (50 mL) and brine (50 mL). The organic layer was dried over $MgSO_4$ and concentrated in vacuo to a thick syrup. The crude product was purified by silica gel column chromatography to afford the desired product PP2 as white needles (8.1 g, 62% yield). ESI MS+ mass calculated $C_{16}H_{29}N_5O_5$: 371.4, found: 394.2 [M+Na]⁺.

General protocol for pegylation of PP1: preparation of (5-Azidovaleryl)-ε-N-(NH-Boc PEG24) lysine (PP4). PP1 (0.74 g, 2.0 mmol) was treated with HCl (2 mL, 4N in dioxane) for 4 h. HPLC-MS showed complete deprotection, 272.2 [M+H]⁺. The reaction was diluted with 1:1 $H_2O$:acetonitrile (10 mL), frozen, and lyophilized overnight to afford PP2 as a white solid in quantitative yield. NHBoc-PEG24 acid (1.1 g, 0.88 mmol) in DMF (3 mL) was activated with HATU (0.34 g, 0.88 mmol), HOBt (0.14 g, 0.88 mmol), and DIEA (0.7 mL, 4.0 mmol) then treated with PP2 (0.24 g, 0.8 mmol) for 2 hours. RP-HPLCMS showed formation of the desired PP4. The crude was purified by RP-HPLC to afford PP4 as a white solid (0.55 g, 46% yield). ESI MS+ mass calculated $C_{67}H_{130}N_6O_{30}$: 1499.77, found: 1499.9 [M+H]⁺, 1400.8 [M−Boc]⁺.

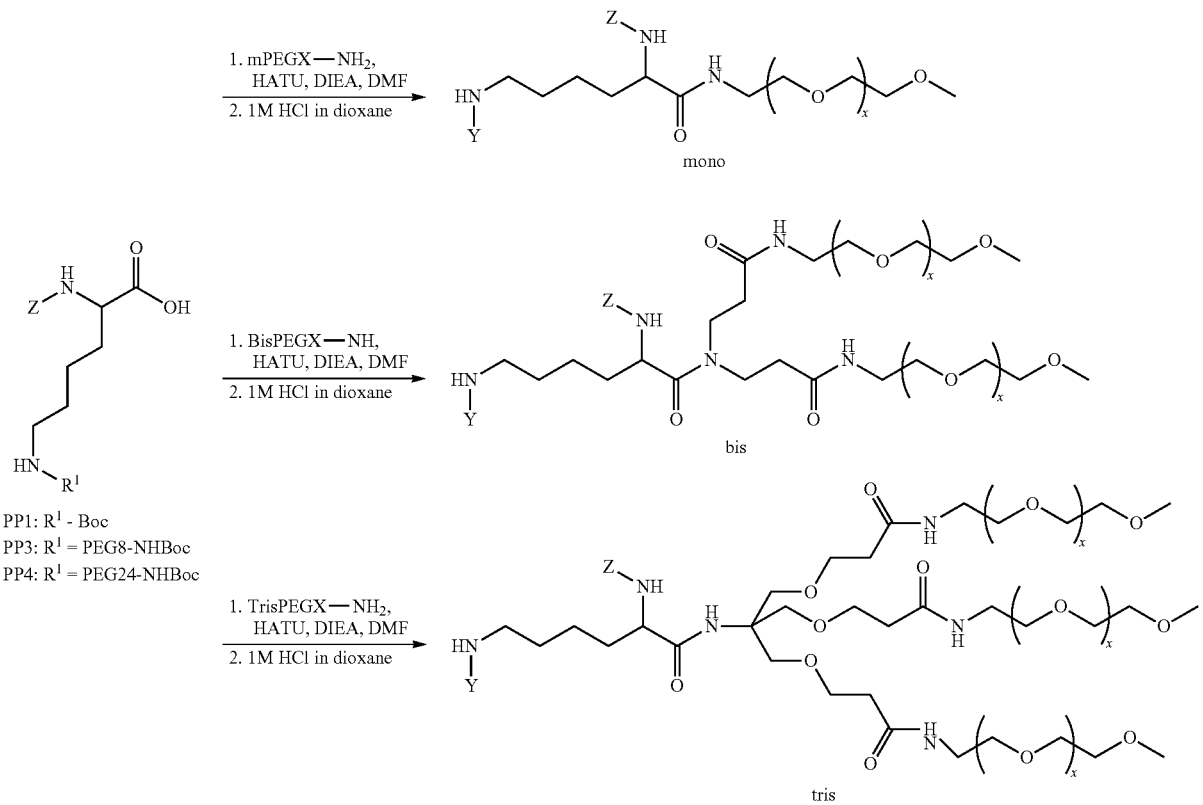

PP1: R¹ - Boc
PP3: R¹ = PEG8-NHBoc
PP4: R¹ = PEG24-NHBoc

BisPegX-NH2 and TrisPegX-NH2 (where X=various PEG lengths) were prepared from commercially available starting materials using procedures described in WO2015/188197.

General protocol for pegylation of PP2, PP3, and PP4: Lysine PP1 (38 mg, 0.1 mmol) dissolved in DMF (1 mL) was treated with HATU (37 mg, 0.1 mmol), N,N-diisopropylethylamine (49 mL, 0.3 mmol), and mPEG48-NH$_2$ (200 mg, 0.09 mmol). RP-HPLC-MS showed complete PEG48 addition to PP1. The crude was purified by RP-HPLC to afford NHBoc PP7 as a white solid (97 mg, 42% yield). ESI MS+ mass calculated $C_{113}H_{224}N_6O_{52}$: 2499.03, found: 833.7 [M+3H]$^{3+}$, 625.6 [M+4H]$^{4+}$. PP7 was deprotected with HCl (2 mL, 4N in dioxane) for 4 h. HPLC-MS showed complete deprotection, as observed by the disappearance of the peak having a mass of the starting material. The reaction was diluted with 1:1 H$_2$O:acetonitrile (10 mL), frozen, and lyophilized overnight to quantitatively afford a white solid PP8. ESI MS+ mass calculated $C_{108}H_{216}N_6O_{50}$: 2398.88, found: 1199.8 [M+2H]$^{2+}$, 800.3 [M+3H]$^{3+}$, 600.5 [M+4H]$^{4+}$, 480.6 [M+5H]$^{5+}$.

205
206
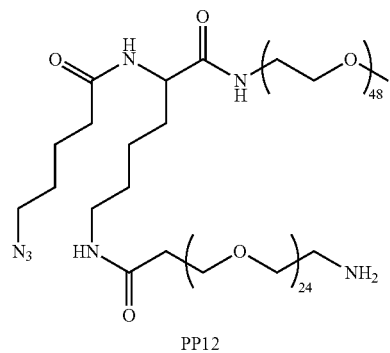
PP12
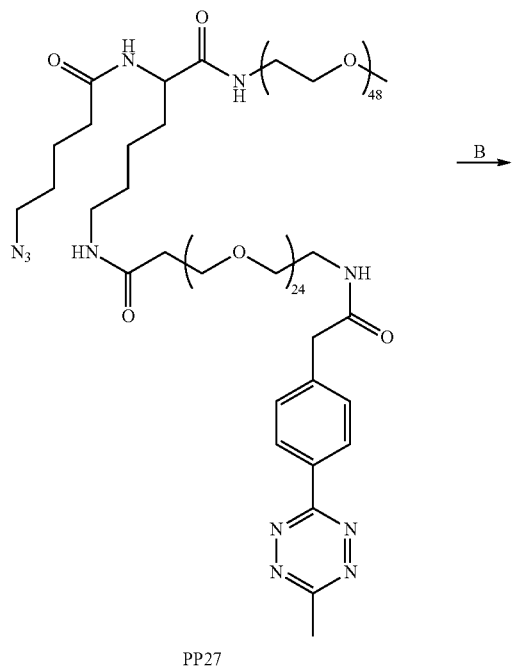
PP27
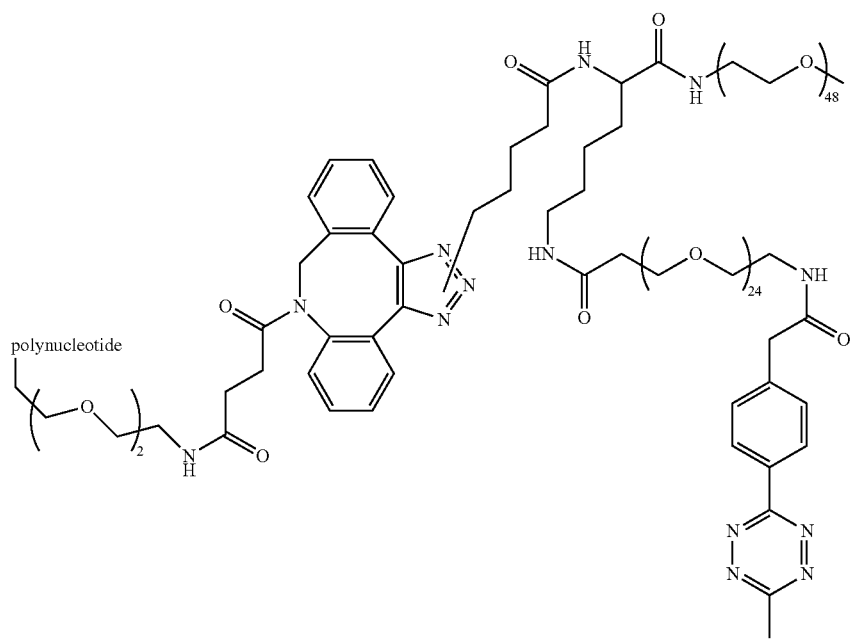
PP28
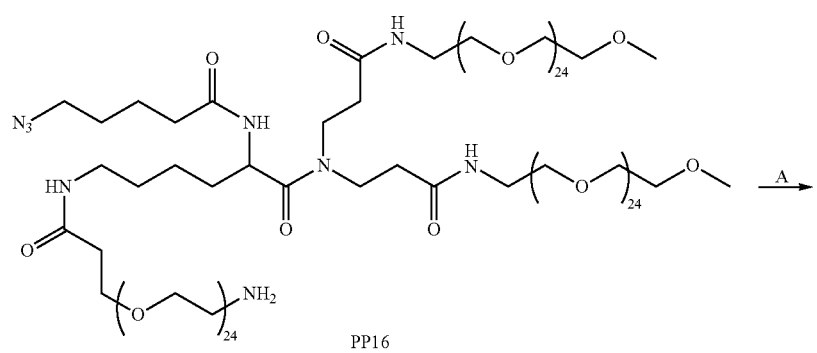
PP16

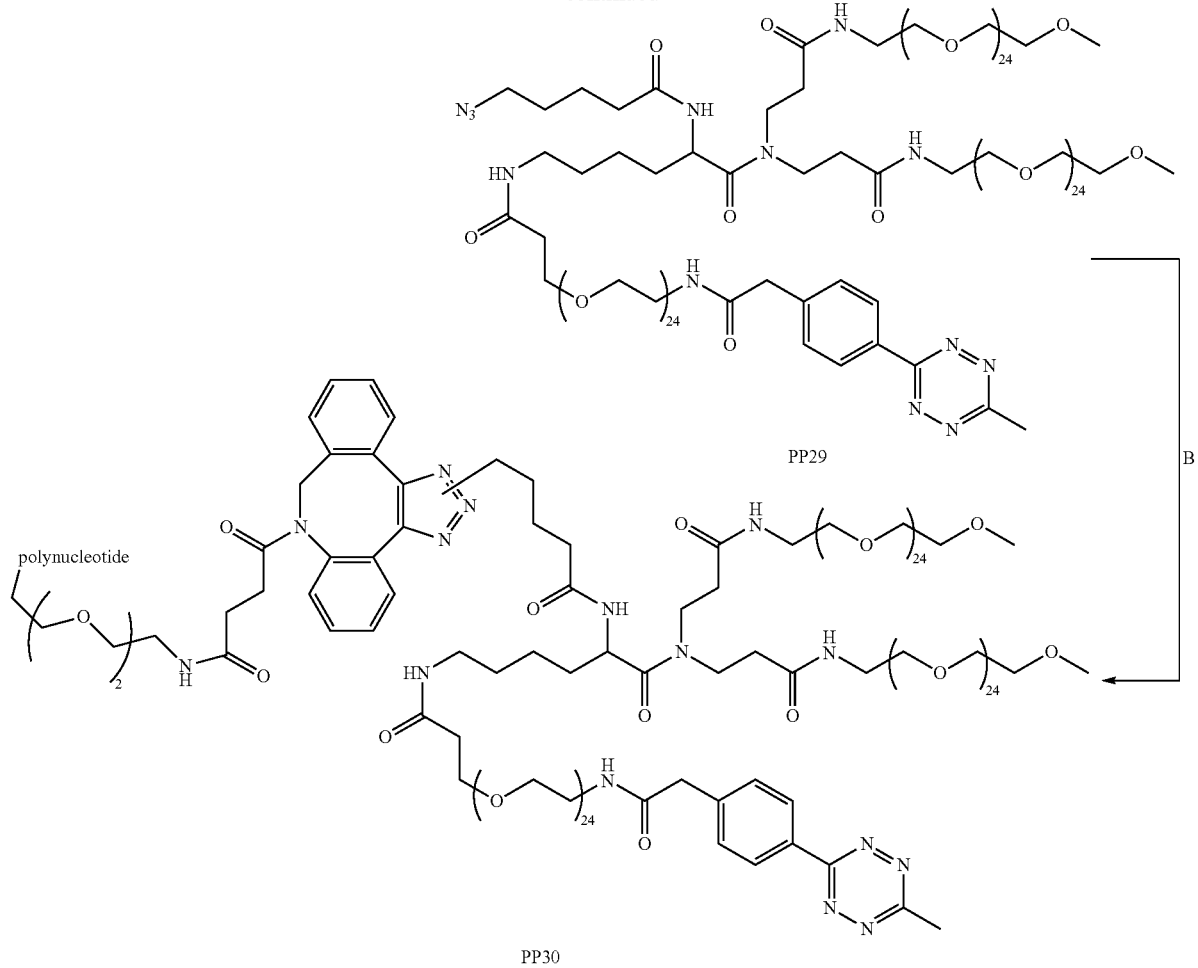

PP29

PP30

In this Scheme, conditions are:

A) 6-methytetrazine-OSu, HATU, Hünig's base, DMF; and

B) DBCO-CpG, acetonitrile/H₂O;

where-6-methyl tetrazine-OSu is of the following formula:

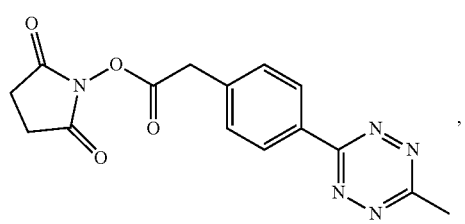 [SMILES: Cc1nnc(-c2ccc(CC(=O)ON3C(=O)CCC3=O)cc2)nn1]

and

DBCO-CpG is of the following formula:

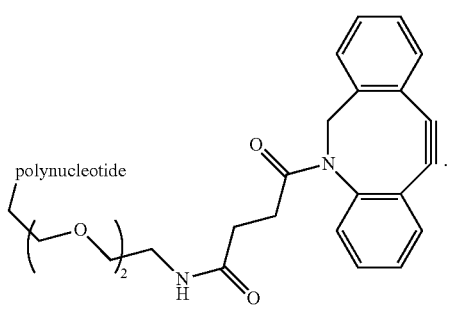

General Protocol for Preparation of Linkers Loaded with Polynucleotides (PP28 and PP30).

Tetrazine-conjugation handle of PP12 and PP16: PP12 (43 mg, 0.12 mmol) was dissolved in DMF (0.5 mL), treated with HATU (4.6 mg, 0.12 mmol), DIEA (12.7 µL, 0.73 mmol), and, after 5 min, with 6-methyl-tetrazine-OSu (19.9 mg, 0.61 mmol). The crude reaction was stirred for 30 min at room temperature RP-HPLCMS showed complete coupling of 6-methyl-tetrazine carboxylate to PP12. The crude was purified by RP-HPLC, and the pooled fractions were lyophilized to afford PP27 as a purple solid (39 mg, 85% yield). ESI MS+ mass calculated $C_{170}H_{325}N_{11}O_{76}$: 3739.47, found: 833.7 $[M+3H]^{3+}$, 625.6 $[M+4H]^{4}$. Pure PP27 was treated in DBCO-CpG in acetonitrile:water (1:1) and incubated at 37° C. for 1-2 hours and an additional 1 hour at room temperature to give PP28. PP28 was purified by preparative AEX (20 mM phosphate and 20 mM phosphate-1 M sodium bromide).

Alternative one-pot route to CpG loaded linkers PP28 and PP30. PP12 (400 nmol) is treated with DBCO-CpG (420 nmol) in acetonitrile:water (1:1) and incubated at 37° C. for 1-2 hours then an additional 1 hour at room temperature. Tetrazine-OSu (4000 nmol) in DMSO stock solution is added to crude PP12-DBCO-CpG solution and the purple solution is reacted for 3 hours at room temperature for 1-2 hours to afford PP28. The crude PP28 was purified by preparative RP-HPLC (50 mM TEAA in water and 10% acetonitrile:water) or preparative AEX (20 mM phosphate and 20 mM phosphate-1M sodium bromide).

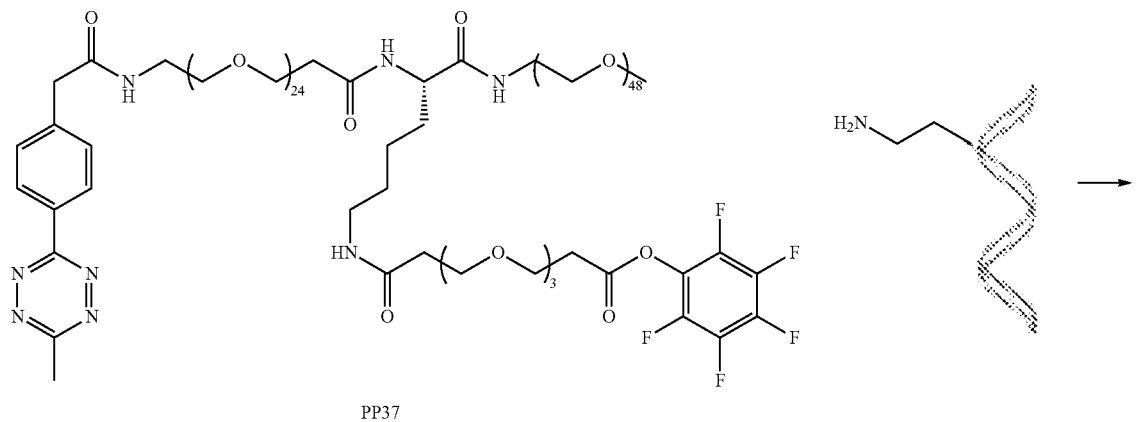

PP37

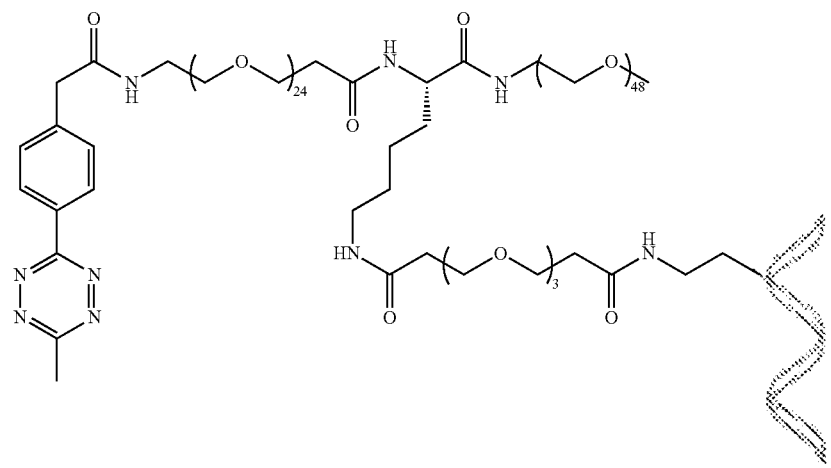

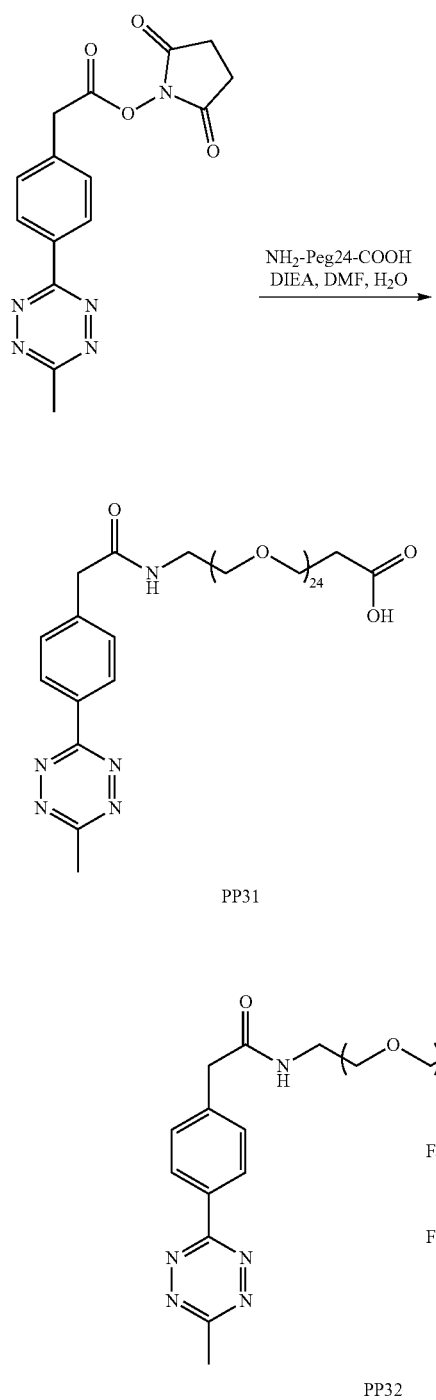

PP31

PP32

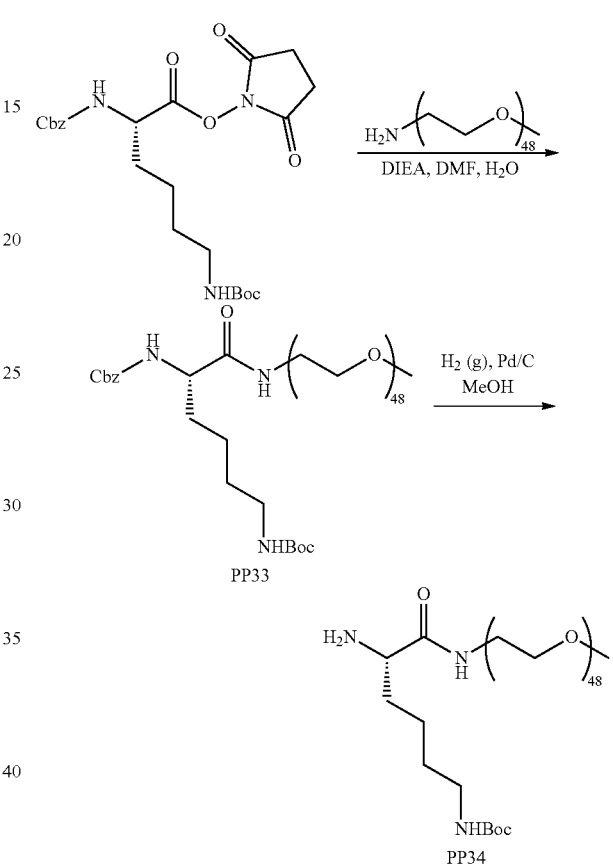

PP33

PP34

Preparation of Tetrazine-PEG24-OPFP (PP32). To a solution of amino-PEG24-carboxylic acid (1.0 g, 0.9 mmol) and diisopropylethylamine (0.8 mL, 4.4 mmol) in DMF/water (1:1, 12 mL) under Ar (g) was added methyltetrazinephenylacetyl succinimidyl ester (370 mg, 1.1 mmol) in DMF (3 mL) dropwise with stirring. Reaction stirred at room temperature for 2 hours. RP-HPLC/MS indicated formation of product. Solvent was removed in vacuo and crude was purified by RP-HPLC (TFA modifier) to provide PP31, 1.1 g (80%). ESI MS for $C_{62}H_{111}N_5O_{27}$ calculated 1358.56, observed [M+H]$^+$ 1358.8. To a solution of PP31 (109 mg, 0.08 mmol) in dichloromethane (3 mL) under Ar (g) was added anhydrous pyridine (32 mg, 0.4 mmol) and pentafluorophenyl trifluoroacetate (67 mg, 0.24 mmol). Reaction stirred at room temperature overnight. Solvent was removed in vacuo. Crude product was redissolved in EtOAc and washed with aq. NaHCO$_3$ (5% w/v) (3×) and brine (1×). Organic phase was dried over Na$_2$SO$_4$, filtered, and concentrated in vacuo to give PP32 quantitatively. Used in next step without further purification. ESI MS for $C_{68}H_{110}F_5N_5O_{27}$ calculated 1524.61, observed [M+2H]$^{2+}$763.0.

Preparation of PP34. To a solution of mPEG48-amine (2.15 g, 1.00 mmol) and diisopropylethylamine (0.87 mL, 5.00 mmol) in DMF/water (1:1, 10 mL) under Ar (g) was added Na-Cbz-Nε-Boc-L-Lysine succinimidyl ester (570 mg, 1.2 mmol) in DMF (5 mL) dropwise with stirring. Reaction mixture was stirred at room temperature for 2 hours. RP-HPLC/MS indicated formation of product, PP33. The reaction mixture was concentrated in vacuo and purified by silica gel chromatography (CH$_2$Cl$_2$:MeOH 0-10%). Recovered PP33 was used directly in next reaction. ESI MS for $C_{116}H_{223}N_3O_{53}$ calculated 2508.0, observed [M+3H]$^{3+}$ 836.7, [M+4H]$^{4+}$ 627.9. A solution of PP33 (1.00 mmol) in MeOH was flushed with nitrogen (g), and Palladium on activated carbon (10% wt, catalytic) was added. The solution was alternately evacuated and purged with hydrogen (g) (3×). RP-HPLC/MS after 2 hours showed formation of PP34. The heterogeneous mixture was filtered through a bed of Celite and washed with copious amounts of methanol. Removal of the solvent in vacuo, yielded PP34, (2.0 g, 84% yield, over 2 steps). ESI MS for $C_{108}H_{217}N_3O_{51}$ calculated 2373.87, observed [M+3H]$^{3+}$792.0.

213 214

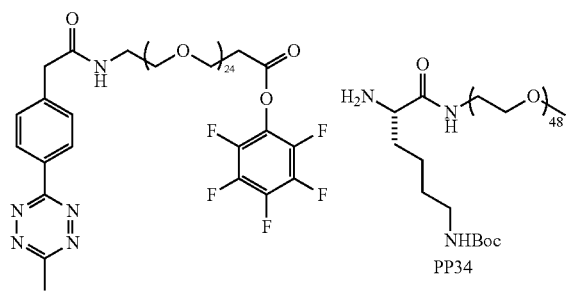
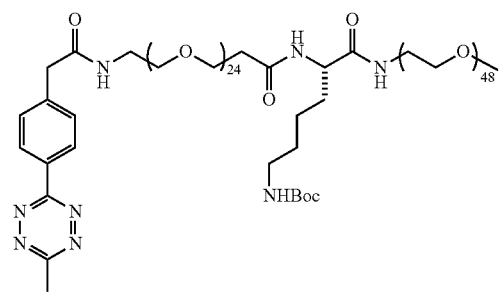

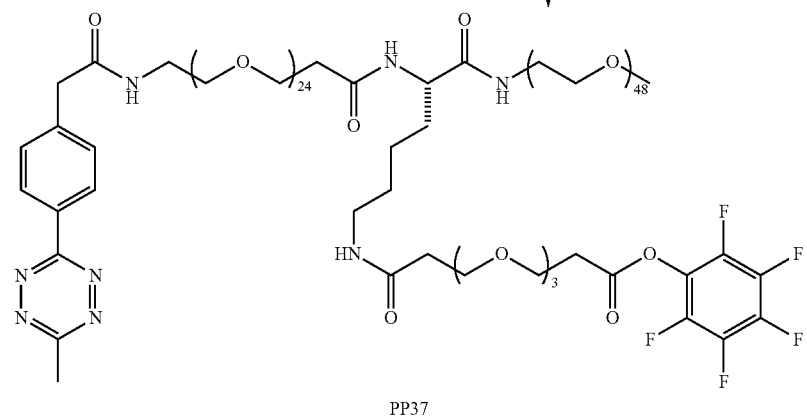

Preparation of PP37. To a solution of PP32 (124 mg, 0.08 mmol) and diisopropylethylamine (31 mg, 0.24 mmol) in DMF/water (1:1, 10 mL) under Ar (g) was added PP34 (230 mg, 0.1 mmol) in DMF/water (1:1, 10 mL) dropwise with stirring. The reaction was stirred at room temperature for 2 hours and RP-HPLC/MS indicated formation of product PP35. Solvent was removed in vacuo and PP35 used in next step without further purification. ESI MS for $C_{170}H_{326}N_8O_{77}$ calculated 3714.4, observed $[M+4H]^{4+}$ 929.5, $[M+5H]^{5+}$ 743.8. Crude PP35 (0.08 mmol) treated with HCl (4 N in dioxane, 5 mL) under Ar (g). Reaction was stirred at room temperature for 2 hours and RP-HPLC/MS indicated complete removal of Boc protecting group. The solvent was removed in vacuo and the amine was acylated with a solution of bis-Peg3-PFP ester (230 mg, 0.4 mmol) in DMF (5 mL) and diisopropylethylamine (140 uL, 0.8 mmol). After 2 hours, RP-HPLC/MS indicated formation of product PP37 Solvent was removed in vacuo and crude was purified by RP-HPLC (TFA modifier) to provide PP37 as a tetra-TFA salt, 31 mg in 8.7% yield. ESI MS for $C_{181}H_{333}F_5N_8O_{81}$ calculated 4012.56, observed $[M+3H]^{3+}$ 1338.3, $[M+4H]^{4+}$ 1004.0, $[M+5H]^{5+}$ 803.4, $[M+6H]^{6+}$ 669.

List of the Linkers Containing Auxiliary Moieties:

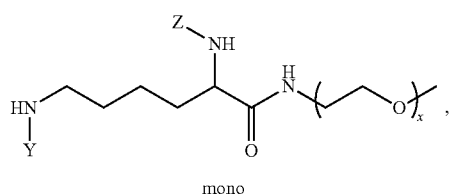

mono

-continued

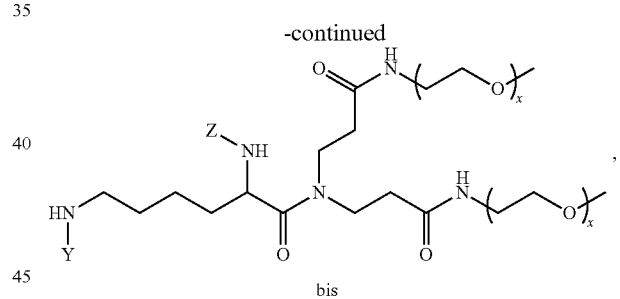

bis

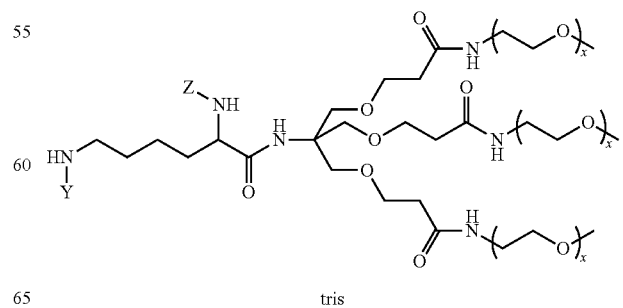

tris

| Linker | Valency | X | Y | Z (tether) | Formula | MS calc. | MS found (ESI+) |
|---|---|---|---|---|---|---|---|
| PP6 | mono | 24 | H | $N_3$-valeramide | $C_{60}H_{120}N_6O_{26}$ | 1341.62 | 1341.7, 671.5 |
| PP8 | mono | 48 | H | $N_3$-valeramide | $C_{108}H_{216}N_6O_{50}$ | 2398.88 | 1199.8, 800.3, 600.5, 480.6 |
| PP10 | mono | 48 | CO-PEG08-$NH_2$ | $N_3$-valeramide | $C_{127}H_{253}N_7O_{59}$ | 2822.38 | 1412.0, 941.7, 706.5, 565.4, 471.4 |
| PP12 | mono | 48 | CO-PEG24-$NH_2$ | $N_3$-valeramide | $C_{159}H_{317}N_7O_{75}$ | 3527.21 | 1176.5, 882.6, 706.3 |
| PP14 | bis | 24 | CO-PEG08-$NH_2$ | $N_3$-valeramide | $C_{134}H_{265}N_9O_{61}$ | 2978.56 | 1490.1, 993.7, 745.6, 596.7, 497.4 |
| PP16 | bis | 24 | CO-PEG24-$NH_2$ | $N_3$-valeramide | $C_{166}H_{329}N_9O_{77}$ | 3683.39 | 1228.6, 921.7, 737.6, 615.0 |
| PP18 | bis | 48 | CO-PEG08-$NH_2$ | $N_3$-valeramide | $C_{230}H_{457}N_9O_{109}$ | 5093.08 | 1247.2, 1019.6, 849.8, 728.6, 637.7 |
| PP20 | bis | 48 | CO-PEG24-$NH_2$ | $N_3$-valeramide | $C_{262}H_{521}N_9O_{125}$ | 5797.93 | 1450.3, 1160.4, 967.1, 829.1, 725.8 |
| PP22 | tris | 24 | H | $N_3$-valeramide | $C_{171}H_{339}N_9O_{80}$ | 3801.52 | 1268.0, 951.2, 761.2 |
| PP24 | tris | 24 | CO-PEG08-$NH_2$ | $N_3$-valeramide | $C_{190}H_{376}N_{10}O_{89}$ | 4225.02 | 1409.3, 1057.0, 846.0, 705.2, 604.6 |
| PP26 | tris | 24 | CO-PEG24-$NH_2$ | $N_3$-valeramide | $C_{222}H_{440}N_{10}O_{105}$ | 4929.87 | 1233.3, 968.8 |
| PP27 | mono | 48 | CO-PEG24-Tetrazine | $N_3$-valeramide | $C_{170}H_{325}N_{11}O_{76}$ | 3739.47 | 1247.2, 935.7, 748.8, 624.1, 535.3 |
| PP28 | mono | 48 | CO-PEG24-Tetrazine | p313 + $N_3$-valeramide | | 8893.7 | 8891, deconvoluted ESI- |
| PP29 | bis | 24 | CO-PEG24-Tetrazine | $N_3$-valeramide | $C_{177}H_{337}N_{13}O_{78}$ | 3895.66 | 974.8, 780.0 |
| PP30 | bis | 24 | CO-PEG24-Tetrazine | p313 + $N_3$-valeramide | | 9049.9 | 9046, deconvoluted ESI- |
| PP37 | mono | 48 | PFP-PEG3 | CO-PEG24-Tetrazine | $C_{181}H_{333}N_8O_{81}$ | 4012.56 | 1338.3, 1004.0, 803.4, 669.6 |
| PP38 | bis | 48 | CO-PEG24-Tetrazine | p313 + $N_3$-valeramide | | 11163.2 | 11159, deconvoluted ESI- |
| PP39 | tris | 24 | CO-PEG24-Tetrazine | p313 + $N_3$-valeramide | | 10281.1 | 10292, deconvoluted ESI- |

In the above table, groups identified as Y or Z have the following structures:

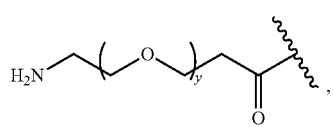

CO—PEG08—$NH_2$ (y = 8)
CO—PEG24—$NH_2$ (y = 24)

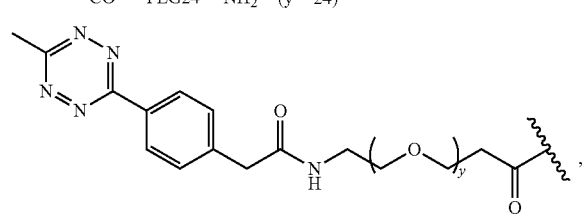

CO—PEG08-Tetrazine (y = 8)
CO—PEG24-Tetrazine (y = 24)

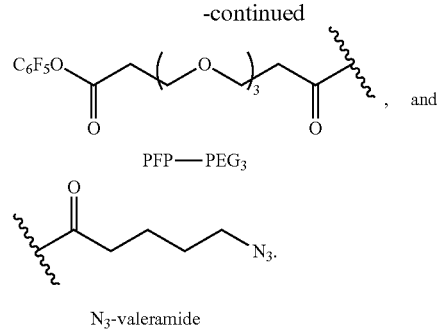

PFP—$PEG_3$ $N_3$-valeramide

In the table above, group Z identified as "p313+$N_3$-valeramide" refers to a product of a cycloaddition reaction between p313 and a linker having $N_3$-valeramide as Z.

The phosphoramidite monomers shown in Table 1 were synthesized using the standard synthetic procedures described herein and in WO 2015/188197.

The bicyclic oxazaphospholidine monomers used in chiral phosphorothioate oligonucleotide synthesis were prepared using literature protocol as reported by Wada, *J. Am. Chem. Soc.* 130:16031-16037, 2008.

TABLE 1

| Compound # | Structure | ³¹P NMR (δ in ppm) and/or ESI MS | Yield (%) |
|---|---|---|---|
| dT1 | 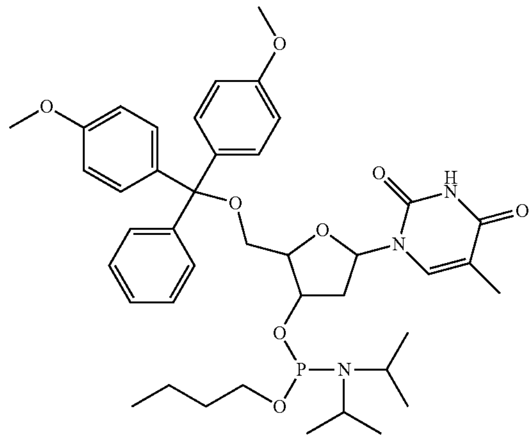 [SMILES: CCCCOP(OC1CC(n2cc(C)c(=O)[nH]c2=O)OC1COC(c1ccccc1)(c1ccc(OC)cc1)c1ccc(OC)cc1)N(C(C)C)C(C)C] | ESI MS calculated 747.8, observed 746.9 [M − H] ³¹P NMR (202 MHz, CDCl₃): δ147.50, 147.00 | |
| dC1 | 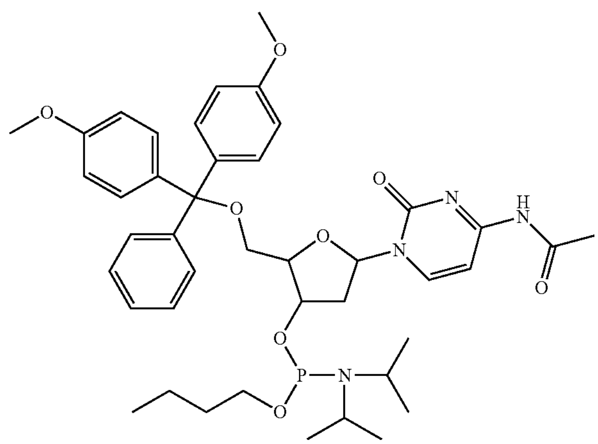 [SMILES: CCCCOP(OC1CC(n2ccc(NC(C)=O)nc2=O)OC1COC(c1ccccc1)(c1ccc(OC)cc1)c1ccc(OC)cc1)N(C(C)C)C(C)C] | — | |
| dA1 | 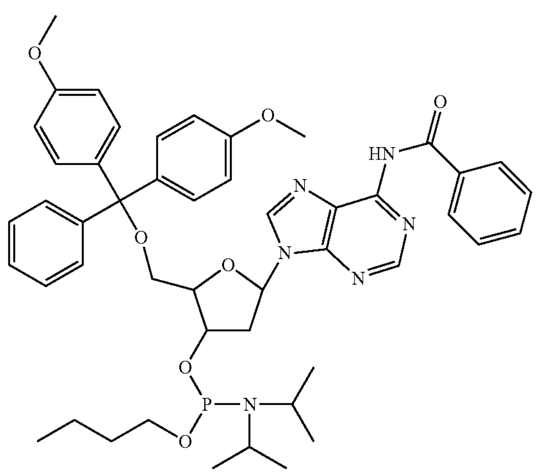 [SMILES: CCCCOP(OC1CC(n2cnc3c(NC(=O)c4ccccc4)ncnc32)OC1COC(c1ccccc1)(c1ccc(OC)cc1)c1ccc(OC)cc1)N(C(C)C)C(C)C] | ESI MS calculated 860.97, observed 859.9 [M − H], 862.0 [M + H] ³¹P NMR (202 MHz, CDCl₃): δ147.47, 147.35 | |

TABLE 1-continued
| Compound # | Structure | ³¹P NMR (δ in ppm) and/or ESI MS | Yield (%) |
|---|---|---|---|
| dG1 | 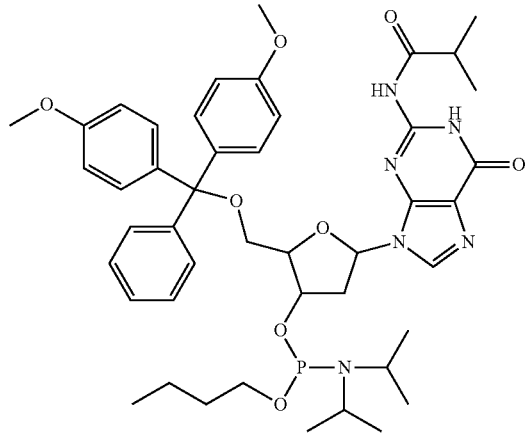 [SMILES: CCCCOP(OC1CC(n2cnc3c(=O)[nH]c(NC(=O)C(C)C)nc32)OC1COC(c1ccccc1)(c1ccc(OC)cc1)c1ccc(OC)cc1)N(C(C)C)C(C)C] | ESI MS calculated 842.96, observed 841.7 [M − H], 843.9 [M + H] ³¹P NMR (202 MHz, CDCl₃): δ147.05, 147.93 | |
| dT2 | 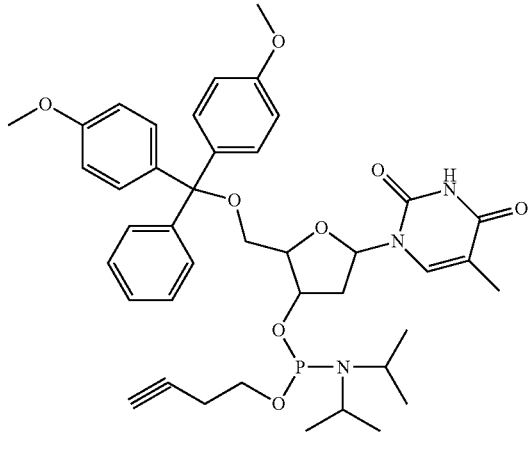 [SMILES: C#CCCOP(OC1CC(n2cc(C)c(=O)[nH]c2=O)OC1COC(c1ccccc1)(c1ccc(OC)cc1)c1ccc(OC)cc1)N(C(C)C)C(C)C] | ESI MS calculated 743.8, observed 742.8 [M − H], 744.7 [M + H] ³¹P NMR (202 MHz, CDCl₃): δ148.26, 147.77 | |
| dC2 | 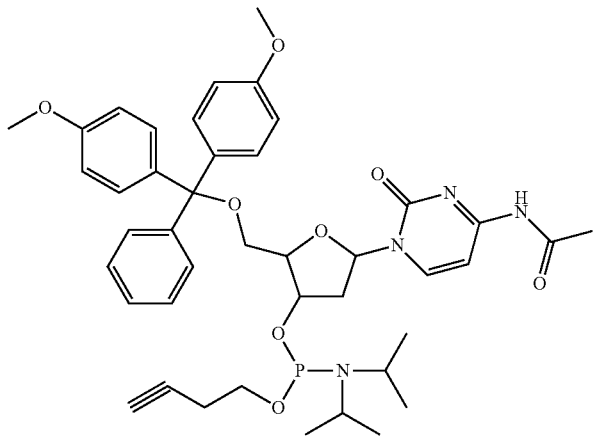 [SMILES: C#CCCOP(OC1CC(n2ccc(NC(C)=O)nc2=O)OC1COC(c1ccccc1)(c1ccc(OC)cc1)c1ccc(OC)cc1)N(C(C)C)C(C)C] | — | |

TABLE 1-continued
| Compound # | Structure | $^{31}$P NMR (δ in ppm) and/or ESI MS | Yield (%) |
|---|---|---|---|
| dA2 | 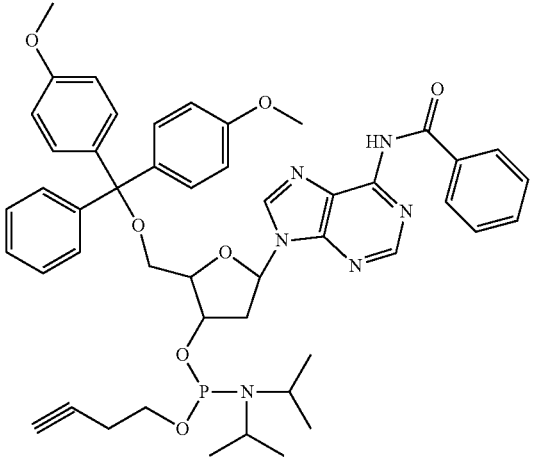 [SMILES: C#CCCOP(OC1CC(n2cnc3c(NC(=O)c4ccccc4)ncnc32)OC1COC(c1ccccc1)(c1ccc(OC)cc1)c1ccc(OC)cc1)N(C(C)C)C(C)C] | — | |
| dG2 | 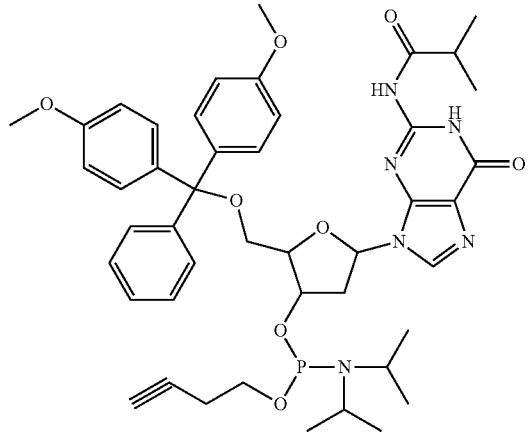 [SMILES: C#CCCOP(OC1CC(n2cnc3c(=O)[nH]c(NC(=O)C(C)C)nc32)OC1COC(c1ccccc1)(c1ccc(OC)cc1)c1ccc(OC)cc1)N(C(C)C)C(C)C] | — | |
| dT3 | 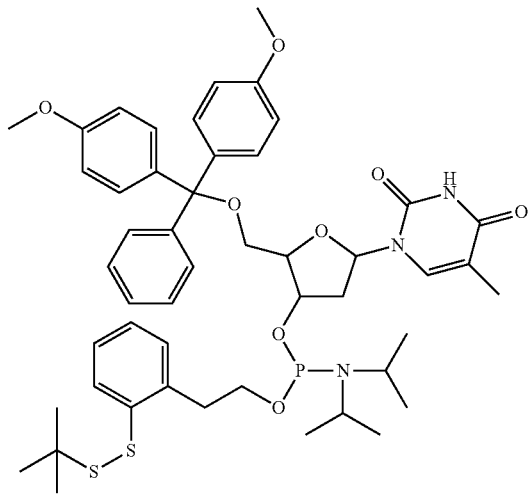 [SMILES: COc1ccc(C(OCC2OC(n3cc(C)c(=O)[nH]c3=O)CC2OP(OCCc2ccccc2SSC(C)(C)C)N(C(C)C)C(C)C)(c2ccccc2)c2ccc(OC)cc2)cc1] | ESI MS calculated 916.1, observed 915.6 [M − H] $^{31}$P NMR (202 MHz, CDCl$_3$): δ147.72, 147.21 | |

TABLE 1-continued
| Compound # | Structure | 31P NMR (δ in ppm) and/or ESI MS | Yield (%) |
|---|---|---|---|
| dC3 | 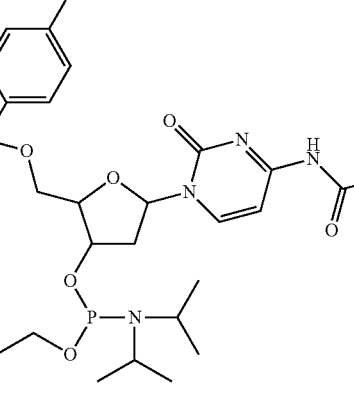 | — | |
| dA3 | 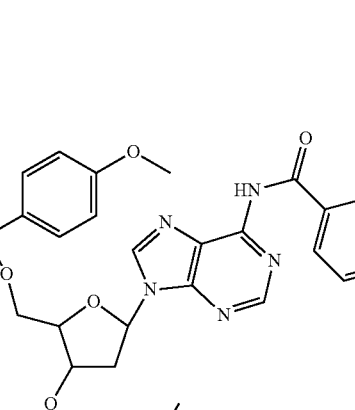 | — | |
| dG3 | 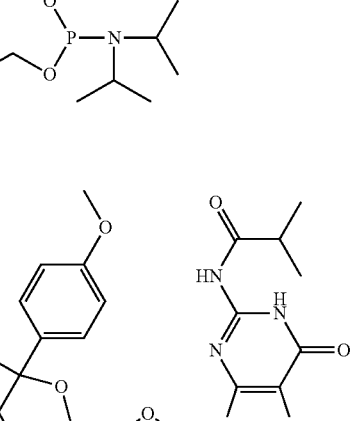 | — | |

TABLE 1-continued
| Compound # | Structure | ³¹P NMR (δ in ppm) and/or ESI MS | Yield (%) |
|---|---|---|---|
| dT4 | 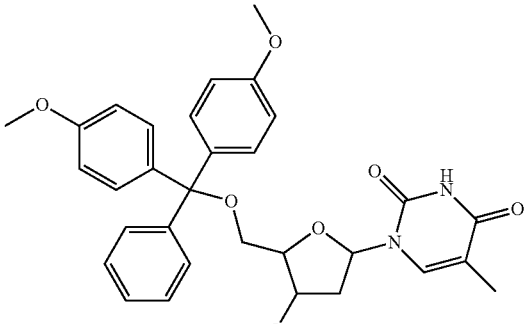 | ESI MS calculated 1045.2, observed 1046.3 [M + H]<br>³¹P NMR (202 MHz, CDCl₃): δ148.38, 148.27 | |
| dC4 | 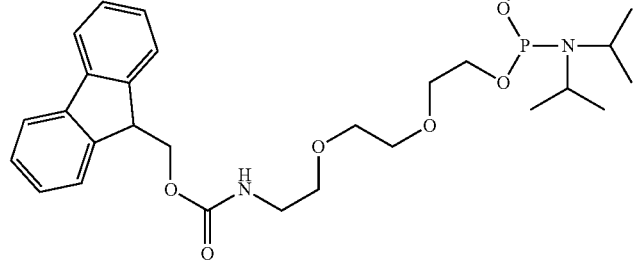 | ESI MS calculated 1088.2, observed 1089.0 [M + H]<br>³¹P NMR (202 MHz, CDCl₃): δ149.29, 148.66 | |

TABLE 1-continued
| Compound # | Structure | ³¹P NMR (δ in ppm) and/or ESI MS | Yield (%) |
|---|---|---|---|
| dA4 | 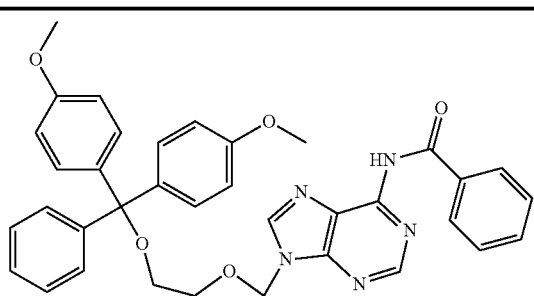 | ESI MS calculated 1158.3, observed 1157.5 [M − H], 1159.0 [M + H] ³¹P NMR (202 MHz, CDCl₃): δ148.38 | |
| dG4 | 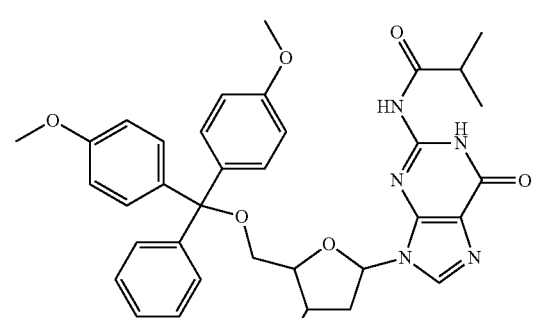 | ESI MS calculated 1140.3, observed 1139.1 [M − H], 1141.2 [M + H] ³¹P NMR (202 MHz, CDCl₃): δ147.76 | |

TABLE 1-continued

| Compound # | Structure | ³¹P NMR (δ in ppm) and/or ESI MS | Yield (%) |
|---|---|---|---|
| dT5 | 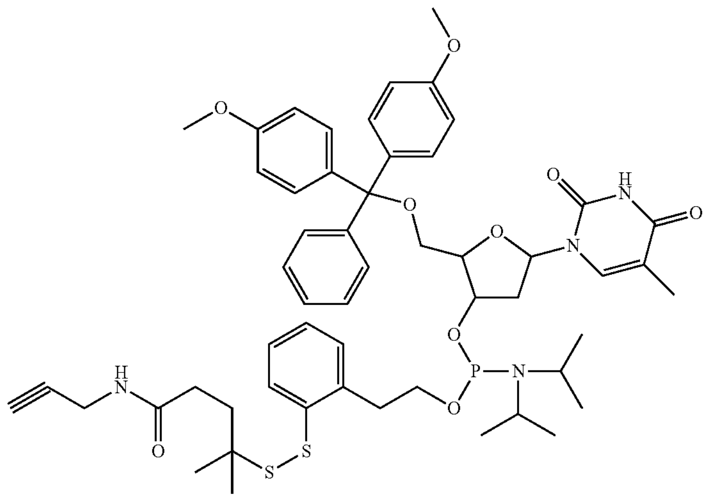 [SMILES: C#CCNC(=O)CCC(C)(C)SSc1ccccc1CCOP(OC1CC(n2cc(C)c(=O)[nH]c2=O)OC1COC(c1ccccc1)(c1ccc(OC)cc1)c1ccc(OC)cc1)N(C(C)C)C(C)C] | ESI MS calculated 1011.2, observed 978.6 [M − H] ³¹P NMR (202 MHz, CDCl₃): δ147.51, 147.32 | |
| dC5 | 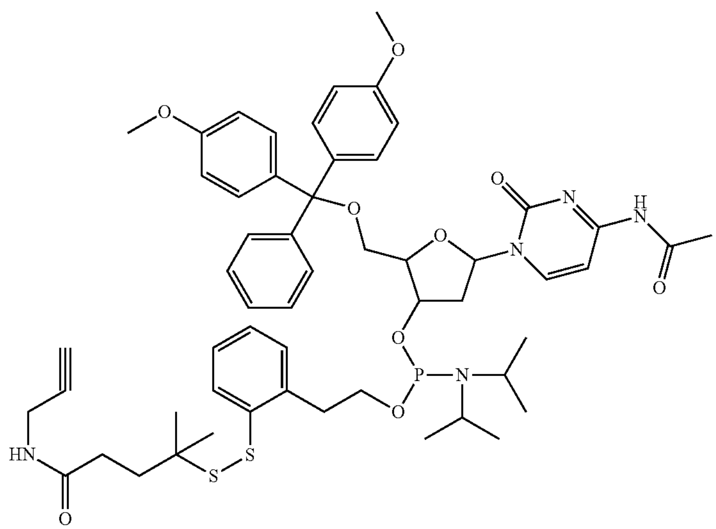 [SMILES: C#CCNC(=O)CCC(C)(C)SSc1ccccc1CCOP(OC1CC(n2ccc(NC(C)=O)nc2=O)OC1COC(c1ccccc1)(c1ccc(OC)cc1)c1ccc(OC)cc1)N(C(C)C)C(C)C] | — | |
| dA5 | 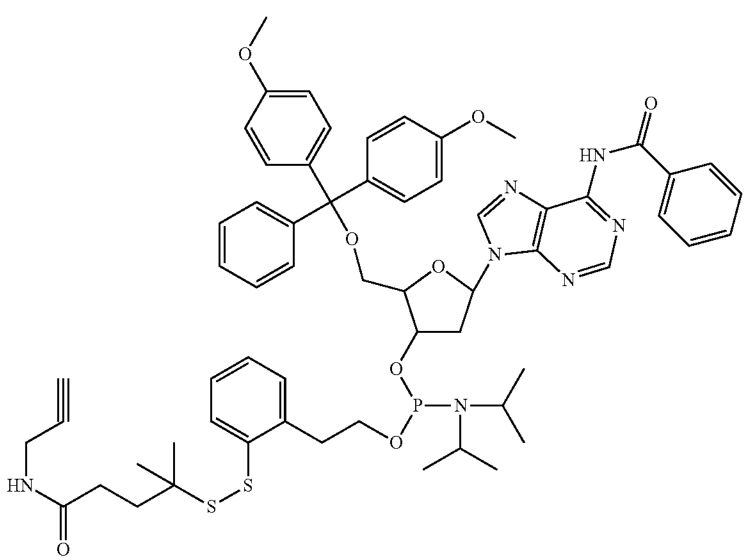 [SMILES: C#CCNC(=O)CCC(C)(C)SSc1ccccc1CCOP(OC1CC(n2cnc3c(NC(=O)c4ccccc4)ncnc32)OC1COC(c1ccccc1)(c1ccc(OC)cc1)c1ccc(OC)cc1)N(C(C)C)C(C)C] | — | |

TABLE 1-continued

| Compound # | Structure | ³¹P NMR (δ in ppm) and/or ESI MS | Yield (%) |
|---|---|---|---|
| dG5 | 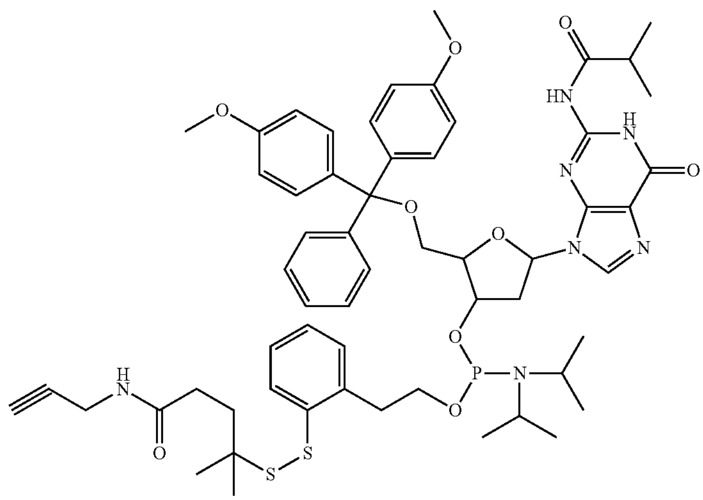 [SMILES: C#CCNC(=O)CCC(C)(C)SSc1ccccc1CCOP(OC1CC(n2cnc3c(=O)[nH]c(NC(=O)C(C)C)nc32)OC1COC(c1ccccc1)(c1ccc(OC)cc1)c1ccc(OC)cc1)N(C(C)C)C(C)C] | — | |
| dT6 | 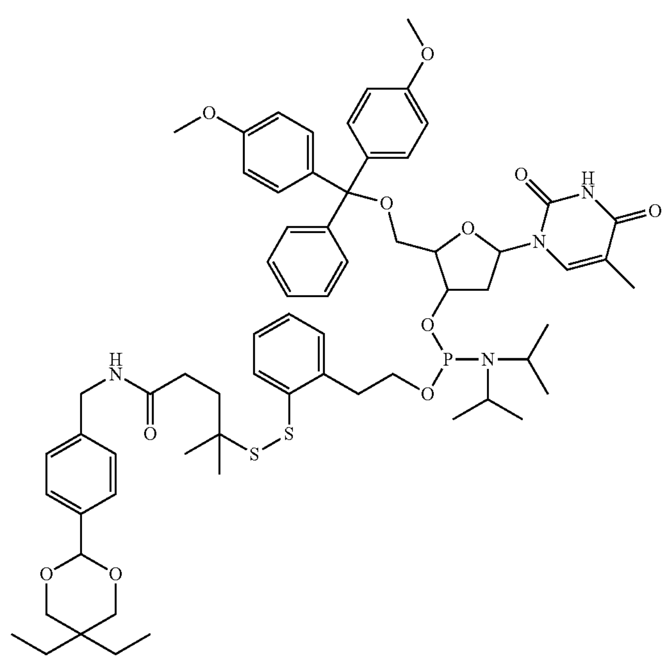 [SMILES: CCC1(CC)COC(c2ccc(CNC(=O)CCC(C)(C)SSc3ccccc3CCOP(OC3CC(n4cc(C)c(=O)[nH]c4=O)OC3COC(c3ccccc3)(c3ccc(OC)cc3)c3ccc(OC)cc3)N(C(C)C)C(C)C)cc2)OC1] | — | |

TABLE 1-continued
| Compound # | Structure | $^{31}$P NMR (δ in ppm) and/or ESI MS | Yield (%) |
|---|---|---|---|
| dC6 | 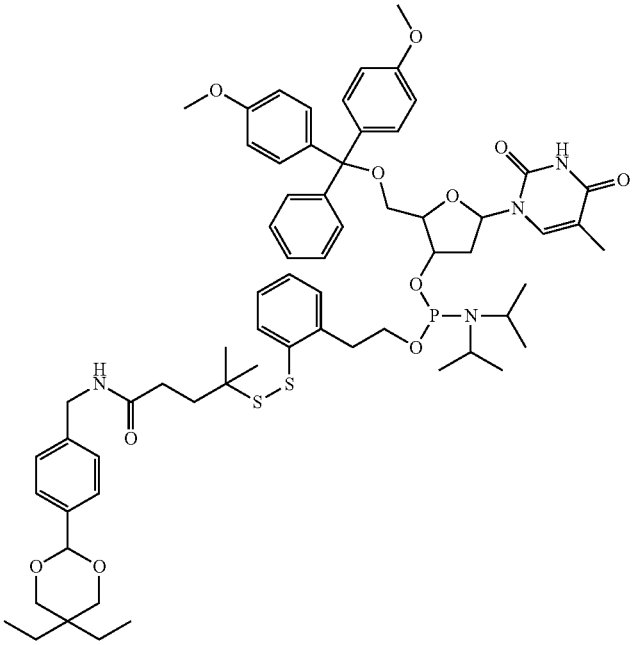 [SMILES: CCC1(CC)COC(c2ccc(CNC(=O)CCC(C)(C)SSc3ccccc3CCOP(OC3CC(n4cc(C)c(=O)[nH]c4=O)OC3COC(c3ccccc3)(c3ccc(OC)cc3)c3ccc(OC)cc3)N(C(C)C)C(C)C)cc2)OC1] | — | — |
| dA6 | 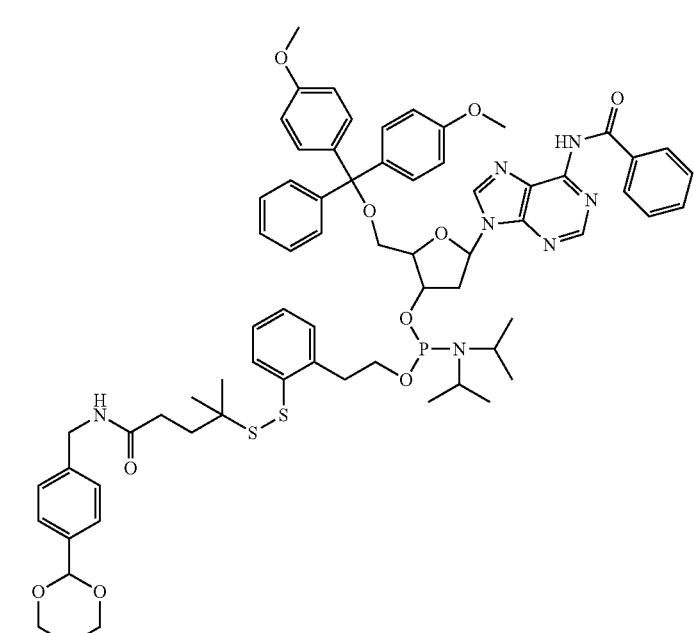 | — | — |

TABLE 1-continued
| Compound # | Structure | ³¹P NMR (δ in ppm) and/or ESI MS | Yield (%) |
|---|---|---|---|
| dG6 | 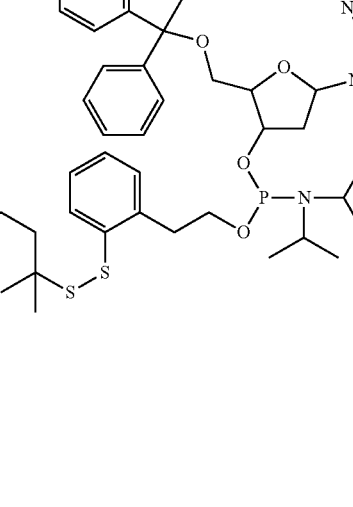 | — | |
| dT7 | 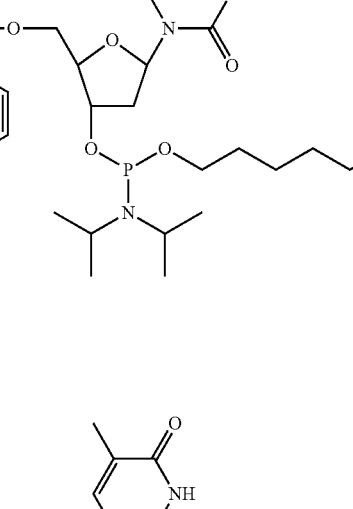 | ³¹P NMR (202 MHz, CDCl₃): δ 147.05 (d, J 8.08 Hz), 146.58 (d, J 8.08 Hz) ESI MS calculated 992.45, observed 994.3 (M + H), 992.0 (M − H) | 42 |
| dT8 | 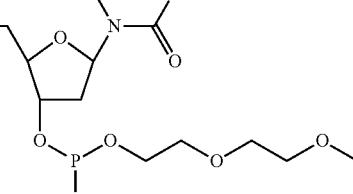 | ³¹P NMR (202 MHz, CDCl₃): δ 147.80 ESI MS calculated 881.99, observed 880.9 (M − H), 904.9 (M + Na) | 14 |

TABLE 1-continued

| Compound # | Structure | 31P NMR (δ in ppm) and/or ESI MS | Yield (%) |
|---|---|---|---|
| dU7 (Rp) | 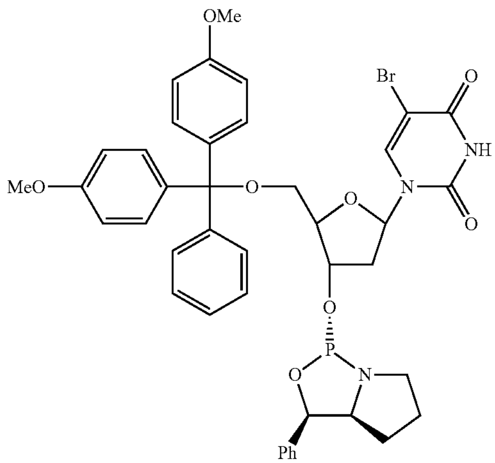 | 31P NMR (202 MHz, CDCl3): δ156.19 (s) | 31 |
| dU8 (Sp) | 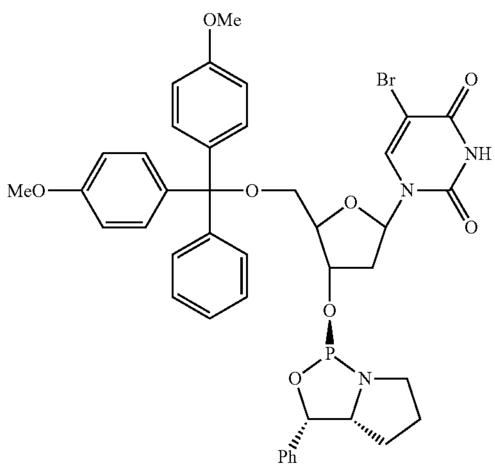 | 31P NMR (202 MHz, CDCl3): δ155.78 (s) | 27 |
| dC7 (Rp) | 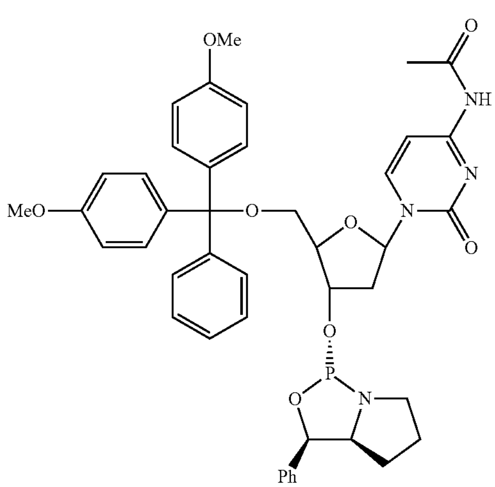 | 31P NMR (202 MHz, CDCl3): δ156.75 (s) | 21 |

TABLE 1-continued
| Compound # | Structure | $^{31}$P NMR (δ in ppm) and/or ESI MS | Yield (%) |
|---|---|---|---|
| dC8 (Sp) | 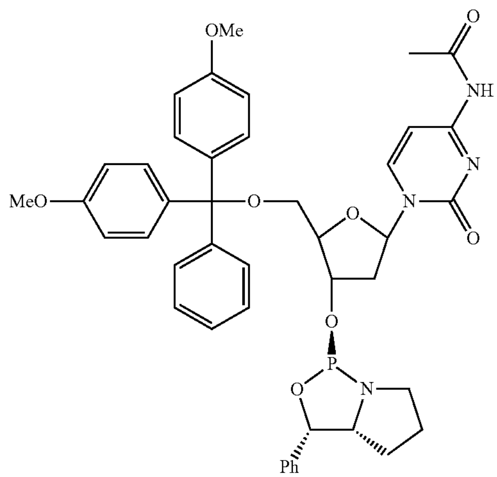 | $^{31}$P NMR (202 MHz, CDCl$_3$): δ156.08 (s) | 25 |
Chiral Abasic Spacers—Compounds X7, X8, X9 and X10:
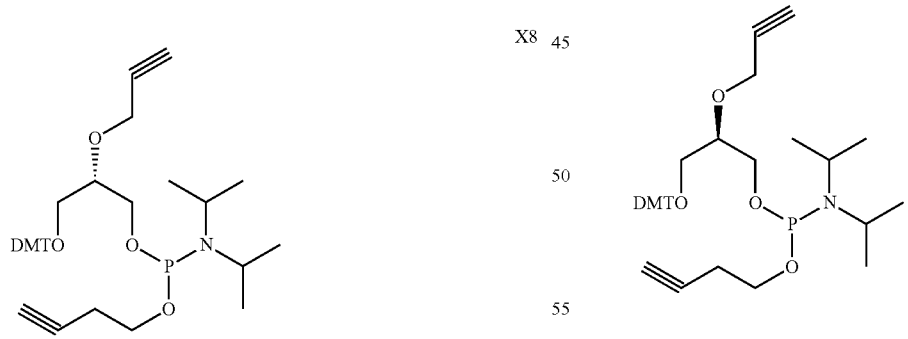
X7 and X8 Synthesis:
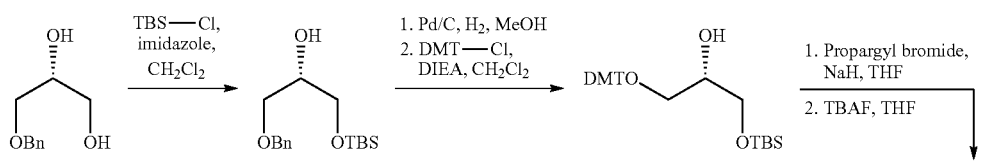

-continued
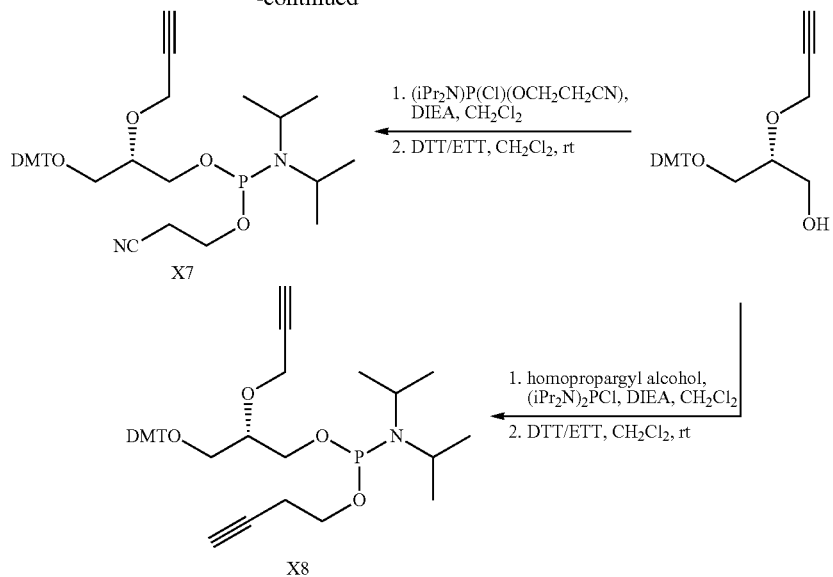
X9 and X10 Synthesis:
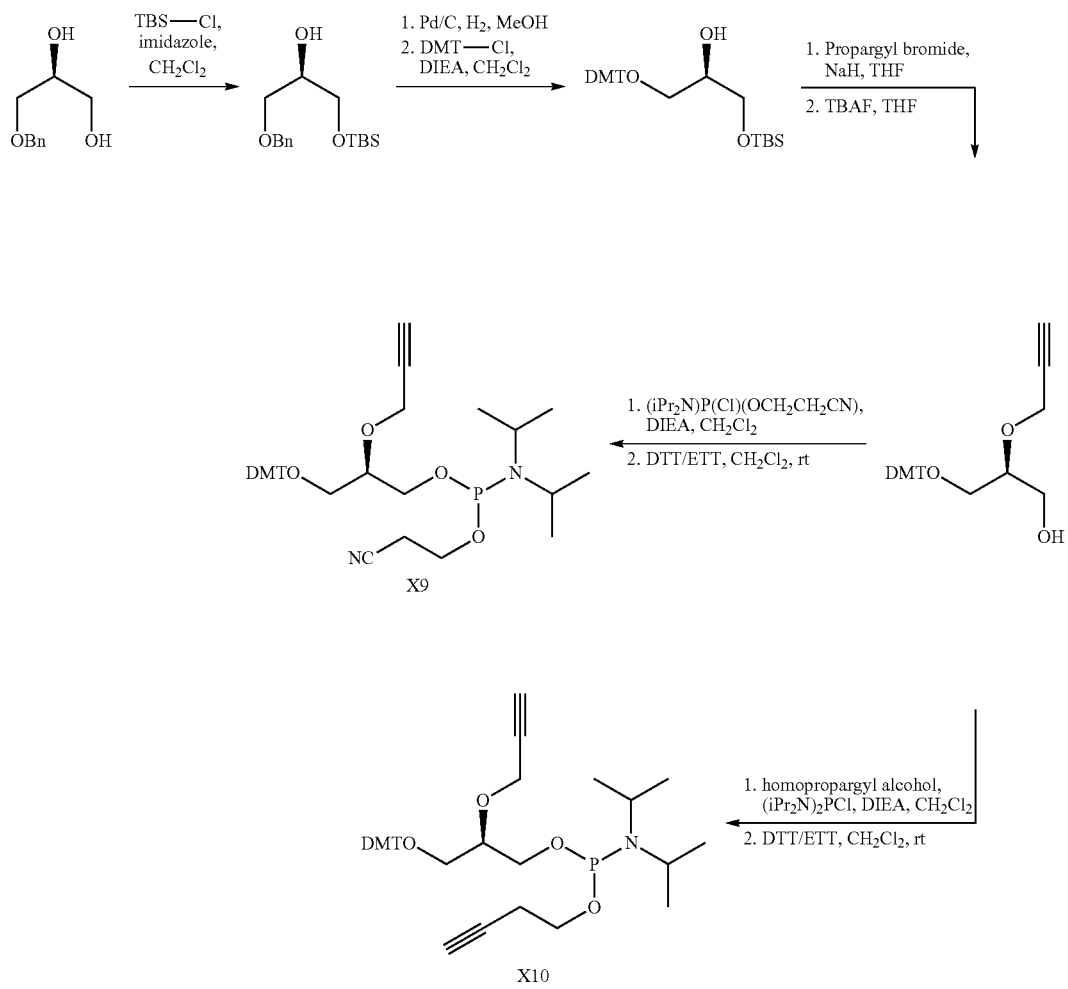

The following are further hydrophilic nucleoside phosphoramidites that can be prepared using methods known in the art and methods described herein:

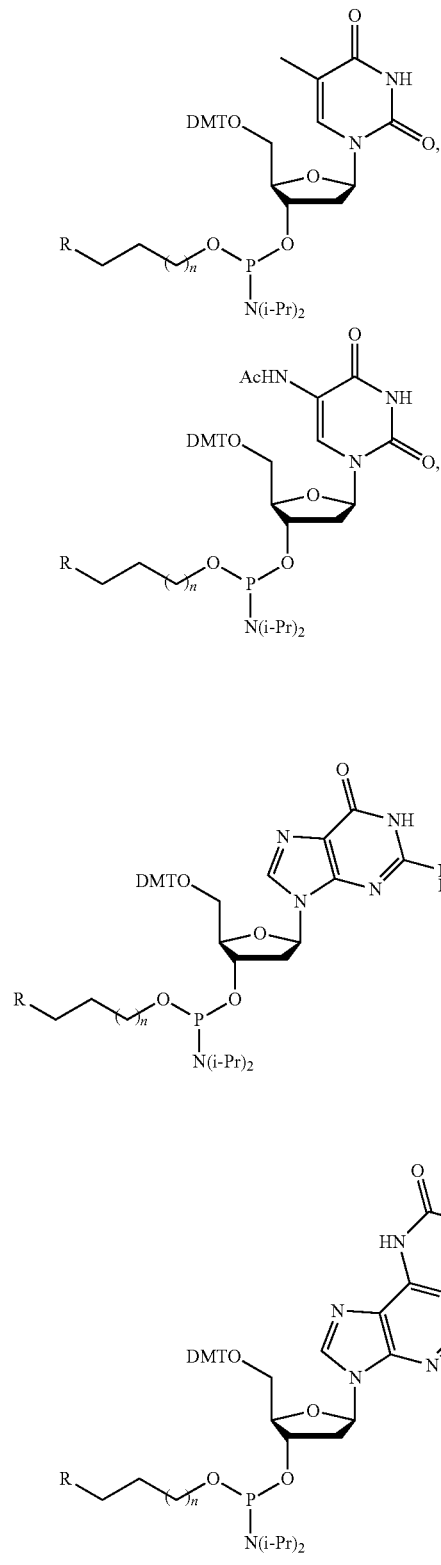

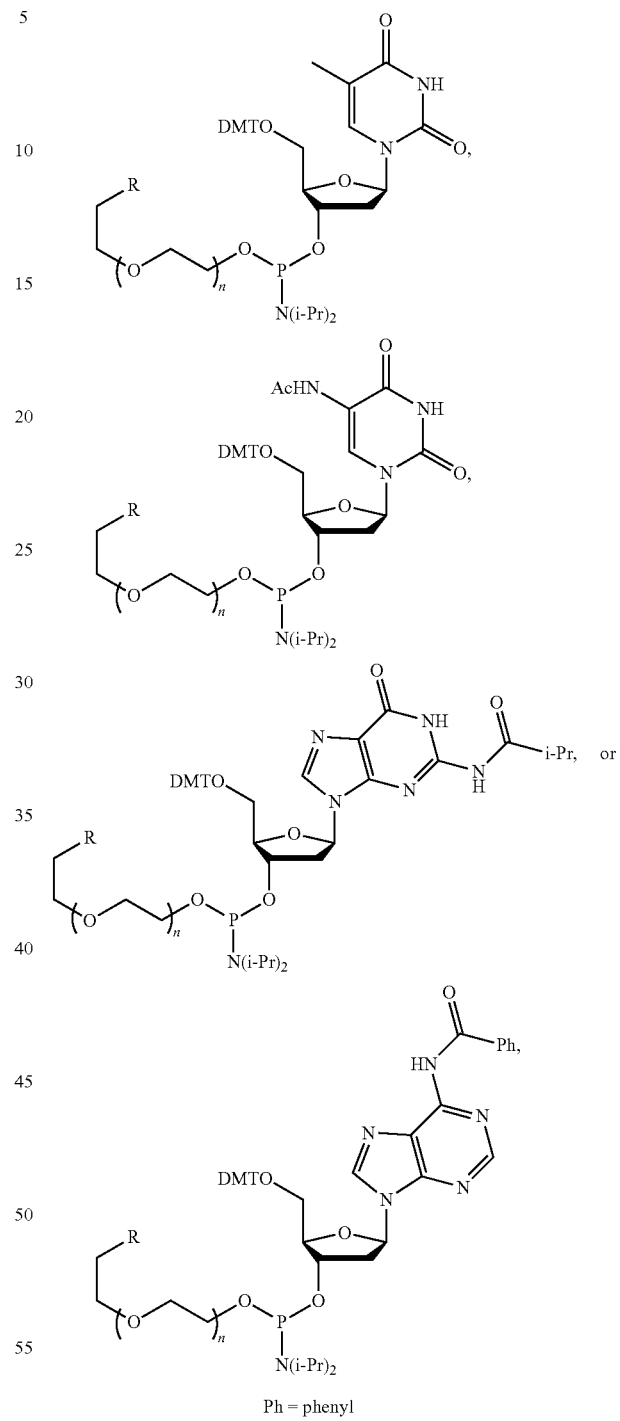

where R is OH, optionally substituted amino, or —$CO_2R^1$ ($R^1$ is H or a counterion), and n is an integer from 1 to 4, Ph = phenyl where R is OH, OAc, OMe, optionally substituted amino, or $CO_2R^1$ ($R^1$ is H or a counterion), and n is an integer from 1 to 51.

The following are further substituted nucleoside phosphoramidites that can be prepared using methods known in the art and methods described herein:

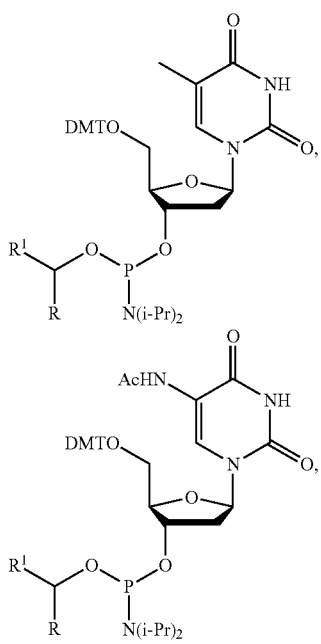
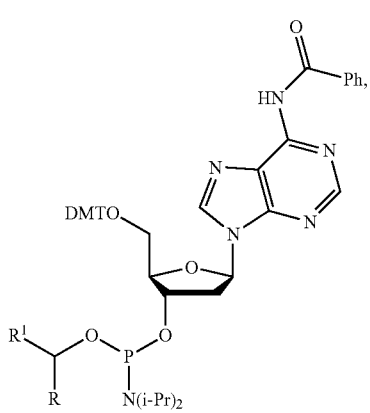
Ph = phenyl
where each of R and R[1] is independently H or optionally substituted $C_{1-6}$ alkyl (e.g., Me, Et, i-Pr, or n-Bu).
The following phosphoramidites are purchased from Glen Research (Sterling, Va.) or ChemGenes (Wilmington, Mass.) or prepared using standard protocols described herein:
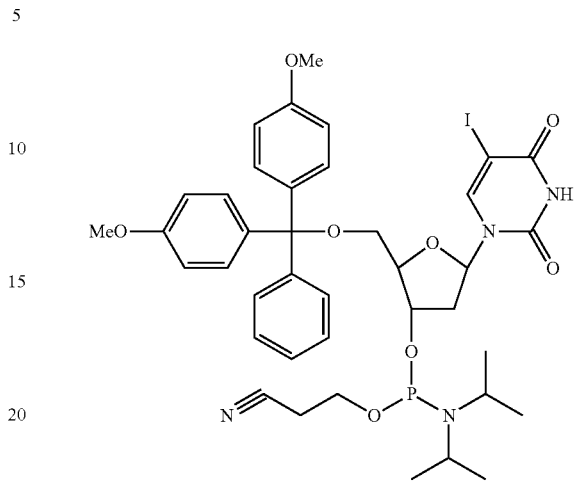
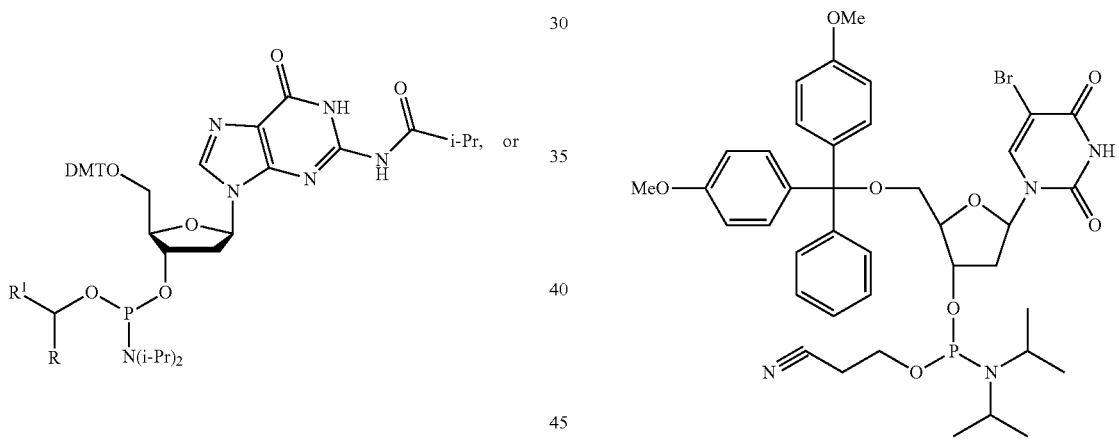

247
-continued
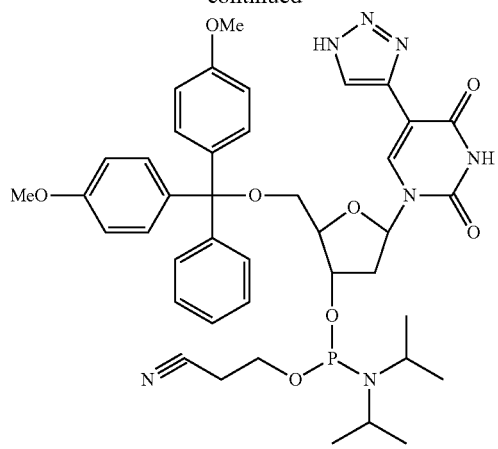
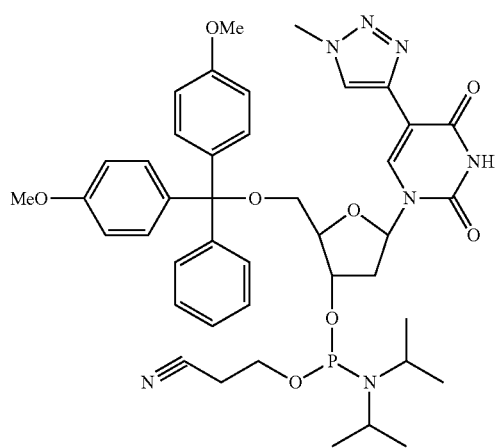
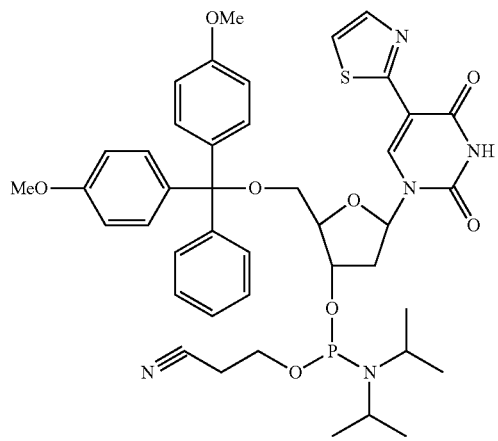
248
-continued
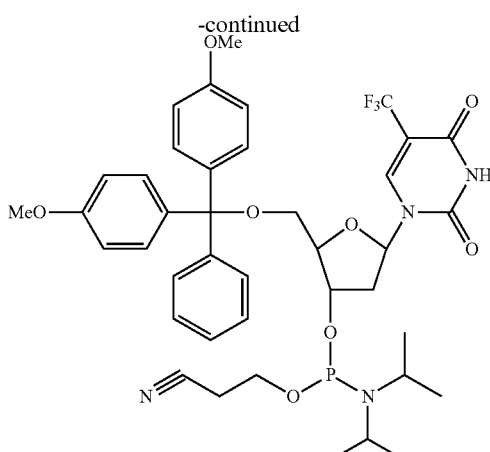
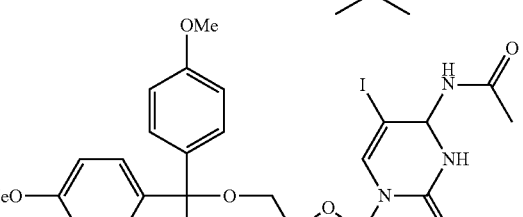
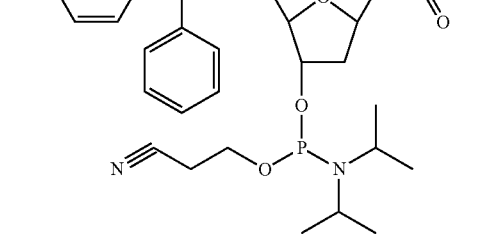
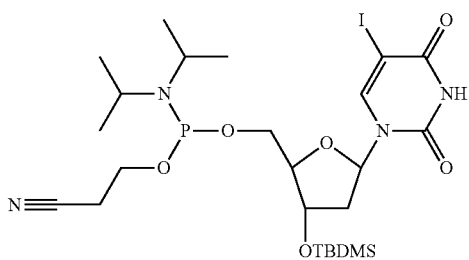
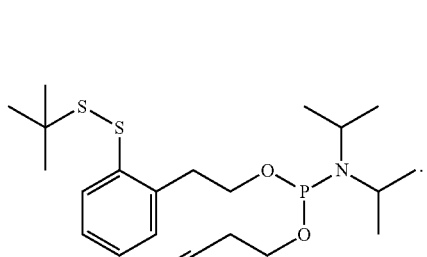
These intermediates may be used in the preparation of polynucleotides of the invention (e.g., polynucleotides containing a 5'-terminal modified nucleoside). Non-limiting examples of 5'-terminal modified nucleosides are 5-halouridine, 5-alkynyluridine, 5-heteroaryluridine, and 5-halocytidine.

5′-Capping:
a) 5′-5′-Capping:
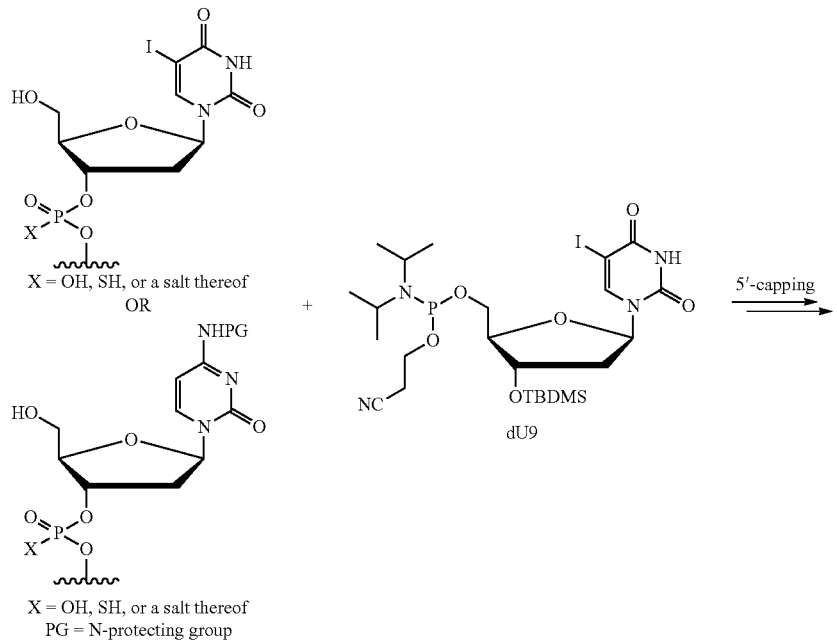
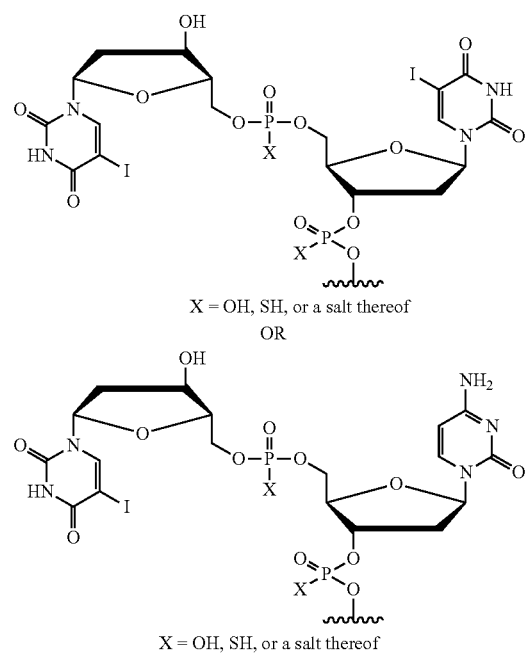

b) 5'-Phosphate or phosphorothioate capping:

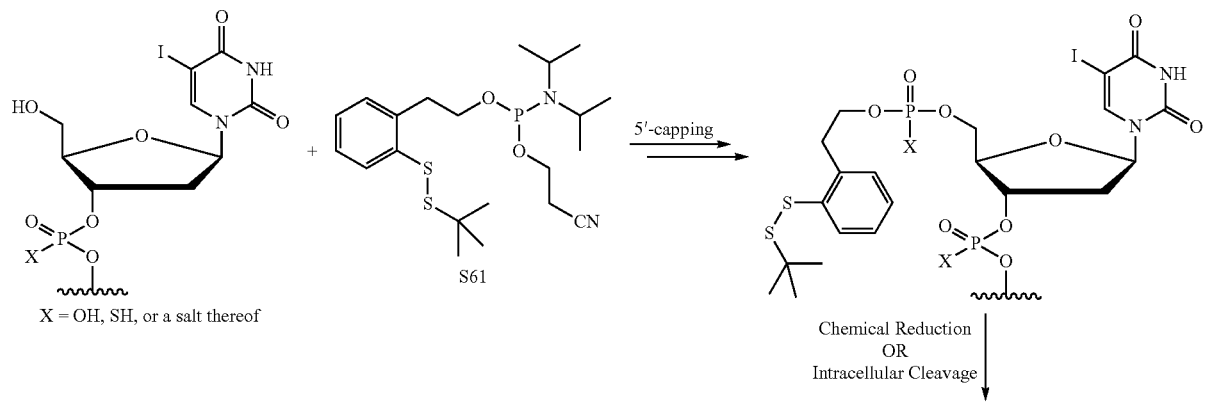

-continued

X = OH, SH, or a salt thereof

Synthesis of Small Molecule-based Targeting Moieties

Exemplary compounds useful for the preparation of small molecule-based targeting moieties are described in WO 2015/188197 (e.g., compounds M1-M30 described in WO 2015/188197).

Synthesis of Glucitol Auxiliary Moieties

Exemplary compounds useful for the preparation of glucitol-based auxiliary moieties are described in WO 2015/188197 (e.g., compounds POH1-POH10 described in WO 2015/188197).

General Polynucleotide Synthesis:

General Scheme:

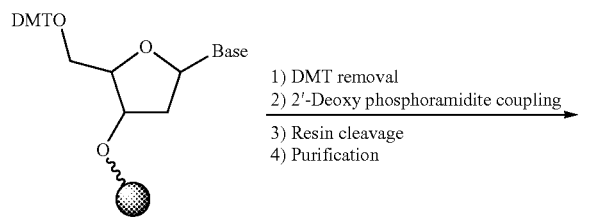

-continued

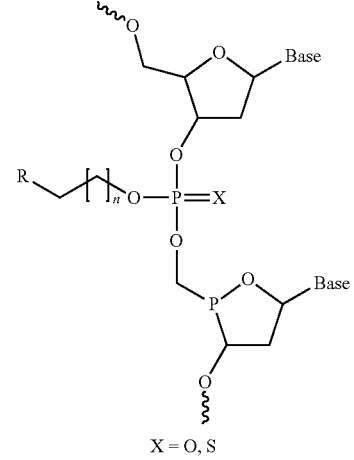

Experimental Details

Automated polynucleotide synthesis (1 µmol scale) was carried out on MerMade 6 or 12 with the following reagents and solvents:

Oxidizer—0.02M I₂ in THF/pyridine/H₂O (60 s oxidation per cycle),

Sulfurizing Reagent II—dithiazole derivative/pyridine/acetonitrile (0.05 M, in 6:4 pyridine:acetonitrile) (60 s per cycle)

Deblock—3% trichloroacetic acid (2×40 s deblocks per cycle),

Cap Mix A—THF/2,6-lutidine/Ac2O (60 s capping per cycle), and

Cap Mix B—16% methyl imidazole in THE (60 s capping per cycle)

Exceptions to standard polynucleotide synthesis conditions were as follows:
 CPG supports with a non-nucleosidic linker called Unylinker was used.
 All 2'-deoxyribose-phosphoramidites were resuspended to 100 mM in 100% anhydrous acetonitrile prior to synthesis, except some of the modified 2'-deoxy-phosphoramidites were dissolved to 100 mM in THE/acetonitrile mixture (1:4) depend on the solubility of the starting material.
 Phosphoramidite activation was performed with a 2.5-fold molar excess of 5-benzylthio-1H-tetrazole (BTT). Activated 2'-deoxyribose-phosphoramidites were coupled for 2×1 minute coupling per insertion and modified phosphoramidites were coupled for 2×3 minute coupling per insertion.
 Sulfurization of the backbone was performed with 0.05M Sulfurizing Reagent II in pyridine/acetonitrile (6:4) for 1 min.

Polynucleotide Deprotection & Purification Protocol:

Following automated polynucleotide synthesis, solid support, and base protecting groups (such as A-Bz, C-Ac, G-iBu, etc.) and methyl esters of phosphotriesters were cleaved and de-protected in 1 mL of AMA (1:1 ratio of 36% aq. ammonia and 40% methylamine in methanol) for 2 h or more at room temperature followed by centrifugal evaporation.

Crude polynucleotide pellets were resuspended in 100 μL of 50% acetonitrile, briefly heated to 65° C. and vortexed thoroughly.

For polynucleotide purification, 100 μL crude polynucleotides were injected onto RP-HPLC with the following buffers/gradient:
 Buffer A=50 mM TEAA in Water;
 Buffer B=90% Acetontrile; and
 Flow Rate=1 mL/min;
 Gradient:
  0-2 min (100% Buffer A/0% Buffer B),
  2-42 min (0% to 60% Buffer B), and
  42-55 min (60% to 100% Buffer B).

DBCO Conjugation and Purification Protocol:

DBCO NHS ester was conjugated to the crude 2'-deoxy DMT-polynucleotide as described here. The crude polynucleotide pellet was suspended into 45 μL DMSO, briefly heated to 65° C. and vortexed thoroughly. 5 μL of DIPEA was added followed by DBCO-NHS ester (30 eq), which was pre-dissolved in DMSO (1M). The reaction was allowed to stand for 10 minutes or until product formation was confirmed by MALDI. Total 80 μL of crude polynucleotide samples were injected onto RP-HPLC with the following buffers/gradient:
 Buffer A=50 mM TEAA in Water
 Buffer B=90% Acetonitrile
 Flow Rate=1 mL/min
 Gradient:
  0-2 min (90% Buffer A/10% Buffer B)
  2-42 min (0% to 60% Buffer B)
  42-55 min (60% to 100% Buffer B).

Across the dominant RP-HPLC peaks, 0.5 mL fractions were collected and analyzed by MALDI-TOF mass spectrometry to confirm presence of desired mass. Mass-selected, purified fractions were frozen and lyophilized. Once dry, fractions were re-suspended, combined with corresponding fractions, frozen and lyophilized.

DMT Cleavage: lyophilized pellets were suspended in 20 μL of 50% acetonitrile and added 80 μL of acetic acid, samples were kept standing at room temperature for 1 h, frozen and lyophilized. The dried samples were re-dissolved in 20% acetonitrile and desalted through NAP 10 (Sephadex™-G25 DNA Grade) columns. Collected, pure fractions were frozen and lyophilized for final product.

General Conjugation Schemes Using Abasic Spacers:

Click reaction—General Scheme:

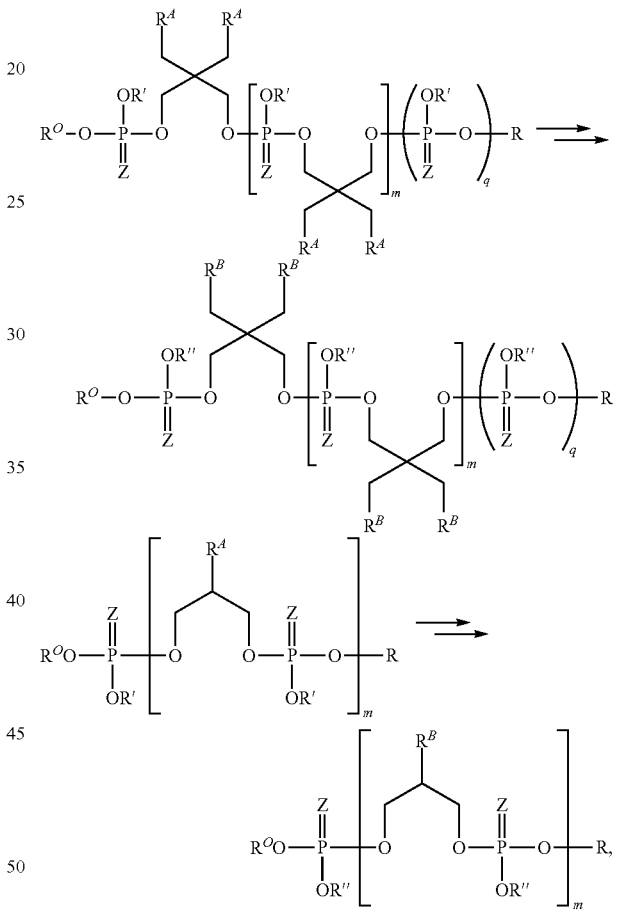

where
 each q is 0 or 1;
 each m is an integer from 0 to 5;
 Z is O or S;
 $R^O$ is a bond to a nucleoside in a polynucleotide;
 R is a bond to H, a nucleoside in a polynucleotide, to solid support, or to a capping group (e.g., —(CH₂)₃—OH);
 each R' is independently H, -$Q^1$-$Q^{41}$, a bioreversible group, or a non-bioreversible group;
 each R" is independently H, -$Q^1$-$Q^4$-$Q^2$-T, a bioreversible group, or a non-bioreversible group;
 each $R^A$ is independently H or —$OR^C$, where $R^C$ is -$Q^1$-$Q^{41}$, a bioreversible group, a non-bioreversible group, or a bond to solid support;

each $R^B$ is independently H or —$OR^D$, where $R^D$ is -$Q^1$-$Q^4$-$Q^2$-T, a bioreversible group, or a non-bioreversible group;
where
each $Q^1$ is independently a divalent, trivalent, tetravalent, or pentavalent group, in which one valency is bonded to $Q^4$ or $Q^{41}$; a second valency is open, and each of the remaining valencies, when present, is independently bonded to an auxiliary moiety;
each $Q^2$ is independently a divalent, trivalent, tetravalent, or pentavalent group, in which one valency is bonded to $Q^4$; a second valency is bonded to T, and each of the remaining valencies, when present, is independently bonded to an auxiliary moiety;
$Q^4$ is 1,2,3-triazole-1,4-diyl, optionally substituted $C_{6-16}$ triazoloheterocyclylene (e.g., 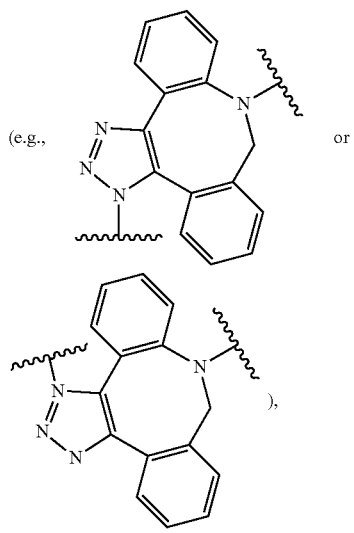 or

), optionally substituted $C_{8-16}$ triazolocycloalkenylene (e.g., 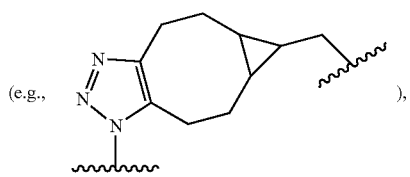 [SMILES: *CC1C2CCc3nnn(*)c3CCC12] ), or a dihydropyridazine group (e.g., trans- 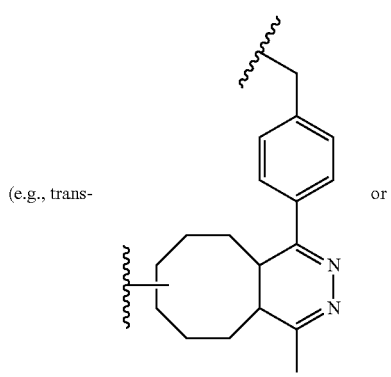 or

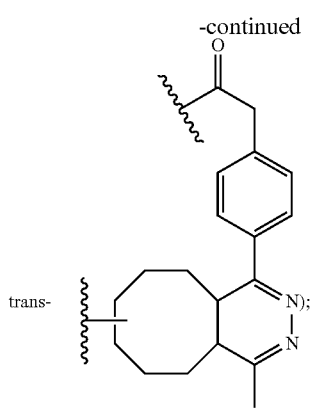

trans- );

$Q^{A1}$ is optionally substituted $C_{2-12}$ alkynyl, optionally substituted $C_{6-16}$ heterocyclyl containing an endocyclic carbon-carbon triple bond (e.g., 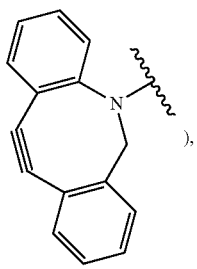 ), optionally substituted $C_{8-16}$ cycloalkynyl (e.g., 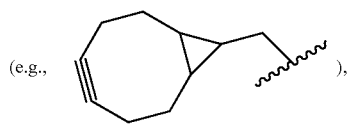 [SMILES: *CC1C2CCC#CCCC12] ), or optionally substituted $C_{4-8}$ strained cycloalkenyl (e.g., rans-cyclooctenyl); and
T is a targeting moiety,
provided that the starting materials contain at least one -$Q^1$-$Q^{A1}$, and products contain -$Q^1$-$Q^4$-$Q^2$-T; and
provided that the starting materials and products contain 0 or 1 bonds to a solid support.

Conjugation Methods
Cu-Catalyzed Click Reaction
Copper-THPTA Complex Preparation
A 5 mM aqueous solution of copper sulfate pentahydrate ($CuSO_4$-$5H_2O$) and a 10 mM aqueous solution of tris(3-hydroxypropyltriazolylmethyl)amine (THPTA) were mixed 1:1 (v/v) (1:2 molar ratio) and allowed to stand at room temperature for 1 hour. This complex can be used to catalyze Huisgen cycloaddition, e.g., as shown in the general conjugation schemes below.
General Procedure (100 nM Scale):
To a solution of 710 µL of water and 100 µL tert-butanol (10% of final volume) in a 1.7 mL Eppendorf tube was added 60 µL of the copper-THPTA complex followed by 50 µL of a 2 mM solution of the oligo, 60 µL of a 20 mM aqueous sodium ascorbate solution and 20 µL of a 10 mM solution of targeting moiety-azide. After thorough mixing the solution was allowed to stand at room temperature for 1 hour. Completion of the reaction was confirmed by gel analysis. The reaction mixture is added to a screw cap vial containing 5-10 fold molar excess of SiliaMetS® TAAcONa (resin bound EDTA sodium salt). The mixture is stirred for 1 hour. This mixture is then eluted through an Illustra™ Nap™-10 column Sephadex™. The resulting solution is then frozen and lyophilized overnight.

Conjugation Through Amide Linkage:

Conjugation through amidation may be performed under the amidation reaction conditions known in the art. See, e.g., Aaronson et al., *Bioconjugate Chem.* 22:1723-1728, 2011.

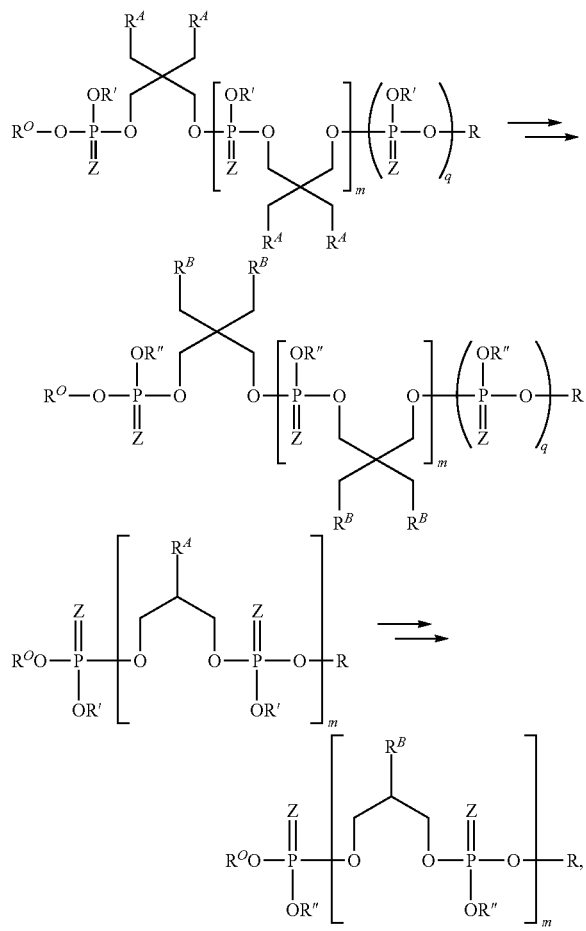

where
each q is 0 or 1;
each m is an integer from 0 to 5;
Z is O or S;
$R^O$ is a bond to a nucleoside in a polynucleotide;
R is a bond to H, a nucleoside in a polynucleotide, to solid support, or to a capping group (e.g., —(CH$_2$)$_3$—OH);
each R' is independently H, -Q$^1$-Q$^{41}$, a bioreversible group, or a non-bioreversible group;
each R'' is independently H, -Q$^1$-Q$^4$-Q$^1$-T, a bioreversible group, or a non-bioreversible group;
each $R^A$ is independently H or —OR$^C$, where R$^C$ is-Q$^1$-Q$^{41}$, a bioreversible group, or a non-bioreversible group;
each $R^B$ is independently H or —OR$^D$, where R$^D$ is -Q$^1$-Q$^4$-Q$^2$-T, a bioreversible group, or a non-bioreversible group;

where
each Q$^1$ is independently a divalent, trivalent, tetravalent, or pentavalent group, in which one valency is bonded to Q$^4$ or Q$^{41}$, the second valency is open, and each of the remaining valencies, when present, is independently bonded to an auxiliary moiety;
each Q$^2$ is independently a divalent, trivalent, tetravalent, or pentavalent group, in which one valency is bonded to Q$^4$, the second valency is bonded to T, and each of the remaining valencies, when present, is independently bonded to an auxiliary moiety;
Q$^4$ is optionally substituted C$_{2-12}$ heteroalkylene containing —C(O)—N(H)— or —N(H)—C(O)—;
Q$^{41}$ is —NHR$^{N1}$ or —COOR$^{12}$, where R$^{N1}$ is H, N-protecting group, or optionally substituted C$_{1-6}$ alkyl, and R$^{12}$ is H, optionally substituted C$_{1-6}$ alkyl, or O-protecting group; and
T is a targeting moiety,
provided that the starting materials contain at least one -Q$^1$-Q$^{41}$, and products contain -Q$^1$-Q$^4$-Q$^2$-T.

Solution Phase Conjugation:

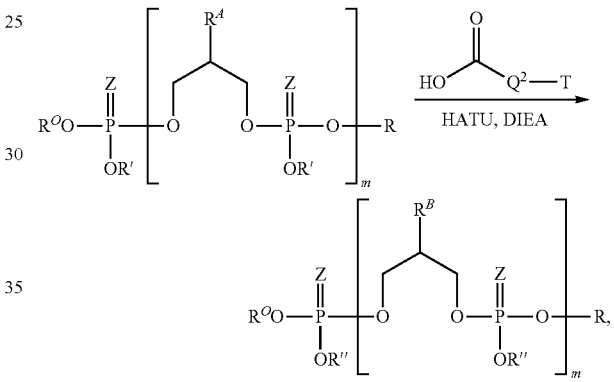

where
m is an integer from 0 to 5;
Z is O or S;
$R^O$ is a bond to a nucleoside in a polynucleotide;
R is a bond to H, a nucleoside in a polynucleotide, or to a capping group;
each R' is independently H, -Q$^1$-NH$_2$, a bioreversible group, or a non-bioreversible group; each R'' is independently H, -Q$^1$-NH—CO-Q$^2$-T, a bioreversible group, or a non-bioreversible group;
each $R^A$ is independently H or —OR$^C$, where R$^C$ is -Q$^1$-NH$_2$, a bioreversible group, or a non-bioreversible group;
each $R^B$ is independently H or —OR$^D$, where R$^D$ is -Q$^1$-NH—CO-Q$^2$-T, a bioreversible group, or a non-bioreversible group;
where
each Q$^1$ is independently a divalent, trivalent, tetravalent, or pentavalent group, in which one valency is bonded to —NH—CO— or —NH$_2$, the second valency is open, and each of the remaining valencies, when present, is independently bonded to an auxiliary moiety;
each Q$^2$ is independently a divalent, trivalent, tetravalent, or pentavalent group, in which one valency is bonded to —NH—CO—, the second valency is a bond to T, and each of the remaining valencies, when present, is independently bonded to an auxiliary moiety; and T is a targeting moiety, provided that the starting material contains -Q¹-NH₂, and the product contains -Q¹-NH—CO-Q²-T.

On-Support Conjugation:

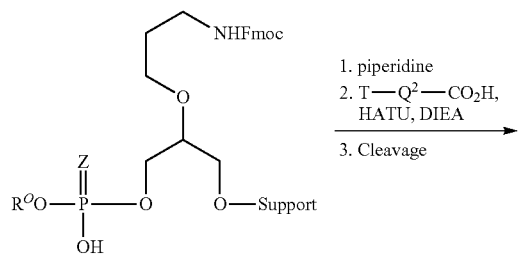

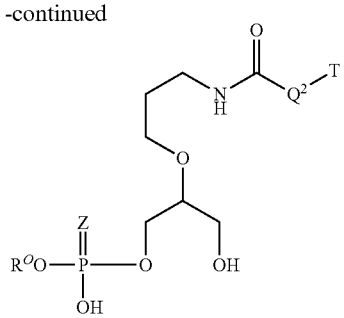

where
Z is O or S;
$R^O$ is a bond to a nucleoside in a polynucleotide;
each $Q^2$ is independently a divalent, trivalent, tetravalent, or pentavalent group, in which one valency is bonded to —NH—CO—, the second valency is a bond to T, and each of the remaining valencies, when present, is independently bonded to an auxiliary moiety; and
T is a targeting moiety.

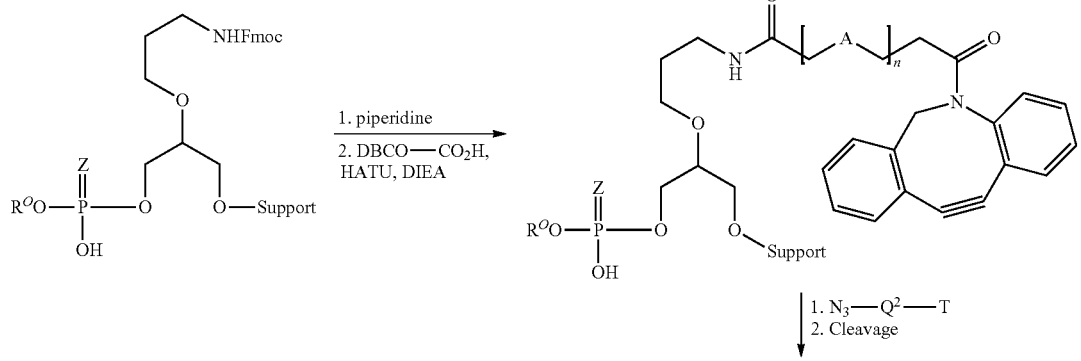

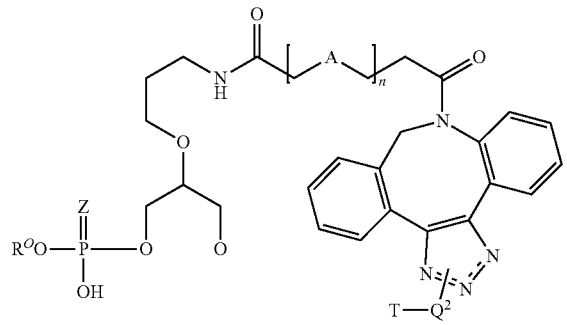

where
n is an integer from 1 to 8;
A is O or —CH$_2$—;
Z is O or S;
R$^O$ is a bond to a nucleoside in a polynucleotide;

each Q$^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and
T is a targeting moiety.

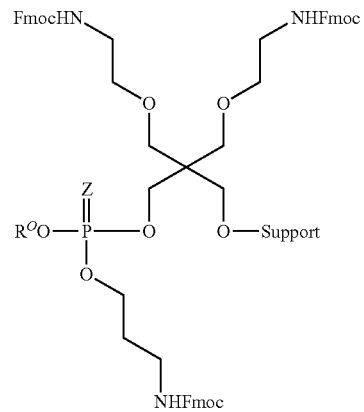

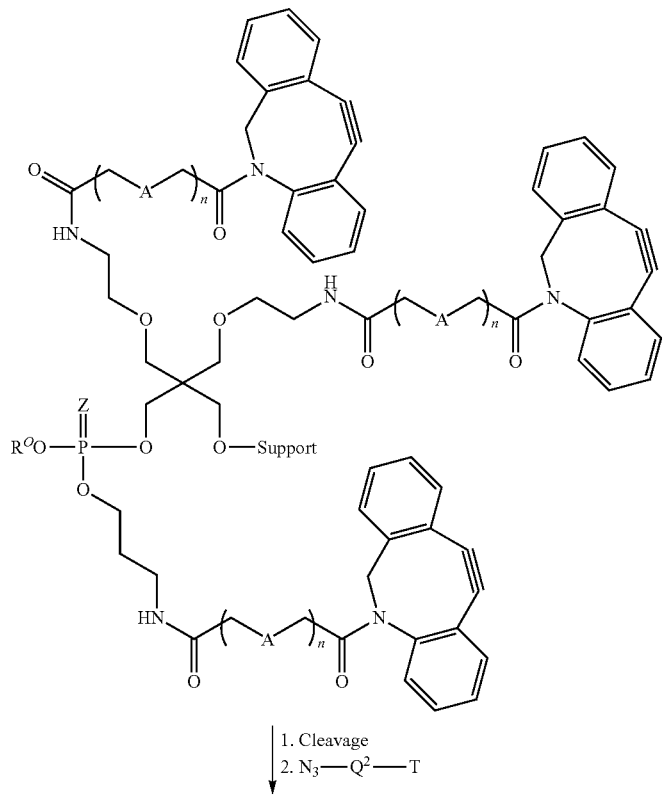

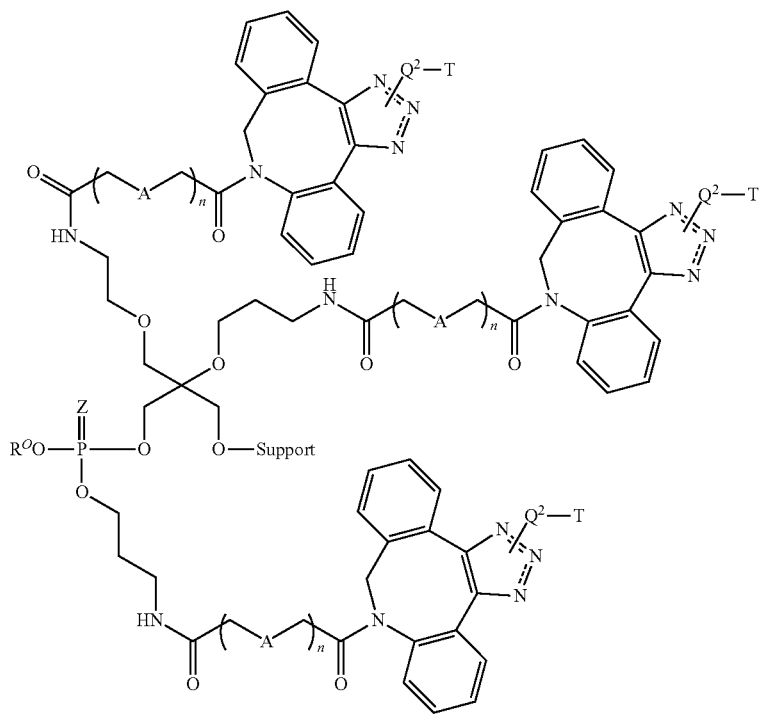

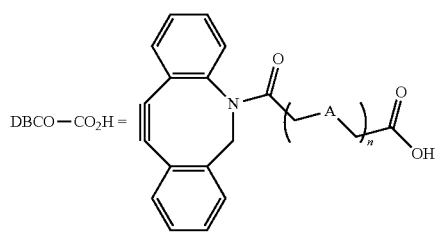

where
n is an integer from 1 to 8;
A is O or —CH$_2$—;
Z is O or S;
R$^O$ is a bond to a nucleoside in a polynucleotide;
each Q$^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and
T is a targeting moiety.

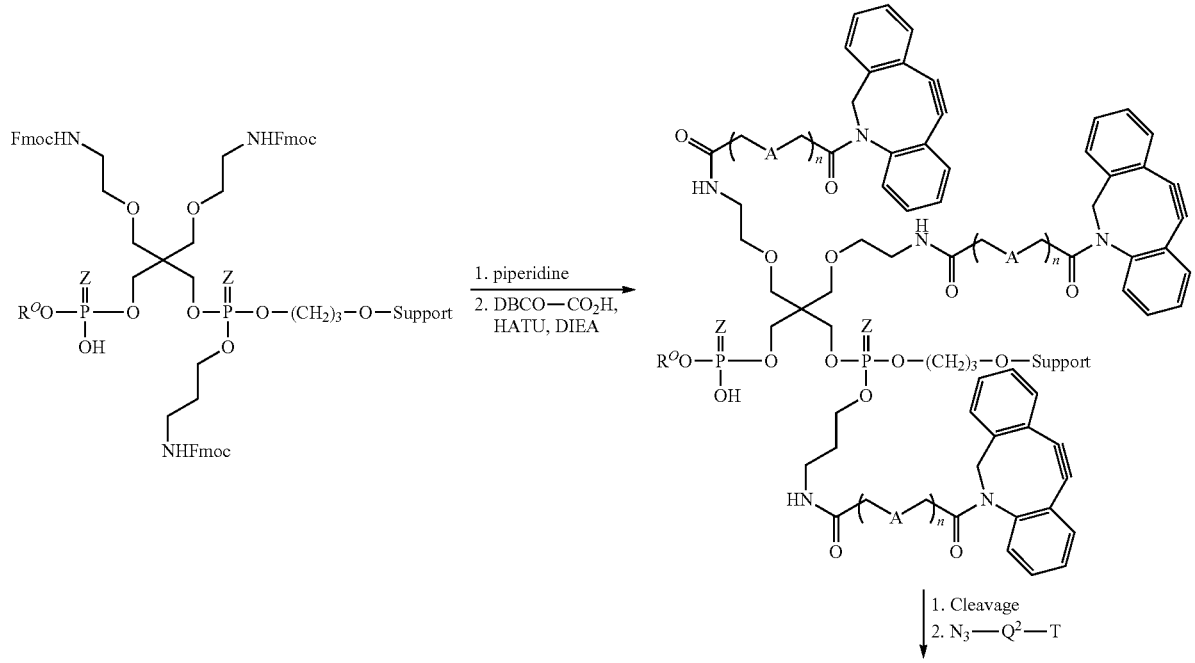

-continued

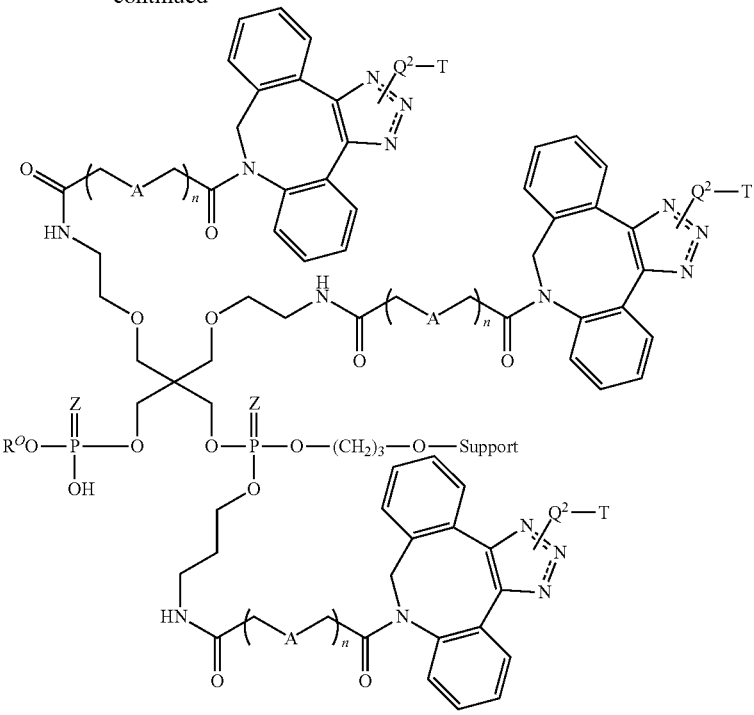

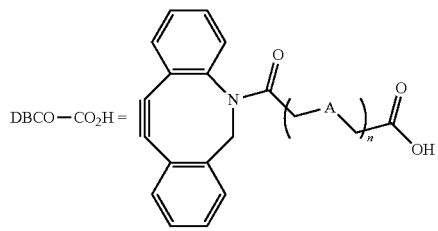

where n is an integer from 1 to 8;

A is O or —$CH_2$—;

Z is O or S;

$R^O$ is a bond to a nucleoside in a polynucleotide;

each $Q^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and each T is independently a targeting moiety.

Representative Example of Fmoc Deprotection of a Phosphotriester:

A polynucleotide including a phosphotriester with Fmoc-protected amine was subjected to deprotection conditions resulting in Fmoc deprotection without observable conversion of the phosphotriester into a phosphodiester.

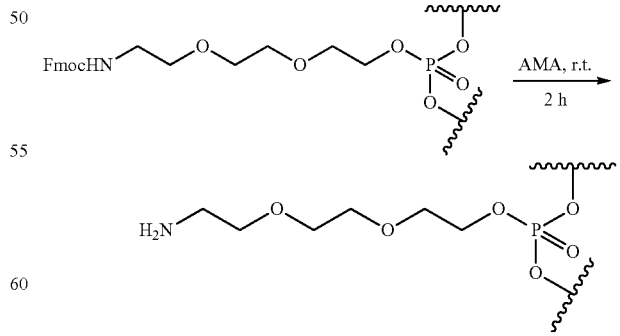

DBCO-NHS Conjugation to p68—Representative Example:

DBCO-NHS conjugation to the amino group in the phosphotriester was complete in 10 min at room temperature, as evidenced by mass spectrometric analysis.

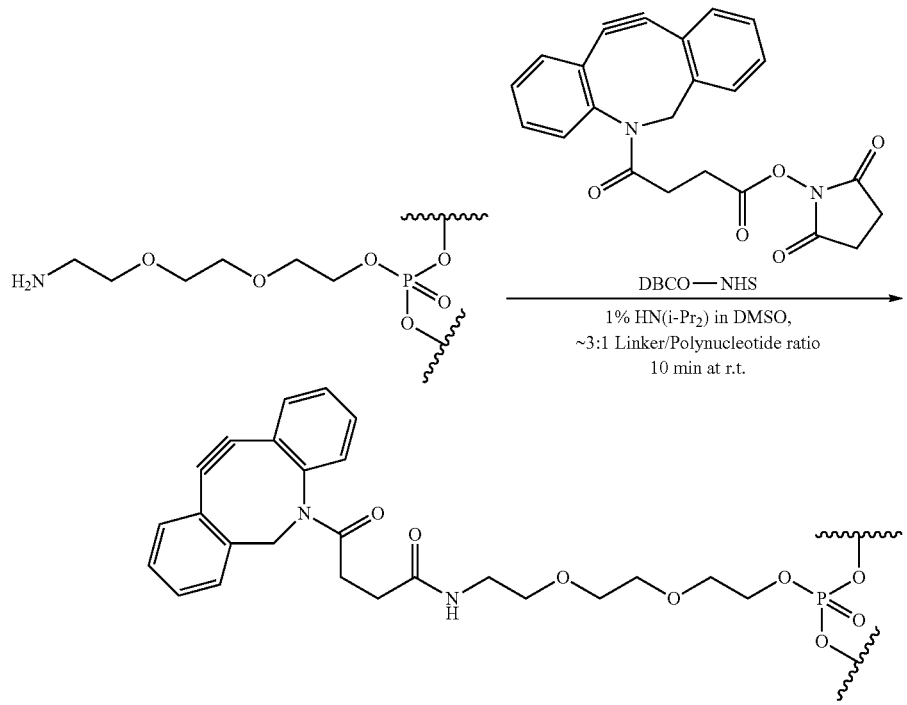

RP-HPLC purification of p68 (see Table 2) containing a DBCO conjugating group was performed using the following conditions:
Buffer A=50 mM TEAA in Water;
Buffer B=90% Acetontrile; and
Flow Rate=1 mL/min;
Gradient:
0-2 min (100% Buffer A/0% Buffer B),
2-22 min (0% to 100% Buffer B), and
22-25 min (100% Buffer B).

A similar procedure may be used to prepare a polynucleotide using, e.g., 2'-modified nucleoside phosphoramidites, such as those described herein. Such a procedure is provided in International Patent application PCT/US2015/034749; the disclosure of the disulfide phosphotriester oligonucleotide synthesis in PCT/US2015/034749 is hereby incorporated by reference.

The general procedure described herein was followed to prepare immunomodulating polynucleotides listed in Table 2.

TABLE 2

| Compound # | Sequence (5' to 3') | SEQ ID NO: | A | B | C | D | E | F | G | H | I | J |
|---|---|---|---|---|---|---|---|---|---|---|---|---|
| p1 | tcgtcgttttgtcgttttgtcgtt | 1 | 120 | 110 | 175 | 50 | >1000 | | | | | |
| p2 | NH2-C6-tcgtcgttttgtcgttttgtcgtt | 2 | | | | | | | | | | |
| p3 | NH2-C6-S-S-C6-tcgtcgttttgtcgttttgtcgtt | 3 | | | | | | | | | | |
| p4 | DBCO-tcgtcgttttgtcgttttgtcgtt | 4 | >1000 | | >1000 | | | | | | | |
| p5 | DBCO-C6-S-S-C6-tcgtcgttttgtcgttttgtcgtt | 5 | | | | | | | | | | |
| p6 | TCGTCGTTTTGTCGTTTGTCGTT | 6 | | | | >1000 | >1000 | >1000 | | | | |
| p7 | DBCO-C6-S-S-C6-TCGTCGTTTTGTCGTTTGTCGTT | 7 | | | | | | | | | | |
| p8 | tgctgcttttgtgcttttgtgctt | 8 | | | | >1000 | >1000 | >1000 | | | | |
| p9 | DBCO-C6-S-S-C6-tgctgcttttgtg cttttgtgctt | 9 | | | | | | | | | | |
| p10 | tcgtcgttttgtcgttttgtcgtt | 10 | | | | | | | | | | |
| p11 | TCGTCGTTTTGTCGTTTGTCGTT | 11 | | | | | | | | | | |
| p12 | DBCO-C6-S-S-C6-tcgtcgttttgtcgttttgtcgtt | 12 | | | | | | | | | | |
| p13 | DBCO-C6-S-S-C6-TCGTCGTTTTGTCGTTTGTCGTT | 13 | | | | | | | | | | |
| p14 | DBCO-tcgtcgttttgtcgttttgtcgtt | 14 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p15 | DBCO-TCGTCGTTTTGTCGTTTTGTCGTT | 15 | | | | | | | | | | |
| p16 | DBCO-tccatgacgttcctgacgtt | 16 | | | | | | | | | | |
| p17 | DBCO-TCCATGACGTTCCTGACGTT | 17 | | | | | | | | | | |
| p18 | tccatgacgttcctgacgtt | 18 | | | 1000 | >1000 | 40 | 22.6 | 24.4 | 26 | | |
| p19 | DBCO-tccatgacgttcctgacgtt | 19 | | | | | | >1000 | | >1000 | | |
| p20 | TCCATGACGTTCCTGACGTT | 20 | | | | >1000 | >1000 | >1000 | | | | |
| p21 | DBCO-TCCATGACGTTCCTGACGTT | 21 | | | | | | | | | | |
| p22 | tccatgagcttcctgagctt | 22 | | | | | | >1000 | | >1000 | | |
| p23 | DBCO-tccatgagcttcctgagctt | 23 | | | | | | | | | | |
| p24 | dtcgtcgtiftgtcgttttgtcgtt | 24 | 500 | >1000 | | | | | | | | |
| p25 | tcgtcgttdttgtcgttttgtcgtt | 25 | >1000 | 800 | | | | | | | | |
| p26 | tcgtcgtiftgdtcgttttgtcgtt | 26 | >1000 | >1000 | | | | | | | | |
| p27 | tcgtcgttttgtcgttdttgtcgtt | 27 | 500 | 800 | | | | | | | | |
| p28 | tcgtcgtifigtcgttttgtcgtdt | 28 | 300 | 800 | | | | | | | | |
| p29 | tcgcgacgttcgcccgacgttcggta | 29 | | | 300 | >1000 | >1000 | 92.8 | | 58 | | |
| p30 | DBCO-tcgcgacgttcgcccgacgttcggta | 30 | | | | | | 183.7 | | 28 | | |
| p31 | tccatgacgttcctgatgct | 31 | | | 1000 | >1000 | 40 | 29.6 | | 27 | | |
| p32 | DBCO-tccatgacgttcctgatgct | 32 | | | | >1000 | >1000 | | | | | |
| p33 | tcgacgttcgtcgttcgtcgttc | 33 | | | 450 | | | 103.2 | | 275 | | |
| p34 | DBCO-tcgacgttcgtcgttcgtcgttc | 34 | | | | | | | | | | |
| p35 | tcgtcgttttgtcgttttgtcgtt | 35 | | | | | | | | | | |
| p36 | DBCO-tcgtcgtifigtcgtifigtcgtt | 36 | | | | | | | | | | |
| p37 | tccatgacgttcctgacgtt | 37 | | | | | | 164.3 | 180 | 28.3 | | |
| p38 | DBCO-tccatgacgttcctgacgtt | 38 | | | | | | | | | | |
| p39 | tccatgacgttcctgacgtt-C3 | 39 | | | | | | 122.2 | 130.8 | | | |
| p40 | TCCATGACGTTCCTGACGTT | 40 | | | | | | >1000 | | | | |
| p41 | TCCATGACGTTCCTGACGTT-C3 | 41 | | | | | | >1000 | | | | |
| p42 | tccatgacgttcctgacgtt | 42 | | | | | | 22.6 | 25.6 | | | |
| p43 | tccatgacgttcctgacgtt-C3 | 43 | | | | | | 19.2 | | | | |
| p44 | TCCATGACGTTCCTGACGTT | 44 | | | | | | >1000 | | | | |
| p45 | TCCATGACGTTCCTGACGTT-C3 | 45 | | | | | | | | | | |
| p46 | tccatgacgttcctgacgtt | 46 | | | | | | 876 | | | | |
| p47 | tccatgacgttcctgacgtt | 47 | | | | | | 615 | | | | |
| p48 | tccatgacgttcctgacgtt | 48 | | | | | | 197.2 | | | | |
| p49 | tccatgacgttcctgacgtt | 49 | | | | | | 75.2 | | | | |
| p50 | tccatgacgttcctgacgtt | 50 | | | | | | 71.3 | | | | |
| p51 | tccatgacgttcctgacgtt | 51 | | | | | | 9.3 | | | | |
| p52 | tccatgacgttcctgacgtt | 52 | | | | | | 29.1 | | | | |
| p53 | GGgggacgatcgtcGGGGGG | 53 | | | | | | | | | | |
| p54 | tcgtcgtcgttcgaacgacgttgat | 54 | | | | | | | | 816 | | |
| p55 | tcgtcgttttcggcgcgcgccg | 55 | | | | | | | | 31.4 | | |
| p56 | tcgcgaacgttcgccgcgttcgaacgcgg | 56 | | | | | | | | 45.5 | | |
| p57 | tcgtcgacgatcggcgcgcgccg | 57 | | | | | | | | | | |
| p58 | tccatgacgttcctgacgtt | 58 | | | | | | | | | | |
| p59 | tccatgacgttcctgacgtt | 59 | | | | | | | | | | |
| p60 | tccatgacgttcctgacgtt | 60 | | | | | | | | | | |
| p61 | tccatgacgttcctgacgtt | 61 | | | | | | | | | | |
| p62 | tccatgacgttcctgacgtt | 62 | | | | | | | | | | |
| p63 | tccatgacgttcctgacgtt | 63 | | | | | | | | | | |
| p64 | tccatgacgttcctgacgtt | 64 | | | | | | | | | | |
| p65 | TCCATGACGTTCCTGACGTT | 65 | | | | | | | | | | |
| p66 | TCCATGACGTTCCTGACGTT | 66 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p67 | TCCATGACG*TT*CCTGACGTT | 67 | | | | | | | | | | |
| p68 | TCCATGACGTT*T*CCTGACGTT | 68 | | | | | | | | | | |
| p69 | TCCATGACGTTCC*T*GACGTT | 69 | | | | | | | | | | |
| p70 | TCCATGACGTTCCTGACGTT | 70 | | | | | | | | | | |
| p71 | TCCATGACGTTCCTGACGT*T* | 71 | | | | | | | | | | |
| p72 | tcgtcgttttgtcgttttgtcgt*t* | 72 | | | | | | | | | | |
| p73 | TCGTCGTTTTGTCGTTTTGTCGT*T* | 73 | | | | | | | | | | |
| p74 | tccatgacgttcctgatgc*t* | 74 | | | | | | | | | | |
| p75 | TCCATGACGTTCCTGATGC*T* | 75 | | | | | | | | | | |
| p76 | *T*CGTCGTTTTGTCGTTTTGTCGTT | 76 | | | | | | | | | | |
| p77 | TC*G*TCGTTTTGTCGTTTTGTCGTT | 77 | | | | | | | | | | |
| p78 | TCGTCG*T*TTTGTCGTTTTGTCGTT | 78 | | | | | | | | | | |
| p79 | TCGTCGT*T*TTGTCGTTTTGTCGTT | 79 | | | | | | | | | | |
| p80 | TCGTCGTT*T*TGTCGTTTTGTCGTT | 80 | | | | | | | | | | |
| p81 | TCGTCGTTT*T*GTCGTTTTGTCGTT | 81 | | | | | | | | | | |
| p82 | TCGTCGTTTTG*T*CGTTTTGTCGTT | 82 | | | | | | | | | | |
| p83 | TCGTCGTTTTGTCG*T*TTGTCGTT | 83 | | | | | | | | | | |
| p84 | TCGTCGTTTTGTCGT*T*TGTCGTT | 84 | | | | | | | | | | |
| p85 | TCGTCGTTTTGTCGTT*T*TGTCGTT | 85 | | | | | | | | | | |
| p86 | TCGTCGTTTTGTCGTTT*T*GTCGTT | 86 | | | | | | | | | | |
| p87 | TCGTCGTTTTGTCGTTTT*G*TCGTT | 87 | | | | | | | | | | |
| p88 | TCGTCGTTTTGTCGTTTTG*T*CGTT | 88 | | | | | | | | | | |
| p89 | tccatGACGTTCCTGACGTT | 89 | | | | | | >1000 | | | | |
| p90 | tccatgacgtTCCTGACGTT | 90 | | | | | | 1000 | | | | |
| p91 | tccatgacgttcctgACGTT | 91 | | | | | | 49 | | | | |
| p92 | tccatGACGTTCCTGACGTT | 92 | | | | | | >1000 | | | | |
| p93 | tccatgacgtTCCTGACGTT | 93 | | | | | | >1000 | | | | |
| p94 | tccatgacgttcctgACGTT | 94 | | | | | | 145 | | | | |
| p95 | TC*G*TCGTTTTGTCGTTTTGTCGTT | 95 | | | | | | | | | | |
| p96 | TC*G*TCGTTTTGTCGTTTTGTCGTT | 96 | | | | | | | | | | |
| p97 | TCGT*C*GTTTTGTCGTTTTGTCGTT | 97 | | | | | | | | | | |
| p98 | TCGTC*G*TTTTGTCGTTTTGTCGTT | 98 | | | | | | | | | | |
| p99 | TCGTCGTTTT*G*TCGTTTTGTCGTT | 99 | | | | | | | | | | |
| p100 | TCGTCGTTTTGT*C*GTTTTGTCGTT | 100 | | | | | | | | | | |
| p101 | TCGTCGTTTTGTC*G*TTTTGTCGTT | 101 | | | | | | | | | | |
| p102 | TCGTCGTTTTGTCGTTTT*G*TCGTT | 102 | | | | | | | | | | |
| p103 | TCGTCGTTTTGTCGTTTTGT*C*GTT | 103 | | | | | | | | | | |
| p104 | TCGTCGTTTTGTCGTTTTGTC*G*TT | 104 | | | | | | | | | | |
| p105 | *T*CCATGACGTTCCTGACGTT | 105 | | | | | | | | | | |
| p106 | T*CC*ATGACGTTCCTGACGTT | 106 | | | | | | | | | | |
| p107 | TC*C*ATGACGTTCCTGACGTT | 107 | | | | | | | | | | |
| p108 | TCC*A*TGACGTTCCTGACG*TT* | 108 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p109 | TCCA*T*GACGTTCCTGA CGTT | 109 | | | | | | | | | | |
| p110 | TCCATG*A*CGTTCCTGA CGTT | 110 | | | | | | | | | | |
| p111 | TCCATGA*C*GTTCCTGA CGTT | 111 | | | | | | | | | | |
| p112 | TCCATGAC*G*TTCCTGA CGTT | 112 | | | | | | | | | | |
| p113 | TCCATGACG*T*TCCTGA CGTT | 113 | | | | | | | | | | |
| p114 | TCCATGACGT*T*CCTGA CGTT | 114 | | | | | | | | | | |
| p115 | TCCATGACGTT*C*CTGA CGTT | 115 | | | | | | | | | | |
| p116 | TCCATGACGTTC*C*TGA CGTT | 116 | | | | | | | | | | |
| p117 | TCCATGACGTTCC*T*GA CGTT | 117 | | | | | | | | | | |
| p118 | TCCATGACGTTCCT*G*A CGTT | 118 | | | | | | | | | | |
| p119 | TCCATGACGTTCCTG*A* CGTT | 119 | | | | | | | | | | |
| p120 | TCCATGACGTTCCTGA *C*GTT | 120 | | | | | | | | | | |
| p121 | TCCATGACGTTCCTGA C*G*TT | 121 | | | | | | | | | | |
| p122 | TCCATGACGTTCCTGA CG*T*T | 122 | | | | | | | | | | |
| p123 | IR700-tccatgacgttcctgacgtt | 123 | | | | | | | | | | |
| p124 | IR700-TCCATGACGTTCCTGA CG*T*T | 124 | | | | | | | | | | |
| p125 | tcgtcgtttcgtcgttttgtcgtt | 125 | | | | | | | | | | |
| p126 | DBCO-TCGTCGTTTTGTCGTTT TGTCGTT | 126 | | | | | | | | | | |
| p127 | DBCO-TCGTCGTTTTGTCGTTT TGTCGTT | 127 | | | | | | | | | | |
| p128 | TGCTGCTTTTGTGCTTT TGTGCTT | 128 | | | | | | | | | | |
| p129 | tcattgGAAAACGTTCTTC GGGGCGTTctt | 129 | | | | | | | | | | |
| p130 | tcattgGAAAAGCTTCTTG CGGGGCTTctt | 130 | | | | | | | | | | |
| p131 | TCATTGGAAAACGTTC TTCGGGGCGTTCTT | 131 | | | | | | | | | | |
| p132 | AAGAACGCCCCGAAGA ACGTTTTCCAATGA | 132 | | | | | | | | | | |
| p133 | TCATTGGAAAACGTTC TTCGGGGCGTTCTT | 133 | | | | | | | | | | |
| p134 | AAGAACGCCCCGAAGA ACGTTTTCCAATGA | 134 | | | | | | | | | | |
| p135 | TCATTGGAAAACGTTC TTCGGGGCGTTCTT | 135 | | | | | | | | | | |
| p136 | AAGAACGCCCCGAAG AACGTTTTCCAATGA | 136 | | | | | | | | | | |
| p137 | TCATTGGAAAACGTTC TTCGGGGCGTTCTT | 137 | | | | | | | | | | |
| p138 | AAGAACGCCCCGAAG AACGTTTTCCAATGA | 138 | | | | | | | | | | |
| p139 | tccatGACGTTCCTGAcgtt | 139 | | | | | | | | | | |
| p140 | TCCATGACGTTCCTGA cgtt | 140 | | | | | | | | | | |
| p141 | tccatGACGTTCCTGACG tt | 141 | | | | | | | | | | |
| p142 | tccatGACGTTCCTGACG *TT* | 142 | | | | | | | | | | |
| p143 | tccatGACGTTCCTGACG *TT* | 143 | | | | | | | | | | |
| p144 | AACGACAAACGACAA AACGACGA | 144 | | | | | | | | | | |
| p145 | AACGACAAACGACAA AACGACG*A* | 145 | | | | | | | | | | |
| p146 | TCGTCGTTTTGTCGTTT TGTCGtT | 146 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p147 | TCGTCGTTTTGTCGTTT TgtcgtT | 147 | | | | | | | | | | |
| p148 | TCGTCGTTTTGTCGTT<u>T</u> TGTCGtT | 148 | | | | | | | | | | |
| p149 | TCGTCGTTTTGTCGTT<u>T</u> TgtcgtT | 149 | | | | | | | | | | |
| p150 | tcgtcGTTTTGTCGTTTT GTCG<u>T</u>T | 150 | | | | | | | | | | |
| p151 | tcgtcgttttgtcgttttgtcg<u>T</u>T | 151 | | | | | | | | | | |
| p152 | tcgtcGTTTTGTCGTTTT GTCG<u>T</u>T | 152 | | | | | | | | | | |
| p153 | tcgtcGTTTTGTCGTTTT GTCG<u>tt</u> | 153 | | | | | | | | | | |
| p154 | tcgtcGTTTTGTCGTTTT GTCG<u>Tt</u> | 154 | | | | | | | | | | |
| p155 | TTCG<u>T</u>CGTTTTGTCGTT TTGTCGTT | 155 | | | | | | | | | | |
| p156 | TTTCG<u>T</u>CGTTTTGTCGT TTTGTCGTT | 156 | | | | | | | | | | |
| p157 | GTTTCG<u>T</u>CGTTTTGTC GTTTTGTCGTT | 157 | | | | | | | | | | |
| p158 | GTTTCG<u>T</u>CGTTTTGTC GTTTTGTCGTT | 158 | | | | | | | | | | |
| p159 | GTTTCG<u>T</u>CGTTTTGTC GTTTTGTCGTT | 159 | | | | | | | | | | |
| p160 | GTTTCG<u>T</u>CGTTTTGTC GTTTTGTCGTT | 160 | | | | | | | | | | |
| p161 | TCG<u>T</u>CGTTTTGTCGTTT TGTCGTT-C3 | 161 | | | | | | | | | | |
| p162 | TCGTCGTTTTGTCGTT<u>T</u> T | 162 | | | | | | | | | | |
| p163 | UCGTCGTTTTGTCGTT TTGTCG<u>tt</u>-C3 | 163 | | | | | | | | | | |
| p164 | C3- UCGTCGTTTTGTCGTT TTGTCG<u>TT</u>-C3 | 164 | | | | | | | | | | |
| p165 | TCGUCGTTTTGTCGTT TTGTCGTT-C3 | 165 | | | | | | | | | | |
| p166 | C3- TCGUCGTTTTGTCGTT TTGTC<u>TT</u>-C3 | 166 | | | | | | | | | | |
| p167 | UCGUCGTTTTGTCGTT TTGTCG<u>T</u>T-C3 | 167 | | | | | | | | | | |
| p168 | C3- UCGUCGTTTTGTCGTT TTGTCG<u>T</u>T-C3 | 168 | | | | | | | | | | |
| p169 | UCG<u>T</u>CGTTTTGTCGTT TTGTCGTT-C3 | 169 | | | | | | | | | | |
| p170 | C3- UCG<u>T</u>CGTTTTGTCGTT TTGTCGTT-C3 | 170 | | | | | | | | | | |
| p171 | TCGTCGTTTTGTCGTTT T | 171 | | | | | | | | | | |
| p172 | TCG<u>T</u>CGTTTTGTCGTT | 172 | | | | | | | | | | |
| p173 | TCG<u>T</u>CGTTTTGTCG | 173 | | | | | | | | | | |
| p174 | TCG<u>T</u>CGTTTTGT | 174 | | | | | | | | | | |
| p175 | UCG<u>T</u>CGTTTTGTCGTT TT | 175 | | | | | | | | | | |
| p176 | UTCG<u>T</u>CGTTTTGTCGT T | 176 | | | | | | | | | | |
| p177 | UCG<u>T</u>CGTTTTGTCG | 177 | | | | | | | | | | |
| p178 | UCG<u>T</u>CGTTTTGT | 178 | | | | | | | | | | |
| p179 | UCGUCGTTTTGTCGTT TTGTCG<u>T</u>T-C3 | 179 | | | | | | | | | | |
| p180 | UCGTCGTTTTGTCGTT TTGTCG<u>T</u>T-C3 | 180 | | | | | | | | | | |
| p181 | UCGTCG<u>T</u>TTTGTCGTT TTGTCGTT-C3 | 181 | | | | | | | | | | |
| p182 | UCGTCG<u>T</u>TTTGTCGTT TTGTCGTT-C3 | 182 | | | | | | | | | | |
| p183 | UCGTCGTTTTGTCGTT TTGTCGTT-C3 | 183 | | | | | | | | | | |
| p184 | TCCATGACGTTCCTGA TGC<u>T</u>-C3 | 184 | | | | | | | | | | |
| p185 | tccatgacgttcctgatgc<u>t</u>-C3 | 185 | | | | | | | | | | |
| p186 | <u>t</u>ccatgacgttcctgatgct-C3 | 186 | | | | | | | | | | |
| p187 | UCG<u>T</u>CGTTTGTCGTT- C3 | 187 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p188 | *U*CG*T*CGTTGTCGTT-C3 | 188 | | | | | | | | | | |
| p189 | *U*CG*T*CGTGTCGTT-C3 | 189 | | | | | | | | | | |
| p190 | *U*CG*T*CGTTCGTT-C3 | 190 | | | | | | | | | | |
| p191 | *U*CG*T*CGTCGTT-C3 | 191 | | | | | | | | | | |
| p192 | *U*GC*T*GCTTTTGTGCTTTTGTGCTT | 192 | | | | | | | | | | |
| p193 | TCCATGACGTTCCTGACGT*T*-C3 | 193 | | | | | | | | | | |
| p194 | tccatgacgttcctgacgt*t*-C3 | 194 | | | | | | | | | | |
| p195 | *T*CCATGACGTTCCTGACGTT-C3 | 195 | | | | | | | | | | |
| p196 | *t*ccatgacgttcctgacgtt-C3 | 196 | | | | | | | | | | |
| p197 | TAACGACAAAACGACAAAACGACGA | 197 | | | | | | | | | | |
| p198 | AACGACAAAACGACAAAACGACGA*T*-C3 | 198 | | | | | | | | | | |
| p199 | *U*CG*T*CGttttgtCGTT-C3 | 199 | | | | | | | | | | |
| p200 | *U*CG*T*CGttttgtCGTT-C3 | 200 | | | | | | | | | | |
| p201 | *U*CG*T*CGttTTGTCGTT-C3 | 201 | | | | | | | | | | |
| p202 | *U*CG*T*CGTTttGTCGTT-C3 | 202 | | | | | | | | | | |
| p203 | *U*CG*T*CGTTTTgtCGTT-C3 | 203 | | | | | | | | | | |
| p204 | *U*CG*T*CGTTTTGTCGTT-C3 | 204 | | | | | | | | | | |
| p205 | *U*CG*T*CGTTTTGTCGTT-C3 | 205 | | | | | | | | | | |
| p206 | *U*CG*T*CGTTTTGTCGTT-C3 | 206 | | | | | | | | | | |
| p207 | *U*CG*T*CGTTTTGTCGTT-C3 | 207 | | | | | | | | | | |
| p208 | *U*CG*T*CGTTTTGTCGTT-C3 | 208 | | | | | | | | | | |
| p209 | *U*CG*T*CGTT-C3 | 209 | | | | | | | | | | |
| p210 | *U*CGTCG*T*T-C3 | 210 | | | | | | | | | | |
| p211 | *U*CG*T*TT-C3 | 211 | | | | | | | | | | |
| p212 | *U*CGTT*T*-C3 | 212 | | | | | | | | | | |
| p213 | *U*CGTCGTGTCG*T*T-C3 | 213 | | | | | | | | | | |
| p214 | *U*CGTCGTGTTT*T*T-C3 | 214 | | | | | | | | | | |
| p215 | *U*CGTTTTGTCG*T*T-C3 | 215 | | | | | | | | | | |
| p216 | *U*CGTTTGTCG*T*T-C3 | 216 | | | | | | | | | | |
| p217 | *U*CGTTGTCG*T*T-C3 | 217 | | | | | | | | | | |
| p218 | *U*CGTGTCG*T*T-C3 | 218 | | | | | | | | | | |
| p219 | *U*GC*T*GCTTTTGTCGTT-C3 | 219 | | | | | | | | | | |
| p220 | *U*CG*T*CGTTTTGTCG*T*T-C3 | 220 | | | | | | | | | | |
| p221 | *U*CG*T*CGTTTTGTCG*T*T-C3 | 221 | | | | | | | | | | |
| p222 | GGGACGATCGTC*T* | 222 | | | | | | | | | | |
| p223 | ggGACGATCGTC*T*gg | 223 | | | | | | | | | | |
| p224 | ggGACGA*T*CGTCTgg | 224 | | | | | | | | | | |
| p225 | *U*CG*T*CGTGTCGTT-C3 | 225 | | | | | | | | | | |
| p226 | *U*CG*T*CGTGTCGTT-C3 | 226 | | | | | | | | | | |
| p227 | *U*CG*T*CGTGTCGTT-C3 | 227 | | | | | | | | | | |
| p228 | *U*CG*T*CGTGTCGTT-C3 | 228 | | | | | | | | | | |
| p229 | *U*CG*T*CGTGTCG*T*T-C3 | 229 | | | | | | | | | | |
| p230 | *U*CGTCGTGTCG*T*T-C3 | 230 | | | | | | | | | | |
| p231 | *U*CG*T*Cgtgt*C*G*T*T-C3 | 231 | | | | | | | | | | |
| p232 | tcgtcgttttgtcgttttgtcgc*T*T-C3 | 232 | | | | | | | | | | |
| p233 | *u*gtcgttttgtcgttttgtcg*T*T-C3 | 233 | | | | | | | | | | |
| p235 | tcgtcgttttgtcg*t*T-C3 | 235 | | | | | | | | | | |
| p236 | *u*cgtcgttttgtcg*t*T-C3 | 236 | | | | | | | | | | |
| p237 | tcgtcgtgtcg*t*T-C3 | 237 | | | | | | | | | | |
| p238 | *u*cgtcgtgtcg*t*T-C3 | 238 | | | | | | | | | | |
| p239 | *U*Cg*t*Cgtgt*C*g*T*T-C3 | 239 | | | | | | | | | | |
| p240 | *U*CgtCgtgtCg*t*t-C3 | 240 | | | | | | | | | | |
| p241 | *U*Cgtcgtgtcg*t*t-C3 | 241 | | | | | | | | | | |
| p242 | *U*cgtcgtgtcg*t*t-C3 | 242 | | | | | | | | | | |
| p243 | *u*cgtcgtgtcg*t*t-C3 | 243 | | | | | | | | | | |
| p244 | *U*Cg*t*cgtcgtt-C3 | 244 | | | | | | | | | | |
| p245 | *U*cg*t*cgtcgtt-C3 | 245 | | | | | | | | | | |
| p246 | *u*cg*t*cgtcgtt-C3 | 246 | | | | | | | | | | |
| p247 | *U*Cg*t*cgttttgtcgttttgtcgtt-C3 | 247 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p248 | Ucg*t*cgttttgtcgttttgtcgtt-C3 | 248 | | | | | | | | | | |
| p249 | u cg *t*cgttttgtcgttttgtcgtt-C3 | 249 | | | | | | | | | | |
| p250 | UCGTCgtgtCGTT-C3 | 250 | | | | | | | | | | |
| p251 | UCG*T*CgtgtCgtt-C3 | 251 | | | | | | | | | | |
| p252 | UCg*T*Cgtgt Cgtt-C3 | 252 | | | | | | | | | | |
| p253 | UCG'*T*CgtgtCGTT-C3 | 253 | | | | | | | | | | |
| p254 | UCG*T*CgtgtCG'TT-C3 | 254 | | | | | | | | | | |
| p255 | UCG*T*CgtgtCGT'T-C3 | 255 | | | | | | | | | | |
| p256 | UCG*T*CgtgtCGTT'-C3 | 256 | | | | | | | | | | |
| p257 | UCG*T*CgtgtCGT'T'-C3 | 257 | | | | | | | | | | |
| p258 | UCG*T*CgtgtCG'T'T'-C3 | 258 | | | | | | | | | | |
| p259 | UCGT'CgtgtCG*T*T-C3 | 259 | | | | | | | | | | |
| p260 | UCGTCgtgtCG*T*T'-C3 | 260 | | | | | | | | | | |
| p261 | UCGT'CgtgtCG*T*T'-C3 | 261 | | | | | | | | | | |
| p262 | Ucgucgtgtcg*t*t-C3 | 262 | | | | | | | | | | |
| p263 | Ucgtcgtgucgtt-C3 | 263 | | | | | | | | | | |
| p264 | TAACGACACGACGA | 264 | | | | | | | | | | |
| p265 | AACGACACGACGA T | 265 | | | | | | | | | | |
| p266 | ucgtcgtgucgtt-C3 | 266 | | | | | | | | | | |
| p267 | cg*t*cgtgtcgtt-C3 | 267 | | | | | | | | | | |
| p268 | cg*t*cgtg*u*cgtt-C3 | 268 | | | | | | | | | | |
| p269 | Tcg*t*cgtgtcgtt-C3 | 269 | | | | | | | | | | |
| p270 | tcg*t*cgtgtcgtt-C3 | 270 | | | | | | | | | | |
| p271 | Ucgtcgtgtcgtt-C3 | 271 | | | | | | | | | | |
| p272 | ucgtcgtgtcgtt-C3 | 272 | | | | | | | | | | |
| p273 | ugc*t*gctgtgctt-C3 | 273 | | | | | | | | | | |
| p274 | ucg*a*gctgtcgtt-C3 | 274 | | | | | | | | | | |
| p275 | ucg*t*cgtgacgtt-C3 | 275 | | | | | | | | | | |
| p276 | ucg*a*cgtgacgtt-C3 | 276 | | | | | | | | | | |
| p277 | acg*a*cgtgacgtt-C3 | 277 | | | | | | | | | | |
| p278 | acg*a*cgtgacg*t*t-C3 | 278 | | | | | | | | | | |
| p279 | ucng*t*cgtgtcgtt-C3 | 279 | | | | | | | | | | |
| p280 | ucg*t*cngtgtcgtt-C3 | 280 | | | | | | | | | | |
| p281 xxxxxx | ucg*t*cgtgtcngtt-C3 | 281 | | | | | | | | | | |
| p282 | ucngtcngtgtcngtt-C3 | 282 | | | | | | | | | | |
| p283 | acngacngtgacngtt-C3 | 283 | | | | | | | | | | |
| p284 | acngacngtgacngtt-C3 | 284 | | | | | | | | | | |
| p285 | ucgtcgtgtcgtT-OH | 285 | | | | | | | | | | |
| p286 | ucg*t*cgtgtcgtt-C3 | 286 | | | | | | | | | | |
| p287 | ucg*t*cgtgtcgtT | 287 | | | | | | | | | | |
| p288 | ucgtcgtgtcgtt-C3 | 288 | | | | | | | | | | |
| p289 | ucgtcgtgtcgtT | 289 | | | | | | | | | | |
| p290 | tcgtcgtgtcgtt-C3 | 290 | | | | | | | | | | |
| p291 | tcgtcgtgtcgtT | 291 | | | | | | | | | | |
| p292 | ucgtcgtgacgt*t*-C3 | 292 | | | | | | | | | | |
| p293 | ucgacgtgacgt*t*-C3 | 293 | | | | | | | | | | |
| p294 | tccatgucgttccttgat*t*-C3 | 294 | | | | | | | | | | |
| p295 | tccatgucgttcctt*t*-C3 | 295 | | | | | | | | | | |
| p296 | tccatgucgttct*t*-C3 | 296 | | | | | | | | | | |
| p297 | tccatgucgt*t*-C3 | 297 | | | | | | | | | | |
| p298 | tucg*t*cgtgtcgtt-C3 | 298 | | | | | | | | | | |
| p299 | uucg*t*cgtgtcgtt-C3 | 299 | | | | | | | | | | |
| p300 | uucg*t*cgtgtcgtt-C3 | 300 | | | | | | | | | | |
| p301 | tcgucgtgtcg*t*t-C3 | 301 | | | | | | | | | | |
| p302 | tcgUcgtgtcg*t*t-C3 | 302 | | | | | | | | | | |
| p303 | tcgUcgtgtcgtt-C3 | 303 | | | | | | | | | | |
| p304 | ucgtcgtgacg*t*t-C3 | 304 | | | | | | | | | | |
| p305 | ucgacgtgacg*t*t-C3 | 305 | | | | | | | | | | |
| p306 | C3-PO-ucg*t*cgtgtcgtt-C3 | 306 | | | | | | | | | | |
| p307 | fucg*t*cgtgtcgtt-C3 | 307 | | | | | | | | | | |
| p308 | bucg*t*cgtgtcgtt-C3 | 308 | | | | | | | | | | |
| p309 | C3-PS-ucg*t*cgtgtcgtt-C3 | 309 | | | | | | | | | | |
| p310 | ucg*t*cgtgtcg tt-C3 | 310 | | | | | | | | | | |
| p311 | ucg*t*cgtgtcgtt-C3 | 311 | | | | | | | | | | |
| p312 | tcgucgtgtcg*t*t | 312 | | | | | | | | | | |
| p313 | tucg*t*cgtgacgtt-C3 | 313 | | | | | | | | | | |
| p314 | uucg*t*cgtgacgtt-C3 | 314 | | | | | | | | | | |
| p315 | NH2C6-ucg*t*cgtgacgtt-C3 | 315 | | | | | | | | | | |
| p316 | C3-uucg*t*cgtgacgtt-C3 | 316 | | | | | | | | | | |
| p317 | tcg*a*cgtgucgtt-C3 | 317 | | | | | | | | | | |
| p318 | tcgacgtgacgtt-C3 | 318 | | | | | | | | | | |
| p319 | ucg*a*cgtgucgtt-C3 | 319 | | | | | | | | | | |
| p320 | ucgtccatgacgtt-C3 | 320 | | | | | | | | | | |
| p321 | ucgtccatgucgtt-C3 | 321 | | | | | | | | | | |
| p322 | tcgtccatgucgtt-C3 | 322 | | | | | | | | | | |
| p323 | bucg*t*cgtgacgtt-C3 | 323 | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p324 | catgucgttcctt*t*-C3 | 324 | | | | | | | | | | |
| p325 | tgucgttcctt*t*-C3 | 325 | | | | | | | | | | |
| p326 | tatgucgttcctt*t*-C3 | 326 | | | | | | | | | | |
| p327 | tccatgacgttcctt*t*-C3 | 327 | | | | | | | | | | |
| p328 | ugc*t*gctgagctt-C3 | 328 | | | | | | | | | | |
| p329 | ugc*a*gctgagctt-C3 | 329 | | | | | | | | | | |
| p330 | fTcg*t*cgtgtcgtt-C3 | 330 | | | | | | | | | | |
| p331 | ftcg*t*cgtgtcgtt-C3 | 331 | | | | | | | | | | |
| p332 | ucg*t*cgtgtcgtt-C3 | 332 | | | | | | | | | | |
| p333 | ucg*t*cgtgtcgtt-C3 | 333 | | | | | | | | | | |
| p334 | ucg*t*cgtgtcgtt-C3 | 334 | | | | | | | | | | |
| p335 | ucg*t*cgtgtcgtt-C3 | 335 | | | | | | | | | | |
| p336 | ucg*t*cgtgtcgtt-C3 | 336 | | | | | | | | | | |
| p337 | ucg*t*cgtgtcgtt-C3 | 337 | | | | | | | | | | |
| p338 | tatgugcttcctt*t*-C3 | 338 | | | | | | | | | | |
| p339 | bucg*t*cgp*t*gtcgp*t*t-C3 | 339 | | | | | | | | | | |
| p340 | bucgtcgp*t*cgtpt-c3 | 340 | | | | | | | | | | |
| p341 | bucg*t*cgtgtcg*t*p*t*-C3 | 341 | | | | | | | | | | |
| p342 | bucg*t*cgp*t*cgtt-C3 | 342 | | | | | | | | | | |
| p343 | bucg*t*cgp*t*gtcgtt-C3 | 343 | | | | | | | | | | |
| p344 | bucg*t*cgtgtcgp*t*p*t*-C3 | 344 | | | | | | | | | | |
| p345 | *t*ugc*t*gctgagctt-C3 | 345 | | | | | | | | | | |
| p346 | tuc*t*gctgagctt-C3 | 346 | | | | | | | | | | |
| p347 | tugctgctgagctt-C3 | 347 | | | | | | | | | | |
| p348 | ucg*t*cgtgtcgtt-C3 | 348 | | | | | | | | | | |
| p349 | ucg*t*cgtgtcgtt-C3 | 349 | | | | | | | | | | |
| p350 | ucg*t*cgtgtcgtt-C3 | 350 | | | | | | | | | | |
| p351 | ucg*t*cgtgtcgtt-C3 | 351 | | | | | | | | | | |
| p352 | ucg*t*cgtgtcgtt-C3 | 352 | | | | | | | | | | |
| p353 | tucgtcgtgacgtt-C3 | 353 | | | | | | | | | | |
| p354 | tugctgctgagctt-C3 | 354 | | | | | | | | | | |
| p355 | ucg*T*cgtgtcg*T*t-C3 | 355 | | | | | | | | | | |
| p356 | ucg*T*cgtgtcgtt-C3 | 356 | | | | | | | | | | |
| p357 | ucg*T*cgtgtcg*T*t-C3 | 357 | | | | | | | | | | |
| p358 | ucgtcgtgtcg*t*t-C3 | 358 | | | | | | | | | | |
| p359 | ucg*T*cgtgtcg*t*t-C3 | 359 | | | | | | | | | | |
| p360 | ucgtcgtgtcg*T*t-C3 | 360 | | | | | | | | | | |
| p361 | ucg*T*cgtgtcgtt-C3 | 361 | | | 102 | | | | | | | |
| p362 | ucg*T*cgtgtcg Tet-C3 | 362 | | | 175 | | | | | | | |
| p363 | ucg*T*cgtgtcGett-C3 | 363 | | | 365 | | | | | | | |
| p364 | ucg*T*cgtgtCegtt-C3 | 364 | | | 523 | | | | | | | |
| p365 | ucg*T*cgtgTecgtt-C3 | 365 | | | 260 | | | | | | | |
| p366 | ucg*T*cgtGetcgtt-C3 | 366 | | | 390 | | | | | | | |
| p367 | ucg*T*cgTegtcgtt-C3 | 367 | | | 287 | | | | | | | |
| p368 | ucg*T*cGetgtcgtt-C3 | 368 | | | 223 | | | | | | | |
| p369 | ucg*T*Cegtgtcgtt-C3 | 369 | | | 242 | | | | | | | |
| p370 | ucGe*T*cgtgtcgtt-C3 | 370 | | | 158 | | | | | | | |
| p371 | uCeg*T*cgtgtcgtt-C3 | 371 | | | 160 | | | | | | | |
| p372 | ucgTecgtgtcg*T*t-C3 | 372 | | | 194 | | | | | | | |
| p373 | tucgtcgtgacgttX5-C3 | 373 | | | | | | | | | | |
| p374 | tucgtcgtgacgtX5t-C3 | 374 | | | | | | | | | | |
| p375 | tucgtcgtgacgX5tt-C3 | 375 | | | | | | | | | | |
| p376 | tucgtcgtgacX5gtt-C3 | 376 | | | | | | | | | | |
| p377 | tucgtcgtgaX5cgtt-C3 | 377 | | | | | | | | | | |
| p378 | tucgtcgtgX5acgtt-C3 | 378 | | | | | | | | | | |
| p379 | tucgtcgtX5gacgtt-C3 | 379 | | | | | | | | | | |
| p380 | tucgtcgX5tgacgtt-C3 | 380 | | | | | | | | | | |
| p381 | tucgtcX5gtgacgtt-C3 | 381 | | | | | | | | | | |
| p382 | tucgtX5cgtgacgtt-C3 | 382 | | | | | | | | | | |
| p383 | tucgX5tcgtgacgtt-C3 | 383 | | | | | | | | | | |
| p384 | tucX5gtcgtgacgtt-C3 | 384 | | | | | | | | | | |
| p385 | tuX5cgtcgtgacgtt-C3 | 385 | | | | | | | | | | |
| p386 | tX5ucgtcgtgacgtt-C3 | 386 | | | | | | | | | | |
| p387 | X5tucgtcgtgacgtt-C3 | 387 | | | | | | | | | | |
| p388 | tucgx5cgtgacgtt-C3 | 388 | | | | | | | | | | |
| p389 | tucgx5cgtgacgtt-C3 | 389 | | | | | | | | | | |
| p390 | Uecg*T*cgtgtcgtt-C3 | 390 | | | 533 | | | | | | | |
| p391 | UeCeg*T*cgtgtcgtt-C3 | 391 | | | 1080 | | | | | | | |
| p392 | UeCeGe*T*cgtgtcgtt-C3 | 392 | | | 1691 | | | | | | | |
| p393 | Uecg*T*cgtgtCeGeTe-C3 | 393 | | | 2211 | | | | | | | |
| p394 | UeCeGe*T*cgtgtCeGeTe-C3 | 394 | | | inact. | | | | | | | |
| p395 | UeCeGe*T*CeGeTeGeTeCeGeTeTe-C3 | 395 | | | | | | | | | | |
| p396 | uCeg*T*cegtgtCegtt-C3 | 396 | | | 704 | | | | | | | |
| p397 | ucg*T*cGetGetcGett-C3 | 397 | | | 3494 | | | | | | | |
| p398 | ucg*T*cgTegTecgTet-C3 | 398 | | | 2423 | | | | | | | |
| p399 | uCeg*T*cgTegTecgTet-C3 | 399 | | | 4261 | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p400 | ucgTecgTegTecgTt-C3 | 400 | | | 1805 | | | | | | | |
| p401 | uCegTecgTegTecgTt-C3 | 401 | | | 2509 | | | | | | | |
| p402 | uCegTcgtgtcGett-C3 | 402 | | | 356 | | | | | | | |
| p403 | uCegTcgtgtCegtt-C3 | 403 | | | 482 | | | | | | | |
| p404 | uCegTcgttgtcgTet-C3 | 404 | | | 203 | | | | | | | |
| p405 | uCegTcgtTegtcgTet-C3 | 405 | | | 809 | | | | | | | |
| p406 | uCegTcgTetgtcg Tet-C3 | 406 | | | 510 | | | | | | | |
| p407 | uCegTcgX3gtcgTet-C3 | 407 | | | 286 | | | | | | | |
| p408 | uCegTcgX3tgtcgTet-C3 | 408 | | | 266 | | | | | | | |
| p409 | uCegTcgTegtcgTet-C3 | 409 | | | 875 | | | | | | | |
| p410 | uCegTcgX3gtcgTet-C3 | 410 | | | 193 | | | | | | | |
| p411 | X3ucTcgtgtcgtt-C3 | 411 | | | 124 | | | | | | | |
| p412 | uX3cgTcgtgtcgtt-C3 | 412 | | | inact. | | | | | | | |
| p413 | ucX3gTcgtgtcgtt-C3 | 413 | | | 225 | | | | | | | |
| p414 | ucgX3Tcgtgtcgtt-C3 | 414 | | | 131 | | | | | | | |
| p415 | ucgTX3cgtgtcgtt-C3 | 415 | | | 124 | | | | | | | |
| p416 | ucgTcX3gtgtcgtt-C3 | 416 | | | 85 | | | | | | | |
| p417 | ucgTcgX3tgtcgtt-C3 | 417 | | | 92 | | | | | | | |
| p418 | ucgTcgtX3gtcgtt-C3 | 418 | | | 93 | | | | | | | |
| p419 | ucgTcgtgX3tcgtt-C3 | 419 | | | 189 | | | | | | | |
| p420 | ucgTcgtgtX3cgtt-C3 | 420 | | | 227 | | | | | | | |
| p421 | ucgTcgtgtcX3gtt-C3 | 421 | | | 95 | | | | | | | |
| p422 | ucgTcgtgtcgX3tt-C3 | 422 | | | 135 | | | | | | | |
| p423 | ucgTcgtgtcgtX3t-C3 | 423 | | | 202 | | | | | | | |
| p424 | ucgTcgtgtcgttX3-C3 | 424 | | | 113 | | | | | | | |
| p425 | bucgTcgtgtcgtt-C3 | 425 | | | | | | | | | | |
| p426 | ccgTcgtgtcgtt-C3 | 426 | | | | | | | | | | |
| p427 | 1ucgTcgtgtcgtt-C3 | 427 | | | | | | | | | | |
| p428 | 10cgTcgtgtcgtt-C3 | 428 | | | | | | | | | | |
| p429 | oducgTcgtgtcgtt-c3 | 429 | | | | | | | | | | |
| p430 | oucgTcgtgtcgtt-c3 | 430 | | | | | | | | | | |
| p431 | odsucgTcgtgtcgtt-c3 | 431 | | | | | | | | | | |
| p432 | sucgTcgtgtcgtt-c3 | 432 | | | | | | | | | | |
| p433 | bu'cgTcgtgtcgtt-C3 | 433 | | | 96 | | | | | | | |
| p434 | bu$^s$cgTcgtgtcgtt-C3 | 434 | | | 125 | | | | | | | |
| p435 | buc'gTcgtgtcgtt-C3 | 435 | | | 148 | | | | | | | |
| p436 | buc$^s$gTcgtgtcgtt-C3 | 436 | | | 112 | | | | | | | |
| p437 | bu$^s$c'gTcgtgtcgtt-C3 | 437 | | | | | | | | | | |
| p438 | bu$^s$c$^s$gTcgtgtcgtt-C3 | 438 | | | | | | | | | | |
| p439 | buCegTcgtgtcgtt-C3 | 439 | | | | | | | | | | |
| p440 | buCegTcgtgtCegtt-C3 | 440 | | | | | | | | | | |
| p441 | buCegTCegtgtCegtt-C3 | 441 | | | | | | | | | | |
| p442 | buCegTcgtgtcgTet-C3 | 442 | | | | | | | | | | |
| p443 | buCegTcgTegtcgTet-C3 | 443 | | | | | | | | | | |
| p444 | Biotin-AfAfCfGfAfCfAfCfGfAfAfCfGfAf | 444 | | | | | | | | | | |
| p445 | buCsigTcgtgtcgtt-c3 | 445 | | | | | | | | | | |
| p446 | bucgTcgtgtcgTsit-c3 | 446 | | | | | | | | | | |
| p447 | buCsigTCsigtgtCsigtt-c3 | 447 | | | | | | | | | | |
| p448 | buCsigTcgtgtcgTsit-c3 | 448 | | | | | | | | | | |
| p449 | buCsigTcgTsigtcgTsit-c3 | 449 | | | | | | | | | | |
| p450 | tucgtcgtgacgtt-c3 | 450 | | | | | | | | | | |
| p451 | tucgacgtgacgtt-c3 | 451 | | | | | | | 60 | | | 18 | 100 |
| p452 | tucgacgtt-c3 | 452 | | | | | | | inact. | | | 100 | inact. |
| p453 | tuacgtt-c3 | 453 | | | | | | | inact. | | | inact. | inact. |
| p454 | tacgtt-c3 | 454 | | | | | | | inact. | | | inact. | inact. |
| p455 | tucgtt-c3 | 455 | | | | | | | inact. | | | inact. | inact. |
| p456 | tacgt-c3 | 456 | | | | | | | inact. | | | inact. | inact. |
| p457 | tucgt-c3 | 457 | | | | | | | inact. | | | inact. | inact. |
| p458 | tucgucgtgacgtt-c3 | 458 | | | | | | | | | | 36 | 119 |
| p459 | tucgucgtt-c3 | 459 | | | | | | | | | | 132 | inact. |
| p460 | tuacgut-c3 | 460 | | | | | | | | | | inact. | inact. |
| p461 | tacgut-c3 | 461 | | | | | | | | | | inact. | inact. |
| p462 | tucgut-c3 | 462 | | | | | | | | | | 223 | inact. |
| p463 | gucgtt-c3 | 463 | | | | | | | | | | inact. | inact. |
| p464 | gacgtt-c3 | 464 | | | | | | | | | | inact. | inact. |
| p465 | gucgut-c3 | 465 | | | | | | | | | | inact. | inact. |
| p466 | gacgut-c3 | 466 | | | | | | | | | | inact. | inact. |
| p469 | tbucgtcgtgacgtt-c3 | 469 | | | | | | | | | | | |
| p470 | bucgTcgtgtcg-c3 | 470 | | | | | | | | | | | |
| p471 | bucgTcgtgt-c3 | 471 | | | | | | | | | | | |
| p472 | bucgtcgtgT-c3 | 472 | | | | | | | | | | | |
| p473 | bucgTcgt-c3 | 473 | | | | | | | | | | | |
| p474 | bucgtcgT-c3 | 474 | | | | | | | | | | | |
| p475 | bucgTt-c3 | 475 | | | | | | | | | | | |
| p476 | bucgtT-c3 | 476 | | | | | | | | | | | |
| p477 | tucgtcgtgacgtmtm-c3 | 477 | | | | | | | | | | | |

TABLE 2-continued

| Compound # | Sequence (5' to 3') | SEQ ID NO: | A | B | C | D | E | F | G | H | I | J |
|---|---|---|---|---|---|---|---|---|---|---|---|---|
| p478 | tmtmucg*t*cgtcgtgacgtt-c3 | 478 | | | | | | | | | | |
| p479 | tmtmucg*t*cgtcgtgacgtmtm-c3 | 479 | | | | | | | | | | |
| p480 | tucg*t*cgtcgtgacgt(m)t(m)-c3 | 480 | | | | | | | | | | |
| p481 | t(m)t(m)ucg*t*cgtcgtgacgtt-c3 | 481 | | | | | | | | | | |
| p482 | tuc'g*t*cgtcgtgacgtt-c3 | 482 | | | | | | 399 | | | | |
| p483 | tuc$^s$g*t*cgtcgtgacgtt-c3 | 483 | | | | | | 577 | | | | |
| p484 | tu$^r$cg*t*cgtcgtgacgtt-c3 | 484 | | | | | | 410 | | | | |
| p485 | tu$^s$cg*t*cgtcgtgacgtt-c3 | 485 | | | | | | 245 | | | | |
| p486 | t(m)t(m)ucg*t*cgtcgtgacgt(m)t(m)-c3 | 486 | | | | | | | | | | |
| p487 | bucg*t*cgtgtcgtt(m)-c3 | 487 | | | | | | | | | | |
| p488 | bucg*t*cgtgtcgt(m)t(m)-c3 | 488 | | | | | | | | | | |
| p489 | bucg*t*cgtgtcgt(m)T-c3 | 489 | | | | | | | | | | |

In table 2,
column A provides IL-6 expression in DB cells (EC$_{50}$, nM);
column B provides IL-10 expression in DB cells (EC$_{50}$, nM);
column C provides NFκB activation in Ramos blue cells (EC$_{50}$, nM);
column D provides NFκB activation Hela-hTLR9-NFκB-luc cells (EC$_{50}$, nM);
column E provides NFκB activation Hela-mTLR9-NFκB-luc cells (EC$_{50}$, nM);
column F provides IL-6 secretion in mouse splenocytes (EC$_{50}$, nM);
column G provides IL-6 secretion in mouse splenocytes after 24 h preincubation in 95% mouse plasma (EC$_{50}$, nM);
column H provides IL-6 secretion in mouse bone marrow differentiated DC (EC$_{50}$, nM);
Column I provides NFκB activation in mouse HEK-Blue cells after 2 h transfection with RNAiMax (EC$_{50}$, nM); and
Column J provides NFκB activation in human HEK-Blue cells after 2h transfection with RNAiMax (EC$_{50}$, nM).
The key descriptors for the sequences provided throughout the Tables included herein are as follows:
lower case = nucleoside-3'-phosphorothioate;
UPPER CASE = ucleoside-3'-phosphate;
italics lower case = nucleoside having a 3'tBuDS-Ph(ortho)triester (PS);
ITALICS UPPER CASE = nucleoside having a 3'tBuDS-Ph(ortho)triester (PO);
dt = dT(DBC0);
bold double underlined t = DBCO-C6-dT;
bold lower case = nucleoside having a 3'n-butyl triester (PS);
BOLD UPPER CASE = nucleoside having a 3'n-butyl triester (PO);
italic bold lower case = nucleoside having a 3'homopropargyl triester (hPro) (PS);
italic underlined lower case = nucleoside having a 3'DBCO-NH-PEG2 triester (N1) (PS);
ITALIC UNDERLINED UPPER CASE = nucleoside having a 3'DBCO-NH-PEG2 triester (N1) (PO);
double underlined t = dT PEG2-NH$_2$ triester (PS);
double underlined T = dT PEG2-NH$_2$ triester (PO);
italic double underlined lower case = nucleoside having a 3'PEG2-NH$_2$ triester (N1)(PS);
ITALIC DOUBLE UNDERLINED UPPER CASE = nucleoside having a 3'PEG2-NH$_2$ triester (N1) (P0);
BOLD ITALIC UNDERLINED UPPER CASE U = 5-iodo-2'-deoxyuridine (PO);
bold italic underlined lower case u = 5-iodo-2'-deoxyuridine (PS);
BOLD UNDERLINED = 2'-fluoronucleotide (PO);
an apostrophe indicates that the nucleotide identified by a letter to the left of the apostrophe contains a 2'-OMe-modified ribose;
underlined ng = 7-deaza-2'-deoxyguanosine (PS);
underlined pT = PEG4 dT triester (PO);
underlined pt = PEG4 dT triester (PS);
fT = 5-trifluoromethyl-thymidine (PO);
fU = 5-fluoro-2'-deoxyuridine (PO);
bU = 5-bromo-2'-deoxyuridine (PO);
ft = 5-trifluoromethyl-thymidine (PS);
fu = 5-fluoro-2'-deoxyuridine (PS);
bu = 5-bromo-2'-deoxyuridine (PS);
C3 = C3 spacer (-(CH{hd 2)$_3$-OH)(PO);
c3 = C3 spacer (-(CH$_2$)$_3$-OH) (PS);
C6 = hexane-1,6-diyl;
NH$_2$C$_6$ = 6-aminohex-1-yl;
Te = thymidine having a 3'ethyl triester (PO);
Ge = guanosine having a 3'ethyl triester (PO);
Ce = cytidine having a 3'ethyl triester (PO);
Ue = 5-iodouridine having a 3'ethyl triester (PO);
ue = 5-iodouridine having a 3'ethyl triester (PS);
iu = 5'- 5' cap based on 5-iodo-2'-deoxyuridine (PS);
iU = 5'- 5' cap based on 5-iodo-2'-deoxyuridine (PO);
X5 = X5-DBCO (PO);
x5 = x5-DBCO (PS);
X3 = X3 abasic spacer (PO); and
IR700 is a dye.
Here, the descriptor (PO) stands for 3'-phosphate; and (PS) stands for 3'-phosphorothioate;
od = 5'-orthosulfide phosphodiester;
o = 5'-phosphate (PO);
ods = 5'-orthosulfide phosphorothioate;
s = 5'-phosphorothioate (PS);
superscript "r" = Rp PS;
superscript "s" = Sp PS;
Af = 2'-fluoro-adenosine (PO);

TABLE 2-continued

| Compound # | Sequence (5' to 3') | SEQ ID NO: | A | B | C | D | E | F | G | H | I | J |
|---|---|---|---|---|---|---|---|---|---|---|---|---|

Figure 1A:
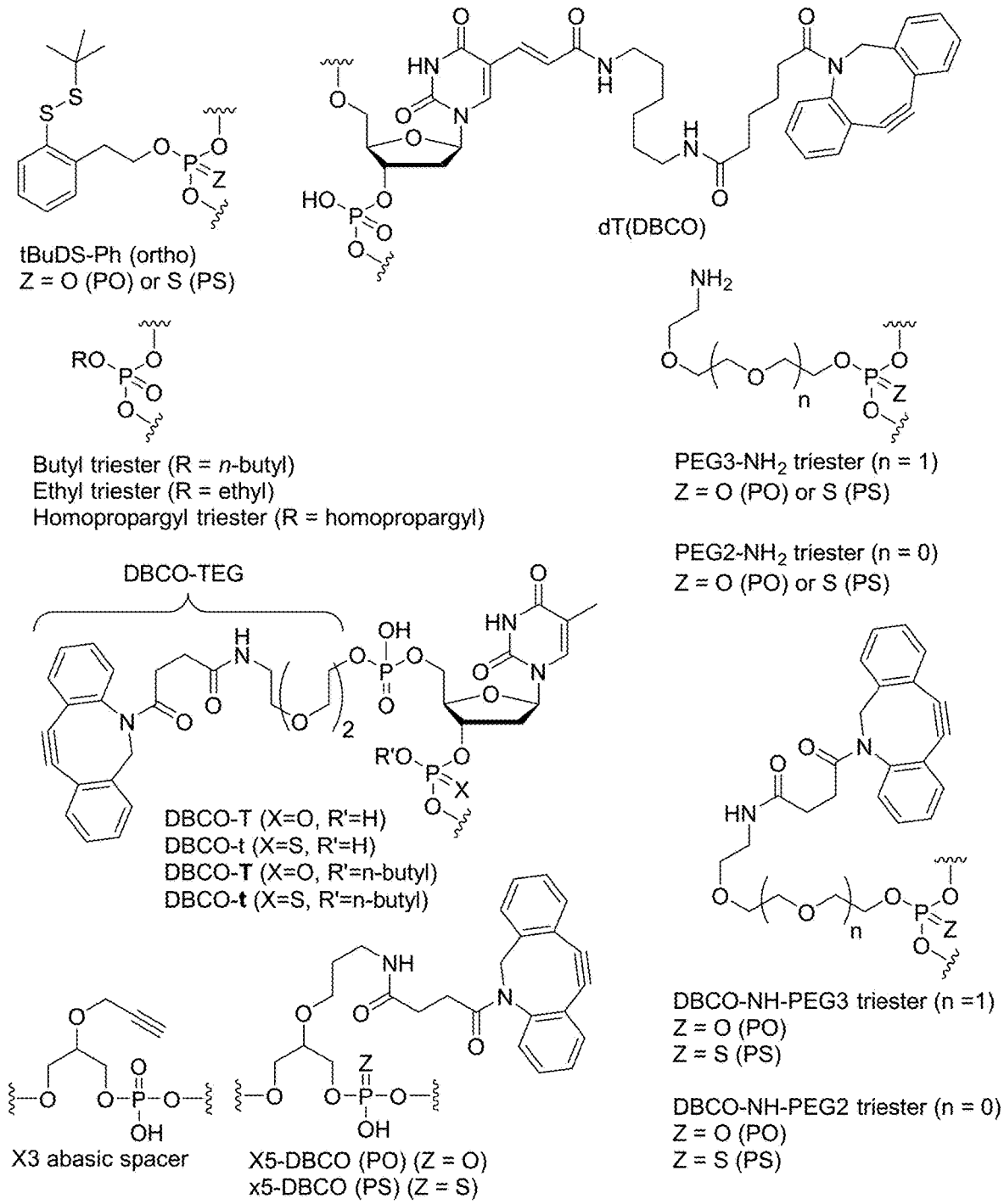
FIG. 1A is a series of structures showing abbreviations with corresponding structures. The abbreviations are those used in Table 2.
Figure 1B:
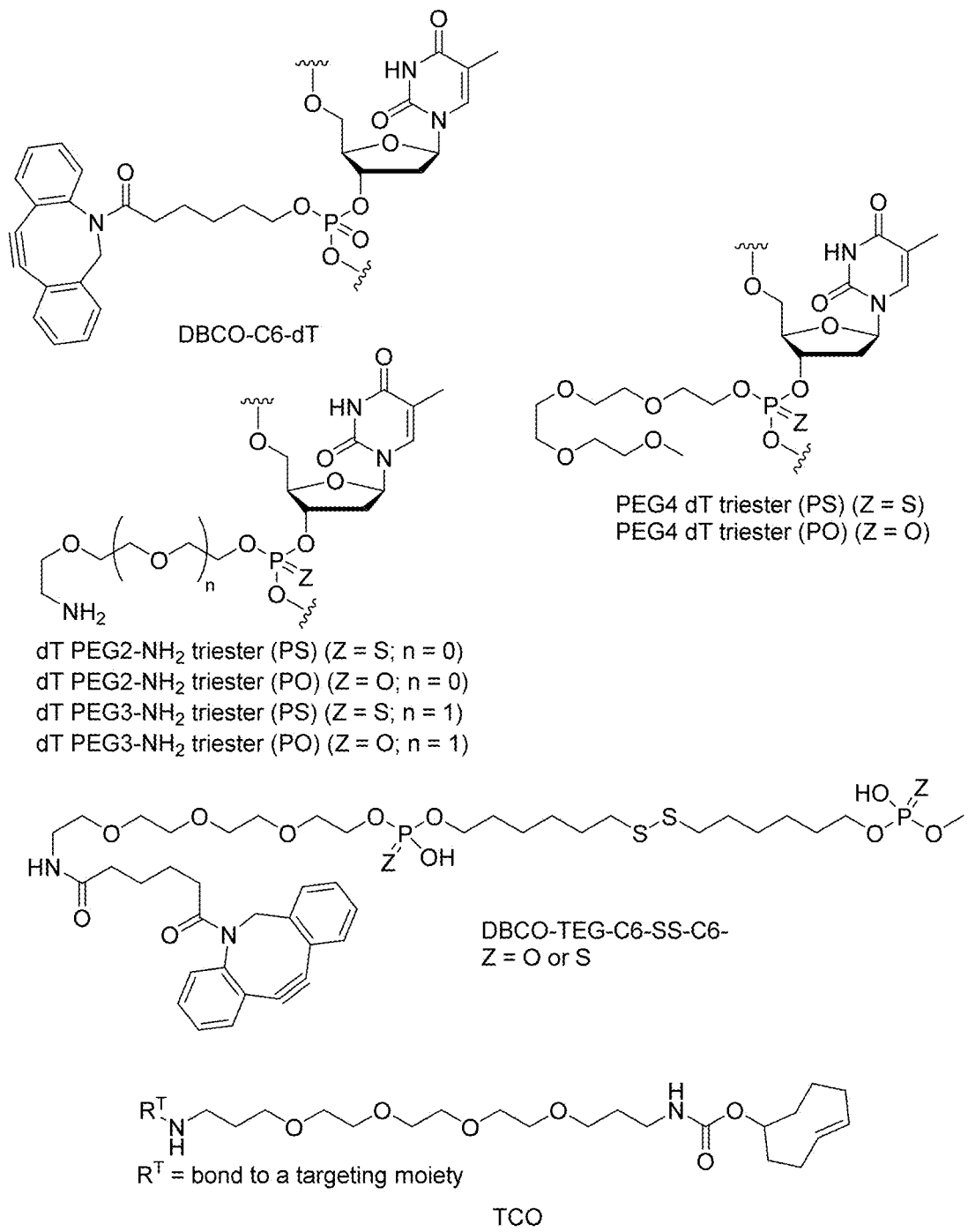
FIG. 1B is a series of structures showing abbreviations with corresponding structures. The abbreviations are those used in Table 2.

Csi = dC O-silyltriester (PO);
Tsi = dT O-silyltriester (PO);
tm = 2'-OMe thymidine (PS);
t(m) = 2'-OMOE thymidine (PS).
Structures are shown in FIGs. 1A and 1B.

Figure 2:
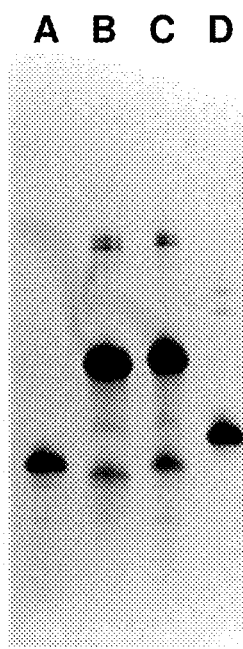
FIG. 2 is an image of an ethidium bromide-stained denaturing gel of single-stranded CpG ODNs (lanes A (p145) and D (p88)) and annealed double-stranded CpG ODNs (lanes B (p88/p144) and C (p88/p145)).

Double-Stranded CpGs:
Annealing and Gel Analysis:

Polynucleotide p88 (1 mL, 5 mM stock) was added to p144 (3.3 mL, 2 mM stock) with DPBS (24.7 mL). Polynucleotide p88 was treated with p145 in a similar manner. The mixtures were heated to 65° C. for 10 min. Analysis by TBE urea gel showed complete annealing of the p88 (see FIG. 2). 1 μL of each sample was removed, added to 5 μL of formamide loading buffer, and loaded per well onto a 15% TBE-urea gel, 200 volts for 40 min followed by ethidium bromide (EtBr) staining. See Table 2 for structures of p88, p144, and p145.

```
Double stranded-CpG using p88/p144 -
Representative example (1):
                              (SEQ ID NO: 234)
TCGTCGTTTTGTCGTTTTGTCGTT

AGCAGCAAAACAGCAAAACAGCAA

Double stranded-CpG using p88/p145 -
Representative example (2):
                              (SEQ ID NO: 467)
TCGTCGTTTTGTCGTTTTGTCGTT

AGCAGCAAAACAGCAAAACAGCAA
```

Example 2: Preparation of the Exemplary Conjugates of the Invention

In the below preparation the following antibodies have been used: anti-CD38 antibody is Ab79 disclosed in WO 2012/092616, the disclosure of this antibody is incorporated herein by reference in its entirety; anti-CD79b antibody is huMA79bv28 disclosed in WO 2014/011521, the disclosure of this antibody is incorporated herein by reference in its entirety; anti-CD30 antibody is brentuximab; anti-CD22 antibody is 10F4 disclosed in US 20140127197, the disclosure of this antibody is incorporated herein by reference in its entirety; and anti-CD20 antibody is rituximab.

Other antibodies may be incorporated in the conjugates described herein, e.g., anti-DEC205 antibody can be an antibody disclosed in US 2010/0098704 (e.g., with light chain having the sequence:
EIVLTQSPAT LSLSPGERAT LSCRASQSVS SYLAWYQQKP GQAPRLLIYD ASNRATGIPA RFSGSGSGTD FTLTISSLEP EDFAVYYCQQ RRNWPLTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 468); and the heavy chain having the sequence: QVQLVESGGGVVQPGRSLRLS-CAASGFTFSNYGMYWVRQAPGKGLEWVAVIWYDG-SNKYYADSVKGR FTISRDNSKNTLYLQMNSLRAED-TAVYYCARDLWGWYFDYWGQGTLVTVSSAS TKGPSVFPLAPSSKST SGGTAALGCLVKDYF-PEPVTVSWNSGALTSGVHTFPAVLQSSGLYS-LSSVVTVPSSSLGTQTYICNVNHK PSNTKVDKRVE-PKSCDKTHTCPPCPAPELLGGPSVFLFPPKPKDTLMIS-RTPEVTCVVVDVSHEDPEVKF NWYVDGVEVHNAKTKPREEQYN-STYRVVSVLTVLHQDWLNGKEYKCKVSNKALPA-PIEKTISKAKGQPR EPQVYTLPPSREEMTKNQVSLT-CLVKGFYPSDIAVEWESNGQPENNYKTTPPVLDS DGSFFLYSKLTVDK SRWQQGNVFSCSVMHEALHN-HYTQKSLSLSPGLLQGG) (SEQ ID NO: 490); anti-CD303 antibody can have a light chain sequence DIQLTQSPSSLSASVGDRVTITCK-ASQSVDYDGDSYMWYQQKPGKAPKLLI-YAASTLESGVPS RFSGSGSGTDFTLTISSLQPEDFA-TYYCQQANEDPRTFGQGTKVEIKRTVAAPS VFIFPPSDE QLKSGTASWCLLNNFY-PREAKVQWKVDNALQSGNSQESVTEQDSKDSTYS-LSSTLTLSKAAYE KHKVYACE-VTHQGLSSPVTKSFNRGEC (SEQ ID NO: 491), and a heavy chain sequence: DVQLVESGGGLVKPGGSLRLS-CAASGFTFSTYTMSWVRQAPGKGLEWVA-TISPGDSFGYYYPDSVQGR FTISRDNAKNS-LYLQMNSLRAEDTAVYYCTRDIYYNYGAWFAY WGQGTLVTVSSASTKGPSVFPLAPSS KSTSGGTAAL-GCLVKDYFPEPVTVSWNSGALTSGVHTFPAVLQSSG-LYSLSSVVTVPSSSLGTQTYICNV NHKPSNTKVDKKVEPKSCDKTHTCPPCPA-PELLGGPSVFLFPPKPKDTLMISRTPE-VTCWVDVSHEDPE VKFNWYVDGVEVHNAKTKPREEQYN-STYRWSVLTVLHQDWLNGKEYKCKVSNKALPA-PIEKTISKAKGQ PREPQVYTLPPSRDELTKNQVSLT-CLVKGFYPSDIAVEWESNGQPENNYKTTPPVLDS DGSFFLYSKLTV DKSRWQQGNVFSCSVMHEALHN-HYTQKSLSLSPGLLQGG (SEQ ID NO: 492); anti-CD40 antibody can be lucatumumab or dacetuzumab; anti-CD74 antibody can be milatuzumab; anti-CD304 antibody can be vesencumab; and anti-CD38 antibody can be daratumumab, SAR650984 (Sanofi-Immunogen), or MOR202 (Morphosys-Celgene). These antibodies can include a Q-tag (e.g., LLQGG (SEQ ID NO: 493) within the heavy chain or GGGLLQGG (SEQ ID NO: 494) within the light chain).

Other antibodies may be incorporated in the conjugates described herein, e.g.: anti-PD-L1 antibody can be antibody described in mAbs (2016), 8, 593 and U.S. Pat. No. 8,217,149 with light chain having the sequence: DIQMTQSPSSL-SASVGDRVTITCRASQDVSTA-VAWYQQKPGKAPKLLIYSASFLYSGVP SRFSGSGSGTDFTLTISSLQPEDFATYYCQQYLYH-PATFGQGTKVEIKADAAPTVSIFPPSSEQLTSGGAS VVCFLNNFYPKDINVKWKIDGSERQNGVLN-SWTDQDSKDSTYSMSSTLTLTKDEYERHNSYT-CEATHKT STSPIVKSFNRNEC (SEQ ID NO: 495), and the heavy chain sequence: EVQLVESGG-GLVQPGGSLRLSCAASGFTFSDSWIHWVRQAPGK-GLEWVAWISPYGGSTYYADSVKGRF TISADTSKN-TAYLQMNSLRAEDTAVYYCARRHWPGGFDYWG QGTLVTVSSAKTTAPSVYPLAPVCGDTT GSSVTLGCLVKGYF-PEPVTLTWNSGSLSSGVHTFPAVLQSD- LYTLSSSVTVTSSTWPSQSITCNVAHPAS STKVDK-
KIEPRGPTIKPCPPCKCPAPNLLGGPSVFIFPPKIKD
VLMISLSPIVTCVVVAVSEDDPDVQISWFV
NNVEVHTAQTQTHREDYASTLRVVSAL-
PIQHQDWMSGKEFKCKVNNKDLPAPIER-
TISKPKGSVRAPQV YVLPP-
PEEEMTKKQVTLTCMVTDFMPEDIYVEWTNNGK
TELNYKNTEPVLDSDGSYFMYSKLRVEKKNW
VERNSYSCSVVHEGLHNHHTTKSFSRTPGLLQGG
(SEQ ID NO: 496)

A. General Procedure for Conjugation to Q-Tagged Antibody Mediated by Microbial Transglutaminase (mTG)

TABLE 3

Exemplary Setup of Transglutaminase-mediated Conjugation

| Molecule | Conc. (µM) | Volume (µL) | Linker:Ab | Ab:mTG | Antibody (nmol) |
|---|---|---|---|---|---|
| Q-tagged anti-CD22 antibody | 99 | 253 | — | — | 25 |
| $N_3$-PEG23-$NH_2$ | 100000 | 25 | 100.0 | — | — |
| mTG | 20 | 125 | — | 10.0 | — |
| Tris buffer, pH 8.5 | — | 97 | — | — | — |
| Final volume | — | 500 | — | — | — |

Figure 3A:
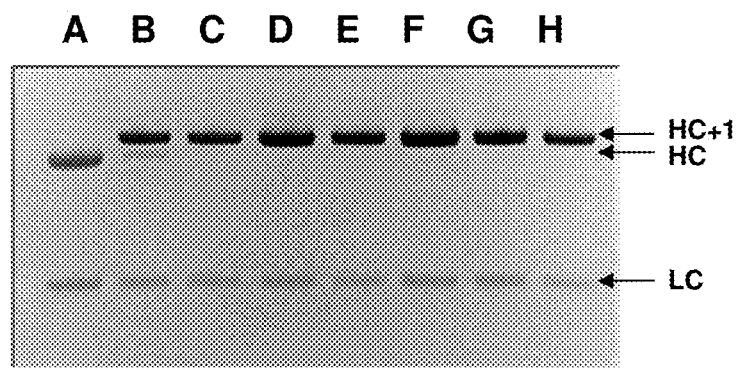
FIG. 3A is an image of ethidium bromide-stained reducing gels of a Q-tagged anti-CD38 antibody before (lane A) and after mouse transglutaminase-mediated conjugation with a polynucleotide (p76, p77, p78, p79, p80, p81, and p82 corresponding to lanes B, C, D, E, F, G, and H, respectively. HC+1 indicates bands of a Q-tagged anti-CD38 antibody heavy chain conjugated to a polynucleotide. HC indicates bands of a Q-tagged anti-CD38 antibody heavy chain. LC indicates an anti-CD38 antibody light chain.
Figure 3B:
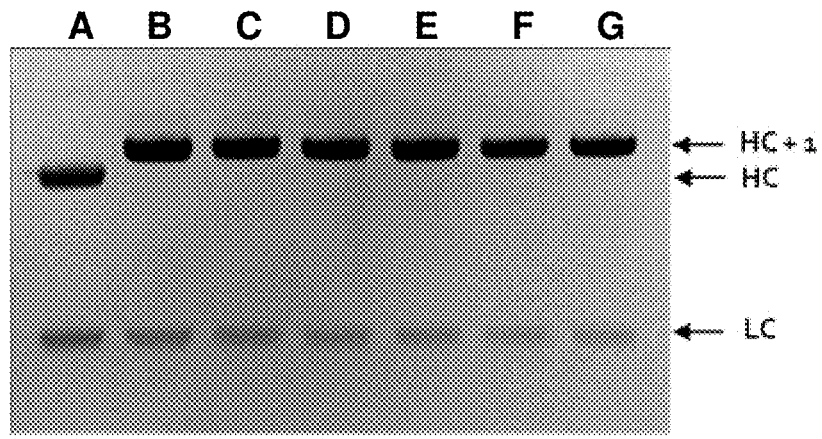
FIG. 3B is an image of ethidium bromide-stained reducing gels of a Q-tagged anti-CD38 antibody before (lane A) and after microbial transglutaminase-mediated conjugation with a polynucleotide p83, p84, p85, p86, p87, and p88 corresponding to lanes B, C, D, E, F, and G, respectively. HC+1 indicates bands of a Q-tagged anti-CD38 antibody heavy chain conjugated to a polynucleotide. HC indicates bands of a Q-tagged anti-CD38 antibody heavy chain. LC indicates an anti-CD38 antibody light chain.

General conditions for enzymatic conjugation:
Final antibody concentration = 50 µM
Antibody:Transglutaminase (mTG) ratio: 10:1
Linker:Ab ratio: 100:1
mTG MW = 38 kDa, 100 mU/mg, $\varepsilon_{280}$ = 71850 $M^{-1}$ $cm^{-1}$
2% w/v = 20 mg/mL = 5 µM in tris buffer
Tris buffer: 25 mM Tris, 150 mM NaCl, pH 8.5
Linker solution in tris buffer or DMSO
DMSO ≤ 5% v/v of final volume General Protocol:

To a solution of a Q-tagged antibody (e.g., Q-tagged anti-CD22 antibody or Q-tagged anti-CD38 antibody, designated as CD22-Q and CD38-Q, respectively) in tris buffer was added sequentially azido amino linker and mTG. The mixture was warmed to 37° C. for 2 h, at which time, the excess linker and mTG were removed by buffer exchanging the antibody with the pendent azido-linker (Ab-$N_3$) through an Amicon 30 kD spin concentrator using DPBS as an eluent. A sample of Ab-$N_3$ was then reduced and characterized for degree of linker conjugation by RP-HPLC, as described below. Subsequent Huisgen cycloaddition of an alkyne in a phosphotriester of the CpG polynucleotide with azido in Ab-$N_3$ furnished an exemplary conjugate of the invention (see FIGS. 3A and 3B).

B. General Procedure for Conjugation to an Antibody Through the Use of Activated Carboxylic Acid Esters (e.g., TFP or PFP)

TABLE 4

Exemplary Setup for Antigen-binding Moiety (e.g., Antibody) Conjugation with TFP-ester- or PFP-ester-capped azido-PEG

| Molecule | Conc. (µM) | Volume (µL) | Linker:Ab | Antibody (nmol) |
|---|---|---|---|---|
| LC-containing antigen-binding moiety (e.g., rituximab) | 167 | 1700 | — | 28 |

TABLE 4-continued

Exemplary Setup for Antigen-binding Moiety (e.g., Antibody) Conjugation with TFP-ester- or PFP-ester-capped azido-PEG

| Molecule | Conc. (µM) | Volume (µL) | Linker:Ab | Antibody (nmol) |
|---|---|---|---|---|
| TFP-PEGn-$N_3$ or PFP-PEGn-$N_3$ n = 3, 7, 11, 24, or 35 | 100000 | 8.5 | 3.0 | — |
| DPBS | — | 291 | — | — |
| Final volume | — | 2000 | — | — |

General Protocol:

To a solution of an antibody in DPBS buffer, was added azido-PEG24-PFP, and the resulting mixture was left overnight at room temperature, at which time, the excess azido-PEG24-PFP was removed by buffer exchanging the produced Ab-$N_3$ through an Amicon 30 kD spin concentrator using DPBS as an eluent. A sample of Ab-$N_3$ was then reduced and characterized for degree of linker conjugation by RP-HPLC, as described below. Subsequent Huisgen cycloaddition of an alkyne in a phosphotriester of the CpG polynucleotide with azido in Ab-$N_3$ furnished an exemplary conjugate of the invention.

Antibody/Double-Stranded Immunomodulating Polynucleotide Conjugation Protocol

Figure 4A:
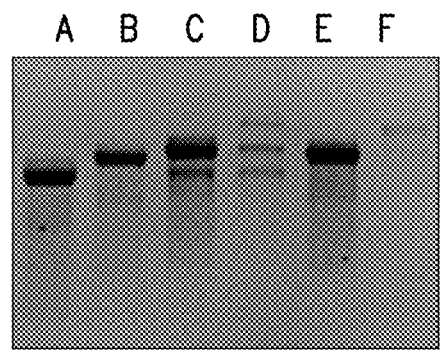
FIG. 4A is an image of an ethidium bromide-stained denaturing gel of a Q-tagged anti-CD38 conjugated to an azide linker before (lane A) and after conjugation through dipolar cycloaddition to a single-stranded polynucleotide (lane B, a Dari conjugate with p88) or to a double-stranded polynucleotide (lanes C, D, E, and F). Lane C corresponds to the isolated first AEX peak for the conjugate of Q-tagged anti-CD38 antibody linked by a metal-free 1,3-dipolar cycloaddition to p88/p145 double-stranded CpG. Lane D corresponds to the isolated second AEX peak for the conjugate of Q-tagged anti-CD38 antibody linked by a metal-free 1,3-dipolar cycloaddition to p88/p145 double-stranded CpG. Lane E corresponds to the isolated first AEX peak for the conjugate of Q-tagged anti-CD38 antibody linked by a metal-free 1,3-dipolar cycloaddition to p88/p144 double-stranded CpG. Lane F corresponds to the isolated second AEX peak for the conjugate of Q-tagged anti-CD38 antibody linked by a metal-free 1,3-dipolar cycloaddition to p88/p144 double-stranded CpG.

The fully annealed double stranded CpG polynucleotides (p88/p144 and p88/p145) were added to anti-CD38Q-$N_3$ antibody (39 mL, 40 mM). The mixture was heated to 37° C. for 2 h and purified by chromatography on an anion exchange resin (AEX). Two major peaks were collected, concentrated through an Amicon 30 kD concentrator, and analyzed by tri-glycine denaturing gel, 200 volts for 1 h followed by ethidium bromide staining (see FIG. 4A).

Anti-CD20 Antibody Immunomodulating Polynucleotide Conjugate

Figure 4B:
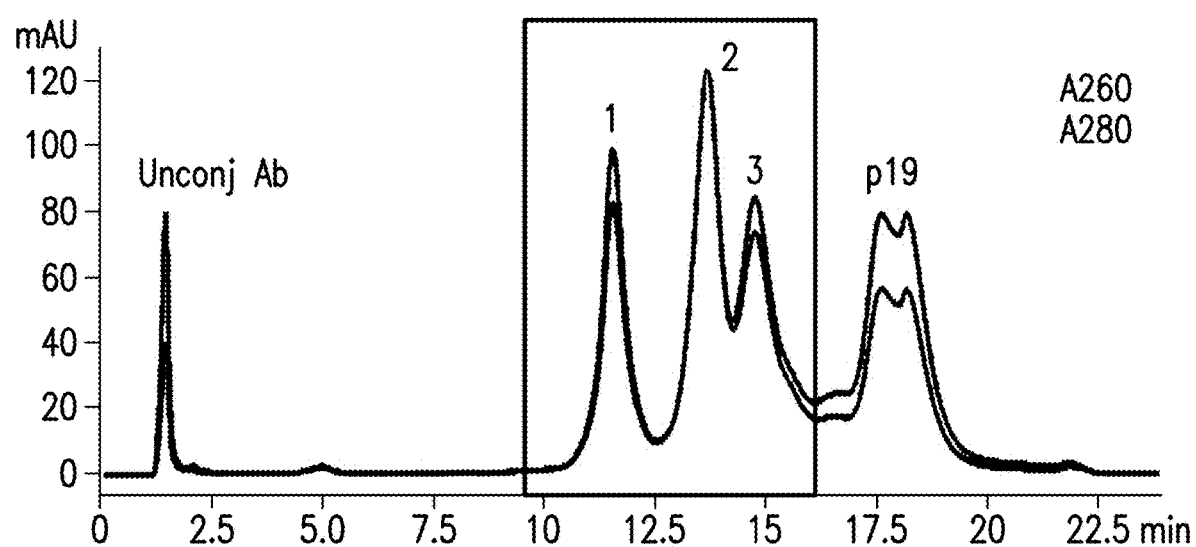
FIG. 4B is a graph showing AEX-HPLC traces for a crude mixture containing rituximab-p19 conjugate showing signals based on absorbance at 280 nm and at 260 nm. There are three peaks corresponding to rituximab-p19 conjugate.
Figure 4C:
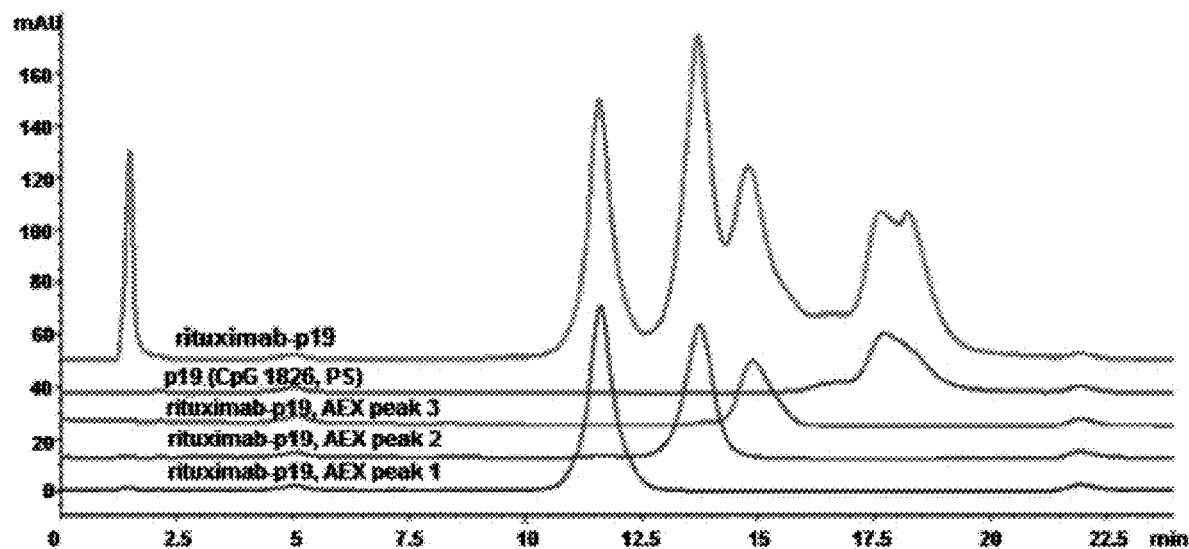
FIG. 4C is a graph showing a composite of AEX-HPLC traces for: the crude mixture, p19, and rituximab-p19 AEX peaks 1, 2, and 3, which are enumerated in FIG. 4B.
Figure 4D:
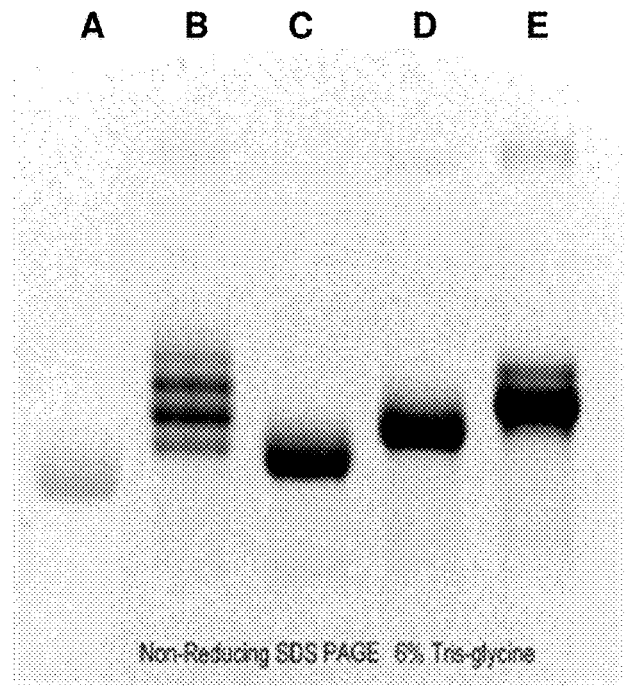
FIG. 4D is an image of a denaturing SDS PAGE 6% tris-glycine gel comparing rituximab-PEG24-N3 (lane A), crude conjugation reaction mixture (lane B), and isolated rituximab-p19 AEX peaks 1 (lane C), 2 (lane D), and 3 (lane E).

A conjugate containing rituximab conjugated through TFP-$PEG_{24}$-$N_3$ linker to an immunostimulating polynucleotide (p19), where the TFP portion was linked to rituximab and azide was linked to the immunostimulating polynucleotide. The crude mixture of the conjugate was purified by AEX-HPLC under the following conditions:

Buffer A: 20 mM sodium phosphate, 15% iPrOH (aq.)
Buffer B: 20 mM sodium phosphate, 1M sodium bromide, 15% iPrOH (aq.)
Column: Thermo Scientific Dionex DNASwift, 5×150 mm
10-95% buffer B in 10 min, then wash and re-equilibrate
Gradient: 10-95% B in 10 minutes, wash 5 min 95% B The AEX-HPLC trace of the crude mixture is shown in FIG. 4B (the peak areas for peaks 1, 2, and 3 are 28%, 40%, and 32%, respectively, of the total area of peaks 1, 2, and 3). FIG. 4C shows the combined HPLC traces for the crude mixture and the isolated peaks identified by numbers 1, 2, and 3 in FIG. 4B. FIG. 4D provides comparison of rituximab-$PEG_{24}$-$N_3$, the crude reaction mixture, and isolated peaks 1, 2, and 3. Rituximab-p19-DAR1 (drug-antibody ratio=1, i.e., there is one antibody conjugated to one p19 polynucleotide) was identified by its molecular weight (MW=155400).

The conjugation procedures described herein have been used to prepare exemplary conjugates of the invention listed in Table 6.

Quantitation of Unconjugated and Conjugated Heavy Chain by RP-HPLC

Ab-$N_3$ samples were analyzed prior to Huisgen cycloaddition to assess the conjugation efficiency for the azido linker. First, reduction of Ab-$N_3$ (5 µM) with DTT (20 mM DTT) and 5 M guanidine-HCl was carried out at 65° C. for 30 min. The resulting proteinaceous products were analyzed by RP-HPLC under the following conditions:

Column: Pursuit Diphenyl 5, 4.6×250 mm, 5 μm
Column Temp: 60° C.
MPA: 0.1% TFA in water, MPB: 0.1% TFA in acetonitrile
Gradient: 35-50% MPB in 17 minutes
Detection at 280 nm The percentages of unconjugated heavy chains and conjugated heavy chains (HC-$N_3$) are provided in Table 5 and are based on the percentages of the total of peak areas for conjugated and unconjugated heavy chains.

TABLE 5

Quantitation of the Extent of Conjugation of Antibody HC

| Reaction | % unconjugated HC | % HC—$N_3$ |
|---|---|---|
| Q-tagged anti-CD79b + $N_3$-PEG23-$NH_2$ | 13 | 86 |
| Q-tagged anti-CD38 + $N_3$-PEG23-$NH_2$ | 24 | 76 |
| Q-tagged anti-CD22 + $N_3$-PEG23-$NH_2$ (overnight, at RT) | 23 | 77 |
| Q-tagged anti-CD22 + $N_3$-PEG23-$NH_2$ (overnight, at RT + 3 h, at 37° C.) | 23 | 77 |

Conjugates Having Polynucleotide Phosphate Backbone can Elute Faster Through Anion Exchange Column than Conjugates Having Phosphorothioate Backbone Conjugates containing Q-tagged anti-CD38 antibody conjugated to a CpG polynucleotide were prepared as described herein. In this experiment, the CpG polynucleotides used in the synthesis were p19, p21, and p88. The isolated conjugates were subjected to AEX-HPLC analysis under the following conditions:

Method A: 10-95% B in 10 min, then wash & re-equilibrate
Method B: 10-50% B in 10 min, then wash & re-equilibrate
Column: Thermo Scientific Dionex DNASwift, analytical 5×150 mm
Buffer A: 20 mM sodium phosphate, 15% iPrOH (aq.)
Buffer B: 20 mM sodium phosphate, 1 M sodium bromide, 15% i-PrOH (aq.)

The retention times for the peaks corresponding to SB-037 (anti-CD38Q-p19) conjugate in the AEX-HPLC trace were greater than those corresponding to SB-038 (anti-CD38Q-p21).

TABLE 6-A

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-001 | CD22 | HC—Q-tag | $NH_2$—PEG8—$N_3$ | p4 | 5'-DBCO—TEG | 4 | | | | | |
| SB-003 | CD22 | HC—Q-tag | $NH_2$—PEG8—$N_3$ | p5 | 5'-DBCO—TEG—C6—SS—C6 | 20 | | | | | |
| SB-004 | CD38 | HC—Q-tag | $NH_2$—PEG8—$N_3$ | p4 | 5'-DBCO—TEG | 10 | 20 | >10 | | | |
| SB-005 | CD38 | HC—Q-tag | $NH_2$—PEG8—$N_3$ | p5 | 5'-DBCO—TEG—C6—SS—C6 | 100 | | | | | |
| SB-006 | CD79b | HC—Q-tag | $NH_2$—PEG8—$N_3$ | p4 | 5'-DBCO—TEG | | | | | | |
| SB-007 | CD79b | HC—Q-tag | $NH_2$—PEG8—$N_3$ | p5 | 5'-DBCO—TEG—C6—SS—C6 | | | | | | |
| SB-008 | CD38 | HC—Q-tag | $NH_2$—PEG8—$N_3$ | p7 | 5'-DBCO—TEG—C6—SS—C6 | 26 | 20 | >10 | | | |
| SB-009 | CD38 | HC—Q-tag | $NH_2$—PEG8—$N_3$ | p9 | 5'-DBCO—TEG—C6—SS—C6 | >200 | | | | | |
| SB-010 | CD38 | HC—Q-tag | $NH_2$—PEG8—$N_3$ | p12 | 5'-DBCO—TEG—C6—SS—C6 | | | | | | |
| SB-011 | CD38 | HC—Q-tag | $NH_2$—PEG8—$N_3$ | p13 | 5'-DBCO—TEG—C6—SS—C6 | 75 | 40 | | | | |
| SB-012 | CD38 | HC—Q-tag | $NH_2$—PEG23—$N_3$ | p24 | dT(DBCO) | 20 | | | | | |
| SB-013 | CD38 | HC—Q-tag | $NH_2$—PEG23—$N_3$ | p25 | dT(DBCO) | 100 | | | | | |
| SB-014 | CD38 | HC—Q-tag | $NH_2$—PEG23—$N_3$ | p26 | dT(DBCO) | >200 | | | | | |
| SB-015 | CD38 | HC—Q-tag | $NH_2$—PEG23—$N_3$ | p27 | dT(DBCO) | >200 | | | | | |
| SB-016 | CD38 | HC—Q-tag | $NH_2$—PEG23—$N_3$ | p28 | dT(DBCO) | 50 | | | | | |
| SB-017 | rituximab | LC—TFP-tag | TFP—PEG24—$N_3$ | p7 | 5'-DBCO—TEG—C6—SS—C6 | >200 | >200 | | | | |
| SB-018 | rituximab | LC—TFP-tag | TFP—PEG24—$N_3$ | p13 | 5'-DBCO—TEG—C6—SS—C6 | >200 | >200 | | | | |
| SB-019 | rituximab | LC—TFP-tag | TFP—PEG24—$N_3$ | p17 | 5'-DBCO—TEG | | | | | | |
| SB-020 | rituximab | LC—TFP-tag | TFP—PEG24—$N_3$ | p21 | 5'-DBCO—TEG | | | | | | |
| SB-021 | rituximab | LC—TFP-tag | TFP—PEG24—$N_3$ | p4 | 5'-DBCO—TEG | >200 | | | | | |
| SB-02-1 | CD22 | HC—Q-tag | $NH_2$—PEG8—$N_3$ | p4 | 5'-DBCO—TEG | >10 | | >10 | | | |
| SB-022 | rituximab | LC—TFP-tag | TFP—PEG24—$N_3$ | p5 | 5'-DBCO—TEG—C6—SS—C6 | >200 | >200 | | | | |
| SB-02-2 | CD22 | HC—Q-tag | $NH_2$—PEG8—$N_3$ | p4 | 5'-DBCO—TEG | >10 | | >10 | | | |
| SB-023 | rituximab | LC—TFP-tag | TFP—PEG24—$N_3$ | p9 | 5'-DBCO—TEG—C6—SS—C6 | | | | | | |
| SB-024 | rituximab | LC—TFP-tag | TFP—PEG24—$N_3$ | p12 | 5'-DBCO—TEG—C6—SS—C6 | | | | | | |
| SB-025 | rituximab | LC—TFP-tag | TFP—PEG24—$N_3$ | p16 | 5'-DBCO—TEG | | | | | | |
| SB-026 | rituximab | LC—TFP-tag | TFP—PEG24—$N_3$ | p19 | 5'-DBCO—TEG | | | | | | |
| SB-027 | rituximab | LC—TFP-tag | TFP—PEG24—$N_3$ | p30 | 5'-DBCO—TEG | | | | | | |
| SB-028 | rituximab | LC—TFP-tag | TFP—PEG24—$N_3$ | p32 | 5'-DBCO—TEG | | | | | | |
| SB-029 | rituximab | LC—TFP-tag | TFP—PEG24—$N_3$ | p34 | 5'-DBCO—TEG | | | | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-030 | rituximab | LC—TFP-tag | TFP—PEG24—N$_3$ | p36 | 5'-DBCO—TEG | >200 | | | | | |
| SB-031 | rituximab | LC—TFP-tag | TFP—PEG24—N$_3$ | p38 | 5'-DBCO—TEG | | | | | | |
| SB-032 | CD79b | HC—Q-tag | NH$_2$—PEG23—N$_3$ | p4 | 5'-DBCO—TEG | | | | | | |
| SB-033 | CD79b | HC—Q-tag | NH$_2$—PEG23—N$_3$ | p19 | 5'-DBCO—TEG | | | | | | |
| SB-034 | CD79b | HC—Q-tag | NH$_2$—PEG23—N$_3$ | p30 | 5'-DBCO—TEG | | | | | | |
| SB-035 | CD79b | HC—Q-tag | NH$_2$—PEG23—N$_3$ | p32 | 5'-DBCO—TEG | | | | | | |
| SB-036 | CD79b | HC—Q-tag | NH$_2$—PEG23—N$_3$ | p34 | 5'-DBCO—TEG | | | | | | |
| SB-037 | CD38 | HC—Q-tag | NH$_2$—PEG23—N$_3$ | p19 | 5'-DBCO—TEG | >100 | | | | | |
| SB-038 | CD38 | HC—Q-tag | NH$_2$—PEG23—N$_3$ | p21 | 5'-DBCO—TEG | 70 | | | | | |
| SB-039 | CD38 | HC—Q-tag | NH$_2$—PEG23—N$_3$ | p23 | 5'-DBCO—TEG | 18 | | | | | |
| SB-040 | CD38 | HC—Q-tag | NH$_2$—PEG23—N$_3$ | p30 | 5'-DBCO—TEG | 12 | | | | | |
| SB-041 | CD38 | HC—Q-tag | NH$_2$—PEG23—N$_3$ | p34 | 5'-DBCO—TEG | 20 | | | | | |
| SB-042 | CD38 | HC—Q-tag | NH$_2$—PEG23—N$_3$ | p38 | 5'-DBCO—TEG | | | | | | |
| SB-043 | CD38 | HC—Q-tag | NH$_2$—PEG23—N$_3$ | p71 | 3'-DBCO—NH—PEG2 triester | | | | | | |
| SB-044 | rituximab | LC—TFP-tag | TFP—PEG24—N$_3$ | p71 | 3'-DBCO—NH—PEG2 triester | >100 | | | | | |
| SB-045 | CD38 | HC—Q-tag | NH$_2$—PEG23—N$_3$ | p76 | DBCO—NH—PEG2 triester | | | >10 | | | |
| SB-046 | CD38 | HC—Q-tag | NH$_2$—PEG23—N$_3$ | p77 | DBCO—NH—PEG2 triester | | | 0.1 | 0.2 | | |
| SB-047 | CD38 | HC—Q-tag | NH$_2$—PEG23—N$_3$ | p78 | DBCO—NH—PEG2 triester | | | 0.05 | | | |
| SB-048 | CD38 | HC—Q-tag | NH$_2$—PEG23—N$_3$ | p79 | DBCO—NH—PEG2 triester | | | 0.6 | | | |
| SB-049 | CD38 | HC—Q-tag | NH$_2$—PEG23—N$_3$ | p80 | DBCO—NH—PEG2 triester | | | 0.04 | | | |
| SB-050 | CD38 | HC—Q-tag | NH$_2$—PEG23—N$_3$ | p81 | DBCO—NH—PEG2 triester | | | 0.1 | | | |
| SB-051 | CD38 | HC—Q-tag | NH$_2$—PEG23—N$_3$ | p82 | DBCO—NH—PEG2 triester | | | 0.09 | | | |
| SB-052 | CD38 | HC—Q-tag | NH$_2$—PEG23—N$_3$ | p83 | DBCO—NH—PEG2 triester | | | 0.4 | | | |
| SB-053 | CD38 | HC—Q-tag | NH$_2$—PEG23—N$_3$ | p84 | DBCO—NH—PEG2 triester | | | 0.1 | 0.3 | | |
| SB-054 | CD38 | HC—Q-tag | NH$_2$—PEG23—N$_3$ | p85 | DBCO—NH—PEG2 triester | | | 0.09 | | | |
| SB-055 | CD38 | HC—Q-tag | NH$_2$—PEG23—N$_3$ | p86 | DBCO—NH—PEG2 triester | | | 0.1 | | | |
| SB-056 | CD38 | HC—Q-tag | NH$_2$—PEG23—N$_3$ | p87 | DBCO—NH—PEG2 triester | | | 0.05 | | | |
| SB-057 | CD38 | HC—Q-tag | NH$_2$—PEG23—N$_3$ | p88 | DBCO—NH—PEG2 triester | | | 0.1 | 0.3 | | |
| SB-058 | rituximab | LC—TFP-tag | TFP—PEG24—N$_3$ | p76 | DBCO—NH—PEG2 triester | | | | | | |
| SB-059 | rituximab | LC—TFP-tag | TFP—PEG24—N$_3$ | p77 | DBCO—NH—PEG2 triester | | | | | | |
| SB-060 | rituximab | LC—TFP-tag | TFP—PEG24—N$_3$ | p78 | DBCO—NH—PEG2 triester | | | | | | |
| SB-061 | rituximab | LC—TFP-tag | TFP—PEG24—N$_3$ | p79 | DBCO—NH—PEG2 triester | | | | | | |
| SB-062 | rituximab | LC—TFP-tag | TFP—PEG24—N$_3$ | p80 | DBCO—NH—PEG2 triester | | | | | | |
| SB-063 | rituximab | LC—TFP-tag | TFP—PEG24—N$_3$ | p81 | DBCO—NH—PEG2 triester | | | | | | |
| SB-064 | rituximab | LC—TFP-tag | TFP—PEG24—N$_3$ | p82 | DBCO—NH—PEG2 triester | | | | | | |
| SB-065 | rituximab | LC—TFP-tag | TFP—PEG24—N$_3$ | p83 | DBCO—NH—PEG2 triester | | | 2.4 | | | |
| SB-066 | rituximab | LC—TFP-tag | TFP—PEG24—N$_3$ | p84 | DBCO—NH—PEG2 triester | | | | | | |
| SB-067 | rituximab | LC—TFP-tag | TFP—PEG24—N$_3$ | p85 | DBCO—NH—PEG2 triester | | | | | | |
| SB-068 | rituximab | LC—TFP-tag | TFP—PEG24—N$_3$ | p86 | DBCO—NH—PEG2 triester | | | 0.24 | | | |
| SB-069 | rituximab | LC—TFP-tag | TFP—PEG24—N$_3$ | p87 | DBCO—NH—PEG2 triester | | | | | | |
| SB-070 | rituximab | LC—TFP-tag | TFP—PEG24—N$_3$ | p88 | DBCO—NH—PEG2 triester | | | | | | |
| SB-071-2 | CD22 | HC—Q-tag | NH$_2$—PEG23—N$_3$ | P7 | 5'-DBCO—TEG—C6—SS—C6 | >10 | | >10 | | | |
| SB-072-2 | CD22 | HC—Q-tag | NH$_2$—PEG23—N$_3$ | p76 | DBCO—NH—PEG2 triester | >10 | | >10 | | | |
| SB-073-1 | CD22 | HC—Q-tag | NH$_2$—PEG23—N$_3$ | p88 | DBCO—NH—PEG2 triester | >10 | | >10 | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-073-2 | CD22 | HC—Q-tag | NH$_2$—PEG23—N$_3$ | p88 | DBCO—NH—PEG2 triester | 2.2 | 1.1 | 0.4 | | | |
| SB-074 | rituximab | LC—TFP-tag | TFP—PEG24—N$_3$ | p95 | DBCO—NH—PEG2 triester | | | | | | |
| SB-075 | rituximab | LC—TFP-tag | TFP—PEG24—N$_3$ | p97 | DBCO—NH—PEG2 triester | | | | | | |
| SB-076 | rituximab | LC—TFP-tag | TFP—PEG24—N$_3$ | p103 | DBCO—NH—PEG2 triester | | | | | | |
| SB-077 | CD79b | HC—Q-tag | NH$_2$—PEG23—N$_3$ | p88 | DBCO—NH—PEG2 triester | | | | | | |
| SB-078 | CD38 | HC—Q-tag | NH$_2$—PEG23—N$_3$ | p95 | DBCO—NH—PEG2 triester | | | 1.9 | | | |
| SB-079 | CD38 | HC—Q-tag | NH$_2$—PEG23—N$_3$ | p97 | DBCO—NH—PEG2 triester | | | 1.6 | | | |
| SB-080 | CD38 | HC—Q-tag | NH$_2$—PEG23—N$_3$ | p100 | DBCO—NH—PEG2 triester | | | >30 | | | |
| SB-081 | CD38 | HC—Q-tag | NH$_2$—PEG23—N$_3$ | p103 | DBCO—NH—PEG2 triester | | | 2.7 | | | |
| SB-082 | CD38 | HC—Q-tag | NH$_2$—PEG3—N$_3$ | p88 | DBCO—NH—PEG2 triester | | | | | | |
| SB-083 | CD38 | HC—Q-tag | NH$_2$—PEG7-N$_3$ | p88 | DBCO—NH—PEG2 triester | | | | | | |
| SB-084 | CD38 | HC—Q-tag | NH$_2$—PEG11-N$_3$ | p88 | DBCO—NH—PEG2 triester | | | | | | |
| SB-085 | CD38 | HC—Q-tag | NH$_2$—PEG35-N$_3$ | p88 | DBCO—NH—PEG2 triester | | | | | | |
| SB-086 | CD38 | HC—Q-tag | NH$_2$—PEG23—N$_3$ | p150 | DBCO—NH—PEG2 triester | | | 0.44 | | | |
| SB-087 | CD38 | HC—Q-tag | NH$_2$—PEG23—N$_3$ | p152 | DBCO—NH—PEG2 triester | | | 0.5 | | | |
| SB-088 | CD38 | HC—Q-tag | NH$_2$—PEG23—N$_3$ | p153 | DBCO—NH—PEG2 triester | | | 0.36 | | | |
| SB-089 | CD38 | HC—Q-tag | NH$_2$—PEG23—N$_3$ | p154 | DBCO—NH—PEG2 triester | | | 0.46 | | | |
| SB-090 | CD38 | HC—Q-tag | NH$_2$—PEG23—N$_3$ | p155 | DBCO—NH—PEG2 triester | | | 0.23 | | | |
| SB-091 | CD38 | HC—Q-tag | NH$_2$—PEG23—N$_3$ | p156 | DBCO—NH—PEG2 triester | | | 0.28 | | | |
| SB-092 | CD38 | HC—Q-tag | NH$_2$—PEG23—N$_3$ | p157 | DBCO—NH—PEG2 triester | | | 0.3 | | | |
| SB-093 | CD38 | HC—Q-tag | NH$_2$—PEG23—N$_3$ | p158 | DBCO—NH—PEG2 triester | | | >10 | | | |
| SB-094 | CD38 | HC—Q-tag | NH$_2$—PEG23—N$_3$ | p159 | DBCO—NH—PEG2 triester | | | >10 | | | |
| SB-095 | CD38 | HC—Q-tag | NH$_2$—PEG23—N$_3$ | p160 | DBCO—NH—PEG2 triester | | | >10 | | | |
| SB-096 | CD38 | HC—Q-tag | NH$_2$—PEG23—N$_3$ | p161 | DBCO—NH—PEG2 triester | | | 0.33 | | | |
| SB-097 | CD38 | HC—Q-tag | NH$_2$—PEG23—N$_3$ | p162 | DBCO—NH—PEG2 triester | | | 0.53 | | | |
| SB-098 | CD38 | HC—Q-tag | NH$_2$—PEG23—N$_3$ | p163 | DBCO—NH—PEG2 triester | | | 0.12 | | | |
| SB-099 | rituximab | HC—Q-tag | NH$_2$—PEG23—N$_3$ | p163 | DBCO—NH—PEG2 triester | | | 0.14 | | | |
| SB-100 | CD38 | HC—Q-tag | NH$_2$—PEG23—N$_3$ | p164 | DBCO—NH—PEG2 triester | | | 1.2 | | | |
| SB-101 | CD38 | HC—Q-tag | NH$_2$—PEG23—N$_3$ | p165 | DBCO—NH—PEG2 triester | | | 0.11 | | | |
| SB-102 | CD38 | HC—Q-tag | NH$_2$—PEG23—N$_3$ | p166 | DBCO—NH—PEG2 triester | | | 0.25 | | | |
| SB-103 | CD38 | HC—Q-tag | NH$_2$—PEG23—N$_3$ | p167 | DBCO—NH—PEG2 triester | | | 0.06 | | | |
| SB-104 | CD38 | HC—Q-tag | NH$_2$—PEG23—N$_3$ | p168 | DBCO—NH—PEG2 triester | | | 0.29 | | | |
| SB-105 | CD38 | HC—Q-tag | NH$_2$—PEG23—N$_3$ | p169 | DBCO—NH—PEG2 triester | | | 0.05 | | | |
| SB-106 | CD38 | HC—Q-tag | NH$_2$—PEG23—N$_3$ | p170 | DBCO—NH—PEG2 triester | | | 0.34 | | | |
| SB-107 | rituximab | LC—PFP | TFP—PEG24—N$_3$ | p163 | DBCO—NH—PEG2 triester | | | 0.55 | | | |
| SB-108 | CD38 | HC—Q-tag | NH$_2$—PEG23—N$_3$ | p179 | DBCO—NH—PEG2 triester | | | 0.12 | | | |
| SB-109 | CD38 | HC—Q-tag | NH$_2$—PEG23—N$_3$ | p179 | DBCO—NH—PEG2 triester | | | 0.11 | | | |
| SB-110 | CD38 | HC—Q-tag | NH$_2$—PEG23—N$_3$ | p180 | DBCO—NH—PEG2 triester | | | 0.1 | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-111 | CD38 | HC—Q-tag | $NH_2$—PEG23—$N_3$ | p180 | DBCO—NH—PEG2 triester | | | 0.11 | | | |
| SB-112 | CD38 | HC—Q-tag | $NH_2$—PEG23—$N_3$ | p181 | DBCO—NH—PEG2 triester | | | 0.07 | | | |
| SB-113 | CD38 | HC—Q-tag | $NH_2$—PEG23—$N_3$ | p182 | DBCO—NH—PEG2 triester | | | 0.12 | | | |
| SB-114 | CD38 | HC—Q-tag | $NH_2$—PEG23—$N_3$ | p183 | DBCO—NH—PEG2 triester | | | 0.1 | | | |
| SB-115 | CD38 | HC—Q-tag | $NH_2$—PEG23—$N_3$ | p183 | DBCO—NH—PEG2 triester | | | 0.09 | | | |
| SB-116 | CD38 | HC—Q-tag | $NH_2$—PEG23—$N_3$ | p171 | DBCO—NH—PEG2 triester | | | 0.44 | | | |
| SB-117 | CD38 | HC—Q-tag | $NH_2$—PEG23—$N_3$ | p172 | DBCO—NH—PEG2 triester | | | 0.52 | | | |
| SB-118 | CD38 | HC—Q-tag | $NH_2$—PEG23—$N_3$ | p173 | DBCO—NH—PEG2 triester | | | 0.91 | | | |
| SB-119 | CD38 | HC—Q-tag | $NH_2$—PEG23—$N_3$ | p174 | DBCO—NH—PEG2 triester | | | 1.5 | | | |
| SB-120 | CD38 | HC—Q-tag | $NH_2$—PEG23—$N_3$ | p175 | DBCO—NH—PEG2 triester | | | 0.07 | | | |
| SB-121 | CD38 | HC—Q-tag | $NH_2$—PEG23—$N_3$ | p176 | DBCO—NH—PEG2 triester | | | 0.11 | | | |
| SB-122 | CD38 | HC—Q-tag | $NH_2$—PEG23—$N_3$ | p176 | DBCO—NH—PEG2 triester | | | 0.08 | | | |
| SB-123 | CD38 | HC—Q-tag | $NH_2$—PEG23—$N_3$ | p176 | DBCO—NH—PEG2 triester | | | 0.05 | | | |
| SB-124 | CD38 | HC—Q-tag | $NH_2$—PEG23—$N_3$ | p176 | DBCO—NH—PEG2 triester | | | 0.05 | | | |
| SB-125 | CD38 | HC—Q-tag | $NH_2$—PEG23—$N_3$ | p176 | DBCO—NH—PEG2 triester | | | 0.05 | | | |
| SB-126 | CD38 | HC—Q-tag | $NH_2$—PEG23—$N_3$ | p177 | DBCO—NH—PEG2 triester | | | 0.12 | | | |
| SB-127 | CD38 | HC—Q-tag | $NH_2$—PEG23—$N_3$ | p178 | DBCO—NH—PEG2 triester | | | 0.34 | | | |
| SB-128 | rituximab | HC—Q-tag | $NH_2$—PEG23—$N_3$ | p176 | DBCO—NH—PEG2 triester | | | 0.16 | | | |
| SB-129 | rituximab | HC—Q-tag | $NH_2$—PEG23—$N_3$ | p176 | DBCO—NH—PEG2 triester | | | 0.16 | | | |
| SB-130 | rituximab | HC—Q-tag | $NH_2$—PEG23—$N_3$ | p184 | DBCO—NH—PEG2 triester | | | >10 | | | |
| SB-131 | rituximab | HC—Q-tag | $NH_2$—PEG23—$N_3$ | p185 | DBCO—NH—PEG2 triester | | | >10 | | | |
| SB-132 | rituximab | HC—Q-tag | $NH_2$—PEG23—$N_3$ | p186 | DBCO—NH—PEG2 triester | | | >10 | | | |
| SB-133 | CD38 | HC—Q-tag | $NH_2$—PEG23—$N_3$ | p187 | DBCO—NH—PEG2 triester | | | 0.08 | | | |
| SB-134 | CD38 | HC—Q-tag | $NH_2$—PEG23—$N_3$ | p188 | DBCO—NH—PEG2 triester | | | 0.08 | | | |
| SB-135 | CD38 | HC—Q-tag | $NH_2$—PEG23—$N_3$ | p189 | DBCO—NH—PEG2 triester | | | 0.09 | | | |
| SB-136 | CD38 | HC—Q-tag | $NH_2$—PEG23—$N_3$ | p190 | DBCO—NH—PEG2 triester | | | 0.16 | | | |
| SB-137 | CD38 | HC—Q-tag | $NH_2$—PEG23—$N_3$ | p191 | DBCO—NH—PEG2 triester | | | 0.21 | | | |
| SB-138 | CD38 | HC—Q-tag | $NH_2$—PEG23—$N_3$ | p199 | DBCO—NH—PEG2 triester | | | 0.14 | | | |
| SB-139 | CD38 | HC—Q-tag | $NH_2$—PEG23—$N_3$ | p200 | DBCO—NH—PEG2 triester | | | 0.08 | | | |
| SB-140 | CD38 | HC—Q-tag | $NH_2$—PEG23—$N_3$ | p201 | DBCO—NH—PEG2 triester | | | 0.12 | | | |
| SB-141 | CD38 | HC—Q-tag | $NH_2$—PEG23—$N_3$ | p202 | DBCO—NH—PEG2 triester | | | 0.13 | | | |
| SB-142 | CD38 | HC—Q-tag | $NH_2$—PEG23—$N_3$ | p203 | DBCO—NH—PEG2 triester | | | 0.08 | | | |
| SB-143 | CD38 | HC—Q-tag | $NH_2$—PEG23—$N_3$ | p204 | DBCO—NH—PEG2 triester | | | 0.14 | | | |
| SB-144 | CD38 | HC—Q-tag | $NH_2$—PEG23—$N_3$ | p205 | DBCO—NH—PEG2 triester | | | 0.13 | | | |
| SB-145 | CD38 | HC—Q-tag | $NH_2$—PEG23—$N_3$ | p206 | DBCO—NH—PEG2 triester | | | 0.19 | | | |
| SB-146 | CD38 | HC—Q-tag | $NH_2$—PEG23—$N_3$ | p207 | DBCO—NH—PEG2 triester | | | 0.02 | | | |
| SB-147 | CD38 | HC—Q-tag | $NH_2$—PEG23—$N_3$ | p208 | DBCO—NH—PEG2 triester | | | 0.03 | | | |
| SB-148 | rituximab | HC—Q-tag | $NH_2$—PEG23—$N_3$ | p088 | DBCO—NH—PEG2 triester | | | 0.42 | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-149 | rituximab | HC—Q-tag | NH$_2$—PEG23—N$_3$ | p151 | DBCO—NH—PEG2 triester | | | 21 | | | |
| SB-150 | CD38 | HC—Q-tag | NH$_2$—PEG23—N$_3$ | p200 | DBCO—NH—PEG2 triester | | | 0.12 | | | |
| SB-151 | CD38 | HC—Q-tag | NH$_2$—PEG23—N$_3$ | p201 | DBCO—NH—PEG2 triester | | | 0.072 | | | |
| SB-152 | CD38 | HC—Q-tag | NH$_2$—PEG23—N$_3$ | p209 | DBCO—NH—PEG2 triester | | | 0.41 | | | |
| SB-153 | CD38 | HC—Q-tag | NH$_2$—PEG23—N$_3$ | p210 | DBCO—NH—PEG2 triester | | | 0.71 | | | |
| SB-154 | CD38 | HC—Q-tag | NH$_2$—PEG23—N$_3$ | p211 | DBCO—NH—PEG2 triester | | | 1 | | | |
| SB-155 | CD38 | HC—Q-tag | NH$_2$—PEG23—N$_3$ | p212 | DBCO—NH—PEG2 triester | | | 0.75 | | | |
| SB-156 | CD38 | HC—Q-tag | NH$_2$—PEG23—N$_3$ | p213 | DBCO—NH—PEG2 triester | | | 0.25 | | | |
| SB-157 | CD38 | HC—Q-tag | NH$_2$—PEG23—N$_3$ | p214 | DBCO—NH—PEG2 triester | | | 0.22 | | | |
| SB-158 | CD38 | HC—Q-tag | NH$_2$—PEG23—N$_3$ | p215 | DBCO—NH—PEG2 triester | | | 0.11 | | | |
| SB-159 | CD38 | HC—Q-tag | NH$_2$—PEG23—N$_3$ | p216 | DBCO—NH—PEG2 triester | | | 0.24 | | | |
| SB-160 | CD38 | HC—Q-tag | NH$_2$—PEG23—N$_3$ | p217 | DBCO—NH—PEG2 triester | | | 0.37 | | | |
| SB-161 | CD38 | HC—Q-tag | NH$_2$—PEG23—N$_3$ | p218 | DBCO—NH—PEG2 triester | | | 0.7 | | | |
| SB-162 | CD38 | HC—Q-tag | NH$_2$—PEG23—N$_3$ | p219 | DBCO—NH—PEG2 triester | | | n/a | | | |
| SB-163 | CD38 | HC—Q-tag | NH$_2$—PEG23—N$_3$ | p222 | DBCO—NH—PEG2 triester | | | >3 | | | |
| SB-164 | CD38 | HC—Q-tag | NH$_2$—PEG23—N$_3$ | p223 | DBCO—NH—PEG2 triester | | | >3 | | | |
| SB-165 | CD38 | HC—Q-tag | NH$_2$—PEG23—N$_3$ | p224 | DBCO—NH—PEG2 triester | | | >1000 | | | |
| SB-166 | CD38 | HC—Q-tag | NH$_2$—PEG23—N$_3$ | p225 | DBCO—NH—PEG2 triester | | | 0.33 | | | |
| SB-167 | CD38 | HC—Q-tag | NH$_2$—PEG23—N$_3$ | p226 | DBCO—NH—PEG2 triester | | | 0.23 | | | |
| SB-168 | CD38 | HC—Q-tag | NH$_2$—PEG23—N$_3$ | p227 | DBCO—NH—PEG2 triester | | | 0.62 | | | |
| SB-169 | CD38 | HC—Q-tag | NH$_2$—PEG23—N$_3$ | p228 | DBCO—NH—PEG2 triester | | | 0.12 | | | |
| SB-170 | CD38 | HC—Q-tag | NH$_2$—PEG23—N$_3$ | p229 | DBCO—NH—PEG2 triester | | | 0.3 | | | |
| SB-171 | CD38 | HC—Q-tag | NH$_2$—PEG23—N$_3$ | p230 | DBCO—NH—PEG2 triester | | | 0.3 | | | |
| SB-172 | CD38 | HC—Q-tag | NH$_2$—PEG23—N$_3$ | p231 | DBCO—NH—PEG2 triester | | | 0.19 | | | |
| SB-173 | CD38 | HC—Q-tag | NH$_2$—PEG23—N$_3$ | p199 | DBCO—NH—PEG2 triester | | | 0.096 | | | |
| SB-174 | CD38 | HC—Q-tag | NH$_2$—PEG23—N$_3$ | p231 | DBCO—NH—PEG2 triester | | | 0.095 | | | |
| SB-175 | CD38 | HC—Q-tag | NH$_2$—PEG23—N$_3$ | p232 | DBCO—NH—PEG2 triester | | | 42 | | | |
| SB-176 | CD38 | HC—Q-tag | NH$_2$—PEG23—N$_3$ | p233 | DBCO—NH—PEG2 triester | | | 9.1 | | | |
| SB-177 | CD38 | HC—Q-tag | NH$_2$—PEG23—N$_3$ | p233 | DBCO—NH—PEG2 triester | | | 33 | | | |
| SB-178 | CD38 | HC—Q-tag | NH$_2$—PEG23—N$_3$ | p235 | DBCO—NH—PEG2 triester | | | 9.4 | | | |
| SB-179 | CD38 | HC—Q-tag | NH$_2$—PEG23—N$_3$ | p236 | DBCO—NH—PEG2 triester | | | 1.5 | | | |
| SB-180 | CD38 | HC—Q-tag | NH$_2$—PEG23—N$_3$ | p237 | DBCO—NH—PEG2 triester | | | 15 | | | |
| SB-181 | CD38 | HC—Q-tag | NH$_2$—PEG23—N$_3$ | p238 | DBCO—NH—PEG2 triester | | | 1 | | | |
| SB-182 | CD38 | HC—Q-tag | NH$_2$—PEG23—N$_3$ | p239 | DBCO—NH—PEG2 triester | | | 0.03 | | | |
| SB-183 | CD38 | HC—Q-tag | NH$_2$—PEG23—N$_3$ | p240 | DBCO—NH—PEG2 triester | | | 0.04 | | | |
| SB-184 | CD38 | HC—Q-tag | NH$_2$—PEG23—N$_3$ | p241 | DBCO—NH—PEG2 triester | | | 0.04 | | | |
| SB-185 | CD38 | HC—Q-tag | NH$_2$—PEG23—N$_3$ | p242 | DBCO—NH—PEG2 triester | | | 0.23 | | | |
| SB-186 | CD38 | HC—Q-tag | NH$_2$—PEG23—N$_3$ | p243 | DBCO—NH—PEG2 triester | | | 0.29 | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-187 | CD38 | HC—Q-tag | NH$_2$—PEG23—N$_3$ | p244 | DBCO—NH—PEG2 triester | | | 0.02 | | | |
| SB-188 | CD38 | HC—Q-tag | NH$_2$—PEG23—N$_3$ | p245 | DBCO—NH—PEG2 triester | | | 0.11 | | | |
| SB-189 | CD38 | HC—Q-tag | NH$_2$—PEG23—N$_3$ | p246 | DBCO—NH—PEG2 triester | | | 0.86 | | | |
| SB-190 | CD38 | HC—Q-tag | NH$_2$—PEG23—N$_3$ | p247 | DBCO—NH—PEG2 triester | | | 0.76 | | | |
| SB-191 | CD38 | HC—Q-tag | NH$_2$—PEG23—N$_3$ | p248 | DBCO—NH—PEG2 triester | | | 2.4 | | | |
| SB-192 | CD38 | HC—Q-tag | NH$_2$—PEG23—N$_3$ | p249 | DBCO—NH—PEG2 triester | | | 2.7 | | | |
| SB-193 | CD38 | HC—Q-tag | NH$_2$—PEG23—N$_3$ | p250 | DBCO—NH—PEG2 triester | | | 0.09 | | | |
| SB-194 | CD38 | HC—Q-tag | NH$_2$—PEG23—N$_3$ | p251 | DBCO—NH—PEG2 triester | | | 0.067 | | | |
| SB-195 | CD38 | HC—Q-tag | NH$_2$—PEG23—N$_3$ | p252 | DBCO—NH—PEG2 triester | | | 0.064 | | | |
| SB-196 | CD38 | HC—Q-tag | NH$_2$—PEG23—N$_3$ | p253 | DBCO—NH—PEG2 triester | | | 0.045 | | | |
| SB-197 | CD38 | HC—Q-tag | NH$_2$—PEG23—N$_3$ | p254 | DBCO—NH—PEG2 triester | | | 0.042 | | | |
| SB-198 | CD38 | HC—Q-tag | NH$_2$—PEG23—N$_3$ | p255 | DBCO—NH—PEG2 triester | | | 0.033 | | | |
| SB-199 | CD38 | HC—Q-tag | NH$_2$—PEG23—N$_3$ | p256 | DBCO—NH—PEG2 triester | | | 0.039 | | | |
| SB-200 | CD38 | HC—Q-tag | NH$_2$—PEG23—N$_3$ | p257 | DBCO—NH—PEG2 triester | | | 0.039 | | | |
| SB-201 | CD38 | HC—Q-tag | NH$_2$—PEG23—N$_3$ | p258 | DBCO—NH—PEG2 triester | | | 0.044 | | | |
| SB-202 | CD38 | HC—Q-tag | NH$_2$—PEG23—N$_3$ | p259 | DBCO—NH—PEG2 triester | | | inact. | | | |
| SB-203 | CD38 | HC—Q-tag | NH$_2$—PEG23—N$_3$ | p260 | DBCO—NH—PEG2 triester | | | 0.044 | | | |
| SB-204 | CD38 | HC—Q-tag | NH$_2$—PEG23—N$_3$ | p261 | DBCO—NH—PEG2 triester | | | inact. | | | |
| SB-205 | CD38 | HC—Q-tag | PP6 | p239 | DBCO—NH—PEG2 triester | | | 0.73 | | | |
| SB-206 | CD38 | HC—Q-tag | PP6 | p242 | DBCO—NH—PEG2 triester | | | 0.25 | | | |
| SB-207 | CD38 | HC—Q-tag | NH$_2$—PEG23—N$_3$ | p262 | DBCO—NH—PEG2 triester | | | 2.9 | | | |
| SB-208 | CD38 | HC—Q-tag | NH$_2$—PEG23—N$_3$ | p262 | DBCO—NH—PEG2 triester | | | 0.09 | | | |
| SB-209 | CD38 | HC—Q-tag | NH$_2$—PEG23—N$_3$ | p263 | DBCO—NH—PEG2 triester | | | 0.17 | | | |
| SB-210 | CD38 | HC—Q-tag | NH$_2$—PEG3—N$_3$ | p238 | DBCO—NH—PEG2 triester | | | 2.6 | | | |
| SB-211 | CD38 | HC—Q-tag | NH$_2$—PEG3—N$_3$ | p245 | DBCO—NH—PEG2 triester | | | 0.1 | | | |
| SB-212 | CD38 | HC—Q-tag | NH$_2$—PEG3—N$_3$ | p246 | DBCO—NH—PEG2 triester | | | 2.7 | | | |
| SB-213 | CD38 | HC—Q-tag | NH$_2$—PEG3—N$_3$ | p293 | DBCO—NH—PEG2 triester | | | inact. | | | |
| SB-214 | CD38 | HC—Q-tag | NH$_2$—PEG23—N$_3$ | p267 | DBCO—NH—PEG2 triester | | | 93 | | | |
| SB-215 | CD38 | HC—Q-tag | NH$_2$—PEG23—N$_3$ | p268 | DBCO—NH—PEG2 triester | | | >2000 | | | |
| SB-216 | CD38 | HC—Q-tag | NH$_2$—PEG23—N$_3$ | p269 | DBCO—NH—PEG2 triester | | | 1.2 | | | |
| SB-217 | CD38 | HC—Q-tag | NH$_2$—PEG23—N$_3$ | p270 | DBCO—NH—PEG2 triester | | | 6.2* | | | |
| SB-218 | CD38 | HC—Q-tag | PP6 | p246 | DBCO—NH—PEG2 triester | | | 3.2 | | | |
| SB-219 | CD38 | HC—Q-tag | NH$_2$—PEG3—N$_3$ | p275 | DBCO—NH—PEG2 triester | | | 3.7 | | | |
| SB-220 | CD38 | HC—Q-tag | NH$_2$—PEG3—N$_3$ | p276 | DBCO—NH—PEG2 triester | | | 3.4 | | | |
| SB-221 | CD38 | HC—Q-tag | NH$_2$—PEG3—N$_3$ | p243 | DBCO—NH—PEG2 triester | | | 4 | | | |
| SB-222 | CD38 | HC—Q-tag | NH$_2$—PEG3—N$_3$ | p245 | DBCO—NH—PEG2 triester | | | ~3.9 | | | |
| SB-223 | CD38 | HC—Q-tag | PP6 | p245 | DBCO—NH—PEG2 triester | | | ~7.5 | | | |
| SB-224 | mouseCD22 | HC—Q-tag | PP6 | p275 | DBCO—NH—PEG2 triester | | | | | 19 | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-225 | mouseCD22 | HC—Q-tag | PP6 | p276 | DBCO—NH—PEG2 triester | | | | | 13 | |
| SB-226 | mouseCD22 | HC—Q-tag | PP6 | p292 | DBCO—NH—PEG2 triester | | | | | 45* | |
| SB-227 | mouseCD22 | HC—Q-tag | PP6 | p293 | DBCO—NH—PEG2 triester | | | | | 39* | |
| SB-228 | mouseCD20 | HC—Q-tag | PP6 | p275 | DBCO—NH—PEG2 triester | | | | | 21 | |
| SB-229 | mouseCD20 | HC—Q-tag | PP6 | p276 | DBCO—NH—PEG2 triester | | | | | 13 | |
| SB-230 | mouseCD22 | HC—Q-tag | PP6 | p304 | DBCO—NH—PEG2 triester | | | | | 53* | |
| SB-231 | mouseCD22 | HC—Q-tag | PP6 | p305 | DBCO—NH—PEG2 triester | | | | | 37* | |
| SB-232 | mouseCD20 | HC—Q-tag | PP6 | p304 | DBCO—NH—PEG2 triester | | | | | 53* | |
| SB-233 | mouseCD20 | HC—Q-tag | PP6 | p305 | DBCO—NH—PEG2 triester | | | | | 42* | |
| SB-234 | CD38 | HC—Q-tag | $NH_2$—PEG3—$N_3$ p298 | | DBCO—NH—PEG2 triester | | | 5.7* | | | |
| SB-235 | CD38 | HC—Q-tag | $NH_2$—PEG3—$N_3$ p299 | | DBCO—NH—PEG2 triester | | | 6.5* | | | |
| SB-236 | CD38 | HC—Q-tag | $NH_2$—PEG3—$N_3$ p300 | | DBCO—NH—PEG2 triester | | | 4.4* | | | |
| SB-237 | CD38 | HC—Q-tag | $NH_2$—PEG3—$N_3$ p301 | | DBCO—NH—PEG2 triester | | | 18* | | | |
| SB-238 | CD38 | HC—Q-tag | $NH_2$—PEG3—$N_3$ p302 | | DBCO—NH—PEG2 triester | | | 9.1* | | | |
| SB-239 | CD38 | HC—Q-tag | $NH_2$—PEG3—$N_3$ p285 | | DBCO—NH—PEG2 triester | | | 2.3 | | | |
| SB-240 | CD38 | HC—Q-tag | $NH_2$—PEG3—$N_3$ p306 | | DBCO—NH—PEG2 triester | | | 3.9* | | | |
| SB-241 | CD38 | HC—Q-tag | $NH_2$—PEG3—$N_3$ p307 | | DBCO—NH—PEG2 triester | | | n/a | | | |
| SB-242 | CD38 | HC—Q-tag | $NH_2$—PEG3—$N_3$ p308 | | DBCO—NH—PEG2 triester | | | 4.5* | | | |
| SB-243 | CD38 | HC—Q-tag | $NH_2$—PEG3—$N_3$ p309 | | DBCO—NH—PEG2 triester | | | n/a | | | |
| SB-244 | CD38 | HC—Q-tag | $NH_2$—PEG3—$N_3$ p310 | | DBCO—NH—PEG2 triester | | | 4.9 | | | |
| SB-245 | CD38 | HC—Q-tag | $NH_2$—PEG23—$N_3$ p301 | | DBCO—NH—PEG2 triester | | | 13* | | | |
| SB-246 | CD38 | HC—Q-tag | $NH_2$—PEG23—$N_3$ p301 | | DBCO—NH—PEG2 triester | | | 7.6 | | | |
| SB-247 | CD38 | HC—Q-tag | $NH_2$—PEG23—$N_3$ p302 | | DBCO—NH—PEG2 triester | | | 3.5 | | | |
| SB-248 | CD38 | HC—Q-tag | $NH_2$—PEG23—$N_3$ p303 | | DBCO—NH—PEG2 triester | | | n/a | | | |
| SB-249 | CD38 | HC—Q-tag | $NH_2$—PEG3—$N_3$ p243 | | DBCO—NH—PEG2 triester | | | 6.2 | | | |
| SB-250 | CD38 | HC—Q-tag | $NH_2$—PEG23—$N_3$ p298 | | DBCO—NH—PEG2 triester | | | 7.1* | | | |
| SB-251 | CD38 | HC—Q-tag | $NH_2$—PEG23—$N_3$ p299 | | DBCO—NH—PEG2 triester | | | 7.7* | | | |
| SB-252 | CD38 | HC—Q-tag | $NH_2$—PEG23—$N_3$ p300 | | DBCO—NH—PEG2 triester | | | 5.1* | | | |
| SB-253 | CD38 | HC—Q-tag | $NH_2$—PEG23—$N_3$ p308 | | DBCO—NH—PEG2 triester | | | 2.2 | | | |
| SB-254 | CD38 | HC—Q-tag | $NH_2$—PEG23—$N_3$ p310 | | DBCO—NH—PEG2 triester | | | 2.5 | | | |
| SB-255 | CD38 | LC—Q-tag | $NH_2$—PEG23—$N_3$ p298 | | DBCO—NH—PEG2 triester | | | 5.9* | | | |
| SB-256 | CD38 | LC—Q-tag | $NH_2$—PEG23—$N_3$ p300 | | DBCO—NH—PEG2 triester | | | 4.2* | | | |
| SB-257 | CD38 | LC—Q-tag | $NH_2$—PEG23—$N_3$ p246 | | DBCO—NH—PEG2 triester | | | 0.57 | | | |
| SB-258 | CD20 | HC—Q-tag | $NH_2$—PEG23—$N_3$ p276 | | DBCO—NH—PEG2 triester | | | | | | 8.6 |
| SB-259 | mouseCD20 | HC—Q-tag | $NH_2$—PEG23—$N_3$ p276 | | DBCO—NH—PEG2 triester | | | | | | 7.4 |
| SB-260 | CD38 | HC—Q-tag | $NH_2$—PEG23—$N_3$ p311 | | DBCO—NH—PEG2 triester | | | 3.6* | | | |
| SB-261 | CD38 | HC—Q-tag | $NH_2$—PEG23—$N_3$ p312 | | DBCO—NH—PEG2 triester | | | 4.6* | | | |
| SB-262 | CD38 | HC—Q-tag | $NH_2$—PEG23—$N_3$ p306 | | DBCO—NH—PEG2 triester | | | 3.1* | | | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-263 | mouseCD20 | HC—Q-tag | NH$_2$—PEG23—N$_3$ | p313 | DBCO—NH—PEG2 triester | | | | | | 4.9 |
| SB-264 | mouseCD20 | HC—Q-tag | NH$_2$—PEG23—N$_3$ | p314 | DBCO—NH—PEG2 triester | | | | | | 4.9 |
| SB-265 | mouseCD20 | HC—Q-tag | NH$_2$—PEG23—N$_3$ | p316 | DBCO—NH—PEG2 triester | | | | | | 14 |
| SB-266 | mouseCD22 | HC—Q-tag | NH$_2$—PEG23—N$_3$ | p314 | DBCO—NH—PEG2 triester | | | | | 1.7 | |
| SB-267 | CD20 | HC—Q-tag | NH$_2$—PEG23—N$_3$ | p313 | DBCO—NH—PEG2 triester | | | | | | 8.9 |
| SB-268 | CD20 | HC—Q-tag | NH$_2$—PEG23—N$_3$ | p314 | DBCO—NH—PEG2 triester | | | | | | 8.1 |
| SB-269 | CD20 | HC—Q-tag | NH$_2$—PEG23—N$_3$ | p316 | DBCO—NH—PEG2 triester | | | | | | 12* |
| SB-270 | CD38 | HC—Q-tag | NH$_2$—PEG23—N$_3$ | p330 | DBCO—NH—PEG2 triester | | | 2.0* | | | |
| SB-271 | CD38 | HC—Q-tag | NH$_2$—PEG23—N$_3$ | p331 | DBCO—NH—PEG2 triester | | | n/a | | | |
| SB-272 | CD38 | HC—Q-tag | NH$_2$—PEG7-N$_3$ | p246 | DBCO—NH—PEG2 triester | | | 3.1 | | | |
| SB-273 | CD38 | HC—Q-tag | NH$_2$—PEG11-N$_3$ | p246 | DBCO—NH—PEG2 triester | | | 2.7 | | | |
| SB-274 | CD38 | LC—Q-tag | NH$_2$—PEG3—N$_3$ | p246 | DBCO—NH—PEG2 triester | | | 3.1 | | | |
| SB-275 | CD38 | LC—Q-tag | NH$_2$—PEG7-N$_3$ | p246 | DBCO—NH—PEG2 triester | | | 1.9 | | | |
| SB-276 | CD38 | LC—Q-tag | NH$_2$—PEG11-N$_3$ | p246 | DBCO—NH—PEG2 triester | | | 1.2 | | | |
| SB-277 | mouseCD22 | HC—Q-tag | PP6 | p313 | DBCO—NH—PEG2 triester | | | | | 1.4 | |
| SB-278 | CD38 | HC—Q-tag | PP10 | p246 | DBCO—NH—PEG2 triester | | | 2.8 | | | |
| SB-279 | CD38 | HC—Q-tag | PP14 | p246 | DBCO—NH—PEG2 triester | | | 1.1 | | | |
| SB-280 | CD38 | HC—Q-tag | PP18 | p246 | DBCO—NH—PEG2 triester | | | 1.3 | | | |
| SB-281 | CD38 | HC—Q-tag | PP24 | p246 | DBCO—NH—PEG2 triester | | | 3.7 | | | |
| SB-282 | CD38 | HC—Q-tag | NH$_2$—PEG23—N$_3$ | p334 | DBCO—C6-dT | | | 1.2* | | | |
| SB-283 | CD38 | HC—Q-tag | NH$_2$—PEG23—N$_3$ | p335 | DBCO—C6-dT | | | 1.9* | | | |
| SB-284 | CD38 | HC—Q-tag | NH$_2$—PEG23—N$_3$ | p347 | DBCO—NH—PEG2 triester | | | >30 | | | |
| SB-285 | CD38 | HC—Q-tag | NH$_2$—PEG23—N$_3$ | p348 | DBCO—NH—PEG2 triester | | | >30 | | | |
| SB-286 | CD38 | HC—Q-tag | NH$_2$—PEG23—N$_3$ | p349 | DBCO—NH—PEG2 triester | | | >30 | | | |
| SB-287 | CD38 | HC—Q-tag | NH$_2$—PEG23—N$_3$ | p350 | DBCO—NH—PEG2 triester | | | 3.7* | | | |
| SB-288 | CD38 | HC—Q-tag | NH$_2$—PEG23—N$_3$ | p351 | DBCO—NH—PEG2 triester | | | 0.8 | | | |
| SB-289 | CD38 | HC—Q-tag | NH$_2$—PEG23—N$_3$ | p355 | DBCO—NH—PEG2 triester | | | 0.67 | | | |
| SB-290 | CD38 | HC—Q-tag | NH$_2$—PEG23—N$_3$ | p355 | DBCO—NH—PEG2 triester | | | 1.44 | | | |
| SB-291 | CD38 | HC—Q-tag | NH$_2$—PEG23—N$_3$ | p356 | DBCO—NH—PEG2 triester | | | 0.47 | | | |
| SB-292 | CD38 | HC—Q-tag | NH$_2$—PEG23—N$_3$ | p357 | DBCO—NH—PEG2 triester | | | 1.94 | | | |
| SB-293 | CD38 | HC—Q-tag | NH$_2$—PEG23—N$_3$ | p358 | DBCO—NH—PEG2 triester | | | 1.02 | | | |
| SB-294 | CD38 | HC—Q-tag | NH$_2$—PEG23—N$_3$ | p359 | DBCO—NH—PEG2 triester | | | 2.43 | | | |
| SB-295 | mouseCD22 | HC—Q-tag | NH$_2$—PEG23—N$_3$ | p373 | X5—DBCO | | | | | 44 | |
| SB-296 | mouseCD22 | HC—Q-tag | NH$_2$—PEG23—N$_3$ | p374 | X5—DBCO | | | | | 47 | |
| SB-297 | mouseCD22 | HC—Q-tag | NH$_2$—PEG23—N$_3$ | p375 | X5—DBCO | | | | | 103 | |
| SB-298 | mouseCD22 | HC—Q-tag | NH$_2$—PEG23—N$_3$ | p376 | X5—DBCO | | | | | 243 | |
| SB-299 | mouseCD22 | HC—Q-tag | NH$_2$—PEG23—N$_3$ | p377 | X5—DBCO | | | | | 64 | |
| SB-300 | mouseCD22 | HC—Q-tag | NH$_2$—PEG23—N$_3$ | p378 | X5—DBCO | | | | | 29 | |
| SB-301 | mouseCD22 | HC—Q-tag | NH$_2$—PEG23—N$_3$ | p379 | X5—DBCO | | | | | 10 | |
| SB-302 | mouseCD22 | HC—Q-tag | NH$_2$—PEG23—N$_3$ | p380 | X5—DBCO | | | | | 7 | |
| SB-303 | mouseCD22 | HC—Q-tag | NH$_2$—PEG23—N$_3$ | p381 | X5—DBCO | | | | | 13 | |
| SB-304 | mouseCD22 | HC—Q-tag | NH$_2$—PEG23—N$_3$ | p382 | X5—DBCO | | | | | 13 | |
| SB-305 | mouseCD22 | HC—Q-tag | NH$_2$—PEG23—N$_3$ | p383 | X5—DBCO | | | | | 25 | |
| SB-306 | mouseCD22 | HC—Q-tag | NH$_2$—PEG23—N$_3$ | p384 | X5—DBCO | | | | | 19 | |
| SB-307 | mouseCD22 | HC—Q-tag | NH$_2$—PEG23—N$_3$ | p385 | X5—DBCO | | | | | inact | |
| SB-308 | mouseCD22 | HC—Q-tag | NH$_2$—PEG23—N$_3$ | p386 | X5—DBCO | | | | | 28 | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-309 | mouseCD22 | HC—Q-tag | $NH_2$—PEG23—$N_3$ | p387 | X5—DBCO | | | | | 20 | |
| SB-310 | mouseCD22 | HC—Q-tag | $NH_2$—PEG23—$N_3$ | p388 | X5—DBCO | | | | | 8 | |
| SB-311 | mouseCD22 | HC—Q-tag | $NH_2$—PEG23—$N_3$ | p389 | X5—DBCO | | | | | 5* | |
| SB-312 | CD38 | HC—Q-tag | $NH_2$—PEG23—$N_3$ | p361 | DBCO—NH—PEG2 triester | | | 0.67 | | 1 | |
| SB-313 | CD38 | HC—Q-tag | $NH_2$—PEG23—$N_3$ | p362 | DBCO—NH—PEG2 triester | | | 0.85 | | | |
| SB-314 | CD38 | HC—Q-tag | $NH_2$—PEG23—$N_3$ | p363 | DBCO—NH—PEG2 triester | | | 1.09 | | | |
| SB-315 | CD38 | HC—Q-tag | $NH_2$—PEG23—$N_3$ | p364 | DBCO—NH—PEG2 triester | | | 1.77 | | | |
| SB-316 | CD38 | HC—Q-tag | $NH_2$—PEG23—$N_3$ | p365 | DBCO—NH—PEG2 triester | | | 1.33 | | | |
| SB-317 | CD38 | HC—Q-tag | $NH_2$—PEG23—$N_3$ | p366 | DBCO—NH—PEG2 triester | | | 2.84 | | | |
| SB-318 | CD38 | HC—Q-tag | $NH_2$—PEG23—$N_3$ | p367 | DBCO—NH—PEG2 triester | | | 2.17 | | | |
| SB-319 | CD38 | HC—Q-tag | $NH_2$—PEG23—$N_3$ | p368 | DBCO—NH—PEG2 triester | | | 1.33 | | | |
| SB-320 | CD38 | HC—Q-tag | $NH_2$—PEG23—$N_3$ | p369 | DBCO—NH—PEG2 triester | | | 0.76 | | | |
| SB-321 | CD38 | HC—Q-tag | $NH_2$—PEG23—$N_3$ | p370 | DBCO—NH—PEG2 triester | | | 0.84 | | | |
| SB-322 | CD38 | HC—Q-tag | $NH_2$—PEG23—$N_3$ | p371 | DBCO—NH—PEG2 triester | | | 0.5 | 6.7 | | |
| SB-323 | CD38 | HC—Q-tag | $NH_2$—PEG23—$N_3$ | p372 | DBCO—NH—PEG2 triester | | | 0.66 | | | |
| SB-324 | CD38 | HC—Q-tag | $NH_2$—PEG23—$N_3$ | p390 | DBCO—NH—PEG2 triester | | | 3.9* | | | |
| SB-325 | CD38 | HC—Q-tag | $NH_2$—PEG23—$N_3$ | p391 | DBCO—NH—PEG2 triester | | | inact. | | | |
| SB-326 | CD38 | HC—Q-tag | $NH_2$—PEG23—$N_3$ | p392 | DBCO—NH—PEG2 triester | | | inact. | | | |
| SB-327 | CD38 | HC—Q-tag | $NH_2$—PEG23—$N_3$ | p396 | DBCO—NH—PEG2 triester | | | 7.1* | | | |
| SB-328 | CD38 | HC—Q-tag | $NH_2$—PEG23—$N_3$ | p397 | DBCO—NH—PEG2 triester | | | inact. | | | |
| SB-329 | CD38 | HC—Q-tag | $NH_2$—PEG23—$N_3$ | p398 | DBCO—NH—PEG2 triester | | | inact. | | | |
| SB-330 | CD38 | HC—Q-tag | $NH_2$—PEG23—$N_3$ | p399 | DBCO—NH—PEG2 triester | | | inact. | | | |
| SB-331 | CD38 | HC—Q-tag | $NH_2$—PEG23—$N_3$ | p400 | DBCO—NH—PEG2 triester | | | inact. | | | |
| SB-332 | CD38 | HC—Q-tag | $NH_2$—PEG23—$N_3$ | p404 | DBCO—NH—PEG2 triester | | | | 10.4 | | |
| SB-333 | CD38 | HC—Q-tag | $NH_2$—PEG23—$N_3$ | p405 | DBCO—NH—PEG2 triester | | | | 25.8 | | |
| SB-334 | CD38 | HC—Q-tag | $NH_2$—PEG23—$N_3$ | p407 | DBCO—NH—PEG2 triester | | | | 7.1 | | |
| SB-335 | CD38 | HC—Q-tag | $NH_2$—PEG23—$N_3$ | p409 | DBCO—NH—PEG2 triester | | | | 51.6 | | |
| SB-336 | CD38 | HC—Q-tag | $NH_2$—PEG23—$N_3$ | p410 | DBCO—NH—PEG2 triester | | | | 10.3 | | |
| SB-337 | mouseCD22 | HC—Q-tag | $NH_2$—PEG23—$N_3$ | p313 | DBCO—NH—PEG2 triester | | | | | 48 | |
| SB-338 | mouseCD22 | HC—Q-tag | PP12 | p313 | DBCO—NH—PEG2 triester | | | | | | |
| SB-339 | mouseCD22 | HC—Q-tag | $NH_2$—PEG23—$N_3$ | p346 | DBCO—NH—PEG2 triester | | | | | | |
| SB-340 | BDCA2 | HC—Q-tag | $NH_2$—PEG23—$N_3$ | p228 | DBCO—NH—PEG2 triester | | | | | | |
| SB-341 | BDCA2 | HC—Q-tag | $NH_2$—PEG23—$N_3$ | p222 | DBCO—NH—PEG2 triester | | | | | | |
| SB-342 | BDCA2 | HC—Q-tag | $NH_2$—PEG23—$N_3$ | p176 | DBCO—NH—PEG2 triester | | | | | | |
| SB-343 | BDCA4 | HC—Q-tag | $NH_2$—PEG23—$N_3$ | p176 | DBCO—NH—PEG2 triester | | | | | | |
| SB-344 | CD22 | HC—Q-tag | PP16 | p313 | DBCO—NH—PEG2 triester | | | | | | |
| SB-345 | CD38 | HC—Q-tag | $NH_2$—PEG23—$N_3$ | p151 | DBCO—NH—PEG2 triester | | | | | | |
| SB-346 | CD38 | HC—Q-tag | $NH_2$—PEG23—$N_3$ | p192 | DBCO—NH—PEG2 triester | | | | | | |
| SB-347 | CD38 | HC—Q-tag | $NH_2$—PEG23—$N_3$ | p425 | DBCO—NH—PEG2 triester | | | | | 2.5 | |

TABLE 6-A-continued

| Conjugate Compound # | Antibody (Ab) | Ab-Conjugation Site | Complementary Reactive Group | Sequence | Conjugating Group | A | B | C | D | E | F |
|---|---|---|---|---|---|---|---|---|---|---|---|
| SB-348 | CD38 | HC—Q-tag | NH$_2$—PEG23—N$_3$ | p426 | DBCO—NH—PEG2 triester | | | | | 24 | |
| SB-349 | CD38 | HC—Q-tag | NH$_2$—PEG23—N$_3$ | p427 | DBCO—NH—PEG2 triester | | | | | 0.016 | |
| SB-350 | CD38 | HC—Q-tag | NH$_2$—PEG23—N$_3$ | p428 | DBCO—NH—PEG2 triester | | | | | | |
| SB-351 | CD38 | HC—Q-tag | PP6 | p243 | DBCO—NH—PEG2 triester | | | | | | |
| SB-352 | CD38 | HC—Q-tag | PP6 | p245 | DBCO—NH—PEG2 triester | | | | | | |
| SB-353 | CD38 | HC—Q-tag | PP10 | p308 | DBCO—NH—PEG2 triester | | | | | | |
| SB-354 | CD38 | HC—Q-tag | PP14 | p308 | DBCO—NH—PEG2 triester | | | | | | |
| SB-355 | CD38 | HC—Q-tag | PP18 | p308 | DBCO—NH—PEG2 triester | | | | | | |
| SB-356 | CD38 | HC—Q-tag | PP24 | p308 | DBCO—NH—PEG2 triester | | | | | | |
| SB-357 | mouseCD22 | HC—Q-tag | PP6 | p294 | DBCO—NH—PEG2 triester | | | | | | |
| SB-358 | mouseCD22 | HC—Q-tag | PP6 | p295 | DBCO—NH—PEG2 triester | | | | | | |
| SB-359 | mouseCD22 | HC—Q-tag | PP6 | p296 | DBCO—NH—PEG2 triester | | | | | | |
| SB-360 | mouseCD22 | HC—Q-tag | PP6 | p297 | DBCO—NH—PEG2 triester | | | | | | |
| SB-361 | mouseCD22 | HC—Q-tag | PP26 | p313 | DBCO—NH—PEG2 triester | | | | | | |
| SB-362 | mouseCD22 | HC—Q-tag | PP38 | p313 | DBCO—NH—PEG2 triester | | | | | | |
| SB-363 | mouseCD22 | HC—Q-tag | PP27 + TCO | p313 | DBCO—NH—PEG2 triester | | | | | | |
| SB-364 | mouseCD22 | HC—Q-tag | PP29 + TCO | p313 | DBCO—NH—PEG2 triester | | | | | | |
| SB-365 | mouseCD22 | HC—Q-tag | PP39 + TCO | p313 | DBCO—NH—PEG2 triester | | | | | | |
| SB-366 | mouseCD22 | HC—Q-tag | PP39 + TCO | p313 | DBCO—NH—PEG2 triester | | | | | | |

In Table 6-A, column A provides IL-6 expression in DB cells (EC50, nM); column B provides IL-10 expression in DB cells (EC50, nM); column C provides NFκB activation Ramos blue cells (EC50, nM); column D provides NFκB activation in Ramos blue cells after 24 h preincubation in mouse serum (EC50, nM); column E provides IL-6 induction by qPCR in mouse A20 lymphoma cells (EC50, nM); and column F provides IL-6 induction in mouse A20-hCD20 Lymphoma cells (EC50, nM). All DBCO/azido conjugations were performed under metal-free 1,3-dipolar cycloaddition reaction conditions; DAR1 indicates a polynucleotide/antibody ratio of 1; DAR2 indicates a polynucleotide/antibody ratio of 2; and n/a stands for no activation.
In table 6-A, * indicates sub-optimal activation.
In table 6-A, CD38 stands for an anti-CD38 antibody; CD22 stands for an anti-CD22 antibody; CD79b stands for an anti-CD79b antibody; mouseCD22 stands for anti-mouseCD22 antibody; BDCA2 stands for anti-BDCA2 antibody; and BDCA4 stands for anti-BDCA4 antibody.
In Table 6-A, TCO is trans-cyclooctenyl-based group bonded to a targeting moiety. TCO has a structure illustrated in FIG. 1B.

TABLE 6-B

| Conjugate Compound # | Antibody (Ab) | Ab-Conjugation Site | Complementary Reactive Group | Sequence | Conjugating Group | CpG Conjugation | A | B | C | D | E |
|---|---|---|---|---|---|---|---|---|---|---|---|
| SB-367 | CD38 | HC—Q-tag | NH2—PEG23—N3 | p429 | DBCO—NH—PEG2 triester | Cu free Click | | | | | |
| SB-368 | CD38 | HC—Q-tag | NH2—PEG23—N3 | p431 | DBCO—NH—PEG2 triester | Cu free Click | | | | | |
| SB-369 | CD38 | HC—Q-tag | NH2—PEG23—N3 | p433 | DBCO—NH—PEG2 triester | Cu free Click | 1 | | | | |
| SB-370 | CD38 | HC—Q-tag | NH2—PEG23—N3 | p434 | DBCO—NH—PEG2 triester | Cu free Click | 1.5 | | | | |
| SB-371 | CD38 | HC—Q-tag | NH2—PEG23—N3 | p435 | DBCO—NH—PEG2 triester | Cu free Click | 0.9 | | | | |
| SB-372 | CD38 | HC—Q-tag | NH2—PEG23—N3 | p436 | DBCO—NH—PEG2 triester | Cu free Click | 2.2 | | | | |
| SB-373 | CD38 | HC—Q-tag | NH2—PEG23—N3 | p438 | DBCO—NH—PEG2 triester | Cu free Click | 2.3 | | | | |
| SB-374 | CD38 | HC—Q-tag | NH2—PEG23—N3 | p439 | DBCO—NH—PEG2 triester | Cu free Click | | | | | |
| SB-375 | CD38 | HC—Q-tag | NH2—PEG23—N3 | p440 | DBCO—NH—PEG2 triester | Cu free Click | | | | | |
| SB-376 | CD38 | HC—Q-tag | NH2—PEG23—N3 | p441 | DBCO—NH—PEG2 triester | Cu free Click | | | | | |

TABLE 6-B-continued

| Conjugate Compound # | Antibody (Ab) | Ab-Conjugation Site | Complementary Reactive Group | Sequence | Conjugating Group | CpG Conjugation | A | B | C | D | E |
|---|---|---|---|---|---|---|---|---|---|---|---|
| SB-377 | CD38 | HC—Q-tag | NH2—PEG23—N3 | p442 | DBCO—NH—PEG2 triester | Cu free Click | | | | | |
| SB-378 | mouseCD22 | HC—Q-tag | NH2—PEG23—N3 | p439 | DBCO—NH—PEG2 triester | Cu free Click | | | | | |
| SB-379 | mouseCD22 | HC—Q-tag | NH2—PEG23—N3 | p440 | DBCO—NH—PEG2 triester | Cu free Click | | | | | |
| SB-380 | mouseCD22 | HC—Q-tag | NH2—PEG23—N3 | p441 | DBCO—NH—PEG2 triester | Cu free Click | | | | | |
| SB-381 | mouseCD22 | HC—Q-tag | NH2—PEG23—N3 | p442 | DBCO—NH—PEG2 triester | Cu free Click | | | | | |
| SB-382 | mouseCD22 | HC—Q-tag | NH2—PEG23—N3 | p425 | DBCO—NH—PEG2 triester | Cu free Click | | | | | |
| SB-383 | CD38 | HC—Q-tag | NH2—PEG23—N3 | p445 | DBCO—NH—PEG2 triester | Cu free Click | 0.6 | | | | |
| SB-384 | CD38 | HC—Q-tag | NH2—PEG23—N3 | p446 | DBCO—NH—PEG2 triester | Cu free Click | 1 | | | | |
| SB-385 | CD38 | HC—Q-tag | NH2—PEG23—N3 | p447 | DBCO—NH—PEG2 triester | Cu free Click | 6.9 | | | | |
| SB-386 | CD38 | HC—Q-tag | NH2—PEG23—N3 | p448 | DBCO—NH—PEG2 triester | Cu free Click | 0.7 | | | | |
| SB-387 | CD38 | HC—Q-tag | NH2—PEG23—N3 | p449 | DBCO—NH—PEG2 triester | Cu free Click | inact. | | | | |
| SB-388 | mouseCD19 | HC—Q-tag | NH2—PEG12—N3 | p313 | DBCO—NH—PEG2 triester | Cu free Click | | | | | |
| SB-389 | PDL-1 | HC—Q-tag | NH2—PEG23—N3 | p313 | DBCO—NH—PEG2 triester | Cu free Click | | | | | |
| SB-390 | mouseCD22 | HC—Q-tag | NH2—PEG23—N3 | p450 | DBCO—NH—PEG2 triester | Cu free Click | | inact. | 0.2 | | |
| SB-391 | mouseCD22 | HC—Q-tag | NH2—PEG23—N3 | p451 | DBCO—NH—PEG2 triester | Cu free Click | | inact. | 0.05 | | |
| SB-392 | mouseCD22 | HC—Q-tag | NH2—PEG23—N3 | p452 | DBCO—NH—PEG2 triester | Cu free Click | | inact. | inact. | | |
| SB-393 | mouseCD22 | HC—Q-tag | NH2—PEG23—N3 | p453 | DBCO—NH—PEG2 triester | Cu free Click | | inact. | inact. | | |
| SB-394 | mouseCD22 | HC—Q-tag | NH2—PEG23—N3 | p454 | DBCO—NH—PEG2 triester | Cu free Click | | inact. | inact. | | |
| SB-395 | mouseCD22 | HC—Q-tag | NH2—PEG23—N3 | p455 | DBCO—NH—PEG2 triester | Cu free Click | | | | | |
| SB-396 | mouseCD22 | HC—Q-tag | NH2—PEG23—N3 | p456 | DBCO—NH—PEG2 triester | Cu free Click | | | | | |
| SB-397 | mouseCD22 | HC—Q-tag | NH2—PEG23—N3 | p457 | DBCO—NH—PEG2 triester | Cu free Click | | | | | |
| SB-398 | mouseCD22 | HC—Q-tag | NH2—PEG23—N3 | p458 | DBCO—NH—PEG2 triester | Cu free Click | | | | | |
| SB-399 | mouseCD22 | HC—Q-tag | NH2—PEG23—N3 | p459 | DBCO—NH—PEG2 triester | Cu free Click | | | | | |
| SB-400 | mouseCD22 | HC—Q-tag | NH2—PEG23—N3 | p460 | DBCO—NH—PEG2 triester | Cu free Click | | | | | |
| SB-401 | mouseCD22 | HC—Q-tag | NH2—PEG23—N3 | p461 | DBCO—NH—PEG2 triester | Cu free Click | | | | | |
| SB-402 | mouseCD22 | HC—Q-tag | NH2—PEG23—N3 | p462 | DBCO—NH—PEG2 triester | Cu free Click | | | | | |
| SB-403 | mouseCD22 | HC—Q-tag | NH2—PEG123—N3 | p463 | DBCO—NH—PEG2 triester | Cu free Click | | | | | |
| SB-404 | mouseCD22 | HC—Q-tag | NH2—PEG23—N3 | p464 | DBCO—NH—PEG2 triester | Cu free Click | | | | | |
| SB-405 | mouseCD22 | HC—Q-tag | NH2—PEG23—N3 | p465 | DBCO—NH—PEG2 triester | Cu free Click | | | | | |
| SB-406 | mouseCD22 | HC—Q-tag | NH2—PEG23—N3 | p466 | DBCO—NH—PEG2 triester | Cu free Click | | | | | |
| SB-407 | mouseCD22 | HC—Q-tag | NH2—PEG23—N3 | p469 | DBCO—NH—PEG2 triester | Cu free Click | | | | | |
| SB-408 | mouseCD22 | HC—Q-tag | NH2—PEG23—N3 | p425 | DBCO—NH—PEG2 triester | Cu free Click | | | | | |
| SB-409 | CD38 | HC—Q-tag | NH2—PEG23—N3 | p470 | DBCO—NH—PEG2 triester | Cu free Click | 0.8 | | | | |
| SB-410 | CD38 | HC—Q-tag | NH2—PEG23—N3 | p471 | DBCO—NH—PEG2 triester | Cu free Click | inact. | | | | |
| SB-411 | CD38 | HC—Q-tag | NH2—PEG23—N3 | p472 | DBCO—NH—PEG2 triester | Cu free Click | inact. | | | | |
| SB-412 | CD38 | HC—Q-tag | NH2—PEG23—N3 | p473 | DBCO—NH—PEG2 triester | Cu free Click | inact. | | | | |
| SB-413 | CD38 | HC—Q-tag | NH2—PEG23—N3 | p474 | DBCO—NH—PEG2 triester | Cu free Click | inact. | | | | |
| SB-414 | CD38 | HC—Q-tag | NH2—PEG23—N3 | p475 | DBCO—NH—PEG2 triester | Cu free Click | inact. | | | | |

TABLE 6-B-continued

| Conjugate Compound # | Antibody (Ab) | Ab-Conjugation Site | Complementary Reactive Group | Sequence | Conjugating Group | CpG Conjugation | A | B | C | D | E |
|---|---|---|---|---|---|---|---|---|---|---|---|
| SB-415 | CD38 | HC—Q-tag | NH2—PEG23—N3 | p476 | DBCO—NH—PEG2 triester | Cu free Click | inact. | | | | |
| SB-416 | humanCD22 | HC—Q-tag | NH2—PEG23—N3 | p313 | DBCO—NH—PEG2 triester | Cu free Click | | | | | |
| SB-417 | mouseCD22 | HC—Q-tag | NH2—PEG23—N3 | p313 | DBCO—NH—PEG2 triester | Cu free Click | | 2.2 | | | |
| SB-418 | mouseCD22 | HC—Q-tag | NH2—PEG11—N3 | p313 | DBCO—NH—PEG2 triester | Cu free Click | | 2 | | | |
| SB-419 | mouseDEC205 | HC—Q-tag | NH2—PEG12—N3 | p313 | DBCO—NH—PEG2 triester | Cu free Click | | | | | |
| SB-420 | mouseCD22 | HC—Q-tag | NH2—PEG3—N3 | p480 | DBCO—NH—PEG2 triester | Cu free Click | | inact. | | | |
| SB-421 | mouseCD22 | HC—Q-tag | NH2—PEG23—N3 | p481 | DBCO—NH—PEG2 triester | Cu free Click | | 0.8 | | | |
| SB-422 | humanCD22 | HC—Q-tag | NH2—PEG23—N3 | p480 | DBCO—NH—PEG2 triester | Cu free Click | | | | | |
| SB-423 | humanCD22 | HC—Q-tag | NH2—PEG23—N3 | p481 | DBCO—NH—PEG2 triester | Cu free Click | | | | | |
| SB-424 | mouseCD22 | HC—Q-tag | NH2—PEG23—N3 | p486 | DBCO—NH—PEG2 triester | Cu free Click | | inact. | | | |
| SB-425 | humanCD22 | HC—Q-tag | NH2—PEG23—N3 | p486 | DBCO—NH—PEG2 triester | Cu free Click | | | | 4.7 | 4.1 |
| SB-426 | humanCD22 | HC—Q-tag | NH2—PEG23—N3 | p308 | DBCO—NH—PEG2 triester | Cu free Click | | | | 5.2 | 4.9 |
| SB-427 | humanCD22 | HC—Q-tag | NH2—PEG23—N3 | p487 | DBCO—NH—PEG2 triester | Cu free Click | | | | 6 | 5.7 |
| SB-428 | humanCD22 | HC—Q-tag | NH2—PEG23—N3 | p488 | DBCO—NH—PEG2 triester | Cu free Click | | | | 6.7 | 7 |
| SB-429 | humanCD22 | HC—Q-tag | NH2—PEG23—N3 | p489 | DBCO—NH—PEG2 triester | Cu free Click | | | | | |
| SB-430 | humanCD22 | HC—Q-tag | NH2—PEG23—N3 | p425 | DBCO—NH—PEG2 triester | Cu free Click | | | | | |

In Table 6-2, column A provides NFκB activation Ramos blue cells (EC$_{50}$, nM); column B provides IL-6 secretion in mouse splenocytes, DAR1 (EC$_{50}$, nm); column C provides IL-6 secreition in mouse splenocytes, DAR2 (EC$_{50}$, nm); column D provides NFκB activation in Daudi-NFκB-Luc cells, DAR1 (EC$_{50}$, nm); column E provides NFκB activation in Daudi-NFκB-Luc cells, DAR2 (EC$_{50}$, nm).
In table 6-2, CD38 stands for an anti-CD38 antibody; CD22 stands for an anti-CD22 antibody; mouseCD22 stands for anti-mouseCD22 antibody; DAR1 indicates a polynucleotide/antibody ratio of 1; DAR2 indicates a polynucleotide/antibody ratio of 2.

Example 3. In Vitro and In Vivo Profiling of the Exemplary Conjugates of the Invention Cells: Human DB, Daudi, Raji, Ramos, SUDHL10, and NCI-H929, and mouse A20 cells were purchased from the American Type Culture Collection (ATCC) and were cultured in RPMI containing 10% FBS. Ramos-blue and HEK-Blue-hTLR9 cells were purchased from Invivogen and were maintained according to supplier's recommendations. TLR9 expression of all the cells was confirmed by qPCR.

Flow cytometry: Cell surface expression of receptors of interest was measured by FACS analysis using CyFlow ML flow cytometer (Partec) and commercially available antibodies (Biolegend, BD Biosciences, San Diego).

In Vitro Profiling of Immunostimulating Polynucleotides or Conjugates Thereof:

In some experiments, the activity of immunostimulating polynucleotides or conjugates thereof was assessed using human or mouse lymphoma cells. In these experiments, test compounds were added to cells (1-4×10$^5$/well) in 96-well plates and incubated at 37° C., 5% CO$_2$ for 24-72 h. At the end of the incubation period, the culture media was removed and used to assess cytokine secretion (DB cells) or alkaline phosphatases secretion as a measure of NFκB activation (Ramos-blue, HEK-Blue-hTLR9 cells). Secreted cytokines were measured by commercially available ELISA kits. The remaining cells were lysed, total RNA purified and cytokine gene expression (IL-6 and IL-10) was quantified by qPCR, and normalized to house-keeping genes (B2M, GAPDH, or PPIB). Gene expression for other cytokines (e.g., IL-8, IL-12a, and IL-12b) can also be determined using methods known in the art, e.g., qPCR.

In some experiments, immunostimulating polynucleotides were profiled in HeLa cells stably expressing human or mouse TLR-9 and an NFkB-luciferase reporter plasmid. Intracellular luciferase activity was quantified by the addition of luciferin (Britelite, Perkin Elmer) and the luminescence signal was captured using Victor2 luminometer (Perkin Elmer).

In some experiments, the activity of immunostimulating polynucleotides was assessed using freshly isolated mouse splenocytes. Spleens from C57B16 mice were harvested, diced through sterile 70 µm filters using ice-cold PBS. Cells were then washed with PBS and the red blood cells were lysed using commercial RBC lysis buffer. Cells were washed again with PBS at 4° C., re-suspended in RPMI containing 10% FBS and seeded in 96-well plates (2×10$^5$ cells/well) and incubated at 37° C., 5% CO$_2$ for 2-4 h. Test compounds were then added and incubated at 37° C., 5% CO$_2$ for additional 24-72 h. The supernatant was carefully removed and cytokine levels were quantitated by ELISA. The cells were lysed, total RNA was purified, and the gene expression was measured by qPCR using standard methods.

In some experiments, test compounds were evaluated for cytokine secretion upon incubation with mouse bone marrow differentiated dendritic cells (DC). In these experiments mouse primary bone marrow progenitor cells were isolated from the femurs and tibias of C57B16 mice according to published protocols. Cells were immediately washed with PBS at 4° C. and red blood cells lysed using a commercial lysis buffer. Cell were suspended at $1.2 \times 10^6$ cells/ml in RPMI containing 10% fetal calf serum, seeded in 96-well plates, and differentiated to DCs with either recombinant mouse GM-CSF (100 ng/ml) and mouse TNFα (10 ng/ml) or with the addition of FLT3L for 7 days. Test compounds were added and incubated for 24-72 hrs. Cytokine secretion was measured in the culture supernatant by ELISA and cells were lysed and used to assess gene expression by qPCR using standard methods.

In some experiments, test compounds were incubated in 95% plasma from mice, rats, monkeys, or heathy humans to assess stability. In these experiments, blood (EDTA) was collected from at least 3 individuals; plasma was isolated by centrifugation and pooled. Test compounds were spiked in plasma in sealed tubes and incubated at 37° C. for 1-72 hrs, after which the compounds were diluted in RPMI+10% FBS to the appropriate concentrations and assessed for functional activity in the test systems outlined above.

In some experiments, the effect of test compounds on lymphocyte proliferation can be evaluated using methods known in the art, e.g., using Cell Titer Glo kit (Promega) after incubation with $1 \times 10^5$ cells/well for 1, 2, 4 or 7 days.

In some experiments, the effect of test compounds on cellular apoptosis can be assessed using methods known in the art, e.g., by annexin-V cell surface expression by FACS using CyFlow ML flow cytometer (Partec).

Cellular dependent cytotoxic (CDC) activity of the conjugates of the invention was assessed as follows. Daudi cells were cultured in RPMI1640 GlutaMAX supplemented with 10% FBS and Pen/Strep. Daudi cells were plated onto a 96-well format by centrifuging cells, removing media, and resuspending in OPTIMEM supplemented with 10% human serum (SIGMA cat #S1764, LOT #SLBQ0752V, 46CH50) at a concentration of $0.8 \times 10^6$ cells/mL and volume of 50 μL/well. Compound dilution plates were prepared in OPTIMEM at double concentration, and 50 μL per well of compound dilution were added giving a final concentration of human serum at 5%. The plated cultures were incubated at 37° C. under 5% $CO_2$ for 2 hours. Alamar Blue viability reagent (10 μL/well) was added, and the resulting cultures were incubated at 37° C. under 5% $CO_2$ for 3-18 h. The results were read out on a plate reader using fluorescence (EX560 and EM590).

Cytokine induction of the conjugates of the invention in human peripheral blood mononuclear cells (hPBMCs) was assessed as follows. Human PBMCs were isolated from LRS obtained from the San Diego Blood Bank. Plasmacytoid dendritic cells were isolated from hPBMCs with a MACs kit (Miltenyi Biotec) and immediately were plated onto a 96-well format ($5 \times 10^4$ cells/well density) in Complete RPMI. Compounds were added after 2 hours and incubated at 37° C. under 5% $CO_2$ for 20 hours. Following the incubation, the media was collected and cytokine levels were determined by ELISA (BioLegend).

The results of the in vitro profiling experiments are summarized in Tables 2 and 6-23 and in FIGS. 5-33.

Figure 5:
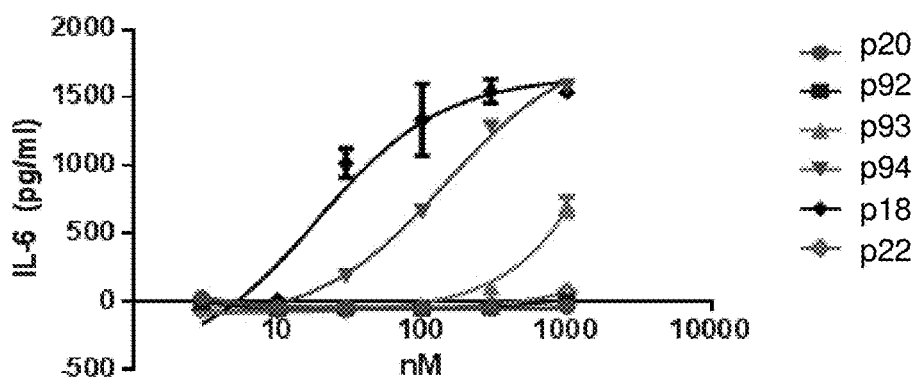
FIG. 5 is a graph showing the efficacy of the murine immunostimulating polynucleotides to induce IL-6 dose-dependently in murine splenocytes. The illustrated data indicate that, for murine immunostimulating polynucleotide sequence of p18, at least 15 phosphorothioates are preferable to achieve immunostimulating activity. In the absence of conjugated targeting moieties, a phosphorothioate backbone is an important feature controlling the efficacy of immunostimulating polynucleotides to induce IL-6.

FIG. 5 shows that CpG polynucleotide unconjugated to an antibody requires phosphorothioate backbone to induce cytokine, as determined by the levels of the expression of IL-6.

Figure 6:
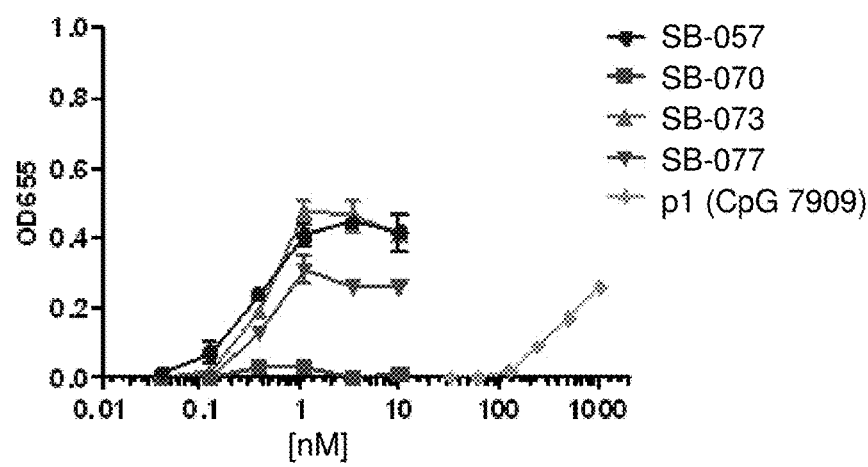
FIG. 6 is a graph showing the efficacy of the immunoconjugates of the invention and CpG 7909 in the activation of NFκB dose-dependently in Ramos Blue cells, as measured by the levels of alkaline phosphatases after 5.5 h of treatment. The x-axis provides the concentration (nM) of the conjugate on the log scale.
Figure 7:
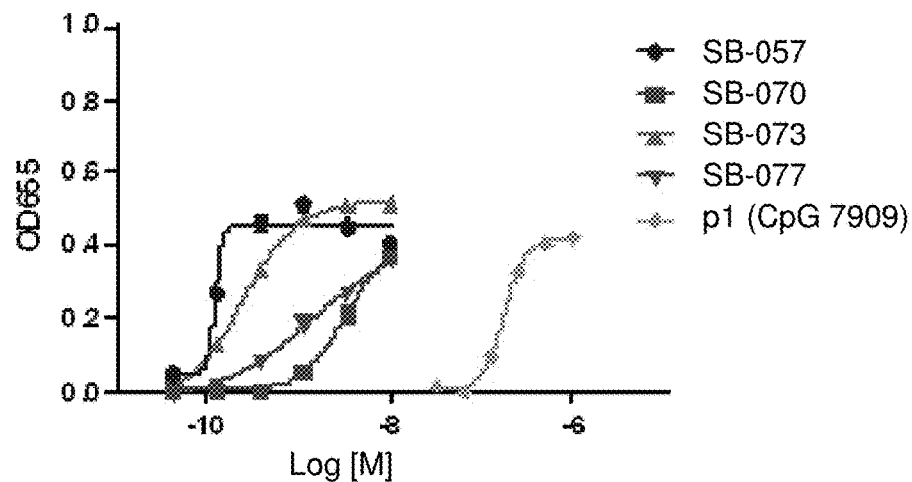
FIG. 7 is a graph showing the efficacy of the immunoconjugates and CpG 7909 in the activation of NFκB dose-dependently in Ramos Blue cells, as measured by the levels of alkaline phosphatases after 24 h of treatment and 2.5 h of QB incubation. The xaxis provides log of the concentration (M) of the conjugates on the linear scale.
Figure 8:
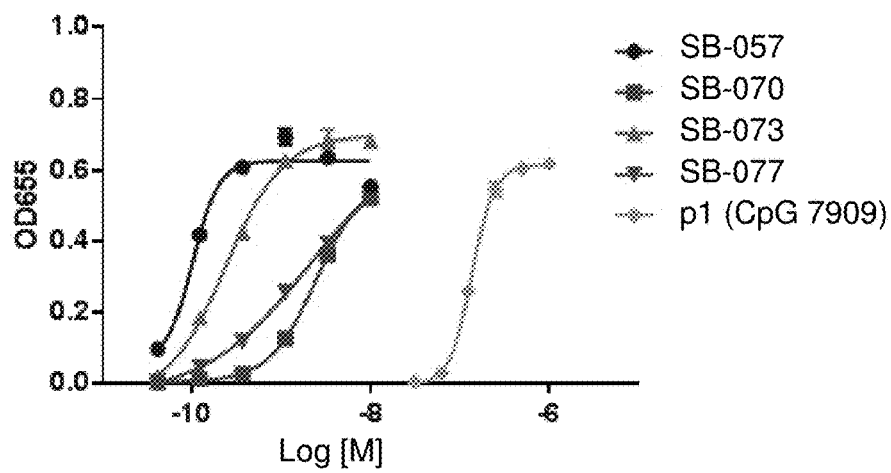
FIG. 8 is a graph showing the efficacy of the immunoconjugates in the activation of NFκB dose-dependently in Ramos Blue cells, as measured by the levels of alkaline phosphatases after 48 h of treatment and 2.5 h of QB incubation. The xaxis shows log of the concentration (M) of the conjugates on the linear scale.
Figure 9:
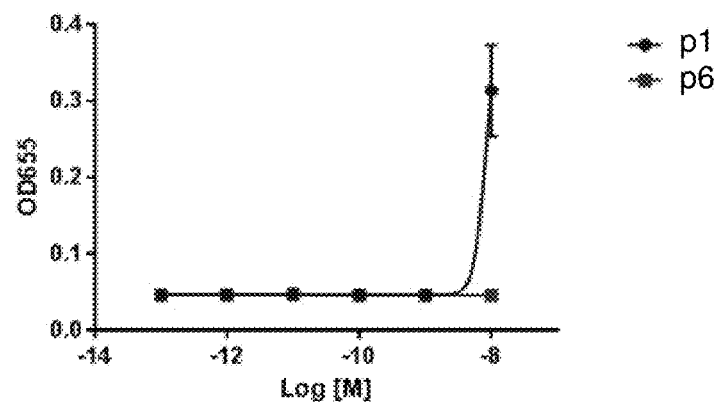
FIG. 9 is a graph comparing the efficacy of p1 and p6 polynucleotides in the activation of NFκB dose-dependently in Ramos Blue cells, as measured by the levels of alkaline phosphatases.
Figure 10:
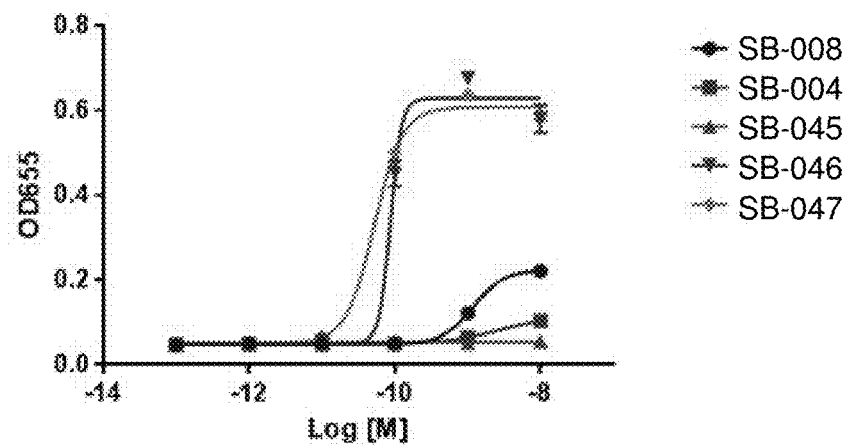
FIG. 10 is a graph showing the efficacy of the immunoconjugates in the activation of NFκB dose-dependently in Ramos Blue cells, as measured by the levels of alkaline phosphatases.
Figure 11:
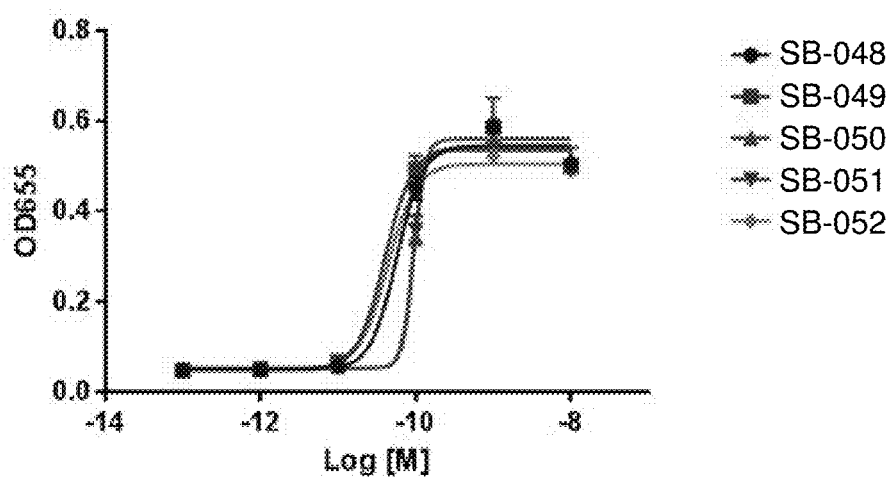
FIG. 11 is a graph showing the efficacy of the immunoconjugates in the activation of NFκB dose-dependently in Ramos Blue cells, as measured by the levels of alkaline phosphatases.
Figure 12:
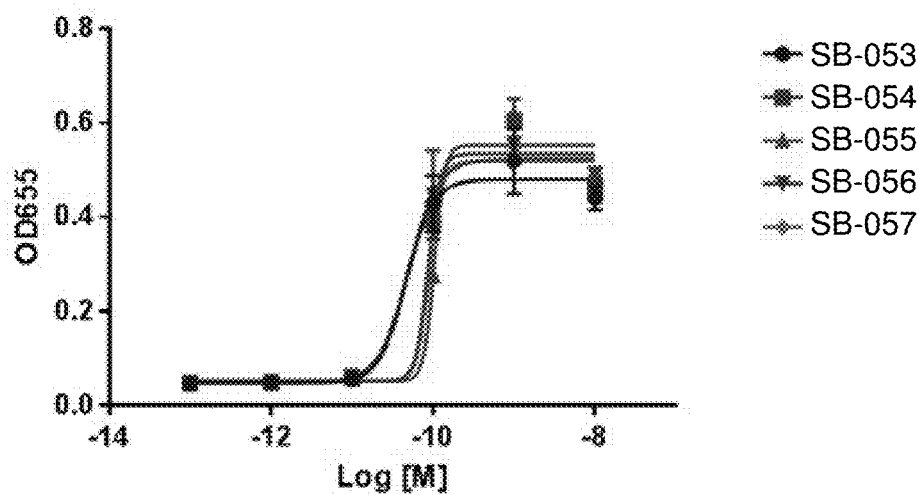
FIG. 12 is a graph showing the efficacy of the immunoconjugates in the activation of NFκB dose-dependently in Ramos Blue cells, as measured by the levels of alkaline phosphatases.
Figure 13:
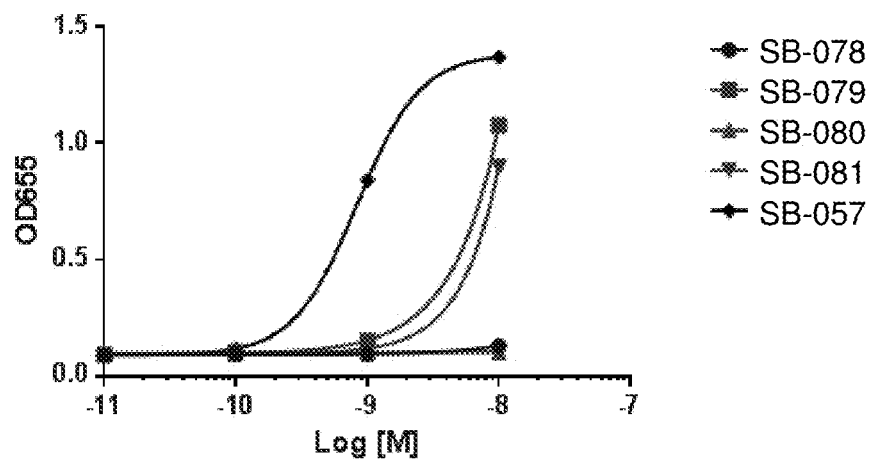
FIG. 13 is a graph showing the efficacy of the immunoconjugates in the activation of NFκB dose-dependently in Ramos Blue cells, as measured by the levels of alkaline phosphatases.
Figure 14:
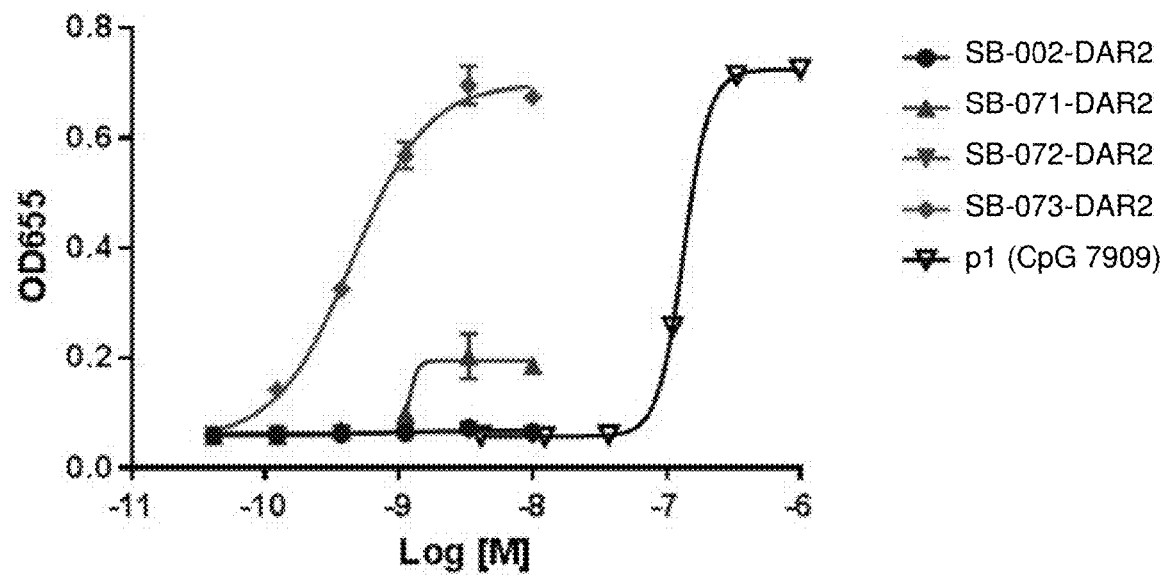
FIG. 14 is a graph showing the efficacy of the immunoconjugates in the activation of NFκB dose-dependently in Ramos Blue cells, as measured by the levels of alkaline phosphatases.
Figure 15:
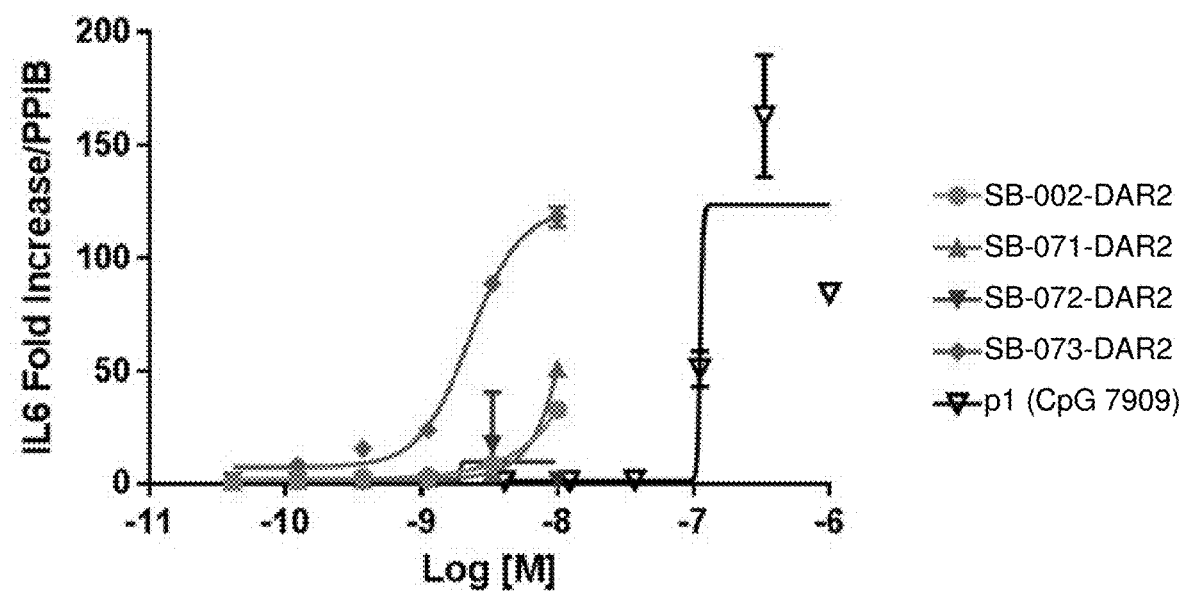
FIG. 15 is a graph showing the efficacy of the immunoconjugates in the dose-dependent induction of IL-6 in DB cells. The y-axis shows the multiplier for the increase of IL6 secretion normalized to PPIB levels.

FIGS. 6-8 provide a comparison of TLR9 agonist activities of exemplary conjugates of the invention and the unconjugated CpG polynucleotide with phosphorothioate backbone.

FIGS. 9-15 show (1) that phosphorothioates are important for TLR9 agonist activity of immunostimulating polynucleotides in the absence of a conjugated targeting moiety, and (2) that conjugation of a targeting moiety to a phosphate bonded to 5'-terminal nucleoside of a CpG polynucleotide reduces its TLR9 agonist activity.

Figure 16:
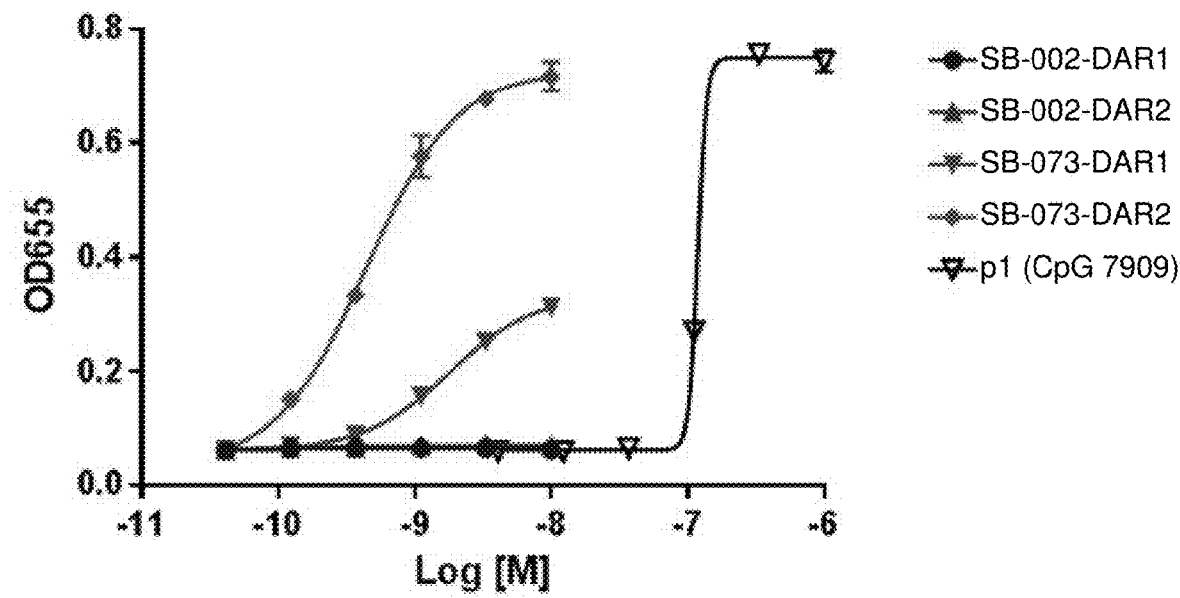
FIG. 16 is a graph showing the efficacy of the immunoconjugates in the dose-dependent induction of NFκB in Ramos Blue cells. This figure compares the conjugates having one polynucleotide (Dari) or two polynucleotides (Dar2) to activate NFκB.
Figure 17:
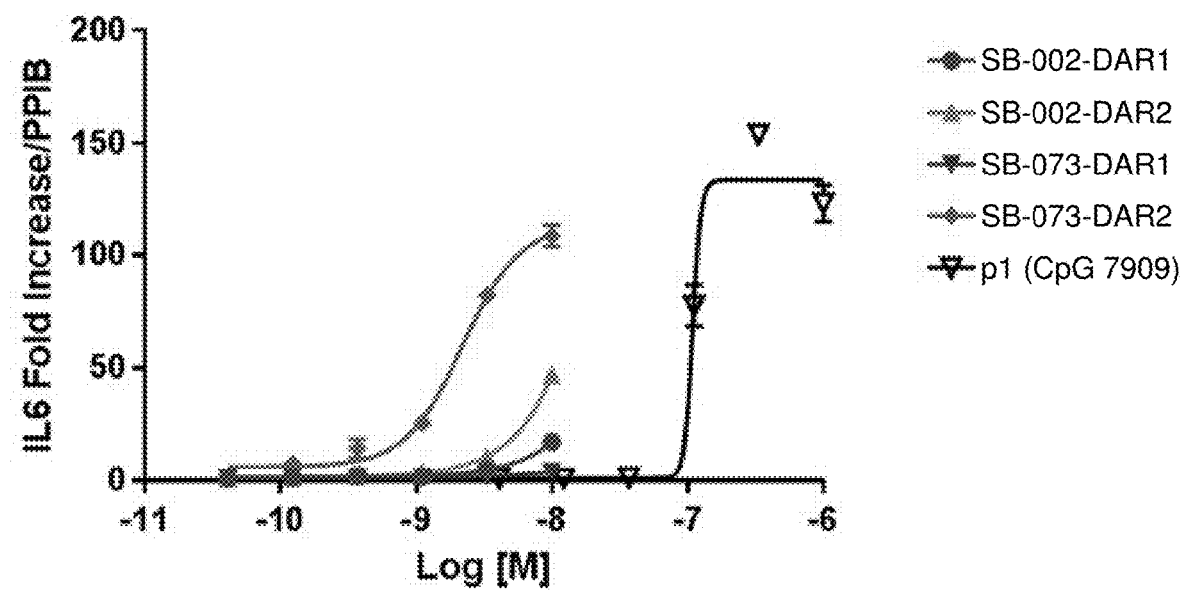
FIG. 17 is a graph showing the efficacy of the immunoconjugates in the dose-dependent induction of IL-6 in DB cells. This figure compares the conjugates having one polynucleotide (Dari) or two polynucleotides (Dar2) to induce IL6. The y-axis shows the multiplier for the increase of IL6 secretion normalized to PPIB levels.

FIGS. 16 and 17 show that a conjugate of the invention including two polynucleotides can exhibit immunostimulating activity, as measured by the NFκB activation, that is higher relative to the conjugate of the invention including one polynucleotide.

Table 7 shows that the inclusion of 5'-terminal 5-iodouridine enhances activity of the immunostimulating polynucleotides.

TABLE 7

| Conjugate | Polynucleotide | Sequence (5' to 3') | Conjugate EC50 (nM) | Length | SEQ ID NO: |
|---|---|---|---|---|---|
| SB-109 | p179 | UCG*U*CGTTTTGTCGTTTTGTCG*TT*-C3 | 0.12 | 24 | 179 |
| SB-110 | p180 | UCGTCGTTTTGTCGTTTTGTCG*TT*-C3 | 0.12 | 24 | 180 |
| SB-112 | p181 | UCGTCG*T*TTTGTCGTTTTGTCGTT-C3 | 0.07 | 24 | 181 |
| SB-113 | p182 | UCGTCG*T*TTTGTCGTTTTGTCGTT-C3 | 0.12 | 24 | 182 |
| SB-096 | p161 | TCG*T*CGTTTTGTCGTTTTGTCGTT-C3 | 0.33 | 24 | 161 |
| SB-114 | p183 | UCG*T*CGTTTTGTCGTTTTGTCGTT-C3 | 0.10 | 24 | 183 |
| SB-098 | p163 | UCGTCGTTTTGTCGTTTTGTCG*tt*-C3 | 0.12 | 24 | 163 |
| SB-057 | p88 | TCGTCGTTTTGTCGTTTTGTCG*TT* | 0.36 | 24 | 88 |

Tables 8 and 9 show that 3'-truncation of immunostimulating polynucleotide sequences and shorter spacing between ISS may not be detrimental and may even improve the immunostimulating activity of an immunostimulating polynucleotide. These tables also show that as few as two ISS may be sufficient for immunostimulation.

TABLE 8

| Conjugate | Polynucleotide | Sequence (5' to 3') | Conjugate EC50 (nM) | Length | SEQ ID NO: |
|---|---|---|---|---|---|
| SB-098 | p163 | UCGTCGTTTTGTCGTTTTGTCGtt-C3 | 0.16 | 24 | 163 |
| SB-114 | p183 | UCGTCGTTTTGTCGTTTTGTCGTT-C3 | 0.07 | 24 | 183 |
| SB-120 | p175 | UCGTCGTTTTGTCGTTTT | 0.05 | 18 | 175 |
| SB-121 | p176 | UTCGTCGTTTTGTCGTT | 0.10 | 16 | 176 |
| SB-126 | p177 | UCGTCGTTTTGTCG | 0.05 | 14 | 177 |
| SB-127 | p178 | UCGTCGTTTTGT | 0.27 | 12 | 178 |
| SB-116 | p171 | TCGTCGTTTTGTCGTTTT | 0.44 | 18 | 171 |
| SB-117 | p172 | TCGTCGTTTTGTCGTT | 0.52 | 16 | 172 |
| SB-118 | p173 | TCGTCGTTTTGTCG | 0.91 | 14 | 173 |
| SB-118 | p174 | TCGTCGTTTTGT | 1.5 | 12 | 174 |
| SB-097 | p162 | TCGTCGTTTTGTCGTTTT | 0.53 | 18 | 162 |

TABLE 9

| Conjugate | Polynucleotide | Sequence (5' to 3') | Conjugate EC50 (nM) | Length | SEQ ID NO: |
|---|---|---|---|---|---|
| SB-115 | p183 | UCGTCGTTTTGTCGTTTTGTCGTT-C3 | 0.07 | 24 | 183 |
| SB-121 | p176 | UTCGTCGTTTTGTCGTT | 0.10 | 16 | 176 |
| SB-133 | p187 | UCGTCGTTTGTCGTT-C3 | 0.08 | 15 | 187 |
| SB-134 | p188 | UCGTCGTTGTCGTT-C3 | 0.08 | 14 | 188 |
| SB-135 | p189 | UCGTCGTGTCGTT-C3 | 0.08 | 13 | 189 |
| SB-136 | p190 | UCGTCGTTCGTT-C3 | 0.16 | 12 | 190 |
| SB-137 | p191 | UCGTCGTCGTT-C3 | 0.21 | 11 | 191 |

Figure 18:
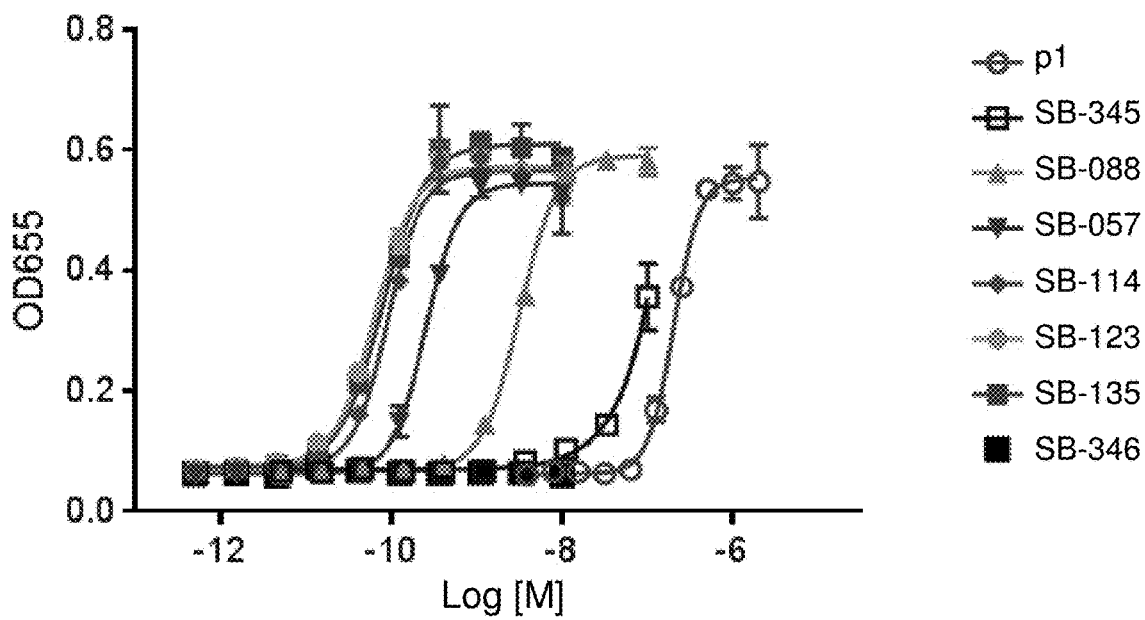
FIG. 18 is a graph showing the efficacy of the immunoconjugates containing immunostimulating polynucleotides of varying length in activating NFκB in Ramos-Blue cells, as measured by alkaline phosphatase readout.

FIG. 18 shows that conjugates containing immunostimulating polynucleotides having all internucleoside phosphoesters that are phosphorothioate-based exhibit activity that is comparable to that of free p1 and that conjugates containing short immunostimulating polynucleotides exhibit activity that is comparable to that of the conjugates containing full-length immunostimulating polynucleotides. The data shown in FIG. 18 are listed in Table 10.

TABLE 10

| Conjugate | Polynucleotide | Sequence (5' to 3') | Conjugate EC50 (nM) | Length | SEQ ID NO: |
|---|---|---|---|---|---|
| SB-345 | p151 | tcgtcgttttgtcgttttgtcgtT | ~200 | 24 | 151 |
| SB-088 | p153 | tcgtcGTTTTGTCGTTTTGTCGtt | 3.2 | 24 | 153 |
| SB-057 | p88 | TCGTCGTTTTGTCGTTTTGTCGTT | 0.25 | 24 | 88 |
| SB-115 | p183 | UCGTCGTTTTGTCGTTTTGTCGTT-C3 | 0.09 | 24 | 183 |
| SB-123 | p176 | UTCGTCGTTTTGTCGTT | ~0.06 | 16 | 176 |
| SB-135 | p189 | UCGTCGTGTCGTT-C3 | 0.08 | 13 | 189 |
| SB-346 | p192 | UGCTGCTTTTGTGCTTTTGTGCTT | inactive | 24 | 192 |
| — | p1 | tcgtcgttttgtcgtttgtcgtt | 200 | 24 | 1 |

Figure 19:
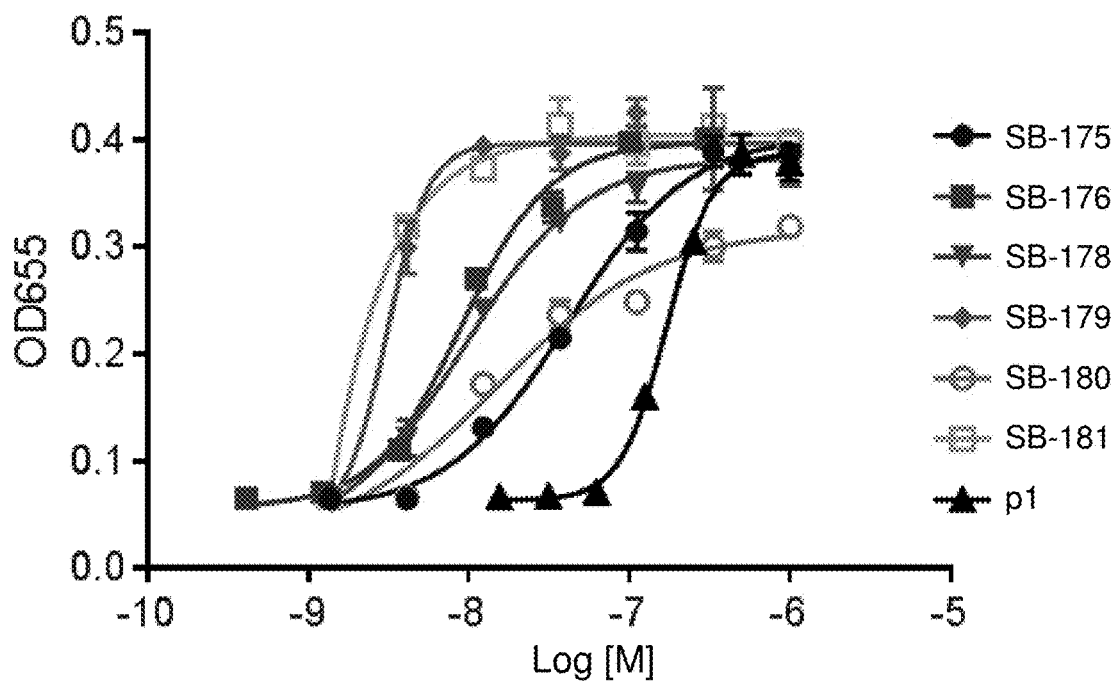
FIG. 19 is a graph showing the efficacy of the immunoconjugates containing immunostimulating polynucleotides of varying length in activating NFκB in Ramos-Blue cells, as measured by alkaline phosphatase readout.

FIG. 19 shows that conjugates containing shorter immunostimulating polynucleotides having all internucleoside phosphoesters that are phosphorothioate-based exhibit activity that is superior that of the conjugated containing longer immunostimulating polynucleotides having all internucleoside phosphoesters that are phosphorothioate-based. The data shown in FIG. 19 are summarized in Table 11.

TABLE 11

| Conjugate | Polynucleotide | Sequence (5' to 3') | Conjugate EC50 (nM) | Length | SEQ ID NO: |
|---|---|---|---|---|---|
| SB-175 | p232 | tcgtcgttttgtcgttttgtcgtT-C3 | 42 | 24 | 232 |
| SB-176 | p233 | UcgtcgttttgtcgttttgtcgtT-C3 | 9.1 | 24 | 233 |
| SB-178 | p235 | tcgtcgttttgtcgtT-C3 | 9.5 | 16 | 235 |
| SB-179 | p236 | UcgtcgttttgtcgtT-C3 | <3 | 16 | 236 |
| SB-180 | p237 | tcgtcgtgtcgtT-C3 | 15 | 13 | 237 |
| SB-181 | p238 | UcgtcgtgtcgtT-C3 | <3 | 13 | 238 |
| – | p1 | tcgtcgttttgtcgttttgtcgtt | 170 | 24 | 1 |

Figure 20:
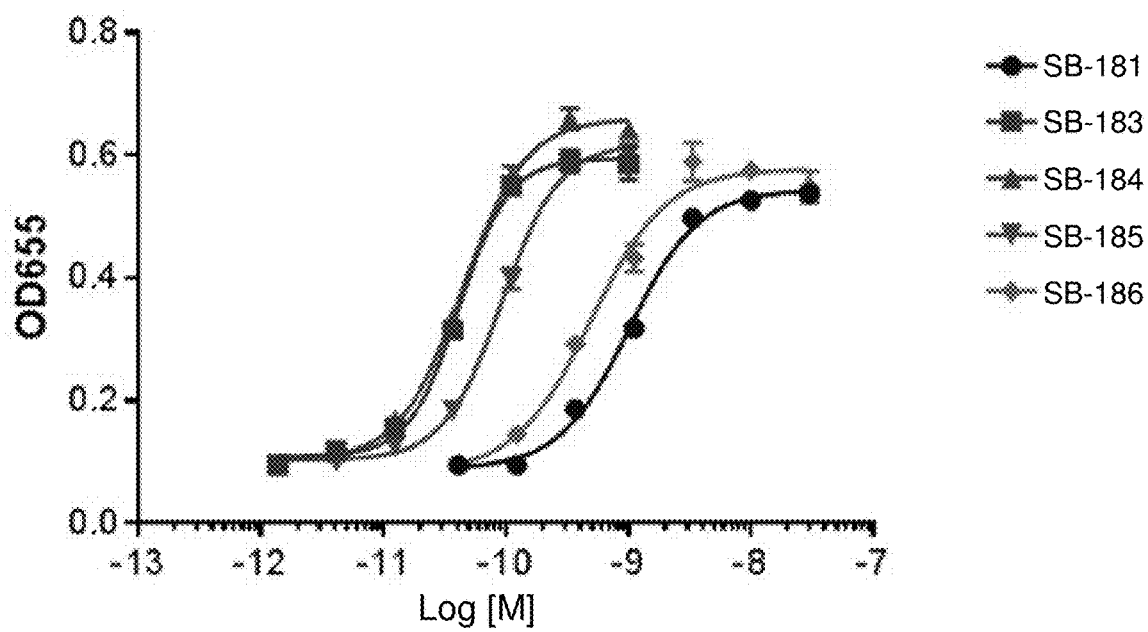
FIG. 20 is a graph showing the comparison of the immunostimulating activity of conjugates containing polynucleotides with 5'-terminal 5-iodo-2-deoxyuridine that is bonded to an internucleoside phosphodiester phosphate to the immunostimulating activity of conjugates containing polynucleotides with 5'-terminal 5-iodo-2-deoxyuridine that is bonded to an internucleoside phosphodiester phosphorothioate. The immunostimulating activities were assessed through the measurement of the NFκB activation in Ramos-Blue cells, as measured by alkaline phosphatase readout.
Figure 21:
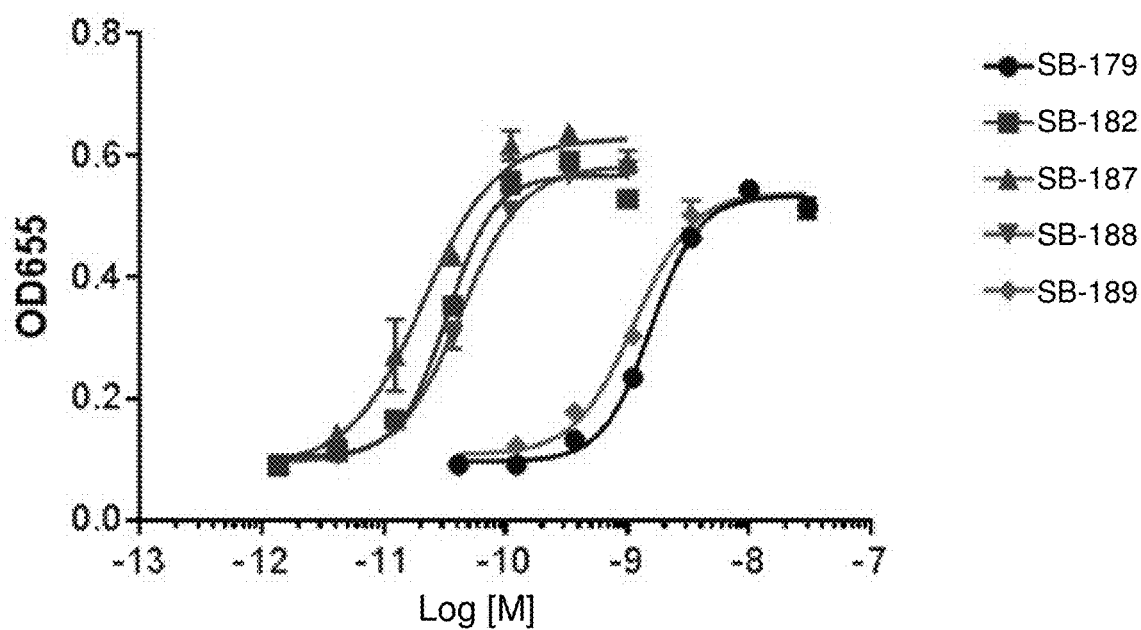
FIG. 21 is a graph showing the comparison of the immunostimulating activity of conjugates containing polynucleotides with 5'-terminal 5-iodo-2-deoxyuridine that is bonded to an internucleoside phosphodiester phosphate to the immunostimulating activity of conjugates containing polynucleotides with 5'-terminal 5-iodo-2-deoxyuridine that is bonded to an internucleoside phosphodiester phosphorothioate. The immunostimulating activities were assessed through the measurement of the NFκB activation in Ramos-Blue cells, as measured by alkaline phosphatase readout.

FIGS. 20 and 21 show that immunostimulating polynucleotides having phosphate-based internucleoside phosphoester(s) within the 5'-terminal ISS exhibit higher immunostimulating activity than immunostimulating polynucleotides having phosphorothioate-based internucleoside phosphoester(s) within 5'-terminal ISS. The data shown in FIGS. 20 and 21 are summarized in Table 12.

TABLE 12

| Conjugate | Polynucleotide | Sequence (5' to 3') | Conjugate EC50 (nM) | SEQ ID NO: |
|---|---|---|---|---|
| SB-181 | p238 | UcgtcgtgtcgtT-C3 | 1.00 | 238 |
| SB-183 | p240 | UCgtCgtgtCgtt-C3 | 0.04 | 240 |
| SB-184 | p241 | Ucgtcgtgtcgtt-C3 | 0.04 | 241 |
| SB-185 | p242 | Ucgtcgtgtcgtt-C3 | 0.09 | 242 |
| SB-186 | p243 | Ucgtcgtgtcgtt-C3 | 0.49 | 243 |
| SB-179 | p236 | UcgtcgttttgtcgtT-C3 | 1.55 | 236 |
| SB-182 | p239 | UCgtCgtgtCgTT-C3 | 0.03 | 239 |
| SB-187 | p244 | Ucgtcgtgtcgtt-C3 | 0.02 | 244 |
| SB-188 | p245 | Ucgtcgtgtcgtt-C3 | 0.04 | 245 |
| SB-189 | p246 | Ucgtcgtgtcgtt-C3 | 1.14 | 246 |

Figure 22:
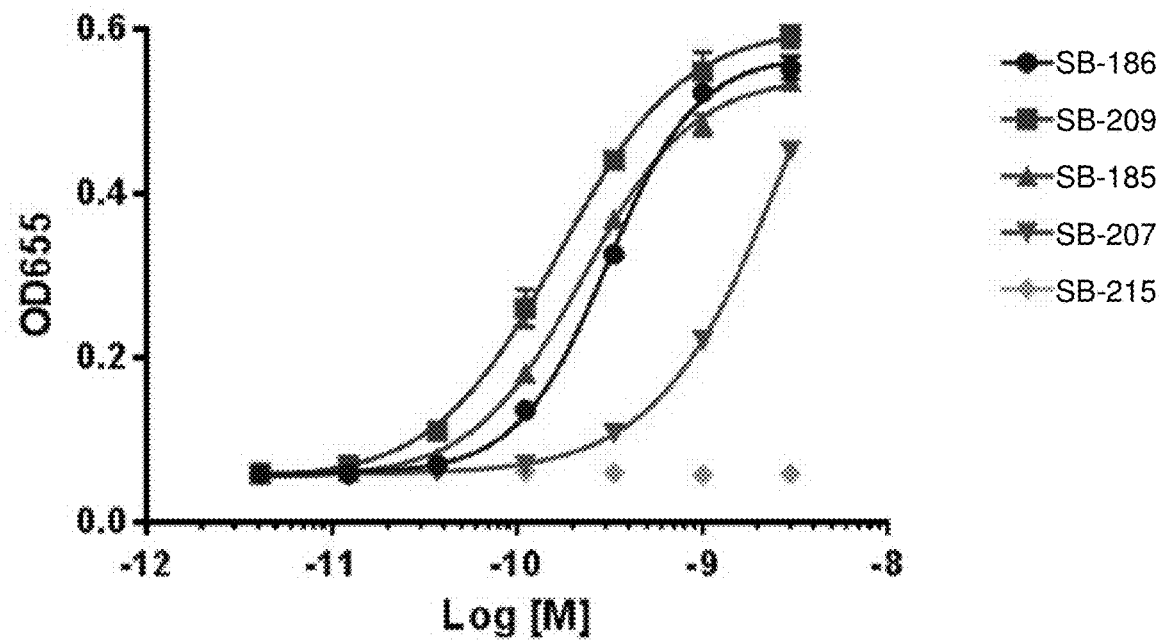
FIG. 22 is a graph showing the comparison of the immunostimulating activities of conjugates containing one or more 5-iodo-2-deoxyuridines. The immunostimulating activities were assessed through the measurement of the NFκB activation in Ramos-Blue cells, as measured by alkaline phosphatase readout.

FIG. 22 shows that 5'-terminal human ISS sequence is preferably UCG. The data shown in FIG. 22 are summarized in Table 13.

TABLE 13

| Conjugate | Polynucleotide | Sequence (5' to 3') | Conjugate EC50 (nM) | SEQ ID NO: |
|---|---|---|---|---|
| SB-186 | p243 | Ucgtcgtgtcgtt-C3 | 0.3 | 243 |
| SB-185 | p242 | Ucgtcgtgtcgtt-C3 | 0.2 | 242 |
| SB-207 | p262 | Ucgucgtgtcgtt-C3 | 2.9 | 262 |
| SB-209 | p263 | Ucgtcgtgucgtt-C3 | 0.2 | 263 |
| SB-215 | p268 | cgtcgtgucgtt-C3 | inactive | 268 |

Figure 23:
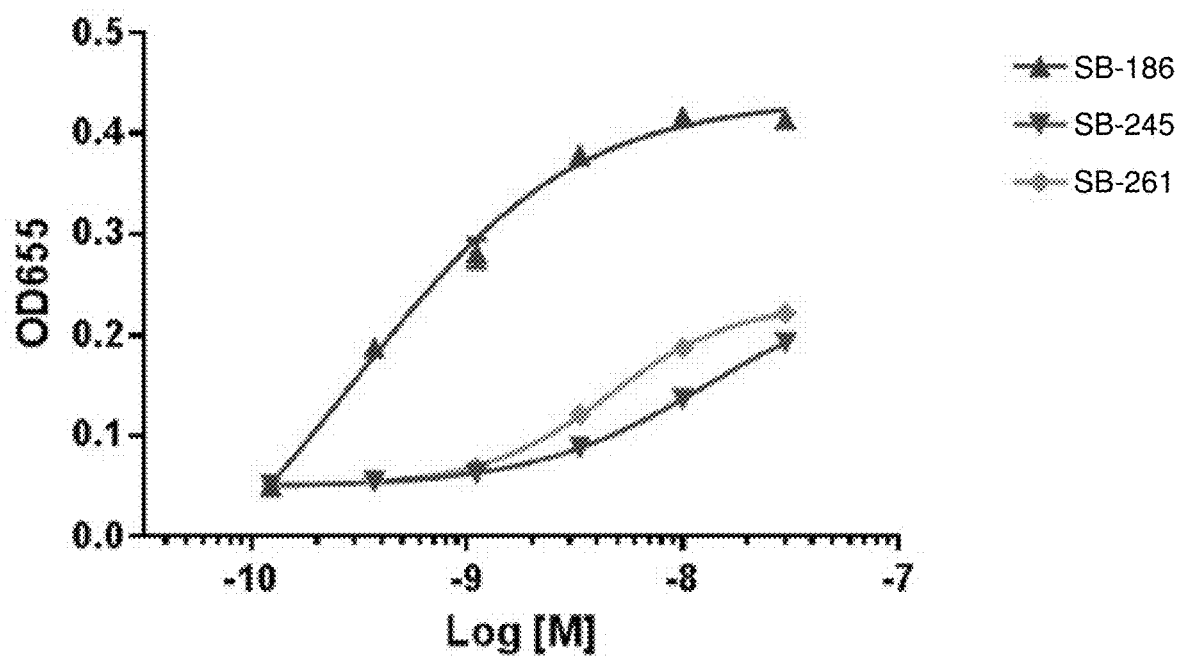
FIG. 23 is a graph showing the comparison of the immunostimulating activities of conjugates containing or lacking 5-iodo-2-deoxyuridine. The immunostimulating activities were assessed through the measurement of the NFκB activation in Ramos-Blue cells, as measured by alkaline phosphatase readout.

FIG. 23 shows that inclusion of 5-iodouridine in 5'-terminal ISS has a stronger enhancing effect on immunostimulating activity of an immunostimulating polynucleotide. The data shown in FIG. 23 are summarized in Table 14.

TABLE 14

| Conjugate | Polynucleotide | Sequence (5' to 3') | Conjugate EC50 (nM) | SEQ ID NO: |
|---|---|---|---|---|
| SB-186 | p243 | ucgtcgtgtcg__tt__-C3 | 0.3 | 243 |
| SB-245 | p301 | tcgucgtgtcg__tt__-C3 | >30 | 301 |
| SB-261 | p312 | tcgUcgtgtcg__tt__-C3 | >30 | 312 |

Figure 24:
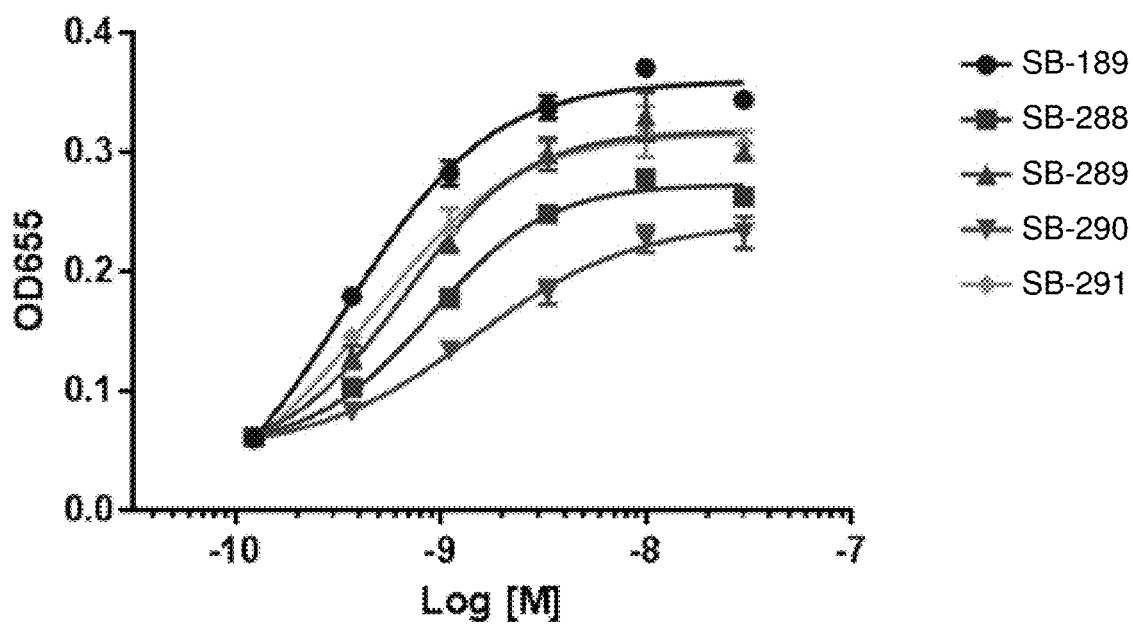
FIG. 24 is a graph showing the comparison of immunostimulating activities of conjugates containing internucleoside phosphotriesters that are phosphate-based or phosphorothioate-based. The immunostimulating activity was assessed through the measurement of the NFκB activation in Ramos-Blue cells, as measured by alkaline phosphatase readout.
Figure 25:
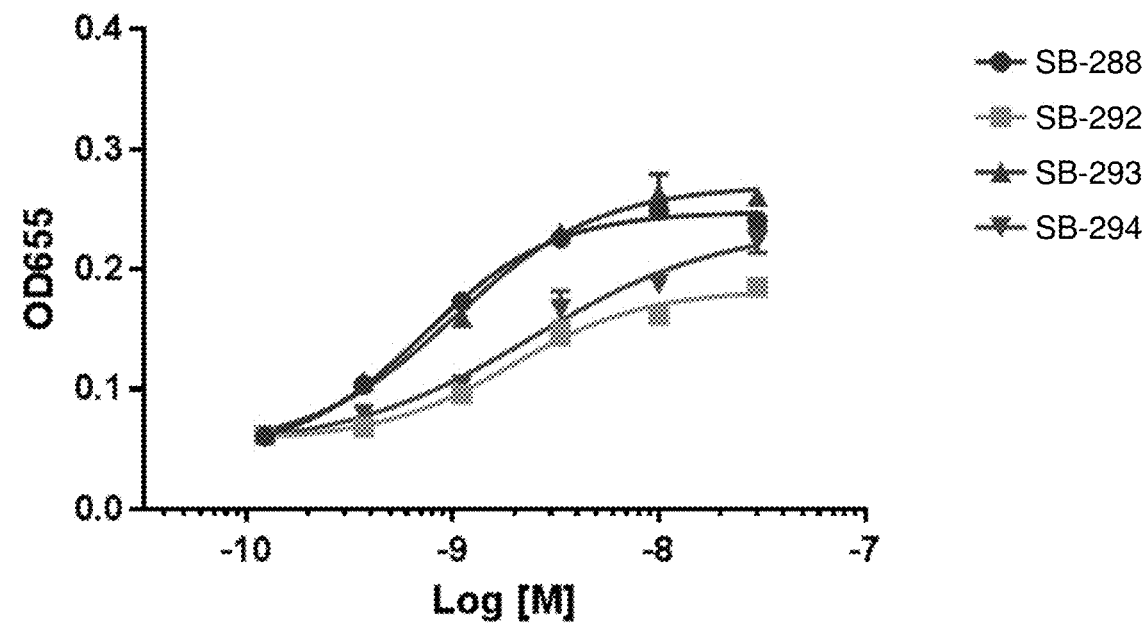
FIG. 25 is a graph showing the comparison of immunostimulating activities of conjugates containing internucleoside phosphotriesters that are phosphate-based or phosphorothioate-based. The immunostimulating activity was assessed through the measurement of the NFκB activation in Ramos-Blue cells, as measured by alkaline phosphatase readout.

FIGS. 24 and 25 show that the immunostimulating activity of polynucleotides containing phosphate-based internucleoside phosphotriesters may be higher than that of the corresponding polynucleotides containing phosphorothioate-based internucleoside phosphotriesters. The data shown in FIGS. 24 and 25 are summarized in Table 15.

TABLE 15

| Conjugate | Polynucleotide | Sequence (5' to 3') | Conjugate EC50 (nM) | SEQ ID NO: |
|---|---|---|---|---|
| SB-189 | p246 | ucg__t__cgtgtcgtt-C3 | 0.34 | 246 |
| SB-288 | p351 | ucg__t__cgtgtcgtt-C3 | 0.89 | 351 |
| SB-289 | p355 | ucg__T__cgtgtcgTt-C3 | 0.67 | 355 |
| SB-290 | p355 | ucg__T__cgtgtcgtt-C3 | 1.44 | 355 |
| SB-291 | p356 | ucg__T__cgtgtcgTt-C3 | 0.47 | 356 |
| SB-292 | p357 | ucgtcgtgtcg__t__t-C3 | 1.94 | 357 |
| SB-293 | p358 | ucgTcgtgtcg__t__t-C3 | 1.02 | 358 |
| SB-294 | p359 | ucgtcgtgtcg__T__t-C3 | 2.43 | 359 |

Table 16 shows that phosphotriester insertions are tolerated in the immunostimulating polynucleotides.

TABLE 16

| Conjugate | Polynucleotide | Sequence (5' to 3') | Polynucleotide EC50 (nM) | Conjugate EC50 (nM) | SEQ ID NO: |
|---|---|---|---|---|---|
| — | p1 | tcgtcgttttgtcgttttgtcgtt | 170 | — | 1 |
| — | p246 | ucg__t__cgtgtcgtt-C3 | 104 | — | 246 |
| SB-312 | p361 | ucg__T__cgtgtcgtt-C3 | 102 | 0.67 | 361 |
| SB-313 | p362 | ucg__T__cgtgtcgTet-C3 | 175 | 0.85 | 362 |
| SB-314 | p363 | ucg__T__cgtgtcGett-C3 | 365 | 1.09 | 363 |
| SB-315 | p364 | ucg__T__cgtgtCegtt-C3 | 523 | 1.77 | 364 |
| SB-316 | p365 | ucg__T__cgtgTecgtt-C3 | 260 | 1.33 | 365 |
| SB-317 | p366 | ucg__T__cgtGetcgtt-C3 | 390 | 2.84 | 366 |
| SB-318 | p367 | ucg__T__cgTegtcgtt-C3 | 287 | 2.17 | 367 |
| SB-319 | p368 | ucg__T__cGetgtcgtt-C3 | 223 | 1.33 | 368 |
| SB-320 | p369 | ucg__T__Cegtgtcgtt-C3 | 242 | 0.76 | 369 |
| SB-321 | p370 | ucGe__t__cgtgtcgtt-C3 | 158 | 0.84 | 370 |
| SB-322 | p371 | uCeg__t__cgtgtcgtt-C3 | 160 | 0.5 | 371 |
| SB-323 | p372 | ucgTecgtgtcg__T__t-C3 | 194 | 0.66 | 372 |

Tables 17 and 18 shows that abasic spacer insertions are tolerated in the immunostimulating polynucleotides.

TABLE 17

| Poly-nucleotide | Sequence (5' to 3') | EC50 (nM) | SEQ ID NO: |
|---|---|---|---|
| p371 | uCeg*T*cgtgtcgtt-C3 | 189 | 371 |
| p402 | uCeg*T*cgtgtcGett-C3 | 356 | 402 |
| p403 | uCeg*T*cgtgtCegtt-C3 | 482 | 403 |
| p404 | uCeg*T*cgttgtcgTet-C3 | 203 | 404 |
| p405 | uCeg*T*cgtTegtcgTet-C3 | 809 | 405 |
| p406 | uCeg*T*cgTetgtcgTet-C3 | 510 | 406 |
| p407 | uCeg*T*cgtX3gtcgTet-C3 | 286 | 407 |
| p408 | uCeg*T*cgX3tgtcgTet-C3 | 266 | 408 |
| p409 | uCeg*T*cgtTegtcgTet-C3 | 875 | 409 |
| p410 | uCeg*T*cgX3gtcgtt-C3 | 193 | 410 |
| p361 | ucg*T*cgtgtcgtt-C3 | 102 | 361 |
| p411 | X3ucg*T*cgtgtcgtt-C3 | 124 | 411 |

TABLE 17-continued

| Poly-nucleotide | Sequence (5' to 3') | EC50 (nM) | SEQ ID NO: |
|---|---|---|---|
| p412 | uX3cg*T*cgtgtcgtt-C3 | inactive | 412 |
| p413 | ucX3g*T*cgtgtcgtt-C3 | 225 | 413 |
| p414 | ucgX3*T*cgtgtcgtt-C3 | 131 | 414 |
| p415 | ucg*T*X3cgtgtcgtt-C3 | 124 | 415 |
| p416 | ucg*T*cX3gtgtcgtt-C3 | 85 | 416 |
| p417 | ucg*T*cgX3tgtcgtt-C3 | 92 | 417 |
| p418 | ucg*T*cgtX3gtcgtt-C3 | 93 | 418 |
| p419 | ucg*T*cgtgX3tcgtt-C3 | 189 | 419 |
| p420 | ucg*T*cgtgtX3cgtt-C3 | 227 | 420 |
| p421 | ucg*T*cgtgtcX3gtt-C3 | 95 | 421 |
| p422 | ucg*T*cgtgtcgX3tt-C3 | 135 | 422 |
| p423 | ucg*T*cgtgtcgtX3t-C3 | 202 | 423 |
| p424 | ucg*T*cgtgtcgttX3-C3 | 113 | 424 |

TABLE 18

| Conjugate | Polynucleotide | Sequence (5' to 3') | Conjugate EC50(nM) | SEQ ID NO: |
|---|---|---|---|---|
| SB-295 | p373 | tucgtcgtgacgttX5-C3 | 44 | 373 |
| SB-296 | p374 | tucgtcgtgacgtX5t-C3 | 47 | 374 |
| SB-297 | p375 | tucgtcgtgacgX5tt-C3 | 103 | 375 |
| SB-298 | p376 | tucgtcgtgacX5gtt-C3 | 243 | 376 |
| SB-299 | p377 | tucgtcgtgaX5cgtt-C3 | 64 | 377 |
| SB-300 | p378 | tucgtcgtgX5acgtt-C3 | 29 | 378 |
| SB-301 | p379 | tucgtcgtX5gacgtt-C3 | 10 | 379 |
| SB-302 | p380 | tucgtcgX5tgacgtt-C3 | 7 | 380 |
| SB-303 | p381 | tucgtcX5gtgacgtt-C3 | 13 | 381 |
| SB-304 | p382 | tucgtX5cgtgacgtt-C3 | 13 | 382 |
| SB-305 | p383 | tucgX5tcgtgacgtt-C3 | 25 | 383 |
| SB-306 | p384 | tucX5gtcgtgacgtt-C3 | 19 | 384 |
| SB-307 | p385 | tuX5cgtcgtgacgtt-C3 | inactive | 385 |
| SB-308 | p386 | tX5ucgtcgtgacgtt-C3 | 28 | 386 |
| SB-309 | p387 | X5tucgtcgtgacgtt-C3 | 20 | 387 |
| SB-310 | p388 | tucgx5cgtgacgtt-C3 | 8 | 388 |
| SB-311 | p389 | tucgx5cgtgacgtt-C3 | 5* | 389 |
| SB-337 | p313 | tucg*t*cgtgacgtt-C3 | 48 | 313 |

*sub-optimal activation

Figure 26A:
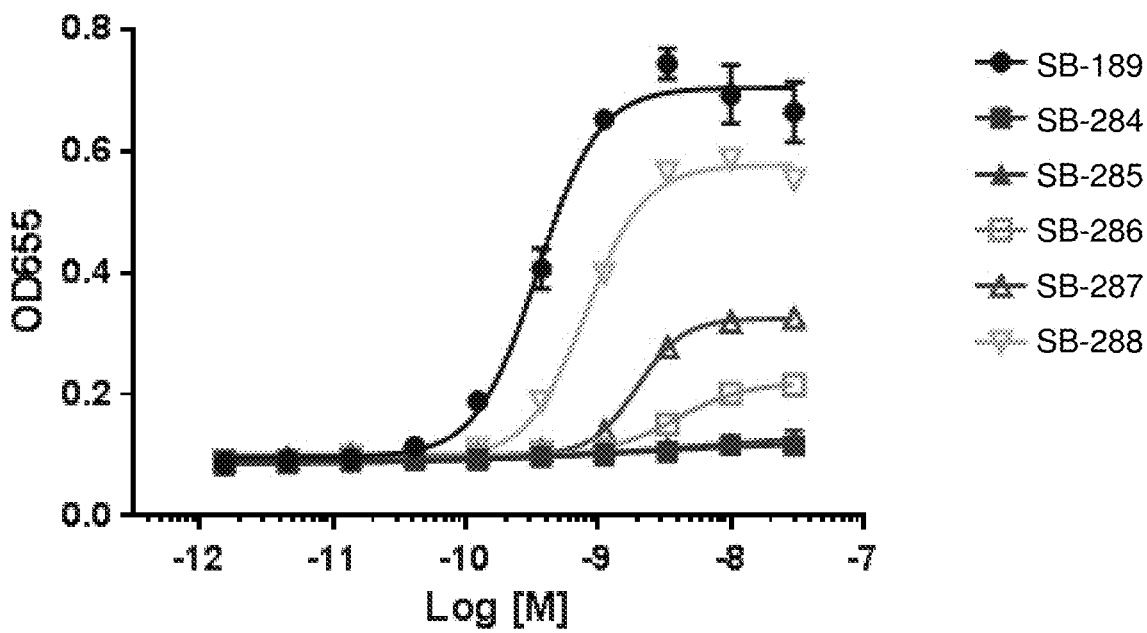
FIG. 26A is a graph showing the comparison of immunostimulating activities of conjugates containing one or more phosphorothioate-based internucleoside phosphotriesters. The immunostimulating activity was assessed through the measurement of the NFκB activation in Ramos-Blue cells, as measured by alkaline phosphatase readout.
Figure 26B:
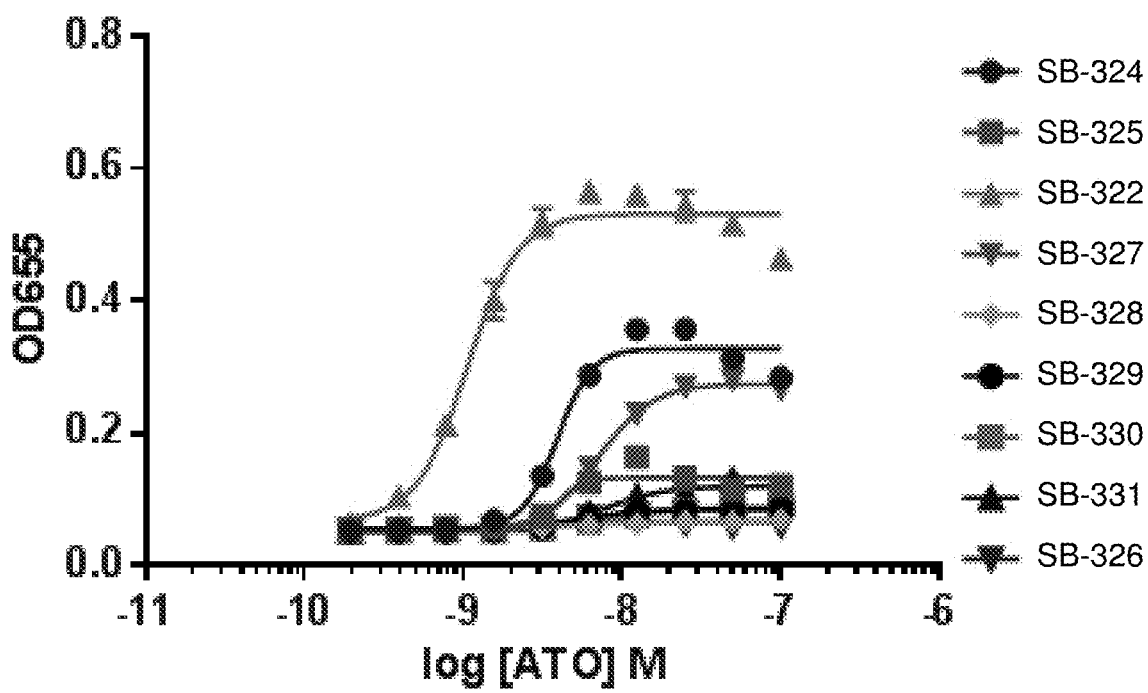
FIG. 26B is a graph showing the comparison of immunostimulating activities of conjugates containing one or more phosphorothioate-based internucleoside phosphotriesters. The immunostimulating activity was assessed through the measurement of the NFκB activation in Ramos-Blue cells, as measured by alkaline phosphatase readout.

FIGS. 26A and 26B shows that the higher content of phosphorothioate-based internucleoside phosphotriesters influences the immunostimulating activity of immunostimulating polynucleotides. This effect is particularly pronounced in the immunostimulating polynucleotides having phosphorothioate-based internucleoside phosphotriesters disposed more distally from the 3'-terminus. The data shown in FIGS. 26A and 26B are summarized in Table 19.

TABLE 19

| Conjugate | Polynucleotide | Sequence (5' to 3') | EC50 (nM) | SEQ ID NO: |
|---|---|---|---|---|
| SB-189 | p246 | ucgtcgtgtcgtt-C3 | 0.35 | 246 |
| SB-284 | p347 | ucgtcgtgtcgtt-C3 | 2.46 | 347 |
| SB-285 | p348 | ucgtcgtgtcgtt-C3 | 4.92 | 348 |
| SB-286 | p349 | ucgtcgtgtcgtt-C3 | 3.74 | 349 |
| SB-287 | p350 | ucgtcgtgtcgtt-C3 | 1.98 | 350 |
| SB-288 | p351 | ucgtcgtgtcgtt-C3 | 0.80 | 351 |
| SB-324 | p390 | UcgTcgtgtcgtt-C3 | 3.9 | 390 |
| SB-325 | p391 | UaCegTcgtgtcgtt-C3 | 3.9* | 391 |
| SB-322 | p371 | uCegTcgtgtcgtt-C3 | 1.1 | 371 |
| SB-327 | p396 | uCegTCegtgtCegtt-C3 | 7.1* | 396 |
| SB-328 | p397 | ucgTcGetGetcGett-C3 | 6.6** | 397 |
| SB-329 | p398 | ucgTcgTegTecgTet-C3 | 5.6** | 398 |
| SB-330 | p399 | uCegTcgTegTecgTet-C3 | 9.4** | 399 |
| SB-331 | p400 | ucgTecgTegTecgTt-C3 | 7.9** | 400 |
| SB-326 | p392 | UaCeGeTcgtgtcgtt-C3 | ca. 3.2** | 392 |

*sub-optimal activation
**inactive

Table 20 shows that longer linkers linking a targeting moiety to an immunostimulating polynucleotide may enhance the immunostimulating activity of the conjugate relative to a conjugate having a shorter linker.

TABLE 20

| Conjugate | Polynucleotide | EC50 (nM) | (PEGx)* |
|---|---|---|---|
| SB-189 | p246 | 0.3 | 23 |
| SB-273 | p246 | 2.7 | 11 |
| SB-272 | p246 | 3.1 | 7 |
| SB-212 | p246 | 3.1 | 3 |
| SB-257 | p246 | 0.2 | 23 |
| SB-276 | p246 | 1.2 | 11 |
| SB-275 | p246 | 1.9 | 7 |
| SB-274 | p246 | 3.1 | 3 |

*(PEGx) indicates the number of ethylene glycol units in the complementary reactive group attached to the antibody.

Figure 27:
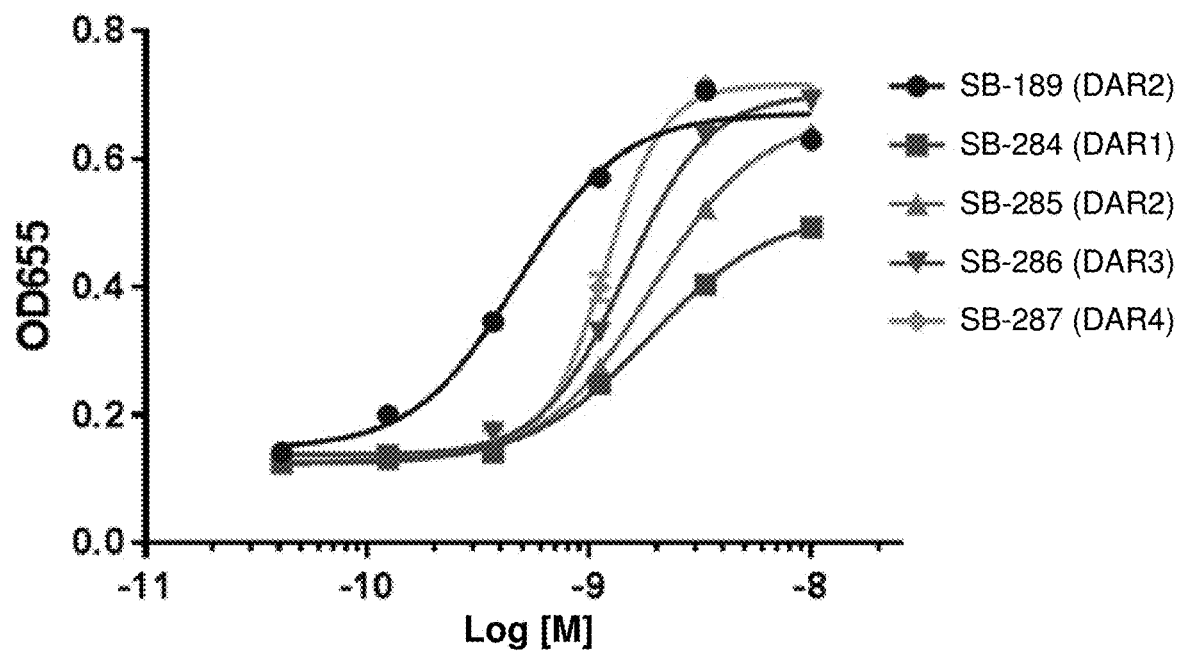
FIG. 27 is a graph showing the comparison of immunostimulating activities of conjugates containing an antibody and one or more immunostimulating polynucleotides. The immunostimulating activity was assessed through the measurement of the NFκB activation in Ramos-Blue cells, as measured by alkaline phosphatase readout.

FIG. 27 shows that conjugation to an antibody heavy chain through Q-tag can provide conjugates exhibiting superior immunostimulating activity relative to conjugation to an antibody light chain through using PFP chemistry. The data shown in FIG. 27 are summarized in Table 21.

TABLE 21

| Conjugate | Antibody | Polynucleotide | Conjugation | DAR* | EC50 (nM) |
|---|---|---|---|---|---|
| SB-099 | rituximab | p163 | HC Q-tag | 2 | 0.48 |
| SB-107 | rituximab | p163 | LC PFP | 1 | 1.85 |
| SB-107 | rituximab | p163 | LC PFP | 2 | 1.88 |

TABLE 21-continued

| Conjugate | Antibody | Polynucleotide | Conjugation | DAR* | EC50 (nM) |
|---|---|---|---|---|---|
| SB-107 | rituximab | p163 | LC PFP | 3 | 1.45 |
| SB-107 | rituximab | p163 | LC PFP | 4 | 1.17 |

*DAR represents the polynucleotide/antibody ratio.

Figure 28:
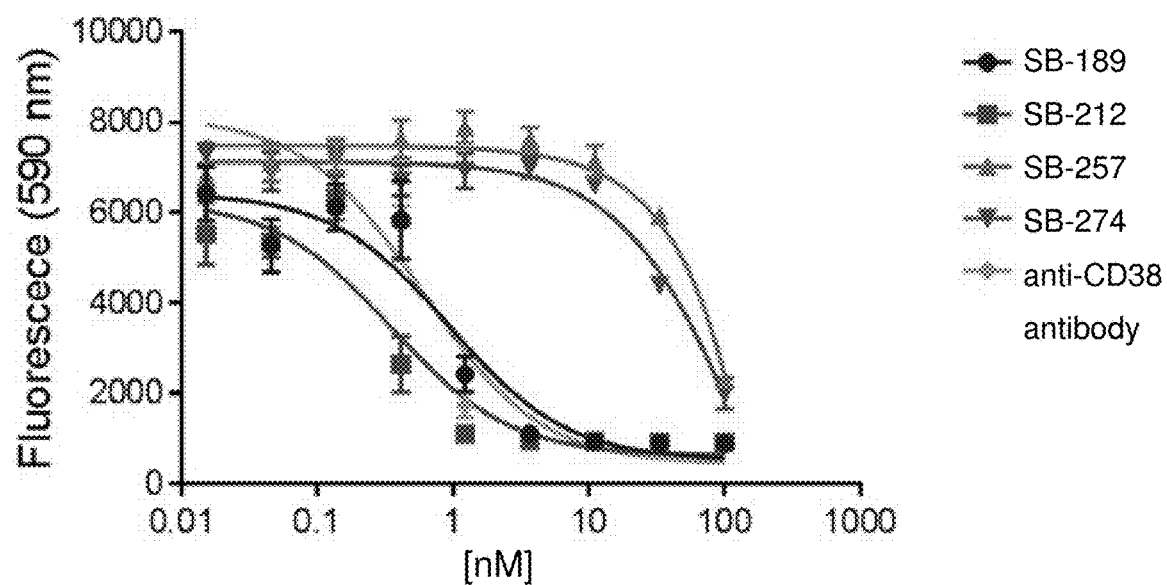
FIG. 28 is a graph showing the comparison of cellular dependent cytotoxicity (CDC) of immunostimulating polynucleotides conjugated through a heavy chain Q-tag or a light chain Q-tag in an antibody. The CDC assay was performed in Daudi cells incubated with the conjugates in human sera, and the cytotoxicity was measured by fluorescence.

FIG. 28 shows that antibody heavy chain conjugates can exhibit superior immunostimulating activity relative to antibody light chain conjugates. The data shown in FIG. 28 are summarized in Table 22.

TABLE 22

| Conjugate | Antibody | Conjugation | Polynucleotide | (PEGx)* | EC50 (nM) |
|---|---|---|---|---|---|
| — | anti-CD38 | — | — | — | 0.6 |
| SB-189 | anti-CD38 | HC Q-tag | p246 | 23 | 0.9 |
| SB-212 | anti-CD38 | HC Q-tag | p246 | 3 | 0.4 |
| SB-257 | anti-CD38 | LC Q-tag | p246 | 23 | >50 |
| SB-274 | anti-CD38 | LC Q-tag | p246 | 3 | >50 |

*(PEGx) indicates the number of ethylene glycol units in the complementary reactive group attached to the antibody that is formed from NH$_2$-PEGx-N$_3$.

Figure 29:
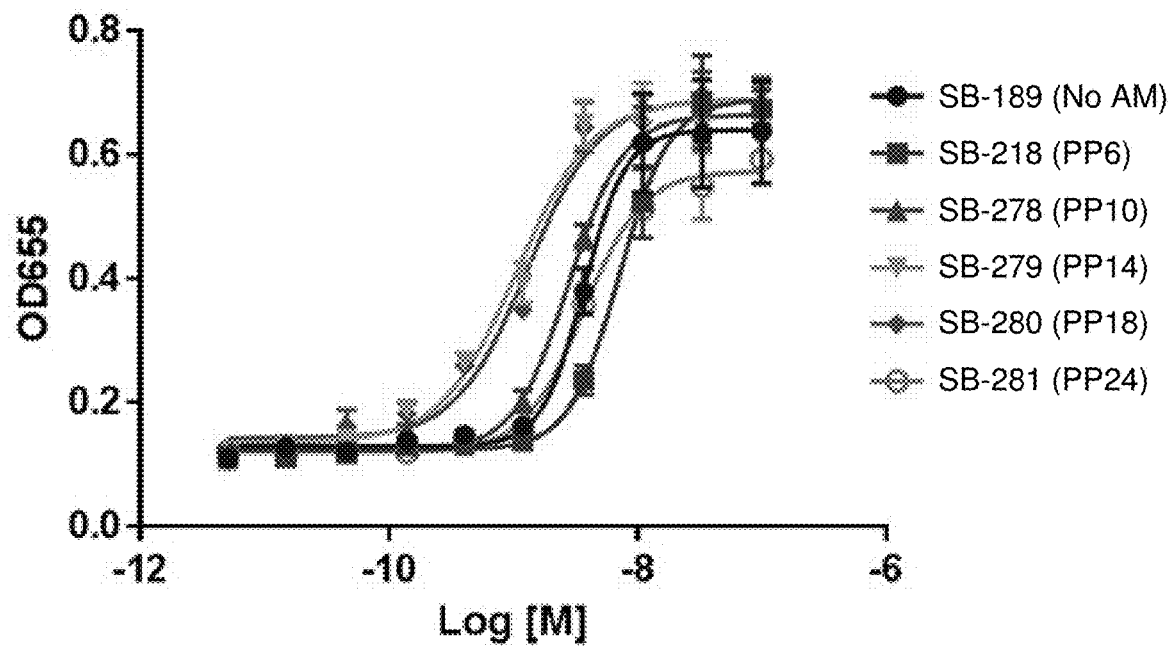
FIG. 29 is a graph showing the comparison of immunostimulating activities of conjugates having auxiliary moieties. The immunostimulating activity was assessed through the measurement of the NFκB activation in Ramos-Blue cells, as measured by alkaline phosphatase readout. The designator in parenthesis indicates the linker/auxiliary moiety structure used in the conjugate, no AM indicates that conjugate SB-189 does not contain an auxiliary moiety.

FIG. 29 shows that inclusion of auxiliary moieties (e.g., poly(ethylene glycol)s) can enhance the immunostimulating activity of a conjugate of the invention. The data shown in FIG. 29 are summarized in Table 23.

TABLE 23

| Conjugate | Antibody | Conjugation | Polynucleotide | (PEGx)* | EC50 (nM) |
|---|---|---|---|---|---|
| SB-212 | anti-CD38 | HC Q-tag | p246 | PEG3 | 3.7 |
| SB-218 | anti-CD38 | HC Q-tag | p246 | PP6 | 7.2 |
| SB-278 | anti-CD38 | HC Q-tag | p246 | PP10 | 2.8 |
| SB-279 | anti-CD38 | HC Q-tag | p246 | PP14 | 1.1 |
| SB-280 | anti-CD38 | HC Q-tag | p246 | PP18 | 1.3 |
| SB-281 | anti-CD38 | HC Q-tag | p246 | PP24 | 3.7 |

*(PEGx) indicates the complementary reactive group used in the conjugates.

Table 24 shows that the inclusion of PEG auxiliary moieties did not significantly influence the self-delivery of immunostimulating polynucleotides unconjugated to a targeting moiety. The data in Table 24 is for the IL6 secretion in A20 cells, as measured by ELISA, after 20 hours of incubation of the cells with the immunostimulating polynucleotides.

TABLE 24

| Polynucleotide | Sequence (5' to 3') | (PEGx)* | EC50 (nM) | SEQ ID NO: |
|---|---|---|---|---|
| p313 | tucgtcgtgacgtt-C3 | PP12 | 111 | 313 |
| p313 | tucgtcgtgacgtt-C3 | PP16 | 139 | 313 |
| p313 | tucgtcgtgacgtt-C3 | PP20 | 123 | 313 |
| p313 | tucgtcgtgacgtt-C3 | PP26 | 96 | 313 |
| p347 | tugctgctgagctt-C3 | — | 39 | 347 |

*(PEGx) indicates the complementary reactive group used in the conjugates.

Figure 30:
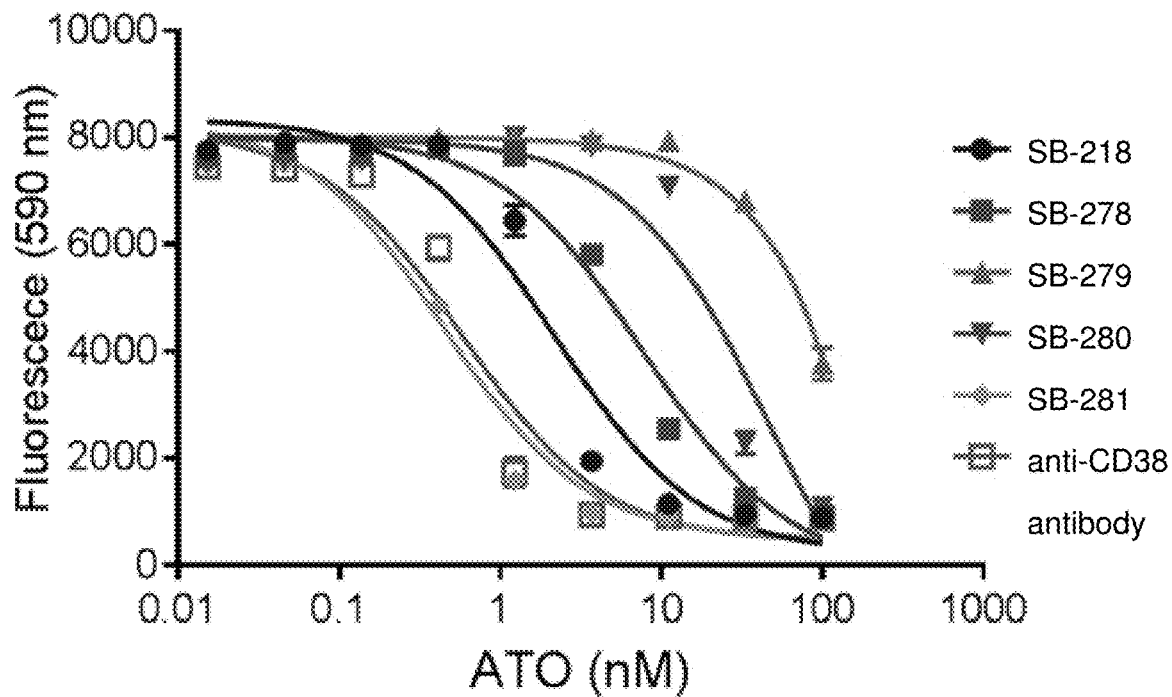
FIG. 30 is a graph showing the comparison of CDC activities of conjugates having auxiliary moieties. The CDC assay was performed in Daudi cells incubated with the conjugates in human sera, and the cytotoxicity was measured by fluorescence.

FIG. 30 shows that auxiliary moieties can influence cellular dependent cytotoxicity of the conjugates. The data shown in FIG. 30 is summarized in Table 25.

TABLE 25

| Conjugate | Antibody | Conjugation | Polynucleotide | (PEGx)* | EC50 (nM) |
|---|---|---|---|---|---|
| SB-218 | anti-CD38 | HC Q-tag | p246 | PP6 | 2.2 |
| SB-278 | anti-CD38 | HC Q-tag | p246 | PP10 | 7.7 |
| SB-279 | anti-CD38 | HC Q-tag | p246 | PP14 | >100 |
| SB-280 | anti-CD38 | HC Q-tag | p246 | PP18 | 47 |
| SB-281 | anti-CD38 | HC Q-tag | p246 | PP24 | 0.5 |

*(PEGx) indicates the complementary reactive group used in the conjugates.

Figure 31:
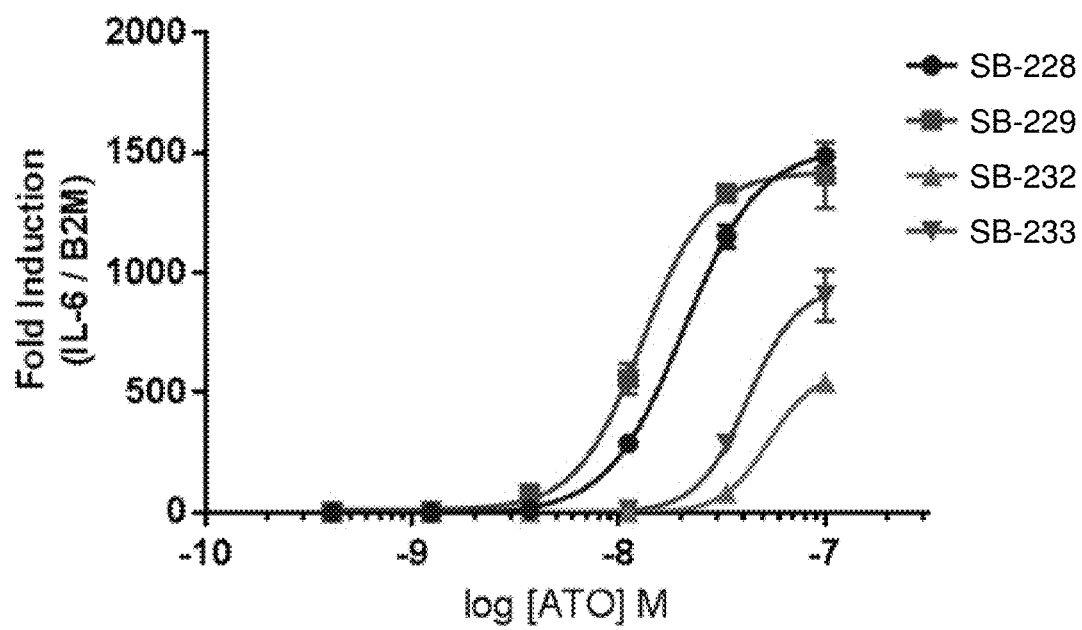
FIG. 31 is a graph showing the induction of IL6 in A20 mouse B-cell lymphoma cells using conjugates containing a truncated murine cross-reactive human immunostimulating polynucleotide (p275) linked through a Q-tag to a murine anti-CD22 antibody.
Figure 32:
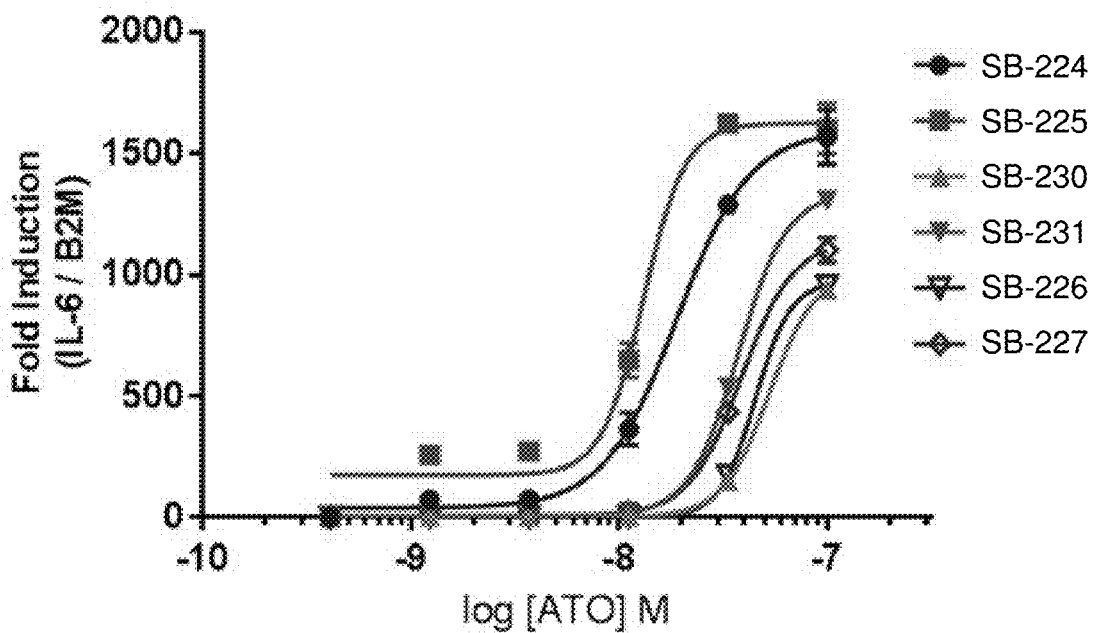
FIG. 32 is a graph showing the induction of IL6 in A20 mouse B-cell lymphoma cells using conjugates containing a truncated murine cross-reactive human immunostimulating polynucleotide (p275) linked through a Q-tag to a murine anti-CD22 antibody.

FIGS. 31 and 32 show the induction of IL6 in mouse A20 cells using conjugates containing truncated immunostimulating polynucleotides. The antibody utilized in these assays was a murine anti-CD20 antibody or murine anti-CD22 antibody. Q-tag was used for conjugation of the polynucleotides to the antibody. The data shown in FIGS. 31 and 32 are summarized in Table 26.

Table 26

[1] (PEGx) indicates the complementary reactive group used in the conjugates.
* indicates suboptimal activation.

the induction of interferon-α in purified plasmacytoid cells. The anti-BCDA4 antibody and its conjugate (SB-343) were used as controls.

Figure 35:
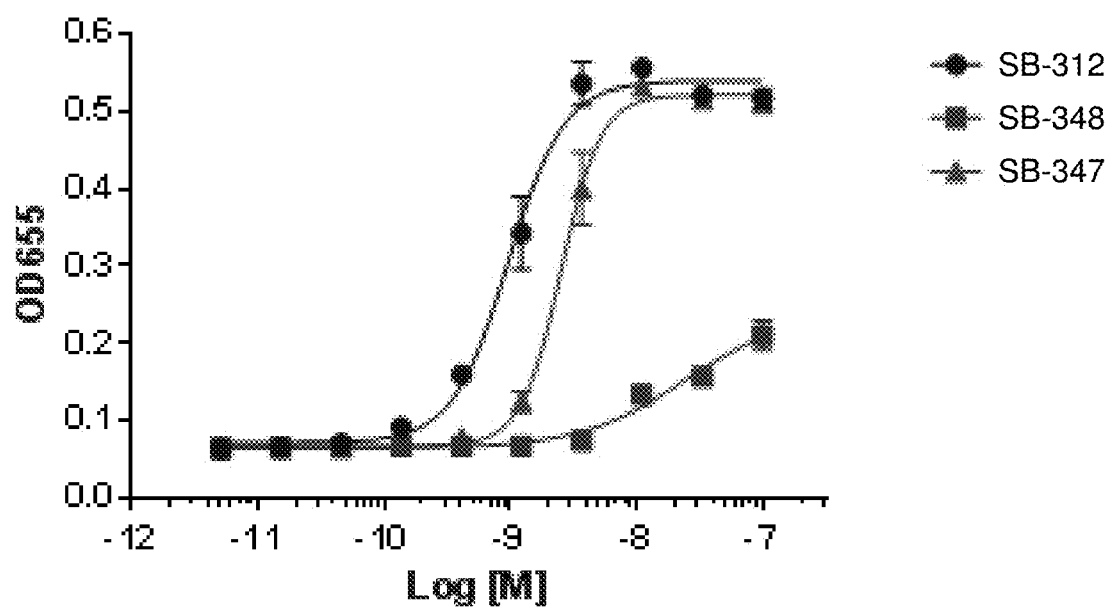
FIG. 35 is a graph showing the comparison of immunostimulatory activity of the polynucleotides with various 5'-terminal modifications and internucleoside triesters.
Figure 36:
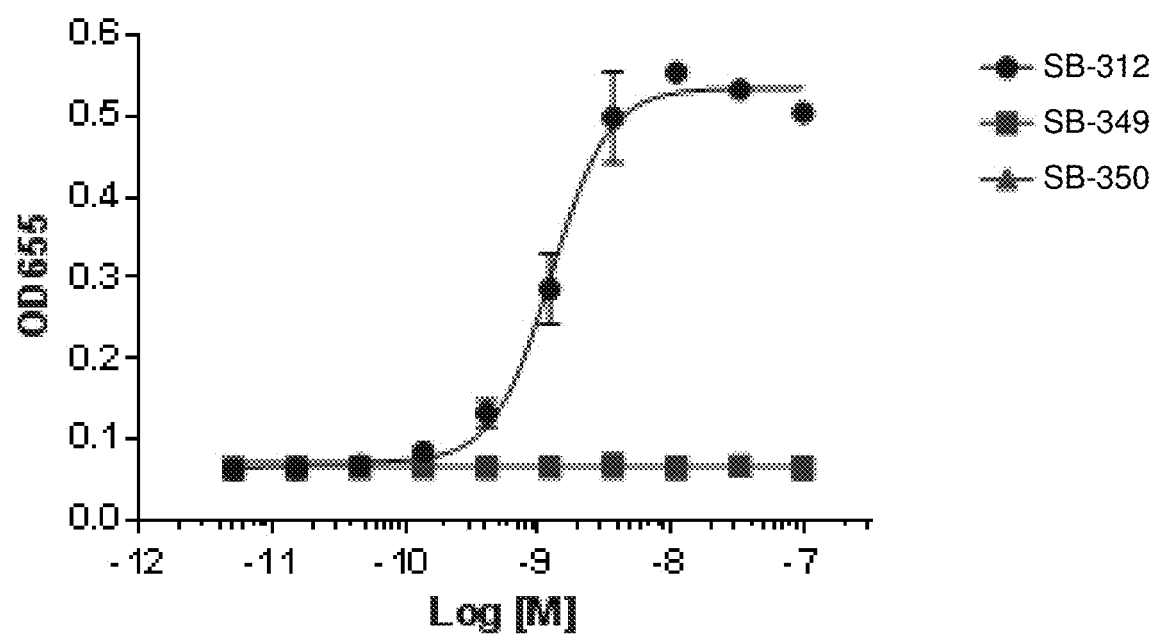
FIG. 36 is a graph showing the comparison of immunostimulatory activity of the polynucleotides with various 5'-terminal modifications and internucleoside triesters.

FIGS. 35 and 36 show immunostimulating activities of polynucleotides with various 5'-modification and inter-

TABLE 26

| Conjugate | Antibody | Polynucleotide | Sequence (5' to 3') | (PEGx)[1] | EC50 (nM) | SEQ ID NO: |
|---|---|---|---|---|---|---|
| SB-228 | anti-CD20 | p275 | ucgtcgtgacgtt-C3 | PP6 | 21 | 275 |
| SB-229 | anti-CD20 | p276 | ucgacgtgacgtt-C3 | PP6 | 13 | 276 |
| SB-232 | anti-CD20 | p304 | ucgtcgtgacgtt-C3 | PP6 | 53* | 304 |
| SB-233 | anti-CD20 | p305 | ucgacgtgacgtt-C3 | PP6 | 42* | 305 |
| SB-224 | anti-CD22 | p275 | ucgtcgtgacgtt-C3 | PP6 | 19 | 275 |
| SB-225 | anti-CD22 | p276 | ucgacgtgacgtt-C3 | PP6 | 13 | 276 |
| SB-230 | anti-CD22 | p304 | ucgtcgtgacgtt-C3 | PP6 | 53* | 304 |
| SB-231 | anti-CD22 | p305 | ucgacgtgacgtt-C3 | PP6 | 37* | 305 |
| SB-226 | anti-CD22 | p292 | ucgtcgtgacgtt-C3 | PP6 | 45* | 292 |
| SB-227 | anti-CD22 | p293 | ucgacgtgacgtt-C3 | PP6 | 39* | 293 |

[1](PEGx) indicates the complementary reactive group used in the conjugates.
*indicates suboptimal activation.

Figure 33A:
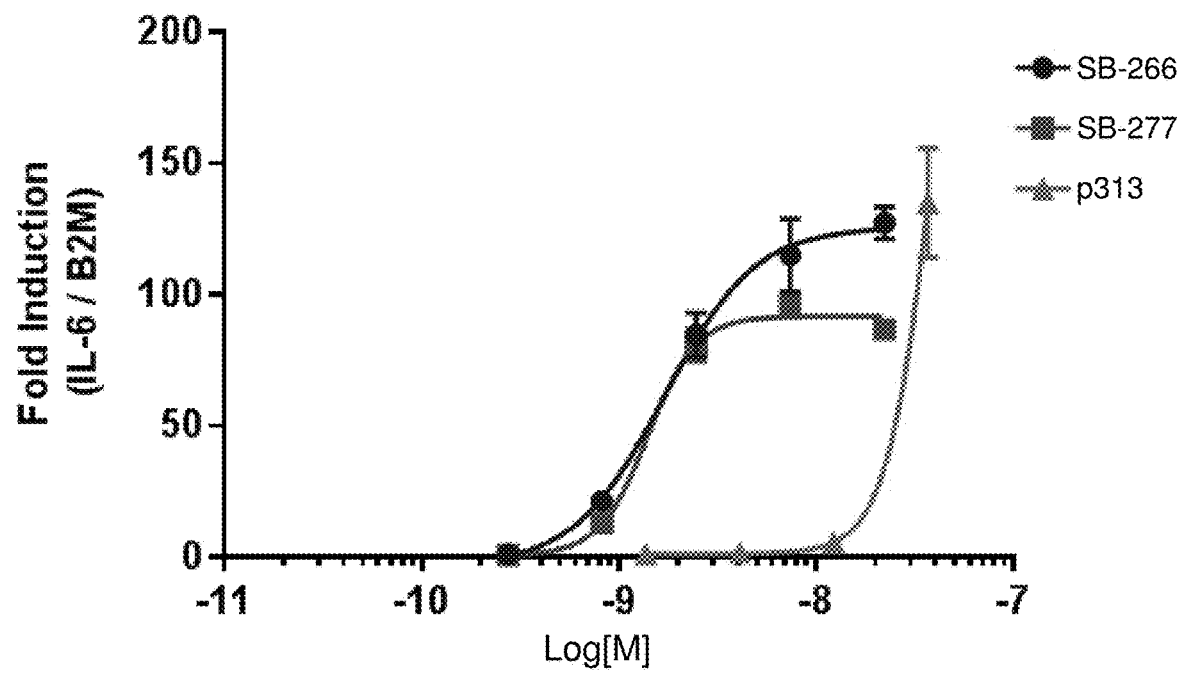
FIG. 33A is a graph showing the induction of IL6 in A20 mouse B-cell lymphoma cells using conjugates containing immunostimulating polynucleotides or an unconjugated immunostimulating polynucleotide.

FIG. 33A shows the induction of IL6 in mouse A20 cells using exemplary conjugates and an immunostimulating polynucleotide. The antibody utilized in these assays was a murine anti-CD22 antibody. Q-tag was used for conjugation of the polynucleotides to the antibody. The data shown in FIG. 33A are summarized in Table 27.

nucleoside triesters at 24 h, as measured by NFκB activation using QuantiBlue.

In Vivo Profiling in a Solid Tumor Model

A20 mouse B-cell lymphoma cells were purchased from the American Type Culture Collection (ATCC) and cultured

TABLE 27

| Conjugate | Polynucleotide | Sequence (5' to 3') | (PEGx)* | EC50 (nM) | SEQ ID NO: |
|---|---|---|---|---|---|
| SB-266 | p314 | uucgtcgtgacgtt-C3 | PEG23 | 1.70 | 314 |
| SB-277 | p313 | tucgtcgtgacgtt-C3 | PP8 | 1.40 | 313 |
| — | p313 | tucgtcgtgacgtt-C3 | — | 40.8 | 313 |

*(PEGx) indicates the complementary reactive group used in the conjugates. PEG23 is a complementary reactive group formed from $NH_2$-PEG23-$N_3$.

Figure 33B:
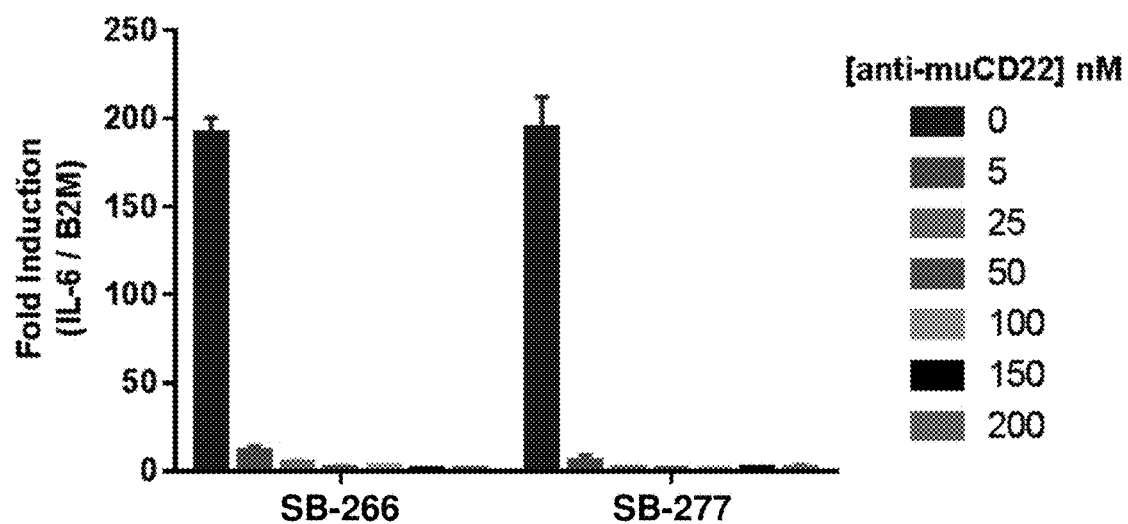
FIG. 33B is a graph showing the induction of IL6 in A20 mouse B-cell lymphoma cells by conjugates containing an anti-mouse CD22 antibody and an immunostimulating polynucleotide in the presence of varying concentration of the free anti-mouse CD22 antibody.

FIG. 33B shows that the activity of the immunostimulating conjugates is antagonized by the presence of the excess (0-10 fold) free antibody targeting the same receptor as that which is targeted by the antibody included in the immunostimulating conjugate. The IL6 secretion was used to assess the immunostimulating efficiency of the conjugates and unconjugated polynucleotides. These data indicate that (1) the targeting moiety improves the immunostimulating activity of the polynucleotides of the invention, and (2) the intracellular delivery of the immunostimulating polynucleotides in the conjugates of the invention is likely cell surface receptor-mediated. Accordingly, the enhancement in the immunostimulating activity of the conjugates relative to the unconjugated polynucleotides is likely due to the improvement in the intracellular delivery of the immunostimulating polynucleotides.

Figure 34A:
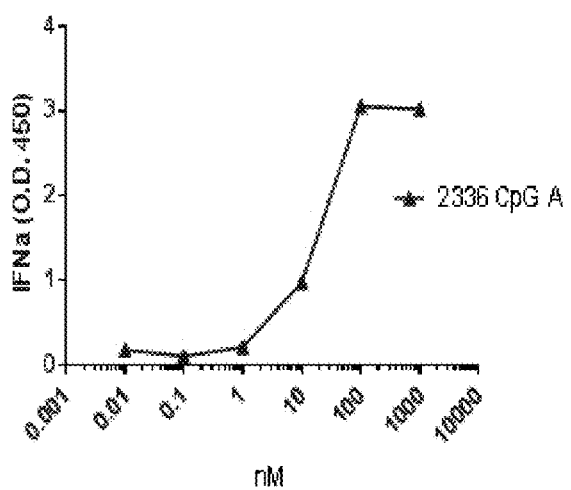
FIG. 34A is a graph showing the induction of interferon-α in human PBMC by CpG-2336, a class A CpG ODN.
Figure 34B:
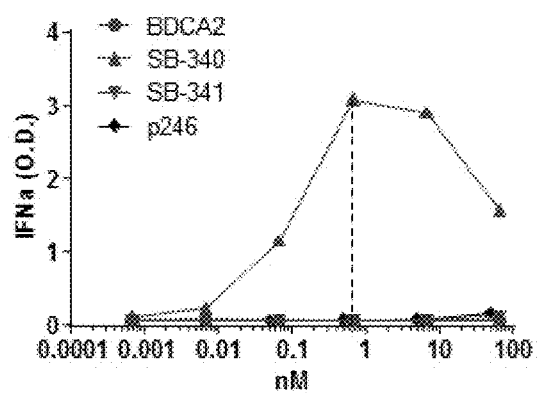
FIG. 34B is a graph showing the induction of interferon-α in human PBMC using conjugate SB-340. Anti-BDCA2 antibody, SB-341, and p246 were used as controls in this experiment. The Y-axis provides optical density in arbitrary units at the wavelength of 450 nm.
Figure 34C:
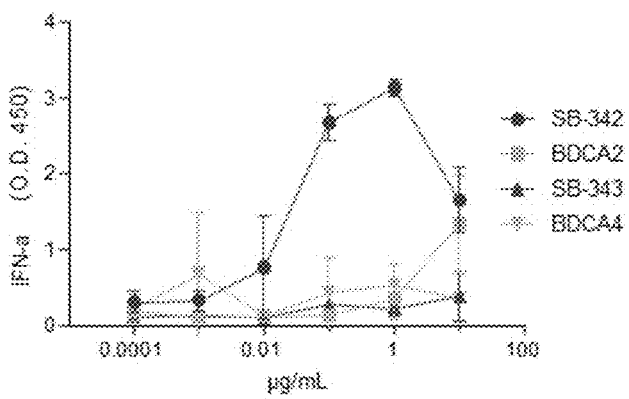
FIG. 34C is a graph showing the induction of interferon-α in purified plasmacytoid cells using conjugate SB-342. Anti-BDCA2 antibody, anti-BDCA4 antibody, and SB-343 were used as controls in this experiment.

FIG. 34A shows the induction of interferon-α in human PBMC by CpG-2336, a class A CpG ODN. FIG. 34B shows the induction of interferon-α in human PBMC using conjugate SB-340. Anti-BDCA2 antibody, SB-341, and p246 were used as controls in this experiment. FIG. 34C shows in RPMI medium containing 10% FBS. On the day of experiment, the cells were harvested, re-suspended in HBSS and inoculated subcutaneously (5×10[6] cells per mouse) into 6-8 week old female Balb/c mice (Charles River). After 10 days, the mice were randomized, each group having 8-10 mice were given three doses of the test article (an immunostimulating polynucleotide or a conjugate), every other day (Q2D), by either intratumoral (I.T., 25 μL) or intravenous (I.V., 100 μL) injection. Tumor volume was used to assess the treatment efficacy. Tumor volume was calculated twice per week using the formula: $V=(L \times W^2)/2$, where V is tumor volume, L is tumor length, and W is tumor width.

Figure 37A:
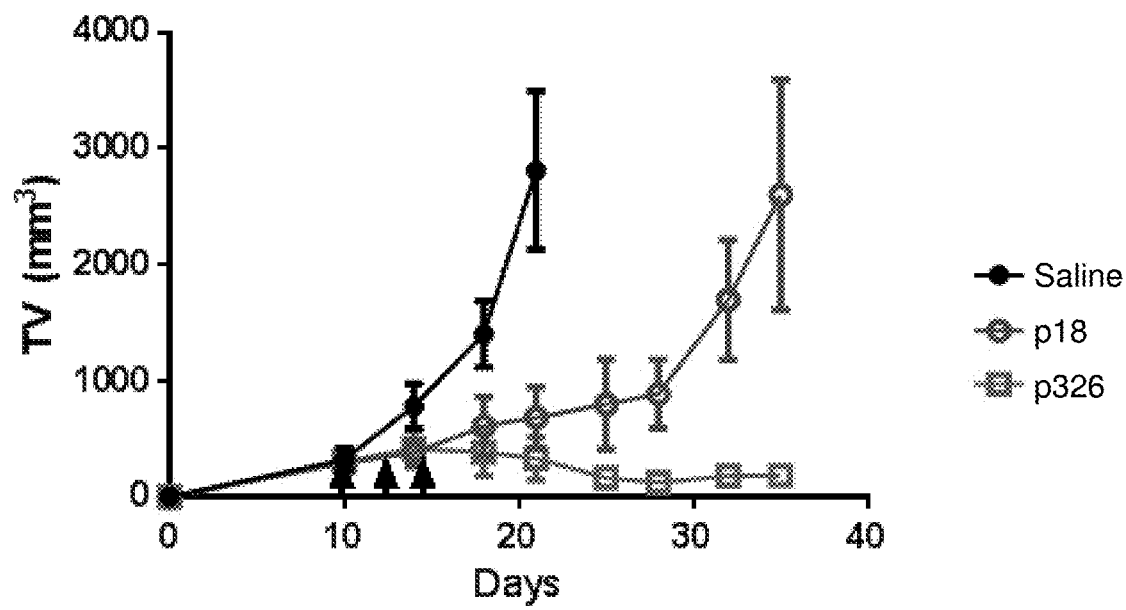
FIG. 37A is a graph showing tumor volume growth progression following inoculation of a mouse with A20 mouse B-cell lymphoma cells and the subsequent, triple, intratumoral administration of a vehicle (saline) or an immunostimulating polynucleotide of the invention (p326) and a control (p18). The administration times are indicated with the arrows on the X-axis.
Figure 37B:
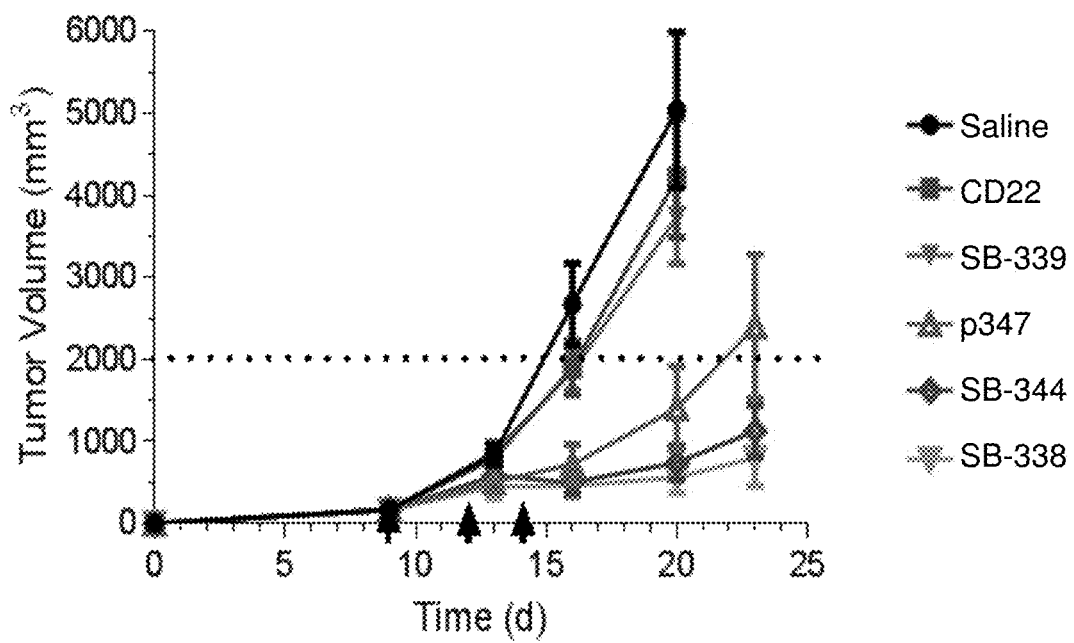
FIG. 37B is a graph showing tumor volume growth progression following inoculation of a mouse with A20 mouse B-cell lymphoma cells and the subsequent, triple, intravenous administration of a vehicle (saline), an immunostimulating polynucleotide (p3), an anti-CD22 antibody (CD22), or conjugates SB-338, SB-339, or SB-344. The administration times are indicated with the arrows on the X-axis.

FIGS. 37A and 37B show that the treatment of a tumor with an immunostimulating polynucleotide of the invention can stop and even reverse the tumor growth. In these experiments, the immunostimulating polynucleotides of the invention were administered intratumorally or intravenously at times identified with arrows along the X-axes of the charts. These data also show that the conjugates are superior in their anti-tumor activity relative to the free individual components of the conjugates. The details of the in vivo profiling tests shown in FIG. 37B are provided in table 28.

TABLE 28

| Conjugate | Antibody | Polynucleotide | Sequence (5' to 3') | (PEGx)* | mg/kg | CpG nmol | Description | SEQ ID NO: |
|---|---|---|---|---|---|---|---|---|
| — | — | — | — | — | — | — | Saline | |
| — | muCD22 | — | — | — | 9 | — | Ab alone | |
| SB-339 | muCD22 | p346 | tgctgctgagctt-C3 | 23 | 10 | 0.9 | control | 346 |
| SB-344 | muCD22 | p313 | tucgtcgtgacgtt-C3 | PP16 | 10 | 0.9 | — | 313 |
| SB-345 | muCD22 | p313 | tucgtcgtgacgtt-C3 | PP12 | 10 | 0.9 | — | 313 |
| — | — | p347 | tugctgctgagctt-C3 | | 14.5 (μg/kg) | 0.9 | CpG alone | 347 |

*(PEGx) indicates the complementary reactive group used in the conjugates.

Figure 38A:
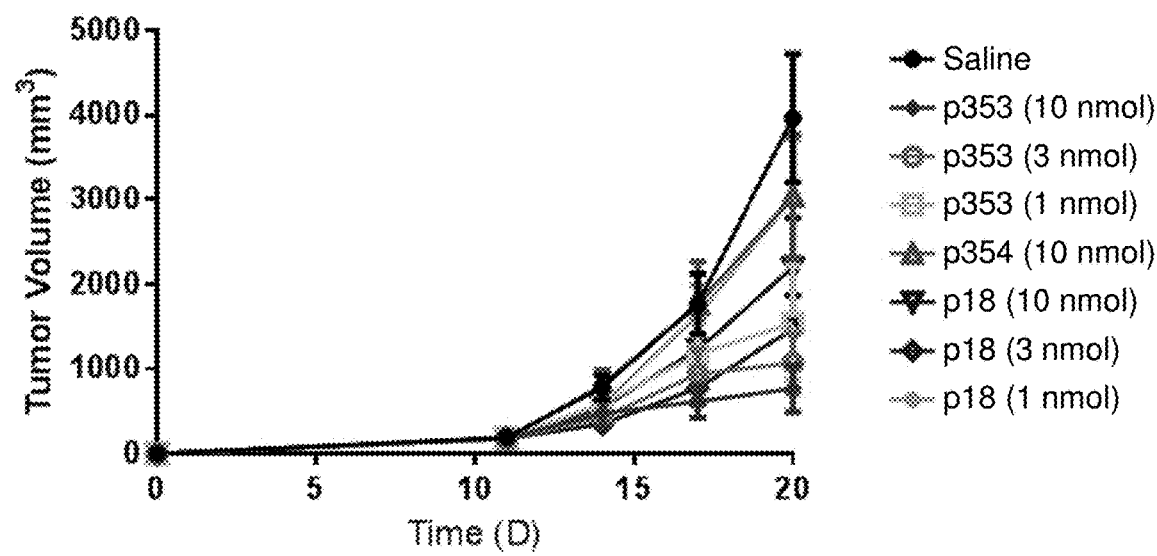
FIG. 38A is a graph showing tumor volume growth progression following inoculation of a mouse with A20 mouse B-cell lymphoma cells and the subsequent, triple, intratumoral administration of a vehicle (saline) or an immunostimulating polynucleotide.

FIG. 38A shows that the treatment of a tumor with an immunostimulating polynucleotide of the invention can reduce tumor growth, as compared to unmodified immunostimulating polynucleotides or immunostimulating polynucleotides lacking a 5'-terminal ISS. In these experiments, the immunostimulating polynucleotides of the invention were administered intratumorally.

Figure 38B:
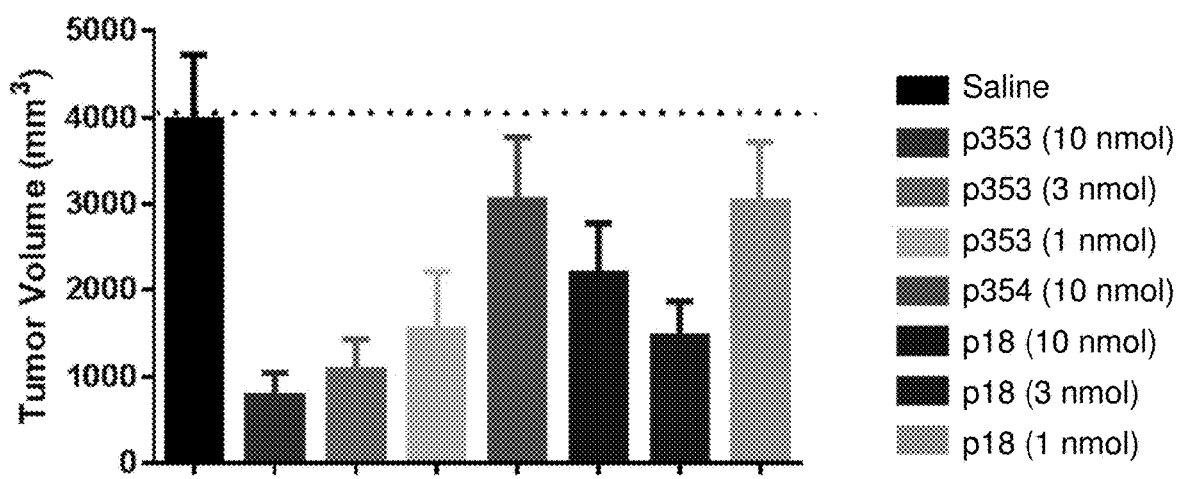
FIG. 38B is a graph showing tumor volume values on day 20 after the inoculation of a mouse with A20 mouse B-cell lymphoma cells and the subsequent, triple, intratumoral administration of a vehicle (saline) or an immunostimulating polynucleotide.

FIG. 38B shows the tumor volumes on day 20 after subcutaneous inoculation of the tested mice with A20 mouse B-cell lymphoma cells and subsequent intratumoral administration of three doses of saline, an immunostimulating polynucleotide of the invention, or an unmodified immunostimulating polynucleotide, as described above. In these experiments, the immunostimulating polynucleotides of the invention were administered intratumorally.

Figure 39A:
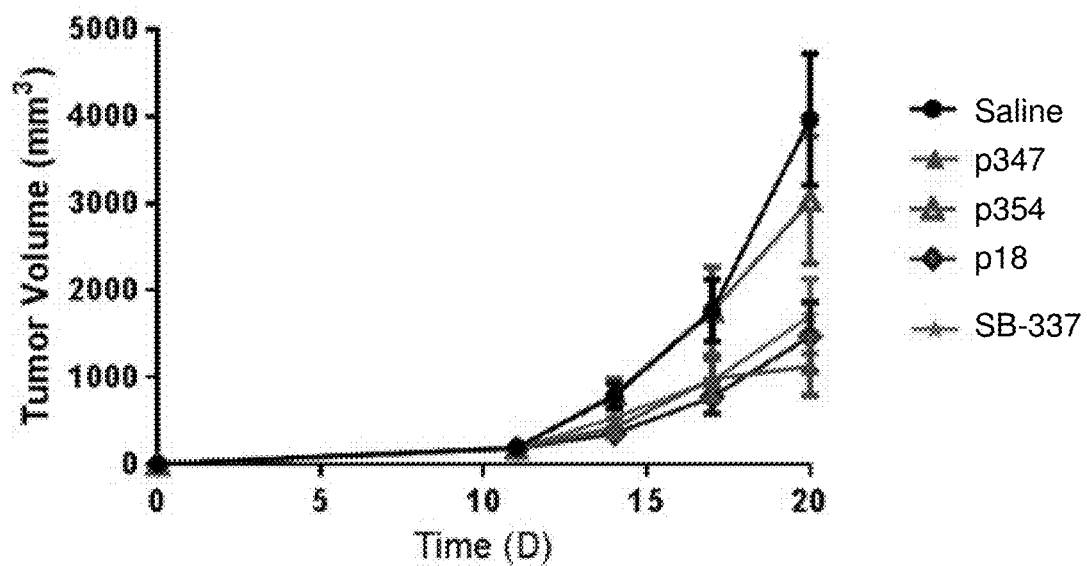
FIG. 39A is a graph showing tumor volume growth progression following the inoculation of a mouse with A20 mouse B-cell lymphoma cells and (i) the subsequent, single, intravenous administration of a conjugate of the invention (SB-337), or (ii) the subsequent, triple, intratumoral administration of a vehicle (saline) or an immunostimulating polynucleotide.

FIG. 39A shows that the intravenous administration of a conjugate of the invention can be as effective in treating a tumor as direct intratumoral administration of an unconjugated immunostimulating polynucleotide of the invention. Saline and unconjugated immunostimulating polynucleotides were administered intratumorally, and SB-337 was administered intravenously.

Figure 39B:
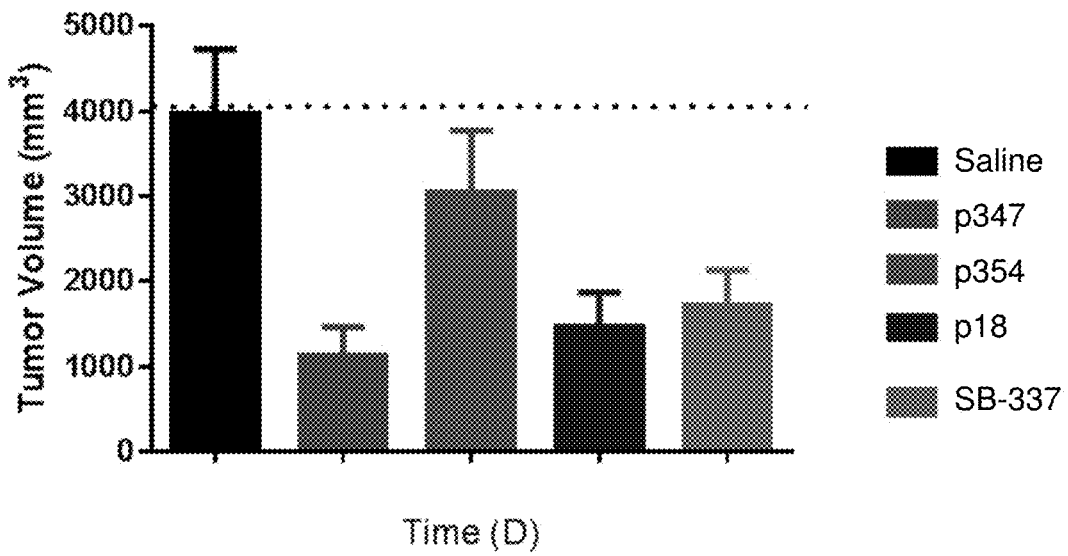
FIG. 39B is a graph showing tumor volume values on day 20 after the inoculation of a mouse with A20 mouse B-cell lymphoma cells and (i) the subsequent, single, intravenous administration of a conjugate of the invention (SB-337), or (ii) the subsequent, triple, intratumoral administration of a vehicle (saline) or an immunostimulating polynucleotide.

FIG. 39B shows the tumor volumes on day 20 after subcutaneous inoculation of the tested mice with A20 mouse B-cell lymphoma cells and subsequent administration of three doses of saline, an immunostimulating polynucleotide, or a conjugate, as described above. Saline and immunostimulating polynucleotides were administered intratumorally in three doses, and SB-337 was administered intravenously once.

In Vivo Profiling in a Liquid Tumor Model

A20 mouse B-cell lymphoma cells were purchased from the American Type Culture Collection (ATCC) and cultured in RPMI medium containing 10% FBS. On the day of experiment, the cells were harvested, re-suspended in HBSS and inoculated intravenously ($5 \times 10^6$ cells per mouse) into 6-8 week old female Balb/c mice (Charles River). Starting on the following day, 8-10 mice/group were given three doses of the test article (an immunostimulating polynucleotide or a conjugate), every other day (Q2D), by intravenous (I.V., 100 μL) injection. On day 47, the surviving mice were re-challenged with ($5 \times 10^6$ A20 cells per mouse). A new control group was added matching in age and size and was inoculated with A20 mouse tumor cells. Non-inoculated, non-treated littermates were included as controls. Survival rate (%) was monitored to assess the treatment efficacy.

Figure 40:
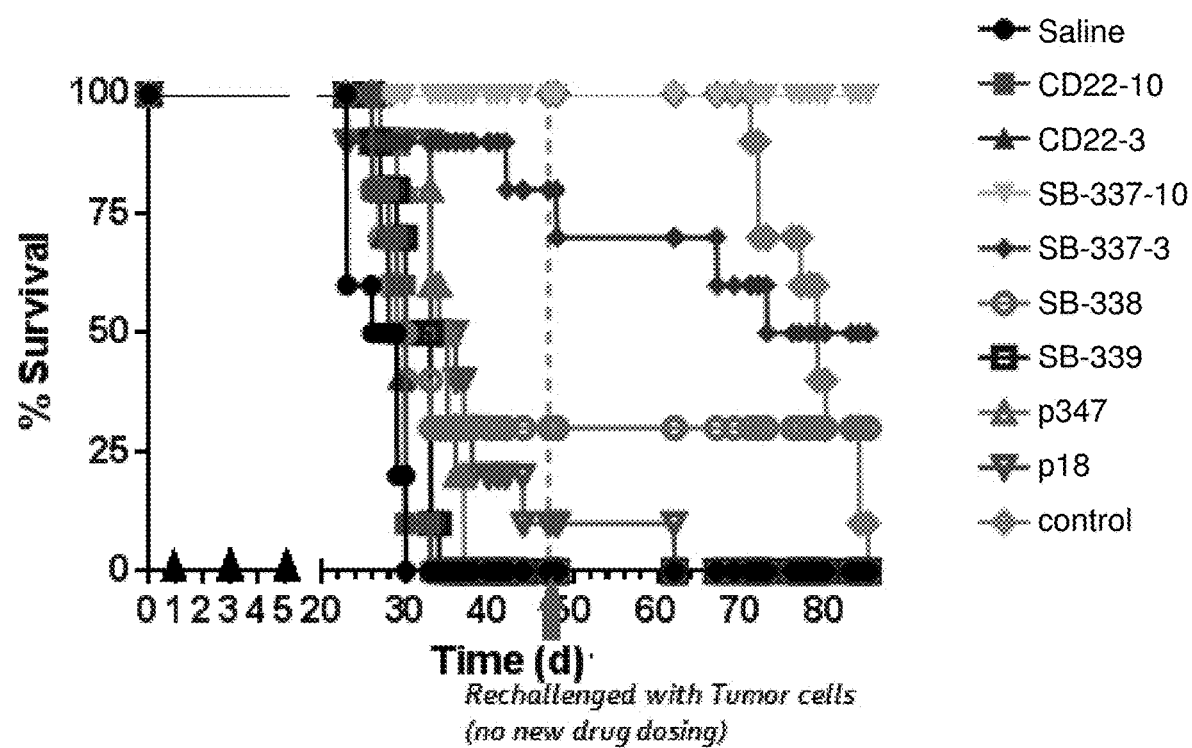
FIG. 40 is a graph showing the survival rates (%) for Balb/c mice inoculated with A20 mouse lymphoma cells and subsequently treated with saline, free antibodies, antibody-immunostimulating polynucleotide conjugates, or free immunostimulating polynucleotides. The control group are non-inoculated, untreated Balb/c mice. The lines identified as CD22-10 and CD22-3 provide mouse survival rates (%) for the treatment regimens: 10 mg/kg of the free anti-mouse CD22 antibody and 3 mg/kg of the free anti-mouse CD22 antibody, respectively. The lines identified as SB-337-10 and SB-337-3 provide mouse survival rates (%) for the treatment regimens: 10 mg/kg of SB-337 and 3 mg/kg of SB-337, respectively.

FIG. 40 shows the survival rates for mice populations undergoing treatment with saline, conjugates of the invention, or immunostimulating polynucleotides. The details of the in vivo profiling tests shown in FIG. 40 are provided in table 29.

TABLE 29

| Description | Antibody | Polynucleotide | Sequence (5' to 3') | (PEGx)* | mg/kg | # of doses | CpG nmol/dose | SEQ ID NO: |
|---|---|---|---|---|---|---|---|---|
| Saline | — | — | — | — | — | 3 | — | |
| - | muCD22 | — | — | — | 10 | 3 | — | |
| - | muCD22 | — | — | — | 3 | 3 | — | |
| SB-337 | muCD22 | p313 | tu cgtcgtgacgtt-C3 | 23 | 10 | 3 | 3 | 313 |
| SB-337 | muCD22 | p313 | tu cgtcgtgacgtt-C3 | 23 | 3 | 3 | 1 | 313 |
| SB-338 | muCD22 | p313 | tu cgtcgtgacgtt-C3 | PP12 | 10 | 1 | 3 | 313 |
| SB-339 | muCD22 | p346 | tu gctgctgagctt-C3 | 23 | 10 | 3 | 3 | 346 |
| — | — | p347 | tu gctgctgagctt-C3 | — | 3** | 3 | 3 | 347 |
| — | — | p18 | tccatgacgttcctgacgtt | — | 3** | 3 | 3 | 18 |

**μg/dose.

Example 4. Serum Stability of Immunostimulating Polynucleotides

Figure 41A:
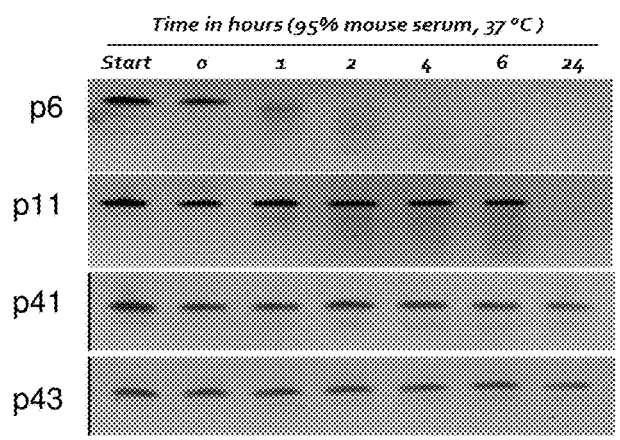
FIG. 41A is an image of a denaturing gel of samples of polynucleotides incubated in mouse serum at 37° C. for up to 24 hours.
Figure 41B:
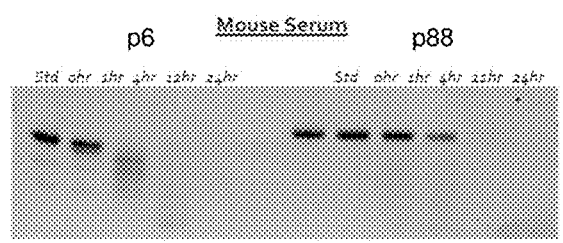
FIG. 41B is an image of a denaturing gel of samples of polynucleotides incubated in mouse serum at 37° C. for up to 24 hours.
Figure 41C:
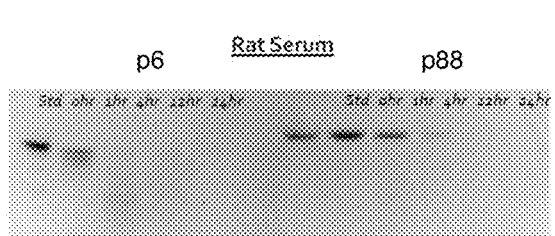
FIG. 41C is an image of a denaturing gel of samples of polynucleotides incubated in rat serum at 37° C. for up to 24 hours.
Figure 41D:
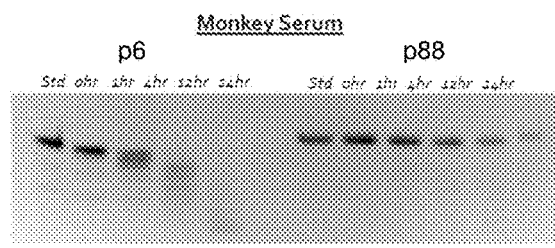
FIG. 41D is an image of a denaturing gel of samples of polynucleotides incubated in monkey serum at 37° C. for up to 24 hours.
Figure 41E:
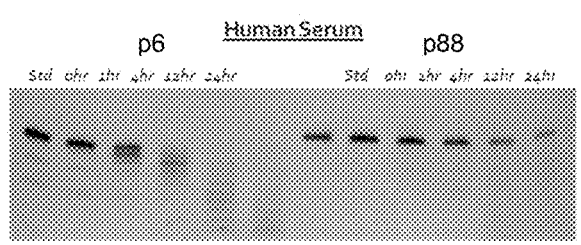
FIG. 41E is an image of a denaturing gel of samples of polynucleotides incubated in human serum at 37° C. for up to 24 hours.

Protocol: 1 µL of 2 mM stock solution (CpG polynucleotide having a phosphotriester) was placed in 19 µL of fresh mouse serum. 20 µL samples were placed in PCR plates and heated on thermocycler at 37° C. 2 µL sample removed at indicated time points, added to 18 µL of formamide loading buffer and frozen prior to gel analysis. 2 µL were loaded per well onto a 15% TBE-urea gel, 200 volts for 30 min followed by ethidium bromide staining (see FIGS. 41A and 41B). The stability of CpG polynucleotides containing phosphotriesters was also assessed in rat serum, monkey serum, and human serum (see FIGS. 41C, 41D, and 41E).

Serum Stability Analyses of Immunostimulating Polynucleotides by AEX HPLC:

An immunostimulating polynucleotide (40 µM in water) was diluted to a final concentration of 8 µM in 80% mouse serum. Aliquots were taken at specified time points (typically at 4 h, 24 h, and 48h) and quenched with 1:1 10 mM EDTA. Samples were analyzed by anion exchange HPLC on a DNAPac PA200, 4×250 mm column at 60° C. using mobile phase A: 20 mM sodium phosphate pH 8, 15% v/v isopropanol and mobile phase B: 20 mM sodium phosphate pH 8, 1.5 M sodium bromide, 15% v/v isopropanol; gradient of 20-98% mobile phase B in 10 minutes; 0.6 mL/min flow rate with detection at 260 nm. In the HPLC trace, the main peak was integrated for each time point, and % peak area relative to the non-aged sample was calculated. Same method was used to analyze the stability of the immunostimulating polynucleotides in rat serum, monkey serum, and human serum.

Figure 42:
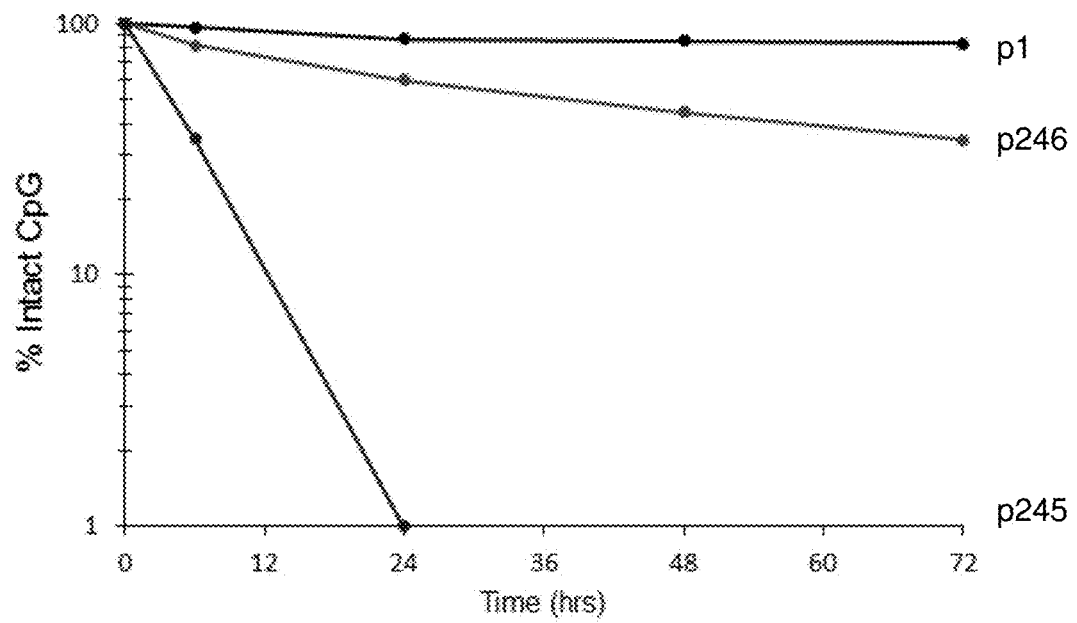
FIG. 42 is a graph showing the effect of phosphate-based and phosphorothioate-based internucleoside phosphodiesters at the 5'-terminus of an immunostimulating polynucleotide on the polynucleotide stability in 80% mouse serum.

FIG. 42 shows that an immunostimulating polynucleotide containing an internucleoside phosphorothioate bonded to the 5'-terminal nucleoside exhibits higher serum stability than an immunostimulating polynucleotide containing an internucleoside phosphate bonded to the 5'-terminal nucleoside. As shown in Table 30, the immunostimulating polynucleotides having an internucleoside phosphate at the 5'-terminus can exhibit higher immunostimulating activity relative to the immunostimulating polynucleotides having an internucleoside phosphorothioate at the 5'-terminus, as measured by NFκB activation.

TABLE 30

| Conjugate | Polynucleotide | Sequence (5' to 3') | EC50 (nM) | SEQ ID NO: |
|---|---|---|---|---|
| — | p1 | tcgtcgttttgtcgttttgtcgtt | 200 | 1 |
| SB-189 | p246 | u cgtcgtgtcgtt-C3 | 1.14 | 246 |
| SB-188 | p245 | U cgtcgtgtcgtt-C3 | 0.04 | 245 |

Figure 43:
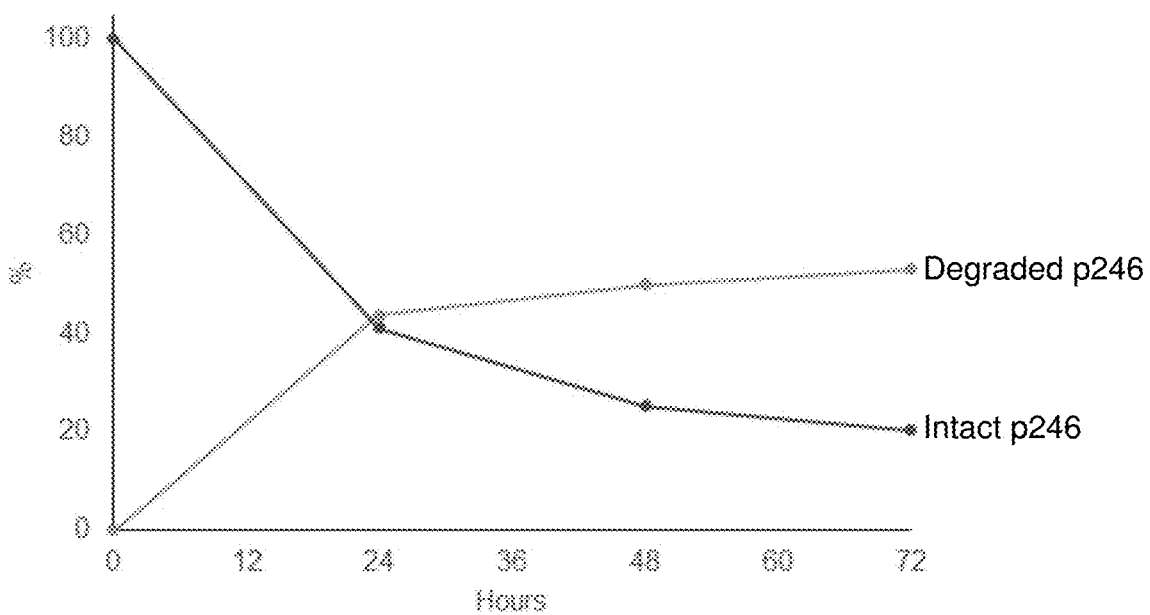
FIG. 43 is a graph showing the proportions of degraded p246 and intact p246 in an aging experiment in 80% mouse serum.

FIG. 43 shows that 5-iodouridine-containing immunostimulating polynucleotides can undergo degradation in serum over time through the loss of iodine, as determined through the observation of the increase in the HPLC peak area corresponding to the material with m/z that is less than the mass of the intact p246 by 127 Da.

Figure 44:
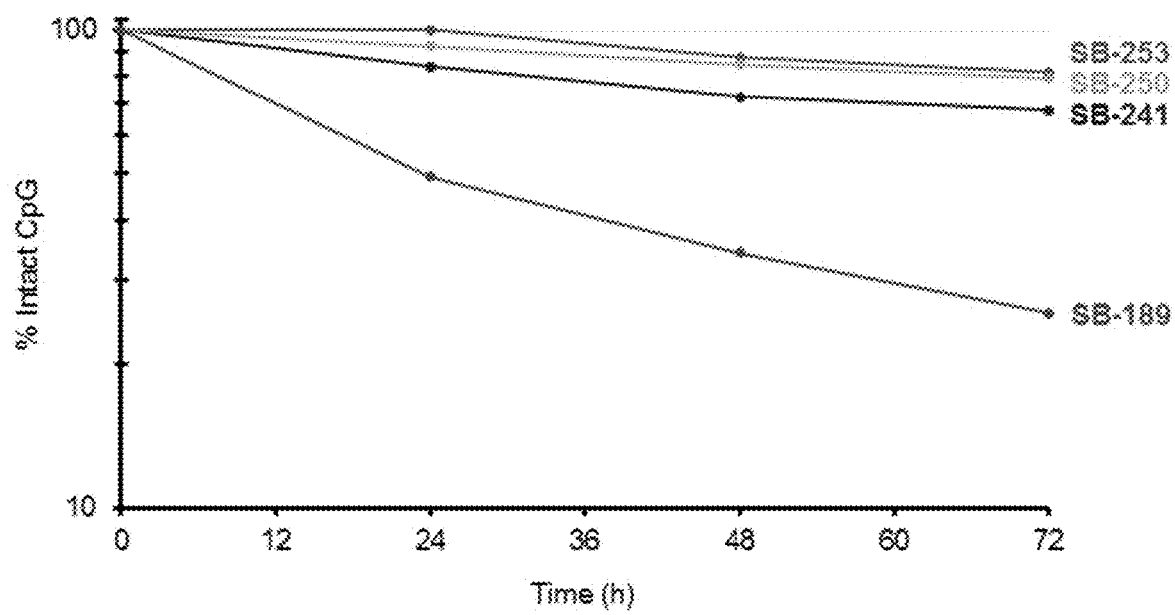
FIG. 44 is a graph showing the effect of 5'-terminal nucleotide structures on the stability of the polynucleotides in 80% mouse serum.

FIG. 44 shows that 5-bromouridine can provide immunostimulating polynucleotides with the superior combination of serum stability and immunostimulating activity. The data shown in FIG. 44 is summarized in Table 31.

TABLE 31

| Y-(PO/PS)-X- cgtcgtgtcgtt -C3 | | | | | |
|---|---|---|---|---|---|
| Conjugate | Polynucleotide | X | Y | (PO/PS) | EC50 (nM) |
| SB-189 | p246 | Iodo-dU | — | PS | 0.8 |
| SB-217 | p270 | dT | — | PS | >30** |
| SB-260 | p311 | dU | — | PS | 37** |
| SB-253 | p308 | Bromo-dU | — | PS | 2.3 |
| SB-262 | p306 | Iodo-dU | C3 | PO | 3.1** |
| SB-270 | p330 | CF$_3$-dT | — | PO | 2.0** |
| SB-271 | p331 | CF$_3$-dT | — | PS | inactive |
| SB-250 | p298 | Iodo-dU | dT | PS | 7.1** |
| SB-251 | p299 | Iodo-dU | Iodo-dU | PS | 7.7** |
| SB-252 | p300 | Iodo-dU | dU | PS | 5.1** |
| SB-241 | p307 | Fluoro-dU | — | PS | inactive |

**indicates suboptimal activation.

Iodo-dU is 5-iodo-2'-deoxyuridine, dT is thymidine, dU is 2'-deoxyuridine, CF$_3$-dT is 5-trifluoromethyl-thymidine, Fluoro-dU is 5-fluoro-2'-deoxyuridine, and C3 is a C3 spacer —(CH$_2$)$_3$—OH.

Figure 45:
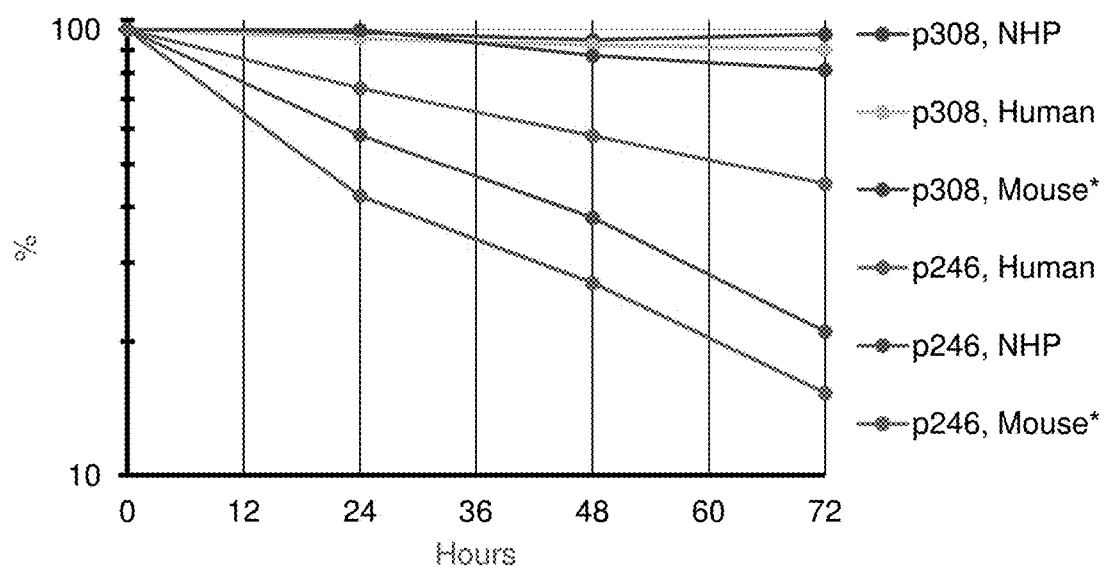
FIG. 45 is a graph showing the effect of 5'-terminal nucleotide structures on the stability of the polynucleotides in 80% mouse serum, 80% non-human primate (NHP) serum, and 80% human serum. The mouse serum data are marked with an asterisk, as these data were obtained in a separate study.

FIG. 45 shows the stabilities of polynucleotides in sera (non-human primate (NHP), human, or mouse), as measured by the percentage of the remaining intact polynucleotide at predetermined time intervals. The data in FIG. 43 is summarized in Table 32.

TABLE 32

| | p246 | | | p308 | | |
|---|---|---|---|---|---|---|
| Hour | NHP | Human | Mouse | NHP | Human | Mouse |
| 0 | 100 | 100 | 100 | 100 | 100 | 100 |
| 24 | 58.0 | 73.9 | 42.3 | 98.5 | 95.4 | 99.9 |
| 38 | 37.8 | 57.9 | 27.0 | 94.9 | 92.3 | 87.5 |
| 72 | 21.0 | 45.1 | 15.3 | 97.7 | 90.4 | 81.4 |

The values recited in this table are percentages of the intact polynucleotides measured at predetermined time intervals after the start of the incubation.

Representative Examples of Human Immunostimulating Conjugates

TABLE 33

| SB # | Ab | PP# | Stretcher | Tether | CpG |
|---|---|---|---|---|---|
| SB-205 | human CD38 | PP6 | mono H | 5-N$_3$-valeramide | p239 |
| SB-206 | human CD38 | PP6 | mono H | 5-N$_3$-valeramide | p242 |
| SB-351 | human CD38 | PP6 | mono H | 5-N$_3$-valeramide | p243 |
| SB-352 | human CD38 | PP6 | mono H | 5-N$_3$-valeramide | p245 |

TABLE 33-continued

| SB # | Ab | PP# | | Stretcher | Tether | CpG |
|---|---|---|---|---|---|---|
| SB-218 | human CD38 | PP6 | mono | H | 5-$N_3$-valeramide | p246 |
| SB-278 | human CD38 | PP10 | mono | CO-PEG08-$NH_2$ | 5-$N_3$-valeramide | p246 |
| SB-279 | human CD38 | PP14 | bis | CO-PEG08-$NH_2$ | 5-$N_3$-valeramide | p246 |
| SB-280 | human CD38 | PP18 | bis | CO-PEG08-$NH_2$ | 5-$N_3$-valeramide | p246 |
| SB-281 | human CD38 | PP24 | tris | CO-PEG08-$NH_2$ | 5-$N_3$-valeramide | p246 |
| SB-353 | human CD38 | PP10 | mono | CO-PEG08-$NH_2$ | 5-$N_3$-valeramide | p308 |
| SB-354 | human CD38 | PP14 | bis | CO-PEG08-$NH_2$ | 5-$N_3$-valeramide | p308 |
| SB-355 | human CD38 | PP18 | bis | CO-PEG08-$NH_2$ | 5-$N_3$-valeramide | p308 |
| SB-356 | human CD38 | PP24 | tris | CO-PEG08-$NH_2$ | 5-$N_3$-valeramide | p308 |

Representative Examples of Murine Immunostimulating Conjugates

TABLE 34

| SB # | Ab | PP# | | Stretcher | Tether | CpG |
|---|---|---|---|---|---|---|
| SB-224 | mouse CD22Q | PP6 | mono | H | 5-$N_3$-valeramide | p275 |
| SB-225 | mouse CD22Q | PP6 | mono | H | 5-$N_3$-valeramide | p276 |
| SB-226 | mouse CD22Q | PP6 | mono | H | 5-$N_3$-valeramide | p292 |
| SB-227 | mouse CD22Q | PP6 | mono | H | 5-$N_3$-valeramide | p293 |
| SB-357 | mouse CD22Q | PP6 | mono | H | 5-$N_3$-valeramide | p294 |
| SB-358 | mouse CD22Q | PP6 | mono | H | 5-$N_3$-valeramide | p295 |
| SB-359 | mouse CD22Q | PP6 | mono | H | 5-$N_3$-valeramide | p296 |
| SB-360 | mouse CD22Q | PP6 | mono | H | 5-$N_3$-valeramide | p297 |
| SB-230 | mouse CD22Q | PP6 | mono | H | 5-$N_3$-valeramide | p304 |
| SB-231 | mouse CD22Q | PP6 | mono | H | 5-$N_3$-valeramide | p305 |
| SB-277 | mouse CD22Q | PP8 | mono | H | 5-$N_3$-valeramide | p313 |
| SB-338 | mouse CD22Q | PP12 | mono | CO—PEG24—NH2 | 5-$N_3$-valeramide | p313 |
| SB-344 | mouse CD22Q | PP16 | bis | CO—PEG24—NH2 | 5-$N_3$-valeramide | p313 |
| SB-361 | mouse CD22Q | PP26 | tris | CO—PEG24—NH2 | 5-$N_3$-valeramide | p313 |
| SB-362 | mouse CD22Q | PP38 | mono | CO—PEG24-Tetrazine | 5-$N_3$-valeramide | p313 |
| SB-363 | mouse CD22Q | PP27 + TCO* | mono | CO—PEG24-Tetrazine | 5-$N_3$-valeramide | p313 |
| SB-364 | mouse CD22Q | PP29 + TCO* | bis | CO—PEG24-Tetrazine | 5-$N_3$-valeramide | p313 |
| SB-365 | mouse CD22Q | PP39 + TCO* | bis | CO—PEG24-Tetrazine | 5-$N_3$-valeramide | p313 |
| SB-366 | mouse CD22Q | PP39 + TCO* | tris | CO—PEG24-Tetrazine | 5-$N_3$-valeramide | p313 |

*TCO is trans-cyclooctenyl-based group bonded to a targeting moiety. TCO has a structure illustrated in FIG. 1B.

Example 5

This Example shows that the CpG polynucleotides conjugated to antibodies (CpG-Abs) provided herein are efficacious in the treatment of various liquid and solid tumors. Specifically B-cell targeted CpG-Abs can affect the innate and adaptive immune responses in a subject with cancer. Such B-cell targeted CpG-Abs can be useful for the treatment of non-B-cell tumors (e.g., colon carcinoma), including of tumors not expressing the CpG-Ab target (e.g., CD22) and not expressing the target of the CpG-Ab immunomodulating polynucleotide (e.g., TLR9 agonist). In addition CpG-Abs targeted to non-B-cell antigen presenting cells (APCs), such as plasmacytoid dendritic cells or macrophages, are useful in the treatment of liquid tumors (e.g., lymphoma). Broad antitumor efficacy of CpG-Abs was observed following their systemic administration to a subject. The antitumor effect of CpG-Abs, including of B-cell targeted CpG-Abs was found to involve cell mediated immunity and to be dependent on a host's T-cell function such as CD8+ T-cell function. CpG-Abs including, for example, B-cell targeted CpG-Abs increased CD4+ and CD8+ T-cell infiltration of solid tumors. Moreover, CpG-Abs were found to provide adaptive and long-lasting anti-tumor immunity. Synergistic effects with checkpoint inhibitors, such as anti-PD1 antibodies and anti-PD-L1 antibodies were observed. CpG-Ab were designed to have a clean complement profile, and, e.g., not to activate complement C3.

Example 6. B-Cell Targeting CpG-Ab Conjugate is Efficacious in Treating Disseminated (Liquid) B-Cell Lymphomas A disseminated (liquid) B-cell lymphoma disease model was created by intravenous injection of immune competent BALB/c mice (8-10 mice/group) with A20 lymphoma cells (TLR9*/CD22*). Test compounds were administered intravenously on days 1, 3 and 5 post cell injection and animal survival was monitored for 40 days.

An immunostimulating polynucleotide was synthetized and conjugated to a mouse-anti-CD22 monoclonal antibody (mAb) as described in Examples 1 and 2 above. This conjugate (SB-337 as shown in Table 6-A) is referred to as CpG-mAb (CD22) in the following examples. A synthetic polynucleotide replacing the CpG dinucleotide with GpC dinucleotides was similarly made and conjugated to the anti-CD22 mAb to serve as a control conjugate (SB-339) in the following experiments.

Mice were injected with A20 lymphoma cells on Day 0 as described above. Then, on Day 1, 3 and 5 each, mice were given intravenous injections of (i) 3 mg/kg CpG-mAb (CD22); (ii) 10 mg/kg CpG-mAb (CD22); (iii) unconjugated CpG (p347 as shown in Table 2); (iv) 10 mg/kg CD22 mAb (CD22); or (v) 10 mg/kg GpC-mAb (control conjugate). Additionally, a negative control group received only saline solution on Day 1, 3 and 5. Survival rates of the groups were monitored for 40 days.

Figure 46B:
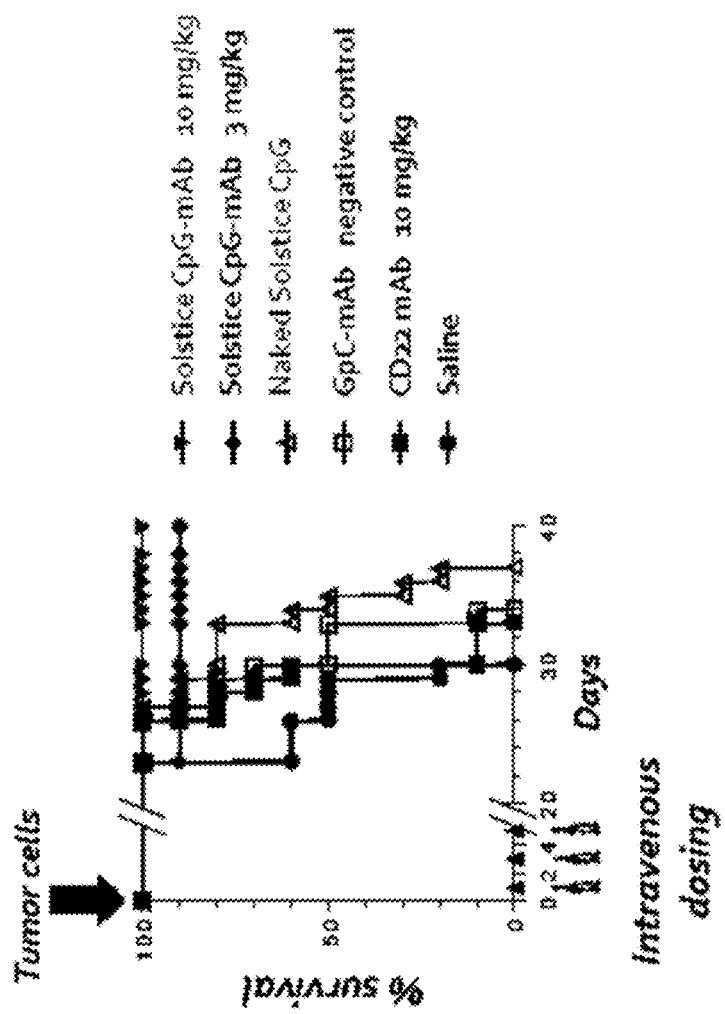
FIG. 46B shows the survival rate of mice having disseminated B-cell lymphoma that were treated on Days 1, 3 and 5 with (i) 3 mg/kg CpG (p313)-mAb (CD22) conjugate (closed diamond); (ii) 10 mg/kg CpG-mAb (CD22) (closed triangle); (iii) naked CpG ODN (open triangle); (iv) 10 mg/kg CD22 mAb (closed square); (v) 10 mg/kg GpC-mAb control conjugate (open square); or (vi) saline solution (closed circle).
Figure 46A:
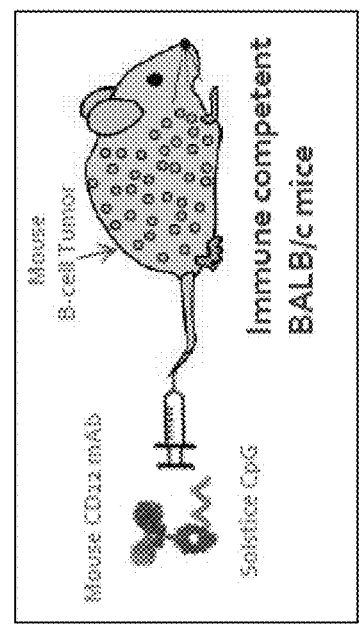
FIG. 46A illustrates the experimental scheme as described in Example 6, where mice having disseminated B-cell lymphoma were given intravenous doses of CpG-Ab (CpG ODN conjugated to a mouse anti-CD22 mAb).

As shown in FIG. 46B, mice treated with CpG-mAb had significantly longer survival as compared to the negative control group. The treatment exhibited dosage dependent effect. Particularly, the group receiving 10 mg/kg CpG-mAb (CD22) sustained 100% survival rate within the 40-day observation window, slightly better than the outcome of the group receiving 3 mg/kg CpG-mAb (CD22), which sustained 90% survival rate.

Further, treatment with naked CpG ODN or anti-CD22 mAb alone also prolonged group survival as compared the negative control group receiving solely the saline solution, although both groups died off within the 40-day observation window. Treatment with the GpC-mAb control also prolonged group survival as compared to the negative control, which effect may be attributable to the anti-CD22 mAb component of the control conjugate.

These data suggest that CpG ODN and CpG-Ab conjugates containing the CpG ODN and an antibody targeting a B cell surface antigen as provided herein are efficacious in treating disseminated B-cell lymphomas.

Next, survivors from the first tumor challenge were subjected to a second tumor challenge on Day 47. Particularly, a second dose of A20 lymphoma cells ($5 \times 10^6$ cells) was injected intravenously into survivors that were treated with 10 mg/kg or 3 mg/kg CpG-mAb (CD22) on Days 1, 3 and 5. A naive control group was given the same dose of A20 lymphoma cells on Day 47. Survival rate of the group of mice were continued to be monitored for 43 days (i.e., 90 days in total after the first tumor challenge).

Figure 46C:
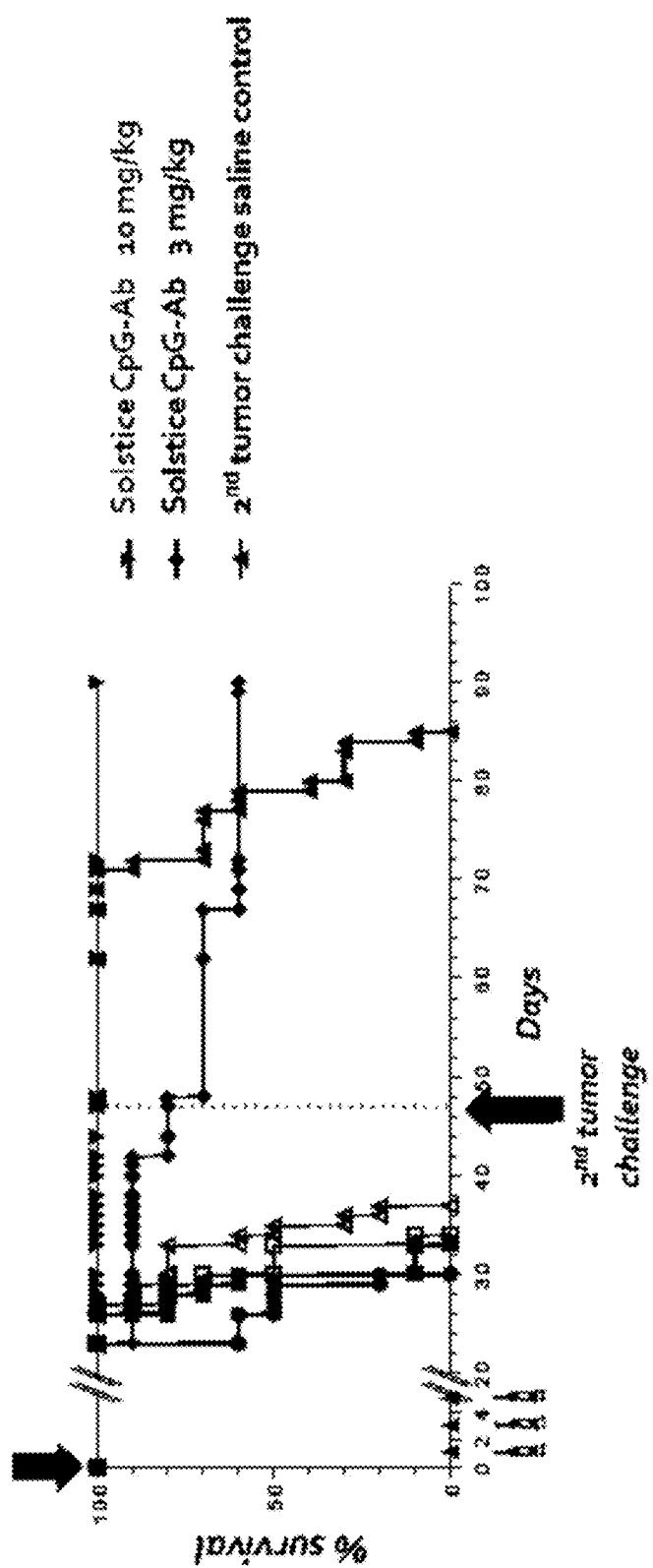
FIG. 46C shows the survival rates of mice which survived from the first tumor challenge and subsequently subjected to a second tumor challenge on Day 47. No treatment was given to the survivor after the second tumor challenge. Survivors treated with 10 mg/kg CpG-mAb (CD22) on Days 1, 3, and 5 (down triangle); survivors treated with 3 mg/kg CpG-mAb (CD22) on Days 1, 3, and 5 (diamond); second control group challenged with tumor cells on Day 47 and treated with saline solution (up triangle).

As shown in FIG. 46C, consistent with the outcome of the first tumor challenge, the naive control group also died off within 40 days after they received the A20 cells on Day 47 (i.e., died off around Day 85). Both the 10 mg/kg and 3 mg/kg treatment groups exhibited significantly better survival rates than the control group. Particularly, as shown in FIG. 46C, the 10 mg/kg treatment group maintained 100% survival rate, and the 3 mg/kg treatment group maintained 60% survival rate at the end of the 90-day observation window, even though the mice did not receive any treatment after the last dose of CpG-mAb (CD22) on Day 5.

Next, the prolonged anti-tumor effect was further monitored after the survivors from the first and second tumor challenges were subjected to a third tumor challenge. Particularly, a solid B-cell lymphoma disease model was created in the survivor mice by implanting $5 \times 10^6$ A20 lymphoma cells (TLR9+/CD22+) subcutaneously on the mouse shoulder on Day 90. A naive control group was implanted with the same dose of A20 lymphoma cells on Day 90. The sizes of the tumor engraftments were monitored for 30 days (i.e., between Day 90 and Day 120).

Figure 46D:
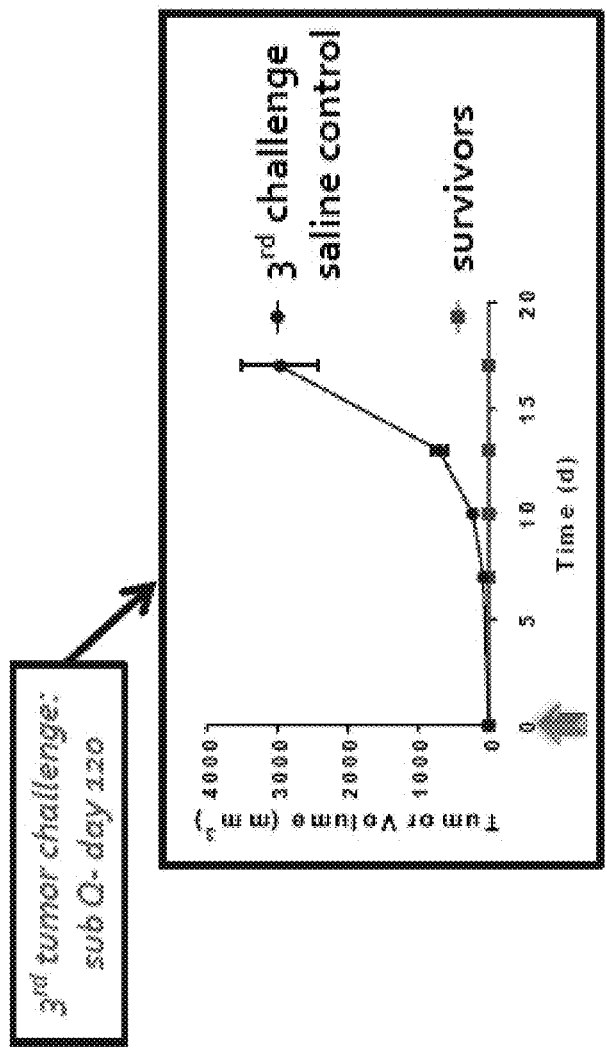
FIG. 46D shows the experiment where mice survived from the first and second tumor challenges were subsequently subjected to a third tumor challenge on Day 90. No treatment was given to the survivors after the second or third tumor challenge. A third control group was challenged with tumor cells on Day 90 and treated with saline solution. The tumor volumes of survivors (square) and the control group (circle) were monitored between Day 90 and Day 120.

Particularly, as shown in FIG. 46D, the tumor volume increased rapidly in the control group, reaching a size above 3000 mm$^3$ within 20 days. In contrast, the survivor group remained tumor free throughout the 30-day observation period, even though the survivors did not receive any additional treatment after the last dose of CpG-mAb (CD22) on Day 5. These experiments indicates that soluble tumor survivors also survived solid tumor challenge. The survivors acquired anti-tumor immunity that strongly inhibited new tumor engraftments later on.

Taken together, these data suggest that the CpG-Ab conjugates provided herein are capable of inducing sustained adaptive immunity against tumor in a subject.

Example 7. B-Cell Targeting CpG-Ab Conjugate is Efficacious in Treating Solid B Cell Lymphomas A solid B-cell lymphoma disease model was created by implanting $5 \times 10^6$ A20 lymphoma cells (TLR9*/CD22*) in immune competent BALB/c mice. The cells were injected subcutaneously on the mouse shoulder and tumor growth was monitored. The CpG-mAb (CD22) conjugate and the GpC-mAb control conjugate were made as described above.

Mice were implanted with A20 lymphoma cells on Day 0 as described above. Then, on Day 9, 12 and 14 each, mice were given intravenous injections of (i) 3 mg/kg CpG-mAb (CD22); (ii) 10 mg/kg CpG-mAb (CD22); (iii) naked CpG ODN; (iv) 10 mg/kg CD22 mAb (closed square); or (v) 10 mg/kg GpC-mAb (control conjugate). Additionally, a negative control group received only saline solution on Day 9, 12 and 14. Tumor volumes of the groups of mice were monitored for 23 days. The results are shown in FIGS. 47B to 47E.

Figure 47B:
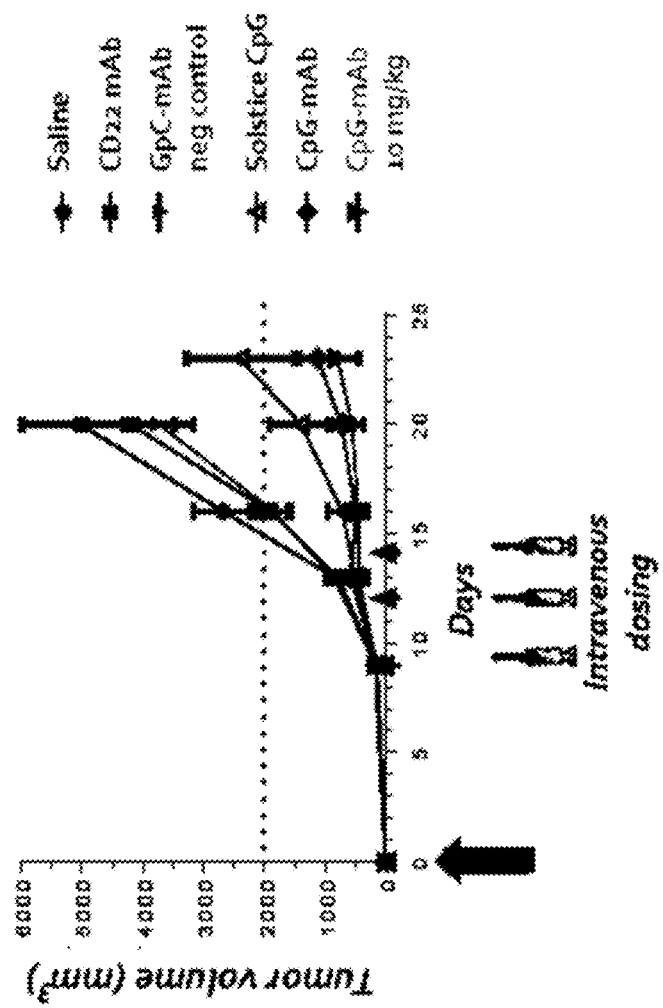
FIG. 47B shows the tumor volume of mice having solid B-cell lymphoma that were treated on Day 9, 12 and 14 with (i) 3 mg/kg CpG-mAb (CD22) (open diamond); (ii) 10 mg/kg CpG-mAb (CD22) (large closed triangle); (iii) naked CpG ODN (open triangle); (iv) 10 mg/kg CD22 mAb (closed square); (v) 10 mg/kg GpC-mAb control conjugate (small closed square), or (vi) saline solution (closed circle).
Figure 47A:
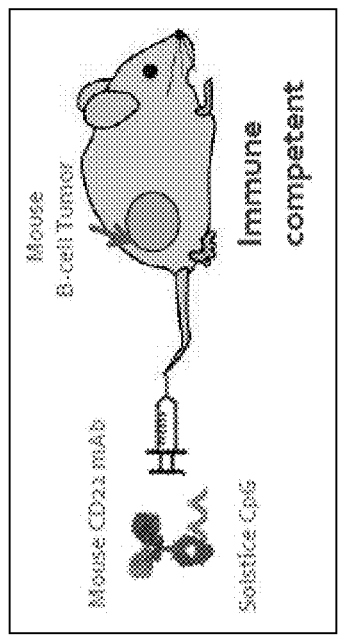
FIG. 47A illustrates the experimental scheme as described in Example 7, where mice having solid B-cell lymphoma were given intravenous doses of CpG-Ab (CpG ODN conjugated to a mouse anti-CD22 mAb).
Figure 47C:
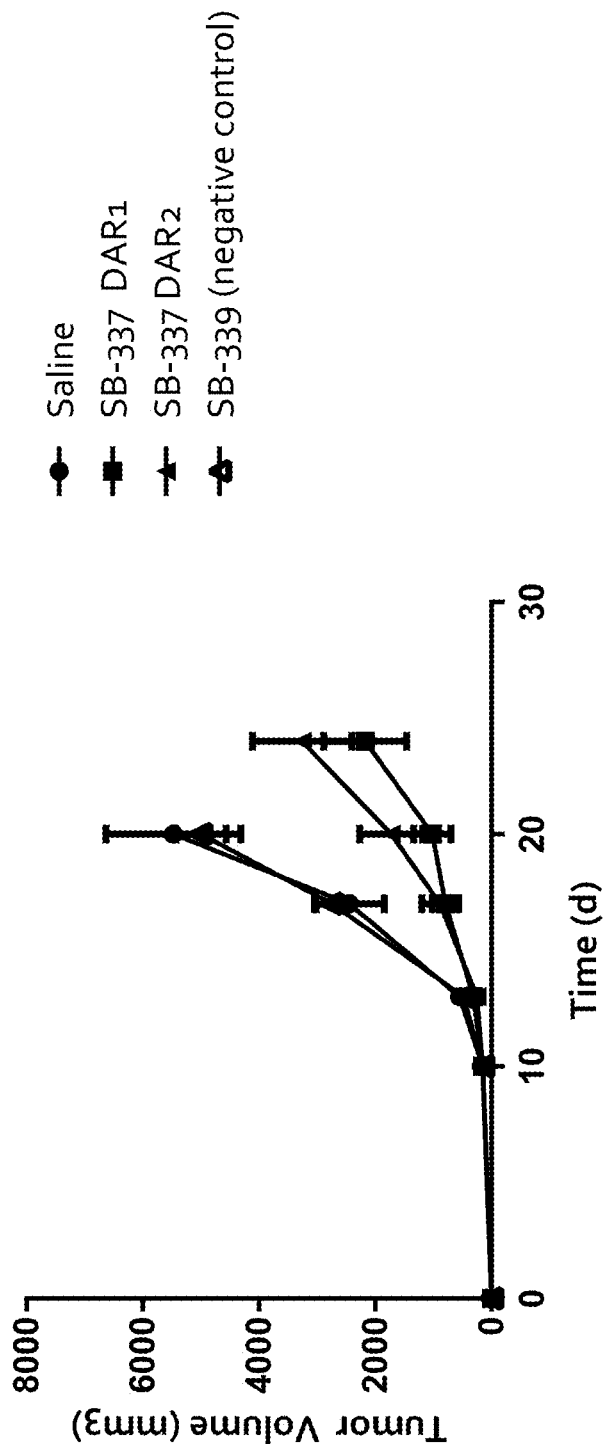
FIG. 47C shows the tumor volume of mice having solid B-cell lymphoma that were treated with SB-337 DAR1 at 10 mg/kg or SB-337 DAR2 at 10 mg/kg in comparison with controls (saline and SB-339).
Figure 47D:
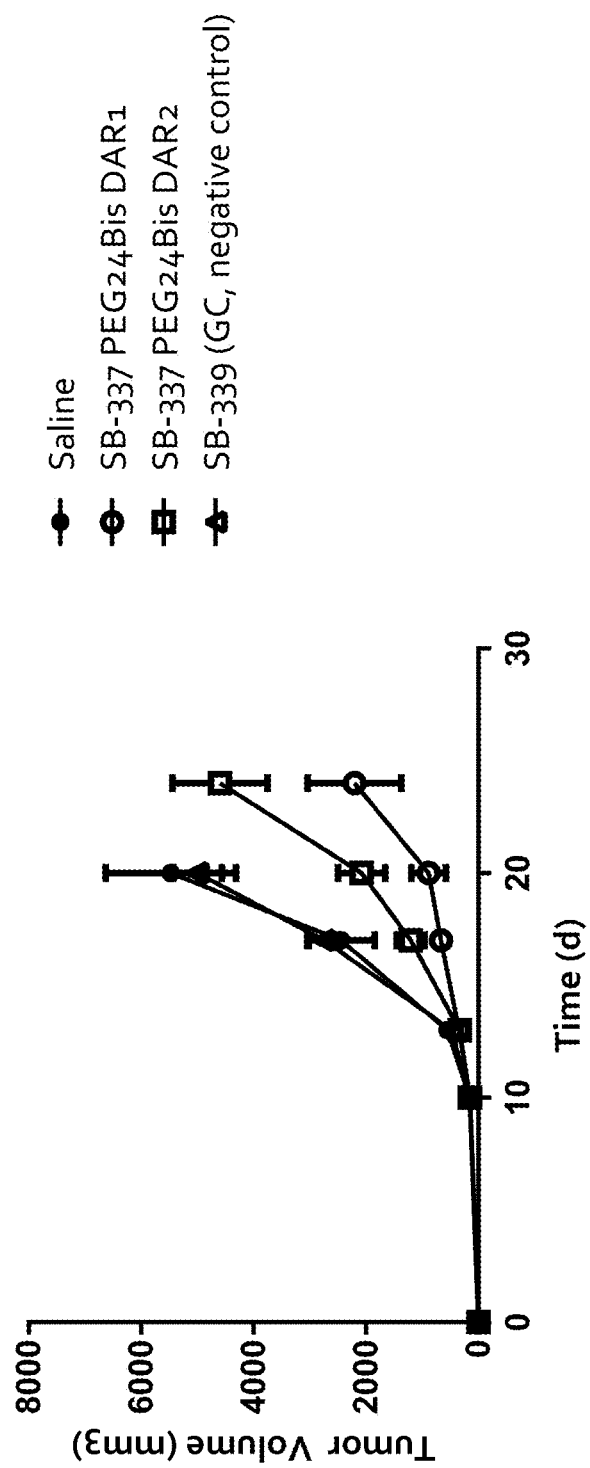
FIG. 47D shows the tumor volume of mice having solid B-cell lymphoma that were treated with SB-337 PEG24Bis DAR1 at 10 mg/kg or SB-337 PEG24Bis DAR2 at 10 mg/kg in comparison with controls (saline and SB-339).
Figure 47E:
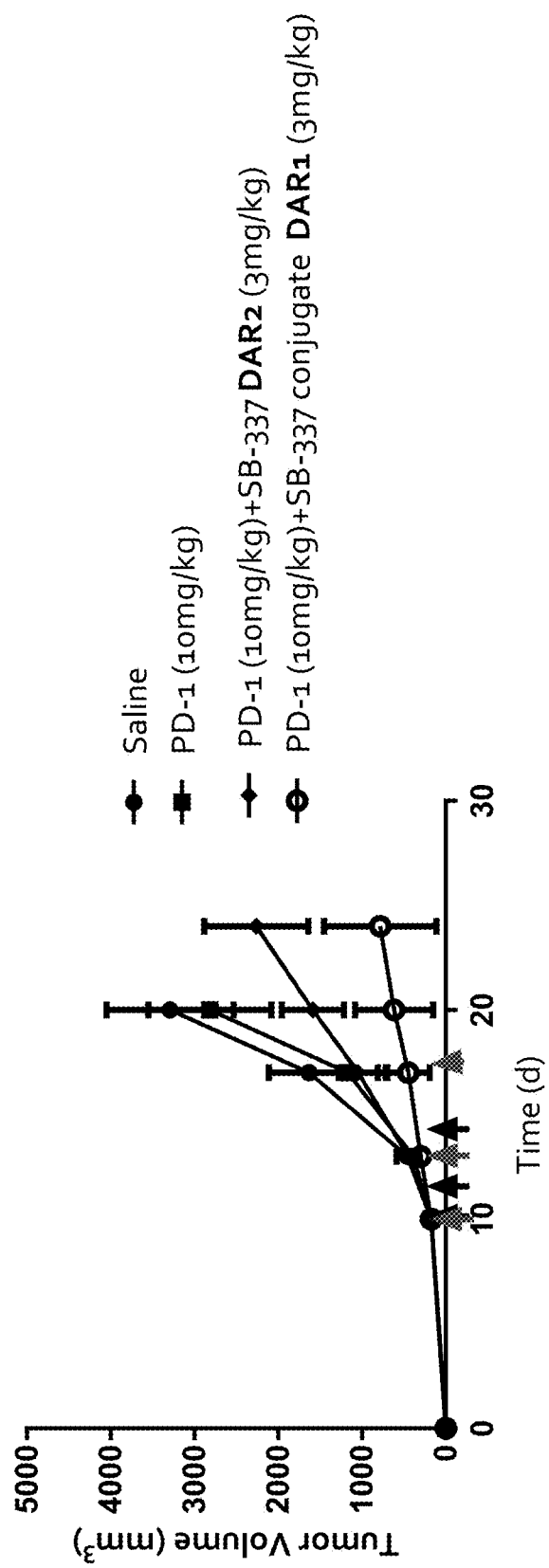
FIG. 47E shows the tumor volume of mice having solid B-cell lymphoma that were treated with PD-1 at 10 mg/kg, PD-1 at 10 mg/kg plus SB-337 DAR1 at 3 mg/kg; or PD-1 at 10 mg/kg plus SB-337 DAR2 at 3 mg/kg in comparison with a saline control.
Figure 47F:
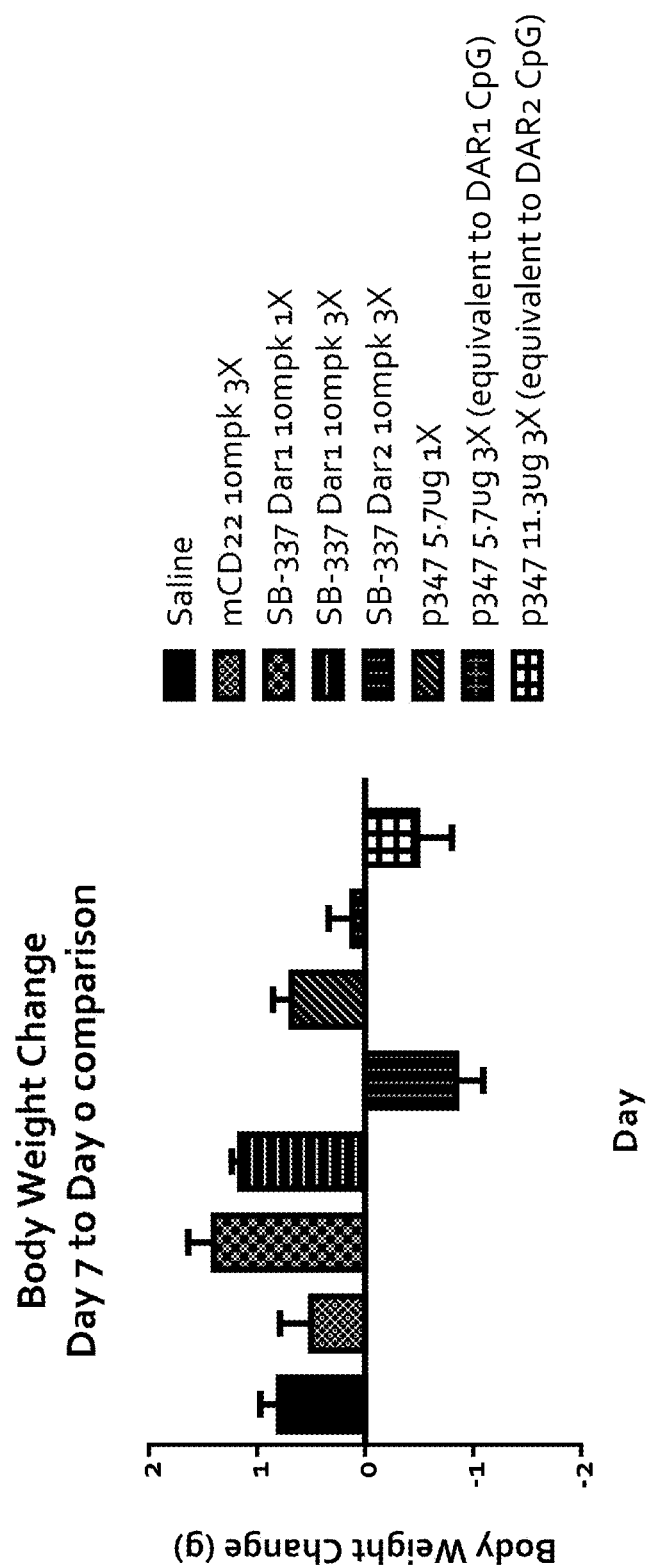
FIG. 47F shows the effect of p347, SB-337 DAR1, and SB-337 DAR2 on the weights of mice in comparison with controls (saline and mCD22).

As shown in FIG. 47B, mice treated with CpG-mAb (CD22) had significantly smaller tumor volume as compared to the negative control group. Tumor volumes of all mice treated with CpG-mAb (CD22) remained under 2000 mm$^3$ at the end of the 25-day period. The treatment exhibited dosage dependent effect. Particularly, the group receiving 10 mg/kg CpG-mAb (CD22) had smaller tumor volume at the end of the 25-day period as compared to the group receiving 3 mg/kg CpG-mAb (CD22). Further, treatment with naked CpG ODN alone also resulted in significantly smaller tumor volumes than the negative control group, with the tumor volume remaining under 2000 mm$^3$ for at least 20 days. Taken together, these data suggest that CpG ODN and CpG-Ab conjugates containing the CpG ODN and an antibody targeting a B cell surface antigen are efficacious in treating solid B-cell lymphomas. The effect of CpG-mAb (CD22) conjugates on the weights of mice were also studies and the results are shown in FIG. 47F.

Example 8. B-Cell Targeting CpG-Ab Conjugate is Efficacious in Treating Non-B Cell Carcinomas A colon carcinoma disease model was created by implanting 0.2×10$^6$ CT26 cells (CD22-/PD-L1(low)/TLR9-) subcutaneously on the flank of immune competent BALB/c mice. The CpG-mAb (CD22) conjugate was made as described above.

Mice were implanted with CT26 cells on Day 0 as described above. Then, the mice were given intravenous injections of (i) CpG-mAb (CD22) alone; (ii) anti-PD-1 antibody alone; (iii) CpG-mAb (CD22) in combination with anti-PD-1 antibody; or (iv) saline solution. Particularly, 3 mg/kg CpG-mAb (CD22) was initially injected on Day 5, and the dosing was repeated on Day 8 and Day 11. 10 mg/kg Anti-PD-1 was initially injected on Day 6, and the dosing repeated on Day 9 and 12. Tumor volumes of the groups of mice were monitored for 18 days.

Figure 48B:
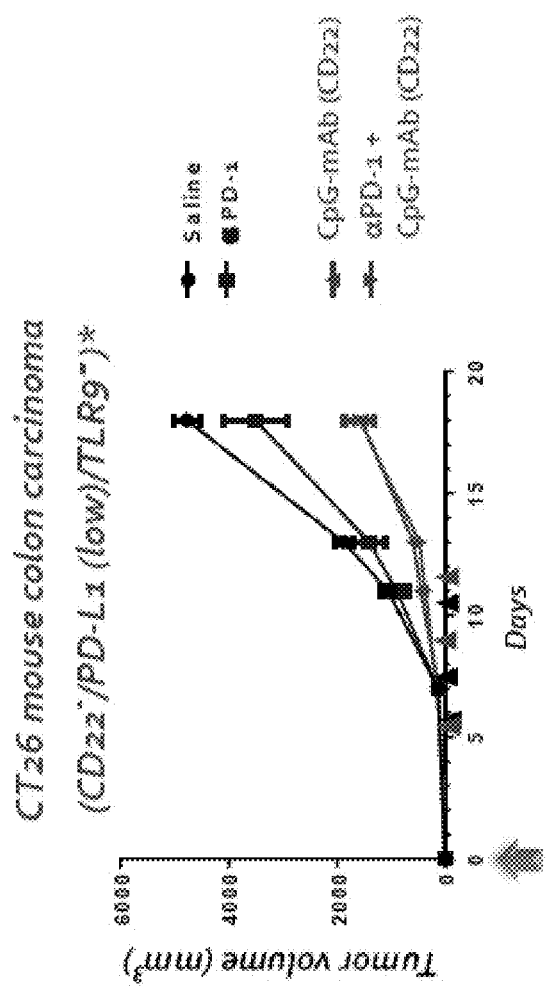
FIG. 48B shows the tumor volume of mice having solid B-cell lymphoma model after receiving (i) 3 mg/kg CpG-mAb (CD22) (up triangle); (ii) anti-PD-1 antibody (closed square); (iii) 3 mg/kg CpG-mAb (CD22) in combination with anti-PD-1 antibody (down triangle); and (iv) saline solution (closed circle).
Figure 48A:
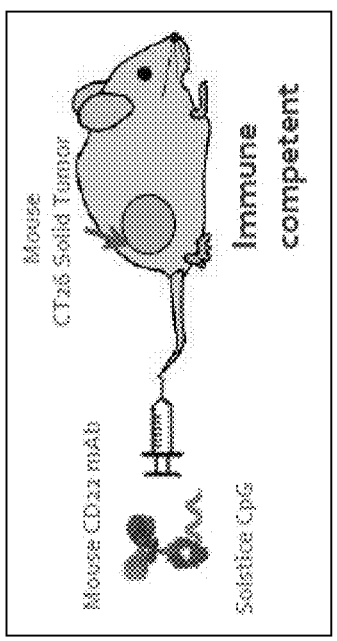
FIG. 48A illustrates the experimental scheme as described in Example 8, where mice having solid colon carcinoma were given intravenous doses of B-cell targeting CpG-Ab (CpG ODN conjugated to a mouse anti-CD22 mAb) alone or in combination with anti-PD-1 antibody.

As shown in FIG. 48B, treatment with CpG-mAb (CD22) or anti-PD-1 alone, or the two agents in combination all reduced the tumor volume significantly at the end of the observation period as compared to the control group. The anti-tumor effect of the combination treatment was more prominent than treatment with anti-PD-1 alone.

Taken together, these data together suggest that systematic administration of the B-cell targeting CpG-mAb (CD22) conjugate is efficacious for treating solid tumors, even though the solid tumors cells themselves do not express TLR9 or the antigen target of the CpG-mAb (CD22) conjugate. The anti-tumor effect can be attributed to B-cell activation upon administration of the B-cell targeting CpG-mAb (CD22) conjugate. Furthermore, a combination therapy using both an anti-PD-1 antibody and a B-cell targeting CpG-mAb (CD22) conjugate is more efficacious in treating the solid tumor as compared to treatment with the anti-PD-1 antibody alone.

Example 9. Anti-Tumor Effect of CpG-Ab Conjugate in Competent Immune Systems

Next, experiments were performed to evaluate anti-tumor effect of CpG-Ab conjugates in immuno-competent and immuno-compromised systems. Solid B-cell lymphoma models were created by implanting 5×10$^6$ A20 lymphoma cells (TLR9$^+$/CD22$^+$) in immune competent BALB/c mice and immuno-compromised Nu/Nu mice and SCID mice, respectively. The CpG-mAb (CD22) conjugate was made as described above.

| Strain | T-cell immunity | B-cell Immunity | NK Cell Immunity |
|--------|-----------------|-----------------|------------------|
| Balb/C | + | + | + |
| Nu/Nu | − | + | + |
| SCID | − | − | +/− |

Figure 49A:
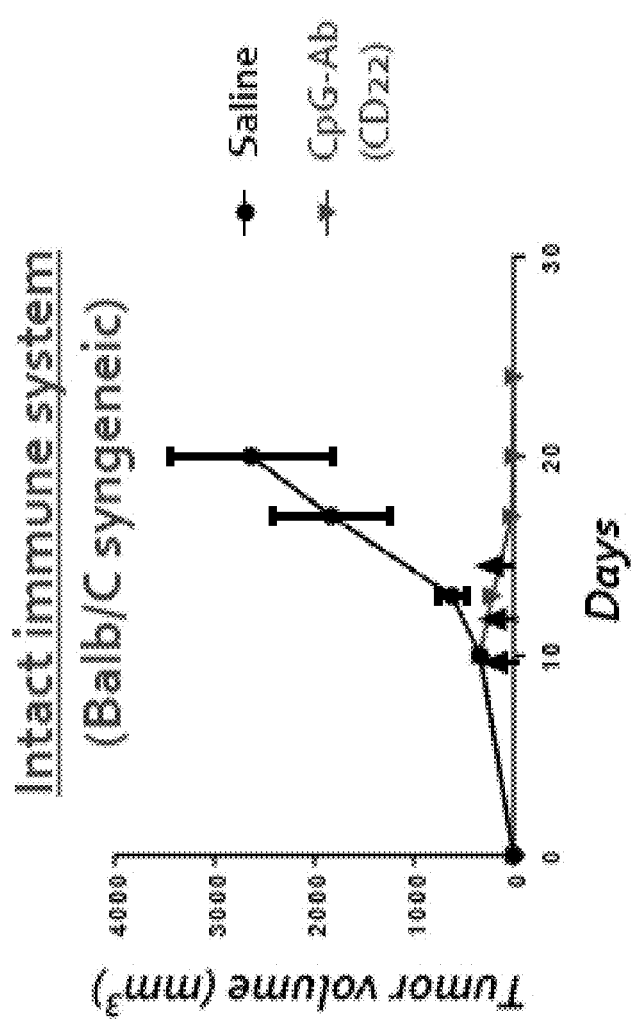
FIG. 49A shows the tumor volume in immune-competent Balb/C mice having solid B-cell lymphoma after receiving (i) 10 mg/kg CpG-mAb (CD22) (triangle) or saline solution (circle).

In the immuno-competent group, 10 mg/kg CpG-mAb (CD22) was administered intravenously on Days 10, 12 and 14. A negative control group received intravenous injection of only saline solutions on the above days. Tumor volumes were monitored for 20 days. As shown in FIG. 49A, intravenous administration of CpG-mAb (CD22) resulted in the tumor-free phenotype in the immune-competent Balb/C mice, while the tumor volume of the control group continued to increase during the observation period.

Figure 49B:
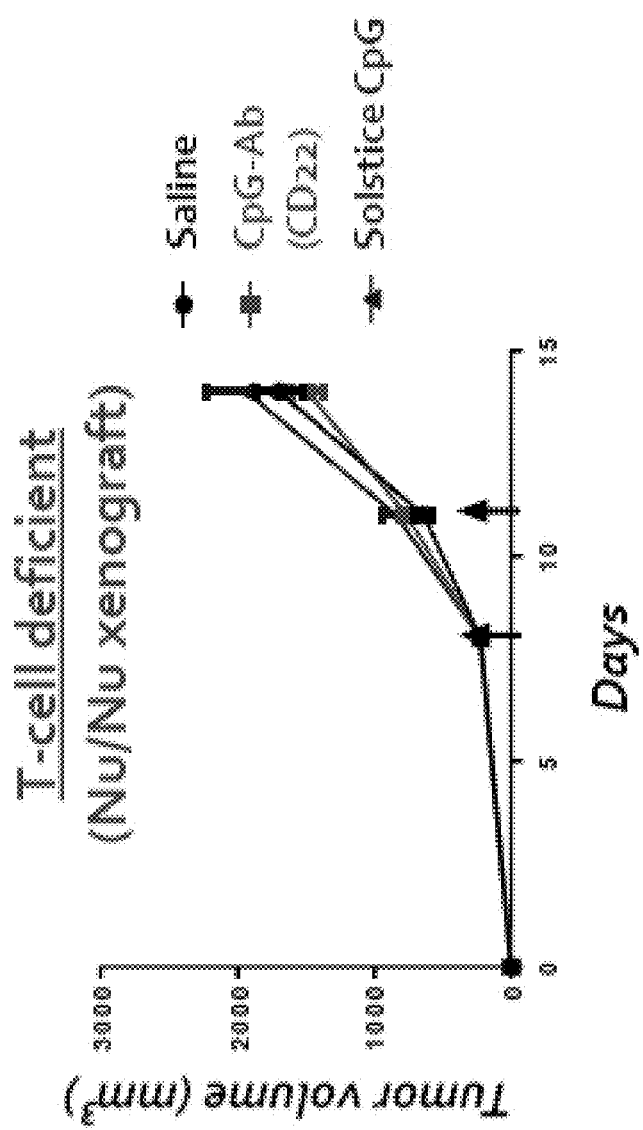
FIG. 49B shows the tumor volume in immune-compromised Nu/Nu mice having solid B-cell lymphoma after receiving (i) 10 mg/kg CpG-mAb (CD22) (square), (ii) naked CpG ODN (triangle) or (iii) saline solution (circle).
Figure 49C:
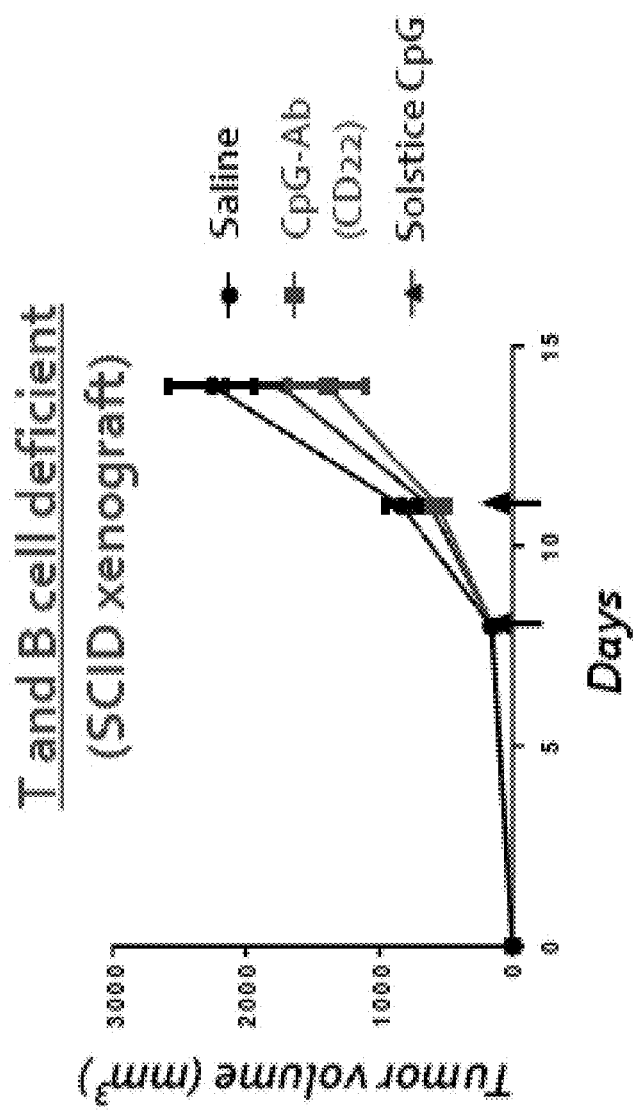
FIG. 49C shows the tumor volume in immune-compromised SCID mice having solid B-cell lymphoma after receiving (i) 10 mg/kg CpG-mAb (CD22) (square), (ii) naked CpG ODN (triangle) or (iii) saline solution (circle).

In the immuno-compromised groups, 10 mg/kg CpG-mAb (CD22) or naked CpG was administered intravenously on Days 8 and 11. A negative control group received i.v. injection of only saline solutions on the above days. Tumor volumes were monitored for 15 days. As shown in FIGS. 49B and 49C, i.v. administrations of the naked CpG ODN or the CpG-mAb (CD22) conjugate did not affect tumor growth in the immune-compromised Nu/Nu mice or SCID mice, as compared to the negative control group.

Taken together, these data suggest that the anti-tumor effect of the CpG-Ab conjugate is dependent upon T-cell immunity.

Example 10. Anti-Tumor Effect of CpG-Ab Conjugate is CD8$^+$ T-Cell Dependent

Next, experiments were conducted to examine activities of lymphocyte that are required for the anti-tumor effect of the CpG-Ab conjugates. Particularly, anti-tumor effects of the CpG-Ab conjugates were evaluated in CD4+ T cell depleted mice, CD8+ T cell depleted mice, and NK cell depleted mice which was achieved by intraperitoneal injection of anti-CD4 antibody (500 ug/mouse on days −2, −1, 0, 5, 8, 12), anti-CD8 antibody (100 ug/mouse on days −2, −1, 0, 5, 8, 12), or anti-asialo GM1 antibody (25 ug/mouse on days −2, −1,0, 5, 8, 12), respectively. Cell depletion was confirmed by FACS analysis. All depletion antibodies were purchased from Bioexcell.

Disseminated B-cell lymphoma model mice were created as described above. The CpG-mAb (CD22) conjugate was made as described above.

In these lymphocyte depletion experiments, mice were injected with A20 lymphoma cells (5×10$^6$) on Day 0 as described above. Then, on Day 1, 3 and 5 each, mice were given intravenous injections of (i) 3 mg/kg CpG-mAb (CD22) and anti-CD4 depletion antibody, 500 ug/mouse on days −2, −1, 0, 5, 8, 12 to deplete CD4+ T cell); (ii) 3 mg/kg CpG-mAb (CD22) and 25 ug/mouse of anti-asialo GM1 antibody on days −2, −1, 0, 5, 8, 12 to deplete NK cells; and (iii) 3 mg/kg CpG-mAb (CD22) and anti-CD8 depletion antibody, 100 ug/mouse on days −2, −1, 0, 5, 8, 12 to deplete to deplete CD8+ T cells. Additionally, a positive control group received 3 mg/kg CpG-mAb (CD22) on Day 1, 3, and 5, and a negative control group received only saline solution on Day 1, 3 and 5. Survival rates of the groups were monitored for 85 days.

Figure 50A:
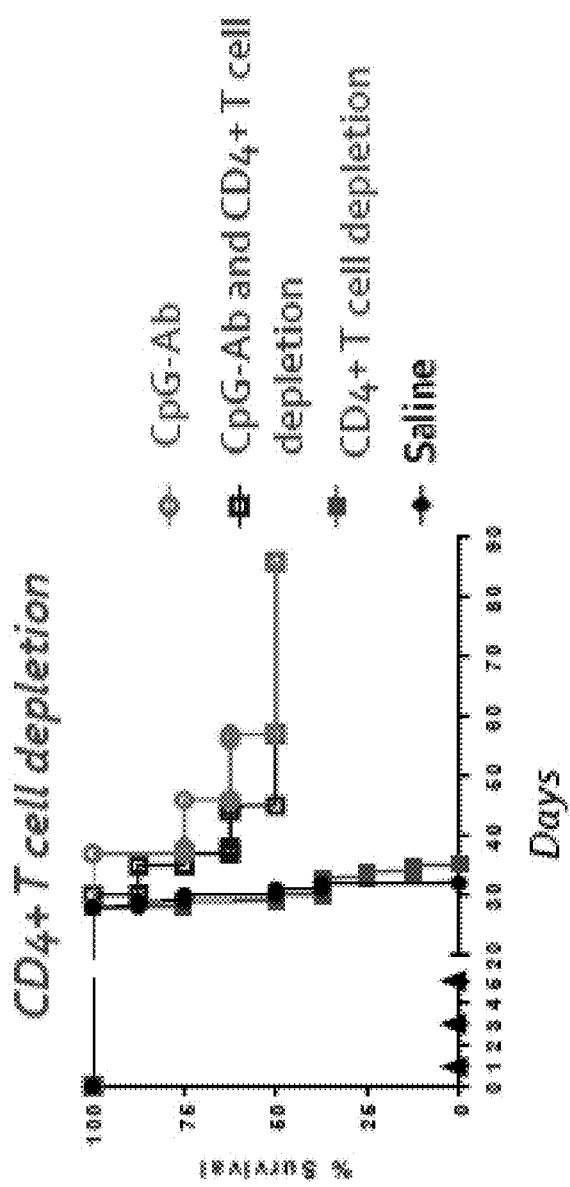
FIG. 50A shows the survival rate of mice having soluble B-cell lymphoma after receiving (i) CpG-mAb (CD22) alone (open circle); (ii) CpG-mAb (CD22) and CD4+ T cell depletion treatment (open square); (iii) CD4+ T cell depletion treatment (closed square); or (iv) saline solution (closed circle).

As shown in FIG. 50A, mice received CpG-mAb (CD22) treatment showed significantly better survival as compared to the groups not treated with CpG-mAb (CD22). CD4+ T cell depletion did not significantly affect survival. Particularly, the two groups of mice treated with CpG-mAb (CD22) (with and without the T-cell depletion treatment) both maintained 50% survival rate for at least 85 days after challenged with tumor cells, while the two groups of mice without CpG-mAb (CD22) treatment (with and without the T-cell depletion treatment) both died off within 40 days.

Figure 50B:
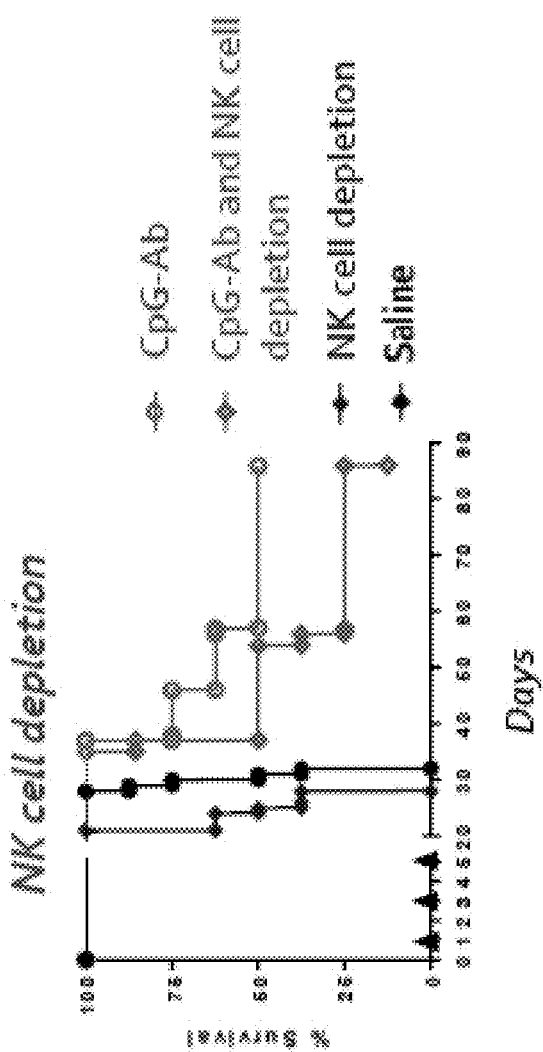
FIG. 50B shows the survival rate of mice having soluble B-cell lymphoma after receiving (i) CpG-mAb (CD22) alone (open circle); (ii) CpG-mAb (CD22) and nature killer (NK) cell depletion treatment (open square); (iii) NK cell depletion treatment (closed square); or (iv) saline solution (closed circle).
Figure 50C:
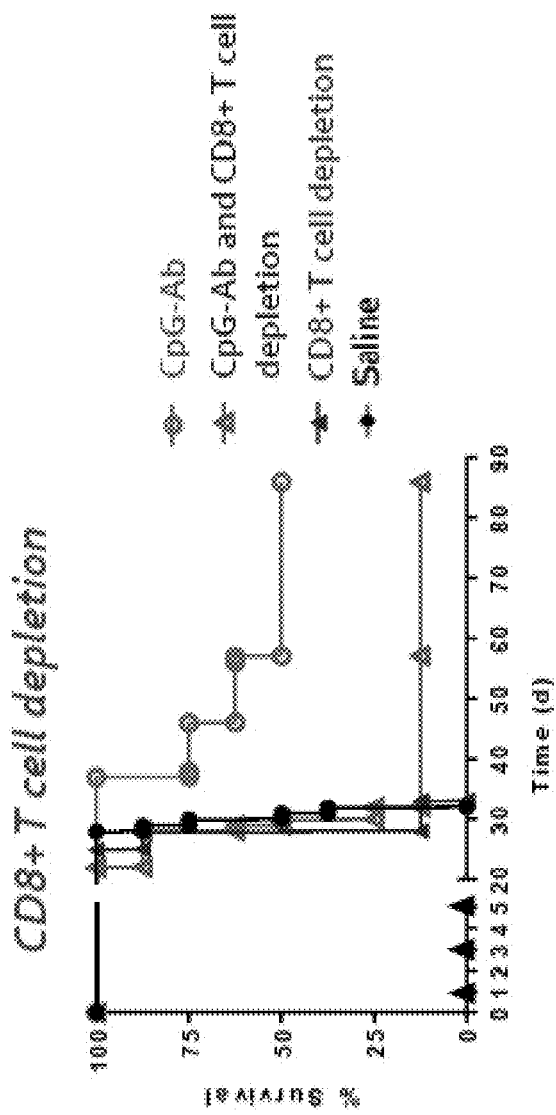
FIG. 50C shows the survival rate of mice having soluble B-cell lymphoma after receiving (i) CpG-mAb (CD22) alone (open circle); (ii) CpG-mAb (CD22) and CD8+ T cell depletion treatment (open square); (iii) CD8+ T cell depletion treatment (closed square); or (iv) saline solution (closed circle).

Depletion of NK cells or CD8+ cells both resulted in worse survival in mice treated with CpG-mAb (CD22). As shown in FIG. 50B, the group receiving both CpG-mAb (CD22) and NK cell depletion treatments exhibited about 90% survival rate on Day 40, and about 10% survival rate on Day 85. More prominently, as shown in FIG. 50C, more than 90% CD8+ T cell depleted mice died within 30 days even after CpG-mAb (CD22) treatment. This result was similar to the outcome observed in the control group (where all mice died around Day 30). These data suggest that the anti-tumor effect CpG-Ab is at least CD8+ T cell dependent.

Example 11. CpG-Ab Conjugate Increases T-Cell Tumor Infiltration

Solid B-cell lymphoma model mice were created as described above. The CpG-mAb (CD22) conjugate was made as described above.

Mice received intravenous administration of 10 mg/kg CpG-mAb (CD22) conjugate 10, 12 and 14 days after challenged with A20 lymphoma cells subcutaneously on day 0. Tumors harvested on Day 17 were subsequently digested by incubation in digestion buffer containing 1 mg/mL collagenase IV, 100 U/mL DNAse I in HBSS at 37° C. for 30 min. Then, the digested cells were filtered through a 70 um sieve, washed, incubated on ice with anti-CD4-PE or anti-CD8-PE antibodies and analyzed by FACS.

Figure 51B:
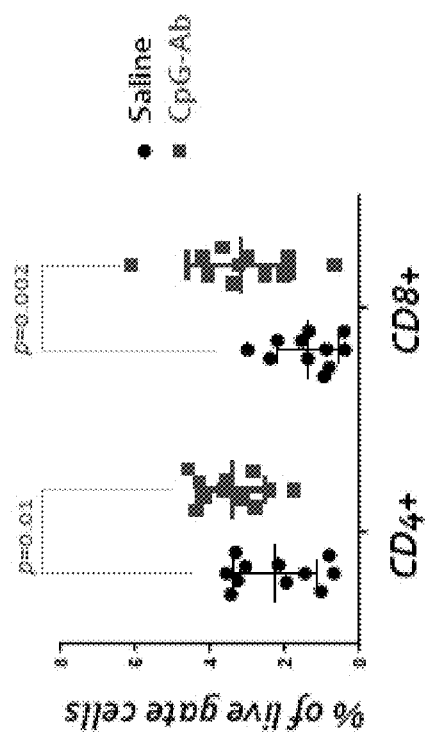
FIG. 51B shows the percentage of CD4+ or CD8+ live gate cells in tumors harvested from mice having solid B-cell lymphoma treated with (i) CpG-Ab (square) or (ii) saline solution (circle).
Figure 51A:
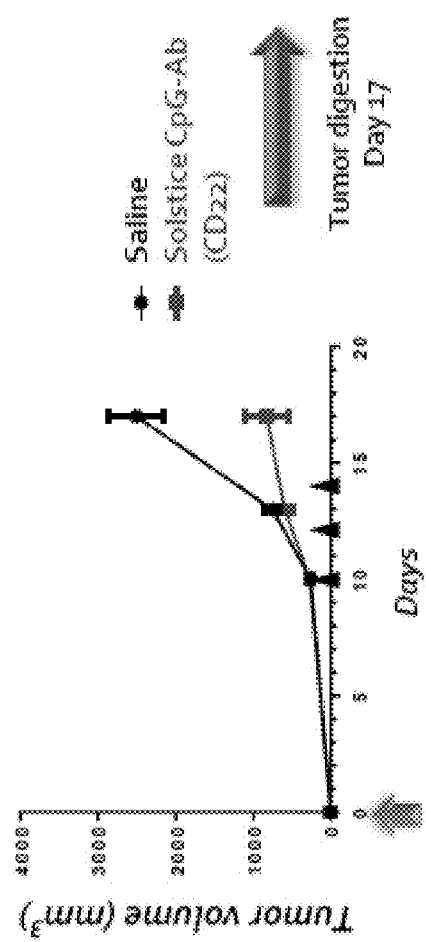
FIG. 51A shows the tumor volume in mice having solid B-cell lymphoma after receiving CpG-mAb (CD22) (square) or saline solution (circle). Mice were sacrificed and tumor were harvested on Day 17 for digestion.
Figure 51C:
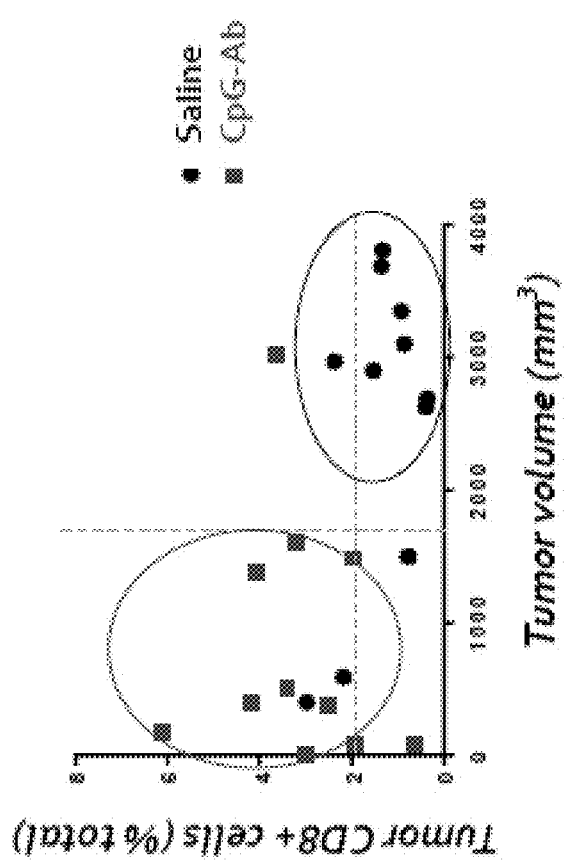
FIG. 51C shows the correlation between the percentage of CD8+ tumor cells and the tumor volume in mice treated with (i) CpG-Ab (square) or (ii) saline solution (circle).

As shown in FIG. 51A, tumor growth was slower in the group treated with CpG-mAb (CD22) as compared to the control group. The tumor volume on Day 17 from CpG-mAb (CD22) treated mice was significantly smaller than the control mice. As shown in FIG. 51B, percentages of CD4+ cells and CD8+ cells in tumor tissue were both significantly higher in the treated group than the control group, Further, as shown in FIG. 51C, the tumor volume inversely correlates with the percentage of CD8+ cells in the tumor.

Taken together, these data suggest that systemic administration of CpG-Ab conjugates into mice having a solid tumor can significantly increase T-cell infiltration into the tumor. The increased number of immune cells, particularly CD8+ T cells, in the tumor and/or tumor microenvironment facilitates immune attacking on the tumor and inhibitors of tumor growth.

Example 12. Synergistic Effect of CpG-Ab Conjugates and Antibodies of Immune Checkpoint Proteins Experiments were performed to evaluate the anti-tumor effect of combination therapy using both CpG-Ab conjugates and an immune checkpoint protein antibody.

Solid B-cell lymphoma model mice were created as described above. The CpG-mAb (CD22) conjugate was made as described above. Anti-PD1 antibody (clone J43) was purchased from Bioxcell and anti-PDL1 antibody (atezolizumab) was made in house.

Mice were implanted with A20 lymphoma cells on Day 0 as described above. Then, the mice were given intravenous injections of (i) CpG-mAb (CD22); (ii) intraperitoneal injection of anti-PD-1 antibody or anti-PD-L1 antibody; (iii) CpG-mAb (CD22) in combination with the anti-PD-1 antibody or CpG-mAb (CD22) in combination with the anti-PD-L1 antibody; or (iv) saline solution. Particularly, for the groups receiving CpG-mAb (CD22) (alone or in combination with the immune checkpoint protein antibody), a first dose of 3 mg/kg CpG-mAb (CD22) was initially administered on Day 10, and then the same dosing was repeated on Day 12 and 14. Additionally, for the groups receiving an immune checkpoint protein antibody (alone or in combination with CpG-mAb (CD22)), a first dose of 10 mg/kg immune checkpoint protein antibody was initially administered on Day 10, and then the same dosing was repeated on Day 13 and 16. Tumor volumes of the group of mice were monitored.

Figure 52A:
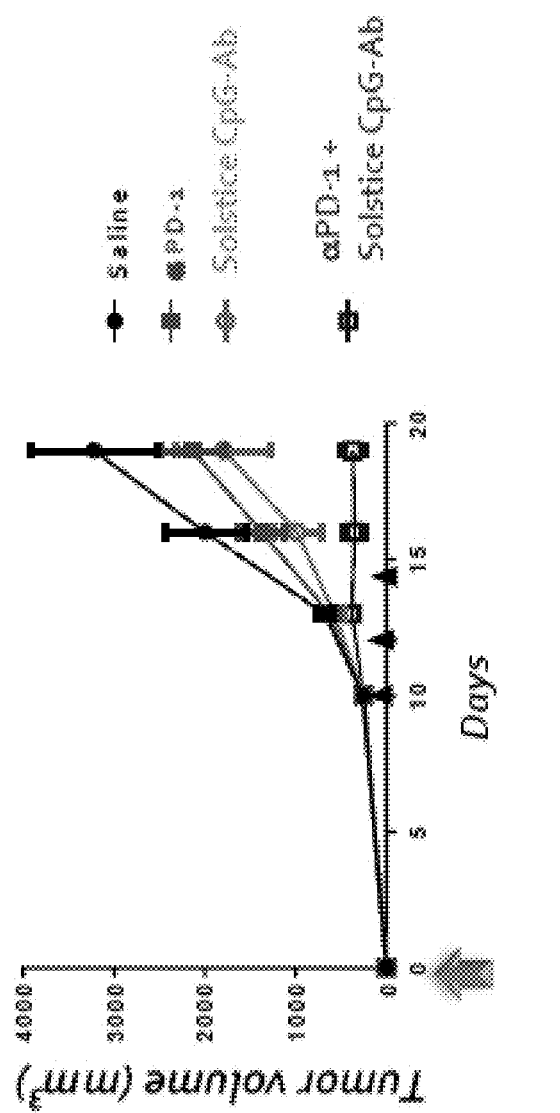
FIG. 52A shows the tumor volume in mice having solid B-cell lymphoma after receiving (i) CpG-mAb (CD22) alone (open circle); (ii) anti-PD-1 antibody alone (closed square); (iii) CpG-mAb (CD22) in combination with anti-PD-1 antibody (open square); or (iv) saline solution (closed circle).
Figure 52B:
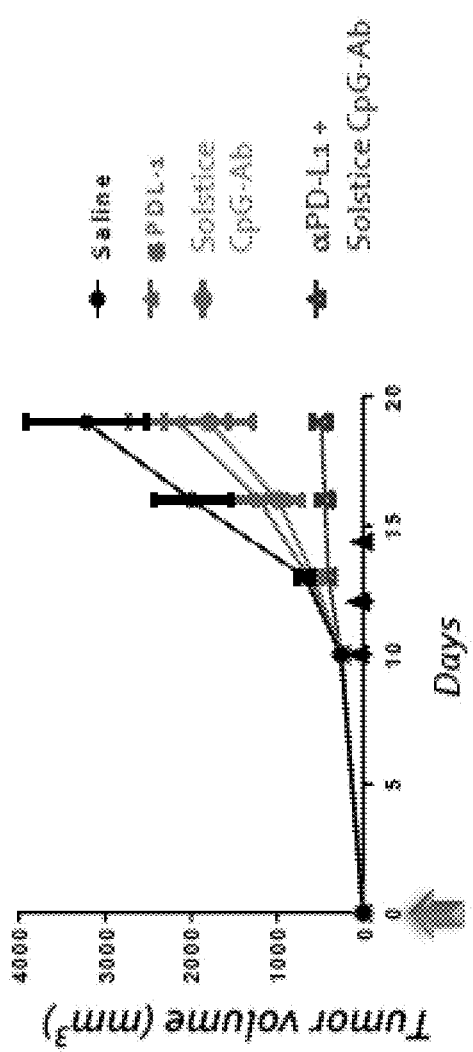
FIG. 52B shows the tumor volume in mice having solid B-cell lymphoma after receiving (i) CpG-mAb (CD22) alone (open circle); (ii) anti-PD-L1 antibody alone (closed triangle); (iii) CpG-mAb (CD22) in combination with anti-PD-L1 antibody (open triangle); or (iv) saline solution (closed circle).

It was observed from this experiment that CpG-mAb (CD22) and the immune checkpoint protein antibody synergistically produced a stronger tumor-inhibiting effect as compared to treatment with either of the two agents separately. Particularly, as shown in FIGS. 52A and 52B, mice treated with the combination therapy had significantly smaller tumor size as compared to treatment with CpG-mAb (CD22) or the immune checkpoint antibody alone.

Figure 52C:
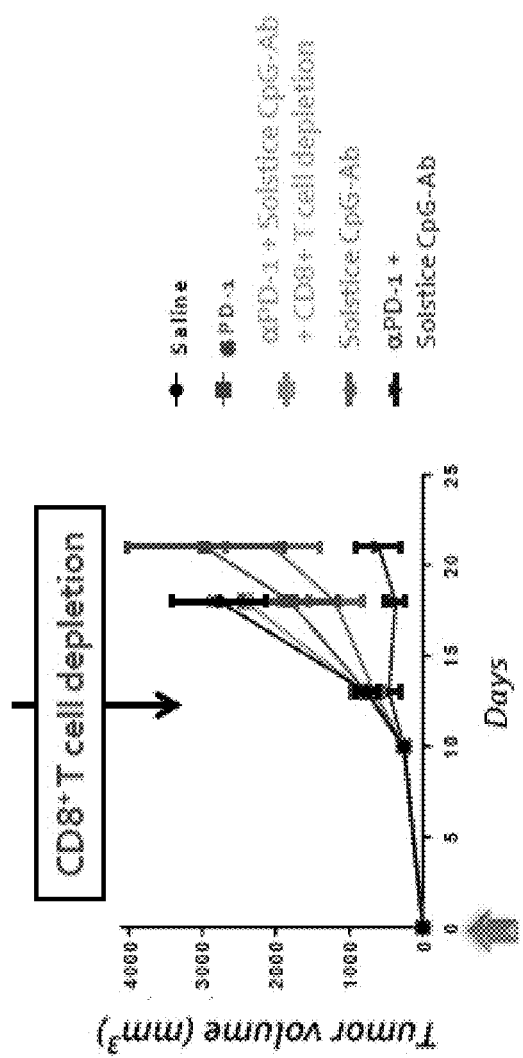
FIG. 52C shows the tumor volume in mice having solid B-cell lymphoma after receiving (i) CpG-mAb (CD22) alone (open circle); (ii) anti-PD-1 antibody alone (closed square); (iii) CpG-mAb (CD22) in combination with anti-PD-1 antibody (open square); (iv) CpG-mAb (CD22) in combination with anti-PD-1 antibody and CD8+ T cell depletion treatment; or (v) saline solution (closed circle).

To examine whether the observed synergistic effect is also dependent on CD8+ T cell activity, an additional group of mice was given (i) 10 mg/kg CpG-mAb (CD22) on each of Days 10, 12 and 14, (ii) 10 mg/kg anti-PD-1 antibody on each of Days 10, 13 and 16, and (iii) antiCD8 antibody (200 ug/mouse, intraperitoneal, starting on days 0 and dosed twice/week throughout the experiment to deplete CD8+ T cells. As shown in FIG. 52C, like the saline treated control group, the tumor volume of this experimental group increased rapidly, suggesting the synergistic effect in inhibiting tumor growth of the combination therapy using both CpG-mAb (CD22) and an immune checkpoint protein antibody is also CD8+ T cell dependent.

Further, mice treated with the combination therapy using both CpG-mAb (CD22) and anti-PD-1 antibody and survived the first tumor challenge were subjected to a second tumor challenge. Particularly, survivors from the combination treatment group was given a second dose of A20 cells subcutaneously on the shoulder on Day 30. The survivor group did not receive any additional treatment after the second tumor challenge. A naive control group was given the same dose of tumor cells. The tumor volume was further monitored for 25 days (i.e., between Day 30 and Day 55).

Figure 53A:
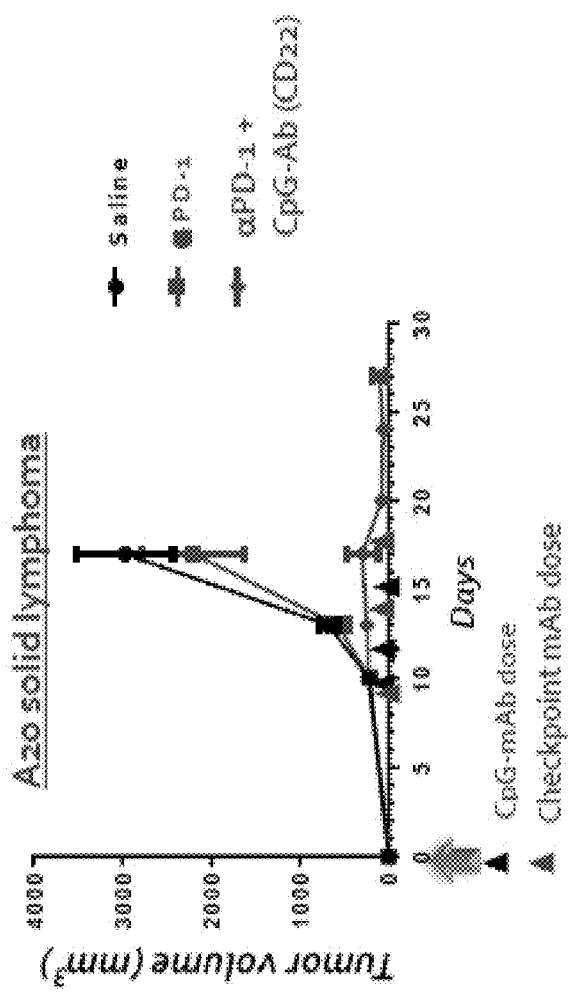
FIG. 53A shows the average tumor volume in mice having solid B-cell lymphoma after receiving (i) anti-PD-1 antibody alone (square); (ii) CpG-mAb (CD22) in combination with anti-PD-1 antibody (diamond); or (iii) saline solution (circle).
Figure 53B:
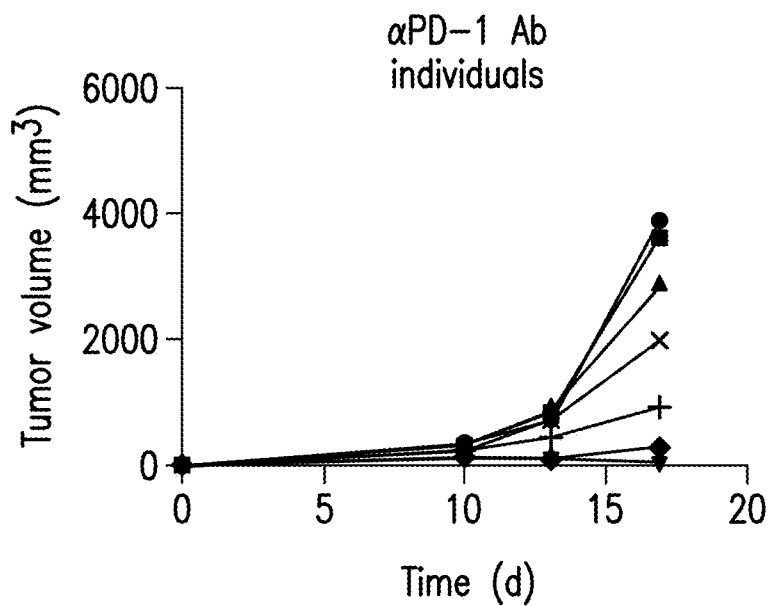
FIG. 53B shows the tumor volumes in individual mice having solid B-cell lymphoma after receiving anti-PD-1 antibody alone.
Figure 53C:
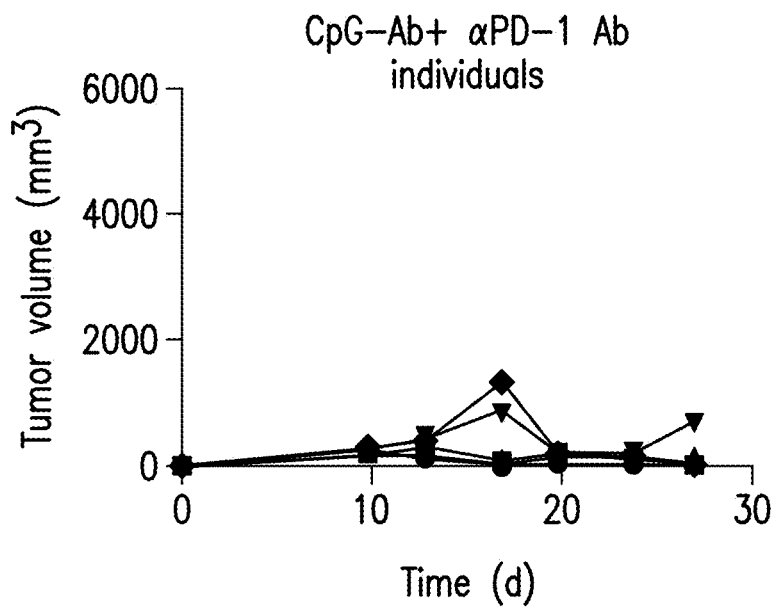
FIG. 53C shows the tumor volumes in individual mice having solid B-cell lymphoma after receiving the CpG-mAb (CD22)/anti-PD-1 antibody combination treatment.

As shown in FIGS. 53A through 53C, in contrast to the control group or the group treated with anti-PD-1 antibody alone, the CpG-Ab/anti-PD-1 combination significantly inhibited tumor growth in all individuals throughout the observation period. Further, the combination treatment regressed staged tumors in two individuals starting around D18.

Figure 53D:
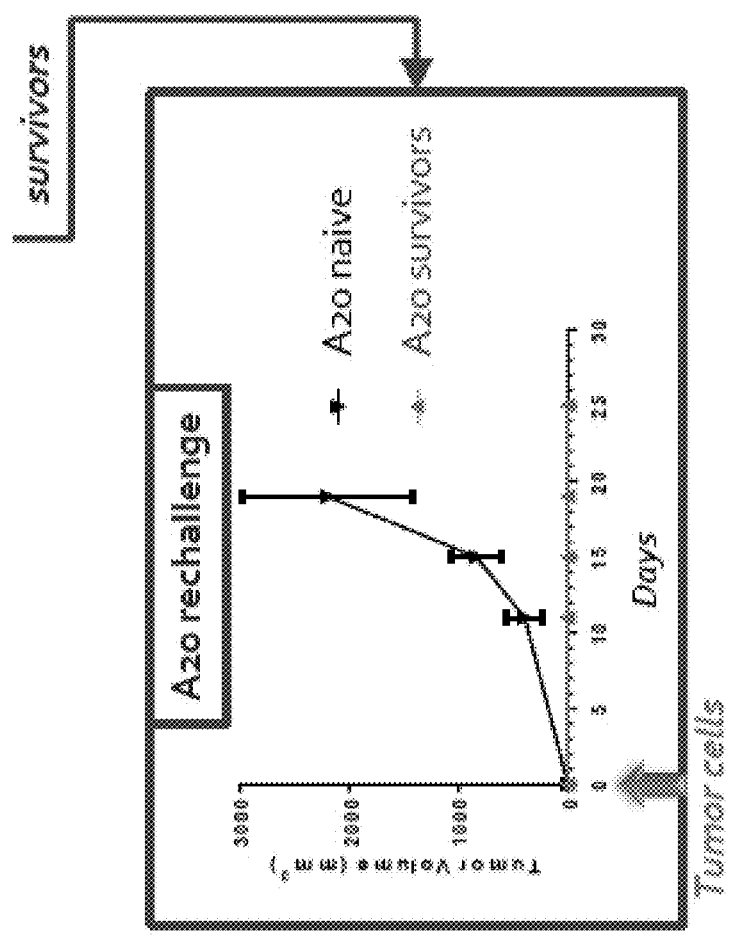
FIG. 53D shows the tumor volume of survivors from the first tumor challenge (up triangle) and a naive control group (down triangle) after the second tumor challenge.

The survivors from the combination treatment group were subjected to the second tumor challenge as described above. As shown in FIG. 53D, after the second tumor challenge, the tumor volume in the naive control group increased rapidly, reaching an average volume above 2000 $mm^3$ within 20 days. In contrast, the survivor group remained tumor free throughout the 25-day observation window. These results suggest that the combination therapy using the CpG-Ab conjugate and an immune checkpoint protein antibody can induce sustained adaptive immunity against tumor in a subject.

Example 13. Synergistic Effect of CpG-Ab Conjugates and T Cell Agonists

Next, Experiments were performed to evaluate the anti-tumor effect of combination therapy using both CpG-Ab conjugates and a T cell agonist.

Solid B-cell lymphoma model mice were created as described above. The CpG-mAb (CD22) conjugate was made as described above.

Mice were implanted with A20 lymphoma cells on Day 0 as described above. Then, the mice were given intravenous injections of (i) CpG-mAb (CD22); (ii) intraperitoneal injection of anti-OX-40 antibody (clone OX-86, 10 mg/kg, Bioxcell), anti-ICOS antibody (clone 7E.17G9, 10 mg/kg, Bioxcell), or anti-4-1BB antibody (clone 3H3, 1 mg/kg, Bioxcell); (iii) CpG-mAb (CD22) in combination with anti-OX-40 antibody, CpG-mAb (CD22) in combination with anti-ICOS antibody, or CpG-mAb (CD22) in combination with anti-4-1 BB antibody; or (iv) saline solution. Particularly, for the group receiving CpG-mAb (CD22) (alone or in combination with a T-cell stimulatory antibody), a first dose of 3 mg/kg CpG-mAb (CD22) was initially administered on Day 10, and then the same dosing was repeated on Day 12 and 14. Additionally, for the group receiving a T-cell stimulatory antibody (alone or in combination with CpG-mAb (CD22)) a first dose of the T-cell stimulating antibody was administered on Day 10, and then the same dosing was repeated on Day 13 and 17. Tumor volumes of the group of mice were monitored.

Figure 54A:
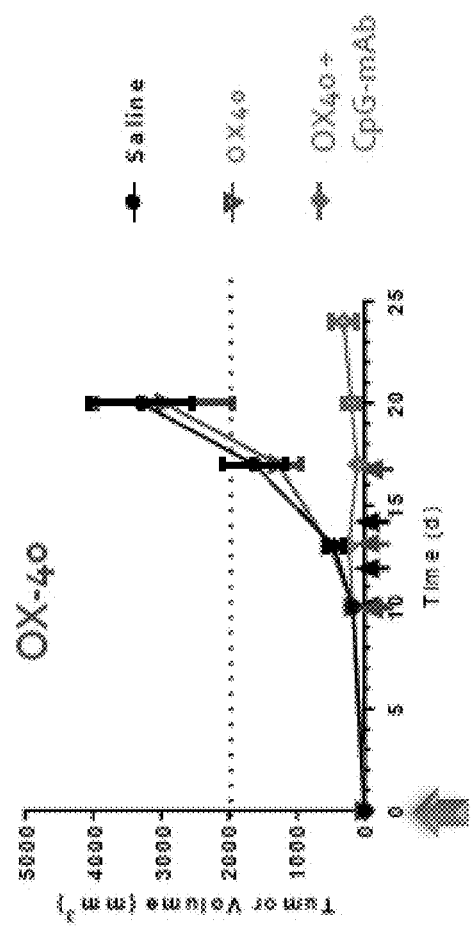
FIG. 54A shows the tumor volume in mice having solid B-cell lymphoma after receiving (i) (i) anti-OX40 antibody alone (triangle); (ii) CpG-mAb (CD22) in combination with anti-OX40 antibody (diamond); or (iii) saline solution (circle).
Figure 54B:
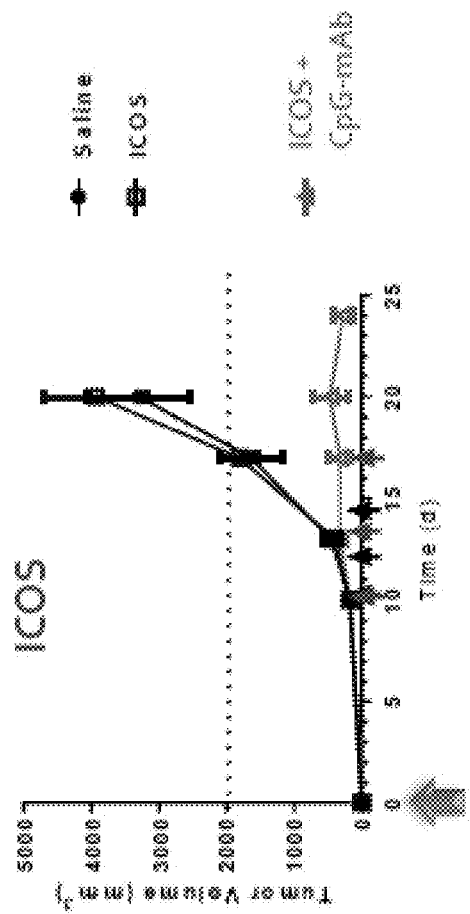
FIG. 54B shows the tumor volume in mice having solid B-cell lymphoma after receiving (i) (i) anti-ICOS antibody alone (square); (ii) CpG-mAb (CD22) in combination with anti-ICOS antibody (triangle); or (iii) saline solution (circle).
Figure 54C:
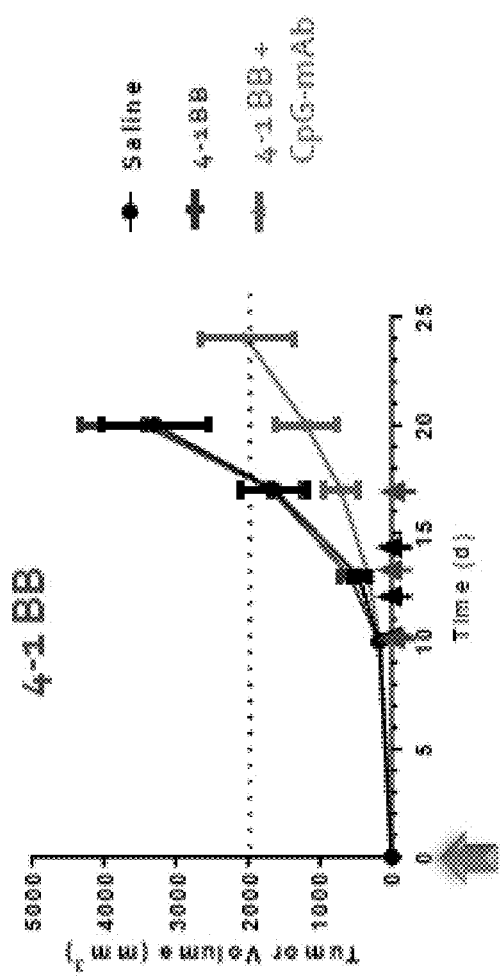
FIG. 54C shows the tumor volume in mice having solid B-cell lymphoma after receiving (i) anti-4-1 BB antibody alone (diamond); (ii) CpG-mAb (CD22) in combination with anti-4-1 BB antibody (triangle); or (iii) saline solution (circle).

It was observed from this experiment that CpG-mAb (CD22) and the T-cell stimulatory antibody synergistically produced a tumor-inhibiting effect that was not observed in treatment with the T-cell stimulatory antibody alone. Particularly, as shown in FIGS. 54A through 54C, mice treated with the combination therapy had significantly smaller tumor size as compared to the negative control group or the group treated with the T-cell stimulatory antibody (anti-OX-40, anti-ICOS, or anti-4-1 BB) alone.

Example 14. B-Cell Targeting CpG-Ab Elicits Tumor Antigen Specific Cytotoxic T-Cell Response in Splenocytes A colon carcinoma disease model was created by as described above. The CpG-mAb (CD22) conjugate was made as described above.

Figure 55A:
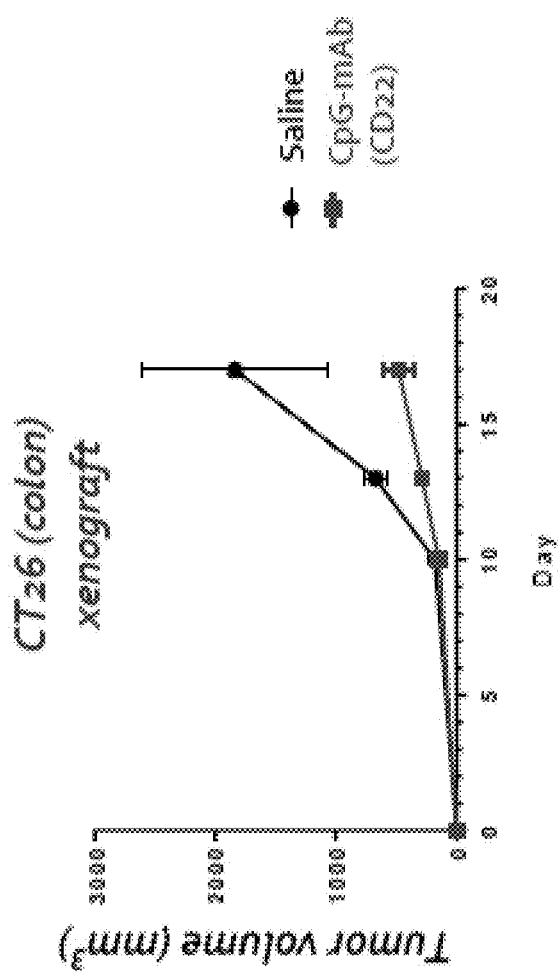
FIG. 55A shows the tumor volume in mice having colon carcinoma after receiving (i) 10 mg/kg CpG-mAb (CD22) or (i) saline solution on each of Days 10, 13 and 16.

Mice were implanted with CT26 cells on Day 0 as described above. Then, the mice were given intravenous injections of 10 mg/kg CpG-mAb (CD22) or saline solution on Days 10, 13, and 16. Tumor volumes of the groups of mice were monitored for 17 days. As shown in FIG. 55A, treatment with the CpG-mAb (CD22) significantly inhibited tumor growth as compared to the control group.

Figure 55B:
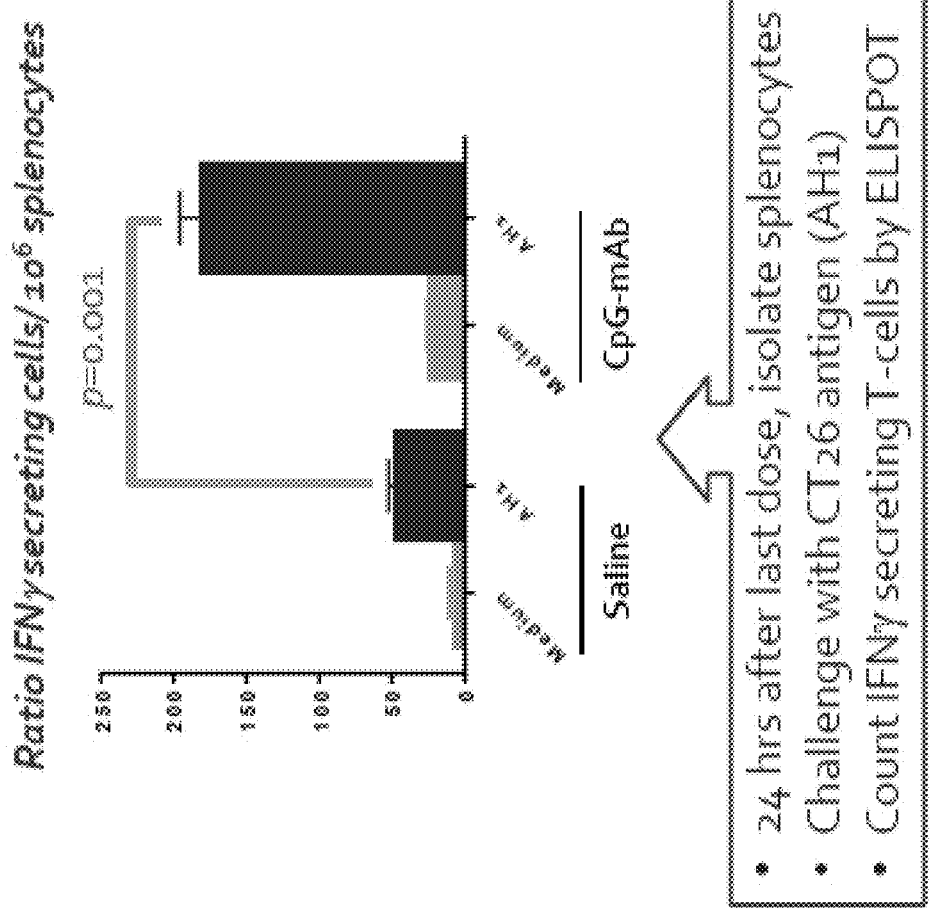
FIG. 55B shows the number of IFN-gamma secreting cells in $10^6$ splenocytes isolated from mice treated with (i) CpG-mAb (CD22) or (i) saline solution, before or after stimulating the cells with the AH1 antigen.

On Day 17 (24 hours after the last dose), the mice were sacrificed, the splenocytes were isolated and plated ($4 \times 10^5$ cells/well) in ELISPOT plates coated with anti-IFN-gamma antibody. The cells were challenged with a CT26 cell surface antigen (AH1 peptide) at 100 ug/ml for 24 hours at 37° C. and the IFN-gamma secreting T cells were counted. As shown in FIG. 55B, the number of IFN-gamma secreting cells significantly increased in the group treated with CpG-mAb (CD22) as compared to the control. These data suggest that the B-cell targeting CpG-Ab conjugate is capable of eliciting tumor antigen specific cytotoxic T-cell response upon administration to a subject.

Example 15. CpG-Ab Conjugates Targeting Dendritic Cells Elicit Anti-tumor Adaptive Immunity A solid B-cell lymphoma disease model was created by as described above. Immunostimulating polynucleotide having the sequence of SEQ ID NO: 313 (p313) was synthesized and conjugated to an anti-CD205 antibody or an anti-PD-L1 antibody as described in Examples 1 and 2. These conjugates are referred to as CpG-Ab (CD205) and CpG-Ab (PD-L1), respectively.

Mice were implanted with A20 cells on Day 0 as described above. Then, the mice were given intravenous injections of (i) 10 mg/kg CpG-Ab (CD205); (ii) 10 mg/kg CpG-Ab (PD-L1); or (iii) saline solution, on Days 10, 12, and 14. Tumor volumes of the groups of mice were monitored for about 41 days.

Figure 56A:
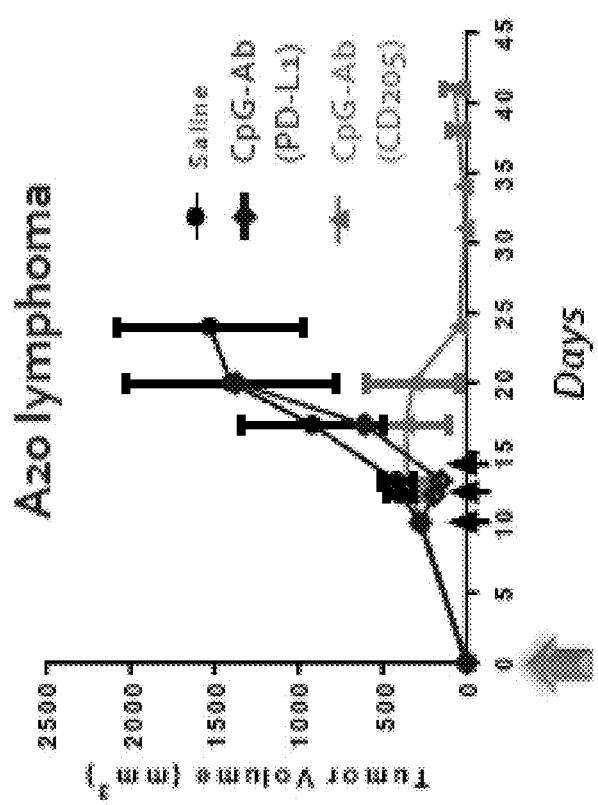
FIG. 56A shows the average tumor volume in mice having solid B-cell lymphoma after receiving intravenous doses of (i) 10 mg/kg CpG-Ab (PD-L1) (diamond); (i) 10 mg/kg CpG-Ab (CD205) (triangle); or (iii) saline solution on each of Days 10, 12 and 14.
Figure 56B:
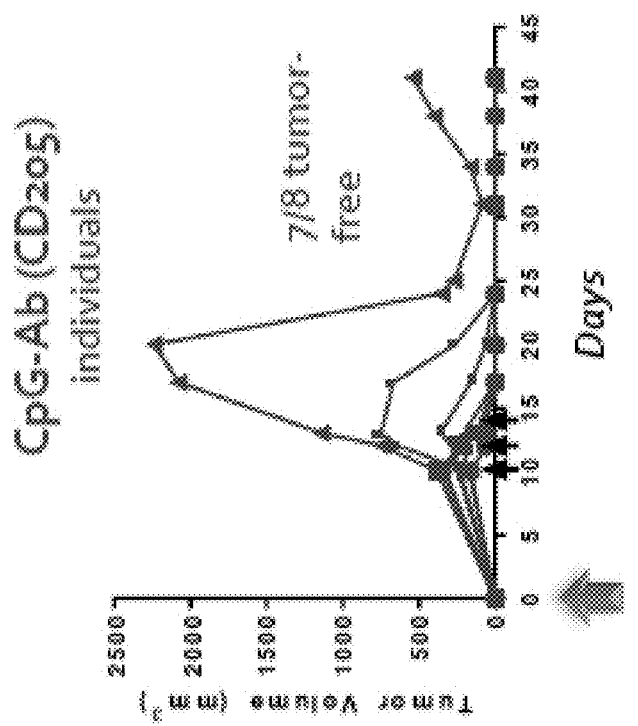
FIG. 56B shows the tumor volumes in individual mice having B-cell lymphoma after receiving intravenous doses of 10 mg/kg CpG-Ab (CD205) on Days 10, 12, and 14.

As shown in FIG. 56A, treatment with the CpG-Ab (CD205) significantly inhibited tumor growth as compared to the control group. As further shown in FIG. 56B, the CpG-Ab (CD205) conjugate regressed tumor growth in all 8 individuals in the group, and resulted in the tumor-free phenotype in 7 out of the 8 individuals in total.

Figure 56C:
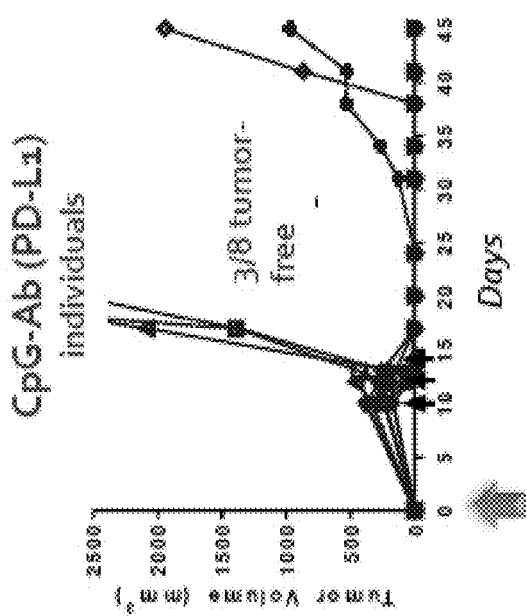
FIG. 56C shows the tumor volumes in individual mice having B-cell lymphoma after receiving intravenous doses of 10 mg/kg CpG-Ab (PD-L1) on Days 10, 12, and 14.

As shown in FIG. 56C, treatment with the CpG-Ab (PD-L1) regressed tumor growth and resulted in the tumor-free phenotype in 3 out of the 8 individuals in total.

Figure 56D:
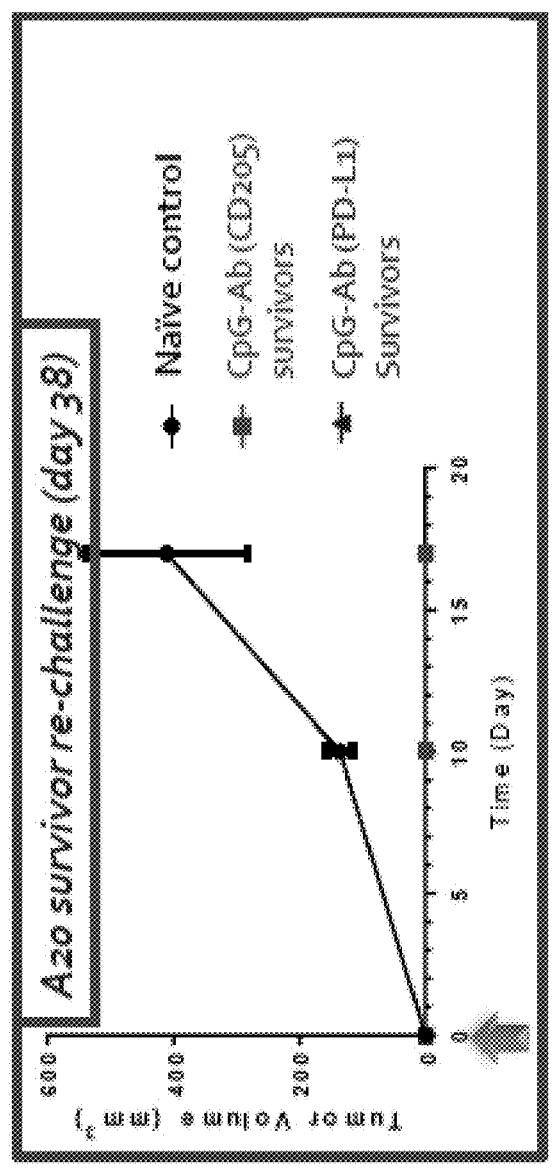
FIG. 56D shows the tumor volume of survivors from the first tumor challenge which were treated with CpG-Ab (CD205) (square) or treated with CpG-Ab (PD-L1) (triangle) and a naïve control group (circle) after the second tumor challenge given at Day 38.

Furthermore, survivors from the groups treated with the CpG-Ab conjugates were subjected to a second tumor challenge. Particularly, survivors were given $5 \times 10^6$ of A20 cells subcutaneously on Day 37 without further treatment. A naive group of mice having solid B-cell lymphoma were given the same dose of A20 cells. The tumor volume of the groups of mice were observed for 17 days after the second challenge. As shown in FIG. 56D, the tumor volume increased rapidly in the control group, while survivors from the CpG-Ab (PD-L1) treatment group or CpG-Ab (CD205) treatment group remained tumor-free throughout the 17-day observation window.

In a separate experiment, four groups of mice having solid B-cell lymphoma (8 individuals/group) were treated with intravenous doses of (i) 10 mg/kg CpG-Ab (CD205) conjugate; (ii) 10 mg/kg mouse anti-CD205 monoclonal antibody; (iii) 10 mg/kg rat IgG, or (iv) saline solution, on each of Days 10, 12, and 14. The tumor volume of the groups of mice were monitored for 27 days.

Figure 57A:
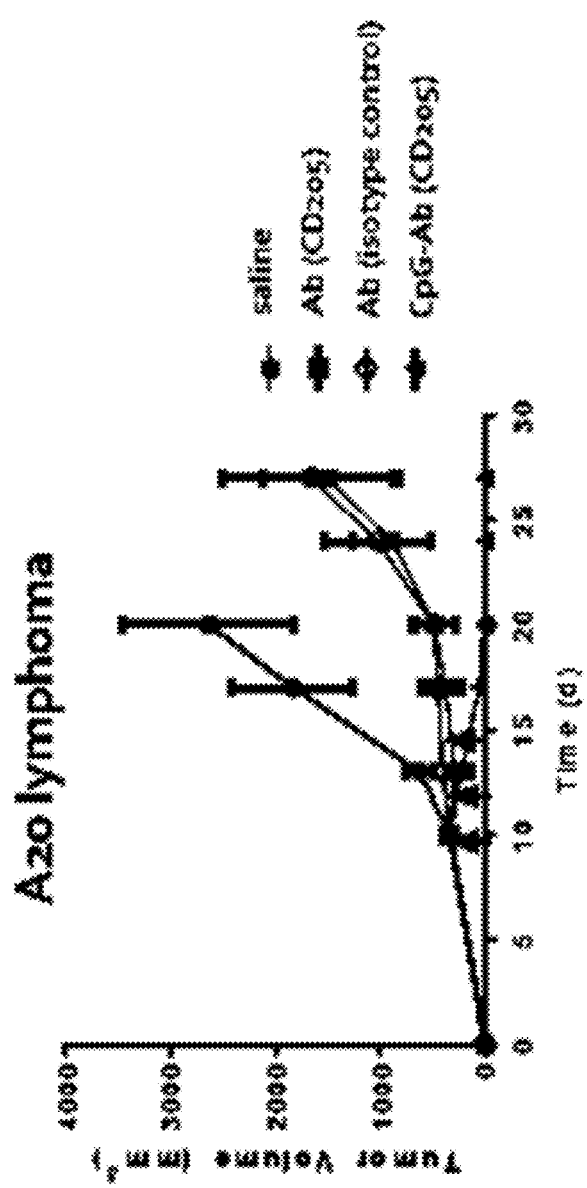
FIG. 57A shows the average tumor volume in mice having solid B-cell lymphoma after receiving intravenous doses of (i) 10 mg/kg CpG-Ab (CD205) (triangle); (ii) 10 mg/kg anti-CD205 antibody (square); (iii) 10 mg/kg mouse IgG (open circle); or (iv) saline solution (closed circle), on each of Days 10, 12 and 14.
Figure 57B:
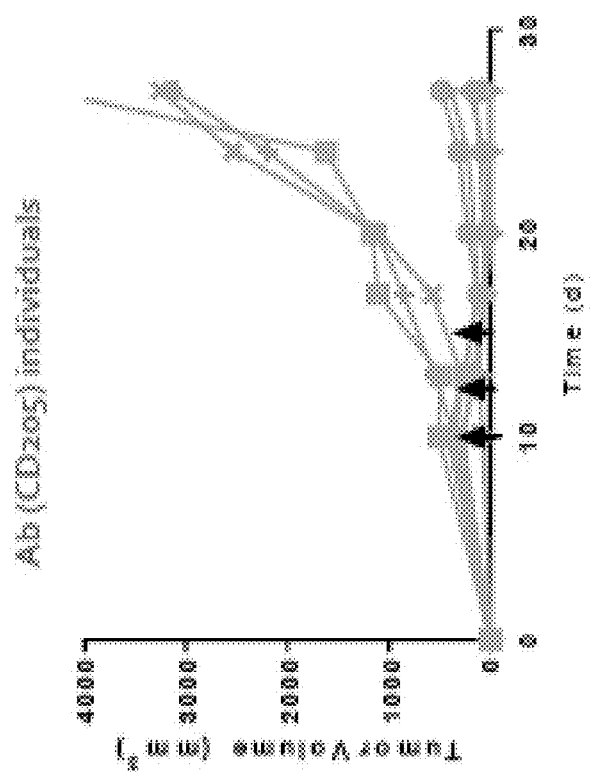
FIG. 57B shows the tumor volumes in individual mice having solid B-cell lymphoma after receiving intravenous doses of 10 mg/kg anti-CD205 antibody on each of Days 10, 12 and 14.
Figure 57C:
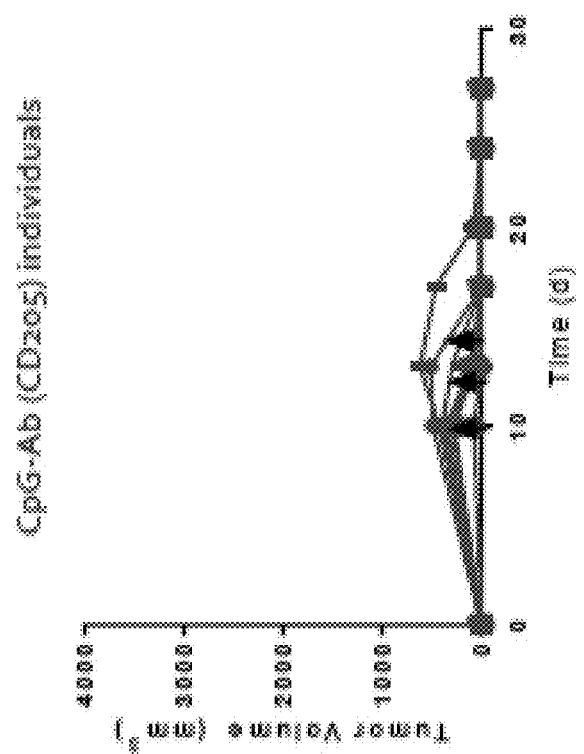
FIG. 57C shows the tumor volumes in individual mice having solid B-cell lymphoma after receiving intravenous doses of 10 mg/kg CpG-Ab (CD205) on each of Days 10, 12 and 14.
Figure 57D:
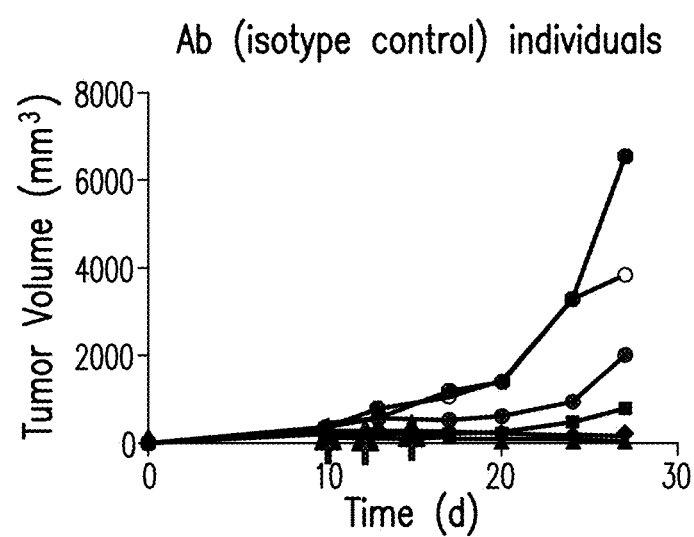
FIG. 57D shows the tumor volumes in individual mice having solid B-cell lymphoma after receiving intravenous doses of 10 mg/kg rat IgG2a antibody on each of Days 10, 12 and 14.

As shown in FIGS. 57A and 57C, treatment with the CpG-Ab (CD205) conjugate regressed tumor growth and eventually resulted in the tumor-free phenotype in all 8 individuals of the treatment group. Also, tumors regressed in mice treated with anti-DEC205 antibody and rat IgG control antibody. This is perhaps due to the fact that both antibodies, as IgG2, possess an active Fc effector function which resulted in moderate anti-tumoral activity, although none of the mice were tumor free. Thus, despite the fact that the anti-DEC205 antibody showed anti-tumoral activity, the CpG-CD205 conjugate was significantly more efficacious as all the mice were tumor free.

Taken together, these data suggest that CpG-Ab conjugates targeting dendritic cells can elicit sustained adaptive immunity against tumor upon administration to a subject.

Example 16 CpG-CD19 Conjugates Show Good Efficacy

A solid B-cell lymphoma disease model was created by implanting $4 \times 10^6$ A20 lymphoma cells in mice, as described above. Briefly, the cells were injected subcutaneously and tumor growth was measured using a caliper. The CpG-mAb conjugate and the naked CpG were made as described above.

Figure 60A:
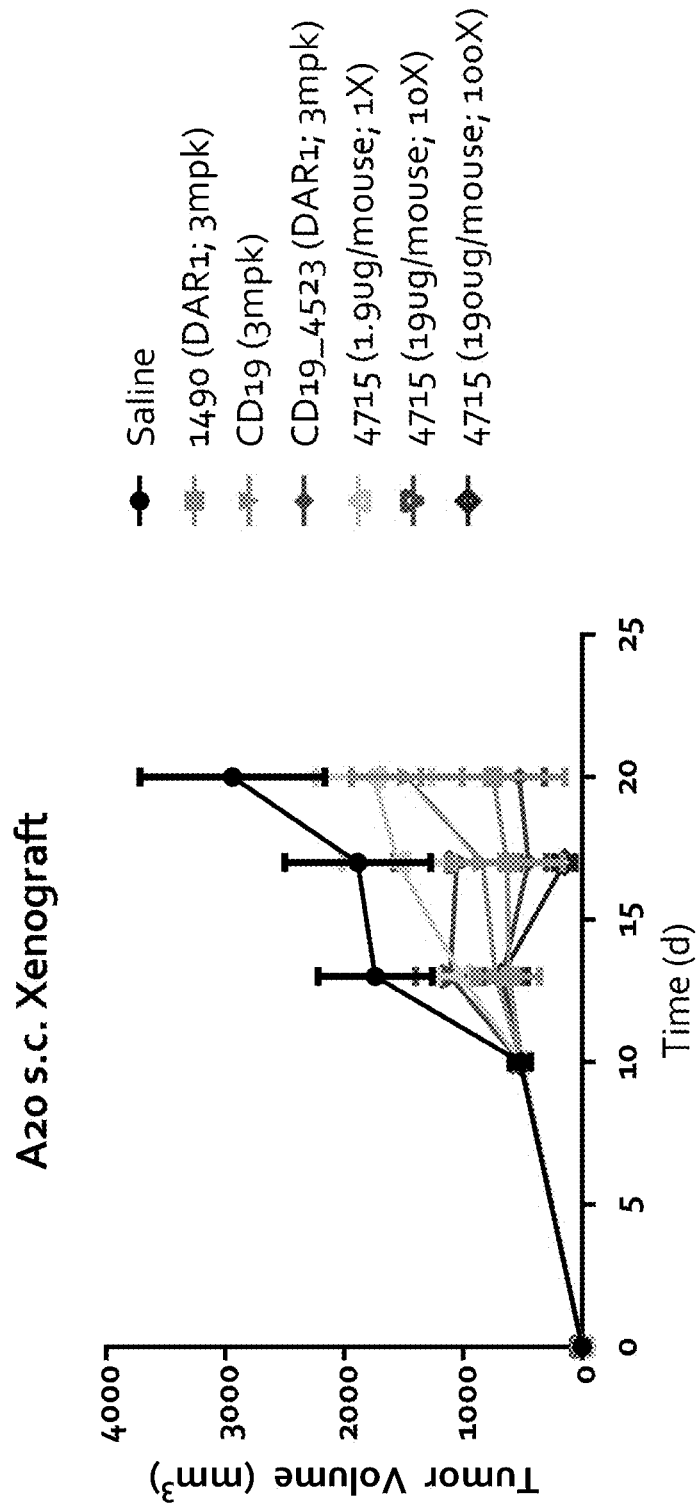
FIG. 60A shows the average tumor volume growth progression of mice with A20 mouse B-cell lymphoma cell xenografts following intravenous doses of (i) saline solution (closed circle); (ii) 3 mg/kg CpG-Ab (4523-CD22; SB-337) (square); (Hi) 3 mg/kg CD19-mAb (down closed triangle); (iv) 3 mg/kg CpG-Ab (4523-CD19; SB-388) (closed diamond); (v) 1.9 µg/mouse naked CpG (P347) (up triangle); (vi) 19 µg/mouse naked CpG (p347) (down open triangle); (vii) 190 µg/mouse naked CpG (P347) (open diamond); on each of Days 10, 12 and 14.

Mice were implanted with A20 lymphoma cells on Day 0. Mice were staged for 10 days and then treated on Day 10, 12 and 14, and tumor growth was measured until Day 20 (FIG. 60A). Treatment included intravenous injections of (i) 3 mg/kg CpG-Ab (SB-337; p313 conjugated to CD22) (square); (iii) 3 mg/kg anti-CD19 (down closed triangle); (iv) 3 mg/kg CpG-Ab (SB-388; p313 conjugated to CD19) (closed diamond); (v) 1.9 µg/mouse free CpG (p347) (up triangle); (vi) 19 µg/mouse free CpG (p347) (down open triangle); or (vii) 190 µg/mouse free CpG (p347) (open diamond). Additionally, a negative control group received only saline solution (closed circle). Tumor volumes of the groups of mice were measured using a caliper starting at Day 10, and continued until Day 20 (FIG. 60A). On Day 20, the mice were sacrificed and the tumor volume was measured (FIG. 60B). The results indicated that the CpG-Ab conjugate (SB-388) that contained p313 conjugated to CD19 displayed good efficacy, and the efficacy was similar to the CpG-Ab conjugate (SB-337) that contained the same CpG (p313), but was conjugated to CD22.

In addition, the body weight change of the mice, discounting the change in tumor weight, was assessed (FIG. 60C). The preliminary safety results indicated that the CD19 CpG-Ab (SB-388) was less toxic than its equivalent dose of CpG, based on the body weight change.

In the current and following examples, CpG-4715 corresponds to p347 as shown in Table 2; CpG-4523 corresponds to p313 as shown in Table 2. SB-1490 corresponds to SB-337 as shown in Table 6-A; and SB-3055 corresponds to SB-388 as shown in FIG. 6-B.

Example 17 Intratumoral Dosing of CpG4715 in Solid Tumors is Efficacious

To assess the intratumoral dosing of CpG in solid tumors, albino C57B1I/6 mice (n=8/group) were inoculated subcutaneously on the flank with 1×10$^6$ B16F10 melanoma cells. The tumors were allowed to grow for seven days, and then p347 was injected intratumorally (30 µg in 50 µL of saline) on days 7, 9, 11, and 13. As a negative control, 50 µL of saline was injected intratumorally in the saline treated group. Tumor volumes were monitored until day 27. The results indicated that p347 is efficacious in solid tumor types, as indicated by the smaller tumor volume in mice treated with p347, relative to saline (FIG. 61A).

In addition, the systemic effect of the CpG was monitored by re-challenging the B16F10 melanoma cells into the mice by injecting 1×10$^6$ B16F10 melanoma cells intravenously into the tail vein on day 14. Tumor volumes were monitored until day 27, whereupon the mice were sacrificed and their lungs were excised to assess tumor metastases. The results revealed that upon re-challenging the mice by injecting non-treated melanoma cells into the tail vein, there were less lung metastases in the p347 treated group compared to the saline treated group (FIG. 61B). Collectively, these results indicated that CpG provides a systemic effect, and the prolonged effect from immune activation is able to reduce the total number of metastases to the lung.

To determine the mechanism of action pertaining to the systemic effect more carefully, the CT-26 colorectal mouse model was employed, as described above. Briefly, the tumors were allowed to grow for seven days, and then p347 was injected intratumorally (10 µg in 50 µL of saline) on days 7, 10, 12, and 14. As a negative control 50 µL of saline was injected intratumorally in the saline treated group. The tumor volumes were monitored until day 21 (FIG. 61C). In agreement with the B16F10 melanoma model, intratumor dosing of CpG4715 was efficacious in CT26 solid tumors. Importantly, the results indicated host TLR9 is sufficient for function of CpG treatment, since CT26 cells are TLR9-.

Example 18 Anti-Tumor Effect of CpG-Ab Conjugate is B-Cell Dependent

Figures 62A, 62B:
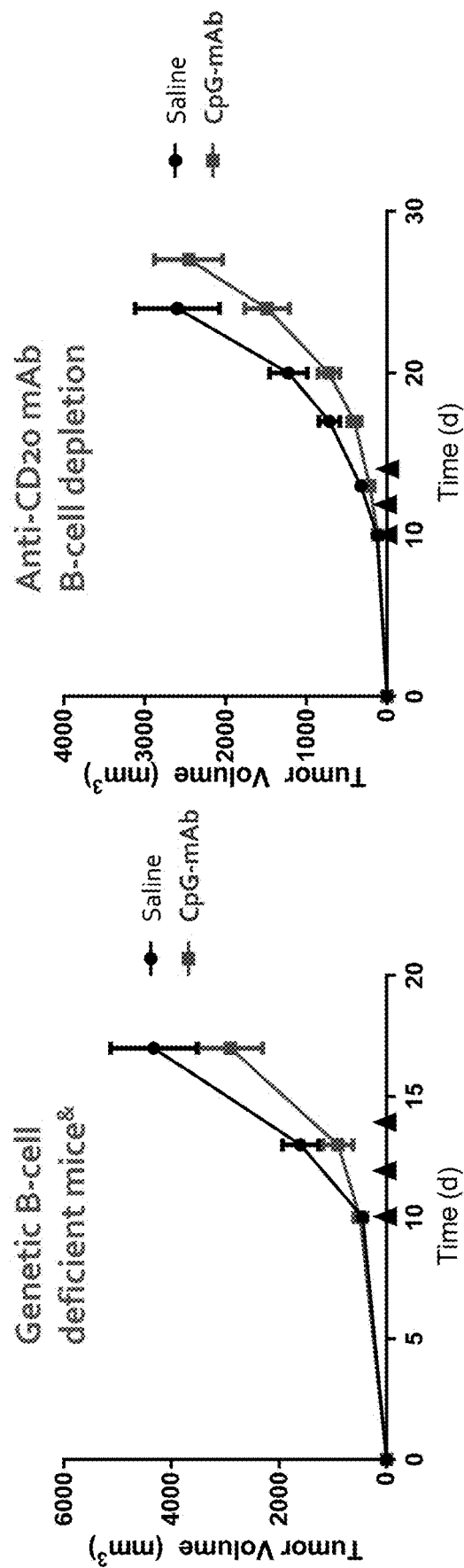
FIG. 62A shows the average tumor volume growth progression of genetic B-cell deficient mice using CT26 colorectal model following intravenous dosing of (i) saline solution (circle); or (ii) 10 mg/kg CpG-mAb (SB-337) (square); on each of Days 10, 12, and 14.
FIG. 62B shows the average tumor volume growth progression of anti-CD20 mAb B-cell depleted mice using CT26 colorectal model following intravenous dosing of (i) saline solution (circle); or (ii) 10 mg/kg CpG-mAb (SB-337) (square); on each of Days 10, 12, and 14.

Experiments were performed to evaluate the role of B cells on the activity of CpG. To this effect, the CT26 colorectal model was used, as described above, in Jh knock-out mice that are genetic B-cell deficient (Igh-J$^{tm1Dhu}$N?+ N2; Taconic Biosciences, Inc) (FIG. 62A). These mice have a deletion of the endogenous murine J segments of the Ig heavy chain locus, resulting in the cells of the B lineage being drastically altered both in developmental progression and in cell quantity. The mice contain no mature (immunoglobulin-bearing) B-lymphocytes in the spleen, bone marrow, lymph nodes, peripheral blood or peritoneum, and they have no detectable IgM or IgG in the sera.

CT26 xenografts were created, as described above. The tumors were grown for seven days, and then mice were treated intravenously with 10 mg/kg CpG-mAb (CD22-CpG; SB-337), or saline on days 10, 12, and 14 (FIG. 62A). The tumor volume was monitored for 17 days, with no significant difference being observed between the saline and CpG-mAb groups. This indicated that B-cells are required for CpG activity.

The results were further supported using a CT-26 colorectal model in a mouse background that had B-cells depleted by administering mice immunocompetent mice with anti-CD20 mAb (FIG. 62B). The tumor volume was measured for 27 days. The anti-tumor effect of the CpG-mAb treatment group was significantly reduced as compared to treatment without B cell depletion. This result further supported that CpG activity is B-cell dependent.

Figure 63A:
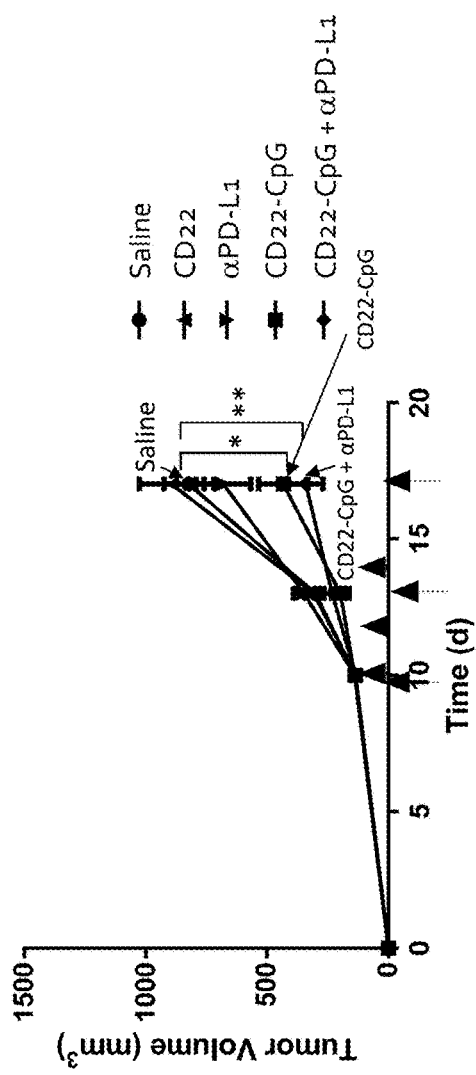
FIG. 63A shows the average tumor volume growth progression of mice using a MC38 colorectal syngeneic model following dosing of (i) saline solution (circle); (ii) 10 mg/kg anti-CD22 (upward triangle); (iii) 10 mg/kg anti-PD-L1 (downward triangle); (iv) 10 mg/kg CD22-CpG (SB-337) (square); or (v) 10 mg/kg CD22-CpG (SB-337)+10 mg/kg anti-PD-L1 (diamond). Anti-CD22 and CD22-CpG were dosed intravenously on Days 10, 12, and 14; anti-PD-L1 was dosed intraperitoneally on Days 10, 13, and 17. * p=0.01; **p=0.001.
Figure 63B:
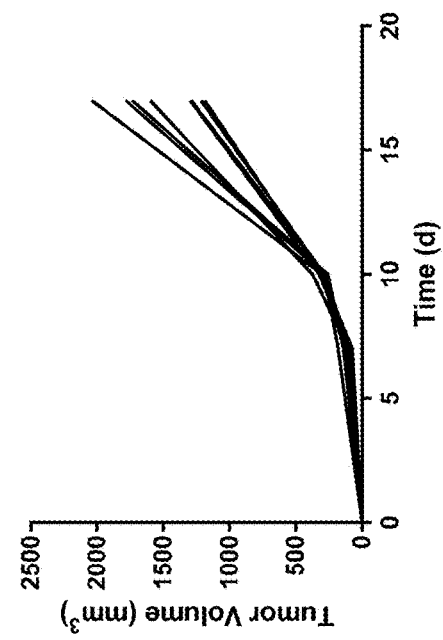
FIG. 63B shows the tumor volume growth progression of each mouse using a MC38 colorectal syngeneic model following intravenous dosing saline on Days 10, 12, and 14

Example 19 B-Cell Activation Enhances CpG Anti-Tumor Activity in Syngeneic Mouse Models A syngeneic model of colorectal cancer was performed using MC38 colorectal cancer cells to assess the effect of B-cell activation on CpG anti-tumor activity. MC38 colorectal cancer cells are antigen/TLR9 negative. Briefly, albino female C57B1I/6 mice (n=8/group) were inoculated subcutaneously on the flank with 0.3×10$^6$ MC38 cells. The xenografts were grown for 10 days, and then the test compounds were injected with (i) saline solution (circle); (ii) 10 mg/kg anti-CD22 (upward triangle); (iii) 10 mg/kg anti-PD-L1 (downward triangle); (iv) 10 mg/kg CD22-CpG (SB-337) (square); or (v) 10 mg/kg CD22-CpG (SB-337)+10 mg/kg anti-PD-L1 (diamond). Anti-CD22 and CD22-CpG were dosed intravenously on Days 10, 12, and 14; anti-PD-L1 was dosed intraperitoneally on Days 10, 13, and 17 (FIG. 63A). The tumor volumes were monitored until day 17 (FIG. 63A).

The results indicated that treatment with 10 mg/kg CD22-CpG (SB-337) (square) significantly reduced the tumor volume, relative to saline treatment (FIG. 63A). Similarly, treatment with 10 mg/kg CD22-CpG (SB-337)+10 mg/kg anti-PD-L1 (diamond) significantly reduced the tumor volume, compared to saline treated mice. The results for the individual mice for each of the treatments is also indicated (FIG. 63B-FIG. 63F).

In addition, the assessment of B-cell activation was performed using the B16F10 melanoma model. Briefly, $1 \times 10^6$ B16F10 melanoma cell were inoculated subcutaneously on the flank of mice, and tumors were allowed to grow for 10 days. Mice were then dosed with (i) saline solution (circle); (ii) 10 mg/kg anti-CD22 (square); (iii) 10 mg/kg CD22-CpG (SB-337) (triangle); or (iv) 10 mg/kg CD22-CpG (SB-337)+ 10 mg/kg anti-PD-L1 (diamond) on Days 10, 12, and 14 (FIG. 64A). Anti-CD22 and CD22-CpG were dosed intravenously; anti-PD-L1 (Atezolizumab) was dosed intraperitoneally. The results indicated that CD22-CpG treatment reduced tumor volume (p=0.08). Similarly, treatment with CD22-CpG+anti-PD-L1 significantly reduced tumor volume (p=0.03).

Consistent with the colorectal and melanoma models, mice inoculated with LLC1 Lewis lung cancer cells showed similar results. Mice were inoculated with LLC1 Lewis lung cancer cells and the average tumor volume growth progression of mice was followed. Starting at day 7 the mice were treated with (i) saline solution (circle); (ii) 10 mg/kg CD22-CpG (SB-337) (circle); (iii) 10 mg/kg anti-PD1 (square); (iv) 10 mg/kg CD22-CpG (SB-337)+10 mg/kg anti-PD1 (upward triangle) (v) 10 mg/kg anti-PD-L1 (downward triangle); (vi) 10 mg/kg CD22-CpG+10 mg/kg anti-PD-L1 (diamond) (FIG. 64B). Anti-CD22 and CD22-CpG were dosed intravenously on Days 7, 10, and 13; anti-PD-L1 and anti-PD1 were dosed intraperitoneally on Days 7, 10, and 14. The results showed that mice treated with 10 mg/kg CD22-CpG alone or in combination with 10 mg/kg anti-PD1 (upward triangle) or in combination with 10 mg/kg anti-PD-L1 (diamond) displayed a significant reduction in tumor volume (p=0.023). Taken together, these results indicated that CD22-CpG treatment can reduce LLC1 tumor volume.

Example 20 Efficacy of Targeting CpG to B-Cells or Dendritic Cells

Experiments were performed to compare the efficacy of targeting CpG to B-cells versus targeting CpG to dendritic cells. Using the CT26 colorectal model, as described above, mice were treated intravenously with CpG conjugated to CD22 (CD22-CpG; SB-337) to target B cells, CpG conjugated to DEC205 (DEC205-CpG; SB-419) to target dendritic cells, or saline. Mice were treated with 10 mg/kg of CpG-Ab on days 12, 17, 20, and 24. Tumor volumes were measured and the average volume (FIG. 65A), as well as the individual tumor volumes for each mice (FIG. 65B-65D) are presented. The results reveal that targeting either B-cells or dendritic cells with a CpG-Ab conjugate is able to reduce the tumor volume.

Example 21 CpG-Ab Activity is CD4+ T-Cell Dependent in CT26 Colorectal Model, but not in A20 Lymphoma Model To investigate the role of T-cells in the mechanism of action for CpG, two mouse models were employed. In the first model, CT26 colorectal cancer cells were used. Briefly, CT26 mouse models were created as described above, and the average tumor volume growth progression of mice was followed after dosing with (i) saline solution (small circle); (ii) CD4 depletion (big circle); (iii) 3 mg/kg CD22-CpG (SB-337) (square); or (iv) CD4 depletion+3 mg/kg CD22-CpG (SB-337) (diamond). CD22-CpG was dosed intravenously on Days 10, 13; and 15 (FIG. 66A). CD4 depletion was performed using anti-CD4 antibody (clone GK1.5, 400 ug/dose) injected intraperitoneally on days 10, 13 and 17.

The results from this experiment demonstrated that CD4+ T-cell depletion using CD4 antibodies inhibits the CpG-Ab activity in a CT26 colorectal cancer model (FIG. 66A).

In contrast, CpG-Ab activity was not inhibited upon CD4+ T-cell depletion in a A20 lymphoma model. Briefly, the average tumor volume growth progression of mice using an A20 lymphoma model was followed after dosing the mice with (i) saline solution (circle); (ii) CD4 depletion (upward triangle); (iii) 3 mg/kg CD22-CpG (SB-337) (square); or (iv) CD4 depletion+3 mg/kg CD22-CpG (SB-337) (downward triangle) (FIG. 66B). CD22-CpG was dosed intravenously on Days 10, 12; and 14. CD4 depletion was performed using anti-CD4 antibody (clone GK1.5, 400 ug/dose) injected intraperitoneally on days 10, 13 and 17. In this model, CD22-CpG reduced the tumor model, relative to saline. However, CD4 depletion did not affect the CpG-Ab activity.

Example 22 B-Cell CpG-Ab Induces Surface T-Cell Co-Stimulators

The role of T-cell activation in B-cell directed CpG-Ab (SB-1490) was assayed by measuring the expression of surface T-cell co-stimulators on B-cells that were treated with antibody, CpG (p347), or CpG-Ab (SB-337). The mouse spleen was harvested and passed through a 70 micron sieve to generate a single cell suspension. The red blood cells (RBC) were lysed by incubation with RBC lysis buffer for 5 min at room temperature and then quenched with complete media. The B-cells were further isolated by negative selection using a mouse B-cell isolation kit (Miltenyi Biotec). Cells were harvested by gentle centrifugation, washed, and re-suspended at a concentration of $2 \times 10^6$ cells/mL in RPMI containing 10% fetal bovine serum (FBS), and 1% penicillin/streptomycin (PS). Cells were then seeded in 96-well plates, and treated with the test compounds at the indicated concentration (1 nM), and incubated at 37° C. for 72 hours. Cells were then harvested by gentle centrifugation and re-suspended in FACS buffer. After centrifugation again, the cells were then re-suspended in 500 µL FACS buffer. Mouse FcR Blocker was added and incubated for 10 min at room temperature. Cells were transferred to ice and appropriate labeled FACS antibodies (see examples below) were added and incubated on ice for 30 min. Non-specific isotype controls were used. Then, cells were collected in FACS buffer in Eppendorf tubes. Cells were centrifuged, washed once with FACS buffer, and then re-centrifuged. Cells were then re-suspended in 1 mL FACS buffer again, then kept on ice until analysis by CyFlow ML FACS machine. Data was analyzed using Flow Jo software.

The results from the in vitro incubation of mouse spleen B-cells with antibody, free CpG (SB-4715), or CpG-Ab (SB-1490) conjugate revealed that B-cell directed CpG-Ab conjugate induces the surface T-cell co-stimulators, such as CD40, CD70, CD80, CD86, MHC-I, MHC-II, and 4-1 BBL (FIG. 67A).

Similar results were obtained from mice that were treated in vivo. Briefly, mice were treated with 10 mg/kg, three times per week, and CD19+/B220+ B-cells were analyzed 3-days post the final dose. Mouse spleens/lymph nodes were harvested, rinsed with PBS and passed through a 70 micron sieve to generate a single cell suspension. Cells were centrifuged gently and then re-suspended in FACS buffer. FcR Blocker was added (1:20 dilution) and incubated for 10 min at room temperature. Cells were transferred to ice and appropriate labeled FACS antibodies (or non-specific isotype controls) were added and incubated on ice for 30 min. Cells were collected in FACS buffer in Eppendorf tubes.

Cells were centrifuged, then washed once with 1 mL FACS buffer, then centrifuged again. Cells were re-suspended in 1 mL FACS buffer again, then kept on ice until analysis by CyFlow ML FACS machine. Data was analyzed using Flow Jo software. Treatment with CpG-Ab resulted in increased surface expression of CD40, CD80, CD86, and MHC-II, relative to saline (FIG. 67B).

| Marker | Name | Isotype | Fluorophore |
|---|---|---|---|
| CD137L | 4-1BBL | rat IgG2a | PE |
| CD252 | OX40L | rat IgG2b | PE |
| CD274 | PD-L1, B7H1 | rat IgG2b | PE |
| CD275 | ICOSL, B7H2 | rat IgG2a | PE |

Example 23 B-Cell CpG-Ab Induces T-Cell Activation in Secondary Lymphoid Tissues The activation of T-cells in secondary lymphoid tissues was measured by FACS to evaluate the functional effect of B-cell targeted CpG-Ab conjugates. Briefly, Balb/c mice were treated with treated with (i) saline (solid); (ii) 10 mg/kg Ab (anti-CD22) (checkered); (iii) 10 mg/kg CpG-Ab (SB-SB-337) (horizontal); or (iv) an equivalent dose of CpG (p347) (vertical), three times per week. Three days post the last dose the mouse spleen and lymph nodes were harvested, and CD3 T-cells were analyzed by FACS. Mouse spleens/lymph nodes were harvested, rinsed with PBS and passed through a 70 um sieve to generate a single cell suspension. Cells were centrifugated gently and then re-suspended in FACS buffer. FcR Blocker was added (1:20 dilution) and incubated for 10 min at room temperature. Cells were transferred to ice and appropriate labeled FACS antibodies (or non-specific isotype controls) were added and incubated on ice for 30 min. Cells were collected in FACS buffer in Eppendorf tubes. Cells were centrifuged, then washed once with 1 mL FACS buffer, then centrifuged again. Cells were re-suspended in 1 mL FACS buffer again, then kept on ice until analysis by CyFlow ML FACS machine. Data was analyzed using Flow Jo software Activated T-cells were quantified by measuring the percentage of CD71+, CD3+ cells, relative to the total T-cell population (CD3+) (FIG. 68A). Activated T-cells were also quantified by measuring the amount of Ki67+, CD3+ cells, relative to the total T-cell population (CD3+) (FIG. 68B). The FACS results revealed that the B-cell targeting CpG-Ab conjugate, and, to a lesser extent free CpG, increase the percentage of activated T-cells in secondary lymphoid tissues.

Example 24 Adoptively Transferred Lymph Node Cells Inhibit Tumor Growth

Experiments to further analyze the role of T-cell activation in B-cell targeting CpG-Ab conjugates were performed using the CT-26 mouse colorectal cancer model. The CT-26 mouse colorectal model was created as described above. Tumors were staged on day 10 and mice were dosed intravenously with (i) saline solution (circle); (ii) 10 mg/kg CD22-CpG (SB-337) (square); (iii) 10 mg/kg CD22 (upward triangle); or (iv) free CpG (p347) (downward triangle) on days 10, 12, 14 (FIG. 69A). Tumor growth was monitored for 22 days (32 days from the day of inoculation) (FIG. 69A). In agreement with the other results described above, CD22-CpG resulted in lower tumor volumes, relative to the other treatment groups.

On day 32, the mice were sacrificed and lymph nodes (draining and non-draining) were isolated and pooled from mice in each treatment group. The lymph nodes were passed through a 70 mm sieve to generate a single cell suspension. Cells were washed twice with ice-cold PBS and counted. $1 \times 10^7$ cells (approximately 70% T-cells) were mixed with $0.1 \times 10^6$ CT-26 cells in HBSS buffer, and the mixture was inoculated subcutaneously on the flanks of naive BalbC mice, as per standard protocol. Tumor volume was monitored in these mice for 24 days (FIG. 69B). The results indicated that adoptively transferred lymph node cells inhibit tumor growth (FIG. 69C)

Example 25 B-Cell CpG-Ab Induces Innate Immune Response

The effect of B-cell targeting CpG-Ab conjugates on the innate immune response was analyzed by intravenously treating naïve mice with (i) saline (solid); (ii) 10 mg/kg Ab (CD22) (checkered); (iii) 5.7 ug CpG (p347) (horizontal); or (iv) 10 mg/kg CpG-mAb (SB-337). Blood was collected from the tail at the indicated time points and the serum was isolated by centrifugation. Serum cytokine levels was measured by bead-based multiplex analysis (LEGENDplex, Biolegend).

After treating the mice, multiple plasma cytokines associated with the innate immune response (i.e. IL-6, IL-10, IL-1p, IL-12p70, IFNγ, and TNFα) were measured 1 hr, 6 hr, and 24 hr after treatment (FIG. 70A-70F). The results indicated that B-cell targeting CpG-Ab conjugates induce a favorable cytokine profile for T-cell, dendritic cell (DC), and natural killer (NK) cell activation. Notably, IL-1p3 (FIG. 70C), and IL-12p70 (FIG. 70D) concentrations were highly elevated at 6 hr. Furthermore, it was observed that free CpG strongly increased TNFα (FIG. 70F) plasma concentration levels at 1 hr, whereas this effect was not observed with the CpG-mAb conjugate, suggesting that CpG-mAb can have a safety advantage over free CpG.

Example 26 B-Cell CpG-Ab Induces B-Cell Differentiation and Germinal Center Formation To assess whether B-cell CpG-Ab induces B-cell differentiation and germinal center formation the CT-26 colorectal cancer model was employed according to the methods described above. Briefly, mice were inoculated with CT-26 colorectal cancer cells, and allowed to grow for 10 days. Mice were then treated intravenously with saline or 10 mg/kg CpG-mAb (SB-1490) on days 10, 13, and 17 and were sacrificed 24 hours after the last dose. The spleens were isolated single cell preparations were prepared as mentioned above and the percentage of B-cells (B220*; FIG. 71A), GC cells (B220$^+$, IgD$^{lo}$, Fas$^+$; FIG. 71B), and T follicular helper (Tfh) cells (CD4+, CXCR5+, PD-1+; FIG. 71C) relative to the total number of cells in the spleen were determined using FACS analysis. In addition, the relative fold changes of IL-21 (FIG. 71D), Bcl-6 (FIG. 71E), and IRF-4 (FIG. 71F) gene expression were determined using standard qPCR methods. The results demonstrated that CpG-mAb significantly increased the percentage of B-cells, GC cells, and Tfh cells, as well as significantly increased the expression levels of IL-21, Bcl-6, and IRF-4. Taken together, these results demonstrated that B-cell targeting CpG-Ab conjugate induces B-cell differentiation and GC formation.

Example 27 B-Cell CpG-Ab Induces Innate and Adaptive Immune Responses

The effect of B-cell CpG-Ab treatment on the innate and adaptive immune responses was measured using the CT-26 colorectal cancer model. CT-26 colorectal mouse model was created as described above. To assess the innate immune response, tumors were inoculated subcutaneously and grown for ten days. On days 10, 13, and 17 the mice were treated intravenously with saline, or 3 mg/kg of CpG-mAb (SB-337) and were sacrificed 24 hours after the last dose. Cells were isolated from the spleen and lymph nodes, and the gene expression of several genes associated with the innate immune response (i.e. IL-6, IL-10, IL-1β, and TNFα) were measured by qPCR. The results revealed that treatment with the CpG-mAb increased the expression of IL-6, IL-10, and IL-1 in the spleen (FIG. 72A-C) and the draining lymph node (FIG. 73A-C). However, the CpG-mAb did not increase TNFα expression in either the spleen (FIG. 72D) or the draining lymph node (FIG. 73D). Collectively, these results demonstrated that the B-cell targeting CpG-Ab conjugate induces the innate immune response.

Next, the effect of the B-cell CpG-Ab treatment on the adaptive immune response was measuring using the CT-26 solid tumor model. CT-26 colorectal mouse model was created as described above. To assess the adaptive immune response, tumors were inoculated subcutaneously and grown for ten days. On days 10, 13, and 16 the mice were treated intravenously with saline, or 3 mg/kg of CpG-mAb (SB-337) and the mice were sacrificed on day 24, blood was collected by cardiac puncture and serum levels of IgM, IgG and IgG2a were measured by ELISA. Sera was collected from the mice and the levels of IgM, IgG, and IgG2a were measured. For the mice treated with CpG-mAb, IgM (FIG. 74A), IgG (FIG. 74B), IgG2a (FIG. 74C) were all significantly increased, relative to saline treated mice.

The levels of the tumor-specific antibodies were further analyzed by performing an ELISA using the CT-26 tumor antigen AH1 as the substrate. AH1 peptide was coated onto 96-well placets overnight and the wells were then washed three times with ELISA wash buffer to remove excess peptide. Mouse serum samples were added and incubated for 2 hours at room temperature. The wells were then rinsed x3 again and the amount of mouse anti-AH1 IgG2a in the serum was measured using two different commercially available secondary anti-mouse IgG2a-HRP antibodies, $2^{nd}$ Ab1 and $2^{nd}$ Ab2 (FIG. 75). The wells were washed again and a TMB substrate solution (100 µL) was added to each well. After the plate was incubated at room temperature for 15-30 minutes or until desired color is developed, a stop solution (100 µL) was added to each well and the plate was read at 450 nm. In agreement with there being more IgG2a in the sera of the mice, treatment with CpG-mAb resulted in significantly more tumor-specific IgG2a in the sera. These results indicated that the B-cell CpG-Ab induces an adaptive response that produces a class switch to high affinity tumor-specific antibodies.

Example 28 B-Cell CpG-Ab Reduces B-Reg Population

The effect of the B-cell targeting CpG-Ab conjugate on splenic B-reg cells was analyzed. Balb/C mice (n=8) were treated with saline or 10 mg/kg of CpG-Ab (SB-337) on days 1, 4 and 7. The mice were sacrificed 14 days after the last dose. The percentage of splenic Breg cells (CD19+, B220+, $CD1d^{hi}$) was determined, relative to the number of B-cells (B220+) (FIG. 76A). In addition, the percentage of splenic B-reg cells (CD19+, B220+, $CD1d^{hi}$) was determined, relative to the total number of cells (FIG. 76B). Quantification of the percentage of B-reg cells under both parameters revealed that CpG-mAb treatment significantly reduced the B-reg population in the mice, relative to saline treatment (FIG. 76A and FIG. 76B). These results demonstrated that B-cell CpG-Ab reduces the B-reg population.

Example 29 B-Cell CpG-Ab Expands DC Population in Secondary Lymphoid Tissues

To assess the effect of B-cell targeted CpG-Ab treatment on the dendritic cell population in secondary lymphoid tissues the CT-26 solid tumor model was used. Mice were treated intravenously with saline, 5.7 ug/dose CpG (p347), or 10 mg/kg CpG-mAb (SB-337) on days 14, 17, 20. Cells from the spleens were isolated as described above. The percentage of spleen myeloid dendritic cells (mDC; B220-, CD11C+, $DEC205^{hi}$) was calculated, relative to the total number of cells. Quantification of the spleen mDC percentage revealed that both free CpG and the CpG-mAb treatment significantly increased the percentage of mDC cells, relative to saline treatment (p=0.003; p=0.0002, respectively) (FIG. 77A). Furthermore, the percentage of mDC cells after CpG-Ab treatment was significantly increased relative to the free CpG (p=0.002) (FIG. 77A). Taken together, these results demonstrated that CpG-Ab treatment expands the mDC pool in the spleen.

In addition, the percentage of pooled lymph node mDC cells (B220-, CD11C+, CD8+) were determined. Treatment of mice with CpG-mAb resulted in an increased percentage of LN mDCs, in both the draining lymph node (dLN), and the non-draining lymph node (ndLN) (FIG. 77B). However, the effect was not observed upon treatment with free CpG (FIG. 77B), which highlights the differential effect between the CpG-Ab conjugate and free CpG. The results indicated that B-cell targeting CpG-Ab conjugates can expand the dendritic cell population in both the spleen, and the lymph nodes.

Example 30 pDCs Contribute to CpG-Ab Activity

Experiments using the CT26 colorectal cancer model and the A20 lymphoma model were performed to determine the contribution of plasmacytoid dendritic cells (pDCs) on CpG-Ab activity. In the CT-26 colorectal model, tumors were grown for 10 days, and then mice were treated intravenously with saline, or 3 mg/kg CD22-CpG (SB-337) on days 10, 13, and 15. In addition, some mice were intraperitoneally injected with PDCA1 antibody, clone BX444, (300 µg per mouse), alone or in combination with CD22-CpG (SB-337) on days 10, 13, and 17 to deplete the pDC cells. The tumor volume progression was measured, and the results indicated that pDC depletion decreased the efficacy of CD22-CpG in the CT-26 colorectal model (FIG. 78A).

The A20 lymphoma model yielded similar results. A20 lymphoma tumors were grown for 10 days and then mice were treated intravenously with saline, or 3 mg/kg CD22-CpG (SB-337) on days 10, 12, and 14. In addition, some mice were intraperitoneally injected with PDCA1 antibody, clone BX444, (300 µg per mouse), alone or in combination with CD22-CpG (SB-337) on days 10, 13, and 17 to deplete the pDC cells. The tumor volume progression was measured, and the results indicated that pDC depletion decreased the efficacy of CD22-CpG in the A20 lymphoma model (FIG. 78B). Taken together, the results demonstrated that pDCs contribute to CpG-Ab activity.

Example 31 CpG-mAb Increased T-Cell Tumor Infiltrates

The effect of CpG-mAb conjugates on T-Cell Infiltrates was determined using the A20 lymphoma model. Briefly, A20 cells were subcutaneously inoculated into mice, and on days 10, 13, and 17 the mice were intravenously treated with saline or 3 mg/kg of CpG-mAb (SB-337) and animals were sacrificed 24 hours after the last dose. In some experiments, the mice were also treated with 10 mg/kg anti-PD-L1 (FIG. 79D). Tumors from the mice were removed, homogenized at 4° C., mRNA was extracted by standard methods and gene expression analysis was performed by qPCR for T-Cell Genes, such as CD3, CD4, CD8a, and CD8b (FIG. 79A; macrophage Genes, such as CD38, GPR18, iNOS, FPR2, Egr2, Arg1, CD206, Adgre1, CD68, and Cd11b (FIG. 79B); cytokine genes, such as IL-2, IL-4, IL-6, IL-10, IL-13, IL-21, TNFα, IFNγ, and TGFβ (FIG. 79C); and apoptotic enzyme genes, such as granzyme B, and perforin (FIG. 79D). Analysis of the gene expression, relative to peptidyl-propyl isomerase B (PPIB) was determined. The results indicated that CpG-mAb increased the expression of T-Cell genes (FIG. 79A), macrophage genes (FIG. 79B), and certain cytokine genes (FIG. 79C). In addition, CpG-mAb and CpG-mAb+ anti-PD-L1 both increased the expression of apoptotic enzyme genes (FIG. 79D). Collectively, the tumor gene expression profile for the mice treated with CpG-mAb was consistent with the presence and/or activation of immune cells.

Example 32 Human CpG-Ab Activity Confirmed

The effect of CpG-Ab conjugates on primary human B-cells was evaluated by collecting and pooling peripheral blood mononuclear cells (PBMCs) from three donors. Briefly, leukocyte enriched blood (LRS chambers) were obtained from the San Diego Blood Bank. Leukocytes were isolated by standard Ficoll gradient centrifugation protocol. B-cells were further isolated by negative selection using a B-cell Isolation Kit (Miltenyi). B-cells (>95% pure) were re-suspended in RPMI containing 10% FBS and 1% PS and seeded in 96-well plates ($1 \times 10^5$ cells/well). Cells were treated with CpG (p425), CpG-Ab (SB-430), or Ab (hCD22), as indicated, at a range of concentrations and incubated at 37° C. for 48-72 hr.

Following treatment, the culture media was removed and secreted IL-6 levels were measured by ELISA (FIG. 80A). Cells were then harvested and cell surface markers for MHC-II (FIG. 80B), CD86 (FIG. 80C), CD70 (FIG. 80D), and CD20 (FIG. 80E) were measured by FACS. The results indicated that human primary B-cells were more sensitive to CpG-Ab treatment, as determined by the concentration of secreted IL-6 (FIG. 80A), and surface markers for MHC-II (FIG. 80B), CD86 (FIG. 80C), CD70 (FIG. 80D), and CD20 (FIG. 80E).

In addition, human primary splenocytes were analyzed for response to treatment with CpG-Ab conjugates and free CpG. Primary human splenocytes were purchased from Bioreclamation IVT. Cells were re-suspended in RPMI containing 10% FBS and 1% PS ($2 \times 10^6$ cells/ml) and seeded in 96-well plates. Cells were treated with hCD22-hCpG (SB-430), free human CpG p1, or free human CpG (Solstice; p425) at the indicated concentrations and incubated at 37° C. for 24 hrs. The culture media was removed and secreted IL-6 was measured by ELISA. Treatment with hCD22-hCpG was able to increase the concentration of IL-6 at lower doses than free CpG p1 or free human CpG (solstice; p425) (FIG. 81). The $EC_{50}$ values were 0.51 nM, 818 nM, and 338 nM, respectively, which provided further evidence that hCpG-hAb could activate human splenocytes.

Experiments were conducted using a humanized mouse model in NCG mice. This model was created by sequential CRISPR/Cas9 editing of the Prkdc and Il2rg loci in the NOD/Nju mouse, generating a mouse coisogenic to the NOD/Nju. The NOD/Nju carries a mutation in the Sirpa (SIRP a) gene that allows for engrafting of foreign hematopoietic stem cells. The Prkdc knockout generates a SCID-like phenotype lacking proper T-cell and B-cell formation. The knockout of the Il2rggene further exacerbates the SCID-like phenotype while additionally resulting in a decrease of NK cell production. The mice were first treated intraperitoneally with fresh human PBMC and then challenged with subcutaneous injection of Daudi cells ($2.5 \times 10^6$) two days later (FIG. 82A). On days 12, 14, and 16 the mice were treated with saline, 5 mg/kg hCD22 antibody, 5 mg/kg hCD22-CpG (SB-430), or 5.7 µg/dose of free CpG (p425). The average tumor volume was followed for 32 days (FIG. 82B). The results indicated that the mice treated with hCD22-CpG has smaller tumor volumes, relative to the other treatment groups. Collectively, these results indicated that CpG-Ab conjugates are efficacious in human cells.

Example 33

Figure 58:
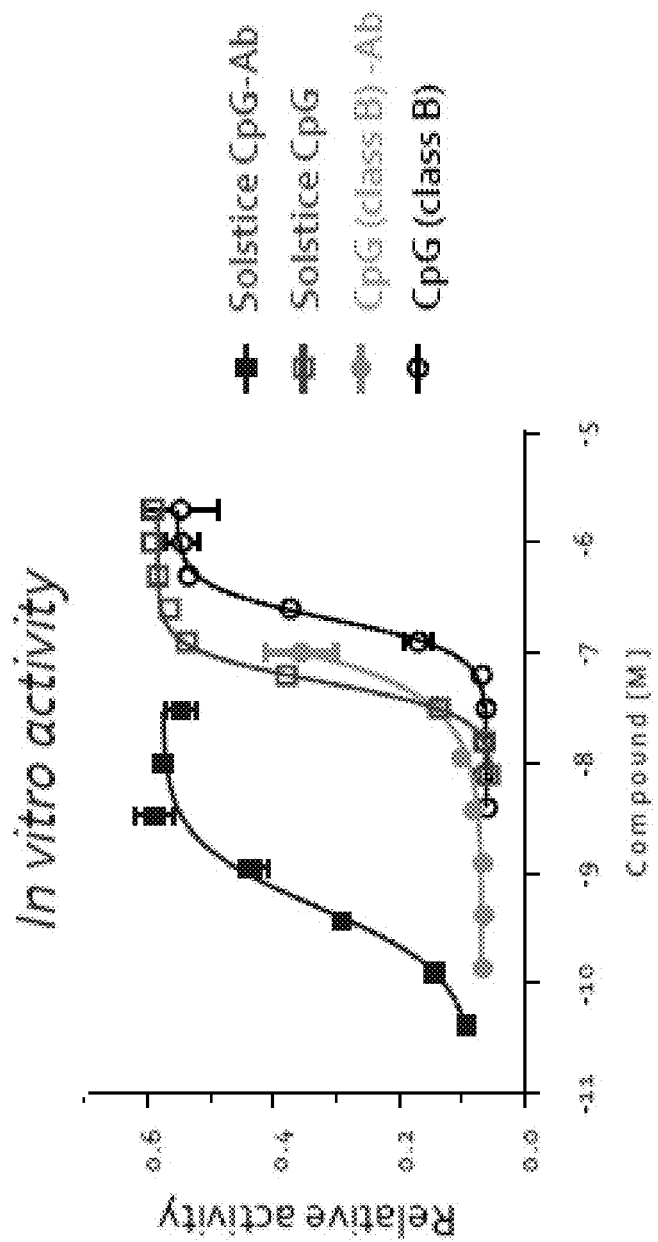
FIG. 58 shows NFκB activation in human Ramos cells after treated with anti-CD38 antibody conjugated to p246 (closed squares), with anti-CD38 antibody conjugated to p4 (closed circles), with unconjugated p246 (open squares) or with unconjugated p4 (open circles).

To demonstrate and compare efficacy of the CpG-containing polynucleotide according to the present disclosure with naturally existing CpG sequences, NFκB activity in human Ramos cells was measured after the cells were incubated with the present CpG-containing polynucleotide either in the free-standing form or in the conjugated form, and with a naturally existing class B CpG sequence either in the free-standing form or in the conjugated form. As shown in FIG. 58B, the present CpG-Ab conjugate had significantly improved activity as compared to the free-standing or conjugated class B CpG.

Example 34

Figure 59:
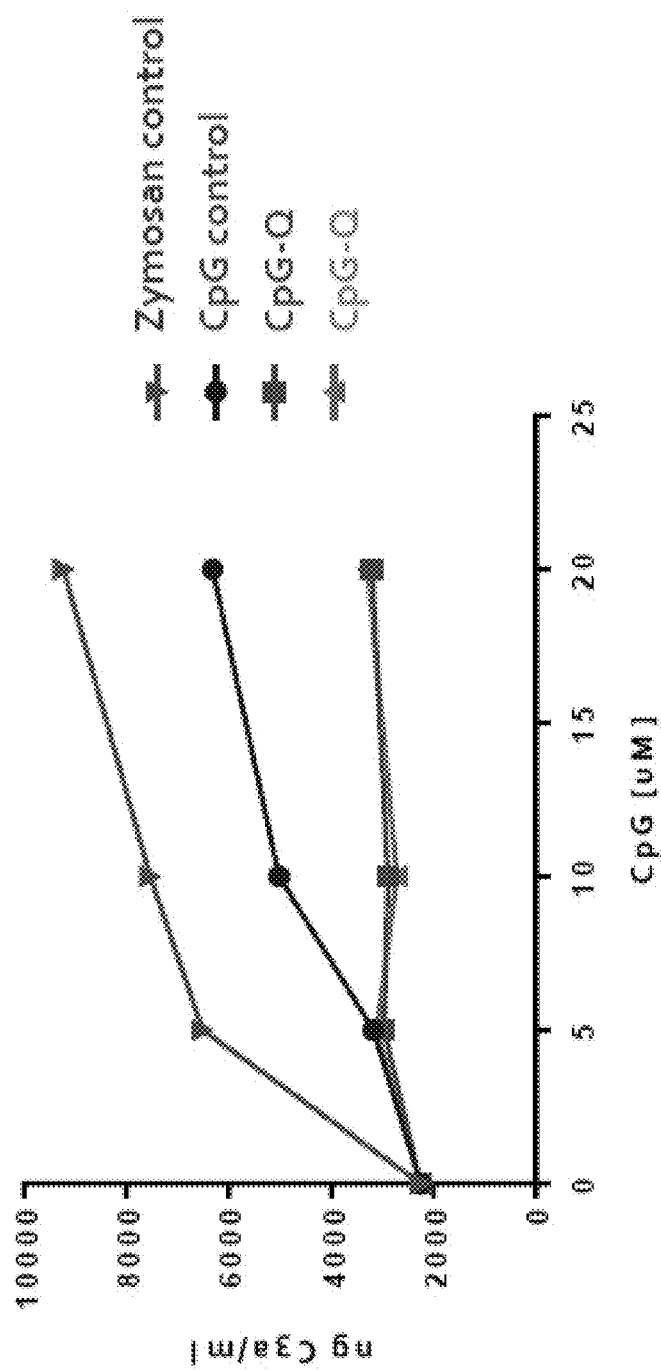
FIG. 59 shows complement activation (as measured by C3 release) after incubating monkey serum with Zymosan (inverted triangle; positive control), p1 (closed circles), or two CpG-containing immunostimulating polynucleotides as provided herein (closed squares and closed triangles).

To evaluate whether the CpG-containing polynucleotide according to the present disclosure activates the complement pathway, C3 release was assessed by incubating monkey serum with zymosan (positive control), naturally existing class B CpG sequence (p1), or two CpG-containing polynucleotides as provided herein. As shown in FIG. 59, the CpG-containing immunostimulating polynucleotide provided herein did not activate the complement pathway.

Example 35: Biological Activity of CpG-Antibody Conjugates Using Mouse Splenocyte Assay Mouse (BALB/c) spleen was harvested and passed through a 70 µm sieve to generate a single cell suspension. Red blood cells were lysed by incubation with RBC lysis buffer for 5 min at room temperature and then quenched with 20:1 complete media. Cells were harvested by gentle centrifugation, washed, and resuspended in RPMI containing 10% FBS and 1% PS ($2 \times 106$ cells/mL) and seeded in 9well plates. Test compounds were added at the indicated concentrations and incubated at 37° C. for 24 hours. The culture media were removed and secreted IL-6 was measured by ELISA. The results are summarized in the table below.

|  | P18 | P347 | SB-337 DAR1 | SB-337 DAR2 |
| --- | --- | --- | --- | --- |
| $EC_{50}$ (nM) | 42 | 219 | 0.07 | 0.11 |

Example 36: Pharmokinetic Studies of CpG-Antibody Conjugates

For a single dosing experiment, a test compound was administered to (BALB/c) mice at 10 mg/kg IV or SC. Serum samples were collected at predetermined time points for analysis and the results are shown in FIG. 83.

For a repeat dosing experiment, a test compound was administered to mice at 10 mg/kg IV on days 1, 7, and 14. Serum samples were collected on day 14 after the last injection at predetermined time points for analysis and the PK profile was compared to another set of mice that received only a single dose of the test compound. The results are shown in FIG. 84.

In another single dosing experiment, a CpG-antibody conjugate was administered to mice at 10 mg/kg IV. Serum samples were collected at 0.08, 1, 6, 24, 48, and 120 hours after administration. The serum samples were analyzed by both antibody and intact CpG-antibody conjugate. The results are shown in FIG. 85.

In yet another single dosing experiment, CpG-antibody conjugates were administered to mice at 10 mg/kg IV. Mice were sacrificed at 0, 0.08, 1, 6, and 24 hours post injection. Serum, liver, and spleen samples were analyzed. The results are shown in FIG. 86.

In yet another single dosing experiment, CpG-antibody conjugates were administered to mice at 10 mg/kg IV. Serum samples were collected at predetermined time points and the results are shown in FIGS. 87A and 87B.

In the above pharmaceutical experiments, the serum samples were analyzed using ELISA assays. To determine the amount of an intact CpG-antibody conjugate remained, serum samples were diluted with a biotinylated-CpG complementary sequence using an ELISA blocking buffer and then incubated for 30 minutes at room temperature. The diluted serum samples were each added at 100 μL to a well in a 96-well plate pre-coated with streptavidin. After the plate was incubated at room temperature for 60 minutes on a plate shaker and washed 3 times with an ELISA wash buffer, a goat anti-mouse IgG-HRP antibody (100 μL) at an optimized dilution in the ELISA blocking buffer was added to each well. After the plate was incubated at room temperature for 30 minutes on a plate shaker and washed 3 times with the ELISA wash buffer, a TMB substrate solution (100 μL) was added to each well. The plate was incubated at room temperature for 15-30 minutes or until desired color is developed, and a stop solution (100 μL) was then added to each well. The plate was read at 450 nm. Intact CpG-antibody conjugate concentrations in serum were calculated using a standard curve starting at 50 nM and serially diluted in the ELISA blocking buffer. The same protocol was also used to determine CpG-antibody conjugates in tissues after the tissues were homogenized.

To analyze for an antibody or the antibody portion of a CpG-antibody conjugate, a 96-well plate was coated with a mouse CD22 extracellular domain diluted in PBS. The plate was incubated at 4° C. overnight, washed 3 times with the ELISA wash buffer, and blocked with the ELISA blocking buffer for at least 60 minutes at room temperature. Serum samples were diluted with an optimized dilution factor in the ELISA blocking buffer. The diluted serum samples were each added at 100 μL to a well in the 96-well plate. After the plate was incubated at room temperature for 60 minutes on a plate shaker and washed 3 times with the ELISA wash buffer, a goat anti-mouse IgG-HRP antibody (100 μL) at an optimized dilution in the ELISA blocking buffer was added to each well of the plate. After the plate was incubated at room temperature for 30 minutes on a plate shaker and washed 3 times with the ELISA wash buffer, a TMB substrate solution (100 μL) was added to each well. After the plate was incubated at room temperature for 15-30 minutes or until desired color is developed, a stop solution (100 μL) was added to each well. The plate was read at 450 nm. CD22 antibody concentrations in serum were calculated using a standard curve starting at 50 nM and serially diluted in the ELISA blocking buffer.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. An oligonucleotide of Formula (A):

$$X^{5'}-(X^N)_b-Y^P-(X^N)_c-X^{3'} \quad (A)$$

or a stereoisomer, a mixture of two or more diastereomers, a tautomer, or a mixture of two or more tautomers thereof; or a pharmaceutically acceptable salt, solvate, or hydrate thereof;

wherein:
  each $X^N$ is independently a nucleotide;
  $X^{3'}$ is a 3' terminal nucleotide;
  $X^{5'}$ is a 5' terminal nucleotide;
  $Y^P$ is an internucleoside phosphotriester; and
  b and c are each an integer ranging from about 0 to about 25; with the proviso that their sum is no less than 5;
  wherein the oligonucleotide comprises a nucleotide with a modified nucleobase.

2. An oligonucleotide having a sequence of $N^1N^2CGN^3CG(T)_xGN^4CGN^5T$ (SEQ ID NO:497), wherein:
  x is an integer ranging from 1 to 4;
  $N^1$ is absent or 2'-deoxythymidine;
  $N^2$ is a 2'-deoxyribonucleotide with a modified nucleobase;
  $N^3$ is T-deoxyadenosine or 2'-deoxythymidine, each optionally comprising a 3'-phosphotriester;
  $N^4$ is T-deoxyadenosine or 2'-deoxythymidine; and
  $N^5$ is 2'-deoxythymidine optionally comprising a 3'-phosphotriester.

3. A method of treating cancer in a subject having cancer, comprising administering to the subject a therapeutically effective amount of the oligonucleotide of claim 1.

4. A method of modulating an endosomal toll-like receptor in a cell comprising the endosomal toll-like receptor, the method comprising contacting the cell with the oligonucleotide of claim 1, under conditions permitting the immunomodulating polynucleotides to be transported into the cell, wherein, after the contacting, the activity of the endosomal toll-like receptor is modulated.

5. A method of inducing one or more cytokines in an antigen-presenting cell comprising an endosomal toll-like receptor, the method comprising contacting the antigen-presenting cell with the oligonucleotide of claim 1 under conditions permitting the one or more immunomodulating polynucleotides to be transported into the cell, wherein, after the contacting, the level of at least one cytokine in the cell is increased,
  wherein the targeting moiety targets the antigen-presenting cell; and
  wherein the immunomodulating polynucleotide is an immunostimulating polynucleotide.

6. The oligonucleotide of claim 1, wherein b is an integer ranging from about 1 to about 15.

7. The oligonucleotide of claim 1, wherein b is an integer of about 2, about 3, about 4, about 11, or about 14.

8. The oligonucleotide of claim 1, wherein c is an integer ranging from about 0 to about 10.

9. The oligonucleotide of claim 1, wherein c is an integer of about 0 or about 8.

10. The oligonucleotide of claim 1, wherein the sum of b and c is ranging from about 5 to about 20.

11. The oligonucleotide of claim 1, wherein the sum of b and c is about 8, about 9, about 10, about 11, about 12, about 13, or about 14.

12. The oligonucleotide of claim 1, wherein each $X^N$ is independently a 2'-deoxyribonucleotide.

13. The oligonucleotide of claim 1, wherein $X^{3'}$ is a 2'-deoxyribonucleotide.

14. The oligonucleotide of claim 1, wherein $X^{3'}$ is 2'-deoxyadenosine, 2'-deoxyguanosine, 2'-deoxycytidine, a 5-halo-2'-deoxycytidine, T-deoxythymidine, 2'-deoxyuridine, or a 5-halo-2'-deoxyuridine.

15. The oligonucleotide of claim 1, wherein $X^{3'}$ is 2'-deoxythymidine.

16. The oligonucleotide of claim 1, wherein $X^{3'}$ is a 2'-modified ribonucleotide.

17. The oligonucleotide of claim 1, wherein $X^{3'}$ is a 2'-methoxy ribonucleotide or 2'-ethoxymethoxy ribonucleotide.

18. The oligonucleotide of claim 1, wherein $X^{5'}$ is a 2'-deoxyribonucleotide.

19. The oligonucleotide of claim 1, wherein $X^{5'}$ is 2'-deoxyadenosine, 2'-deoxyguanosine, 2'-deoxycytidine, a 5-halo-2'-deoxycytidine, T-deoxythymidine, 2'-deoxyuridine, or a 5-halo-2'-deoxyuridine.

20. The oligonucleotide of claim 1, wherein $X^{5'}$ is a 2'-deoxyribonucleotide with a substituted pyrimidine base.

21. The oligonucleotide of claim 1, wherein $X^{5'}$ is a 2'-deoxyribonucleotide with a 5-substituted pyrimidine base.

22. The oligonucleotide of claim 1, wherein $X^{5'}$ is 2'-deoxythymidine, a 5-halo-2'-deoxycytidine, or a 5-halo-2'-deoxyuridine.

23. The oligonucleotide of claim 1, wherein $X^{5'}$ is a 5-halo-2'-deoxycytidine.

24. The oligonucleotide of claim 1, wherein $X^{5'}$ is a 5-halo-2'-deoxyuridine.

25. The oligonucleotide of claim 1, wherein $X^{5'}$ is 2'-deoxythymidine, 5-bromo-2'-deoxycytidine, 5-iodo-2'-deoxycytidine, 5-bromo-2'-deoxyuridine, or 5-iodo-2'-deoxyuridine.

26. The oligonucleotide of claim 1, wherein $X^{5'}$ is 2'-deoxythymidine, 5-bromo-2'-deoxyuridine, or 5-iodo-2'-deoxyuridine.

27. The oligonucleotide of claim 1, wherein $X^{5'}$ has a 3'-phosphorothioate group.

28. The oligonucleotide of claim 27, wherein the 3'-phosphorothioate is chiral.

29. The oligonucleotide of claim 28, wherein $X^{5'}$ has a 3'-phosphorothioate group having a chirality of Rp and $X^{3'}$ is a 2'-methoxy ribonucleotide or 2'-ethoxymethoxy ribonucleotide.

30. The oligonucleotide of claim 28, wherein $X^{5'}$ has a 3'-phosphorothioate group having a chirality of Sp and $X^{3'}$ is a 2'-methoxy ribonucleotide or 2'-ethoxymethoxy ribonucleotide.

31. The oligonucleotide of claim 1, wherein $Y^P$ is:

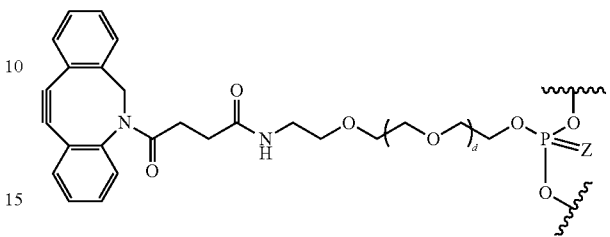

wherein Z is O or S; and d is an integer ranging from about 0 to about 50.

32. The oligonucleotide of claim 1, wherein $Y^P$ is:

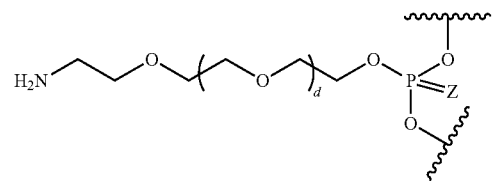

wherein Z is O or S; and d is an integer ranging from about 0 to about 50.

33. The oligonucleotide of claim 1, comprising an additional internucleoside phosphotriester.

34. The oligonucleotide of claim 33, wherein the additional internucleoside phosphotriester is an alkylphosphotriester.

35. The oligonucleotide of claim 1, comprising one or more internucleoside phosphorothioates.

* * * * *